US012767955B2

(12) United States Patent
Gersbach et al.

(10) Patent No.: US 12,767,955 B2
(45) **Date of Patent: *Oct. 20, 2026**

(54) CAS9 FUSION PROTEINS, RNA-GUIDED GENE EDITING, GENE REGULATION COMPOSITIONS, AND METHODS COMPRISING THE SAME

(71) Applicant: Duke University, Durham, NC (US)

(72) Inventors: Charles A. Gersbach, Durham, NC (US); Isaac B. Hilton, Durham, NC (US); Pablo Perez-Pinera, Urbana, IL (US); Ami M. Kabadi, Greensboro, NC (US); Pratiksha I. Thakore, Durham, IL (US); David G. Ousterout, Raleigh, NC (US); Joshua B. Black, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/927,679

(22) Filed: Jul. 13, 2020

(65) Prior Publication Data

US 2021/0032654 A1 Feb. 4, 2021

Related U.S. Application Data

(60) Continuation of application No. 15/991,333, filed on May 29, 2018, now Pat. No. 10,745,714, which is a division of application No. 14/895,316, filed as application No. PCT/US2014/041190 on Jun. 5, 2014, now Pat. No. 10,704,060.

(60) Provisional application No. 61/981,575, filed on Apr. 18, 2014, provisional application No. 61/967,466, filed on Mar. 19, 2014, provisional application No. 61/904,911, filed on Nov. 15, 2013, provisional application No. 61/839,127, filed on Jun. 25, 2013, provisional application No. 61/831,481, filed on Jun. 5, 2013.

(51) Int. Cl.

| | |
|---|---|
| ***C12N 9/22*** | (2006.01) |
| ***A61K 38/46*** | (2006.01) |
| ***A61K 48/00*** | (2006.01) |
| ***C07K 14/47*** | (2006.01) |
| ***C12N 9/96*** | (2006.01) |
| ***C12N 15/85*** | (2006.01) |
| ***C12N 15/90*** | (2006.01) |

(52) U.S. Cl.
CPC ............ *C12N 15/85* (2013.01); *A61K 38/465* (2013.01); *A61K 48/0058* (2013.01); *C07K 14/4708* (2013.01); *C12N 9/22* (2013.01); *C12N 9/96* (2013.01); *C12N 15/907* (2013.01); *A61K 48/005* (2013.01); *C07K 2319/71* (2013.01); *C12N 2740/16043* (2013.01); *C12N 2800/40* (2013.01); *C12N 2840/20* (2013.01); *C12Y 301/00* (2013.01)

(58) Field of Classification Search
CPC .... C12N 9/22; C12N 2310/20; C12N 15/113; C12N 15/11
See application file for complete search history.

(56) References Cited

U.S. PATENT DOCUMENTS

| | | | |
|---|---|---|---|
| 3,687,808 | A | 8/1972 | Merigan, Jr. |
| 4,469,863 | A | 9/1984 | Ts'o et al. |
| 4,476,301 | A | 10/1984 | Imbach et al. |
| 4,501,729 | A | 2/1985 | Boucher et al. |
| 4,554,101 | A | 11/1985 | Hopp |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,737,323 | A | 4/1988 | Martin et al. |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 5,013,830 | A | 5/1991 | Ohsuka et al. |
| 5,023,243 | A | 6/1991 | Tullis |
| 5,034,506 | A | 7/1991 | Summerton et al. |

(Continued)

FOREIGN PATENT DOCUMENTS

| | | | |
|---|---|---|---|
| AU | 2022318664 | A1 | 2/2024 |
| CA | 2749305 | A1 | 7/2010 |

(Continued)

OTHER PUBLICATIONS

US 11,898,176 B2, 02/2024, Gersbach et al. (withdrawn)

(Continued)

*Primary Examiner* — Dana H Shin
(74) *Attorney, Agent, or Firm* — Michael Best & Friedrich LLP

(57) ABSTRACT

Disclosed herein are Clustered Regularly Interspaced Short Palindromic Repeats (CRISPR)/CRISPR-associated (Cas) 9-based system related compositions and methods of using said CRISPR/Cas9-based system related compositions for altering gene expression and genome engineering. Also disclosed herein are compositions and methods of using said compositions for altering gene expression and genome engineering in muscle, such as skeletal muscle and cardiac muscle.

15 Claims, 81 Drawing Sheets

Specification includes a Sequence Listing.

(56) References Cited

U.S. PATENT DOCUMENTS

| | | | |
|---|---|---|---|
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,139,941 | A | 8/1992 | Muzyczka et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,219,740 | A | 6/1993 | Miller et al. |
| 5,220,007 | A | 6/1993 | Pederson et al. |
| 5,235,033 | A | 8/1993 | Summerton et al. |
| 5,245,022 | A | 9/1993 | Weis et al. |
| 5,254,469 | A | 10/1993 | Warren, III |
| 5,256,775 | A | 10/1993 | Froehler |
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,292,873 | A | 3/1994 | Rokita et al. |
| 5,317,098 | A | 5/1994 | Shizuya et al. |
| 5,321,131 | A | 6/1994 | Agrawal et al. |
| 5,366,878 | A | 11/1994 | Pederson et al. |
| 5,367,066 | A | 11/1994 | Urdea et al. |
| 5,371,241 | A | 12/1994 | Brush |
| 5,391,723 | A | 2/1995 | Priest |
| 5,399,676 | A | 3/1995 | Froehler |
| 5,403,711 | A | 4/1995 | Walder et al. |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,470,967 | A | 11/1995 | Huie et al. |
| 5,476,925 | A | 12/1995 | Letsinger et al. |
| 5,478,745 | A | 12/1995 | Samulski et al. |
| 5,484,908 | A | 1/1996 | Froehler et al. |
| 5,486,603 | A | 1/1996 | Buhr |
| 5,489,677 | A | 2/1996 | Sanghvi et al. |
| 5,491,133 | A | 2/1996 | Walder et al. |
| 5,502,177 | A | 3/1996 | Matteucci et al. |
| 5,510,473 | A | 4/1996 | Camerini-otero et al. |
| 5,510,475 | A | 4/1996 | Agrawal et al. |
| 5,512,439 | A | 4/1996 | Horner et al. |
| 5,512,667 | A | 4/1996 | Reed et al. |
| 5,514,785 | A | 5/1996 | Van Ness et al. |
| 5,519,126 | A | 5/1996 | Hecht |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,541,306 | A | 7/1996 | Agrawal et al. |
| 5,541,307 | A | 7/1996 | Cook et al. |
| 5,541,313 | A | 7/1996 | Ruth |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,552 | A | 10/1996 | Magda et al. |
| 5,567,810 | A | 10/1996 | Weis et al. |
| 5,571,799 | A | 11/1996 | Tkachuk et al. |
| 5,574,142 | A | 11/1996 | Meyer et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,593,972 | A | 1/1997 | Weiner et al. |
| 5,595,726 | A | 1/1997 | Magda et al. |
| 5,596,086 | A | 1/1997 | Matteucci et al. |
| 5,596,091 | A | 1/1997 | Switzer |
| 5,597,696 | A | 1/1997 | Linn et al. |
| 5,599,923 | A | 2/1997 | Sessler et al. |
| 5,599,928 | A | 2/1997 | Hemmi et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,633,360 | A | 5/1997 | Bischofberger et al. |
| 5,652,355 | A | 7/1997 | Metelev et al. |
| 5,652,356 | A | 7/1997 | Agrawal |
| 5,658,784 | A | 8/1997 | Eckner et al. |
| 5,663,312 | A | 9/1997 | Chaturvedula et al. |
| 5,677,437 | A | 10/1997 | Teng et al. |
| 5,677,439 | A | 10/1997 | Weis et al. |
| 5,681,941 | A | 10/1997 | Cook et al. |
| 5,688,941 | A | 11/1997 | Cook et al. |
| 5,700,922 | A | 12/1997 | Cook et al. |
| 5,714,331 | A | 2/1998 | Buchardt et al. |
| 5,719,262 | A | 2/1998 | Buchardt et al. |
| 5,741,683 | A | 4/1998 | Zhou et al. |
| 5,750,692 | A | 5/1998 | Cook et al. |
| 5,773,700 | A | 6/1998 | Van Grinsven et al. |
| 5,962,428 | A | 10/1999 | Carrano et al. |
| 6,057,152 | A | 5/2000 | Samulski et al. |
| 6,140,081 | A | 10/2000 | Barbas |
| 6,204,059 | B1 | 3/2001 | Samulski et al. |
| 6,207,453 | B1 | 3/2001 | Maass et al. |
| 6,268,213 | B1 | 7/2001 | Samulski et al. |
| 6,268,490 | B1 | 7/2001 | Imanishi et al. |
| 6,287,860 | B1 | 9/2001 | Monia et al. |
| 6,453,242 | B1 | 9/2002 | Eisenberg et al. |
| 6,462,254 | B1 | 10/2002 | Vernachio et al. |
| 6,491,907 | B1 | 12/2002 | Rabinowitz et al. |
| 6,534,261 | B1 | 3/2003 | Cox, III et al. |
| 6,596,535 | B1 | 7/2003 | Carter |
| 6,660,514 | B1 | 12/2003 | Zolotukhin et al. |
| 6,734,291 | B2 | 5/2004 | Kochkine et al. |
| 6,770,748 | B2 | 8/2004 | Imanishi et al. |
| 6,794,499 | B2 | 9/2004 | Wengel et al. |
| 6,951,753 | B2 | 10/2005 | Shenk et al. |
| 7,034,133 | B2 | 4/2006 | Wengel et al. |
| 7,053,207 | B2 | 5/2006 | Wengel |
| 7,060,809 | B2 | 6/2006 | Wengel et al. |
| 7,074,596 | B2 | 7/2006 | Darzynkiewicz et al. |
| 7,084,125 | B2 | 8/2006 | Wengel |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,449,561 | B1 | 11/2008 | Sommer et al. |

(56) References Cited

U.S. PATENT DOCUMENTS

| | | | |
|---|---|---|---|
| 7,456,683 | B2 | 11/2008 | Takano et al. |
| 7,572,582 | B2 | 8/2009 | Wengel et al. |
| 7,588,772 | B2 | 9/2009 | Kay et al. |
| 7,728,118 | B2 | 6/2010 | Wood et al. |
| 7,745,651 | B2 | 6/2010 | Heyes et al. |
| 7,790,449 | B2 | 9/2010 | Gao et al. |
| 7,799,565 | B2 | 9/2010 | Maclachlan et al. |
| 7,906,111 | B2 | 3/2011 | Wilson et al. |
| 8,278,036 | B2 | 10/2012 | Kariko et al. |
| 8,450,107 | B1 | 5/2013 | Zhang et al. |
| 8,586,526 | B2 | 11/2013 | Gregory et al. |
| 8,697,359 | B1 | 4/2014 | Zhang et al. |
| 8,889,356 | B2 | 11/2014 | Zhang |
| 8,993,233 | B2 | 3/2015 | Zhang et al. |
| 9,139,554 | B2 | 9/2015 | Hope et al. |
| 9,458,205 | B2 | 10/2016 | Gregory et al. |
| 9,738,879 | B2 | 8/2017 | Gersbach et al. |
| 9,828,582 | B2 | 11/2017 | Perez-Pinera et al. |
| 9,834,791 | B2 | 12/2017 | Zhang et al. |
| 9,890,364 | B2 | 2/2018 | Joung et al. |
| 10,011,850 | B2 | 7/2018 | Joung et al. |
| 10,190,106 | B2 | 1/2019 | Wolfe et al. |
| 10,266,850 | B2 | 4/2019 | Doudna et al. |
| 10,676,726 | B2 | 6/2020 | Gersbach et al. |
| 10,676,735 | B2 | 6/2020 | Gersbach et al. |
| 10,704,060 | B2 | 7/2020 | Gersbach et al. |
| 10,711,256 | B2 | 7/2020 | Gersbach et al. |
| 10,745,714 | B2 | 8/2020 | Gersbach et al. |
| 10,836,997 | B2 | 11/2020 | Ko |
| 11,155,796 | B2 | 10/2021 | Gersbach et al. |
| 11,421,251 | B2 | 8/2022 | Gersbach et al. |
| 11,427,817 | B2 | 8/2022 | Josephs et al. |
| 11,970,710 | B2 | 4/2024 | Gersbach et al. |
| 11,976,307 | B2 | 5/2024 | Gersbach et al. |
| 12,428,631 | B2 | 9/2025 | Gersbach et al. |
| 2002/0160940 | A1 | 10/2002 | Case et al. |
| 2003/0124102 | A1 | 7/2003 | Rudnicki et al. |
| 2004/0142025 | A1 | 7/2004 | Maclachlan et al. |
| 2004/0175727 | A1 | 9/2004 | Draghia-Akli et al. |
| 2004/0192593 | A1 | 9/2004 | Draghia-Akli et al. |
| 2004/0204345 | A1 | 10/2004 | Case et al. |
| 2005/0079512 | A1 | 4/2005 | Emerson et al. |
| 2006/0068395 | A1 | 3/2006 | Wood et al. |
| 2006/0171924 | A1 | 8/2006 | Luo et al. |
| 2006/0211647 | A1 | 9/2006 | Khan |
| 2006/0270595 | A1 | 11/2006 | Jullien et al. |
| 2007/0042031 | A1 | 2/2007 | Maclachlan et al. |
| 2007/0042462 | A1 | 2/2007 | Hildinger |
| 2007/0059795 | A1 | 3/2007 | Moore et al. |
| 2007/0185042 | A1 | 8/2007 | Tsai et al. |
| 2007/0192880 | A1 | 8/2007 | Muyan et al. |
| 2008/0070299 | A1 | 3/2008 | Wood et al. |
| 2008/0090291 | A1 | 4/2008 | Wood et al. |
| 2008/0200409 | A1 | 8/2008 | Wilson et al. |
| 2009/0018031 | A1 | 1/2009 | Trinklein et al. |
| 2010/0035968 | A1 | 2/2010 | Rasmussen et al. |
| 2010/0076057 | A1 | 3/2010 | Sontheimer et al. |
| 2010/0261175 | A1 | 10/2010 | Rasmussen et al. |
| 2010/0267018 | A1 | 10/2010 | Wengel et al. |
| 2011/0145940 | A1 | 6/2011 | Voytas et al. |
| 2011/0197290 | A1 | 8/2011 | Fahrenkrug et al. |
| 2011/0236353 | A1 | 9/2011 | Wilson et al. |
| 2011/0263682 | A1 | 10/2011 | De Kimpe et al. |
| 2011/0286957 | A1 | 11/2011 | Prieve et al. |
| 2011/0301073 | A1 | 12/2011 | Gregory et al. |
| 2011/0301218 | A1 | 12/2011 | Bozzoni et al. |
| 2012/0195917 | A1 | 8/2012 | Sahin et al. |
| 2012/0207744 | A1 | 8/2012 | Mendlein et al. |
| 2013/0137173 | A1 | 5/2013 | Zang et al. |
| 2013/0274129 | A1 | 10/2013 | Katzen et al. |
| 2013/0323001 | A1 | 12/2013 | Ueki et al. |
| 2014/0068797 | A1 | 3/2014 | Doudna et al. |
| 2014/0140969 | A1 | 5/2014 | Beausejour et al. |
| 2014/0170753 | A1 | 6/2014 | Zhang |
| 2014/0179006 | A1 | 6/2014 | Zhang |
| 2014/0186958 | A1 | 7/2014 | Zhang et al. |
| 2014/0234975 | A1 | 8/2014 | Silva et al. |
| 2014/0295557 | A1 | 10/2014 | Joung et al. |
| 2014/0309177 | A1 | 10/2014 | Perez-Pinera et al. |
| 2014/0315862 | A1 | 10/2014 | Kaye |
| 2014/0356956 | A1 | 12/2014 | Church et al. |
| 2014/0357530 | A1 | 12/2014 | Zhang et al. |
| 2014/0377868 | A1 | 12/2014 | Joung et al. |
| 2015/0024499 | A1 | 1/2015 | Brouns et al. |
| 2015/0031089 | A1 | 1/2015 | Lindstrom |
| 2015/0044772 | A1 | 2/2015 | Zhao |
| 2015/0045413 | A1 | 2/2015 | De Visser et al. |
| 2015/0056705 | A1 | 2/2015 | Conway et al. |
| 2015/0079064 | A1 | 3/2015 | Gersbach et al. |
| 2015/0159178 | A1 | 6/2015 | Green et al. |
| 2015/0166980 | A1 | 6/2015 | Liu et al. |
| 2015/0225717 | A1 | 8/2015 | Lee et al. |
| 2015/0252358 | A1 | 9/2015 | Maeder et al. |
| 2016/0002634 | A1 | 1/2016 | Sazani et al. |
| 2016/0040189 | A1 | 2/2016 | Kennedy et al. |
| 2016/0058889 | A1 | 3/2016 | Olson et al. |
| 2016/0199419 | A1 | 7/2016 | Miura |
| 2016/0201089 | A1 | 7/2016 | Gersbach et al. |
| 2016/0281166 | A1 | 9/2016 | Bhattacharjee et al. |
| 2016/0354487 | A1 | 12/2016 | Zhang et al. |
| 2017/0002316 | A1 | 1/2017 | Gascón Jiménez et al. |
| 2017/0037396 | A1 | 2/2017 | Lee et al. |
| 2017/0137801 | A1 | 5/2017 | Liras et al. |
| 2017/0198308 | A1 | 7/2017 | Qi et al. |
| 2017/0204407 | A1 | 7/2017 | Gilbert et al. |
| 2017/0260547 | A1 | 9/2017 | Dombrowski et al. |
| 2017/0283831 | A1 | 10/2017 | Zhang et al. |
| 2017/0298331 | A1 | 10/2017 | Gersbach et al. |
| 2017/0327806 | A1 | 11/2017 | Joung et al. |
| 2017/0362635 | A1 | 12/2017 | Chamberlain et al. |
| 2018/0002682 | A1 | 1/2018 | Sternberg et al. |
| 2018/0023064 | A1 | 1/2018 | Gersbach et al. |
| 2018/0073012 | A1 | 3/2018 | Liu et al. |
| 2018/0094238 | A1 | 4/2018 | Perez-Pinera et al. |
| 2018/0127780 | A1 | 5/2018 | Liu et al. |
| 2018/0135023 | A1 | 5/2018 | Wang et al. |
| 2018/0135109 | A1 | 5/2018 | Jayaram et al. |
| 2018/0201951 | A1 | 7/2018 | Guilak et al. |
| 2018/0237771 | A1 | 8/2018 | Kim et al. |
| 2018/0251735 | A1 | 9/2018 | Ko |
| 2018/0271069 | A1 | 9/2018 | Min et al. |
| 2018/0280539 | A1 | 10/2018 | Debs et al. |
| 2018/0291370 | A1 | 10/2018 | Gersbach et al. |
| 2018/0298380 | A1 | 10/2018 | Gao et al. |
| 2018/0305689 | A1 | 10/2018 | Sætrom et al. |
| 2018/0305704 | A1 | 10/2018 | Zhang |
| 2018/0305719 | A1 | 10/2018 | Perez-Pinera et al. |
| 2018/0319850 | A1 | 11/2018 | Payne et al. |
| 2018/0320197 | A1 | 11/2018 | Gersbach et al. |
| 2018/0327740 | A1 | 11/2018 | Gifford et al. |
| 2018/0334685 | A1 | 11/2018 | Yeo et al. |
| 2018/0334688 | A1 | 11/2018 | Gersbach et al. |
| 2018/0353615 | A1 | 12/2018 | Gersbach et al. |
| 2018/0355332 | A1 * | 12/2018 | Steinberg ............. C12N 15/102 |
| 2019/0032049 | A1 | 1/2019 | Naldini et al. |
| 2019/0038776 | A1 | 2/2019 | Pyle et al. |
| 2019/0048337 | A1 | 2/2019 | Hsu et al. |
| 2019/0062790 | A1 | 2/2019 | Doudna et al. |
| 2019/0078119 | A1 | 3/2019 | Wilson et al. |
| 2019/0106710 | A1 | 4/2019 | Zhang et al. |
| 2019/0127713 | A1 | 5/2019 | Gersbach et al. |
| 2019/0134221 | A1 | 5/2019 | Bumcrot et al. |
| 2019/0136229 | A1 | 5/2019 | Josephs et al. |
| 2019/0142972 | A1 | 5/2019 | Burns et al. |
| 2019/0144845 | A9 | 5/2019 | Yin et al. |
| 2019/0151476 | A1 | 5/2019 | Gersbach et al. |
| 2019/0167815 | A1 | 6/2019 | Holmes et al. |
| 2019/0183932 | A1 | 6/2019 | Mackall et al. |
| 2019/0192691 | A1 | 6/2019 | Barrett et al. |
| 2019/0194633 | A1 | 6/2019 | Gersbach et al. |
| 2019/0201402 | A1 | 7/2019 | Jiang et al. |
| 2019/0225955 | A1 | 7/2019 | Liu et al. |
| 2019/0225991 | A1 | 7/2019 | Izpisua et al. |
| 2019/0248854 | A1 | 8/2019 | Tremblay et al. |

(56) References Cited

U.S. PATENT DOCUMENTS

| | | | |
|---|---|---|---|
| 2019/0264232 | A1 | 8/2019 | Hou et al. |
| 2019/0351074 | A1 | 11/2019 | Ahituv et al. |
| 2019/0359959 | A1 | 11/2019 | Jaenisch et al. |
| 2019/0374655 | A1 | 12/2019 | Kabadi et al. |
| 2020/0002731 | A1 | 1/2020 | Frendewey et al. |
| 2020/0056206 | A1 | 2/2020 | Tremblay et al. |
| 2020/0063105 | A1 | 2/2020 | Ng et al. |
| 2020/0080108 | A1 | 3/2020 | Jaskula-Ranga et al. |
| 2020/0080112 | A1 | 3/2020 | Zhang et al. |
| 2020/0109406 | A1 | 4/2020 | Miller et al. |
| 2020/0123533 | A1 | 4/2020 | Wang et al. |
| 2020/0148745 | A1 | 5/2020 | Keravala et al. |
| 2020/0216549 | A1 | 7/2020 | Fukumura et al. |
| 2020/0216810 | A1 | 7/2020 | Metelitsa et al. |
| 2020/0260698 | A1 | 8/2020 | Kyrychenko et al. |
| 2020/0275641 | A1 | 9/2020 | Min et al. |
| 2020/0318139 | A1 | 10/2020 | Gersbach et al. |
| 2020/0332307 | A1 | 10/2020 | Hummel et al. |
| 2020/0347105 | A1 | 11/2020 | Gersbach et al. |
| 2020/0361877 | A1 | 11/2020 | Mahajan et al. |
| 2020/0370042 | A1 | 11/2020 | Olson et al. |
| 2020/0385695 | A1 | 12/2020 | Gersbach et al. |
| 2021/0002665 | A1 | 1/2021 | Gersbach et al. |
| 2021/0024895 | A1 | 1/2021 | Kariko et al. |
| 2021/0040460 | A1 | 2/2021 | Gersbach et al. |
| 2021/0054448 | A1 | 2/2021 | Ng et al. |
| 2021/0254049 | A1 | 8/2021 | Wang et al. |
| 2021/0277379 | A1 | 9/2021 | Gaudelli et al. |
| 2021/0322577 | A1 | 10/2021 | Lande et al. |
| 2021/0363521 | A1 | 11/2021 | Police et al. |
| 2021/0363525 | A1 | 11/2021 | Sætrom et al. |
| 2022/0098561 | A1 | 3/2022 | Gersbach et al. |
| 2022/0177879 | A1 | 6/2022 | Gersbach et al. |
| 2022/0184229 | A1 | 6/2022 | Gersbach et al. |
| 2022/0186199 | A1 | 6/2022 | Cotta-Ramusino et al. |
| 2022/0195406 | A1 | 6/2022 | Gersbach et al. |
| 2022/0244244 | A1 | 8/2022 | Schmedt et al. |
| 2022/0249626 | A1 | 8/2022 | Kmiec et al. |
| 2022/0305141 | A1 | 9/2022 | Gersbach et al. |
| 2022/0307015 | A1 | 9/2022 | Gersbach et al. |
| 2022/0364124 | A1 | 11/2022 | Gersbach et al. |
| 2022/0396790 | A1 | 12/2022 | Gersbach et al. |
| 2023/0032846 | A1 | 2/2023 | Gersbach et al. |
| 2023/0047669 | A1 | 2/2023 | Josephs et al. |
| 2023/0201375 | A1 | 6/2023 | Gersbach et al. |
| 2023/0348870 | A1 | 11/2023 | Gersbach et al. |
| 2023/0349888 | A1 | 11/2023 | Gersbach et al. |
| 2023/0383270 | A1 | 11/2023 | Gersbach et al. |
| 2023/0383297 | A1 | 11/2023 | Gersbach et al. |
| 2023/0392132 | A1 | 12/2023 | Gersbach et al. |
| 2024/0026352 | A1 | 1/2024 | Gersbach et al. |
| 2024/0052328 | A1 | 2/2024 | Kwon et al. |
| 2024/0058425 | A1 | 2/2024 | Gersbach et al. |
| 2024/0067968 | A1 | 2/2024 | Cosgrove et al. |
| 2024/0141341 | A1 | 5/2024 | Gersbach et al. |
| 2024/0279628 | A1 | 8/2024 | Gersbach et al. |
| 2024/0336892 | A1 | 10/2024 | Perez-Pinera et al. |
| 2025/0114482 | A1 | 4/2025 | Gersbach et al. |
| 2025/0262326 | A1 | 8/2025 | Gersbach et al. |

FOREIGN PATENT DOCUMENTS

| | | | |
|---|---|---|---|
| CA | 2981508 | A1 | 10/2016 |
| CA | 3086885 | A1 | 7/2019 |
| CA | 3101477 | A1 | 12/2019 |
| EP | 2620161 | A1 | 7/2013 |
| EP | 3009511 | A2 | 4/2016 |
| EP | 3199632 | A1 | 8/2017 |
| EP | 3712272 | A1 | 9/2020 |
| EP | 3209783 | B1 | 11/2021 |
| EP | 3995584 | A1 | 5/2022 |
| JP | 2003-512827 | A | 4/2003 |
| JP | 2006254854 | A | 9/2006 |
| JP | 2013-509159 | A | 3/2013 |
| JP | 2015-534817 | A | 12/2015 |
| JP | 2016-521452 | A | 7/2016 |
| JP | 2016-521452 | A2 | 7/2016 |
| JP | 2016-521975 | A | 7/2016 |
| JP | 2016-523082 | A | 8/2016 |
| JP | 2018-011546 | A | 1/2018 |
| JP | 2019-103393 | A | 6/2019 |
| JP | 2020-517247 | A | 6/2020 |
| KR | 20190134673 | A | 12/2019 |
| WO | WO 1991/18114 | A1 | 11/1991 |
| WO | WO 1992/000387 | A1 | 1/1992 |
| WO | WO 1993/007883 | A1 | 4/1993 |
| WO | WO 1993/024640 | A2 | 12/1993 |
| WO | WO 1994/016737 | A1 | 8/1994 |
| WO | WO 1998/053058 | A1 | 11/1998 |
| WO | WO 1998/053059 | A1 | 11/1998 |
| WO | WO 1998/053060 | A1 | 11/1998 |
| WO | WO 2000/028004 | A1 | 5/2000 |
| WO | 2001/083793 | A2 | 11/2001 |
| WO | WO 2001/083783 | A2 | 11/2001 |
| WO | WO 2001/092551 | A2 | 12/2001 |
| WO | WO 2002/016536 | A1 | 2/2002 |
| WO | WO 2003/016496 | A2 | 2/2003 |
| WO | WO 2003/042397 | A2 | 5/2003 |
| WO | WO2003/072788 | A1 | 9/2003 |
| WO | 2004/018632 | A2 | 3/2004 |
| WO | WO 2005/033321 | A2 | 4/2005 |
| WO | WO 2006/110689 | A2 | 10/2006 |
| WO | WO 2007/019301 | A2 | 2/2007 |
| WO | WO 2008/006028 | A2 | 1/2008 |
| WO | WO 2008/070859 | A2 | 6/2008 |
| WO | WO 2010/053572 | A2 | 5/2010 |
| WO | WO 2010/075424 | A2 | 7/2010 |
| WO | WO2010/144740 | A1 | 12/2010 |
| WO | WO 2011/036640 | A2 | 3/2011 |
| WO | WO 2011/126808 | A2 | 10/2011 |
| WO | 2011/141820 | A1 | 11/2011 |
| WO | 2011/146121 | A1 | 11/2011 |
| WO | WO 2011/154427 | A1 | 12/2011 |
| WO | WO 2012/136476 | A1 | 10/2012 |
| WO | WO 2012/170930 | A1 | 12/2012 |
| WO | WO 2013/049493 | A1 | 4/2013 |
| WO | WO 2013/098244 | A1 | 7/2013 |
| WO | WO 2013/143555 | A1 | 10/2013 |
| WO | WO 2013/163628 | A2 | 10/2013 |
| WO | WO 2013/176772 | A1 | 11/2013 |
| WO | WO 2013/182683 | A1 | 12/2013 |
| WO | WO 2014/018423 | A2 | 1/2014 |
| WO | 2014/043519 | A1 | 3/2014 |
| WO | WO 2014/059255 | A1 | 4/2014 |
| WO | WO 2014/065596 | A1 | 5/2014 |
| WO | WO 2014/081855 | A1 | 5/2014 |
| WO | 2014/093622 | A2 | 6/2014 |
| WO | 2014/093712 | A1 | 6/2014 |
| WO | 2014/099744 | A1 | 6/2014 |
| WO | WO 2014/089290 | A1 | 6/2014 |
| WO | WO 2014/093479 | A1 | 6/2014 |
| WO | WO 2014/093595 | A1 | 6/2014 |
| WO | WO 2014/093655 | A2 | 6/2014 |
| WO | WO 2014/093661 | A2 | 6/2014 |
| WO | WO 2014/093709 | A1 | 6/2014 |
| WO | WO 2014/144288 | A1 | 9/2014 |
| WO | WO 2014/144592 | A2 | 9/2014 |
| WO | WO 2014/152432 | A2 | 9/2014 |
| WO | WO 2014/172470 | A2 | 10/2014 |
| WO | WO 2014/186585 | A2 | 11/2014 |
| WO | 2014/197568 | A2 | 12/2014 |
| WO | WO 2014/191128 | A1 | 12/2014 |
| WO | WO 2014/197748 | A2 | 12/2014 |
| WO | WO 2014/204726 | A1 | 12/2014 |
| WO | WO 2014/204728 | A1 | 12/2014 |
| WO | WO 2015/006747 | A2 | 1/2015 |
| WO | 2015/021457 | A2 | 2/2015 |
| WO | WO 2015/017519 | A1 | 2/2015 |
| WO | 2015/035139 | A2 | 3/2015 |
| WO | WO2015/035136 | A2 | 3/2015 |
| WO | WO 2015/048690 | A1 | 4/2015 |
| WO | WO 2015/070083 | A1 | 5/2015 |
| WO | 2015/089462 | A1 | 6/2015 |
| WO | WO 2015/089419 | A2 | 6/2015 |

(56) References Cited

FOREIGN PATENT DOCUMENTS

| | | | |
|---|---|---|---|
| WO | WO2015/089427 | A1 | 6/2015 |
| WO | WO 2015/089465 | A1 | 6/2015 |
| WO | WO 2015/089486 | A2 | 6/2015 |
| WO | WO 2015/126927 | A2 | 8/2015 |
| WO | WO 2015/155686 | A2 | 10/2015 |
| WO | WO2015/161276 | A2 | 10/2015 |
| WO | 2015/195621 | A1 | 12/2015 |
| WO | 2016/011080 | A2 | 1/2016 |
| WO | WO2016/011070 | A2 | 1/2016 |
| WO | WO2016/049258 | A2 | 3/2016 |
| WO | WO 2016/054326 | A1 | 4/2016 |
| WO | WO 2016/063264 | A1 | 4/2016 |
| WO | WO 2016/070070 | A1 | 5/2016 |
| WO | WO 2016/081924 | A1 | 5/2016 |
| WO | WO 2016/094880 | A1 | 6/2016 |
| WO | WO2016/114972 | A1 | 7/2016 |
| WO | WO2016/123578 | A1 | 8/2016 |
| WO | WO 2016/130600 | A2 | 8/2016 |
| WO | WO 2016/161380 | A1 | 10/2016 |
| WO | 2016/182893 | A1 | 11/2016 |
| WO | 2016/205613 | A1 | 12/2016 |
| WO | WO 2016/187717 | A1 | 12/2016 |
| WO | WO 2017/015637 | A1 | 1/2017 |
| WO | 2017/016915 | A1 | 2/2017 |
| WO | WO 2017/035416 | A2 | 3/2017 |
| WO | WO 2017/049266 | A2 | 3/2017 |
| WO | WO2017/049407 | A1 | 3/2017 |
| WO | WO 2017/066497 | A2 | 4/2017 |
| WO | WO 2017/070632 | A2 | 4/2017 |
| WO | 2017/074943 | A1 | 5/2017 |
| WO | 2017/075335 | A1 | 5/2017 |
| WO | WO 2017/072590 | A1 | 5/2017 |
| WO | WO 2017/075478 | A2 | 5/2017 |
| WO | WO 2017/095967 | A2 | 6/2017 |
| WO | WO 2017/139505 | A2 | 8/2017 |
| WO | WO 2017/165859 | A1 | 9/2017 |
| WO | 2017/180976 | A1 | 10/2017 |
| WO | WO 2017/180915 | A2 | 10/2017 |
| WO | WO 2017/193029 | A2 | 11/2017 |
| WO | 2018/005805 | A1 | 1/2018 |
| WO | 2018/017483 | A1 | 1/2018 |
| WO | WO2018/002812 | A1 | 1/2018 |
| WO | WO 2018/013932 | A1 | 1/2018 |
| WO | WO 2018/017751 | A1 | 1/2018 |
| WO | WO 2018/017754 | A1 | 1/2018 |
| WO | WO 2018/031762 | A1 | 2/2018 |
| WO | WO 2018/035388 | A1 | 2/2018 |
| WO | WO 2018/035495 | A1 | 2/2018 |
| WO | 2018/039145 | A1 | 3/2018 |
| WO | WO 2018/081504 | A1 | 5/2018 |
| WO | WO 2018/098480 | A1 | 5/2018 |
| WO | 2018/107003 | A1 | 6/2018 |
| WO | 2018/129486 | A2 | 7/2018 |
| WO | WO 2018/129296 | A1 | 7/2018 |
| WO | WO2018/162702 | A1 | 9/2018 |
| WO | 2018/179578 | A1 | 10/2018 |
| WO | 2018/195073 | A2 | 10/2018 |
| WO | WO 2018/191388 | A1 | 10/2018 |
| WO | 2019/009682 | A2 | 1/2019 |
| WO | WO 2019/002590 | A1 | 1/2019 |
| WO | WO 2019/014230 | A1 | 1/2019 |
| WO | WO2019/023291 | A2 | 1/2019 |
| WO | WO 2019/036599 | A1 | 2/2019 |
| WO | WO 2019/038776 | A1 | 2/2019 |
| WO | 2019/046755 | A1 | 3/2019 |
| WO | WO 2019/067786 | A1 | 4/2019 |
| WO | WO 2019/077001 | A1 | 4/2019 |
| WO | WO 2019/079514 | A1 | 4/2019 |
| WO | WO2019/084050 | A1 | 5/2019 |
| WO | WO 2019/092505 | A1 | 5/2019 |
| WO | 2019/113472 | A1 | 6/2019 |
| WO | 2019/120283 | A1 | 6/2019 |
| WO | WO2019/123014 | A1 | 6/2019 |
| WO | WO2019/136216 | A1 | 7/2019 |
| WO | WO 2019/144061 | A1 | 7/2019 |
| WO | 2019/152609 | A1 | 8/2019 |
| WO | 2019/204750 | A1 | 10/2019 |
| WO | WO2019/213626 | A1 | 11/2019 |
| WO | 2020/018918 | A1 | 1/2020 |
| WO | 2020/079033 | A1 | 4/2020 |
| WO | 2020/086881 | A1 | 4/2020 |
| WO | 2020/101042 | A1 | 5/2020 |
| WO | 2020/106916 | A1 | 5/2020 |
| WO | WO 2020/124257 | A1 | 6/2020 |
| WO | WO 2020/132226 | A1 | 6/2020 |
| WO | 2020/168133 | A1 | 8/2020 |
| WO | WO 2020/163396 | A1 | 8/2020 |
| WO | WO 2020/210776 | A1 | 10/2020 |
| WO | WO 2020/214609 | A1 | 10/2020 |
| WO | WO 2020/214613 | A1 | 10/2020 |
| WO | WO 2020/257665 | A1 | 12/2020 |
| WO | WO 2021/026516 | A1 | 2/2021 |
| WO | WO 2021/034984 | A2 | 2/2021 |
| WO | WO 2021/034987 | A1 | 2/2021 |
| WO | WO 2021/055956 | A1 | 3/2021 |
| WO | 2021/076744 | A1 | 4/2021 |
| WO | WO 2021/067878 | A1 | 4/2021 |
| WO | WO 2021/113536 | A1 | 6/2021 |
| WO | 2021/167101 | A1 | 8/2021 |
| WO | PCT/US2021/054292 | | 10/2021 |
| WO | PCT/US2021/054636 | | 10/2021 |
| WO | PCT/US2021/056122 | | 10/2021 |
| WO | PCT/US2021/059270 | | 11/2021 |
| WO | WO 2021/222268 | A1 | 11/2021 |
| WO | WO 2021/222314 | A1 | 11/2021 |
| WO | WO 2021/222327 | A1 | 11/2021 |
| WO | WO 2021/222328 | A1 | 11/2021 |
| WO | WO 2021/226555 | A2 | 11/2021 |
| WO | 2022/038264 | A1 | 2/2022 |
| WO | 2022/055946 | A1 | 3/2022 |
| WO | 2022/087321 | A1 | 4/2022 |
| WO | 2022/104159 | A1 | 5/2022 |
| WO | WO 2022/103935 | A1 | 5/2022 |
| WO | 2022/133062 | A1 | 6/2022 |
| WO | WO 2022/187288 | A2 | 9/2022 |
| WO | 2023/283631 | A2 | 1/2023 |
| WO | WO 2023/010133 | A2 | 2/2023 |
| WO | WO 2023/137471 | A1 | 7/2023 |
| WO | WO 2023/137472 | A2 | 7/2023 |
| WO | PCT/US2023/076920 | | 10/2023 |
| WO | PCT/US2023/078124 | | 10/2023 |
| WO | WO2023/200998 | A2 | 10/2023 |
| WO | WO 2024/015881 | A2 | 1/2024 |
| WO | PCT/US2023/072524 | | 2/2024 |
| WO | WO2024/040253 | A1 | 2/2024 |
| WO | WO 2024/064642 | A2 | 3/2024 |
| WO | PCT/US2024/025594 | | 4/2024 |
| WO | WO2024/081937 | A1 | 4/2024 |
| WO | 2024/092258 | A2 | 5/2024 |
| WO | WO 2024/040254 | A3 | 5/2024 |
| WO | WO 2024/220947 | A2 | 10/2024 |
| WO | 2024/229292 | A2 | 11/2024 |
| WO | WO 2025/038982 | A2 | 2/2025 |
| WO | WO 2025/049903 | A2 | 3/2025 |

OTHER PUBLICATIONS

Mitsunobu et al., Beyond native Cas9: Manipulating genomic information and function, Trends in Biotechnology, vol. 35, pp. 983-996. (Year: 2017).*

Ousterout et al., "Genetic Correction of Duchenne Muscular Dystrophy Using Zinc Finger Nucleases," Mol. Ther., 2013, vol. 21, Supplement 1, 292, p. S111-S112.

Rousseau et al., "New TALENs To Correct the Reading Frame of Exon 54 of the Dystrophin Gene," Mol. Ther., 2013, vol. 21, Supplement 1, 293, p. S112.

Japanese Patent Office Action for Application No. 2019-200973 dated Jan. 11, 2022 (5 pages, English translation Included).

United States Patent Office Action for U.S. Appl. No. 16/858,689 dated Mar. 4, 2022 (8 pages).

United States Patent Office Action for U.S. Appl. No. 15/789,348 dated Mar. 21, 2022 (23 pages).

(56) References Cited

OTHER PUBLICATIONS

U.S. Appl. No. 17/471,935, filed Sep. 10, 2021.
U.S. Appl. No. 17/603,243, filed Oct. 12, 2021.
U.S. Appl. No. 17/603,329, filed Oct. 12, 2021.
U.S. Appl. No. 17/603,330, filed Oct. 12, 2021.
Aartsma-Rus et al., "Antisense-mediated exon skipping: a versatile tool with therapeutic and research applications," RNA 13, 2007, 1609-1624.
Aartsma-Rus et al., "Exploring the frontiers of therapeutic exon skipping for Duchenne muscular dystrophy by double targeting within one or multiple exons," Mol Ther, 2006, 14:401-407.
Aartsma-Rus et al., "Theoretic applicability of antisense-mediated exon skipping for Duchenne muscular dystrophy mutations, " Hum Mutat, 2009, 30:293-299.
Adler et al., "Nonviral direct conversion of primary mouse embryonic fibroblasts to neuronal cells," Molecular therapy, 2012 Nucleic acids 1, e32.
Aiuti et al., "Lentiviral hematopoietic stem cell gene therapy in patients with Wiskott-Aldrich syndrome," Science, 2013, 341(6148): p. 1233151.
Anders et al., "Differential expression analysis for sequence count data," Genome biology 11, 2010, R106.
Anders et al., "Structural basis of PAM-dependent target DNA recognition by the Cas9 endonuclease," Nature, 2014, 513: 569-73.
Anguela et al., "Robust ZFN-mediated genome editing in adult hemophilic mice," Blood, 2013, 122:3283-3287.
Aoki et al., "Bodywide skipping of exons 45-55 in dystrophic mdx52 mice by systemic antisense delivery," Proc Natl Acad Sci USA, 2012, 109:13763-13768.
Arnold et al., "Genome-wide quantitative enhancer activity maps identified by STARR-seq," Science, 2013, 339(6123):1074-7.
Asokan et al., "The AAV Vector Toolkit: Poised at the Clinical Crossroads, " Mol Ther, 2012, 20, 699-708.
Ayyanathan et al., "Regulated recruitment of HP1 to a euchromatic gene induces mitotically heritable, epigenetic gene silencing: a mammalian cell culture model of gene variegation," Genes Dev, 2003, 17, 1855-1869.
Bartsevich et al., "Engineered zinc finger proteins for controlling stem cell fate," Stem Cells 21, 2003, 632-637.
Beerli et al., "Chemically regulated zinc finger transcription factors," J Biol Chem, 2000, 275(42):32617-27.
Beerli et al., "Engineering polydactyl zinc-finger transcription factors," Nat Biotechnol 20, 2002, 135-141.
Beerli et al., "Positive and negative regulation of endogenous genes by designed transcription factors," Proc Natl Acad Sci U S A 97, 2000, 1495-1500.
Beerli et al., "Toward controlling gene expression at will: specific regulation of the erbB-2/HER-2 promoter by using polydactyl zinc finger proteins constructed from modular building blocks," Proc Natl Acad Sci U S A 95, 1998, 14628-14633.
Beltran et al., "Re-activation of a dormant tumor suppressor gene maspin by designed transcription factors," Oncogene 26, 2007, 2791-2798.
Bender et al., "Independent formation of DnaseI hypersensitive sites in the murine beta-globin locus control region," Blood, 2000, 95, 3600-3604.
Benedetti et al., "Repair or Replace? Exploiting Novel Gene and Cell Therapy Strategies for Muscular Dystrophies," FEBS Journal, 2013, 280:4263-4280.
Berghella et al., "Reversible immortalization of human myogenic cells by site-specific excision of a retrovirally transferred oncogene," Human gene therapy 10, 1999, 1607-1617.
Bernstein et al., "The NIH Roadmap Epigenomics Mapping Consortium," Nat Biolechnol, 2010, 28, 1045-1048.
Beverley, "Primer: making sense of T-cell memory," Nat. Clin. Pract. Rheumatol. 2008, 4, 43- 49.
Bhakta et al., "Highly active zinc-finger nucleases by extended modular assembly," Genome Res, 2013, 530-538.
Bidou et al., "Sense from nonsense: therapies for premature stop codon diseases," Trends in Molecular Medicine 18, 2012, 679-688.
Blancafort et al., "Scanning the human genome with combinatorial transcription factor libraries," Nat Biotechnol 21, 2003, 269-274.
Boch et al., "Breaking the code of DNA binding specificity of TAL-type III effectors," Science 326, 2009, 1509.
Boshart et al., "A very strong enhancer is located upstream of an immediate early gene of human cytomegalovirus," Cell, 1985, 41:521-530.
Bowles et al., "Phase 1 Gene Therapy for Duchenne Muscular Dystrophy Using a Translation Optimized AAV Vector," Molecular Therapy 20, 2012, 443-455.
Boyle et al., "High-resolution mapping and characterization of open chromatin across the genome," Cell, 2008. 132(2):311-22.
Brunet et al., "Chromosomal translocations induced at specific loci in human stem cells," Proc Natl Acad Sci USA, 2009, 106:10620-10625.
Buler et al., "Energy-sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, Jan. 13, 2012, vol. 287, No. 3, pp. 1847-1860.
Bultmann et al., "Targeted transcriptional activation of silent oct4 pluripotency gene by combining designer TALEs and inhibition of epigenetic modifiers," Nucleic Acids Res 40, 2012, 5368-5377.
Carrillo et al., "The Multiple Sequence Alignment Problem in Biology" Siam J. Applied Math., 1988, 48, 1073.
Carter et al., "Long-range chromatin regulatory interactions in vivo," Nat Genet, 2002, 32, 623- 626.
Cerletti et al., "Highly efficient, functional engraftment of skeletal muscle stem cells in dystrophic muscles," Cell 134, 2008, 37-47.
Cermak et al., "Efficient design and assembly of custom TALEN and other TAL effector-based constructs for DNA targeting," Nucleic Acids Res 30, 2011, pp. 1-11.
Chakraborty et al., "A CRISPR/Cas9-Based System for Reprogramming Cell Lineage Specification," Stem cell reports 3, 2014, 940-947.
Chapdelaine et al., "Meganucleases can restore the reading frame of a mutual dystrophin," Gene therapy 17, 2010, 846-858.
Chavez et al., "Comparison of Cas9 activators in multiple species," Nat Methods, 2016, 13: 563-67.
Chavez et al., "Highly efficient Cas9-mediated transcriptional programming," Nat Methods 12, 2015, 326-328.
Chen et al., "Expanding the CRISPR imaging toolset with Staphylococcus aureus Cas9 for simultaneous imaging of multiple genomic loci," Nucleic Acids Research, 2016, 44(8): e75, 13 pages.
Chen et al., "Life and death of transcriptional co-activator p300," Epigenetics 6, 2011, 957-961.
Chen et al., "Two upstream enhancers collaborate to regulate the spatial patterning and timing of MyoD transcription during mouse development," Dev Dyn, 2001, 221, 274-288.
Cheng et al., "Multiplexed activation of endogenous genes by CRISPR-on, an RNA-guided transcriptional activator system," Cell Res, 2013, 23(10):1163-1171.
Chew et al., "A multifunctional AAV-CRISPR-Cas9 and its host response," Nat Methods, 2016, 13:868-74.
Cho et al., "Analysis of off-target effects of CRISPR/Cas-derived RNA-guided endonucleases and nickases," Genome Res, 2014, 24:132-141.
Cho et al., "Targeted genome engineering in human cells with the Cas9 RNA-guided endonuclease," Nat Biotechnol 31, 2013, 230-232.
Choy et al., "Eukaryotic activators function during multiple steps of preinitiation complex assembly," Nature 366, 1993, 531-536.
Christian et al., "Targeting DNA double-strand breaks with TAL effector nucleases," Genetics 186, 2010, 757-761.
Chu et al., "SV40 DNA transfection of cells in suspension: analysis of efficiency of transcription and translation of T-antigen," Gene, 1981, 13:197.
Cirak et al., "Exon skipping and dystrophin restoration in patients with Duchenne muscular dystrophy after systemic phosphorodiamidate morpholino oligomer treatment: an open-label, phase 2, dose-escalation study," Lancet 378, 2011, 595-605.

(56) References Cited

OTHER PUBLICATIONS

Cong et al., "Comprehensive interrogation of natural TALE DNA-binding modules and transcriptional repressor domains," Nat Commun 3, 2012, 968.
Cong et al., "Multiplex Genome Engineering Using CRISPR/Cas Systems," Science 339, 2013, 819-823.
Consortium, "An integrated encyclopedia of DNA elements in the human genome," Nature 489, 2012, 57-74.
Cornu et al., "DNA-binding specificity is a major determinant of the activity and toxicity of zinc- finger nucleases," Mol Ther, 2008, 16:352-358.
Cornu et al., "Quantification of zinc finger nuclease-associated toxicity," Meth Mol Biol, 2010, 649:237-245.
Cradick et al., "CRISPR/Cas9 systems targeting beta-globin and CCR5 genes have substantial off-target activity," Nucleic Acids Res, 2013, 41(20):9584-92.
Crawford et al., "Genome-wide mapping of DNase hypersensitive sites using massively parallel signature sequencing (MPSS)," Genome Res. 2006, 16, 123-131.
Crocker et al., "TALE-mediated modulation of transcriptional enhancers in vivo," Nature methods 10, 2013, 762-767.
Darabi et al., "Human ES-and iPS-derived myogenic progenitors restore dystrophin and improve contractility upon transplantation in dystrophic mice," Cell Stem Cell 10, 2012, 610-619.
De Groote et al., "Epigenetic Editing: targeted rewriting of epigenetic marks to modulate expression of selected target genes," Nucleic Acids Res, 2012, vol. 40, No. 21, pp. 10596-10613.
Dean et al., "Inducible transcription of five globin genes in K562 human leukemia cells," Proceedings of the National Academy of Sciences of the United States of America 80, 1983, 5515-5519.
Deltcheva et al., "CRISPR RNA maturation by trans-encoded small RNA and host factor RNase III," Nature, 2011, 471(7340):602-7.
Delvecchio et al., "Structure of the p300 catalytic core and implications for chromatin targeting and HAT regulation," Nat Struct Mol Biol 20, 2013, 1040-1046.
Deng et al., "Reactivation of developmentally silenced globin genes by forced chromatin looping," Cell 158, 2014, 849-860.
Dezawa et al., "Bone marrow stromal cells generate muscle cells and repair muscle degeneration," Science Signaling 309, 2005, 314-317.
Dijkema et al., "Cloning and expression of the chromosomal immune interferon gene of the rat," EMBO J., 1985, 4:761.
Ding et al., "A TALEN Genome-Editing System for Generating Human Stem Cell-Based Disease Models," 2013, Cell Stem Cell 12, 238-251.
Ding et al., "Enhanced efficiency of human pluripotent stem cell genome editing through replacing TALENs with CRISPRs," Cell Stem Cell, 2013, 12:393-394.
Ding et al., "Permanent Alteration of PCSK9 With In Vivo CRISPR-Cas9 Genome Editing," Circulation Research, 2014, vol. 115, No. 5, 488-492.
Doench et al., "Optimized sgRNA design to maximize activity and minimize off-target effects of CRISPR-Cas9," Nat Biotechnol, 2016, 34:184-91.
Doench et al., "Rational design of highly active sgRNAs for CRISPR-Cas9-mediated gene inactivation," Nat Biotechnol, 2014, 32:1262-7.
Dostie et al., "Chromosome Conformation Capture Carbon Copy (5C): a massively parallel solution for mapping interactions between genomic elements," Genome research 16, 2006, 1299-1309.
Doudna et al., "Genome editing. The new frontier of genome engineering with CRISPR-Cas9," Science 346, 2014, 1258096.
Doyle et al., "TAL Effector-Nucleotide Targeter (TALE-NT) 2.0: tools for TAL effector design and target prediction," Nucleic Acids Res 40, 2012, W117-122.
Doyon et al., "Enhancing zinc-finger-nuclease activity with improved obligate heterodimeric architectures," Nat Methods 8, 2010, 74-79.
EBI Accession No. GSP: BCJ39961 (2016).
Edelstein et al., "Gene therapy clinical trials worldwide 1989-2004—an overview," J. Gene Med., 2004, vol. 6, pp. 597-602.
Egger et al., "Epigenetics in human disease and prospects for epigenetic therapy," Nature 429, 2004, 457-463.
Esvelt et al., "Orthogonal Cas9 proteins for RNA-guided gene regulation and editing," Nature Methods 2013, 10(11):1116-21.
Farinelli et al., "Lentiviral vectors for the treatment of primary immunodeficiencies," J Inherit Metab Dis, 2014, 37:525-533.
Farzadfard et al., "Tunable and Multifunctional Eukaryotic Transcription Factors Based on CRISPR/Cas," ACS Synth Biol, 2013, 604-613.
Ferretti et al., "Complete genome sequence of an M1 strain of Streptococcus pyogenes," Proc Natl Acad Sci U S A, 2001, 98(8): 4658-63.
Fine et al., "Trans-spliced Cas9 allows cleavage of HBB and CCR5 genes in human cells using compact expression cassettes," Sci Rep. 2015, 5:10777.
Flanigan et al., "Mutational spectrum of DMD mutations in dystrophinopathy patients: application of modern diagnostic techniques to a large cohort," Human mutation 30, 2009, 1657-1666.
Fonfara et al., "Phylogeny of Cas9 determines functional exchangeability of dual-RNA and Cas9 among orthologous type II CRISPR-Cas systems," Nucleic Acids Res, 2013, 42(4):2577-2590.
Fontenot et al., "Regulatory T cell lineage specification by the forkhead transcription factor foxp3," Immunity, 2005, 22, 329-341.
Fu et al., "High-frequency off-target mutagenesis induced by CRISPR-Cas nucleases in human cells," Nat Biotechnol, 2013, 31(9):822-6.
Fu et al., "Improving CRISPR-Cas nuclease specificity using truncated guide RNAs," Nat Biotechnol 32, 2014, 279-284.
Gaj et al., "Targeted gene knockout by direct delivery of zinc-finger nuclease proteins," Nature Methods, 2012, 9(8):805-807.
Gaj et al., "ZFN, TALEN, and CRISPR/Cas-based methods for genome engineering," Trends Biotechnol, 2013, 31:397-405.
Gao et al., "Comparison of TALE designer transcription factors and the CRISPR/dCas9 in regulation of gene expression by targeting enhancers," Nucleic Acids Res 42, 2014, e155.
Gao et al., "Reprogramming to Pluripotency Using Designer TALE Transcription Factors Targeting Enhancers," Stem Cell Reports, 2013, 1(2):183-97.
Garg et al., "Engineering synthetic TAL effectors with orthogonal target sites, " Nucleic Acids Res 40, 2012, 7584-7595.
Garriga-Canut et al., "Synthetic zinc finger repressors reduce mutant huntingtin expression in the brain of R6/2 mice," Proceedings of the National Academy of Sciences of the United States of America 109, 2012, E3136-3145.
Gersbach et al., "Activating human genes with zinc finger proteins, transcription activator-like effectors and CRISPR/Cas9 for gene therapy and regenerative medicine," Expert Opin Ther Targets, 2014, 18(8):835-9.
Gersbach, "Genome engineering: the next genomic revolution," Nat Methods 11, 2014, 1009-1011.
Gerstein et al., "Architecture of the human regulatory network derived from ENCODE data," Nature 489, 2012, 91-100.
Gertz et al., "Transposase mediated construction of RNA-seq libraries," Genome Res 22, 2012, 134-141.
Gilbert et al., "CRISPR-mediated modular RNA-guided regulation of transcription in eukaryotes," Cell 154, 2013, 442-451.
Gilbert et al., "Genome-Scale CRISPR-Mediated Control of Gene Repression and Activation," Cell 159, 2014, 647-661.
Goemans et al., "Systemic administration of PRO051 in Duchenne's muscular dystrophy," The New England journal of medicine 364, 2011, 1513-1522.
Gorman et al., "The Rous sarcoma virus long terminal repeat is a strong promoter when introduced into a variety of eukaryotic cells by DNA-mediated transfection," Proc. Natl. Acad. Sci. U.S.A., 1982, 79:6777.
Gou et al., "A novel approach for the construction of multiple shRNA expression vectors," J Gene Med, 2007, 9(9):751-63.
Graham et al., "A new technique for the assay of infectivity of human adenovirus 5 DNA," Virol., 1973, 52:456-467.
Graslund et al., "Exploring strategies for the design of artificial transcription factors: targeting sites proximal to known regulatory regions for the induction of gamma-globin expression and the treatment of sickle cell disease," J Biol Chem 280, 2005, 3707-3714.

(56) References Cited

OTHER PUBLICATIONS

Gregorevic et al., "Systemic delivery of genes to striated muscles using adeno-associated viral vectors," Nat Med, 2004, 10:828-834.
Grimmer et al., "Analysis of an artificial zinc finger epigenetic modulator: widespread binding but limited regulation," Nucleic acids research 42, 2014, 10856-10868.
Groner et al., "KRAB-zinc finger proteins and KAP1 can mediate long-range transcriptional repression through heterochromatin spreading," PLoS Genet 6, 2010, e1000869.
Guo et al., "Directed evolution of an enhanced and highly efficient Fokl cleavage domain for zinc finger nucleases," J Mol Biol, 2010, 400:96-107.
Guschin et al., "A rapid and general assay for monitoring endogenous gene modification," Methods Mol Biol 649, 2010, 247-256.
Hamar et al., "Small interfering RNA targeting Fas protects mice against renal ischemia-reperfusion injury," PNAS, 2004, 101:14883-8.
Hardison et al., "Locus control regions of mammalian beta-globin gene clusters: combining phylogenetic analyses and experimental results to gain functional insights," Gene 205, 1997, 73-94.
Hathaway et al., "Dynamics and memory of heterochromatin in living cells," Cell 149, 2012, 1447-1460.
Heintzman et al., "Distinct and predictive chromatin signatures of transcriptional promoters and enhancers in the human genome," Nat Genet 39, 2007, 311-318.
Hilton et al., "Epigenome editing by a CRISPR-Cas9-based acetyltransferase activates genes from promoters and enhancers," Nature biotechnology, 2015, vol. 33, No. 5, pp. 510-519.
Hockemeyer et al., "Efficient targeting of expressed and silent genes in human ESCs and iPSCs using zinc-finger nucleases," Nat Biotechnol, 2009, 27(9):851-7.
Hockemeyer et al., "Genetic engineering of human pluripotent cells using TALE nucleases," Nat Biotechnol 29, 2011, 731-734.
Hoffman et al., "Dystrophin: the protein product of the Duchenne muscular dystrophy locus," Cell, 1987, 51:919.
Hotta et al., "Isolation of human iPS cells using EOS lentiviral vectors to select for pluripotency," Nat Methods 6, 2009, 370-376.
Hou et al., "Efficient genome engineering in human pluripotent stem cells using Cas9 from Neisseria meningitidis," Proc Natl Acad Sci USA, 2013, 110: 15644-15649.
Hsu et al., "Dissecting Neural Function Using Targeted Genome Engineering Technologies," ACS Chem. Neurosci., 2012, pp. 603-610.
Hsu et al., "DNA targeting specificity of RNA-guided Cas9 nucleases," Nature Biotechnology 31, 2013, 827-832.
Hu et al., "Direct activation of human and mouse Oct4 genes using engineered TALE and Cas9 transcription factors," Nucleic Acids Res 42, 2014, 4375-4390.
Humbert et al., "Targeted gene therapies: tools, applications, optimization", Critical Reviews in Biochemistry and Molecular Biology, CRC Press, vol. 47, No. 3, Apr. 2012, pp. 264-281.
Hwang et al., "Efficient genome editing in zebrafish using CRISPR-Cas system," Nat Biotechnol, 2013, 31(3):227-9.
Ikonomi et al., "Levels of GATA-1/GATA-2 transcription factors modulate expression of embryonic and fetal hemoglobins," Gene 261, 2000, 277-287.
Ji et al., "Engineered zinc-finger transcription factors activate OCT4 (POUSFI ), SOX2, KLF4, c-MYC (MYC) and miR302/367," Nucleic Acids Res 42, 2014, 6158-6167.
Jinek et al., "A programmable dual-RNA-guided DNA endonuclease in adaptive bacterial immunity," Science 337, 2012, 816-821.
Jinek et al., "RNA-programmed genome editing in human cells," eLife 2, 2013, e00471.
Jinek et al., "Structures of Cas9 endonucleases reveal RNA-mediated conformational activation," Science, 2014, 343(6176):1247997.
Jörg, "Engineering of the epigenome: synthetic biology to define functional causality and develop innovative therapies," Epigenomics, 2016, 8(2):153-156.
Joung et al., "TALENs: a widely applicable technology for targeted genome editing," Nature Reviews Molecular Cell Biology 14, 2013, 49-55.
Kabadi et al., "Multiplex CRISPR/Cas9-based genome engineering from a single lentiviral vector," Nucleic Acids Res, 2014, 42(19):e147.
Kayali et al., "Site-directed gene repair of the dystrophin gene mediated by PNA-ssODNs," Human Molecular Genetics, vol. 19, No. 16, Aug. 15, 2010, pp. 3266-3281.
Kearns et al., "Cas9 effector-mediated regulation of transcription and differentiation in human pluripotent stem cells," Development, 2014, 141(1):219-23.
Kearns et al., "Functional annotation of native enhancers with a Cas9-histone demethylase fusion," Nat Methods, 2015, 12(5):401-403.
Keung et al., "Using targeted chromatin regulators to engineer combinatorial and spatial transcriptional regulation," Cell 158, 2014, 110-120.
Khoury et al., "Efficient new cationic liposome formulation for systemic delivery of small interfering RNA silencing tumor necrosis factor a in experimental arthritis," Arthritis Rheumatol, 2006, 54: 1867-77.
Kim et al., "Histone acetylation contributes to chromatin looping between the locus control region and globin gene by influencing hypersensitive site formation," Biochim Biophys Acta, 2013, 1829: 963-969.
Kim et al., "Surrogate reporters for enrichment of cells with nuclease-induced mutations," Nat Methods, 2011, 8:941-943.
Kim et al., "TALENs and ZFNs are associated with different mutation signatures," Nat Methods, 2013, 10(3):185.
Kim et al., "Use of the human elongation factor 1a promoter as a versatile and efficient expression system," Gene, 1990, 91:217.
Kimura et al., "Cell-lineage regulated myogenesis for dystrophin replacement: a novel therapeutic approach for treatment of muscular dystrophy," Hum Mol Genet 17, 2008, 2507-2517.
Konermann et al., "Genome-scale transcriptional activation by an engineered CRISPRCas9 complex," Nature, 2015, 517: 583-588.
Konermann et al., "Optical control of mammalian endogenous transcription and epigenetic states," Nature, 2013, 500(7463): 472-6.
Konieczny et al., "Gene and cell-mediated therapies for muscular dystrophy," Muscle Nerve, 2013, 47:649-663.
Kotin, "Prospects for the use of adeno-associated virus as a vector for human gene therapy," Hum. Gene Ther., 1994, 5:793-801.
Kubokawa et al., "Molecular characterization of the 5'-UTR of retinal dystrophin reveals a cryptic intron that regulates translational activity," Molecular Vision, 2010, vol. 16, pp. 2590-2597.
Kuscu et al., "Genome-wide analysis reveals characteristics of off-target sites bound by the Cas9 endonuclease," Nat Biotechnol, 2014, 32(7): 677-83.
Kwa et al., "Chromatin modifying agents—the cutting edge of anticancer therapy," Drug Discovery Today, 2011, 16(13/14):543-547.
Kyte et al., "A Simple Method for Displaying the Hydropathic Character of a Protein," J. Mol. Biol., 1982, 157:105-132.
La Russa et al., "The New State of the Art: Cas9 for Gene Activation and Repression," Molecular and Cellular Biology, 2015, 35(22):3800-3809.
Landen et al., "Intraperitoneal delivery of liposomal siRNA for therapy of advanced ovarian cancer," Cancer Biol. Ther, 2006, 5(12):1708-13.
Langmead et al., "Fast gapped-read alignment with Bowtie 2," Nature methods, 2012, 9: 357-359.
Langmead et al., "Ultrafast and memory-efficient alignment of short DNA sequences to the human genome," Genome biology 10, 2009, R25.
Larson et al., "CRISPR interference (CRISPRi) for sequence-editing control of gene expression," Nat Protoc, 2013, 8(11): 2180-96.
Latta-Mahieu et al., "Gene transfer of a chimeric trans-activator is immunogenic and results in short-lived transgene expression," Human Gene Therapy, Sep. 2002, vol. 13, No. 13, pp. 1611-1620.
Lattanzi et al., "High efficiency myogenic conversion of human fibroblasts by adenoviral vector- mediated MyoD gene transfer. An

(56) References Cited

OTHER PUBLICATIONS alternative strategy for ex vivo gene therapy of primary myopathies," The Journal of clinical investigation 101, 1998, 2119-2128.
Lee et al., "Role of satellite cells versus myofibers in muscle hypertrophy induced by inhibition of the myostatin/activin signaling pathway," Proc Natl Acad Sci U S A, 2012, 109(35):E2353-60.
Lee et al., "Targeted chromosomal deletions in human cells using zinc finger nucleases," Genome research 20, 2010, 81-89.
Lee, "Regulation of muscle mass by myostatin," Annu Rev Cell Dev Biol, 2004, 20: 61-86.
Li et al., "In vivo genome editing restores haemostasis in a mouse model of haemophilia," Nature 475, 2011, 217-221.
Li et al., "Extensive promoter-centered chromatin interactions provide a topological basis for transcription regulation," Cell, 2012, 148: 84-98.
Li et al., "Locus control regions," Blood, 2002, 100: 3077-3086.
Li et al., "Marginal level dystrophin expression improves clinical outcome in a strain of dystrophin/utrophin double knockout mice," PLoS One, 2010, 5:e15286.
Li et al., "Modularly assembled designer TAL effector nucleases for targeted gene knockout and gene replacement in eukaryotes," Nucleic Acids Research, 2011, vol. 39, No. 14, pp. 6315-6325.
Li et al., "The role of chromatin during transcription," Cell, 2007, 128: 707-719.
Li et al., "The Sequence Alignment/Map format and SAMtools," Bioinformatics, 2009, 25: 2078-2079.
Li et al., "Transcription activator-like effector hybrids for conditional control and rewiring of chromosomal transgene expression," Scientific reports 2, 2012, 897.
Liang et al., "Engineering biological systems with synthetic RNA molecules," Mol Cell 43, 2011, 915-926.
Lohmueller et al., "A tunable zinc finger-based framework for Boolean logic computation in mammalian cells," Nucleic Acids Res 40, 2012, 5180-5187.
Love et al., "Moderated estimation of fold change and dispersion for RNA-seq data with DESeq2," Genome biology, 2014, 15: 550.
Lovric et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu et al., "The status of exon skipping as a therapeutic approach to duchenne muscular dystrophy," Molecular Therapy 19, 2011, 9-15.
Lund et al., "Promoter-targeted phage display selections with preassembled synthetic zinc finger libraries for endogenous gene regulation," Journal of Molecular Biology, 2004, vol. 340, pp. 599-613.
Luo et al., "Synthetic DNA delivery systems," Nature Biotechnology, 2000, vol. 18, pp. 33-37.
Maeder et al., "CRISPR RNA-guided activation of endogenous human genes," Nat Methods, 2013, 10: 977-979.
Maeder et al., "Robust, synergistic regulation of human gene expression using TALE activators," Nature Methods, vol. 10, No. 3, pp. 243-246, Feb. 10, 2013, including pp. 1/14-14/14 of Supplementary Material.
Maeder, "Targeted DNA demethylation and activation of endogenous genes using programmable TALE-TET1 fusion proteins," Nat Biotechnol, 2013, 31(12): 1137-42.
Magnenat et al., "In vivo selection of combinatorial libraries and designed affinity maturation of polydactyl zinc finger transcription factors for ICAM-1 provides new insights into gene regulation," J Mol Biol, 2004, 341: 635-649.
Mali et al., "Cas9 as a versatile tool for engineering biology," Nat Methods, 2013, 10(10): 957-63.
Mali et al., "CAS9 transcriptional activators for target specificity screening and paired nickases for cooperative genome engineering," Nat Biotechnol, 2013, 31(9): 833-8.
Mali et al., "RNA-Guided Human Genome Engineering via Cas9," Science 339, 2013, 823-826.
Mamchaoui et al., "Immortalized pathological human myoblasts: towards a universal tool for the study of neuromuscular disorders," Skelet Muscle 1, 2011, 1-11.
Maniatis et al., "Regulation of inducible and tissue-specific gene expression," Science, 1987, 236:1237.
Matsushita et al., "Adeno-associated virus vectors can be efficiently produced without helper virus," Gene Therapy, 1998, 5:938.
McCarty et al., "Self-complementary recombinant adeno-associated virus (scAAV) vectors promote efficient transduction independently of DNA synthesis," Gene Ther, 2001, 8:1248-54.
McDowell et al., "Structural and functional cross-talk between a distant enhancer and the epsilon-globin gene promoter shows interdependence of the two elements in chromatin," Molecular and cellular biology, 1999, 19: 7600-7609.
Memedula et al., "Sequential recruitment of HAT and SWI/SNF components to condensed chromatin by VP16," Curr Biol, 2003, 13, 241-246.
Mendell et al., "Dystrophin immunity in Duchenne's muscular dystrophy," New England Journal of Medicine 363, 2010, 1429-1437.
Mendenhall et al., "Locus-specific editing of histone modification at endogenous enhancers," Nat Biotechnol, 2013, 31(12): 1133-6.
Mercer et al., "Regulation of Endogenous Human Gene Expression by Ligand-Inducible TALE Transcription Factors," ACS Synth Biol, 2013.
Miller et al., "A TALE nuclease architecture for efficient genome editing," Nat Biotechnol 29, 2011, 143-148.
Mittler et al., "A novel docking site on Mediator is critical for activation by VP 16 in mammalian cells," EMBO J, 2003, 22: 6494-6504.
Mizushima et al., "pEF-BOS, a powerful mammalian expression vector," Nucl. Acids. Res., 1990, 18:5322.
Morrissey et al., "Activity of stabilized short interfering RNA in a mouse model of hepatitis B virus replication," Hepatol, 2005, 41: 1349-56.
Moscou et al., "A simple cipher governs DNA recognition by TAL effectors," Science 326, 2009, 1501.
Murphy et al., "The in vitro transcription of the 7SK RNA gene by RNA polymerase III is dependable only on the presence of an upstream promoter," Cell, 1987, 51:81-87.
Mussolino et al., "A novel TALE nuclease scaffold enables high genome editing activity in combination with low toxicity," Nucleic Acids Res 39, 2011, 9283-9293.
Muzycka, "Use of adeno-associated virus as a general transduction vector for mammalian cells," Curr. Top. Microbiol. Immunol., 1992, 158:97-129.
Myslinski et al., "An unusually compact external promoter for RNA polymerase III transcription of the human H1RNA gene," Nucleic Acids Res, 2001, 29:2502-2509.
Negroni et al., "In Vivo Myogenic Potential of Human CD133+ Muscle-derived Stem Cells: A Quantitative Study," Molecular Therapy 17, 2009, 1771-1778.
Nelson et al., "In vivo genome editing improves muscle function in a mouse model of Duchenne muscular dystrophy," Science, 2016, 351, 403-7.
Nishimasu et al., "Crystal structure of cas9 in complex with guide RNA and target DNA Cell," 2014, 156(5): 935-49.
Nissim et al., "Multiplexed and Programmable Regulation of Gene Networks with an Integrated RNA and CRISPR/Cas Toolkit in Human Cells," Mol Cell, 2014, 54: 698-710.
Nordhoff et al., "Comparative analysis of human, bovine, and murine Oct-4 upstream promoter sequences," Mamm Genome, 2001, 12: 309-317.
Ogryzko et al., "The transcriptional coactivators p300 and CBP are histone acetyltransferases," Cell, 1996, 87: 953-959.
Ohshima et al., "Nucleotide sequence of mouse genomic loci including a gene or pseudogene for U6 (4.85) nuclear RNA," Nucleic Acids Res, 1981, 9:5145-5158.
Okkenhaug et al., "PI3K in lymphocyte development, differentiation and activation," Nat. Rev. Immunol., 2003, 3(4): 317-330.
Ong et al., "Enhancer function: new insights into the regulation of tissuespecific gene expression," Nature reviews. Genetics, 2011, 12: 283-293.
Osakabe et al., "FLAG-NLS-SpCas9-2A-GFBSD2 [Binary vector pEgP526-2A-GFBSD2]," National Center for Biotechnology Infor-

(56) References Cited

OTHER PUBLICATIONS mation, Genbank Entry, Retrieved from the Internet on Sep. 18, 2017 <https://www.ncbi.nlm.nih.gov/protein/BAV01234>.
Ousterout et al., "Reading frame correction by targeted genome editing restores dystrophin expression in cells from Duchenne muscular dystrophy patients," Mol Ther, 2013, 21:1718-1726.
Palu et al., "In pursuit of new developments for gene therapy of human diseases," J. Biotechnol, 1999, vol. 68, pp. 1-13.
Papayannakos et al., "Understanding lentiviral vector chromatin targeting: working to reduce insertional mutagenic potential for gene therapy," Gene Ther, 2013, 20(6): 581-8.
Park et al., "Phenotypic alteration of eukaryotic cells using randomized libraries of artificial transcription factors," Nat Biotechnol 21, 2003, 1208-1214.
Pattanayak et al., "High-throughput profiling of off-target DNA cleavage reveals RNA-programmed Cas9 nuclease specificity," Nat Biotechnol, 2013, 31(9): 839-43.
Peault et al., "Stem and progenitor cells in skeletal muscle development, maintenance, and therapy," Molecular Therapy 15, 2007, 867-877.
Perez et al., "Establishment of HIV-1 resistance in CD4+ T cells by genome editing using zinc-finger nucleases," Nature biotechnology 26, 2008, 808-816.
Perez-Pinera et al., "Advances in targeted genome editing," Current Opinion in Chemical Biology 16, 2012, 268-277.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976.
Perez-Pinera et al., "Synergistic and tunable human gene activation by combinations of synthetic transcription factors," Nature Methods, vol. 10, No. 3, pp. 239-244, Feb. 3, 2013, including pp. 1/1-12-12 of Supplementary Material.
Perez-Pinera et al., "Synergistic Transcriptional Activation by Combinations of Engineered TALEs" was publicly presented at the American Society of Gene & Cell Therapy's 15th Annual Meeting in Philadelphia, Pennsylvania during the Late Abstracts Poster Session III: Saturday, May 19, 2012. Abstract 855.
Persons, "Lentiviral vector gene therapy: effective and safe?" Mol Ther, 2010, 18(5): 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant et al., "Current status of pharmaceutical and genetic therapeutic approaches to treat DMD," Molecular Therapy 19, 2011, 830-840.
Polstein et al., "Genome-wide specificity of DNA-binding, gene regulation, and chromatin remodeling by TALE- and CRISPR/Cas9-based transcriptional activators," Genome Res, 2015, 25:1158-1169.
Polstein et al., "Light-inducible spatiotemporal control of gene activation by customizable zinc finger transcription factors," J Am Chem Soc, 2012, 134(40): 16480-3.
Popplewell et al., "Gene correction of a duchenne muscular dystrophy mutation by meganuclease-enhanced exon knock-in," Hum Gene Ther, 2013, 24:692-701.
Qi et al., "Repurposing CRISPR as an RNA-guided platform for sequence-specific control of gene expression," Cell 152, 2013, 1173-1183.
Quinlan et al., "BEDTools: a flexible suite of utilities for comparing genomic features," Bioinformatics 26, 2010, 841-842.
Rada-Iglesias et al., "A unique chromatin signature uncovers early developmental enhancers in humans," Nature 470, 2011, 279-283.
Rahdar et al., "Synthetic CRISPR RNA-Cas9-Guided Genome Editing in Human Cells," Proceedings to the National Academy of Sciences of USA, 2015, vol. 112, No. 51, pp. E7110-7117.
Ran et al., "Double nicking by RNA-guided CRISPR Cas9 for enhanced genome editing specificity," Cell, 2013, 154(6): 1380-9.
Ran et al., "In vivo genome editing using *Staphylococcus aureus* Cas9," Nature 520, 2015, 186-91.
Rebar et al., "Induction of angiogenesis in a mouse model using engineered transcription factors," Nat Med 8, 2002, 1427-1432.
Reynolds et al., "NuRD-mediated deacetylation of H3K27 facilitates recruitment of Polycomb Repressive Complex 2 to direct gene repression," The EMBO Journal 31, 2012, 593-605.
Reyon et al., "FLASH assembly of TALENs for high-throughput genome editing," Nat Biotechnol 30, 2012, 460-465.
Riley, "PD-1 signaling in primary T cells," Immunological Reviews, 2009, 229: 114-125.
Rivenbark et al., "Epigenetic reprogramming of cancer cells via targeted DNA methylation," Epigenetics 7, 2012, 350-360.
Rousseau et al., "Endonucleases: tools to correct the dystrophin gene" The Journal of Gene Medicine, 2011, vol. 13, pp. 522-537.
Saito et al., "Specific activation of microRNA-127 with downregulation of the proto-oncogene BCL6 by chromatin-modifying drugs in human cancer cells," Cancer Cell, 2006, vol. 9, pp. 435-443.
Salmon et al., "Production and titration of lentiviral vectors," Curr Protoc Neurosci, 2006, Chapter 4: Unit 4 21.
Sambrook et al., Molecular Cloning and Laboratory manual, Second Ed., Cold Spring Harbor, 1989, pp. 16.7-16.8.
Schmid-Burgk et al., "A ligation-independent cloning technique for high-throughput of transcription activator-like effector genes," Nat Biotechnol 31, 2012, 76-81.
Scholze et al., "TAL effectors are remote controls for gene activation," Current Opinion in Microbiology, Jan. 2011, vol. 14, pp. 47-53.
Schultz et al., "Recombinant adeno-associated virus transduction and integration," Molecular Therapy 16, 2008, 1189-1199.
Schultz et al., "SETDB1: a novel KAP-1-associated histone H3, lysine 9-specific methyltransferase that contributes to HP1-mediated silencing of euchromatic genes by KRAB zinc-finger proteins," Genes & development 16, 2002, 919-932.
Sebastiano et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seidel et al., "Chromatin-modifygin agents in anti-cancer therapy," Biochimie, 2012, vol. 94, pp. 2264-2279.
Seto et al., "Gene Replacement Therapies for Duchenne Muscular Dystrophy Using Adeno-Associated Viral Vectors," Current Gene Therapy, 2012, 12:139-151.
Sharma et al., "Efficiency of nonhomologous DNA and joining varies among somatic tissues, despite similarity in mechanism," Cellular and Molecular Life Science 68, 2011, 661-676.
Silva et al., "Meganucleases and other tools for targeted genome engineering: perspective and challenges for gene therapy," Current gene therapy, 2011, 11:11-27.
Smith et al., "Myostatin inhibitors as therapies for muscle wasting associated with cancer and other disorders," Curr Opin Support Palliat Care, 2013, 7, 352-60.
Snowden et al., "Gene-specific targeting of H3K9 methylation is sufficient for initiating repression in vivo," Curr Biol 12, 2002, 2159-2166.
Şöllü et al., "Autonomous zinc-finger nuclease pairs for targeted chromosomal deletion," Nucleic acids research 38, 2010, 8269-8276.
Song et al., "Dnase-seq: a high-resolution technique for mapping active gene regulatory elements across the genome from mammalian cells," Cold Spring Harbor protocols 2010, 2010(2):11.
Song et al., "Open chromatin defined by DNaseI and FAIRE identifies regulatory elements that shape cell-type identify," Genome Res 21, 2011, 1757-1767.
Soutschek et al., "Therapeutic silencing of an endogenous gene by systemic administration of modified siRNAs," Nature, 2004, 432: 173-8.
Spitz et al., "Transcription factors: from enhancer binding to developmental control," Nat. Rev. Genet. 2012, 13, 613-626.
Sripathy et al., "The KAP1 corepressor functions to coordinate the assembly of de novo HP1-demarcated microenvironments of

(56) References Cited

OTHER PUBLICATIONS heterochromatin required for KRAB zinc finger protein-mediated transcriptional repression," Molecular and cellular biology 26, 2006, 8623-8638.
Sternberg et al., "Conformational Control of DNA Target Cleavage by CRISPR-Cas9," Nature, 2015, vol. 527, No. 7576, pp. 110-113.
Sternberg et al., "DNA interrogation by the CRISPR RNA-guided endonuclease Cas9," Nature, 2014, 507, 62-67.
Su et al., "Identification of biologically relevant enhancers in human erythroid cells," J Biol Chem 288, 2013, 8433-8444.
Su et al., "In vitro and in vivo mRNA delivery using lipid-enveloped pH-responsive polymer nanoparticles," Mol. Pharmaceutics, 2011, 8, 774-787.
Sun et al., "Optimized TAL effector nucleases (TALENs) for use in treatment of sickle cell disease," Molecular bioSystems 8, 2012, 1255-1263.
Szyf, "Epigenetics, DNA methylation, and chromatin modifying drugs," Annual Review of Pharmacology and Toxicology, 2009, vol. 49, pp. 243-263.
Tabebordbar et al., "In vivo gene editing in dystrophic mouse muscle and muscle stem cells," Science, 2016, 351, 407-11.
Takahashi et al., "Induction of pluripotent stem cells from adult human fibroblasts by defined factors," Cell 1131, 2007, 861-872.
Takeshima et al., "Mutation spectrum of the dystrophin gene in 442 Duchene/Becker muscular dystrophy cases from one Japanese referral center," Journal of Human Genetics, 2010, 55: 379-388.
Tanenbaum et al., "A Protein-Tagging System for Signal Amplification in Gene Expression and Fluorescence Imaging," Cell, 2014, pp. 635-646.
Taniguchi-Ikeda et al., "Pathogenic exon-trapping by SVA retrotransposon and rescue in Fukuyama muscular dystrophy," Nature 478, 2011, 127-131.
Tebas et al., "Gene editing of CCR5 in autologous CD4 T cells of persons infected with HIV," N Engl J Med, 2014, 370:901-910.
Tedesco et al., "Repairing skeletal muscle: regenerative potential of skeletal muscle stem cells," J Clin Invest, 2010, 120:11-19.
Tedesco et al., "Stem Cell-Mediated Transfer of a Human Artificial Chromosome Ameliorates Musculat Dystrophy," Science Translational Medicine 3, 2011, 96ra78-96ra78.
Tedesco et al., "Transplantation of Genetically Corrected Human iPSC-Derived Progenitors in Mice with Limb-Girdle Muscular Dystrophy," Science Translational Medicine 4, 2012, 140ra189.
Thakore et al., "Editing the epigenome: technologies for programmable transcription and epigenetic modulation," Nat Methods. 2016, 13:127-37.
Thakore et al., "Highly specific epigenome editing by CRISPR-Cas9 repressors for silencing of distal regulatory elements," Nat Methods, 2015, 12, 1143-9.
Thakore et al., "RNA-guided transcriptional silencing in vivo with *S. aureus* CRISPR-Cas9 repressors," Nature Communications, 2018, 9(1):1674, 9 pages.
Thomson et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression, " Virol., 1994, 204:304-311.
Thurman et al., "The accessible chromatin landscape of the human genome," Nature 489, 2012, 75-82.
Tone et al., "Smad3 and NFAT cooperate to induce Foxp3 expression through its enhancer," Nat. Immunol., 2008, 9, 194-202.
Truong et al., "Development of an intein-mediated split-Cas9 system for gene therapy," Nucleic Acids Res. 2015, 43: 6450-6458.
Tuan et al., "Transcription of the hypersensitive site HS2 enhancer in erythroid cells," Proceedings of the National Academy of Sciences of the United States of America 89, 1992, 11219-11223.
Uchida et al., "In Vivo Messenger RNA Introduction into the Central Nervous System Using Polyplex Nanomicelle," PLoS One, 2013, 8: e56220.
Uetsuki et al., "Isolation and characterization of the human chromosomal gene for polypeptide chain elongation factor-1 alpha," J. Biol. Chem., 1989, 264:5791.
Urnov et al., "Highly efficient endogenous human gene correction using designed zinc-finger nucleases," Nature 435, 2005, 646-651.
Vakoc et al., "Proximity among distant regulatory elements at the beta-globin locus requires GATA-1 and FOG-1," Molecular cell 17, 2005, 453-462.
Van Putten et al., "Low dystrophin levels in heart can delay heart failure in mdx mice," J Mol Cell Cardiol, 2014, 69C:17-23.
Van Putten et al., "Low dystrophin levels increase survival and improve muscle pathology and function in dystrophin/utrophin double-knockout mice," FASEB J, 2013, 27:2484-2495.
Verma et al., "Gene Therapy: Twenty-first century medicine," Annual Review of Biochemistry, 2005, vol. 74, pp. 711-738.
Verma et al., "Gene therapy—promises, problems and prospects," Nature, 1997, vol. 389, pp. 239-242.
Vierbuchen et al., "Direct conversion of fibroblasts to functional neurons by defined factors," Nature 463, 2010, 1035-1041.
Visel et al., "ChIP-seq accurately predicts tissue-specific activity of enhancers," Nature 457, 2009, 854-858.
Voss et al., "The role of enhancers in the regulation of cell-type-specific transcriptional control," Trends Biochem. Sci., 1986, 11:287.
Wagner et al., "A phase I/IItrial of MYO-029 in adult subjects with muscular dystrophy," Ann Neurol 63, 2008, 561-71.
Wang et al., "Adeno-associated virus vector carrying human minidystrophin genes effectively ameliorates muscular dystrophy in mdx mouse model," Proc Natl Acad Sci US A., 2000, 97(25):13714-13719.
Wang et al., "Epstein-Barr virus nuclear protein 2 interacts with p300, CBP, and PCAF histone acetyltransferases in activation of the LMPI promoter," Proc Natl Acad Sci U S A 97, 2000, 430- 435.
Wang et al., "Genome-wide mapping of HATs and HDACs reveals distinct functions in active and inactive genes," Cell 138, 2009, 1019-1031.
Wang et al., "One-Step Generation of Mice Carrying Mutations in Multiple Genes by CRISPR-Cas-Mediated Genome Engineering," Cell, 2013, 153(4): 910-8.
Wein et al., "Efficient bypass of mutations in dysferlin deficient patient cells by antisense-induced exon skipping," Hum Mutat 31, 2010, 136-142.
Welch et al., "PTC124 targets genetic disorders caused by nonsense mutations," Nature 447, 2007, 87-91.
Whisstock et al., "Prediction of protein function from protein sequence," Q. Rev. Biophysics., 2003, 36(3): 307-340.
Wu et al., "Genome-wide binding of the CRISPR endonuclease Cas9 in mammalian cells," Nat Biotechnol 32, 2014, 670-676.
Yan et al., "Drugging the undruggable: Transcription therapy for cancer," Biochimica et Biophysica Acta (BBA)—Reviews on Cancer, Jan. 2013, vol. 1835, No. 1, pp. 76-85.
Yang, "Optimization of scarless human stem cell genome editing," Nucleic Acids Res, 2013, 41:9049-9061.
Youngblood et al., "Chronic virus infection enforces demethylation of the locus that encodes PD-1 in antigen-specific $CD8^+$ T cells," Immunity, 2011, 35: 400-412.
Yusa et al., "Targeted gene correction of $\alpha$1-antitrypsin deficiency in induced pluripotent stem cells," Nature 478, 2011, 391-394.
Zhang et al. "Efficient construction of sequence-specific TAL effectors for modulating mammalian transcription," Nat Biotechnol 29, 2011, 149-153.
Zhang et al., "Adenovirus-Adeno-Associated Virus Hybrid for Large-Scale Recombinant Adeno-Associated Virus Production," Hum Gene Ther. 2009, 20:922-9.
Zhang et al., "Model-based analysis of ChIP-Seq (MACS)," Genome biology 9, 2008, R137.
Zheng et al., "Foxp3 in control of the regulatory T cell lineage, " Nat. Immunol. 2007, 8, 457-462.
Zheng et al., "Role of conserved non-coding DNA elements in the Foxp3 gene in regulatory T-cell fate," Nature, 2010, 463, 808-812.
Zhou et al., "High-throughput screening of a CRISPR/Cas9 library for functional genomics in human cells," Nature, 2014, 509(7501): 487-491.
Zhu et al., "Cellular senescence in human telomerase reverse transcriptase and cyclin-dependent kinase 4: consequences in aging muscle and therapeutic strategies for muscular dystrophies," Aging cell 6, 2007, 515-523.

(56) References Cited

OTHER PUBLICATIONS

Zincarelli et al., "Analysis of AAV serotypes 1-9 mediated gene expression and tropism in mice after systemic injection," Mol Ther 16, 2008, 1073-80.
Zou et al., "Site-specific gene correction of a point mutation in human iPS cells derived from an adult patient with sickle cell disease," Blood 118, 2011, 4599-4608.
International Search Report and Written Opinion for Application No. PCT/US14/41190 dated Dec. 17, 2014 (14 pages).
International Search Report and Written Opinion for Application No. PCT/US13/38536 dated Nov. 29, 2013 (27 pages).
International Search Report and Written Opinion for Application No. PCT/US14/17221 dated Oct. 26, 2016 (11 pages).
Australian Patent Office Examination Report No. 1 for Application No. 2014274840 dated Mar. 13, 2019 (5 pages).
Canadian Patent Office Action for Application No. 2,914,519 dated May 14, 2020 (4 pages).
Chinese Patent Office Action for Application No. 201480044748.X dated Aug. 20, 2018 (32 pages, English translation included).
Chinese Patent Office Action for Application No. 201480044748.X dated Apr. 26, 2019 (10 pages, English translation included).
Chinese Patent Office Action for Application No. 201480044748.X dated Dec. 16, 2019 (11 pages, English translation included).
Chinese Patent Office Action for Application No. 201480044748.X dated Nov. 24, 2020 (8 pages, English translation included).
European Extended Search Report for Application No. 14806852.1 dated Dec. 8, 2016 (6 pages).
European Patent Office Action for Application No. 14806852.1 dated Sep. 15, 2017 (5 pages).
European Patent Office Action for Application No. 14806852.1 dated Feb. 9, 2018 (4 pages).
European Patent Office Extended Search Report for Application No. 18172956.7 dated Nov. 26, 2018 (5 pages).
European Patent Office Extended Search Report for Application No. 19168481.0 dated Jun. 24, 2019 (5 pages).
European Patent Office Action for Application No. 18172956.7 dated Jul. 7, 2020 (4 pages).
European Patent Office Action for Application No. 14806852.1 dated Oct. 12, 2020 (3 pages).
Japanese Patent Office Action for Application No. 2016-518017 dated Aug. 27, 2018 (9 pages, English translation included).
Japanese Patent Office Action for Application No. 2016-518017 dated Jul. 4, 2019 (7 pages, English translation included).
Japanese Patent Office Action for Application No. 2016-518017 dated Feb. 15, 2021 (15 pages, English translation included).
Japanese Patent Office Action for Application No. 2019-200973 dated Jan. 25, 2021 (4 pages, English translation included).
Korean Patent Office Action for Application No. 10-2016-7000166 dated Mar. 10, 2021 (5 pages, English translation included).
United States Patent Office Action for U.S. Appl. No. 14/220,116 dated Jul. 22, 2015 (26 pages).
United States Patent Office Final Action for U.S. Appl. No. 14/220,116 dated May 4, 2016 (29 pages).
United States Patent Office Action for U.S. Appl. No. 14/220,116 dated Dec. 2, 2016 (16 pages).
United States Patent Office Action for U.S. Appl. No. 14/220,116 dated Jul. 19, 2017 (15 pages).
United States Patent Office Notice of Allowance for U.S. Appl. No. 14/220,116 dated Sep. 19, 2017 (8 pages).
United States Patent Office Action for U.S. Appl. No. 14/397,420 dated Jun. 2, 2016 (8 pages).
United States Patent Office Action for U.S. Appl. No. 14/397,420 dated Oct. 5, 2016 (10 pages).
United States Patent Office Action for U.S. Appl. No. 14/895,316 dated Dec. 15, 2016 (13 pages).
United States Patent Office Action for U.S. Appl. No. 14/895,316 dated Mar. 21, 2018 (8 pages).
United States Patent Office Action for U.S. Appl. No. 14/895,316 dated Oct. 22, 2018 (11 pages).
United States Patent Office Action for U.S. Appl. No. 14/895,316 dated Apr. 19, 2019 (11 pages).
United States Patent Office Notice of Allowance for U.S. Appl. No. 14/895,316 dated Sep. 30, 2019 (9 pages).
United States Patent Office Notice of Allowance for U.S. Appl. No. 14/895,316 dated Jan. 27, 2020 (7 pages).
United States Patent Office Action for U.S. Appl. No. 15/634,425 dated Aug. 8, 2019 (10 pages).
United States Patent Office Notice of Allowance for U.S. Appl. No. 15/634,425 dated Mar. 9, 2020 (8 pages).
United States Patent Office Action for U.S. Appl. No. 15/789,348 dated Feb. 22, 2018 (14 pages).
United States Patent Office Action for U.S. Appl. No. 15/789,348 dated Aug. 13, 2018 (15 pages).
United States Patent Office Action for U.S. Appl. No. 15/789,348 dated May 22, 2019 (13 pages).
United States Patent Office Action for U.S. Appl. No. 15/789,348 dated Dec. 10, 2019 (18 pages).
United States Patent Office Action for U.S. Appl. No. 15/789,348 dated Jun. 26, 2020 (25 pages).
United States Patent Office Action for U.S. Appl. No. 15/991,333 dated Apr. 19, 2019 (12 pages).
United States Patent Office Action for U.S. Appl. No. 15/991,333 dated Oct. 4, 2019 (6 pages).
United State Patent Office Notice of Allowance for U.S. Appl. No. 15/991,333 dated Apr. 13, 2020 (8 pages).
United States Patent Office Action for U.S. Appl. No. 15/549,842 dated May 17, 2019 (29 pages).
United States Patent Office Action for U.S. Appl. No. 15/549,842 dated Oct. 10, 2019 (14 pages).
United States Patent Office Notice of Allowance for U.S. Appl. No. 15/549,842 dated Jan. 30, 2020 (7 pages).
United States Patent Office Action for U.S. Appl. No. 15/789,348 dated Jan. 27, 2021 (16 pages).
United States Patent Office Notice of Allowance for U.S. Appl. No. 16/865,151 dated Mar. 18, 2021 (7 pages).
Korean Patent Office Action for Application No. 10-2021-7017616 Dated Aug. 4, 2021 (8 pages, English translation Included).
Wang et al., "Efficient delivery of genome-editing proteins using bioreducible lipid nanoparticles," Proc Natl Acad USA, 2016, 113(11): 2868-2873.
Yang et al., "Gene Reactivation by 5-Aza-2'-Deoxycytidine-Induced Demethylation Requires SRCAP-Mediated HZA.Z Insertion to Establish Nucleosome Depleted Regions", PLoS Genetics, 2012, vol. 8, Issue 3, e1002604, 12 pages.
Zenser et al., "A new TAP system for isolation of plant protein complexes and subsequent mass-spec analysis," <https://www.sigmaaldrich.com/deepweb/assets/sigmaaldrich/product/documents/388/028/flag_ha_tap_poster.pdf> published 2008, printed as pp. 1/4-4/4.
Australian Patent Office Examination Report No. 1 for Application No. 2020203924 dated Oct. 8, 2021 (3 pages).
United States Patent Office Action for U.S. Appl. No. 15/789,348 dated Sep. 21, 2021 (20 pages).
United States Patent Office Action for U.S. Appl. No. 16/858,689 dated Nov. 16, 2021 (14 pages).
Canadian Patent Office Action for Application No. 2,914,519 dated Dec. 29, 2021 (4 pages).
Japanese Patent Office Action for Application No. 2016-518017 dated Dec. 8, 2021 (12 pages, English translation included).
Korean Patent Office Action for Application No. 10-2021-7017616 Dated Jun. 9, 2022 (5 pages, English translation Included).
European Patent Office Action for Application No. 14806852.1 dated Jun. 3, 2022 (4 pages).
'T Hoen et al., "Generation and characterization of transgenic mice with the full-length human DMD gene," J. Biol. Chem., 2008, 283: 5899-5907.
Acosta et al., "Use of two gRNAs for CRISPR/Cas9 improves bi-allelic homologous recombination efficiency in mouse embryonic stem cells," Genesis, 2018, 56(5): 1-8.
Adamson et al., "A Multiplexed Single-Cell CRISPR Screening Platform Enables Systematic Dissection of the Unfolded Protein Response," Cell, 2016, 167: 1867-1882 e1821.

(56) References Cited

OTHER PUBLICATIONS

Adamson et al., "A Multiplexed Single-Cell CRISPR Screening Platform Enables Systematic Dissection of the Unfolded Protein Response," Cell, 2016, 167: 1867-1882.e21.
Aguilar et al., "Transcriptional and Chromatin Dynamics of Muscle Regeneration after Severe Trauma," Stem Cell Rep, 2016, 7: 983-997.
Ahlenius et al., "FoxO3 regulates neuronal reprogramming of cells from postnatal and aging mice," Proc Natl Acad Sci U S A, 2016, 113: 8514-8519.
Albuquerque et al., "Mammalian nicotinic acetylcholine receptors: from structure to function," Physiol Rev, 2009, 89: 73-120.
Aloia, "Epigenetic Regulation of Cell-Fate Changes That Determine Adult Liver Regeneration After Injury," Front. Cell Dev. Biol., 2021, 9: 643055.
Amabile et al., "Inheritable Silencing of Endogenous Genes by Hit-and-Run Targeted Epigenetic Editing," Cell, 2016, 167(1): 219-232.e14.
Amabile et al., "Permanent Epigenetic Silencing of Human Genes With Artificial Transcriptional Repressors,", Molecular Therapy, 2015, 23(Suppl. 1): S275.
Amoasii et al., "Gene editing restores dystrophin expression in a canine model of Duchenne muscular dystrophy," Science, 2018, 362: 86-91.
Amoasii et al., "Single-cut genome editing restores dystrophin expression in a new mouse model of muscular dystrophy," Sci Transl Med, Nov. 2017, 9(418): eaan8081.
Andersen et al., "Dual role of delta-like 1 homolog (DLK1) in skeletal muscle development and adult muscle regeneration," Development, 2013, 140: 3743-3753.
Arnett et al., "Adeno-associated viral vectors do not efficiently target muscle satellite cells," Molecular Therapy Methods & Clinical Development, 2014, 1: 14038.
Asokan et al., "Reengineering a receptor footprint of adeno-associated virus enables selective and systemic gene transfer to muscle," Nat Biotechnol, 2010, 28: 79-82.
Asrani et al., "Burden of liver diseases in the world," J Hepatol, 2019, 70(1): 151-171.
Bae et al., "Cas-OFFinder: a fast and versatile algorithm that searches for potential off-target sites of Cas9 RNA-guided endonucleases," Bioinformatics, 2014, 30: 1473-1475.
Balboa et al., "Conditionally Stabilized dCas9 Activator for Controlling Gene Expression in Human Cell Reprogramming and Differentiation," Stem Cell Rep, 2015, 5: 448-459.
Baratta et al., "Cellular organization of normal mouse liver: a histological, quantitative immunocytochemical, and fine structural analysis," Histochem Cell Biol, 2009, 131(6): 713-726.
Barberi et al., "Derivation of engraftable skeletal myoblasts from human embryonic stem cells," Nat Med, 2007, 13: 642-648.
Barr et al., "Predominant Expression of Alternative PAX3 and PAX7 Forms in Myogenic and Neural Tumor Cell Lines," Cancer Res, 1999, 59: 5443-5448.
Barrangou et al., "CRISPR provides acquired resistance against viruses in prokaryotes," Science, 2007, 315(5819): 1709-1712.
Bartel et al., "Isolation of new ribozymes from a large pool of random sequences," Science, 1993, 261(5127): 1411-1418.
Bauer et al., "An erythroid enhancer of BCL11A subject to genetic variation determines fetal hemoglobin level," Science 342, 2013, 253-257.
Beaudry et al., "Directed evolution of an RNA enzyme," Science, 1992, 257(5070): 635-641.
Bengtsson et al., "Muscle-specific CRISPR/Cas9 dystrophin gene editing ameliorates pathophysiology in a mouse model for Duchenne muscular dystrophy," Nat Commun, 2017, 8: 1-10.
Bernstein et al., "An integrated encyclopedia of DNA elements in the human genome," Nature, 2012, 489: 57-74.
Bieth et al., "Highly restricted deletion of the SNORD116 region is implicated in Prader-Willi Syndrome," Eur J Hum Genet, 2015, 23: 252-255.
Bittel et al., "Prader-Willi syndrome: clinical genetics, cytogenetics and molecular biology," Expert Rev Mol Med, 2005, 7(14): 1-20.
Black et al., "Targeted Epigenetic Remodeling of Endogenous Loci by CRISPR/Cas9-Based Transcriptional Activators Directly Converts Fibroblasts to Neuronal Cells," Cell Stem Cell, 2016, 19: 406-414.
Bladen et al., "The TREAT-NMD DMD Global Database: analysis of more than 7,000 Duchenne muscular dystrophy mutations, " Human Mutation, 2015, 36(4):395-402.
Blakemore et al., "Editing of Human Genes May Begin by Year's End in the U.S." Smithsonian.com, <https://www.smithsonianmag.com/smart-news/editing-human-genes-may-begin-years-end-us-180959532/?no-ist> 2016.
Blancafort et al., "Writing and rewriting the epigenetic code of cancer cells: from engineered proteins to small molecules," Mol. Pharmacol., 2013, 83(3): 563-576.
Boldrin et al., "Donor satellite cell engraftment is significantly augmented when the host niche is preserved and endogenous satellite cells are incapacitated," Stem Cells, 2012, 30: 1971-1984.
Braasch et al., "Novel Antisense and Peptide Nucleic Acid Strategies for Controlling Gene Expression," Biochemistry, 2002, 41: 4503-4510.
Breaker et al., "Inventing and improving ribozyme function rational design versus iterative selection methods," TIBTECH, 1994, 12: 268-274.
Breaker, "Are engineered proteins getting competition from RNA?," Curr. Op. Biotech., 1996, 7(4): 442-448.
Briguet et al., "Histological parameters for the quantitative assessment of muscular dystrophy in the mdx-mouse," Neuromuscul. Disord., 2004, 14: 675-682.
Briner et al., "Guide RNA Functional Modules Direct Cas9 Activity and Orthogonality," Molecular Cell, 2014, 56(2): 333-339.
Briner et al., "Lactobacillus buchneri genotyping on the basis of clustered regularly interspaced short palindromic repeat (CRISPR) locus diversity," Appl. Environ. Microbiol., 2014, 80: 994-1001.
Brummelkamp et al., "A system for stable expression of short interfering RNAs in mammalian cells," Science, 2002, 296(5567): 550-553.
Brunger et al., "CRISPR/Cas9 Editing of Murine Induced Pluripotent Stem Cells for Engineering Inflammation-Resistant Tissues," Arthritis Rheumatol, 2017, 69: 1111-1121.
Brunger et al., "Genome Engineering of Stem Cells for Autonomously Regulated, Closed-Loop Delivery of Biologic Drugs," Stem Cell Reports, 2017, 8: 1202-1213.
Buenrostro et al., "Transposition of native chromatin for fast and sensitive epigenomic profiling of open chromatin, DNA-binding proteins and nucleosome position," Nat Methods, 2013, 10: 1213-1218.
Buiting, "Prader-Willi syndrome and Angelman syndrome," Am J Med Genet C Semin Med Genet, 2010, 154C(3): 365-376.
Burnett et al., "Deficiency in prohormone convertase PC1 impairs prohormone processing in Prader-Willi syndrome," J Clin Invest, 2017, 127: 293-305.
Busskamp et al., "Rapid neurogenesis through transcriptional activation in human stem cells," Mol Syst Biol, 2014, 10: 760.
Cano-Rodriguez et al., "Writing of H3K4Me3 overcomes epigenetic silencing in a sustained but context-dependent manner," Nat Commun, 2016, 7: 12284.
Cassidy et al., "Prader-Willi syndrome," Eur J Hum Genet, 2009, 17(1): 3-13.
Cassidy et al., "Prader-Willi syndrome," Genet Med, 2012, 14: 10-26.
Cencic et al., "Protospacer adjacent motif (PAM)-distal sequences engage CRISPR Cas9 DNA target cleavage," PLoS one, 2014, 9, e109213, 13 pages.
Chal et al., "Differentiation of pluripotent stem cells to muscle fiber to model Duchenne muscular dystrophy," Nat Biotechnol, 2015, 33: 962-969.
Chamberlain et al., "Progress toward Gene Therapy for Duchenne Muscular Dystrophy," Mol. Ther., 2017, 25: 1125-1131.
Chanda et al., "Generation of induced neuronal cells by the single reprogramming factor ASCL1," Stem Cell Reports, 2014, 3: 282-296.

(56) References Cited

OTHER PUBLICATIONS

Chang et al., "Integrating Combinatorial Lipid Nanoparticle and Chemically Modified Protein for Intracellular Delivery and Genome Editing," Acc. Chem. Res., 2019, 52: 665-675.
Cheloufi et al., "The histone chaperone CAF-1 safeguards somatic cell identity," Nature, 2015, 528: 218-224.
Chen et al., "Acetylation of RelA at discrete sites regulates distinct nuclear functions of NF-kB," The EMBO Journal, 2002, 21(23): 6539-6548.
Chen et al., "Dynamic imaging of genomic loci in living human cells by an optimized CRISPR/Cas systemm," Cell, 2013, 155: 1479-1491.
Chen et al., "Enrichr: interactive and collaborative HTML5 gene list enrichment analysis tool," BMC Bioinformatics, 2013, 14: 128.
Chen et al., "Genome-wide CRISPR screen in a mouse model of tumor growth and metastasis," Cell, 2015, 160: 1246-1260.
Chen et al., "microRNA-1 and microRNA-206 regulate skeletal muscle satellite cell proliferation and differentiation by repressing Pax7," J Cell Biol, 2010, 190: 867-879.
Chen et al., "Targeted activation of diverse CRISPR-Cas systems for mammalian genome editing via proximal CRISPR targeting," Nature Communications, 2017, 8: 14958.
Chen et al., "Vitamin D receptor suppresses proliferation and metastasis in renal cell carcinoma cell lines via regulating the expression of the epithelial Ca2+ channel TRPV5," PLoS One, 2018, 13: e0195844.
Childers et al., "Gene therapy prolongs survival and restores function in murine and canine models of myotubular myopathy," Sci Transl Med, 2014, 6: 220ra210.
Christoffersen et al., "Ribozymes as human therapeutic agents," J. Med. Chem., 1995, 38(12): 2023-2037.
Chronis et al., "Cooperative Binding of Transcription Factors Orchestrates Reprogramming," Cell, 2017, 168: 442-459 e420.
Concise Encyclopedia of Polymer Science And Engineering, 1990, pp. 858-859.
Cooper et al., "Improved induction of immune tolerance to factor IX by hepatic AAV-8 gene transfer," Hum Gene Ther, 2009, 20: 767-776.
Corces et al., "The chromatin accessibility landscape of primary human cancers," Science, 2018, 362(6413): eaav1898.
Cordier et al., "Muscle-specific promoters may be necessary for adeno-associated virus-mediated gene transfer in the treatment of muscular dystrophies," Hum. Gene Ther., 2001, 12: 205-215.
Crooke et al., "Pharmacokinetic properties of several novel oligonucleotide analogs in mice," J. Pharmacol. Exp. Ther., 1996, 277(2): 923-937.
Cruvinel et al., "Reactivation of maternal SNORD116 cluster via SETDB1 knockdown in Prader-Willi syndrome iPSCs," Hum Mol Genet, 2014, 23: 4674-4685.
Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.
D'Alessio et al., "A Systematic Approach to Identify Candidate Transcription Factors that Control Cell Identity," Stem Cell Reports, 2015, 5: 763-775.
Daley et al., "CRISPhieRmix: a hierarchical mixture model for CRISPR pooled screens," Genome Biol, 2018, 19: 159.
Darabi et al., "Functional skeletal muscle regeneration from differentiating embryonic stem cells," Nat Med, 2008, 14: 134-143.
Darmanis et al., "A survey of human brain transcriptome diversity at the single cell level," Proc Natl Acad Sci U S A, 2015, 112: 7285-7290.
Datlinger et al., "Pooled CRISPR screening with single-cell transcriptome readout," Nat. Methods, 2017, 14: 297-301.
De Mesmaeker et al., "Antisense Oligonucleotides," Ace. Chem. Res., 1995, 28: 366-374.
De Smith et al., "A deletion of the HBII-85 class of small nucleolar RNAs (snoRNAs) is associated with hyperphagia, obesity and hypogonadism," Hum Mol Genet, 2009, 18: 3257-3265.
Deconinck et al., "Utrophin-Dystrophin-Deficient Mice as a Model for Duchenne Muscular Dystrophy," Cell, 1997, 90(4): 717-727.
Dempster et al., "Extracting Biological Insights from the Project Achilles Genome-Scale CRISPR Screens in Cancer Cell Lines," Cold Spring Harbor Laboratory, 2019, 35 pages.
Diao et al., "A new class of temporarily phenotypic enhancers identified by CRISPR/Cas9-mediated genetic screening," Genome Res, 2016, 26: 397-405.
Dirks et al., "Triggered amplification by hybridization chain reaction," Proceedings of the National Academy of Sciences of the United States of America, 2004, 101(43): 15275-15278.
Dixit et al., "Perturb-Seq: Dissecting Molecular Circuits with Scalable Single-Cell RNA Profiling of Pooled Genetic Screens," Cell, 2016, 167: 1853-1866.e17.
Du et al., "Genetic interaction mapping in mammalian cells using CRISPR interference," Nat Methods, 2017, 14: 577-580.
Duan et al., "Expanding AAV packaging capacity with transsplicing or overlapping vectors: a quantitative comparison," Molecular Therapy, 2001, 4: 383-391.
Duan et al., "Genome-wide identification of CRISPR/Cas9 off-targets in human genome," Cell research, 2014, 24(8): 1009-12.
Duan, "Systemic AAV Micro-dystrophin Gene Therapy for Duchenne Muscular Dystrophy," Molecular Therapy, 2018, 26(10): 2337-2356.
Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.
Dumont et al., "Dystrophin expression in muscle stem cells regulates their polarity and asymmetric division," Nat Med, 2015, 21: 1455-1463.
Dumont et al., "Intrinsic and extrinsic mechanisms regulating satellite cell function," Development, 2015, 142: 1572-1581.
Dunbar et al., "Gene therapy comes of age," Science, 2018, 359: eaan4672.
Dykeman, "An implementation of the Gillespie algorithm for RNA kinetics with logarithmic time update," Nucleic Acids Research, 2015, 45(12): 5708-5715.
Eguchi et al., "Reprogramming cell fate with a genome-scale library of artificial transcription factors," Proc Natl Acad Sci U S A, 2016, 113: E8257-E8266.
Englisch et al., Chemically Modified Oligonucleotides as Probes and Inhibitors, Angewandle Chemie, International Edition, 1991, 30(6): 613-629.
Eraslan et al., "Deep learning: new computational modelling techniques for genomics," Nat. Rev. Genet., 2019, 20: 389-403.
Ernsberger, "Role of neurotrophin signalling in the differentiation of neurons from dorsal root ganglia and sympathetic ganglia," Cell Tissue Res, 2009, 336: 349-384.
Erwin et al., "Synthetic transcription elongation factors license transcription across repressive chromatin," Science, 2017, 358: 1617-1622.
Fagerlund et al., "The Cpf1 CRISPR-Cas protein expands genome-editing tools," Genome Biology, 2015, 16:251.
Fairclough et al., "Therapy for Duchenne muscular dystrophy: renewed optimism from genetic approaches," Nat. Rev. Genet., 2013, 14: 373-378.
Farasat et al., "A Biophysical Model of CRISPR/Cas9 Activity for Rational Design of Genome Editing and Gene Regulation," PLOS Computational Biology, 2016, 12(1):e1004724.
Farasat, "Sequence-to-Function Models for Efficient Optimization of Metabolic Pathways and Genetic Circuits," Ph. D. Thesis, 2015, 254 pages.
FDA approval brings first gene therapy to the United States, <https://www.fda.gov/newsevents/newsroom/pressannouncements/ucm574058.htm> (Aug. 30, 2017).
FDA approves first drug for spinal muscular atrophy, <https://www.fda.gov/newsevents/newsroom/pressannouncements/ucm534611.htm> (Dec. 23, 2016).
FDA approves first-of-its kind targeted RNA-based therapy to treat a rare disease, <https://www.fda.gov/newsevents/newsroom/pressannouncements/ucm616518.htm> (Aug. 10, 2018).

(56) References Cited

OTHER PUBLICATIONS

FDA approves novel gene therapy to treat patients with a rare form of inherited vision loss, <https://www.fda.gov/newsevents/newsroom/pressannouncements/ucm589467.htm> (Dec. 18, 2017).
FDA grants accelerated approval to first drug for Duchenne muscular dystrophy, <https://www.fda.gov/newsevents/newsroom/pressannouncements/ucm521263.htm> (Sep. 19, 2016).
Flamm et al., "RNA folding at elementary step resolution," Rna, 2000, 6: 325-338.
Flandin et al., "Lhx6 and Lhx8 coordinately induce neuronal expression of Shh that controls the generation of interneuron progenitors," Neuron, 2011, 70: 939-950.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5: 838-843.
Forget, "Molecular basis of hereditary persistence of fetal hemoglobin," Ann N Y Acad Sci, 1998, 850, 38-44.
Frank et al., "HDAC inhibitors cause site-specific chromatin remodeling at PU.1-bound enhancers in K562 cells," Epigenetics Chromatin, 2016, 9: 15.
Friedland et al., "Characterization of *Staphylococcus aureus* Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications, " Molecular Therapy, 2015, 23(Suppl. 1):S224.
Friedland et al., "*Staphyloccocus aureus* Cas9: An Alternative Cas9 for Genome Editing Applications," Retrieved from the Internet: <http://www.editasmedicine.com/data/doc uments/ASGCT%20poster 2015 Ari.pdf> Retrieved on Feb. 28, 2018.
Fu et al., "Landscape of target: guide homology effects on Cas9-mediated cleavage," Nucleic Acids Research, 2014, 42(22): 13778-13787.
Fulco et al., "Activity-by-contact model of enhancer-promoter regulation from thousands of CRISPR perturbations," Nature Genetics, 2019, 51: 1664-1669.
Fulco et al., "Systematic mapping of functional enhancer-promoter connections with CRISPR interference," Science, 2016, 354: 769-773.
Fulmer-Smentek et al., "Association of acetylated histones with paternally expressed genes in the Prader-Willi deletion region," Hum Mol Genet, 2001, 10: 645-652.
Gait, "Oligoribonucleotides," Antisense Research and Applications, 1993, Chapter 16, pp. 290-299.
Gaj et al., "Structure-Guided Reprogramming of Serine Recombinase DNA Sequence Specificity," Proc Natl Acad Sci U S A, 2011, 108(2): 498-503.
Gao et al., "Complex transcriptional modulation with orthogonal and inducible dCas9 regulators," Nat Methods, 2016, 13: 1043-1049.
Gascon et al., "Direct Neuronal Reprogramming: Achievements, Hurdles, and New Roads to Success," Cell Stem Cell, 2017, 21: 18-34.
Gasiunas et al., "Cas9-crRNA ribonucleoprotein complex mediates specific DNA cleavage for adaptive immunity in bacteria," Proc. Natl. Acad. Sci., 2012, 109: E2579-E2586.
Gasperini et al., "A Genome-wide Framework for Mapping Gene Regulation via Cellular Genetic Screens," Cell, 2018, 176(1-2); 377-390.e19.
Gaudelli et al., "Directed evolution of adenine base editors with increased activity and therapeutic application," Nat Biotechnol, Jul. 2020, 38(7): 892-900.
Gaudelli et al., "Programmable base editing of A•T to G•C in genomic DNA without DNA cleavage," Nature, Nov. 2017, 551(7681): 464-471.
Gebeyehu et al., "Novel biotinylated nucleotide—analogs for labeling and colorimetric detection of DNA," Nucl. Acids Res., 1987, 15(11): 4513-4534.
Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Gemberling et al., "Transgenic mice for in vivo epigenome editing with CRISPR-based systems," Nat Methods, 2021, 18(8): 965-974.
Genbank Accenssion AP006627.1 (2016).
Genbank Accenssion BA000004.3 (2016).
Genbank Accenssion BAB04055.1 (2016).
GenBank Accession AF214528.1 (2000).
GenBank Accession No. AAC75803.1 (2018).
GenBank Accession No. AIN33136.1 (2014).
GenBank Accession No. BAB04055.1 (2017).
GenBank Accession No. EOT14076.1 (2013).
GenBank Accession No. AK019325 (2010).
GenBank Accession No. BB730912 (2001).
GenBank Accession No. BC010291 (2006).
GenBank Accession No. BC026642.1 (2007).
GenBank Accession No. BI143915 (2011).
GenBank Accession No. NM_020562.1 (2004).
GenBank Accession X51934.1 (1997).
GenBank P38036.2 (2013).
Gersbach et al., "Targeted plasmid integration into the human genome by an engineered zinc-finger recombinase," Nucleic Acids Res, 2011, 39: 7868-7878.
Ghisletti et al., "Identification and characterization of enhancers controlling the inflammatory gene expression program in macrophages," Immunity, 2010, 32: 317-328.
Gibson et al., "Enzymatic assembly of DNA molecules up to several hundred kilobases," Nature Methods, 2009, 6(5): 343-345.
Gillespie, "A general method for numerically simulating the stochastic time evolution of coupled chemical reactions," Journal of computational physics, 1976, 22: 403-434.
Gilman et al., "Distal CCAAT box deletion in the A gamma globin gene of two black adolescents with elevated fetal A gamma globin," Nucleic Acids Res 16, 1988, 10635-10642.
Goldstein et al., "In Situ Modification of Tissue Stem and Progenitor Cell Genomes," Cell Reports, 2019, 27: 1254-1264.e7.
Gomaa et al., "Programmable Removal of Bacterial Strains by Use of Genome-Targeting CRISPR-Cas Systems," 2014, mBio 5(1): e00928-13.
Gonda "Aerosols for delivery of therapeutic and diagnostic agents to the respiratory tract," Critical Reviews in Therapeutic Drug Carrier Systems, 1990 6:273-313.
Gong et al., "Molecular insights into DNA interference by CRISPR-associated nuclease-helicase Cas3," Proc Natl Acad Sci U S A, 2014, 111(46):16359-64.
Gray et al., "G quadruplexes are genomewide targets of transcriptional helicases XPB and XPD," Nat. Chem. Biol, 2014, 10: 313-318.
Gregorevic et al., "Systemic microdystrophin gene delivery improves skeletal muscle structure and function in old dystrophic mdx mice," Mol Ther, 2008, 16: 657-664.
Grissa et al., "CRISPRFinder: a web tool to identify clustered regularly interspaced short palindromic repeats," Nucleic Acids Res., 2007, 35(Web Server issue):W52-57.
Guo et al., "Harnessing accurate non-homologous end joining for efficient prease deletion in CRISPR/Cas9-mediated genome editing, " Genome Biology, 2018, 19: 170, 20 pages.
Guo, J. et al., "Directed evolution of an enhanced and highly efficient Fokl cleavage domain for zinc finger nucleases," J Mol Biol, 2010, 400(1): 96-107.
Hacein-Bey-Abina et al., "LMO2-associated clonal T cell proliferation in two patients after gene therapy for SCID-X1," Science, 2003, 302: 415-419.
Hakim et al., "Evaluation of Muscle Function of the Extensor Digitorum Longus Muscle Ex vivo and Tibialis Anterior Muscle In situ in Mice," J. Vis. Exp., 2013, 1-8.
Hakim et al., "Systemic gene transfer reveals distinctive muscle transduction profile of tyrosine mutant AAV-1, -6, and -9 in neonatal dogs," Mol. Ther. Methods Clin. Dev., 2014, 1:14002.
Hall et al., "Prevention of Muscle Aging by Myofiber-Associated Satellite Cell Transplantation," Sci Transl Med, 2010, 2: 57ra83.

(56) References Cited

OTHER PUBLICATIONS

Hardy et al., "Comparative Study of Injury Models for Studying Muscle Regeneration in Mice," PLoS One, 2016, 11: e0147198.
Harper et al., "Modular flexibility of dystrophin: implications for gene therapy of Duchenne muscular dystrophy," Nat. Med., 2002, 8: 253-261.
Harrow et al., "GENCODE: The reference human genome annotation for The ENCODE Project," Genome Res, 2012, 22: 1760-1774.
Hart et al., "High-Resolution CRISPR Screens Reveal Fitness Genes and Genotype-Specific Cancer Liabilities," Cell, 2015, 163: 1515-1526.
Hayward et al., "Whole-genome landscapes of major melanoma subtypes," Nature, 2017, 545: 175-180.
He et al., "Molecular Genetic Mechanisms of Hereditary Spherocytosis: Current Perspectives," Acta Haematol., 2018, 139: 60-66.
Heagerty et al., "Time-dependent ROC curves for censored survival data and a diagnostic marker," Biometrics, 2000, 56(2): 337-344.
Heasman, "Morpholino oligos: making sense of antisense?," Dev. Biol., 2002, 243(2): 209-214.
Henikoff et al., "Amino acid substitution matrices from protein blocks," Proc. Natl. Acad. Sci. USA, 1992, 89: 10915-9.
Henning et al., "Epigenetic control of CD8 + T cell differentiation," Nat Rev Immunol, 2018, 18(5): 340-356.
Hilton et al., "Enabling functional genomics with genome engineering," Genome Research, 2015, 25(10):1442-1455.
Himeda et al., "Design and Testing of Regulatory Cassettes for Optimal Activity in Skeletal and Cardiac Muscles," Methods Mol Biol, 2011, 709: 3-19 (Published Online Dec. 2010).
Hori et al., "Simple and reproducible hepatectomy in the mouse using the clip technique," World J Gastroenterol, 2012, 18(22): 2767-2774.
Howarth et al., "A monovalent streptavidin with a single femtomolar biotin binding site," Nature methods, 2006, 3(4): 267-273.
Hsu et al., "Development and applications of CRISPR-Cas9 for genome engineering," Cell, 2014, 157: 1262-1278.
Huang et al., "Generation and comparison of CRISPR-Cas9 and Cre-mediated genetically engineered mouse models of sarcoma," Nature Communications, 2017, 8(15999): 1-11.
Huang et al., "Impaired respiratory function in mdx and mdx/utrn+/− mice," Muscle & Nerve, 2011, 43(2): 263-267.
Huntriss et al., "Imprinted expression of SNRPN in human preimplantation embryos," Am J Hum Genet, 1998, 63: 1009-1014.
Inoue et al., "Runx transcription factors in neuronal development," Neural Dev, 2008, 3: 20.
Isaac et al., "Dystrophin and utrophin "double knockout" dystrophic mice exhibit a spectrum of degenerative musculoskeletal abnormalities," Journal of Orthopaedic Research, 2013, 31(3): 343-349.
Iyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.
Jansen et al., "Identification of genes that are associated with DNA repeats in prokaryotes," Mol Microbiol, 2002, 43(6): 1565-1575.
Jeltsch et al., "Application of DNA methyltransferases in targeted DNA methylation," Appl. Microbiol. Biotechnol., 2007, 75(6): 1233-1240.
Jepsen et al., "Locked nucleic acid: a potent nucleic acid analog in therapeutics and biotechnology," Oligonucleotides, 2004, 14(2): 130-146.
Jiang et al., "A Cas9-guide RNA complex preorganized for target DNA recognition," Science, 2015, 348, 1477-1481.
Jiang et al., "Notch signaling deficiency underlies age-dependent depletion of satellite cells in muscular dystrophy," Disease Models & Mechanisms, 2014, 7: 997-1004.
Jiang et al., "RNA-guided editing of bacterial genomes using CRISPR-Cas systems," Nat. Biotechnol., 2013, 31:233-239.
Jimenez et al., "Activation of the beta-globin locus control region precedes commitment to the erythroid lineage," Proceedings of the National Academy of Sciences, 1992, 89: 10618-10622.
Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.
Jobling et al., "Chitayat-Hall and Schaaf-Yang syndromes:a common aetiology: expanding the phenotype of MAGEL2-related disorders," J Med Genet, 2018, 55: 316-321.
Jooss et al., "Transduction of dendritic cells by DNA viral vectors directs the immune response to transgene products in muscle fibers," J. Virol., 1998, 72: 4212-4223.
Josephs et al., "Structure and specificity of the RNA-guided endonuclease Cas9 during DNA interrogation, target binding and cleavage," Nucleic Acids Research, 2015, 43(18): 8924-8941.
Joyce, "Amplification, mutation and selection of catalytic RNA," Gene, 1989, 82(1): 83-87.
Joyce, "Directed molecular evolution," Scientific American, 1992, 267(6): 90-97.
Jurkowska and Jeltsch, "Silencing of Gene Expression by Targeted DNA Methylation: Concepts and Approaches," Methods Mol. Biol. 649, 2010, Chapter 9: 149-161.
Kabadi et al., "Engineering Synthetic TALE and CRISPR/Cas9 Transcription Factors for Regulating Gene Expression," Methods, 2014, 69(2): 188-197.
Kabanov et al., "A new class of antivirals: antisense oligonucleotides combined with a hydrophobic substituent effectively inhibit influenza virus reproduction and synthesis of virus-specific proteins in MDCK cells," FEBS Lett., 1990, 259: 327-330.
Karlin et al., "Applications and statistics for multiple high-scoring segments in molecular sequences," Proc. Natl. Acad. Sci. USA, 1993, 90: 5873-77.
Kauppinen et al., "Locked nucleic acid (LNA): High affinity targeting of RNA for diagnostics and therapeutics," Drug Discov Today Technol, 2005, 2(3): 287-290.
Keefe et al., "Muscle stem cells contribute to myofibers in sedentary adult mice," Nat Commun, 2015, 6: 7087.
Keil et al., "Brain transcriptome databases: a user's guide," J Neurosci, 2018, 38(10): 2399-2412.
Kempfer et al., "Methods for mapping 3D chromosome architecture," Nat. Rev. Genet., 2020, 21: 207-226.
Keys et al., "A genome-wide screen in the mouse liver reveals sex-specific and cell non-autonomous regulation of cell fitness," bioRxiv preprint doi: https://doi.org/10.1101/2021.01.30.428976, posted Feb. 1, 2021.
Khambata-Ford et al., "Identification of Promoter Regions in the Human Genome by Using a Retroviral Plasmid Library-Based Functional Reporter Gene Assay," Genome Research, 2003, 13: 1765-1774.
Khodakov et al., "Protected DNA strand displacement for enhanced single nucleotide discrimination in double-stranded DNA," Scientific reports, 2015, 5: 8721.
Khurana et al., "Role of non-coding sequence variants in cancer," Nat. Rev. Genet., 2016, 17: 93-108.
Kim et al., "A Histone acetylation contributes to chromatin looping between the locus control region and globin gene by influencing hypersensitive site formation," Biochim Biophys Acta, 2013, 1829: 963-969.
Kim et al., "Epigenetic therapy of Prader-Willi Syndrome," Transl Res, 2019, 208: 105-118.
Kim et al., "Expansion and Purification Are Critical for the Therapeutic Application of Pluripotent Stem Cell-Derived Myogenic Progenitors," Stem Cell Rep, 2017, 9: 12-22.
Kim et al., "Targeting the histone methyltransferase G9a activates imprinted genes and improves survival of a mouse model of Prader-Willi syndrome," Nat Med, 2017, 23: 213-222.
Kim et al., "Engineering and Application of Zinc Finger Proteins and TALEs for Biomedical Research," Mol Cells, 2017, 40(8): 533-541.
Klann et al., "CRISPR-based methods for high-throughput annotation of regulatory DNA," Curr Opin Biotechnol, 2018, 52: 32-41.
Klann et al., "Genome-wide annotation of gene regulatory elements linked to cell fitness," bioRxiv doi: 10.1101/2021.03.08.434470. Preprint posted Mar. 9, 2021, 42 pages.

(56) References Cited

OTHER PUBLICATIONS

Kleinstiver et al., "Broadening the targeting range of *Staphylococcus aureus* CRISPR-Cas9 by modifying PAM recognition," Nature Biotechnology, 2015, 33(12): 1293-1298.
Kleinstiver et al., "Engineered CRISPR-Cas9 nucleases with altered PAM specificities," Nature, 2015, 523(7561): 481-485.
Kleinstiver et al., "Genome-wide specificities of CRISPR-Cas Cpf1 nucleases in human cells," Nature Biotechnology, 2016, 34(8):869-874.
Koblan et al., "Improving cytidine and adenine base editors by expression optimization and ancestral reconstruction," Oct. 2018, 36(9): 843-846.
Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29.
Kocher et al., "Phylogenetic Analysis of the SNORD116 Locus," Genes, 2017, 8(12): 358.
Kodaka et al., "Skeletal Muscle Cell Induction from Pluripotent Stem Cells," Stem Cells Int, Apr. 2017, Article ID 1376151, 16 pages.
Koerber et al., "DNA shuffling of adeno-associated virus yields functionally diverse viral progeny," Mol Ther, 2008, 16: 1703-1709.
Komor et al., "Programmable editing of a target base in genomic DNA without double-stranded DNA cleavage," Nature, 2016, 533(7603): 420-424.
Koo et al., "Functional Rescue of Dystrophin Deficiency in Mice Caused by Frameshift Mutations Using Campylobacter jejuni Cas9," Molecular Therapy, 2018 26(6): 1529-1538.
Koopmans et al., "SynGO: An Evidence-Based, Expert-Curated Knowledge Base for the Synapse," Neuron, 2019, 103: 217-234 e214.
Koppanati et al., "Improvement of the mdx mouse dystrophic phenotype by systemic in utero AAV8 delivery of a minidystrophin gene," Gene Ther, 2010, 17: 1355-1362.
Kornberg et al., "DNA Replication," 1980, pp. 75-77.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14): 3607-3630.
Kreis et al., "The Multifaceted p21 (Cip1/Waf1/CDKN1A) in Cell Differentiation, Migration and Cancer Therapy," Cancers (Basel), 2019, 11(9): 1220.
Kuhnel et al., "Tumor-specific adenoviral gene therapy: Transcriptional repression of gene expression by utilizing p53- signal transduction pathways," Cancer Gene Ther., 2004, 11: 28-40.
Kumar et al., "Artificial evolution and natural ribozymes," FASEB Journal, 1995, 9: 1183-1195.
Kurreck, "Antisense technologies. Improvement through novel chemical modifications," European Journal of Biochemistry, 2003, 270(8): 1628-1644.
Kwon et al., "Myogenic Progenitor Cell Lineage Specification by CRISPR/Cas9-Based Transcriptional Activators," Stem cell reports, 2020, 14: 755-769.
Lacerra et al., "Restoration of hemoglobin A synthesis in erythroid cells from peripheral blood of thalassemic patients," Proc. Natl. Acad. Sci., 2000, 97(17): 9591-9596.
Lai et al., "Partial restoration of cardiac function with ΔPDZ nNOS in aged mdx model of Duchenne cardiomyopathy," Hum Mol Genet., 2014, 23(12): 3189-3199.
Lake et al., "Integrative single-cell analysis of transcriptional and epigenetic states in the human adult brain," Nat Biotechnol, 2018, 36: 70-80.
Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.
Lambert et al., "The Human Transcription Factors," Cell, 2018, 172: 650-665.
Lamey et al., "Pax genes in myogenesis: alternate transcripts add complexity," Histol Histopathol, 2004, 19: 1289-1300.
Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.
Langouet et al., "Zinc finger protein 274 regulates imprinted expression of transcripts in Prader-Willi syndrome neurons," Hum Mol Genet, 2018, 27: 505-515.
Laumont et al., "Noncoding regions are the main source of targetable tumor-specific antigens," Sci. Transl. Med., 2018, 10(470): eaau5516, 11 pages.
Lawrence et al., "Discovery and saturation analysis of cancer genes across 21 tumour types," Nature, 2014, 505: 495-501.
Lee et al., "Activation of innate immunity is required for efficient nuclear reprogramming," Cell, 2012, 151: 547-558.
Lee et al., "Expression of small interfering RNAs targeted against HIV-1 rev transcripts in human cells," Nature Biotechnol, 2002, 20(5): 500-505.
Lee et al., "Nanoparticle delivery of Cas9 ribonucleoprotein and donor DNA in vivo induces homology-directed DNA repair," Nat Biomed Eng, 2017, 1: 889-901.
Lenoir et al., "PICKLES: the database of pooled in-vitro CRISPR knockout library essentiality screens," Nucleic Acids Res, 2018, 46: D776-D780.
Lesnik et al., "Relative thermodynamic stability of DNA, RNA, and DNA: Rna hybrid duplexes: relationship with base composition and structure," Biochemistry, 1995, 34(34): 10807-10815.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.
Levin et al., "Position-dependent effects of locked nucleic acid (LNA) on DNA sequencing and PCR primers," Nuc. Acids. Res., 2006, 34: e142.
Levskaya et al., "Synthetic biology: engineering Escherichia coli to see light," Nature, 2005, 438:441-442.
Li et al., "Chimeric DNA methyltransferases target DNA methylation to specific DNA sequences and repress expression of target genes," Nucleic Acids Res., 2007, 35(1): 100-112.
Li et al., "Engineering and selection of shuffled AAV genomes: a new strategy for producing targeted biological nanoparticles," Mol Ther, 2008, 16: 1252-1260.
Li et al., "Ex vivo cell-based CRISPR/Cas9 genome editing for therapeutic applications," Biomaterials, 2020, 234: 119711.
Li et al., "Precise correction of the dystrophin gene in duchenne muscular dystrophy patient induced pluripotent stem cells by TALEN and CRISPR-Cas9," Stem Cell Reports, 2015, 4: 143-154.
Li et al., "Preservation of muscle force in Mdx3cv mice correlates with low-level expression of a near full-length dystrophin protein," Am. J. Pathol., 2008, 172: 1332-1341.
Li et al., "RSEM: accurate transcript quantification from RNA-Seq data with or without a reference genome," BMC Bioinformatics, 2011, 12: 323.
Li et al., "Synthetic muscle promoters: activities exceeding naturally occurring regulatory sequences," Nature Biotechnology, 1999, 17: 241-245.
Li et al., "The autism-related gene SNRPN regulates cortical and spine development via controlling nuclear receptor Nr4a1," Sci Rep, 2016, 6: 29878.
Lian et al., "Robust cardiomyocyte differentiation from human pluripotent stem cells via temporal modulation of canonical Wnt signaling," Proc Natl Acad Sci, 2012, 109: E1848-E1857.
Liao et al., "In Vivo Target Gene Activation via CRISPR/Cas9-Mediated Trans-epigenetic Modulation," Cell, 2017, 171: 1495-1507.
Liao et al., "The Subread aligner: fast, accurate and scalable read mapping by seed-and-vote," Nucleic Acids Res, 2013, 41: e108.
Lim et al., "Application of CRISPR/Cas9 for the Treatment of Duchenne Muscular Dystrophy," Journal of Personalized Medicine, 2018, 8(4): 1-20.
Limberis et al., "Transduction efficiencies of novel AAV vectors in mouse airway epithelium in vivo and human ciliated airway epi-

(56) References Cited

OTHER PUBLICATIONS thelium in vitro," Molecular therapy: the journal of the American Society of Gene Therapy, 2009, 17: 294-301.
Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.
Liu et al., "Adeno-associated virus-mediated microdystrophin expression protects young mdx muscle from contraction-induced injury," Mol. Ther., 2005, 11: 245-256.
Liu et al., "CRISPR Activation Screens Systematically Identify Factors that Drive Neuronal Fate and Reprogramming," Cell Stem Cell, 2018, 23: 758-771 e758.
Liu et al., "CRISPR-Based Chromatin Remodeling of the Endogenous Oct4 or Sox2 Locus Enables Reprogramming to Pluripotency," Cell Stem Cell, 2018, 22: 252-261 e254.
Liu et al., "Editing DNA Methylation in the Mammalian Genome," Cell, Sep. 2016, 167(1): 233-247.
Liu et al., "Monte Carlo simulation for single RNA unfolding by force," Biophysical journal, 2005, 88(1): 76-84.
Long et al., "Postnatal genome editing partially restores dystrophin expression in a mouse model of muscular dystrophy," Science, 2016, 351(6271): 400-403.
Luo et al., "Repurposing endogenous type I CRISPR-Cas systems for programmable gene repression," Nucleic Acids Research, 2014, 43(1): 674-681.
Ma et al., "Targeted gene suppression by inducing de novo DNA methylation in the gene promoter," Epigenetics Chromatin, 2014, 7: 20.
Machinek et al., "Programmable energy landscapes for kinetic control of DNA strand displacement," Nature communications, 2014, 5: 5324, 9 pages.
Macpherson et al., "Flexible guide-RNA design for CRISPR applications using Protospacer Workbench," Nature biotechnology, 2015, 33(8): 805-806.
Mader et al., "CRISPR RNA-guided activation of endogenous human genes," Nature Methods, 2013, 10(10): 977-979.
Madigan et al., "Engineering AAV receptor footprints for gene therapy," Curr Opin Virol, 2016, 18: 89-96.
Madisen et al., "A robust and high-throughput Cre reporting and characterization system for the whole mouse brain," Nat Neurosci, 2010, 13: 133-140.
Maeder et al., "Robust, synergistic regulation of human gene expression using TALE activators," Nat Methods, 2013, 10(3): 243-245.
Magli et al., "PAX7 Targets, CD54, Integrin a9B1, and SDC2, Allow Isolation of Human ESC/iPSC-Derived Myogenic Progenitors," Cell Rep, 2017, 19: 2867-2877.
Maheshri et al., "Directed evolution of adeno-associated virus yields enhanced gene delivery vectors," Nat Biotechnol, 2006, 24: 198-204.
Majzner et al., "Clinical lessons learned from the first leg of the Car T cell journey," Nature Medicine, 2019, 25(9): 1341-1355.
Makarova et al., "An updated evolutionary classification of CRISPR-Cas systems," Nature Reviews Microbiology, 2015, 13:722-736.
Makarova et al., "Evolution and classification of the CRISPR-Cas systems," Nature Reviews Microbiology, 2011, pp. 467-477.
Mann et al., "Improved antisense oligonucleotide induced exon skipping in the mdx mouse model of muscular dystrophy," J. Gene Med., 2002, 4: 644-654.
Manning et al., "What has the mdx mouse model of duchenne muscular dystrophy contributed to our understanding of this disease?," Journal of Muscle Research and Cell Motility, 2015, 36: 155-167.
Manoharan et al., "Chemical Modifications to Improve Uptake and Bioavailability of Antisense Oligonucleotides," Ann. N. Y. Acad. Sci., 1992, 660: 306-309.
Manoharan et al., "Cholic acid-oligonucleotide conjugates for antisense applications," Bioorg. Med. Chem. Let., 1994, 4(8): 1053-1060.
Manoharan et al., "Introduction of a lipophilic thioether tether in the minor groove of nucleic acids for antisense applications," Bioorg. Med. Chem. Let., 1993, 3(12): 2765-2770.
Manoharan et al., "Lipidic Nucleic Acids," Tetrahedron Lett, 1995, 36: 3651-3654.
Manoharan et al., "Oligonucleotide Conjugates: Alteration of the Pharmacokinetic Properties of Antisense Agents," Nucleosides & Nucleotides, 1995, 14: 969-973.
Martin et al., "A New Access to 2'-O-Alkylated Ribonucleosides and Properties of 2'-O-Alkylated Oligoribonucleotides," Helv. Chim. Acta, 1995, 78: 486-504.
Maruyama et al., "Epigenetic Regulation of Cell Type-Specific Expression Patterns in the Human Mammary Epithelium," PLoS Genetics, 2011, 7(4): e1001369, 15 pages.
Mastellos et al., "Inducing and characterizing liver regeneration in mice: Reliable models, essential "readouts" and critical perspectives," Curr Protoc Mouse Biol., 2013, 3(3): 141-170.
Mathews et al., "Expanded sequence dependence of thermodynamic parameters improves prediction of RNA secondary structure," Journal of Molecular Biology, 1999, 288(5): 911-940.
Maurano et al., "Systematic localization of common disease-associated variation in regulatory DNA," Science, 2012, 337: 1190-1195.
Maxwell et al., "A detailed cell-free transcription-translation-based assay to decipher CRISPR protospacer-adjacent motifs," Methods, 2018, 143: 48-57.
McCarthy et al., "Schaaf-Yang syndrome overview: Report of 78 individuals," Am J Med Genet A, 2018, 176(12): 2564-2574.
McFadden et al., "The Hand1 and Hand2 transcription factors regulate expansion of the embryonic cardiac ventricles in a gene dosage-dependent manner," Development, 2005, 132: 189-201.
McGreevy et al., "Animal models of Duchenne muscular dystrophy: from basic mechanisms to gene therapy," Disease Models Mechanisms, 2015, 8(3): 195-213.
McTigue et al., "Sequence-dependent thermodynamic parameters for locked nucleic acid (LNA)-DNA duplex formation," Biochemistry, 2004, 43(18): 5388-5405.
Mertens et al., "Evaluating cell reprogramming, differentiation and conversion technologies in neuroscience," Nat Rev Neurosci, 2016, 17: 424-437.
Mevissen et al., "Molecular basis of Lys11-polyubiquitin specificity in the deubiquitinase Cezanne," Nature, 2016, 538(7625): 402-405.
Miller et al., "Transcriptional landscape of the prenatal human brain," Nature, 2014, 508: 199-206.
Min et al., "CRISPR Correction of Duchene Muscular Dystrophy," Annual Review of Medicine, Epub Oct. 2018, 70: 239-255.
Mishra et al., "Improved leishmanicidal effect of phosphorotioate antisense oligonucleotides by LDL-mediated delivery," Biochim. Biophys. Acta, 1995, 1264(2): 229-237.
Miyagishi et al., "U6 promoter-driven siRNAs with four uridine 3' overhangs efficiently suppress targeted gene expression in mammalian cells," Nature Biotechnol, 2002, 20(5): 497-500.
Mojica et al., "Intervening sequences of regularly spaced prokaryotic repeats derive from foreign genetic elements," J Molec Evolution, 2005, 60(2): 174-182.
Mojica et al., "Short motif sequences determine the targets of the prokaryotic CRISPR defence system," Microbiology, 2009, 155: 733-740.
Montalbano et al., "High-Throughput Approaches to Pinpoint Function within the Noncoding Genome," Mol. Cell, 2017, 68: 44-59.
Montarras, "Direct Isolation of Satellite Cells for Skeletal Muscle Regeneration," Science, 2005, 309: 2064-2067.
Moore et al., "Transcription Activator-like Effectors: A Toolkit for Synthetic Biology," ACS Synth Biol, 2014, 3(10): 708-716.
Morris et al., "Dissecting engineered cell types and enhancing cell fate conversion via CellNet," Cell, 2014, 158: 889-902.
Muir et al., "Engraftment potential of dermal fibroblasts following in vivo myogenic conversion in immunocompetent dystrophic skeletal muscle," Mol. Ther. Methods Clin. Dev., 2014, 1:14025.
Murray et al., "Codon usage in plant genes," Nucl. Acids Res., 1989, 17:477-498.
Naguibneva et al., "An LNA-based loss-of-function assay for micro-RNAs," Biomed Pharmacother, 2006, 60: 633-638.

(56) References Cited

OTHER PUBLICATIONS

Najm et al., "Orthologous CRISPR-Cas9 enzymes for combinatorial genetic screens," Nat Biotechnol, 2018, 36: 179-189.
Naldini, "Gene therapy returns to centre stage," Nature, 2015, 526: 351-360.
Nam et al., "Cas5d protein processes pre-crRNA and assembles into a Cascade-like interference complex in Subtype I-C/Dvulg CRISPR-Cas system," Structure, 2012, 20:1574-1584.
Nance et al., "AAV9 Edits Muscle Stem Cells in Normal and Dystrophic Adult Mice," Molecular Therapy, 2019, 27: 1568-1585.
Nasevicius et al., "Effective targeted gene 'knockdown' in zebrafish," Nat. Genet., 2000, 26(2): 216-220.
Nelson et al., "Engineering Delivery Vehicles for Genome Editing," Annual review of chemical and biomolecular engineering, 2016, 7: 637-662.
Nelson et al., "Genome engineering: a new approach to gene therapy for neuromuscular disorders," Nat Rev Neurol, 2017, 13: 647-661.
Nelson et al., "Local and Systemic Gene Editing in a Mouse Model of Duchenne Muscular Dystrophy," Molecular Therapy, 2016, 24(Supp 1):S191.
Nelson et al., "Long-term evaluation of AAV-CRISPR genome editing for Duchenne muscular dystrophy," Nature Medicine, 2019, 25(3): 427-432.
Nguyen et al., "Transcriptional Enhancers in the Regulation of T Cell Differentiation," Front. Immunol., 2015, 6: 462.
Nielsen et al., "Sequence-selective recognition of DNA by strand displacement with a thymine-substituted polyamide," Science, 1991, 254: 1497-1500.
Nikfarjam et al., "A Model of Partial Hepatectomy in Mice," Journal of Investigative Surgery, 2004, 17(5): 291-294.
Nowotny et al., "Crystal structures of RNase H bound to an RNA/DNA hybrid: substrate specificity and metal-dependent catalysis," Cell, 2005, 121(7): 1005-1016.
Nuñez et al., "Genome-wide programmable transcriptional memory by CRISPR-based epigenome editing," Cell, 2021, 184(9): P2503-2519.
O'Brien et al., "GT-Scan: identifying unique genomic targets," Bioinformatics, 2014, 30: 2673-2675.
Oberhauser et al., "Effective incorporation of 2'-O-methyl-oligoribonucleotides into liposomes and enhanced cell association through modification with thiocholesterol," Nucl. Acids Res., 1992, 20(3): 533-538.
Obika et al., "Stability and structural features of the duplexes containing nucleoside analogues with a fixed N-type conformation, 2'-O,4'-C-methyleneribonucleosides," Tetrahedron Lett. 1998, 39(30): 5401-5404.
O'Connell et al., "Programmable RNA recognition and cleavage by CRISPR/Cas9," Nature, 2014, 516: 263-266.
Odom et al., "Microutrophin Delivery Through rAAV6 Increases Lifespan and Improves Muscle Function in Dystrophic Dystrophin/Utrophin-deficient Mice," Molecular Therapy, 2008, 16(9): 1539-1545.
O'Geen et al., "dCas9-based epigenome editing suggests acquisition of histone methylation is not sufficient for target gene repression," Nucleic Acids Res, 2017, 45: 9901-9916.
O'Geen et al., "Ezh2-dCas9 and KRAB-dCas9 enable engineering of epigenetic memory in a context-dependent manner," Epigenetics Chromatin, 2019, 12: 26.
Olguin et al., "Pax-7 up-regulation inhibits myogenesis and cell cycle progression in satellite cells: a potential mechanism for self-renewal," Dev Biol, 2004, 275: 375-388.
Orgel, "Selection in vitro," Proc. R. Soc. B, 1979, 205: 435-442.
Orlando et al., "Promoter capture Hi-C-based identification of recurrent noncoding mutations in colorectal cancer," Nat. Genet., 2018, 50: 1375-1380.
Orom et al., "LNA-modified oligonucleotides mediate specific inhibition of microRNA function," Gene, 2006, 372: 137-141.
Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Multiplex CRISPR/Cas9-based genome editing for correction of dystrophin mutations that cause Duchenne muscular dystrophy," Nature Communications, 2015, 6:6244.
Ousterout, "Genetic Correction of Duchenne Muscular Dystrophy using Engineered Nucleases," Dept. of Biomedical Engineering Duke University (Dissertation), 2014, pp. 1-204.
Paddison et al., "Short hairpin RNAs (shRNAs) induce sequence-specific silencing in mammalian cells," Genes & Dev, 2002, 16(8): 948-958.
Paez-Espino et al., "CRISPR immunity drives rapid phage genome evolution in *Streptococcus thermophilus*," mBio, 2015, 6(2): e00262-15.
Pang et al., "Induction of human neuronal cells by defined transcription factors," Nature, 2011, 476: 220-223.
Papapetrou, "Induced pluripotent stem cells, past and future," Science, 2016, 353: 991-992.
Parekh et al., "Mapping Cellular Reprogramming via Pooled Overexpression Screens with Paired Fitness and Single-Cell RNA-Sequencing Readout," Cell Systems, 2018, 7: 548-555.e548.
Park et al., "Multi-Parametric MRI at 14T for Muscular Dystrophy Mice Treated with AAV Vector-Mediated Gene Therapy," PLoS One, 2015, 10(4): e0124914.
Paul et al., "Effective expression of small interfering RNA in human cells," Nature Biotechnol, 2002, 20(5): 505-508.
Pawlikowski et al., "Regulation of skeletal muscle stem cells by fibroblast growth factors," Dev Dyn, 2017, 246: 359-367.
Penczek et al., "Three-dimensional reconstruction of single particles embedded in ice," Ultramicroscopy, 1992, 40, 33-53.
Perez-Pinera et al., "Synergistic and tunable human gene activation by combinations of synthetic transcription factors," Nat Methods, 2013, 10: 239-242.
Pigozzo et al., "Revertant Fibers in the mdx Murine Model of Duchenne Muscular Dystrophy: An Age- and Muscle-Related Reappraisal," PLoS One, 2013, 8(8): e72147.
Pinello et al., "Analyzing CRISPR genome-editing experiments with CRISPResso," Nat Biotechnol, 2016, 34(7):695-697.
Polstein et al., "A light-inducible CRISPR-Cas9 system for control of endogenous gene activation," Nature Chemical Biology, 2015, 11: 198-200.
Ponting et al., "Evolution and functions of long noncoding RNAs," Cell, 2009, 136(4): 629-641.
Povero et al., "Lipid-induced toxicity stimulates hepatocytes to release angiogenic microparticles that require Vanin-1 for uptake by endothelial cells," Sci Signal, 2013, 6(296): ra88.
Powell et al., "A Prader-Willi locus IncRNA cloud modulates diurnal genes and energy expenditure," Hum Molec Genet, 2013, 22: 4318-4328.
Prykhozhij et al., "CRISPR MultiTargeter: A Web Tool to Find Common and Unique CRISPR Single Guide RNA Targets in a Set of Similar Sequences," PLoS One, 2015, 10(3): e0119372.
Puccini et al., "Colorectal cancer: epigenetic alterations and their clinical implications", Biochim Biophys Acta, 2017, vol. 1868, No. 2, pp. 439-448.
Rackham et al., "A predictive computational framework for direct reprogramming between human cell types," Nature Genetics, 2016, 48: 331-335.
Raeburn et al., "Techniques for drug delivery to the airways, and the assessment of lung function in animal models," J. Pharmacol. Toxicol. Meth., 1992, 27:143-159.
Rajagopal et al., "High-throughput mapping of regulatory DNA," Nat. Biotechnol, 2016, 34: 167-174.
Ramachandran et al., "Nitric Oxide Signaling Pathway in Duchenne Muscular Dystrophy Mice: Upregulation of L-arginine Transport," Biochem. J., 2012, 449: 133-142.
Ran et al., "Genome engineering using the CRISPR-Cas9 system," Nature Protocols, 2013, 8(11): 2281-2308.
Rao et al., "Engineering human pluripotent stem cells into a functional skeletal muscle tissue," Nat Commun, 2018, 9: 126.

(56) References Cited

OTHER PUBLICATIONS

Ratcliff et al., "A novel single-molecule study to determine protein-protein-protein association constants," Journal of the American Chemical Society, 2001, 123(24): 5632-5635.
Rauscher et al., "GenomeCRISPR—a database for high-throughput CRISPR/Cas9 screens," Nucleic Acids Res, 2017, 45: D679-D686.
Rheinbay et al., "Analyses of non-coding somatic drivers in 2,658 cancer whole genomes," Nature, 2020, 578: 102-111.
Rhodes et al., "G-quadruplexes and their regulatory roles in biology," Nucleic Acids Res, 2015, 43: 8627-8637.
Richter et al., "Phage-assisted evolution of an adenine base editor with improved Cas domain compatibility and activity, " Nat Biotechnol, Jul. 2020, 38(7): 883-891.
Riordan et al., "Application of CRISPR/Cas9 for biomedical discoveries," Cell & Bioscience, 2015, 5(1):11 pages.
Rmilah et al., "Understanding the marvels behind liver regeneration," Wiley Interdiscip Rev Dev Biol., 2019, 8(3): e340.
Roadmap Epigenomics Consortium, "Integrative analysis of 111 reference human epigenomes," Nature, 2015, 518: 317-330.
Rodriguez et al., "Clustering by fast search and find of density peaks," Science, 2014, 344(6191): 1492-1496.
Roudaut et al., "Restriction of calpain3 expression to the skeletal muscle prevents cardiac toxicity and corrects pathology in a murine model of limb-girdle muscular dystrophy," Circulation, 2013, 128: 1094-1104.
Russa et al. "The New State of the Art: Cas9 for Gene Activation and Repression," Molecular and Cellular Biology, 2015, 35(22):3800-3809.
Rutkauskas et al., "Directional R-loop formation by the CRISPR-Cas surveillance complex cascade provides efficient off-target site rejection," Cell reports, 2015, 10, 1534-1543.
Sacco et al., "Short Telomeres and Stem Cell Exhaustion Model Duchenne Muscular Dystrophy in mdx/mTR Mice," Cell, 2010, 143: 1059-1071.
Sagal et al., "Proneural transcription factor Atoh1 drives highly efficient differentiation of human pluripotent stem cells into dopaminergic neurons," Stem Cells Transl Med, 2014, 3: 888-898.
Sahoo et al., "Prader-Willi phenotype caused by paternal deficiency for the HBII-85 C/D box small nucleolar RNA cluster," Nat Genet, 2008, 40: 719-721.
Saitoh et al., "Parent-of-Origin Histone Acetylation and Reactivation of a Key Imprinted Gene Locus in Prader-Willi Syndrome," Am J Hum Genet, 2000, 66: 1958-1962.
Salmon et al., "Production and titration of lentiviral vectors," Curr Protoc Hum Genet, 2007, Chapter 12, Unit 12.10, Supplement 54, 24 pages.
Salva et al., "Design of tissue-specific regulatory cassettes for high-level rAAV-mediated expression in skeletal and cardiac muscle," Mol. Ther., 2007, 15:320-329.
Sambasivan et al., "Embryonic founders of adult muscle stem cells are primed by the determination gene Mrf4," Developmental Biology, 2013, 381: 241-255.
Sanghvi et al., "Heterocyclic Base Modifications in Nucleic Acids and their Applications in Antisense Oligonucleotides," 1993, Antisense Research and Applications, Chapter 15, pp. 274-285.
Sanjana et al., "High-resolution interrogation of functional elements in the noncoding genome," Science, 2016, 353: 1545-1549.
Sanson et al., "Optimized libraries for CRISPR-Cas9 genetic screens with multiple modalities," Nat Commun, 2018, 9: 5416.
Santalucia et al., "Improved nearest-neighbor parameters for predicting DNA duplex stability," Biochemistry, 1996, 35(11): 3555-3562.
Schaaf et al., "Truncating mutations of MAGEL2 cause Prader-Willi phenotypes and autism," Nat Genet, 2013, 45(11): 1405-1408.
Schifrut et al., "Genome-wide CRISPR Screens in Primary Human T Cells Reveal Key Regulators of Immune Function," Cell, 2018, 175(7): 1958-1971.e15.
Schmidt et al., "GenomeRNAi: a database for cell-based and in vivo RNAi phenotypes, 2013 update," Nucleic Acids Res, 2013, 41: D1021-6.
Schmittgen et al., "Analyzing real-time PCR data by the comparative CT method," Nature Protocols, 2008, 3(6): 1101-1108.
Schreck et al., "DNA hairpins destabilize duplexes primarily by promoting melting rather than by inhibiting hybridization," Nucleic Acids Research, 2015, 43(13): 6181-6190.
Schreck et al., "DNA hairpins primarily promote duplex melting rather than inhibiting hybridization," 2014, arXiv preprint arXiv:1408.4401.
Schultz et al., "SETDBI: a novel KAP-I-associated histone H3, lysine 9-specific methyltransferase that contributes to HPI-mediated silencing of euchromatic genes by KRAB zinc-finger proteins," Genes & Development, 2002, 16: 919-932.
Segal and Meckler, "Genome Engineering at the Dawn of the Golden Age," Annu. Rev. Genomics Hum. Genet., 2013, 14: 135-158.
Semenova et al., "The Cas6e ribonuclease is not required for interference and adaptation by the *E. coli* type I-E CRISPR-Cas system," Nucleic Acids Res, 2015, 43(12):6049-61.
Sengupta et al., "Super-Enhancer-Driven Transcriptional Dependencies in Cancer," Trends Cancer Res, 2017, 3: 269-281.
Sentmanat et al., "A Survey of Validation Strategies for CRISPR-Cas9 Editing," Scientific Reports, 2018, 8: 888.
Sequence alignment: SEQ ID No. 102920 (2019).
Sequence alignment: SEQ ID No. 102921 (2019).
Sequence alignment: SEQ ID No. 103735 (2019).
Sequence alignment: SEQ ID No. 103736 (2019).
Serra et al., "Predicting thermodynamic properties of RNA," Methods in Enzymology, 1995, 259: 242-261.
Shalem et al., "Genome-scale CRISPR-Cas9 knockout screening in human cells," Science, 2014, 343: 84-87.
Sharma et al., "In vivo genome editing of the albumin locus as a platform for protein replacement therapy," Blood, 2015, 126: 1777-1784.
Shea et al., "Synthesis, hybridization properties and antiviral activity of lipid-oligodeoxynucleotide conjugates," Nucl. Acids Res, 1990, 18: 3777-3783.
Shelton et al., "Derivation and Expansion of PAX7-Positive Muscle Progenitors from Human and Mouse Embryonic Stem Cells," Stem Cell Rep, 2014, 3: 516-529.
Shen et al., "Combinatorial CRISPR-Cas9 screens for de novo mapping of genetic interactions," Nat Methods, 2017, 14: 573-576.
Shen et al., "Engraftment of a galactose receptor footprint onto adeno-associated viral capsids improves transduction efficiency," J Biol Chem, 2013, 288(40): 28814-28823.
Shin et al., "Microdystrophin Ameliorates Muscular Dystrophy in the Canine Model of Duchenne Muscular Dystrophy," Mol. Ther., 2013, 21: 750-757.
Shlyakhtenko et al., "Silatrane-based surface chemistry for immobilization of DNA, protein-DNA complexes and other biological materials," Ultramicroscopy, 2003, 97: 279-287.
Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.
Simpson, "Contacts between *Escherichia coli* RNA polymerase and thymines in the lac UV5 promoter," Proc. Natl. Acad. Sci. USA, 1979, 76: 3233-3237.
Singh et al. "Protein Engineering Approaches in the Post-Genomic Era," Current Protein and Peptide Science, 2017, 18: 1-11.
Skene et al., "Genetic identification of brain cell types underlying schizophrenia," Nat Genet, 2018, 50: 825-833.
Soejima et al., "Imprinting centers, chromatin structure, and disease," J Cell Biochem, 2005, 95(2): 226-233.
Song et al., "Non-immunogenic utrophin gene therapy for the treatment of muscular dystrophy animal models," Nature Medicine, 2019, 25(10): 1505-1511.
Stanton et al., "Chemical modification study of antisense gapmers," Nucleic Acid Ther., 2012, 22(5): 344-359.
Stemmer et al., "CCTop: An Intuitive, Flexible and Reliable CRISPR/Cas9 Target Prediction Tool," PLoS One, 2015, 10(4): e0124633.
Stephens, "False discovery rates: a new deal," Biostatistics, 2017, 18: 275-294.

(56) References Cited

OTHER PUBLICATIONS

Stepper et al., "Efficient targeted DNA methylation with chimeric dCas9-Dnmt3a-Dnmt3L methyltransferase," Nucleic Acids Res., 2017, 45(4): 1703-1713.
Stolzenburg et al., "Targeted silencing of the oncogenic transcription factor SOX2 in breast cancer," Nucleic Acids Res., 2012, 40(14): 6725-6740.
Stuelsatz et al., "A Contemporary Atlas of the Mouse Diaphragm: Myogenicity, Vascularity, and the Pax3 Connection" J Histochem Cytochem, 2012, 60(9): 638-657.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sui et al., "A DNA vector-based RNAi technology to suppress gene expression in mammalian cells," PNAS, 2002, 99(8): 5515-5520.
Sun et al., "Phage mutations in response to CRISPR diversification in a bacterial population," Environmental microbiology, 2013, 15(2): 463-470.
Sur et al., "The role of enhancers in cancer," Nat. Rev. Cancer., 2016, 16: 483-493.
Sutcliffe et al., "Deletions of a differentially methylated CpG island at the SNRPN gene define a putative imprinting control region," Nature Genetics, 1994, 8: 52-58.
Suzuki et al., "In vivo genome editing via CRISPR/Cas9 mediated homology-independent targeted integration," Nature, 2016, 540: 144-149.
Svinarchuk et al., "Inhibition of HIV proliferation in MT-4 cells by antisense oligonucleotide conjugated to lipophilic groups," Biochimie, 1993, 75: 49-54.
Szczelkun et al., "Direct observation of R-loop formation by single RNA-guided Cas9 and Cascade effector complexes," Proceedings of the National Academy of Sciences, 2014, 6 pages.
Szostak, "in Vitro Genes," TIBS, 1993, 17: 89-93.
Szymczak et al., "Correction of multi-gene deficiency in vivo using a single 'self-cleaving' 2A peptide-based retroviral vector," Nature Biotechnology, 2004, 22(5): 589-594.
Takahashi et al., "A decade of transcription factor-mediated reprogramming to pluripotency," Nature Reviews, 2016, 17: 183-193.
Takahashi et al., "Induction of pluripotent stem cells from mouse embryonic and adult fibroblast cultures by defined factors," Cell, 2006, 126: 663-676.
Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.
Tam et al., "Benefits and limitations of genome-wide association studies," Nat. Rev. Genet., 2019, 20: 467-484.
Tan et al., "Efficient derivation of lateral plate and paraxial mesoderm subtypes from human embryonic stem cells through GSKi-mediated differentiation," Stem Cells Dev, 2013, 22: 1893-1906.
Tan et al., "Rationally engineered *Staphylococcus aureus* Cas9 nucleases with high genome-wide specificity," Proc. Nat. Acad. Sci. USA, 2019, 116(46): 20969-20976.
Teratani-Ota et al., "Induction of specific neuron types by overexpression of single transcription factors," In Vitro Cell Dev Biol Anim, 2016, 52(9): 961-973.
Theodorou et al., "A high throughput embryonic stem cell screen identifies Oct-2 as a bifunctional regulator of neuronal differentiation," Genes Dev, 2009, 23: 575-588.
Thorgeirsson et al., "A variant associated with nicotine dependence, lung cancer and peripheral arterial disease," Nature, 2008, 452: 638-642.
Tian et al., "CRISPR Interference-Based Platform for Multimodal Genetic Screens in Human iPSC-Derived Neurons," Neuron, 2019, 104: 239-255 e212.
Tinsley et al., "Amelioration of the dystrophic phenotype of mdx mice using a truncated utrophin transgene," Nature, 1996, 384(6607): 349-353.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.
Tsai et al., "GUIDE-seq enables genome-wide profiling of off-target cleavage by CRISPR-Cas nucleases," Nature biotechnology, 2015, 33(2): 187-197.
Tsuchiya et al., "The "Spanning Protocol": A new DNA extraction method for efficient single-cell genetic diagnosis," Journal of Assisted Reproduction Genetics, 2005, 22(11-12):407-14.
Tsunemoto et al., "Diverse reprogramming codes for neuronal identity," Nature, 2018, 557: 375-380.
Tycko et al., "Screening *S. aureus* CRISPR-Cas9 Paired Guide RNAs for Efficient Targeted Deletion in Duchenne Muscular Dystrophy," Editas, Poster presented on May 5, 2016.
Tyle, "Iontophoretic Devices for Drug Delivery," Pharm. Res., 1986, 3: 318-326.
U.S. Appl. No. 17/636,750, filed Feb. 18, 2022, by Gersbach et al.
U.S. Appl. No. 17/636,754, filed Feb. 18, 2022, by Gersbach et al.
Urrutia, "KRAB-containing zinc-finger repressor proteins," Genome Biol., 2003, 4(10): 231.
Usman et al., "Catalytic RNA (Ribozymes) as Drugs," Ann. Rep. Med. Chem., 1995, Chapter 30, pp. 285-294.
Van Arensbergen et al., "Genome-wide mapping autonomous promoter activity in human cells," Nature Biotechnology, 2017, 35(2): 145-153.
Van der Oost et al., "Unravelling the structural and mechanistic basis of CRISPR-Cas systems," Nature Reviews Microbiology, 2014, 12: 479-492.
Van Deutekom et al., "Advances in Duchenne muscular dystrophy gene therapy," Nat. Rev. Genet., 2003, 4: 774-783.
Vaquerizas et al., "A census of human transcription factors: function, expression and evolution," Nat Rev Genet, 2009, 10: 252-263.
Veltrop et al., "A dystrophic Duchenne mouse model for testing human antisense oligonucleotides," PLoS One, 2018, 13(2): e0193289, 18 pages.
Verkhusha et al., "GFP-like flourescent proteins and chromoproteins of the class Anthozoa," Protein Structures: Kaleidoscope of Structural Properties and Functions, 2003, 405-439.
Vierbuchen et al., "Direct lineage conversions: unnatural but useful? ," Nat Biotechnol, 2011, 29: 892-907.
Vierbuchen et al., "Molecular roadblocks for cellular reprogramming," Mol Cell, 2012, 47: 827- 838.
Vorobyov et al., "Expression of two protein isoforms of PAX7 is controlled by competing cleavage-polyadenylation and splicing," Gene, 2004, 342: 107-112.
Wada et al., "Codon usage tabulated from the GenBank genetic sequence data," Nucl. Acids Res., 1990, 18: 2367-2411.
Waddell et al., "DIk1 Is Necessary for Proper Skeletal Muscle Development and Regeneration," PLoS One, 2010, 5(11): e15055.
Waldrop et al., "Update in Duchenne and Becker muscular dystrophy," Current Opinion in Neurology, 2019, 32: 722-727.
Wang et al., "Adeno-associated virus serotype 8 efficiently delivers genes to muscle and heart," Nat. Biotechnol., 2005, 23: 321-328.
Wang et al., "Construction and analysis of compact muscle-specific promoters for AAV vectors," Gene Ther, 2008, 15: 1489-1499.
Wang et al., "Cyclohexene Nucleic Acids (CeNA): Serum Stable Oligonucleotides that Activate RNase H and Increase Duplex Stability with Complementary Rna," J. Am. Chem. Soc., 2000, 122: 8595-8602.
Wang et al., "Gene Essentiality Profiling Reveals Gene Networks and Synthetic Lethal Interactions with Oncogenic Ras," Cell, 2017, 168: 890-903.e15.
Wang et al., "Genetic screens in human cells using the CRISPR-Cas9 system," Science, 2014, 343: 80-84.
Wang et al., "Identification and characterization of essential genes in the human genome," Science, 2015, 350: 1096-1101.
Wang et al., "Potential of Epigenetic Therapy for Pader-Willi Syndrome," Trends in Pharmacological Sciences, 2019, 40(9): 605-608.

(56) References Cited

OTHER PUBLICATIONS

Wang et al., "Systemic human minidystrophin gene transfer improves functions and life span of dystrophin and dystrophin/utrophin-deficient mice," J. Orthop. Res., 2009, 27: 421-426.
Wang et al., "Unbiased detection of off-target cleavage by CRISPR-Cas9 and TALENs using integrase-defective lentiviral vectors," Nature biotechnology, 2015, 33(2): 175-8.
Wapinski et al., "Hierarchical mechanisms for direct reprogramming of fibroblasts to neurons," Cell, 2013, 155: 621-635.
Watkins et al., "Thermodynamic contributions of single internal rA.dA, rC.dC, rG.dG and rU.dT mismatches in RNA/DNA duplexes," Nucleic acids research, 2011, 39(5): 1894-1902.
Wei et al., "Targeting Regnase-1 programs long-lived effector T cells for cancer therapy," Nature, 2019, 576(7787): 471-476.
Weltner et al., "Human pluripotent reprogramming with CRISPR activators," Nat Commun Lond, 2018, 9: 1-12.
Westendorp et al., "E2F7 represses a network of oscillating cell cycle genes to control S-phase progression," Nucleic Acids Res, 2012, 40: 3511-3523.
Wherry, "T cell exhaustion," Nat. Immunology, 2011, 12: 492-499.
Wienert et al., "Editing the genome to introduce a beneficial naturally occurring mutation associated with increased fetal globin," Nat Commun 6, 2015, 7085.
Wiggins et al., "High flexibility of DNA on short length scales probed by atomic force microscopy," Nature nanotechnology, 2006, 1(2): 137-141.
Wilbie et al., "Delivery Aspects of CRISPR/Cas for in Vivo Genome Editing," Acc Chem Res, 2019, 52(6): 1555-1564.
Wiles et al., "CRISPR-Cas9_mediated genome editing and guide RNA design," Mammalian Genome, 2015, 26(9): 501-510.
Willmann et al., "Mammalian animal models for Duchenne muscular dystrophy," Neuromuscular Disorders, 2009, 19(4): 241-249.
Wood, "Neuromuscular disease: CRISPR/Cas9 gene-editing platform corrects mutations associated with Duchenne muscular dystrophy," Nature Reviews Neurology, 2015, 11(4):184.
Wu et al., "A Myogenic Double-Reporter Human Pluripotent Stem Cell Line Allows Prospective Isolation of Skeletal Muscle Progenitors," Cell Rep, 2018, 25: 1966-1981.e4.
Wu et al., "Induction of anion exchanger-1 translation and its opposite roles in the carcinogenesis of gastric cancer cells and differentiation of K562 cells," Oncogene, 2010, 29: 1987-1996.
Wu et al., "Unusual Processing Generates SPA LncRNAs that Sequester Multiple RNA Binding Proteins," Mol Cell, 2016, 64: 534-548.
Wu et al., "Genome-wide binding of the CRISPR endonuclease Cas9 in mammalian cells," Nat Biotechnol, 2014, 32: 670-676.
Wüst et al., "Metabolic Maturation during Muscle Stem Cell Differentiation Is Achieved by miR-1/133a-Mediated Inhibition of the Dlk1-Dio3 Mega Gene Cluster," Cell Metab, 2018, 27: 1026-1039.e6.
Wylie et al., "Distinct transcriptomes define rostral and caudal serotonin neurons," J Neurosci, 2010, 30: 670-684.
Xie et al., "Multiplexed Engineering and Analysis of Combinatorial Enhancer Activity in Single Cells," Mol. Cell, 2017, 66: 285-299. e5.
Xie et al., "sgRNAcas9: a software package for designing CRISPR sgRNA and evaluating potential off-target cleavage sites," PLoS One, 2014, 9(6): e100448.
Xu et al., "CRISPR-mediated Genome Editing Restores Dystrophin Expression and Function in mdx Mice," Molecular Therapy: The Journal of the American Society of Gene Therapy, 2016, 24(3): 564-569.
Xu et al., "Direct lineage reprogramming: strategies, mechanisms, and applications," Cell Stem Cell, 2015, 16: 119-134.
Xu et al., "Human Satellite Cell Transplantation and Regeneration from Diverse Skeletal Muscles," Stem Cell Rep, 2015, 5: 419-434.
Xu et al., "Recent advances in neuroepigenetic editing," Curr Opin Neurobiol, 2019, 59: 26-33.
Xue et al., "Synthetic mRNAs Drive Highly Efficient iPS Cell Differentiation to Dopaminergic Neurons," Stem Cells Transl Med, 2019, 8: 112-123.
Yang et al., "Determination of protein-DNA binding constants and specificities from statistical analyses of single molecules: MutS-DNA interactions," Nucleic acids research, 2005, 33(13): 4322-4334.
Yang et al., "Generation of pure GABAergic neurons by transcription factor programming," Nat Methods, 2017, 14: 621-628.
Yin et al., "Long noncoding RNAs with snoRNA ends," Mol Cell, 2012, 48(2): 219-230.
Yin et al., "Programming biomolecular self-assembly pathways," Nature, 2008, 451(7176): 318- 323.
You et al., "Design of LNA probes that improve mismatch discrimination," Nuc. Acids. Res., 2006, 34(8): e60.
Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.
Young et al., "Creation of a Novel Humanized Dystrophic Mouse Model of Duchenne Muscular Dystrophy and Application of a CRISPR/Cas9 Gene Editing Therapy," Journal of Neuronuscular Diseases, 2017, 4(2): 139-145.
Younossi et al., "Epidemiology of chronic liver diseases in the USA in the past three decades," Gut, 2020, 69(3): 564-568.
Yu et al., "RNA interference by expression of short-interfering RNAs and hairpin RNAs in mammalian cells," PNAS, 2002, 99(9): 6047-6052.
Zetsche et al., "Cpf1 Is a Single RNA-Guided Endonuclease of a Class 2 CRISPR-Cas System," Cell, 2015, 163(3):759-71.
Zhang et al., "Comprehensive Structure-Function Study of Neurogenin3 Disease-Causing Alleles during Human Pancreas and Intestinal Organoid Development," Dev Cell, 2019, 50(3): 367-380.e7.
Zhang et al., "Efficient precise knockin with a double cute HDR donor after CRISPR/Cas9-mediated double-stranded DNA cleavage," Genome Biol, 2017 18(35): 18 pages.
Zhang et al., "Gene activation in human cells using CRISPR/Cpf1-p300 and CRISPR/Cpf1-SunTag systems," Protein Cell, 2018, 9: 380-383.
Zhang et al., "Myoediting: Toward Prevention of Muscular Dystrophy by Therapeutic Genome Editing," Physiological Reviews, 2018, 98(3): 1205-1240.
Zhang et al., "Propagated Perturbations from a Peripheral Mutation Show Interactions Supporting WW Domain Thermostability," Structure, 2018, 26: 1474-1485.
Zhang et al., "Rapid single-step induction of functional neurons from human pluripotent stem cells," Neuron, 2013, 78: 785-798.
Zhao et al., "High-efficiency transfection of primary human and mouse T lymphocytes using RNA electroporation," Mol. Ther., 2006, 13: 151-159.
Zhao et al., "Intracellular delivery of artificial transcription factors fused to the protein transduction domain of HIV-1 Tat," Protein Expr Purif, 2013, 90(1): 27-33.
Zhao et al., "The LIM-homeobox gene Lhx8 is required for the development of many cholinergic neurons in the mouse forebrain," Proc Natl Acad Sci U S A, 2003, 100: 9005-9010.
Zhou et al., "Haploinsufficiency of utrophin gene worsens skeletal muscle inflammation and fibrosis in mdx mice," Journal of the Neurological Sciences, 2008, 264(1): 106-111.
Zhu et al., "The role of histone deacetylase 7 (HDAC7) in cancer cell proliferation: regulation on c-Myc," J. Mol. Med, 2011, 89: 279-289.
Arechavala-Gomeza et al., "Comparative analysis of antisense oligonucleotide sequences for targeted skipping of exon 51 during dystrophin pre-mRNA splicing in human muscle," Human Gene Therapy, 2007, 18: 798-810.
Carroll, "A CRISPR approach to gene targeting," Molecular Therapy, 2012, 20: 1658-1660.
NCBI Reference Sequence XM011532698.1 (2015).
NCBI Reference Sequence NM_004020.2 (2010).
NCBI Reference Sequence NG_028016.2 (2013).
United States Patent Office Notice of Allowance for U.S. Appl. No. 16/890,232 dated Sep. 28, 2022 (8 pages).

(56) References Cited

OTHER PUBLICATIONS

United States Patent Office Action for U.S. Appl. No. 15/789,348 dated Sep. 15, 2022 (21 pages).
United States Patent Office Action for U.S. Appl. No. 16/858,689 dated Oct. 19, 2022 (11 pages).
United States Patent Office Notice of Allowance for U.S. Appl. No. 16/890,232 dated Feb. 2, 2023 (8 pages).
United States Patent Office Notice of Allowance for U.S. Appl. No. 15/789,348 dated Feb. 15, 2023 (11 Pages).
Japanese Patent Office Action for Application No. 2019-200973 dated Nov. 2, 2022 (9 pages, English translation included).
Canadian Patent Office Action for Application No. 2,914,519 dated Jan. 31, 2023 (5 pages).
Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.
Min et al., "CRISPR Correction of Duchene Muscular Dystrophy Exon 44 Deletion Mutations in Mice and Human Cells," Science Advances, 2019, 5: eaav4324.
Robinson-Hamm et al., "Gene therapies that restore dystrophin expression for the treatment of Duchenne muscular dystrophy," Human Genetics, 2016, 135(9): 1029-1040.
United States Patent Office Action for U.S. Appl. No. 16/858,689 dated Mar. 23, 2023 (10 pages).
Japanese Patent Office Action for Application No. 2022-052186 dated Mar. 15, 2023 (4 pages, English translation included).
Yu et al., "Dystrophin-deficient large animal models: translational research and exon skipping," Am J Transl Res, 2015, 7(8): 1314-1331.
Adikusuma et al., "Versatile single-step-assembly CRISPR/Cas9 vectors for dual gRNA expression," 2017, 12(12): e0187236.
Carcagno et al., "Neurogenin3 Restricts Serotonergic Neuron Differentiation to the Hindbrain," The Journal of Neuroscience, 2014, 34(46): 15223-15233.
Kalsner et al., "Prader-Willi, Angelman, and 15q11-q13 Duplication Syndromes," Pediatric Clinics of North America United States, 2015, 62(3): 587-606.
Ohta et al., "Imprinting-Mutation Mechanisms in Prader-Willi Syndrome," The American Journal of Human Genetics, 1999, 64(2): 397-413.
Yang et al., "A dual AAV system enables the Cas9-mediated correction of a metabolic liver disease in newborn mice," Nature Biotechnology, 2016, 34(3): 334-338.
United States Patent Office Action for U.S. Appl. No. 16/927,679 dated Sep. 21, 2023 (6 pages).
U.S. Appl. No. 18/279,996, filed Sep. 1, 2023.
U.S. Appl. No. 18/415,321, filed Jan. 17, 2024.
U.S. Appl. No. 18/405,995, filed Jan. 5, 2024.
U.S. Appl. No. 18/036,862, filed Jan. 25, 2024.
U.S. Appl. No. 18/180,718, filed Feb. 22, 2024.
Trinklein et al., "Identification and functional analysis of human transcriptional promoters," Genome Research, 2003, 13(2): 308-312.
Park et al., "Cas-Designer: a web-based tool for choice of CRISPR-Cas9 target sites," Bioinformatics, 2015, 31(24): 4014-4016.
Shen et al., "Massively parallel cis-regulatory analysis in the mammalian central nervous system," Genome Research, 2015, 26(2): 238-255.
Chhatwal et al., "Identification of cell-type-specific promoters within the brain using lentiviral vectors," Gene Therapy, 2007, 14(7): 575-583.
Chinese Patent Office Action for Application No. 202111496852.0 dated Aug. 29, 2023 (18 pages, English translation included).
United States Patent Office Notice of Allowance for U.S. Appl. No. 15/789,348 dated Jun. 15, 2023 (8 Pages).
United States Patent Office Notice of Allowance for U.S. Appl. No. 16/890,232 dated Jun. 22, 2023 (7 pages).
Abaandou et al., "Affecting HEK293 Cell Growth and Production Performance by Modifying the Expression of Specific Genes," Cells, 2021, 10: 1667, 21 pages.
Alerasool et al., "An efficient KRAB domain for CRISPRi applications in human cells," Nat Methods, 2020, 17: 1093-1096.
Alonso-Camino et al., "CARbodies: Human Antibodies Against Cell Surface Tumor Antigens Selected From Repertoires Displayed on T Cell Chimeric Antigen Receptors," Mol Ther Nucl Acids, 2013, 2: e93, 11 pages.
Azuma et al., "Robust expansion of human hepatocytes in Fah-/-/Rag2-/-/Il2rg-/- mice" Nat Biotechnol., 2007, 25(8): 903-910.
Bhakta et al., "The generation of zinc finger proteins by modular assembly," Methods Mol. Biol., 2010, 649: 3-30.
Bloomfield, "Quasi-Elastic Light Scattering Applications in Biochemistry and Biology," Ann. Rev. Biophys. Bioeng., 1981, 10: 421-450.
Boris-Lawrie et al., "Recent advances in retrovirus vector technology," Cur. Opin. Genet. Develop., 1993, 3: 102-109.
Bouhairie et al., "Familial hypercholesterolemia," Cardiol. Clin., 2015, 33(2): 169-179.
Braliou et al., "The v-ErbA oncoprotein quenches the activity of an erythroid-specific enhancer," Oncogene, 2001, 20(7): 775-87.
Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.
Broude et al., "p21 (CDKN1A) is a negative regulator of p53 stability," Cell Cycle, 2007, 6(12): 1468-1471.
Buckingham, M. et al. "The role of Pax genes in the development of tissues and organs: Pax3 and Pax7 regulate muscle progenitor cell functions." Annu. Rev. Cell Dev. Biol. 23 (2007): 645-673.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.
Cano-Rodriguez et al., "Epigenetic Editing: On the Verge of Reprogramming Gene Expression at Will," Curr Genet Med Rep, 2016, 4: 170-179.
Carlens et al., "Ex vivo T lymphocyte expansion for retroviral transduction: influence of serum-free media on variations in cell expansion rates and lymphocyte subset distribution," Exp Hematol, 2000, 28(10): 1137-46.
Cavalieri et al., "Human T lymphocytes transduced by lentiviral vectors in the absence of TCR activation maintain an intact immune competence," Blood, 2003, 102(2): 497-505.
Aubert et al. "553. AAV-Mediated Delivery of HSV-Specific Homing Endonucleases To Neurons of the Trigeminal Ganglia for HSV-1 Inhibition." Molecular Therapy 22 (2014).
Chen et al., "Fusion protein linkers: property, design and functionality," Adv. Drug Deliv. Rev., 2013, 65(10): 1357-1369.
Chicaybam et al., "An efficient low cost method for gene transfer to T lymphocytes," PLoS One, 2013, 8(3): e60298, 11 pages.
Chylinski et al., "The tracrRNA and Cas9 families of type II CRISPR-Cas immunity systems," RNA Biol., 2013, 10(5): 726-737.
Cooper et al., "T-cell clones can be rendered specific for CD19: toward the selective augmentation of the graft-versus-B-lineage leukemia effect," Blood, 2003, 101(4): 1637-1644.
Cortes-Mancera et al., "Gene-Targeted DNA Methylation: Towards Long-Lasting Reprogramming of Gene Expression?" Adv Exp Med Biol., 2022, 1389: 515-533.
Das et al., "Tet-On Systems For Doxycycline-inducible Gene Expression," Current Gene Therapy, 2016, 16: 156-167.
Defesche et al., "Familial hypercholesterolaemia," Nat. Rev. Dis. Primers, 2017, 3: 17093, 20 pages.
Deng et al., "Highly sensitive electrochemical methyltransferase activity assay," Anal Chem., 2014, 86: 2117-2123.
Fuks, "DNA methylation and histone modifications: teaming up to silence genes," Current Opinion in Genetics & Development, 2005, 15(5): 490-495.
Gersbach et al., "Synthetic zinc finger proteins: the advent of targeted gene regulation and genome modification technologies," Acc. Chem. Res., 2014, 47(8): 2309-18.

(56) References Cited

OTHER PUBLICATIONS

Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.
Gowher et al., "Molecular enzymology of the catalytic domains of the Dnmt3a and Dnmt3b DNA methyltransferases," J. Biol. Chem., 2002, 277(23): 20409-20414.
Hochstrasser et al., "CasA mediates Cas3-catalyzed target degradation during CRISPR RNA-guided interference," PNAS, 2014, 111(18): 6618-23.
Huang et al., "Ch 9: DNA transposons for modification of human primary T lymphocytes," Methods Mol Biol, 2009, 506: 115-126.
Jia et al., "Structure of Dnmt3a bound to Dnmt3L suggests a model for de novo DNA methylation," Nature, 2007, 449(7159): 248-251.
Johnston, "Biolistic transformation: microbes to mice," Nature, 1990, 346: 776-777.
Kao et al., "Ectopic DNMT3L triggers assembly of a repressive complex for retroviral silencing in somatic cells," J Virol., 2014, 88(18): 10680-95.
Kim et al., "Zinc-fingers and homeoboxes 1 (ZHX1) binds DNA methyltransferase (Dnmt) 3B to enhance DNMT3B-mediated transcriptional repression," Biochemical and Biophysical Research Communications, 2007, 355(2): 318-323.
Koste et al., "T-cell receptor transfer into human T cells with ecotropic retroviral vectors," Gene Ther, 2014, 21(5): 533-538.
Lagace, "PCSK9 and LDLR degradation: regulatory mechanisms in circulation and in cells," Curr. Opin. Lipidol., 2014, 25(5): 387-393.
Lei et al., "Targeted DNA methylation in vivo using an engineered dCas9-MQ1 fusion protein," Nat. Commun, 2017, 8: 16026, 10 pages.
Li et al., "Development of fluorescent methods for DNA methyltransferase assay," Methods Appl. Fluoresc., 2017, 5: 012002, 8 pages.
Li et al., "The histone methyltransferase SETDB1 and the DNA methyltransferase DNMT3A interact directly and localize to promoters silenced in cancer cells," J. Biol. Chem., 2006, 281(28): 19489-19500.
Liu et al., "Design of polydactyl zinc-finger proteins for unique addressing within complex genomes," PNAS, 1997, 94(11): 5525-5530.
Ma et al., "Pol III Promoters to Express Small RNAs: Delineation of Transcription Initiation," Molecular Therapy-Nucleic Acids, 2014, 3: e161, 11 pages.
Makarova et al., "Annotation and Classification of CRISPR-Cas Systems," Methods Mol. Biol, 2015, 1311: 47-75.
Manuri et al., "piggyBac transposon/transposase system to generate CD19-specific T cells for the treatment of B-lineage malignancies," Hum Gene Ther, 2010, 21(4): 427-437.
Mavrothalassitis et al., "Proteins of the ETS family with transcriptional repressor activity," Oncogene, 2000, 19: 6524-6532.
Miller et al., "Improved retroviral vectors for gene transfer and expression," BioTechniques, 1989, 7(9): 980-990.
Miller, "Retrovirus packaging cells," Human Gene Therapy, 1990, 1: 5-14.
Milone et al., "Clinical use of lentiviral vectors," Leukemia, 2018, 32(7): 1529-1541.
Mok et al., "Stabilized plasmid-lipid particles: factors influencing plasmid entrapment and transfection properties," Biochimica et Biophysica Acta, 1999, 1419(2): 137-150.
Moon et al., "Recent advances in the CRISPR genome editing tool set," Exp. Mol. Med., 2019, 51(11): 130, 11 pages.
Moussa et al., "Here to stay: Writing lasting epigenetic memories," Cell, 2021, 184(9): 2281-2283.
Murphy et al., "The Transcriptional Repressive Activity of KRAB Zinc Finger Proteins Does Not Correlate with Their Ability to Recruit TRIM28," PLoS One, 2016, 11(9): e0163555, 19 pages.
O'Geen et al., "Determinants of heritable gene silencing for KRAB-dCas9 + DNMT3 and Ezh2-dCas9 + DNMT3 hit-and-run epigenome editing," Nucleic Acids Res, 2022, 50(6): 3239-3253.
Orth et al., "Structural basis of gene regulation by the tetracycline inducible Tet repressor-operator system," natural structural biology, 2000, 7(3): 215-219.
Park et al., "Treating cancer with genetically engineered T cells," Trends Biotechnol, 2011, 29(11): 550-557.
Peterson et al., "PCSK9 function and physiology," J. Lipid Res., 2008, 49(6): 1152-1156.
Pickar-Oliver et al., "The next generation of CRISPR-Cas technologies and applications," Nature Reviews Molecular Cell Biology, 2019, 20(8): 490-507.
Poh et al., "DNA Methyltransferase Activity Assays: Advances and Challenges," Theranostics, 2016, 6(3): 369-391.
Poirier et al., "The proprotein convertase PCSK9 induces the degradation of low density lipoprotein receptor (LDLR) and its closest family members VLDLR and ApoER2" J. Biol. Chem., 2008, 283: 2363-2372.
Policarpi et al., "Epigenetic editing: Dissecting chromatin function in context," Bioessays, 2021, 43(5): e2000316, 16 pages.
Saha et al., "The NIH Somatic Cell Genome Editing program," Nature, 2021, 592: 195-204.
Scarpa et al., "Characterization of recombinant helper retroviruses from moloney-based vectors in ecotropic and amphotropic packaging cell lines," Virology, 1991, 180: 849-852.
Schellenberger et al., "A recombinant polypeptide extends the in vivo half-life of peptides and proteins in a tunable manner," Nature Biotechnology, 2009, 27(12): 1186-1190.
Sharma et al., "Efficient Sleeping Beauty DNA Transposition From DNA Minicircles," Molec Ther Nucl Acids, 2013, 2(2): e74, 10 pages.
Stepper, "Dissertation: CRISPR-Cas9 fusions for synthetic epigenetics," Von der Fakultat 4: Energie-, Verfahrens-und Biotechnik, Institut für Biochemie und Technische Biochemie der Universität Stuttgart, 2020, 148 pages.
Thakore et al., "385. Inhibiting the Myostatin Signaling Pathway using CRISPR/Cas9-Based Repressors." Molecular Therapy 2016, 24: S153.
Tycko et al., "High-Throughput Discovery and Characterization of Human Transcriptional Effectors," Cell, 2020, 183(7): 2020-2035.
Van Tedeloo et al., "High-level transgene expression in primary human T lymphocytes and adult bone marrow CD34+ cells via electroporation-mediated gene delivery," Gene Therapy, 2000, 7(16): 1431-1437.
Verhoeyen et al., "Ch 8: Lentiviral vector gene transfer into human T cells," Methods Mol Biol, 2009, 506: 97-114.
Wang et al., "Phenotypic and functional attributes of lentivirus modified CD19-specific human CD8+ central memory T cells manufactured at clinical scale," J. Immunother, 2012, 35(9): 689-701.
Wright et al., "Rational design of a split-Cas9 enzyme complex," PNAS, 2015, 112(10): 2984-2989.
Wright et al., "Standardized reagents and protocols for engineering zinc finger nucleases by modular assembly," Nat. Protoc., 2006, 1(3): 1637-1652.
Zetsche et al., "A split-Cas9 architecture for inducible genome editing and transcription modulation," Nat. Biotechnol, 2015, 33(2): 139-142.
Echevarria et al., "Exon-skipping advances for Duchenne muscular dystrophy," Human Molecular Genetics, 2018, 27(R2): R163-R172.
Miller, "Non-viral CRISPR/Cas gene editing in vitro and in vivo enabled by synthetic nanoparticle co-delivery of Cas9 mRNA and sgRNA," Angew Chem Int Engl, 2017, 56(4): 1059-1063.
Ryu et al., "Adenine base editing in mouse embryos and an adult mouse model of Duchenne muscular dystrophy," Nature Biotechnology, 2018, 36(6): 536-539.
Rees et al., "Base editing: precision chemistry on the genome and transcriptome of living cells," Nature Reviews Genetics, 2018, 19(12): 770-788.
Nelson et al., "Long-term evaluation of genome editing for Duchenne muscular dystrophy," Duke Presentation, 2019, 123 pages. Retrieved from the Internet: <https://static.seekingalpha.com/uploads/sa_presentations/453/41453/original.pdf>.

(56) References Cited

OTHER PUBLICATIONS

Young, "Development of a Therapeutic CRISPR/Cas9 Plataform for Duchenne Muscular Dystrophy," UCLA Electronic Theses and Dissertations, Jan. 1, 2018, 136 pages.
Kwon et al., "In Vivo Gene Editing of Muscle Stem Cells with Adeno-Associated Viral Vectors in a Mouse Model of Duchenne Muscular Dystrophy," Molecular Therapy, 2020, 19: 320-329.
Chinese Patent Office Action for Application No. 202111496852.0 dated Mar. 27, 2024 (14 pages, English translation included).
European Patent Office Action for Application No. 18172956.7 dated Mar. 26, 2024 (3 pages).
Japanese Patent Office Action for Application No. 2022-052186 dated Oct. 19, 2023 (6 pages, English translation included).
Korean Patent Office Action for Application No. 10-2023-7022139 Dated Nov. 27, 2023 (9 pages, English translation included).
United States Patent Office Action for U.S. Appl. No. 16/858,689 dated Feb. 2, 2024 (16 pages).
United States Patent Office Notice of Allowance for U.S. Appl. No. 16/890,232 dated Mar. 1, 2024 (7 pages).
United States Patent Office Action for U.S. Appl. No. 15/789,348 dated Mar. 13, 2024 (10 pages).
Bulcha et al., "Viral vector platforms within the gene therapy landscape," Signal Transduction and Targeted Therapy, 2021, 6: 53.
Duchêne et al., "CRISPR-Induced Deletion with SaCas Restores Dystrophin Expression in Dystrophic Models In Vitro and In Vivo," Molecular Therapy: The Journal of the American Society of Gene Therapy, 2018, 26(11): 2604-2616.
United States Patent Office Notice of Allowance for U.S. Appl. No. 17/471,935 dated Aug. 19, 2024 (7 pages).
Chinese Patent Office Action for Application No. 202111496852.0 dated Jul. 31, 2024 (21 pages, English translation included).
Canadian Patent Office Action for Application No. 2,914,519 dated Aug. 19, 2024 (7 pages).
Australian Patent Office Examination Report No. 1 for Application No. 2022250450 dated Jun. 12, 2024 (5 pages).
Australian Patent Office Examination Report No. 1 for Application No. 2022250572 dated Jun. 12, 2024 (3 pages).
Hideki et al., Geneseq Accession No. BFK30060, 2018. Reference in U.S. Appl. No. 16/963,034, U.S. Patent Office Action dated Jun. 27, 2024.
Kotterman et al., "Engineering adeno-associated viruses for clinical gene therapy," Nature Reviews, 2014, 15(7): 445-451.
Lenzi et al., "Oversight and Review of Clinical Gene Transfer Protocols: Assessing the Role of the Recombinant DNA Advisory Committee," NCBI Bookshelf, A Service of the National Library of Medicine, National Institute of Health, Washington, DC, National Academies Press, US, 2014, pp. 1-16.
Liao, "Targeted disruption of DNMT1, DNMT3A and DNMT3B in human embryonic stem cells," Nature Genetics, 2015, 47(5): 469-478.
Long et al., "Correction of Diverse Muscular Dystrohpy Mutations in Human Engineered Heart Muscle by Single-Site Genome Editing," Sci Adv, 2018, 4(1): eaap9004.
Maggio et al., "Adenoviral vectors encoding CRISPR/Cas9 multiplexes rescue dystrophin synthesis in unselected populations of DMD muscle cells," Scientific Reports, 2016, 6: 37051.
Shim et al., "Nonviral Delivery Systems for Cancer Gene Therapy: Strategies and Challenges," Current Gene Therapy, 2017, 17(5): 1-18.
Swiech et al., "In vivo interrogation of gene function in the mammalian brain using CRISPR-Cas9," Nature Biotechnology, 2014, 33(1): 102-106 (Supplementary Information included).
Thule et al., "Engineered Insulin Secretion in Human Primary Thyroid Cells," Molecular Therapy, 2012, 20 (Supplement 1): S164, Article 421.
Chao et al., "Several log increase in therapeutic transgene delivery by distinct adeno-associated viral serotype vectors," (2000) Molecular Therapy 2:619.
Chen et al., "In vivo CD8+ T cell CRISPR screening reveals control by Fli1 in infection and cancer," Cell, 2021, 184(5): 1262-1280.
Corces et al., "An improved ATAC-seq protocol reduces background and enables interrogation of frozen tissues," Nature Methods. 2017, 14: 959-962.
Galletti et al., "Two subsets of stem-like CD8+ memory T cell progenitors with distinct fate commitments in humans," Nature Immunology, 2020, 21: 1552-1562.
Gao et al., "Clades of Adeno-Associated Viruses Are Widely Disseminated in Human Tissues," (2004) J. Virology 78:6381-6388.
GenBank Accession No. AF028704.1, (1998).
GenBank Accession No. AF028705.1, (1998).
GenBank Accession No. AF043303.1, (2010).
GenBank Accession No. AF063497.1, (1999).
GenBank Accession No. AF288061.1, (2001).
GenBank Accession No. AF513851.1, (2002).
GenBank Accession No. AFS13852.1, (2015).
GenBank Accession No. AH009962.2, (2016).
GenBank Accession No. AY028223.1, (2001).
GenBank Accession No. AY028226.1, (2001).
GenBank Accession No. AY530579.1, (2004).
GenBank Accession No. J01901.1, (1993).
GenBank Accession No. J02275.1, (1995).
GenBank Accession No. NC_000883.2, (2018).
GenBank Accession No. NC_001358.1, (2015).
GenBank Accession No. NC_001401, (2018).
GenBank Accession No. NC_001510.1, (2018).
GenBank Accession No. NC_001540.1, (2018).
GenBank Accession No. NC_001701.1, (2018).
GenBank Accession No. NC_001729, (2018).
GenBank Accession No. NC_001829.1, (2018).
GenBank Accession No. NC_001862.1, (2004).
GenBank Accession No. NC_001863.1, (2004).
GenBank Accession No. NC_002077, (2018).
GenBank Accession No. NC_006152.1, (2018).
GenBank Accession No. NC_006261.1, (2018).
GenBank Accession No. U89790.1, (1997).
GenBank Accession No. X01457.1, (2005).
Hao et al., "Integrated analysis of multimodal single-cell data," Cell, 2021, 184: 3573-3587.e29.
Hart et al., "Kruppel-like factors in lymphocyte biology," J Immunol, 2012, 188(2): 521-526.
Joung et al., "Transcription Factor Atlas of Directed Differentiation," Cell, 2023, 186(1): 209-229.e26.
Jung et al. "BLIMP1 and NR4A3 transcription factors reciprocally regulate antitumor CAR T cell stemness and exhaustion," Cancer Immunotherapy, 2022, 14: eabn7336.
Kaminskiy et al., "Neglected, yet significant role of FOXP1 in T-cell quiescence, differentiation and exhaustion," Front. Immunol, 2022, 13: 971045.
Krishna et al., "Stem-like CD8 T cells mediate response of adoptive cell immunotherapy against human cancer," Science, 2020, 370: 1328-1334.
Kuleshov et al., "Enrichr: a comprehensive gene set enrichment analysis web server 2016 update," Nucleic Acids Research, 2016, 44: 90-97.
Liao et al., "featureCounts: an efficient general purpose program for assigning sequence reads to genomic features," Bioinformatics, 2013, 30(7): 923-30.
Martin et al., "CCR7 Deficiency in NOD Mice Leads to Thyroiditis and Primary Hyperthyroidism," The Journal of Immunology, 2009, 183(5): 3073-3080.
Mimitou et al., "Expanding the CITE-seq tool-kit: Detection of proteins, transcriptomes, clonotypes and CRISPR perturbations with multiplexing, in a single assay," Nat. Methods, 2019, 16: 409-412.
Mori et al, "Two novel adeno-associated viruses from cynomolgus monkey: pseudotyping characterization of capsid protein," (2004) Virology 330: 375-383.
Muzyczka, "Use of adeno-associated virus as a general transduction vector for mammalian cells," (1992) Curr. Topics Microbial. Immunol. 158: 97-129.
Philip et al., "Chromatin states define tumour-specific T cell dysfunction and reprogramming," Nature, 2017, 545: 452-456.

(56) References Cited

OTHER PUBLICATIONS

Pritykin et al., "A unified atlas of CD8 T cell dysfunctional states in cancer and infection," Mol. Cell 2021, 81: 2477-2493.
Ramirez et al., "deepTools: a flexible platform for exploring deep-sequencing data," Nucleic Acids Research, 2014, 42:W187-91.
Schubert et al., "Autosomal dominant immune dysregulation syndrome in humans with CTLA4 mutations," Nature Medicine, 2014, 20(2): 1410-1416.
Sen et al., "The epigenetic landscape of T cell exhaustion," Science, 2016, 354(6316): 1165-1169.
Vojta et al., "Repurposing the CRISPR-Cas9 system for targeted DNA methylation," Nucleic Acids Research, 2016, 44(12): 5615-5628.
Wherry et al., "Molecular Signature of CD8+ T Cell Exhaustion during Chronic Viral Infection," Immunity, 2007, 27(4): 670-684.
Woolf et al., "Runx3 and Runx1 are required for CD8 T cell development during thymopoiesis," PNAS, 2003, 100(13): 7731-7736.
Yang et al., "The transcriptional regulators Id2 and Id3 control the formation of distinct memory CD8+ T cell subsets," Nat Immunol, 2011, 12: 1221-1229.
Yu et al., "ChIPseeker: an R/Bioconductor package for ChIP peak annotation, comparison and visualization," Bioinformatics, 2015, 31(14): 2382-2383.
Yuan et al., "Genetic Modulation of RNA Splicing with a CRISPR-Guided Cytidine Deaminase," Molecular Cell, 2018, 72(2): 380-394.
Zhang et al., "Model-based analysis of ChIP-Seq (MACS)," Genome Biology, 2008, 9(9): R137.
Zheng et al., "Landscape of Infiltrating T Cells in Liver Cancer Revealed by Single-Cell Sequencing," Cell, 2017, 169: 1342-1356.
Ahern, "Biochemical, Reagents Kits Offer Scientists Good Return On Investment," The Scientist Magazine, (accessed at https://www.the-scientist.com/technology/biochemical-reagents-kits-offer-scientists-good-return-on-investment-58425 on Dec. 14, 2023) (Year: 1995).
Bennett et al., "Detection of mutations in the dystrophin gene via automated DHPLC screening and direct sequencing," BMC Genet, 2001, 2: 17.
Bikard et al., "Programmable repression and activation of bacterial gene expression using an engineered CRISPR-Cas system," Nucleic Acids Research, 2013, 41(15): 7429-7437.
Echigoya et al., "Multiple Exon Skipping in the Duchenne Muscular Dystrophy Hot Spots: Prospects and Challenges," J Pers Med, 2018, 8(4): 41.
Jangid et al., "Biodirectional promoters exhibit characteristic chromatin modification signature associated with transcription elongation in both sense and antisense directions," BMC Genomics, 2018, 19: 313.
Mitsunobu et al., "Beyond Native Cas9: Manipulating Genomic Information and Function," Trends in Biotechnology, 2017, 35(10): 986-996.
NCBI Reference Sequence: NG_012232.1, "*Homo sapiens* dystrophin (DMD), RefSeqGene (LRG_199) on chromosome X," National Library of Medicine (accessed at: https://www.ncbi.nlm.nih.gov/nuccore/NG_012232.1/) (Year: 1993).
NCBI Reference Sequence: WP_038431314.1 "type II CRISPR RNA-guided endonuclease Cas9 [*Streptococcus pyogenes*]," National Library of Medicine (accessed at: https://www.ncbi.nlm.nih.gov/protein/WP_038431314.1) (Year: 2005).
Pinder et al., "Nuclear domain 'knock-in' screen for the evaluation and identification of small molecule enhancers of CRISPR-based genome editing," Nucleic Acids Research, 2015,43(19): 9379-9392.
Shimo et al., "A novel human muscle cell model of Duchenne muscular dystrophy created by CRISPR/Cas9 and evaluation of antisense-mediated exon skipping," Journal of Human Genetics, 2018, 63: 365-375.
Tremblay et al., "Gene Editing for Duchenne Muscular Dystrophy Using the CRISPR/Cas9 Technology: The Importance of Fine-tuning the Approach," Molecular Therapy, The Journal of the American Society of Gene Therapy, 2016, 24(11): 1888-1889.
Warnock et al., "Introduction to Viral Vectors," Viral Vectors for Gene Therapy: Methods in Molecular Biology, 2011, vol. 737, Chapter 1, 25 pages.
European Patent Extended Search Report for Application No. 24163890.7 dated Nov. 28, 2024 (14 pages).
Abdennur et al., "Cooler: scalable storage for Hi-C data and other genomically labeled arrays," Bioinformatics, 2020, 36: 311-316.
Achterberg et al., "The nano-scale mechanical properties of the extracellular matrix regulate dermal fibroblast function," J. Invest. Dermatol, 2014, 134: 1862-1872.
Akter et al., "FAM98A associates with DDX1-C14orf166-FAM98B in a novel complex involved in colorectal cancer progression," Int. J. Biochem. Cell Biol., 2017, 84: 1-13.
Andreu et al.," Mechanical force application to the nucleus regulates nucleocytoplasmic transport," Nat. Cell Biol., 2022, 24: 896-905.
Arda et al., "Quantitative assessment of normal soft-tissue elasticity using shear-wave ultrasound elastography," AJR Am. J. Roentgenol., 2011, 197: 532-536.
Aubel et al., "Mammalian synthetic biology—from tools to therapies," BioEssays, 2010, 32(4): 332-345.
Babic et al., "CYR61, a product of a growth factor-inducible immediate early gene, promotes angiogenesis and tumor growth," Proc. Natl. Acad. Sci. U.S.A., 1998, 95: 6355-6360.
Baek et al., "DNA-free two-gene knockout in Chlamydomonas reinhardtii via CRISPR-Cas9 ribonucleoproteins," Scientific Reports, 2016, 6:30620.
Balko et al., "Activation of MAPK pathways due to DUSP4 loss promotes cancer stem cell-like phenotypes in basal-like breast cancer," Cancer Res, 2013, 73: 6346-6358.
Behan et al., "Prioritization of cancer therapeutic targets using CRISPR-Cas9 screens," Nature, 2019, 568: 511-516.
Benabdallah et al., "Decreased Enhancer-Promoter Proximity Accompanying Enhancer Activation," Mol. Cell, 2019, 76: 473-484.e7.
Beningo et al., "Traction forces of fibroblasts are regulated by the Rho-dependent kinase but not by the myosin light chain kinase," Arch. Biochem. Biophys., 2006, 456: 224-231.
Berginski et al., "The Focal Adhesion Analysis Server: a web tool for analyzing focal adhesion dynamics," F1000Res., 2013, 2: 68.
Bischoff et al., "RanGAP1 induces GTPase activity of nuclear Ras-related Ran," Proc. Natl. Acad. Sci. U.S.A., 1994, 91: 2587-2591.
Bolger et al., "Trimmomatic: a flexible trimmer for Illumina sequence data," Bioinformatics, 2014, 30: 2114-2120.
Braun et al., "Rapid and reversible epigenome editing by endogenous chromatin regulators," Nat Commun, 2017, 8(1): 560.
Canver et al., "BCL11A enhancer dissection by Cas9-mediated in situ saturating mutagenesis," Nature, 2015, 527: 192-197.
Chang et al., "GEF-H1 couples nocodazole-induced microtubule disassembly to cell contractility via RhoA," Mol Biol Cell, 2008, 19: 2147-2153.
Chang et al., "The SWI/SNF complex is a mechanoregulated inhibitor of YAP and TAZ," Nature, 2018, 563: 265-269.
Chen et al., "Connective Tissue Growth Factor: From Molecular Understandings to Drug Discovery," Front Cell Dev Biol, 2020, 8: 593269.
Chen et al., "Geometric control of cell life and death," Science, 1997, 276: 1425-1428.
Chen, "Mechanotransduction—a field pulling together?" J. Cell Sci., 2008, 121: 3285-3292.
Chrzanowska-Wodnicka et al., "Rho-stimulated contractility drives the formation of stress fibers and focal adhesions," J Cell Biol, 1996, 133: 1403-1415.
Clement et al., "CRISPResso2 provides accurate and rapid genome editing sequence analysis," Nat. Biotechnol., 2019, 37: 224-226.
Corces et al., "Omni-ATAC-seq: improved ATAC-seq protocol," Protocol exchange, [Preprint] 2017.
Cosgrove et al., "Mechanosensitive genomic enhancers potentiate the cellular response to matrix stiffnes," Posted Jan. 10, 2024. bioRxiv Jan. 10, 2024:2024.01.10.574997.
Darnell et al. "RNA-seq reveals diverse effects of substrate stiffness on mesenchymal stem cells," Biomaterials, 2018, 181: 182-188.

(56) References Cited

OTHER PUBLICATIONS

Devos et al., "Practical Limits of Fuction Prediction," Proteins: Structure, Function, and Genetics, 2000, 41: 98-107.
Ding et al., "Improving CRISPR-Cas9 Genome Editing Efficiency by Fusion with Chromatin-Modulating Peptides," CRISPR J, 2019, 2: 51-63.
Dobin et al., "STAR: ultrafast universal RNA-seq aligner," Bioinformatics, 2013, 29: 15-21.
Dupont et al., "Mechanical regulation of chromatin and transcription," Nat. Rev. Genet., 2022, 23: 624-643.
Dupont et al., "Role of YAP/TAZ in mechanotransduction," Nature, 2011, 474: 179-183.
Durand et al., "Juicer Provides a One-Click System for Analyzing Loop-Resolution Hi-C Experiments," Cell Syst, 2016, 3: 95-98.
Effendi et al., "Connective Tissue Growth Factor in Idiopathic Pulmonary Fibrosis: Breaking the Bridge," Int. J. Mol. Sci., 2022, 23.
Ehrbar et al., "Elucidating the role of matrix stiffness in 3D cell migration and remodeling," Biophys. J., 2011, 100: 284-293.
Elosegui-Artola et al., "Force triggers YAP nuclear entry by regulating transport across nuclear pores," Cell, 2017, 171: 1397-1410. e14.
Encode Project Consortium, "An integrated encyclopedia of DNA elements in the human genome," Nature, 2012, 2012, 489: 57-74.
Encode Project Consortium, "Expanded encyclopaedias of DNA elements in the human and mouse genomes," Nature, 2020, 583: 699-710.
Engler et al., "Matrix elasticity directs stem cell lineage specification," Cell, 2006, 126: 677-689.
Ernst et al., "ChromHMM: automating chromatin-state discovery and characterization," Nat Methods, 2012, 9: 215-216.
Fan et al., "Hsp90{beta} and p130(cas): novel regulatory factors of MMP-13 expression in human osteoarthritic chondrocytes," Ann. Rheum. Dis., 2009, 68: 976-982.
Finak et al., "MAST: a flexible statistical framework for assessing transcriptional changes and characterizing heterogeneity in single-cell RNA sequencing data," Genome Biol., 2015, 16: 278.
Fiore et al., "Publisher Correction: Mechanics of a multilayer epithelium instruct tumour architecture and function," Nature, 2020, 586: E9.
Freeberg et al., "Mechanical Feed-Forward Loops Contribute to Idiopathic Pulmonary Fibrosis," Am. J. Pathol., 2021, 191: 18-25.
Fulco et al., "Activity-by-contact model of enhancer-promoter regulation from thousands of CRISPR perturbations," Nat. Genet., 2019, 51: 1664-1669.
Galli et al., "YAP Drives Growth by Controlling Transcriptional Pause Release from Dynamic Enhancers," Molecular Cell, 2015, 60(2): P328-337.
Gasperini et al., "A Genome-wide Framework for Mapping Gene Regulation via Cellular Genetic Screens," Cell, 2019, 176: 377-390.e19.
GenBank Accession No. U94396.1 "Human dystrophin (DMD) gene, exon 44 and partial cds," 2016.
Gilbert et al., "CRISPR-mediated modular RNA-guided regulation of transcription in eukaryotes," Cell, 2013, 154: 442-451.
Gordon et al., "lentiMPRA and MPRAflow for high-throughput functional characterization of gene regulatory elements," Nat. Protoc., 2020, 15(8): 2387-2412.
Habermann et al., "Single-cell RNA sequencing reveals profibrotic roles of distinct epithelial and mesenchymal lineages in pulmonary fibrosis," Sci Adv, 2020, 6: eaba197.
Hall et al., "Polarity of the CRISPR roadblock to transcription," Nat. Struct. Mol. Biol., 2022, 29: 1217-1227.
Han et al., "CRISPR screens in cancer spheroids identify 3D growth-specific vulnerabilities," Nature, 2020, 580: 136-141.
Hanmandlu et al., "Transcriptomic and Epigenetic Profiling of Fibroblasts in Idiopathic Pulmonary Fibrosis," Am J Respir Cell Mol Biol, 2022, 66(1): 53-63.
Heinz et al., "Simple combinations of lineage-determining transcription factors prime cis-regulatory elements required for macrophage and B cell identities," Mol. Cell, 2010, 38: 576-589.
Heinz et al., "The selection and function of cell type-specific enhancers," Nat. Rev. Mol. Cell Biol., 2015, 16: 144-154.
Heo et al., "Differentiation alters stem cell nuclear architecture, mechanics, and mechano-sensitivity," Elife, 2016, 5.
Herrera et al., "Extracellular matrix as a driver of progressive fibrosis," J. Clin. Invest., 2018, 128: 45-53.
Ho et al., "Lamin A/C and emerin regulate MKL1-SRF activity by modulating actin dynamics," Nature, 2013, 497: 507-511.
Hoffman et al., "Dynamic molecular processes mediate cellular mechanotransduction," Nature, 2011, 475: 316-323.
Horlbeck et al., "Compact and highly active next-generation libraries for CRISPR-mediated gene repression and activation," Elife, 2016, 5: e19760.
Humphrey et al., "Mechanotransduction and extracellular matrix homeostasis," Nat. Rev. Mol. Cell Biol., 2014, 15: 802-812.
Isaac et al., "Nucleosome breathing and remodeling constrain CRISPR-Cas9 function," Elife, 2016, 5: e13450.
Jang et al., "Mechanical cue-induced YAP instructs Skp2-dependent cell cycle exit and oncogenic signaling," EMBO J., 2017, 36: 2510-2528.
Jeffrey et al., "Targeting dual-specificity phosphatases: manipulating MAP kinase signalling and immune responses," Nat. Rev. Drug Discov., 2007, 6: 391-403.
Jiang et al., "Systematic investigation of cytokine signaling activity at the tissue and single-cell levels," Nat. Methods, 2021, 18: 1181-1191.
Johne et al., "Spred1 and TESK1—two new interaction partners of the kinase MARKK/TAO1 that link the microtubule and actin cytoskeleton," Mol. Biol. Cell, 2008, 19: 1391-1403.
Jones et al., "Mechanoepigenetic regulation of extracellular matrix homeostasis via Yap and Taz," Proc. Natl. Acad. Sci. U.S.A., 2023, 120: e2211947120.
Jones et al., "No place like home: anatomy and function of the stem cell niche," Nat. Rev. Mol. Cell Biol., 2008, 9: 11-21.
Jones et al., "ZNF416 is a pivotal transcriptional regulator of fibroblast mechanoactivation," J. Cell Biol., 2021, 220.
Juric et al., "MAPS: Model-based analysis of long-range chromatin interactions from PLAC-seq and HiChIP experiments," PLoS Comput. Biol., 2019, 15: e1006982.
Katsura et al., "Human Lung Stem Cell-Based Alveolospheres Provide Insights into SARS-CoV-2-Mediated Interferon Responses and Pneumocyte Dysfunction," Cell Stem Cell, 2020, 27(6): 890-904.e8.
Kechin et al., "cutPrimers: A New Tool for Accurate Cutting of Primers from Reads of Targeted Next Generation Sequencing," J. Comput. Biol., 2017, 24: 1138-1143.
Khemlina et al., "The biology of Hepatocellular carcinoma: implications for genomic and immune therapies," Mol. Cancer, 2017, 16: 149.
Kisselev, "Polypeptide Release Factors in Prokaryotes and Eukaryotes: Same Function, Different Structure," Structure, 2002, 10: 8-9.
Klann et al., "CRISPR-Cas9 epigenome editing enables high-throughput screening for functional regulatory elements in the human genome," Nat. Biotechnol., 2017, 35: 561-568.
Korkmaz et al., "Functional genetic screens for enhancer elements in the human genome using CRISPR-Cas9," Nat. Biotechnol., 2016, 34: 192-198.
Krietenstein et al., "Ultrastructural Details of Mammalian Chromosome Architecture," Mol. Cell, 2020, 78(3): 554-565.e7.
Kurppa et al., "Treatment-Induced Tumor Dormancy through YAP-Mediated Transcriptional Reprogramming of the Apoptotic Pathway," Cancer Cell, 2020, 37: 104-122.e12.
Langmead, "Aligning short sequencing reads with Bowtie," Curr. Protoc. Bioinformatics, 2010, Chapter 11, Unit 11.7.
Lau et al., "In vivo epigenome editing and transcriptional modulation using CRISPR technology," Transgenic Res. 2018, 27(6): 489-509.
Le et al., "Mechanical regulation of transcription controls Polycomb-mediated gene silencing during lineage commitment, " Nature Cell Biology, 2016, 18(8): 864-875.

(56) References Cited

OTHER PUBLICATIONS

Lee et al., "The novel PIAS-like protein hZimp10 is a transcriptional co-activator of the p53 tumor suppressor," Nucleic Acids Res., 2007, 35: 4523-4534.
Leight et al., "Matrix rigidity regulates a switch between TGF-β1-induced apoptosis and epithelial-mesenchymal transition," Mol. Biol. Cell, 2012, 23: 781-791.
Li et al., "MicroRNA-21 preserves the fibrotic mechanical memory of mesenchymal stem cells," Nat. Mater., 2017, 16: 379-389.
Liao et al., "featureCounts: an efficient general purpose program for assigning sequence reads to genomic features," Bioinformatics, 2014, 30: 923-930.
Liu et al., "Modulating chromatin accessibility by transactivation and targeting proximal dsgRNAs enhances Cas9 editing efficiency in vivo," Genome Biol, 2019, 20(1): 145.
Love et al., "Moderated estimation of fold change and dispersion for RNA-seq data with DESeq2," Genome Biol., 2014, 15: 550.
Ma et al., "Mechanotransduction and anoikis: death and the homeless cell," Cell Cycle, 2008, 7: 2462-2465.
McBeath et al., "Cell shape, cytoskeletal tension, and RhoA regulate stem cell lineage commitment," Dev. Cell, 2004, 6: 483-495.
McDowell et al., "Glucocorticoid receptor recruits to enhancers and drives activation by motif-directed binding," Genome Res., 2018, 28: 1272-1284.
Meng et al., "RAP2 mediates mechanoresponses of the Hippo pathway," Nature, 2018, 560: 655-660.
Meyers et al., "Computational correction of copy number effect improves specificity of CRISPR-Cas9 essentiality screens in cancer cells," Nat. Genet., 2017, 49: 1779-1784.
Miano, "Serum response factor: toggling between disparate programs of gene expression," J. Mol. Cell. Cardiol., 2003, 35: 577-593.
Mifsud et al., "Mapping long-range promoter contacts in human cells with high-resolution capture Hi-C," Nat. Genet., 2015, 47: 598-606.
Miralles et al., "Actin dynamics control SRF activity by regulation of its coactivator MAL," Cell, 2003, 113: 329-342.
Miroshnikova et al., "Emerging roles of mechanical forces in chromatin regulation," J. Cell Sci., 2017, 130: 2243-2250.
Molineros et al., "Mechanistic Characterization of Variants Identifies an hnRNP-K-Regulated Transcriptional Enhancer Contributing to SLE Susceptibility," Front. Immunol., 2019, 10: 1066.
Moore et al., "Regulation and Relevance of Myofibroblast Responses in Idiopathic Pulmonary Fibrosis," Curr. Pathobiol. Rep., 2013, 1: 199-208.
Morrison et al., "Stem cells and niches: mechanisms that promote stem cell maintenance throughout life," Cell, 2008, 132: 598-611.
Muerdter et al., "Resolving systematic errors in widely used enhancer activity assays in human cells," Nat. Methods, 2018, 15: 141-149.
Murthy et al., "Human distal lung maps and lineage hierarchies reveal a bipotent progenitor," Nature, 2022, 604(7904): 111-119.
Namavar et al., "Classification, diagnosis and potential mechanisms in pontocerebellar hypoplasia," Orphanet J. Rare Dis., 2011, 6: 50.
Nava et al., "Heterochromatin-Driven Nuclear Softening Protects the Genome against Mechanical Stress-Induced Damage," Cell, 2020, 181: 800-817.e22.
Noonan et al., "Genomics of long-range regulatory elements," Annu. Rev. Genomics Hum. Genet., 2010, 11: 1-23.
Oliver-De La Cruz et al., "Substrate mechanics controls adipogenesis through YAP phosphorylation by dictating cell spreading, " Biomaterials, 2019, 205: 64-80.
Open2c et al., "Pairtools: From sequencing data to chromosome contacts," PLoS Comput. Biol., 2024, 20: e1012164.
Paoli et al., "Anoikis molecular pathways and its role in cancer progression," Biochim. Biophys. Acta, 2013, 1833: 3481-3498.
Parker et al., "Fibrotic extracellular matrix activates a profibrotic positive feedback loop," J. Clin. Invest., 2014, 124: 1622-1635.
Paszek et al., "Tensional homeostasis and the malignant phenotype," Cancer Cell, 2005, 8: 241-254.
Paulmann et al., "The OTUD6B-LIN28B-MYC axis determines the proliferative state in multiple myeloma," EMBO J., 2022, 41: e110871.
Pelham Jr et al., "Cell locomotion and focal adhesions are regulated by substrate flexibility," Proc. Natl. Acad. Sci. U.S.A., 1997, 94: 13661-13665.
Piccolo et al., "The biology of YAP/TAZ: hippo signaling and beyond," Physiol. Rev., 2014, 94: 1287-1312.
Plikus et al., "Fibroblasts: Origins, definitions, and functions in health and disease," Cell, 2021, 184: 3852-3872.
Quinlan et al., "BEDTools: a flexible suite of utilities for comparing genomic features," Bioinformatics, 2010, 26: 841-842.
Quinlan, "BEDTools: The Swiss-Army Tool for Genome Feature Analysis," Curr. Protoc. Bioinformatics, 2014, 47: 11.12.1-34.
Ramírez et al., "deepTools: a flexible platform for exploring deep-sequencing data," Nucleic Acids Res., 2014, 42: W187-91.
Ritterhoff et al., "The RanBP2/RanGAP1*SUMO1/Ubc9 SUMO E3 ligase is a disassembly machine for Crm1-dependent nuclear export complexes," Nat. Commun., 2016, 7: 11482.
Robinson et al., "edgeR: a Bioconductor package for differential expression analysis of digital gene expression data," Bioinformatics, 2010, 26: 139-140.
Royer et al., "Mechanobiology in the Comorbidities of Ehlers Danlos Syndrome," Front Cell Dev Biol, 2022, 10: 874840.
Sanson et al., "Optimized libraries for CRISPR-Cas9 genetic screens with multiple modalities," Nat. Commun., 2018, 9: 1-15.
Sanyal et al., "The long-range interaction landscape of gene promoters," Nature, 2012, 489: 109-113.
Schmelzle et al., "Functional role and oncogene-regulated expression of the BH3-only factor Bmf in mammary epithelial anoikis and morphogenesis," Proc. Natl. Acad. Sci. U.S.A., 2007, 104: 3787-3792.
Seo et al., "RNAi-based functional selection identifies novel cell migration determinants dependent on PI3K and AKT pathways," Nat. Commun., 2014, 5: 5217.
Simeonov et al., "Discovery of stimulation-responsive immune enhancers with CRISPR activation," Nature, 2017, 549: 111-115.
Sollis et al., "The NHGRI-EBI GWAS Catalog: knowledgebase and deposition resource," Nucleic Acids Res., 2023, 51: D977-D985.
Song et al., "B-catenin induces A549 alveolar epithelial cell mesenchymal transition during pulmonary fibrosis," Mol. Med. Rep., 2015, 11: 2703-2710.
Stowers et al., "Matrix stiffness induces a tumorigenic phenotype in mammary epithelium through changes in chromatin accessibility," Nat Biomed Eng, 2019, 3: 1009-1019.
Stuart et al., "Comprehensive Integration of Single-Cell Data," Cell, 2019, 177: 1888-1902.e21.
Sun et al., "Effects of Matrix Stiffness on the Morphology, Adhesion, Proliferation and Osteogenic Differentiation of Mesenchymal Stem Cells," Int. J. Med. Sci., 2018, 15: 257-268.
Sun et al., "Force-induced gene up-regulation does not follow the weak power law but depends on H3K9 demethylation," Sci Adv, 2020, 6: eaay9095.
Swift et al., "Nuclear lamin-A scales with tissue stiffness and enhances matrix-directed differentiation," Science, 2013, 341: 1240104.
Tajik et al., "Transcription upregulation via force-induced direct stretching of chromatin," Nat. Mater., 2016, 15: 1287-1296.
Thakore et al., "Highly specific epigenome editing by CRISPR-Cas9 repressors for silencing of distal regulatory elements," Nat. Methods, 2015, 12: 1143-1149.
Torrungruang et al., "DNA binding and gene activation properties of the Nmp4 nuclear matrix transcription factors," J. Biol. Chem., 2002, 277: 16153-16159.
Tycko et al., "Mitigation of off-target toxicity in CRISPR-Cas9 screens for essential non-coding elements," Nat. Commun., 2019, 10: 4063.
Vartiainen et al., "Nuclear actin regulates dynamic subcellular localization and activity of the SRF cofactor MAL," Science, 2007, 316: 1749-1752.
Vicente-Manzanares et al., "Non-muscle myosin II takes centre stage in cell adhesion and migration" Nat. Rev. Mol. Cell Biol., 2009, 10: 778-790.

(56) References Cited

OTHER PUBLICATIONS

Vierbuchen et al., "AP-1 Transcription Factors and the BAF Complex Mediate Signal-Dependent Enhancer Selection," Mol. Cell, 2017, 68: 1067-1082.e12.
Vishwanath et al., "Mechanisms of aortic carboxypeptidase-like protein secretion and identification of an intracellularly retained variant associated with Ehlers-Danlos syndrome," J. Biol. Chem., 2020, 295: 9725-9735.
Wei et al., "HiCAR is a robust and sensitive method to analyze open-chromatin-associated genome organization," Mol. Cell, 2022, 82: 1225-1238.e6.
Wells, "Tissue mechanics and fibrosis," Biochim. Biophys. Acta, 2013, 1832: 884-890.
Witkowski et al., "Conversion of a β-Ketoacyl Synthase to a Malonyl Decarboxylase by Replacement of the Active-Site Cysteine with Glutamine," Biochemistry, 1999, 38: 11643-11650.
Yan et al., "Zinc finger protein 384 enhances colorectal cancer metastasis by upregulating MMP2," Oncol. Rep., 2022, 47.
Yao et al., "The ENCODE4 Consortium, Multi-center integrated analysis of non-coding CRISPR screens," https://doi.org/10.1101/2022.12.21.520137, posted Dec. 22, 2022.
Yu et al., "ChIPseeker: an R/Bioconductor package for ChIP peak annotation, comparison and visualization," Bioinformatics, 2015, 31: 2382-2383.
Zanconato et al., "Genome-wide association between YAP/TAZ/TEAD and AP-1 at enhancers drives oncogenic growth," Nat. Cell Biol., 2015, 17: 1218-1227.
Zhang et al., "BAALC-AS1/G3BP2/c-Myc feedback loop promotes cell proliferation in esophageal squamous cell carcinoma," Cancer Commun., 2021, 41: 240-257.
Zhang et al., "Model-based analysis of ChIP-Seq (MACS)," Genome Biol., 2008, 9: R137.
Zhang et al., "The matricellular protein Cyr61 is a key mediator of platelet-derived growth factor-induced cell migration," J. Biol. Chem., 2015, 290: 8232-8242.
Zhao et al., "Cell detachment activates the Hippo pathway via cytoskeleton reorganization to induce anoikis," Genes Dev., 2012, 26: 54-68.
Zhao et al., "Substrate stiffness regulated migration and angiogenesis potential of A549 cells and HUVECs," J. Cell. Physiol, 2018, 233: 3407-3417.
Zhao et al., "TEAD mediates YAP-dependent gene induction and growth control," Genes Dev., 2008, 22: 1962-1971.
Zhou et al., "Novel identified associations of RGS1 and RASGRP1 variants in IgA Nephropathy," Sci. Rep., 2016, 6: 35781.
Mathias et al., "Unraveling Immune-Related lncRNAs in Breast Cancer Molecular Subtypes," Front. Oncol., 2021, 11: 692170.
Cui et al., "Long non-coding RNA LINC02613 is a prognostic biomarker for breast cancer and correlates with the cell cycle and immune infiltration based on TCGA data," Translational Cancer Research, 2022, 11(4): 615-628.
Hori et al., "Control of Regulatory T Cell Development by the Transcription Factor Foxp3," Science, 2003, 299: 1057-1061.
Reiner et al., "Epigenetics meets GPCR: inhibition of histone H3 methyltransferase (G9a) and histamine H3 receptor for Prader-Willi Syndrome," Scientific Reports, 2020, 10: 13558.
Burr et al., "Mitochondrial Protein Lipoylation and the 2-Oxoglutarate Dehydrogenase Complex Controls HIF1a Stability in Aerobic Conditions," Cell Metab, 2016, 24(5): 740-752.
Leandro et al., "DHTKD1 and OGDH display in vivo substrate overlap and form a hybrid ketoacid dehydrogenase complex," bioRxiv preprint version posted May 22, 2019.
Bailey et al., "ABHD11 maintains 2-oxoglutarate metabolism by preserving functional lipoylation of the 2-oxoglutarate dehydrogenase complex," Nature Communications, 2020, 11: 4046.
Japanese Patent Office Action for Application No. 2023-131956 dated Jun. 12, 2025 (21 pages, English translation included).
Korean Patent Office Action for Application No. 10-2023-7031879 dated Jun. 27, 2025 (4 pages, English translation included).
Chung et al., "Prader-Willi syndrome: reflections on seminal studies and future therapies," Open Biology, 2020, 10: 200195.
Hesselson et al., "Suppression of Ptf1a Activity Induces Acinar-to-Endocrine Conversion," Current Biology, 2011, 21: 712-717.
Australian Patent Office Examination Report No. 1 for Application No. 2025213563 dated Aug. 21, 2025 (4 pages).
U.S. Appl. No. 19/477,032, filed Oct. 20, 2025.
U.S. Appl. No. 19/310,493, filed Aug. 26, 2025.
U.S. Appl. No. 19/480,763, filed Oct. 31, 2025.
Liu et al., "A CRISPR-Cas9 Strategy for Activating the Saccharopolyspora erythraea Erythromycin Biosynthetic Gene Cluster with Knock-in Bidirectional Promoters," ACS Synth. Biol. 2019, 8(5): 1134-1143.
Miyazaki et al., "Characterization of deletion breakpoints in patients with dystrophinopathy carrying a deletion of exons 45-55 of the Duchenne muscular dystrophy (DMD) gene," Journal of Human Genetics, 2009, 54: 127-130.
Razzouk, "CRISPR-Cas9: A cornerstone for the evolution of precision medicine," Annal of Human Genetics, 2018, 82(6): 331-357.
Simeonov et al., "Discovery of stimulation-responsive immune enhancers with CRISPR activation," Nature, 2017, 549(7670): 111-115.
European Patent Office Extended Search Report for Application No. 24163845.1 dated Sep. 16, 2024 (6 pages).
Japanese Patent Office Action for Application No. 2023-131956 dated Sep. 10, 2024 (10 pages, English translation included).
United States Patent Office Notice of Allowance for U.S. Appl. No. 15/789,348 dated Sep. 25, 2024 (9 pages).
United States Patent Office Notice of Allowance for U.S. Appl. No. 16/858,689 dated Nov. 12, 2024 (10 pages).
United States Patent Office Action for U.S. Appl. No. 16/858,689 dated Jun. 5, 2025 (16 pages).
Lee et al., "Synthetically modified guide RNA and donor DNA are a versatile platform for CRISPR-Cas9 engineering," eLife, 2017, 6: e25312.
Kwon et al., "626. Directing Skeletal Myogenic Progenitor Cell Lineage Specification with CRISPR/Cas9 Transcriptional Activators," Molecular Therapy, 2016, 24: S248.
Jiang et al., "CRISPR-Cas9 Structures and Mechanisms," Annu Rev Biophys, 2017, 46: 505-529.
Cataletto et al., "Prader-Willi syndrome: A primer for clinicians," Int J Pediatr Endocrinol, 2011, 2011(1): 12.
Chen et al., "Functional disruption of dystrophin gene in rhesus monkey using CRISPR/Cas9," Human Molecular Genetics, 2015, 24(13): 3764-3774.
Heigwer et al., "E-CRISP: fast CRISPR target site identification," Nature Methods, 2014, 11(2): 122-123.
Nemoto et al., "Rescue of imprinted genes by epigenome editing in human cellular models of Prader-Willi syndrome," Nat Commun, 2025, 16(1): 9442.
Japanese Patent Office Action for Application No. 2024-196641 dated Nov. 27, 2025 (3 pages, English translation included).
United Sates Patent Office Action for U.S. Appl. No. 16/858,689 dated Dec. 5, 2025 (10 pages).
Segal et al., "Attenuation of HIV-1 Replication in Primary Human Cells with a Designed Zinc Finger Transcription Factor," The Journal of Biological Chemistry, 2004, 279(15): 14509-14519.
Dreier et al., "Development of Zinc Finger Domains for Recognition of the 5'-CNN-3' Family DNA Sequences and Their Use in the Construction of Artificial Transcription Factors," The Journal of Biological Chemistry, 2005, 280(42): 35588-35597.
Adikusuma et al., "Versatile single-step-assembly CRISPR/Cas9 vectors for dual gRNA expression," PLoS One, 2017, 12(12): e0187236.
GenBank Accession X96744.1 "H.sapiens PAX7 gene, exon 1(and joined CDS)" (2006).
Bai et al., "Feasibility of using NF1-GRD and AAV for gene replacement therapy in NF1-associated tumors," Gene Ther, 2019, 26(6): 277-286.
Bednarski et al., "Targeted Integration of a Super-Exon into the CFTR Locus Leads to Functional Correction of a Cystic Fibrosis Cell Line Model," PLOS One, 2016, 11(8): e0161072.

(56) References Cited

OTHER PUBLICATIONS

Li et al., "Plant Genome Editing with CRISPR Systems," Methods in Molecular Biology, 2019, 1917: 285-296.
Moutal et al., "CRISPR/Cas9 editing of Nf1 gene identifies CRMP2 as a therapeutic target in neurofibromatosis type 1-related pain that is reversed by (S)-Lacosamide," Pain, 2017, 158(12): 2301-2319.
Australian Patent Office Examination Report No. 2 for Application No. 2025213563 dated Jan. 28, 2026 (6 pages).
Canadian Patent Office Action for Application No. 2,914,519 dated Jan. 20, 2026 (5 pages).
Japanese Patent Office Action for Application No. 2023-131956 dated Jan. 28, 2026 (3 pages, English statement of relevance included).
Addgene, "CRISPR Guide," <https://web.archive.org/web/20200220035811/http://www.addgene.org:80/guides/crispr/>webpage accessed via Wayback Machine on Feb. 20, 2020.
Allen et al., "Using Synthetically Engineered Guide RNAs to Enhance CRISPR Genome Editing Systems in Mammalian Cells," Genome Ed, 2021, 2: 617910.
Butterfield et al., "Characterization of diverse Cas9 orthologs for genome and epigenome editing," PNAS, 2025, 122 (11): e2417674122, 11 pages.
Fedorova et al., "PpCase9 from Pasteurella pneumotropica—a compact Type II-C Cas9 ortholog active in human cells," Nucleic Acids Research, 2020, 13 pages.
GenBank Accession No. NG_054065.1 (2021).
Han et al., "Destabilizing LSD1 by Jade-2 Promotes Neurogenesis: An Antibraking System in Neural Development," Molecular Cell, 2014, 55: 482-494.
Hnisz et al., "Activation of proto-oncogenes by disruption of chromosome neighborhoods," Science, 2016, 351(6280): 1454-1458.
Huang et al., "DNA epigenome editing using CRISPR-Cas SunTag-directed DNMT3A," Genome Biology, 2017, 178:176.
Layer et al., "LMO2 Oncoprotein Stability in T-Cell Leukemia Requires Direct LDB1 Binding," Mol Cell Biol, 2015, 36(3): 488-506.
Lu et al., "Multimode drug inducible CRISPR/Cas9 devices for transcriptional activation and genome editing," Nucleic Acids Research, 2018, 46(5): e25, 15 pages.
Lu et al., "Multimode drug inducible CRISPR/Cas9 devices for transcriptional activation and genome editing," Nucleic Acids Research, 2018, 46(5): Supplemental Materials, 29 pages.
McCormick et al., "The Lmo2 oncogene initiates leukemia in mice by inducing thymocyte self-renewal," Science, 2010, 327(5967): 879-883.
Morita et al., "Targeted DNA demethylation in vivo using dCas9-peptide repeat and scFv-TET1 catalytic domain fusions," Nature Biotechnology, 2016, 34(10): 1060-1065.
Peter et al., "In vivo epigenetic editing of Sema6a promotor reverses transcallosal dysconnectivity caused by C11orf46/Arl14ep rusk gene," Nature Communications, 2019, 10: 4112.
Pflueger et al., "A modular dCas9-Sun Tag DNMT3A epigenome editing system overcomes pervasive off-target activity of direct fusion dCas9-DNMT3A constructs," Genome Research, 2018, 28(8): 1193-1206.
Tarjan et al., "Epigenome editing strategies for the functional annotation of CTCF insulators," Nat Commun, 2019, 10:4258.
Uniprot ID Q4VAX0_HUMAN, entry version 113 Jan. 16, 2019.
Zhou et al., "In vivo simultaneous transcriptional activation of multiple genes in the brain using CRISPR-dCas9-activator transgenic mice, " Nature neuroscience, 2018, 21: 440-446.
Korean Office Action for Application No. 10-2023-7031879 dated Mar. 9, 2026 (10 pages, English translation included).

* cited by examiner

M*DYKDHDGDYKDHDIDYKDDDDK*MAPKKKRKVGRGMDKKYSIGLAIGTNSVGWAVITD
EYKVPSKKFKVLGNTDRHSIKKNLIGALLFDSGETAEATRLKRTARRRYTRRKNRICYLQ
EIFSNEMAKVDDSFFHRLEESFLVEEDKKHERHPIFGNIVDEVAYHEKYPTIYHLRKKLVD
STDKADLRLIYLALAHMIKFRGHFLIEGDLNPDNSDVDKLFIQLVQTYNQLFEENPINASG
VDAKAILSARLSKSRRLENLIAQLPGEKKNGLFGNLIALSLGLTPNFKSNFDLAEDAKLQL
SKDTYDDDLDNLLAQIGDQYADLFLAAKNLSDAILLSDILRVNTEITKAPLSASMIKRYDEH
HQDLTLLKALVRQQLPEKYKEIFFDQSKNGYAGYIDGGASQEEFYKFIKPILEKMDGTEE
LLVKLNREDLLRKQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDKNLPNEKVL
PKHSLLYEYFTVYNELTKVKYVTEGMRKPAFLSGEQKKAIVDLLFKTNRKVTVKQLKEDY
FKKIECFDSVEISGVEDRFNASLGTYHDLLKIIKDKDFLDNEENEDILEDIVLTLTLFEDRE
MIEERLKTYAHLFDDKVMKQLKRRRYTGWGRLSRKLINGIRDKQSGKTILDFLKSDGFAN
RNFMQLIHDDSLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHPVENTQLQNE
KLYLYYLQNGRDMYVDQELDINRLSDYDVDAIVPQSFLKDDSIDNKVLTRSDKNRGKSD
NVPSEEVVKKMKNYWRQLLNAKLITQRKFDNLTKAERGGLSELDKAGFIKRQLVETRQIT
KHVAQILDSRMNTKYDENDKLIREVKVITLKSKLVSDFRKDFQFYKVREINNYHHAHDAY
LNAVVGTALIKKYPKLESEFVYGDYKVYDVRKMIAKSEQEIGKATAKYFFYSNIMNFFKTE
ITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSK
YVNFLYLASHYEKLKGSPEDNEQKQLFVEQHKHYLDEIIEQISEFSKRVILADANLDKVLS
AYNKHRDKPIREQAENIIHLFTLTNLGAPAAFKYFDTTIDRKRYTSTKEVLDATLIHQSITG
LYETRIDLSQLGGDPIAGSKASPKKKRKVGRA*DALDDFDLDMLGSDALDDFDLDMLGS*
*DALDDFDLDMLGSDALDDFDLDML*IN*YPYDVPDYA*S (SEQ ID NO: 1)

FLAG epitope tag = italicized
Nuclear localization sequence = bold
*Streptococcus pyogenes* Cas9 = underlined
VP64 (4x minimal VP16 domain) = italicized and bold
HA epitope tag = italicized and underlined

Fig. 9A

GAGGGCCTATTTCCCATGATTCCTTCATATTTGCATATACGATACAAGGCTG TTAGAGAGATAATTGGAATTAATTTGACTGTAAACACAAAGATATTAGTACA AAATACGTGACGTAGAAAGTAATAATTTCTTGGGTAGTTTGCAGTTTTAAAA TTATGTTTTAAAATGGACTATCATATGCTTATCGTAACTTGAAAGTATTTCGA TTTCTTGGCTTTATATATCTTGTGGAAAGGACGAAACACCGG*GTCTTC*GA*GA AGAC*CT*GTTTTAGAGCTAGAAATAGCAAGTTAAAATAAGGCTAGTCCGTTATC AACTTGAAAAAGTGGCACCGAGTCGGTGC*TTTTTTT (SEQ ID NO:2)

U6 promoter = bold
+1 transcription start site = underlined
BbsI restriction sites to clone in guide RNA = italicized and underlined
Chimeric guide RNA sequence = italicized
Poly-T terminator sequence = bold and underlined

Fig. 9B

Fig. 11A
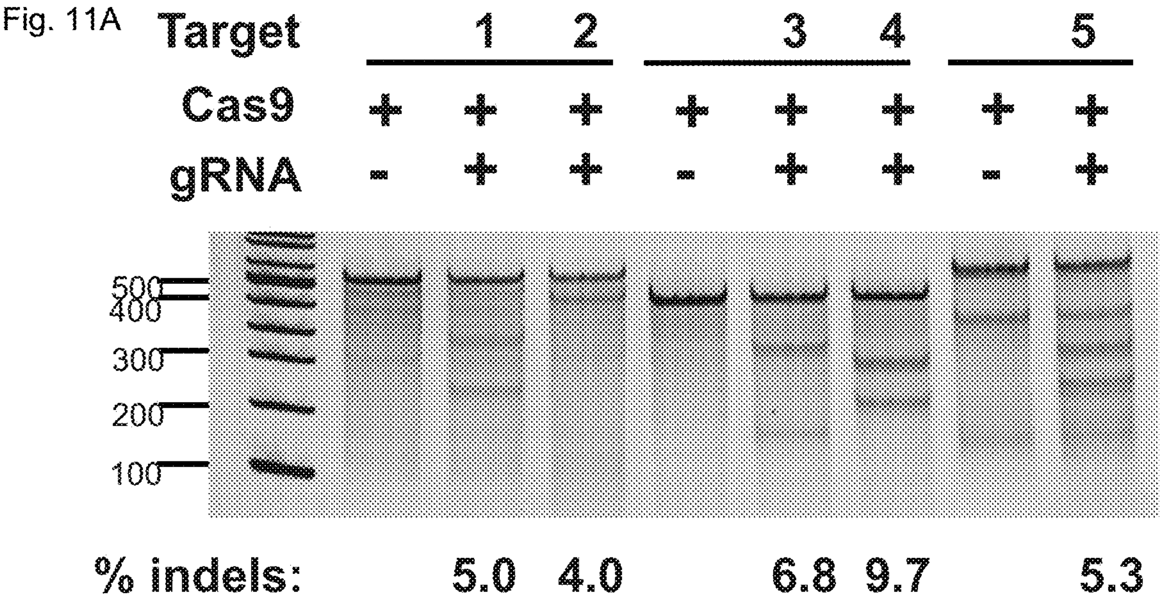
Fig. 11B
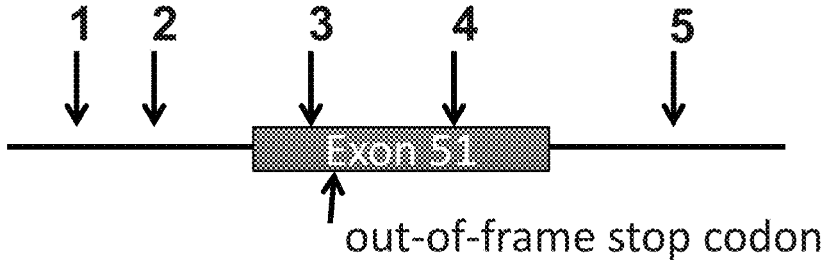
Fig. 11C
Expected cleavage sizes
CR1=352/237
CR2=461/128
CR3=301/150
CR4=272/179
CR5=280/203

Fig. 20A

| SEQ ID NO: | |
|---|---|
| | Intron 50 Exon 51 ▼ PAM |
| 405 | AAAATATTTTAGCTCCTACTCAGACTGTTACTCTGGTGACACAA |
| 406 | TTTTATAAAATCGAGGATGAGTCTGACAATGAGACCACTGTGTT |
| | sgRNA 5'-GCCUACUCAGACUGUUACUC...... |

Fig. 20B

Deletions

| SEQ ID NO: | Sequence | | Length | Frame |
|---|---|---|---|---|
| 407 | TAGCTCCTACTCAGACTGTTACTCTGGTGACACAAC | (x16) | Length | Frame |
| 408 | TAGCTCCTACTCAGACT--------GGTGACCCAAC | | -8 | +2 |
| 409 | TAGCTCCTAC------------TCTGGTGACACAAC | | -12 | +3 |
| 410 | TAGCTCCTACTCAGAC--------TGGTGACACAAC | (x2) | -8 | +2 |
| 411 | TAGCTCCTACTCAGAC--------------------- | | -21 | +3 |
| 412 | TAGCTCCTACTCAGACTGTT---------ACACAAC | | -9 | +3 |
| 413 | TAGCTCCTACTCAGACTG------TGGTGAGGTGAC | | -6 | +3 |
| 414 | TAGCTCCTACTCAGAC----TCTCTGGTGACACAAC | | -4 | +1 |
| 415 | TAGCTCCTACTCAGA-----CCTCTGGTGACACAAC | (x2) | -5 | +2 |
| 416 | TAGCTCCTACTCAGGCTG----TCTGGTGACACAAC | | -4 | +1 |
| 417 | TAGCTCCTACTCAGACT---ACTCTGGTGACACAAC | | -3 | +3 |
| 418 | TAGCTCCTACTCAGAC--------TGTTGACACAAC | | -8 | +2 |
| 419 | -----------------------CTGGTGACACAAC | | -26 | +2 |
| 420 | TAGCTCCTACTCAGACTGTTA-------GACACAAC | | -7 | +1 |
| 421 | TAGCTCCTACTCAGACT---GCTCTGGTGACACAAC | | -3 | +3 |

Insertions

| SEQ ID NO: | Sequence | | Length | Frame |
|---|---|---|---|---|
| 422 | CAGAC---------------TGTTACTCTGGTGAC | (x16) | Length | Frame |
| 423 | CAGACCACCTGTGGTCTCCTA-------CTGGTGAC | | +9 | +3 |

Fig. 20C

Total events: 17/33 (52%)
+1 Frame: 3/17 (18%)
+2 Frame: 7/17 (41%)
+3 Frame: 7/17 (41%)

Fig. 20D

Fig. 22A
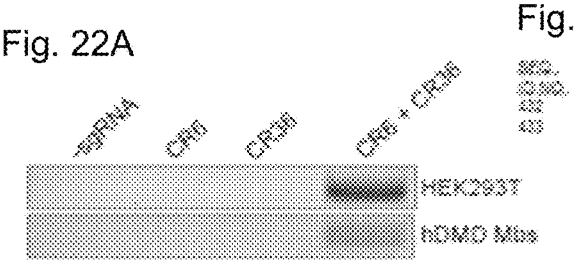
Fig. 22B
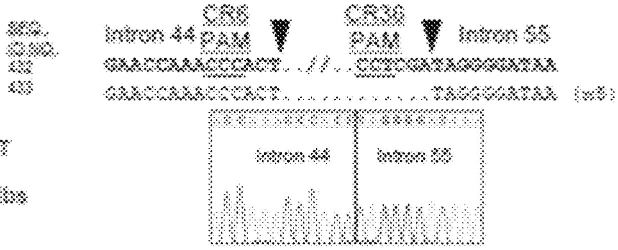
Fig. 22C
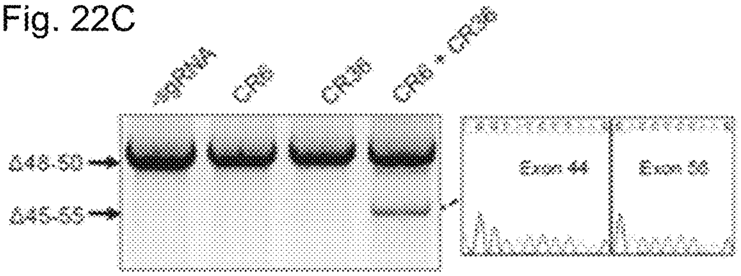
Fig. 22D
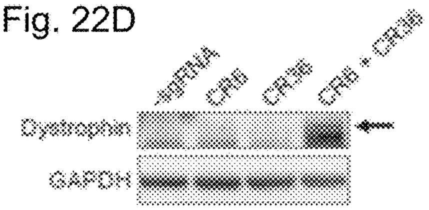
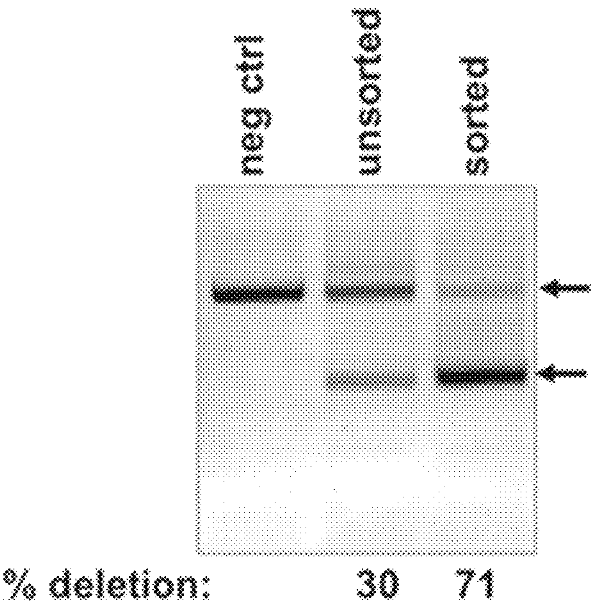
Fig. 23

Survival (%)
100
80
60
40
20
0
Mock
I-SceI
GZF3
-sgRNA
CR1
CR2
CR3
CR5
CR6
CR36

CR3
CR1
CR36
TGT
OT1
OT3
sgRNA:
% indels:
4.9
1.8
3.4
n.d.
1.0

CR1
Chr. X
P1
P2
CR1-OT1
Chr. 16
P5
P6
Primers:
P1/P5
P1/P6
P2/P5
P2/P6
Exp. Size(bp):
489
432
401
339
500 bp
PCR Primers: P2/P5
Sequencing Primer: P2
chrX/intron 50
chr16

CR5
P3
P4
P3/P5
P3/P6
P4/P5
P4/P6
389
311
468
381

Rosa T2A opt DNA sequence (SEQ ID NO: 434)

ATGAGGTCTGACTACAAAGACCATGACGGTGATTATAAAGATCATGACATCGATTACAAGGATGACGATGACAAGAT
GGCCCCCAAGAAGAAGaggaaggtgggcctcgaGCCCGGAGAAAAACCGTACAAGTGCCCTGAGTGCGGAAATCAT
TCTCCGACCCTGGGGCGCTCGTCCGGCACCAAAGGACGCATACAGGGGAAAAGCCGTATAAGTGCCCCGAGTGTGGA
AAGAGCTTCTCGCAGAGAGCCCACCTTGAACGACACCAAAGAACACACACTGGTGAGAAACCCTATAAGTGTCCAGA
GTGCGGCAAATCGTTTAGCAGATCCGATGACTTGGTGCGCCACCAGCGGACACACACGGGTGAAAAGCCCTACAAAT
GCCCGGAGTGTGGGAAGTCGTTTTCAAGGTCGGATCATCTGACTACCCATCAGCGCACCCATACGGGAGCggccgcc
cgcgccctGGTGAAGAGCGAGCTGGAGGAGAAGAAGTCCGAGCTGCGGCACAAGCTGAAGTACGTGCCCCACGAGTA
CATCGAGCTGATCGAGATCGCCAGGAACCCCACCCAGGACCGCATCCTGGAGATGAAGGTGATGGAGTTCTTCATGA
AGGTGTACGGCTACAGGGGAGAGCACCTGGGCGGAAGCAGAAAGCCTGACGGCGCCATCTATACAGTGGGCAGCCCC
ATCGATTACGGCGTGATCGTGGACACAAAGGCCTACAGCGGCGGCTACAATCTGCCTATCGGCCAGGCCGACGAGAT
GCAGAGATACGTGAAGGAGAACCAGACCCGGAATAAGCACATCAACCCCAACGAGTGGTGGAAGGTGTACCCTAGCA
GCGTGACCGAGTTCAAGTTCCTGTTCGTGAGCGGCCACTTCAAGGGCAACTACAAGGCCCAGCTGACCAGGCTGAAC
CGCAAAACCAACTGCAATGGCGCCGTGCTGAGCGTGGAGGAGCTGCTGATCGGCGGCGAGATGATCAAAGCCGGCAC
CCTGACACTGGAGGAGGTGCGGCGCAAGTTCAACAACGGCGAGATCAACTTCGAGGGCAGAGGAAGTCTTCTAACAT
GCGGTGACGTGGAGGAGAATCCCGGCCCTAgatcTGACTACAAAGACCATGACGGTGATTATAAAGATCATGACATC
GATTACAAGGATGACGATGACAAGATGGCCCCCAAGAAGAAGaggaaggtgggcctcgagccGGGAGAGAAGCCGTA
CAAGTGTCCCGAATGTGGAAAGAGCTTCTCACAGTCGGGGGACCTTCGGCGCCACCAGCGCACACATACTGGTGAAA
AGCCGTATAAGTGTCCAGAATGTGGCAAATCATTCTCCACATCAGGGAGCCTGGTCAGGCACCAGCGAACCCACACG
GGTGAGAAGCCCTATAAGTGCCCCGAATGCGGGAAGTCCTTTTCGCAGAGAGCCCACTTGGAGAGGCACCAGAGGAC
CCATACGGGGGAGAAACCTTACAAGTGCCCTGAATGCGGAAAGTCGTTCTCGACCCATCTGGATCTCATCAGACATC
AGAGAACGCACACTGGAGAGAAACCCTACAAATGTCCCGAGTGTGGGAAGTCGTTTAGCCGAAAGGACAATCTCAAA
AACCATCAACGGACACACACGGGTGAAAAACCATACAAATGCCCGGAGTGCGGCAAATCGTTTTCCCAACTTGCGCA
CTTGCGGGCACACCAACGCACGCATACTGGAGCGGCCGCccgcgccCTGGTGAAGAGCGAGCTGGAGGAGAAGAAGT
CCGAGCTGCGGCACAAGCTGAAGTACGTGCCCCACGAGTACATCGAGCTGATCGAGATCGCCAGGAACCCCACCCAG
GACCGCATCCTGGAGATGAAGGTGATGGAGTTCTTCATGAAGGTGTACGGCTACAGGGGAGAGCACCTGGGCGGAAG
CAGAAAGCCTGACGGCGCCATCTATACAGTGGGCAGCCCCATCGATTACGGCGTGATCGTGGACACAAAGGCCTACA
GCGGCGGCTACAATCTGCCTATCGGCCAGGCCGACGAGATGGAGAGATACGTGGAGGAGAACCAGACACGGGATAAG
CACCTCAACCCCAACGAGTGGTGGAAGGTGTACCCTAGCAGCGTGACCGAGTTCAAGTTCCTGTTCGTGAGCGGCCA
CTTCAAGGGCAACTACAAGGCCCAGCTGACCAGGCTGAACCACATCACCAACTGCAATGGCGCCGTGCTGAGCGTGG
AGGAGCTGCTGATCGGCGGCGAGATGATCAAAGCCGGCACCCTGACACTGGAGGAGGTGCGGCGCAAGTTCAACAAC
GGCGAGATCAACTTCTGA

Rosa T2A opt protein sequence (SEQ ID NO: 435)

MRSDYKDHDGDYKDHDIDYKDDDDKMAPKKKRKVGLEPGEKPYKCPECGKSFSDPGALVRHQRTHTGEKPYKCPECG
KSFSQRAHLERHQRTHTGEKPYKCPECGKSFSRSDDLVRHQRTHTGEKPYKCPECGKSFSRSDHLTTHQRTHTGAAA
RALVKSELEEKKSELRHKLKYVPHEYIELIEIARNPTQDRILEMKVMEFFMKVYGYRGEHLGGSRKPDGAIYTVGSP
IDYGVIVDTKAYSGGYNLPIGQADEMQRYVKENQTRNKHINPNEWWKVYPSSVTEFKFLFVSGHFKGNYKAQLTRLN
RKTNCNGAVLSVEELLIGGEMIKAGTLTLEEVRRKFNNGEINFEGRGSLLTCGDVEENPGPRSDYKDHDGDYKDHDI
DYKDDDDKMAPKKKRKVGLEPGEKPYKCPECGKSFSQSGDLRRHQRTHTGEKPYKCPECGKSFSTSGSLVRHQRTHT
GEKPYKCPECGKSFSQRAHLERHQRTHTGEKPYKCPECGKSFSTHLDLIRHQRTHTGEKPYKCPECGKSFSRKDNLK
NHQRTHTGEKPYKCPECGKSFSQLAHLRAHQRTHTGAAARALVKSELEEKKSELRHKLKYVPHEYIELIEIARNPTQ
DRILEMKVMEFFMKVYGYRGEHLGGSRKPDGAIYTVGSPIDYGVIVDTKAYSGGYNLPIGQADEMERYVEENQTRDK
HLNPNEWWKVYPSSVTEFKFLFVSGHFKGNYKAQLTRLNHITNCNGAVLSVEELLIGGEMIKAGTLTLEEVRRKFNN
GEINF

Fig. 33

SASTG capsid sequence (SEQ ID NO: 436)

tggccactccctctatgcgcactcgctcgctcggtggggcctggcgaccaaaggtcgccagacggacgtgctttgca
cgtccggccccaccgagcgagcgagtgcgcatagagggagtggccaactccatcactagaggtatggcagtgacgta
acgcgaagcgcgcgaagcgagaccacgcctaccagctgcgtcagcagtcaggtgaccctttgcgacagtttgcgac
accacgtggccgctgagggtatatattctcgagtgagcgaaccaggagctccatttgaccgcgaaatttgaacgag
cagcagccatgccggggttctacgagattgtcctgaaggtcccgagtgacctggacgagcacctgccgggcatttct
aactcgtttgttaactgggtggccgagaaggaatgggagctgccgccggattctgacatggatccgaatctgattga
gcaggcaccccctgaccgtggccgaaaagcttcagcgcgagttcctggtggagtggcgccgcgtgagtaaggccccgg
aggccctctttttgtccagttcgaaaagggggagacctacttccacctgcacgtgctgattgagaccatcggggtc
aaatccatggtggtcggccgctacgtgagccagattaaagagaagctggtgacccgcatctaccgcggggtcgagcc
gcagcttccgaactggttcgcggtgaccaaaacgcgaaatggcgccgggggcgggaacaaggtggtggacgactgct
acatccccaactacctgctccccaagacccagcccgagctccagtgggcgtggactaacatggaccagtatttaagc
gcctgtttgaatctcgcggagcgtaaacggctggtggcgcagcatctgacgcacgtgtcgcagacgcaggagcagaa
caaagagaatcagaaccccaattctgacgcgccggtcatcaggtcaaaaacctcagccaggtacatggagctggtcg
ggtggctggtggaccgcgggatcacgtcagaaaagcaatggattcaggaggaccaggcctcgtacatctccttcaac
gccgcctccaactcgcggtcccagatcaaggccgcgctggacaatgcctccaagatcatgagcctgacaaagacggc
tccggactacctggtgggcagcaacccgccggaggacattaccaaaaatcggatctaccaaatcctggagctgaacg
ggtacgatccgcagtacgcggcctccgtcttcctgggctgggcgcaaaagaagttcgggaagaggaacaccatctgg
ctctttgggccggccacgacgggtaaaaccaacatcgcggaagccatcgcccacgccgtgcccttctacggctgcgt
aaactggaccaatgagaactttcccttcaacgattgcgtcgacaagatggtgatctggtgggaggagggcaagatga
cggccaaggtcgtggagagcgccaaggccattctgggcggaagcaaggtgcgcgtggaccaaaagtgcaagtcatcg
gcccagatcgaacccactcccgtgatcgtcacctccaacaccaacatgtgcgccgtgattgacgggaacagcaccac
cttcgagcatcagcagccgctgcaggaccggatgtttaaatttgaacttacccgccgtttggaccatgactttggga
aggtcaccaaacaggaagtaaaggactttttccggtgggcttccgatcacgtgactgacgtggctcatgagttctac
gtcagaaagggtggagctaagaaacgccccgcctccaatgacgcggatgtaagcgagccaaaacggcagtgcacgtc
acttgcgcagccgacaacgtcagacgcggaagcaccggcggactacgcggacaggtaccaaaacaaatgttctcgtc
acgtgggcatgaatctgatgctttttccctgtaaaacatgcgagagaatgaatcaaatttccaatgtctgttttacg
catggtcaaagagactgtggggaatgcttccctggaatgtcagaatctcaacccgtttctgtcgtcaaaaagaagac
ttatcagaaactgtgtccaattcatcatatcctggaagggcacccgagattgcctgttcggcctgcgatttggcca
atgtggacttggatgactgtgtttctgagcaataaatgacttaaaccaggtatggctgctgacggttatcttccaga
ttggctcgaggacaacctttctgaaggcattcgtgagtggtgggctctgaaacctggagtccctcaacccaaagcga
accaacaacaccaggacaaccgtcggggtcttgtgcttccgggttacaaatacctcggacccggtaacggactcgac
aaaggagagccggtcaacgaggcggacgcggcagccctcgaacacgacaaagcttacgaccagcagctcaaggccgg
tgacaacccgtacctcaagtacaaccacgccgacgccgagtttcaggagcgtcttcaagaagatacgtcttttgggg
gcaaccttggcagagcagtcttccaggccaaaaagaggatccttgagcctcttggtctggttgaggaagcagctaaa
acggctcctggaaagaagaggcctgtagatcagtctcctcaggaaccggactcatcatctggtgttggcaaatcggg
caaacagcctgccagaaaaagactaaatttcggtcagactggcgactcagagtcagtcccagaccctcaacctctcg
gagaaccaccagcagccccccacaagtttgggatctaatacaatggcttcaggcggtggcgcaccaatggcagacaat
aacgagggtgccgatggagtgggtaattcctcaggaaattggcattgcgattcccaatggctgggcgacagagtcat
caccaccagcaccagaacctgggccctgcccacttacaacaaccatctctacaagcaaatctccagcGCTtcaACGg
gagcttcaaacgacaaccactactttggctacagcaccccttgggggtattttgactttaacagattccactgccac
ttctcaccacgtgactggcagcgactcattaacaacaactggggattccggcccaagaaactcagcttcaagctctt
caacatccaagttaaagaggtcacgcagaacgatggcacgacgactattgccaataaccttaccagcacggttcaag
tgtttacggactcggagtatcagctcccgtacgtgctcgggtcggcgcaccaaggctgtctcccgccgtttccagcg
gacgtcttcatggtccctcagtatggatacctcaccctgaacaacggaagtcaagcggtgggacgctcatcctttta
ctgcctggagtacttcccttcgcagatgctaaggactggaaataacttccaattcagctataccttcgaggatgtac
cttttcacagcagctacgctcacagccagagtttggatcgcttgatgaatcctcttattgatcagtatctgtactac
ctgaacagaacgcaaggaacaacctctggaacaaccaaccaatcacggctgcttttagccaggctgggcctcagtc
tatgtctttgcaggccagaaattggctacctgggccctgctaccggcaacagagactttcaaagactgctaacgaca
acaacaacagtaactttccttggacagcggccagcaaatatcatctcaatggccgcgactcgctggtgaatccagga
ccagctatggccagtcacaaggacgatgaagaaaaatttttccctatgcacggcaatctaatatttggcaaagaagg
gacaacggcaagtaacgcagaattagataatgtaatgattacggatgaagaagagattcgtaccaccaatcctgtgg
caacagagcagtatggaactgtggcaaataacttgcagagctcaaatacagctcccacgactagaactgtcaatgat
caggggggccttacctggcatggtgtggcaagatcgtgacgtgtaccttcaaggacctatctgggcaaagattcctca
cacggatggacactttcatccttctcctctgatgggaggctttggactgaaacatccgcctcctcaaatcatgatca
aaaatactccggtaccggcaaatcctccgacgactttcagcccggccaagtttgcttcatttatcactcagtactcc

Fig. 34A actggacaggtcagcgtggaaattgagtgggagctacagaaagaaaacagcaaacgttggaatccagagattcagta
cacttccaactacaacaagtctgttaatgtggactttactgtagacactaatggtgtttatagtgaacctcgccccta
ttggaacccggtatctcacacgaaacttgtaatcctggttaatcaataaaccgtttaattcgtttcagttgaacttt
ggctcttgtgcacttcttatcttatcttgtttccatggctactgcgtagataagcagcggcctgcggcgcttgcgct
tcgcggtttacaactgctggttaatatttaactctcgccatacctctagtgatggagttggccactccctctatgcg
cactcgctcgctcggtggggcctggacgtgcaaagcacgtccgtctggcgacctttggtcgccaggccccaccgagcg
agcgagtgcgcatagagggagtggccaa

SASTG capsid peptide sequence (SEQ ID NO: 437)

MAADGYLPDWLEDNLSEGIREWWALKPGVPQPKANQQHQDNRRGLVLPGYKYLGPGNGLDKGEPVNEADAAALEHDK
AYDQQLKAGDNPYLKYNHADAEFQERLQEDTSFGGNLGRAVFQAKKRILEPLGLVEEAAKTAPGKKRPVDQSPQEPD
SSSGVGKSGKQPARKRLNFGQTGDSESVPDPQPLGEPPAAPTSLGSNTMASGGGAPMADNNEGADGVGNSSGNWHCD
SQWLGDRVITTSTRTWALPTYNNHLYKQISSASTGASNDNHYFGYSTPWGYFDFNRFHCHFSPRDWQRLINNNWGFR
PKKLSFKLFNIQVKEVTQNDGTTTIANNLTSTVQVFTDSEYQLPYVLGSAHQGCLPPFPADVFMVPQYGYLTLNNGS
QAVGRSSFYCLEYFPSQMLRTGNNFQFSYTFEDVPFHSSYAHSQSLDRLMNPLIDQYLYYLNRTQGTTSGTTNQSRL
LFSQAGPQSMSLQARNWLPGPCYRQQRLSKTANDNNNSNFPWTAASKYHLNGRDSLVNPGPAMASHKDDEEKFFPMH
GNLIFGKEGTTASNAELDNVMITDEEEIRTTNPVATEQYGTVANNLQSSNTAPTTRTVNDQGALPGMVWQDRDVYLQ
GPIWAKIPHTDGHFHPSPLMGGFGLKHPPPQIMIKNTPVPANPPTTFSPAKFASFITQYSTGQVSVEIEWELQKENS
KRWNPEIQYTSNYNKSVNVDFTVDTNGVYSEPRPIGTRYLTRNL

Fig. 34B

DZF16 ZFN target site (SEQ ID NO:442):

5'-CAAACTAGAAATGCCATCTTCCTTGATGTTGGAGGTACCTGC-3'

3'-GTTTGATCTTTACGGTAGAAGGAACTACAACCTCCATGGACG-5'

DZF16-L6 left full amino acid sequence (SEQ ID NO:443)

MDYKDHDGDYKDHDIDYKDDDDKMAPKKKRKVGRLEPGEKPYKCPECGKSFSRKDALRGHQRTHTGEKPY
KCPECGKSFSHRTTLTNHQRTHTGEKPYKCPECGKSFSQRNALAGHQRTHTGEKPYKCPECGKSFSHKNA
LQNHQRTHTGEKPYKCPECGKSFSDPGHLVRHQRTHTGEKPYKCPECGKSFSTSGNLVRHQRTHTGAAAR
ALVKSELEEKKSELRHKLKYVPHEYIELIEIARNPTQDRILEMKVMEFFMKVYGYRGEHLGGSRKPDGAI
YTVGSPIDYGVIVDTKAYSGGYNLPIGQADEMERYVEENQTRDKHLNPNEWWKVYPSSVTEFKFLFVSGH
FKGNYKAQLTRLNHITNCNGAVLSVEELLIGGEMIKAGTLTLEEVRRKFNNGEINF*

DZF16-R6 right full amino acid sequence (SEQ ID NO:444)

MDYKDHDGDYKDHDIDYKDDDDKMAPKKKRKVGRLEPGEKPYKCPECGKSFSQQRSLVGHQRTHTGEKPY
KCPECGKSFSDKKDLTRHQRTHTGEKPYKCPECGKSFSTSGHLVRHQRTHTGEKPYKCPECGKSFSQRAH
LERHQRTHTGEKPYKCPECGKSFSTSGSLVRHQRTHTGEKPYKCPECGKSFSTSGNLVRHQRTHTGAAAR
ALVKSELEEKKSELRHKLKYVPHEYIELIEIARNPTQDRILEMKVMEFFMKVYGYRGEHLGGSRKPDGAI
YTVGSPIDYGVIVDTKAYSGGYNLPIGQADEMQRYVKENQTRNKHINPNEWWKVYPSSVTEFKFLFVSGH
FKGNYKAQLTRLNRKTNCNGAVLSVEELLIGGEMIKAGTLTLEEVRRKFNNGEINF*

Fig. 35

E51C3 target site (SEQ ID NO:445):

5'-(t)ATCTGCCCATGACTGGCGCAGGG(a)-3'

3'-(a)TAGACGGGTACTGACCGCGTCCC(t)-5'

E51C-3L left full amino acid sequence (SEQ ID NO:446)

MDYKDHDGDYKDHDIDYKDDDDKMAPKKKRKVGRLEPGERPFQCRICMRNFSSKQALAVHTRTHTGEKPF
QCRICMRNFSQSTTLKRHLRTHTGEKPFQCRICMRNFSRSDHLSLHLKTHLRGSQLVKSELEEKKSELRH
KLKYVPHEYIELIEIARNPTQDRILEMKVMEFFMKVYGYRGEHLGGSRKPDGAIYTVGSPIDYGVIVDTK
AYSGGYNLPIGQADEMQRYVKENQTRNKHINPNEWWKVYPSSVTEFKFLFVSGHFKGNYKAQLTRLNRKT
NCNGAVLSVEELLIGGEMIKAGTLTLEEVRRKFNNGEINF*

E51C-3R right full amino acid sequence (SEQ ID NO:447)

MDYKDHDGDYKDHDIDYKDDDDKMAPKKKRKVGRLEPGERPFQCRICMRNFSRRAHLQNHTRTHTGEKPF
QCRICMRNFSQSTTLKRHLRTHTGEKPFQCRICMRNFSDGGHLTRHLKTHLRGSQLVKSELEEKKSELRH
KLKYVPHEYIELIEIARNPTQDRILEMKVMEFFMKVYGYRGEHLGGSRKPDGAIYTVGSPIDYGVIVDTK
AYSGGYNLPIGQADEMERYVEENQTRDKHLNPNEWWKVYPSSVTEFKFLFVSGHFKGNYKAQLTRLNHIT
NCNGAVLSVEELLIGGEMIKAGTLTLEEVRRKFNNGEINF*

Fig. 36

DZF15 target site (SEQ ID NO:448):

5'-ACTAGAAATGCCATCTTCCTTGATGTTGGAGGTACCTGCTCT-3'
3'-TGATCTTTACGGTAGAAGGAACTACAACCTCCATGGACGAGA-5'

DZF15-L6 left full amino acid sequence (SEQ ID NO:449)

MDYKDHDGDYKDHDIDYKDDDDKMAPKKKRKVGRLEPGEKPYKCPECGKSFSHRTTLTNHQRTHTGEKPYKCPECGKSFSQRNALAGHQRTHTGEKPYKCPECGKSFSHKNALQNHQRTHTGEKPYKCPECGKSFSDPGHLVRHQRTHTGEKPYKCPECGKSFSTSGNLVRHQRTHTGEKPYKCPECGKSFSQSSNLVRHQRTHTGAAARALVKSELEEKKSELRHKLKYVPHEYIELIEIARNPTQDRILEMKVMEFFMKVYGYRGEHLGGSRKPDGAIYTVGSPIDYGVIVDTKAYSGGYNLPIGQADEMERYVEENQTRDKHLNPNEWWKVYPSSVTEFKFLFVSGHFKGNYKAQLTRLNHITNCNGAVLSVEELLIGGEMIKAGTLTLEEVRRKFNNGEINF*

DZF15-R6 right full amino acid sequence (SEQ ID NO:450)

MDYKDHDGDYKDHDIDYKDDDDKMAPKKKRKVGRLEPGEKPYKCPECGKSFSQRNALAGHQRTHTGEKPYKCPECGKSFSQQRSLVGHQRTHTGEKPYKCPECGKSFSDKKDLTRHQRTHTGEKPYKCPECGKSFSTSGHLVRHQRTHTGEKPYKCPECGKSFSQRAHLERHQRTHTGEKPYKCPECGKSFSTSGSLVRHQRTHTGAAARALVKSELEEKKSELRHKLKYVPHEYIELIEIARNPTQDRILEMKVMEFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFKGNYKAQLTRLNRKTNCNGAVLSVEELLIGGEMIKAGTLTLEEVRRKFNNGEINF*

DZF15-L5 left full amino acid sequence (SEQ ID NO:451)

MDYKDHDGDYKDHDIDYKDDDDKMAPKKKRKVGRLEPGEKPYKCPECGKSFSQRNALAGHQRTHTGEKPYKCPECGKSFSHKNALQNHQRTHTGEKPYKCPECGKSFSDPGHLVRHQRTHTGEKPYKCPECGKSFSTSGNLVRHQRTHTGEKPYKCPECGKSFSQSSNLVRHQRTHTGAAARALVKSELEEKKSELRHKLKYVPHEYIELIEIARNPTQDRILEMKVMEFFMKVYGYRGEHLGGSRKPDGAIYTVGSPIDYGVIVDTKAYSGGYNLPIGQADEMERYVEENQTRDKHLNPNEWWKVYPSSVTEFKFLFVSGHFKGNYKAQLTRLNHITNCNGAVLSVEELLIGGEMIKAGTLTLEEVRRKFNNGEINF*

DZF15-R5 right full amino acid sequence (SEQ ID NO:452)

MDYKDHDGDYKDHDIDYKDDDDKMAPKKKRKVGRLEPGEKPYKCPECGKSFSQQRSLVGHQRTHTGEKPYKCPECGKSFSDKKDLTRHQRTHTGEKPYKCPECGKSFSTSGHLVRHQRTHTGEKPYKCPECGKSFSQRAHLERHQRTHTGEKPYKCPECGKSFSTSGSLVRHQRTHTGAAARALVKSELEEKKSELRHKLKYVPHEYIELIEIARNPTQDRILEMKVMEFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFKGNYKAQLTRLNRKTNCNGAVLSVEELLIGGEMIKAGTLTLEEVRRKFNNGEINF*

Fig. 37

E51C4 target site (SEQ ID NO:453):

5′-(t)GCCATCTTCCTTGATGTTGGAGGT(a)-3′

3′-(a)CGGTAGAAGGAACTACAACCTCCA(t)-5′

E51C-4L left full amino acid sequence (SEQ ID NO:454)

MDYKDHDGDYKDHDIDYKDDDDKMAPKKKRKVGRLEPGERPFQCRICMRNFSSPSKLARHTRTHTGEKPF
QCRICMRNFSVRHNLTRHLRTHTGEKPFQCRICMRNFSQRNNLGRHLKTHTGAAARALVKSELEEKKSEL
RHKLKYVPHEYIELIEIARNPTQDRILEMKVMEFFMKVYGYRGEHLGGSRKPDGAIYTVGSPIDYGVIVD
TKAYSGGYNLPIGQADEMQRYVKENQTRNKHINPNEWWKVYPSSVTEFKFLFVSGHFKGNYKAQLTRLNR
KTNCNGAVLSVEELLIGGEMIKAGTLTLEEVRRKFNNGEINF*

E51C-4R right full amino acid sequence (SEQ ID NO:455)

MDYKDHDGDYKDHDIDYKDDDDKMAPKKKRKVGRLEPGERPFQCRICMRNFSIPNHLARHTRTHTGEKPF
QCRICMRNFSQSAHLKRHLRTHTGEKPFQCRICMRNFSHHNSLTRHLKTHTGAAARALVKSELEEKKSEL
RHKLKYVPHEYIELIEIARNPTQDRILEMKVMEFFMKVYGYRGEHLGGSRKPDGAIYTVGSPIDYGVIVD
TKAYSGGYNLPIGQADEMERYVEENQTRDKHLNPNEWWKVYPSSVTEFKFLFVSGHFKGNYKAQLTRLNH
ITNCNGAVLSVEELLIGGEMIKAGTLTLEEVRRKFNNGEINF*

Fig. 38

SaCas9-NLS (NLS underlined) (SEQ ID NO: 459)

atgaaaaggaactacattctggggctggacatcgggattacaagcgtggggtatgggattattgactatgaaacaag
ggacgtgatcgacgcaggcgtcagactgttcaaggaggccaacgtggaaaacaatgagggacggagaagcaagaggg
gagccaggcgcctgaaacgacggagaaggcacagaatccagagggtgaagaaactgctgttcgattacaacctgctg
accgaccattctgagctgagtggaattaatccttatgaagccagggtgaaaggcctgagtcagaagctgtcagagga
agagttttccgcagctctgctgcacctggctaagcgccgaggagtgcataacgtcaatgaggtggaagaggacaccg
gcaacgagctgtctacaaaggaacagatctcacgcaatagcaaagctctggaagagaagtatgtcgcagagctgcag
ctggaacggctgaagaaagatggcgaggtgagagggtcaattaataggttcaagacaagcgactacgtcaaagaagc
caagcagctgctgaaagtgcagaaggcttaccaccagctggatcagagcttcatcgatacttatatcgacctgctgg
agactcggagaacctactatgagggaccaggagaagggagccccttcggatggaaagacatcaaggaatggtacgag
atgctgatgggacattgcacctattttccagaagagctgagaagcgtcaagtacgcttataacgcagatctgtacaa
cgccctgaatgacctgaacaacctggtcatcaccagggatgaaaacgagaaactggaatactatgagaagttccaga
tcatcgaaaacgtgtttaagcagaagaaaaagcctacactgaaacagattgctaaggagatcctggtcaacgaagag
gacatcaagggctaccgggtgacaagcactggaaaaccagagttcaccaatctgaaagtgtatcacgatattaagga
catcacagcacggaaagaaatcattgagaacgccgaactgctggatcagattgctaagatcctgactatctaccaga
gctccgaggacatccaggaagagctgactaacctgaacagcgagctgacccaggaagagatcgaacagattagtaat
ctgaaggggtacaccggaacacacaacctgtccctgaaagctatcaatctgattctggatgagctgtggcatacaaa
cgacaatcagattgcaatctttaaccggctgaagctggtcccaaaaaaggtggacctgagtcagcagaaagagatcc
caaccacactggtggacgatttcattctgtcacccgtggtcaagcggagcttcatccagagcatcaaagtgatcaac
gccatcatcaagaagtacggcctgcccaatgatatcattatcgagctggctagggagaagaacagcaaggacgcaca
gaagatgatcaatgagatgcagaaacgaaaccggcagaccaatgaacgcattgaagagattatccgaactaccggga
aagagaacgcaaagtacctgattgaaaaaatcaagctgcacgatatgcaggagggaaagtgtctgtattctctggag
gccatccccctggaggacctgctgaacaatccattcaactacgaggtcgatcatattatccccagaagcgtgtcctt
cgacaattcctttaacaacaaggtgctggtcaagcaggaagagaactctaaaaagggcaataggactcctttccagt
acctgtctagttcagattccaagatctcttacgaaacctttaaaaagcacattctgaatctggccaaaggaaagggc
cgcatcagcaagaccaaaaaggagtacctgctggaagagcgggacatcaacagattctccgtccagaaggattttat
taaccggaatctggtggacacaagatacgctactcgcggcctgatgaatctgctgcgatcctatttccgggtgaaca
atctggatgtgaaagtcaagtccatcaacggcgggttcacatcttttctgaggcgcaaatggaagtttaaaaaggag
cgcaacaaagggtacaagcaccatgccgaagatgctctgattatcgcaaatgccgacttcatctttaaggagtggaa
aaagctggacaaagccaagaaagtgatggagaaccagatgttcgaagagaagcaggccgaatctatgcccgaaatcg
agacagaacaggagtacaaggagattttcatcactcctcaccagatcaagcatatcaaggatttcaaggactacaag
tactctcaccgggtggataaaaagcccaacagagagctgatcaatgacaccctgtatagtacaagaaaagacgataa
ggggaatacccctgattgtgaacaatctgaacggactgtacgacaaagataatgacaagctgaaaaagctgatcaaca
aaagtcccgagaagctgctgatgtaccaccatgatcctcagacatatcagaaactgaagctgattatggagcagtac
ggcgacgagaagaacccactgtataagtactatgaagagactgggaactacctgaccaagtatagcaaaaaggataa
tggccccgtgatcaagaagatcaagtactatgggaacaagctgaatgcccatctggacatcacagacgattacccta
acagtcgcaacaaggtggtcaagctgtcactgaagccatacagattcgatgtctatctggacaacggcgtgtataaa
tttgtgactgtcaagaatctggatgtcatcaaaaaggagaactactatgaagtgaatagcaagtgctacgaagaggc
taaaaagctgaaaaagattagcaaccaggcagagttcatcgcctcctttacaacaacgacctgattaagatcaatg
gcgaactgtatagggtcatcggggtgaacaatgatctgctgaaccgcattgaagtgaatatgattgacatcacttac
cgagagtatctggaaaacatgaatgataagcgcccccctcgaattatcaaaacaattgcctctaagactcagagtat
caaaaagtactcaaccgacattctgggaaacctgtatgaggtgaagagcaaaaagcaccctcagattatcaaaaagg
gcagcggaggcaagcgtcctgctgctactaagaaagctggtcaagctaagaaaaagaaa**ggatcctacccatacgat
gttccagattacgct**taa SaCas9 gRNA (SEQ ID NO: 460)

[protospacer]gttttagtactctggaaacagaatctactaaaacaaggcaaaatgccgtgtttatctcgtcaac
ttgttggcgagatttttt

Fig. 40

NmCas9 (NLS 1 underlined NLS 2 underlined/bold, HA tag bold)(SEQ ID NO: 461)

atggtgcctaagaagaagagaaaggtggctgccttcaaacctaattcaatcaactacatcctcggcctcgatatcgg
catcgcatccgtcggctgggcgatggtagaaattgacgaagaagaaaaccccatccgcctgattgatttgggcgtgc
gcgtatttgagcgtgccgaagtaccgaaaacaggcgactcccttgccatggcaaggcgtttggcgcgcagtgttcgc
cgcctgacccgccgtcgcgcccaccgcctgcttcggacccgccgcctattgaaacgcgaaggcgtattacaagccgc
caattttgacgaaaacggcttgattaaatccttaccgaatacaccatggcaacttcgcgcagccgcattagaccgca
aactgacgcctttagagtggtcggcagtcttgttgcatttaatcaaacatcgcggctatttatcgcaacggaaaac
gagggcgaaactgccgataaggagcttggcgctttgcttaaaggcgtagccggcaatgcccatgccttacagacagg
cgatttccgcacaccggccgaattggctttaaataaatttgagaaagaaagcggccatatccgcaatcagcgcagcg
attattcgcatacgttcagccgcaaagatttacaggcggagctgattttgctgtttgaaaaacaaaaagaatttggc
aatccgcatgtttcaggcggccttaaagaaggtattgaaaccctactgatgacgcaacgccctgccctgtccggcga
tgccgttcaaaaaatgttggggcattgcaccttcgaaccggcagagccgaaagccgctaaaaacacctacacagccg
aacgtttcatctggctgaccaagctgaacaacctgcgtattttagagcaaggcagcgagcggccattgaccgatacc
gaacgcgccacgcttatggacgagccatacagaaaatccaaactgacttacgcacaagcccgtaagctgctgggttt
agaagataccgcctttttcaaaggcttgcgctatggtaaagacaatgccgaagcctcaacattgatggaaatgaagg
cctaccatgccatcagccgtgcactggaaaaagaaggattgaaagacaaaaaatccccattaaacctttctcccgaa
ttacaagacgaaatcggcacggcattctccctgttcaaaaccgatgaagacattacaggccgtctgaaagaccgtat
acagcccgaaatcttagaagcgctgttgaaacacatcagcttcgataagttcgtccaaatttccttgaaagcattgc
gccgaattgtgcctctaatggaacaaggcaaacgttacgatgaagcctgcgccgaaatctacggagaccattacggc
aagaagaatacggaagaaaagatttatctgccgccgattcccgccgacgaaatccgcaaccccgtcgtcttgcgcgc
cttatctcaagcacgtaaggtcattaacggcgtggtacgccgttacggctccccagctcgtatccatattgaaactg
caagggaagtaggtaaatcgtttaaagaccgcaaagaaattgagaaacgccaagaagaaaaccgcaaagaccgggaa
aaagccgccgccaaattccgagagtatttccccaatttttgtcggagaacccaaatccaaagatattctgaaactgcg
cctgtacgagcaacaacacggcaaatgcctgtattcgggcaaagaaatcaacttaggccgtctgaacgaaaaaggct
atgtcgaaatcgaccatgccctgccgttctcgcgcacatgggacgacagtttcaacaataaagtactggtattgggc
agcgaaaaccaaaacaaaggcaatcaaaccccttacgaatacttcaacggcaaagacaacagccgcgaatggcagga
atttaaagcgcgtgtcgaaaccagccgtttcccgcgcagtaaaaaacaacggattctgctgcaaaaattcgatgaag
acggctttaaagaacgcaatctgaacgacacgcgctacgtcaaccgtttcctgtgtcaatttgttgccgaccgtatg
cggctgacaggtaaaggcaagaaacgtgtctttgcatccaacggacaaattaccaatctgttgcgcggcttttgggg
attgcgcaaagtgcgtgcggaaaacgaccgccatcacgccttggacgccgtcgtcgttgcctgctcgaccgttgcca
tgcagcagaaaattacccgttttgtacgctataaagagatgaacgcgtttgacggtaaaaccatagacaaagaaaca
ggagaagtgctgcatcaaaaaacacacttcccacaaccttgggaatttttcgcacaagaagtcatgattcgcgtctt
cggcaaaccggacggcaaacccgaattcgaagaagccgataccctagaaaaactgcgcacgttgcttgccgaaaat
tatcatctcgccccgaagccgtacacgaatacgttacgccactgtttgtttcacgcgcgcccaatcggaagatgagc
gggcaagggcatatggagaccgtcaaatccgccaaacgactggacgaaggcgtcagcgtgttgcgcgtaccgctgac
acagttaaaactgaaagacttggaaaaaatggtcaatcgggagcgcgaacctaagctatacgaagcactgaaagcac
ggctggaagcacataaagacgatcctgccaaagcctttgccgagccgttttacaaatacgataaagcaggcaaccgc
acccaacaggtaaaagccgtacgcgtagagcaagtacagaaaaccggcgtatgggtgcgcaaccataacggtattgc
cgacaacgcaaccatggtgcgcgtagatgtgtttgagaaaggcgacaagtattatctggtaccgatttacagttggc
aggtagcgaaagggattttgccggatagggctgttgtacaaggaaaagatgaagaagattggcaacttattgatgat
agtttcaactttaaattctcattacaccctaatgatttagtcgaggttataacaaaaaaagctagaatgtttggtta
ctttgccagctgccatcgaggcacaggtaatatcaatatacgcattcatgatcttgatcataaaattggcaaaaatg
gaatactggaaggtatcggcgtcaaaaccgccctttcattccaaaaataccaaattgacgaactgggcaaagaaatc
agaccatgccgtctgaaaaaacgcccgcctgtccgttacccatacgatgttccagattacgctgcagctccagcagc
gaagaaaaagaagctggattaa NmCas9 short hairpin from Thomson PNAS 2013 (SEQ ID NO: 462)

[protospacer]GTTGTAGCTCCCTTTCTCATTTCGGAAACGAAATGAGAACCGTTGCTACAATAAGGCCGTCTGA
AAAGATGTGCCGCAACGCTCTGCCCCTTAAAGCTTCTGCTTTAAGGGGCTTTTTTT NmCas9 long hairpin from Church Nature Biotech 2013 (SEQ ID NO: 463)

[protospacer]GTTGTAGCTCCCTTTCTCATTTCGCAGTGCTACAATGAAAATTGTCGCACTGCGAAATGAGAACC
GTTGCTACAATAAGGCCGTCTGAAAAGATGTGCCGCAACGCTCTGCCCCTTAAAGCTTCTGCTTTAAGGGGCTTTTT
TT

Fig. 41

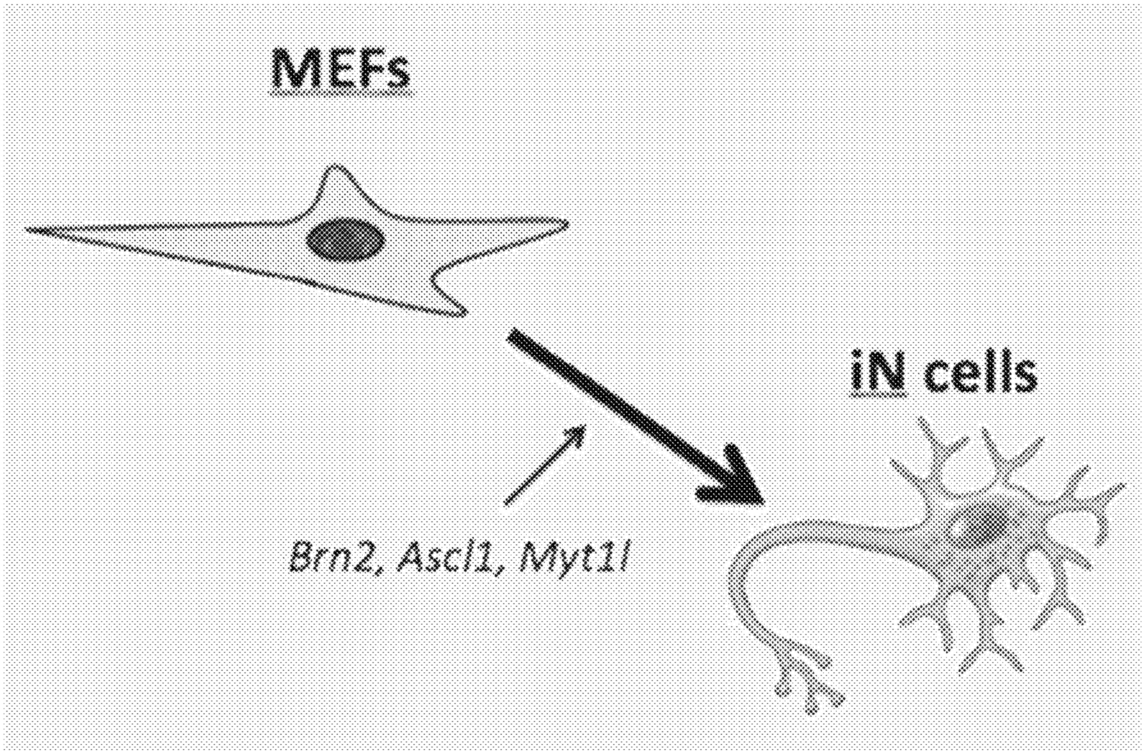
Fig. 48
Fig. 49A
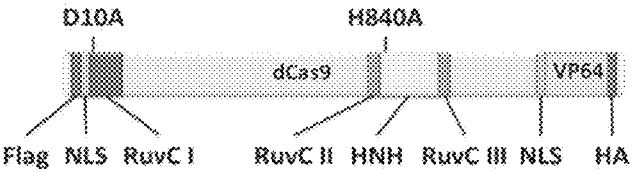
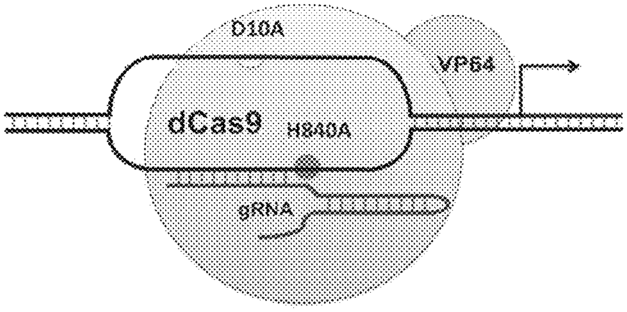
Fig. 49B
Fig. 49C
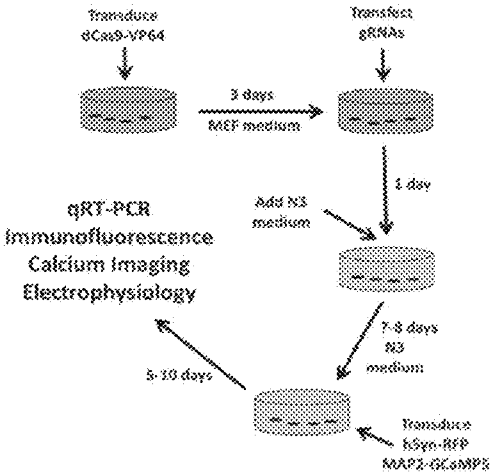

Fig. 50A
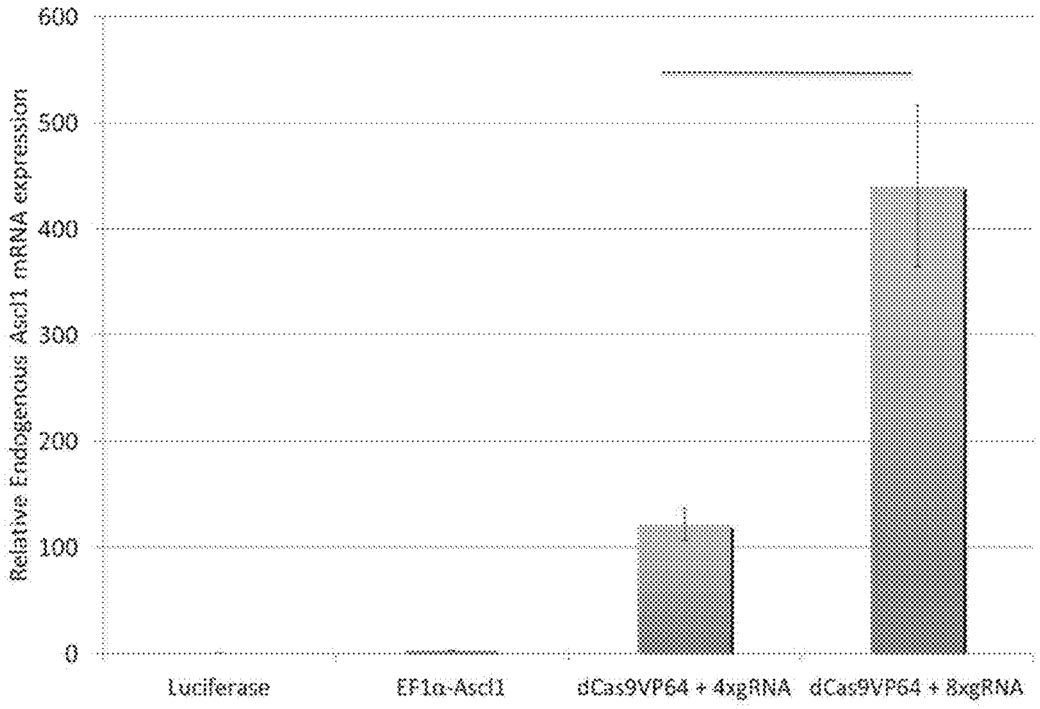
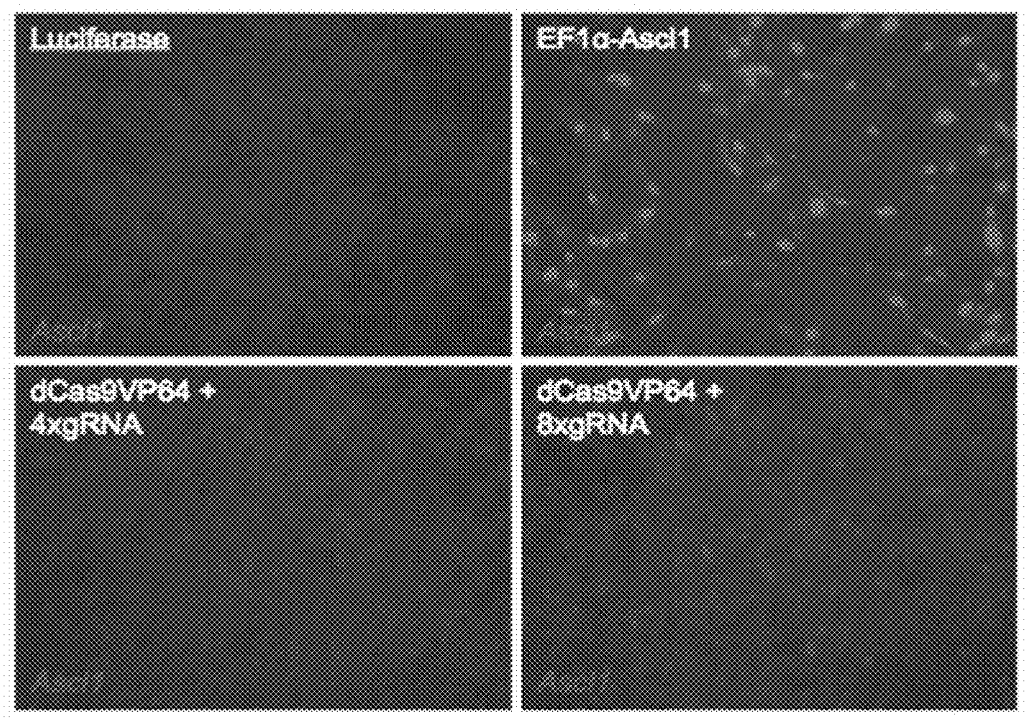
Fig. 50B

Fig. 51A
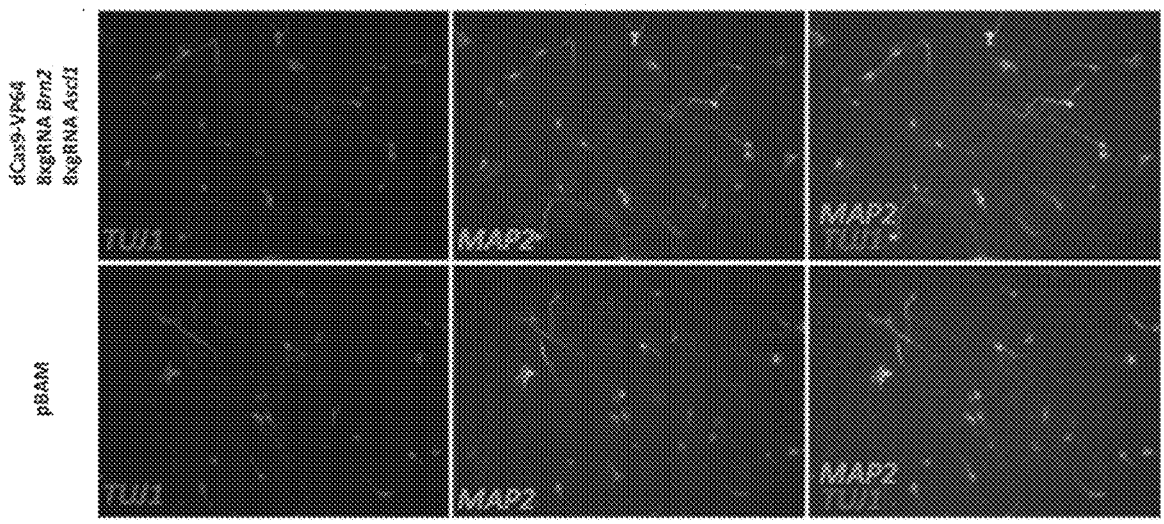
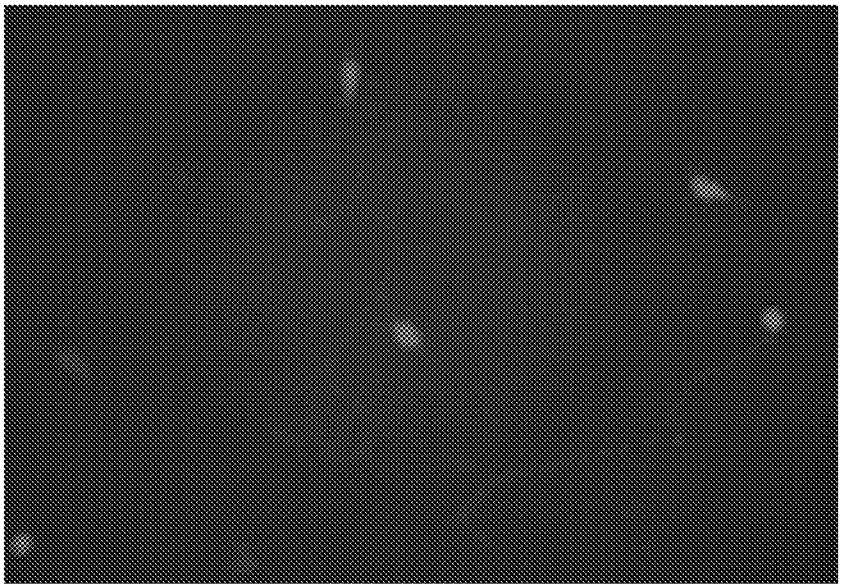
Fig. 51B i. dCas9

M*DYKDHDGDYKDHDIDYKDDDDK*MAPKKKRKVGRGMDKKYSIGLAIGTNSVGWAVITDEY
KVPSKKFKVLGNTDRHSIKKNLIGALLFDSGETAEATRLKRTARRRYTRRKNRICYLQEI
FSNEMAKVDDSFFHRLEESFLVEEDKKHERHPIFGNIVDEVAYHEKYPTIYHLRKKLVDS
TDKADLRLIYLALAHMIKFRGHFLIEGDLNPDNSDVDKLFIQLVQTYNQLFEENPINASG
VDAKAILSARLSKSRRLENLIAQLPGEKKNGLFGNLIALSLGLTPNFKSNFDLAEDAKLQ
LSKDTYDDDLDNLLAQIGDQYADLFLAAKNLSDAILLSDILRVNTEITKAPLSASMIKRY
DEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILT
FRIPYYVGPLARGNSRFAWMTRKSEETITPWNFEEVVDKGASAQSFIERMTNFDKNLPNE
KVLPKHSLLYEYFTVYNELTKVKYVTEGMRKPAFLSGEQKKAIVDLLFKTNRKVTVKQLK
EDYFKKIECFDSVEISGVEDRFNASLGTYHDLLKIIKDKDFLDNEENEDILEDIVLTLTL
FEDREMIEERLKTYAHLFDDKVMKQLKRRRYTGWGRLSRKLINGIRDKQSGKTILDFLKS
DGFANRNFMQLIHDDSLTFKEDIQKAQVSGQGDSLHEHIANLAGSPAIKKGILQTVKVVD
ELVKVMGRHKPENIVIEMARENQTTQKGQKNSRERMKRIEEGIKELGSQILKEHPVENTQ
LQNEKLYLYYLQNGRDMYVDQELDINRLSDYDVDHIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNF
FKTEITLANGEIRKRPLIETNGETGEIVWDKGRDFATVRKVLSMPQVNIVKKTEVQTGGF
SKESILPKRNSDKLIARKKDWDPKKYGGFDSPTVAYSVLVVAKVEKGKSKKLKSVKELLG
ITIMERSSFEKNPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDA
TLIHQSITGLYETRIDLSQLGGDPKKKRKVG

Amino Acid Legend:

*"Flag" Epitope*
Nuclear Localization Sequence
*Streptococcus pyogenes* Cas9 (D10A, H840A)
VP64 Effector
p300 Core Effector
*"HA" Epitope*

Fig. 61A ii. dCas9$^{VP64}$

MDYKDHDGDYKDHDIDYKDDDDKMAPKKKRKVGRGMDKKYSIGLAIGTNSVGWAVITDEY
KVPSKKFKVLGNTDRHSIKKNLIGALLFDSGETAEATRLKRTARRRYTRRKNRICYLQEI
FSNEMAKVDDSFFHRLEESFLVEEDKKHERHPIFGNIVDEVAYHEKYPTIYHLRKKLVDS
TDKADLRLIYLALAHMIKFRGHFLIEGDLNPDNSDVDKLFIQLVQTYNQLFEENPINASG
VDAKAILSARLSKSRRLENLIAQLPGEKKNGLFGNLIALSLGLTPNFKSNFDLAEDAKLQ
LSKDTYDDDLDNLLAQIGDQYADLFLAAKNLSDAILLSDILRVNTEITKAPLSASMIKRY
DEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILT
FRIPYYVGPLARGNSRFAWMTRKSEETITPWNFEEVVDKGASAQSFIERMTNFDKNLPNE
KVLPKHSLLYEYFTVYNELTKVKYVTEGMRKPAFLSGEQKKAIVDLLFKTNRKVTVKQLK
EDYFKKIECFDSVEISGVEDRFNASLGTYHDLLKIIKDKDFLDNEENEDILEDIVLTLTL
FEDREMIEERLKTYAHLFDDKVMKQLKRRRYTGWGRLSRKLINGIRDKQSGKTILDFLKS
DGFANRNFMQLIHDDSLTFKEDIQKAQVSGQGDSLHEHIANLAGSPAIKKGILQTVKVVD
ELVKVMGRHKPENIVIEMARENQTTQKGQKNSRERMKRIEEGIKELGSQILKEHPVENTQ
LQNEKLYLYYLQNGRDMYVDQELDINRLSDYDVDAIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNF
FKTEITLANGEIRKRPLIETNGETGEIVWDKGRDFATVRKVLSMPQVNIVKKTEVQTGGF
SKESILPKRNSDKLIARKKDWDPKKYGGFDSPTVAYSVLVVAKVEKGKSKKLKSVKELLG
ITIMERSSFEKNPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDA
TLIHQSITGLYETRIDLSQLGGDPIAGSKASPKKKRKVGRADALDDFDLDMLGSDALDDF
DLDMLGSDALDDFDLDMLGSDALDDFDLDMLINYPYDVPDYAS

Fig. 61B iii. $dCas9^{p300\ Core}$

*MDYKDHDGDYKDHDIDYKDDDDK*MAPKKKRKVGRGMDKKYSIGLAIGTNSVGWAVITDEY
KVPSKKFKVLGNTDRHSIKKNLIGALLFDSGETAEATRLKRTARRRYTRRKNRICYLQEI
FSNEMAKVDDSFFHRLEESFLVEEDKKHERHPIFGNIVDEVAYHEKYPTIYHLRKKLVDS
TDKADLRLIYLALAHMIKFRGHFLIEGDLNPDNSDVDKLFIQLVQTYNQLFEENPINASG
VDAKAILSARLSKSRRLENLIAQLPGEKKNGLFGNLIALSLGLTPNFKSNFDLAEDAKLQ
LSKDTYDDDLDNLLAQIGDQYADLFLAAKNLSDAILLSDILRVNTEITKAPLSASMIKRY
DEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILT
FRIPYYVGPLARGNSRFAWMTRKSEETITPWNFEEVVDKGASAQSFIERMTNFDKNLPNE
KVLPKHSLLYEYFTVYNELTKVKYVTEGMRKPAFLSGEQKKAIVDLLFKTNRKVTVKQLK
EDYFKKIECFDSVEISGVEDRFNASLGTYHDLLKIIKDKDFLDNEENEDILEDIVLTLTL
FEDREMIEERLKTYAHLFDDKVMKQLKRRRYTGWGRLSRKLINGIRDKQSGKTILDFLKS
DGFANRNFMQLIHDDSLTFKEDIQKAQVSGQGDSLHEHIANLAGSPAIKKGILQTVKVVD
ELVKVMGRHKPENIVIEMARENQTTQKGQKNSRERMKRIEEGIKELGSQILKEHPVENTQ
LQNEKLYLYYLQNGRDMYVDQELDINRLSDYDVDAIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNF
FKTEITLANGEIRKRPLIETNGETGEIVWDKGRDFATVRKVLSMPQVNIVKKTEVQTGGF
SKESILPKRNSDKLIARKKDWDPKKYGGFDSPTVAYSVLVVAKVEKGKSKKLKSVKELLG
ITIMERSSFEKNPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDA
TLIHQSITGLYETRIDLSQLGGDPIAGSKASPKKKRKVGRAIFKPEELRQALMPTLEALY
RQDPESLPFRQPVDPQLLGIPDYFDIVKSPMDLSTIKRKLDTGQYQEPWQYVDDIWLMFN
NAWLYNRKTSRVYKYCSKLSEVFEQEIDPVMQSLGYCCGRKLEFSPQTLCCYGKQLCTIP
RDATYYSYQNRYHFCEKCFNEIQGESVSLGDDPSQPQTTINKEQFSKRKNDTLDPELFVE
CTECGRKMHQICVLHHEIIWPAGFVCDGCLKKSARTRKENKFSAKRLPSTRLGTFLENRV
NDFLRRQNHPESGEVTVRVVHASDKTVEVKPGMKARFVDSGEMAESFPYRTKALFAFEEI
DGVDLCFFGMHVQEYGSDCPPPNQRRVYISYLDSVHFFRPKCLRTAVYHEILIGYLEYVK
KLGYTTGHIWACPPSEGDDYIFHCHPPDQKIPKPKRLQEWYKKMLDKAVSERIVHDYKDI
FKQATEDRLTSAKELPYFEGDFWPNVLEESIKELEQEEEERKREENTSNESTDVTKGDSK
NAKKKNNKKTSKNKSSLSRGNKKKPGMPNVSNDLSQKLYATMEKHKEVFFVIRLIAGPAA
NSLPPIVDPDPLIPCDLMDGRDAFLTLARDKHLEFSSLRRAQWSTMCMLVELHTQSQD*YP*
*YDVPDYAS*

Fig. 61C

CAS9 FUSION PROTEINS, RNA-GUIDED GENE EDITING, GENE REGULATION COMPOSITIONS, AND METHODS COMPRISING THE SAME

CROSS REFERENCE TO RELATED APPLICATIONS

This application is a continuation of U.S. patent application Ser. No. 15/991,333, filed May 29, 2018, which is a divisional of U.S. patent application Ser. No. 14/895,316 filed Dec. 2, 2015, U.S. Pat. No. 10,704,060, which is a national stage filing under 35 U.S.C. 371 of International Patent Application No. PCT/US2014/041190, filed Jun. 5, 2014, which claims the benefit of priority to U.S. Provisional Application No. 61/831,481, filed Jun. 5, 2013, U.S. Provisional Application No. 61/839,127, filed Jun. 25, 2013, U.S. Provisional Application No. 61/904,911, filed Nov. 15, 2013, U.S. Provisional Application No. 61/967,466, filed Mar. 19, 2014, and U.S. Provisional Application No. 61/981,575, filed Apr. 18, 2014, all of which are incorporated herein by reference in their entirety.

STATEMENT OF GOVERNMENT INTEREST

This invention was made with government support under federal grant numbers DP2-OD008586 and R01DA036865 awarded by NIH and CBET-1151035 awarded by the National Science Foundation. The U.S. Government has certain rights to this invention.

SEQUENCE LISTING

The instant application contains a Sequence Listing which has been submitted electronically in ASCII format and is hereby incorporated by reference in its entirety. Said ASCII copy, created on Jul. 6, 2018, is named "028193-9164-US04_As_Filed_Subst_Sequence_Listing" and is 331,257 bytes in size.

TECHNICAL FIELD

The present disclosure relates to the field of gene expression alteration, genome engineering and genomic alteration of genes using Clustered Regularly Interspaced Short Palindromic Repeats (CRISPR)/CRISPR-associated (Cas) 9-based systems and viral delivery systems. The present disclosure also relates to the field of genome engineering and genomic alteration of genes in muscle, such as skeletal muscle and cardiac muscle.

BACKGROUND

Synthetic transcription factors have been engineered to control gene expression for many different medical and scientific applications in mammalian systems, including stimulating tissue regeneration, drug screening, compensating for genetic defects, activating silenced tumor suppressors, controlling stem cell differentiation, performing genetic screens, and creating synthetic gene circuits. These transcription factors can target promoters or enhancers of endogenous genes, or be purposefully designed to recognize sequences orthogonal to mammalian genomes for transgene regulation. The most common strategies for engineering novel transcription factors targeted to user-defined sequences have been based on the programmable DNA-binding domains of zinc finger proteins and transcription-activator like effectors (TALEs). Both of these approaches involve applying the principles of protein-DNA interactions of these domains to engineer new proteins with unique DNA-binding specificity. Although these methods have been widely successful for many applications, the protein engineering necessary for manipulating protein-DNA interactions can be laborious and require specialized expertise.

Additionally, these new proteins are not always effective. The reasons for this are not yet known but may be related to the effects of epigenetic modifications and chromatin state on protein binding to the genomic target site. In addition, there are challenges in ensuring that these new proteins, as well as other components, are delivered to each cell. Existing methods for delivering these new proteins and their multiple components include delivery to cells on separate plasmids or vectors which leads to highly variable expression levels in each cell due to differences in copy number. Additionally, gene activation following transfection is transient due to dilution of plasmid DNA, and temporary gene expression may not be sufficient for inducing therapeutic effects. Furthermore, this approach is not amenable to cell types that are not easily transfected. Thus another limitation of these new proteins is the potency of transcriptional activation.

Site-specific nucleases can be used to introduce site-specific double strand breaks at targeted genomic loci. This DNA cleavage stimulates the natural DNA-repair machinery, leading to one of two possible repair pathways. In the absence of a donor template, the break will be repaired by non-homologous end joining (NHEJ), an error-prone repair pathway that leads to small insertions or deletions of DNA. This method can be used to intentionally disrupt, delete, or alter the reading frame of targeted gene sequences. However, if a donor template is provided along with the nucleases, then the cellular machinery will repair the break by homologous recombination, which is enhanced several orders of magnitude in the presence of DNA cleavage. This method can be used to introduce specific changes in the DNA sequence at target sites. Engineered nucleases have been used for gene editing in a variety of human stem cells and cell lines, and for gene editing in the mouse liver. However, the major hurdle for implementation of these technologies is delivery to particular tissues in vivo in a way that is effective, efficient, and facilitates successful genome modification.

Hereditary genetic diseases have devastating effects on children in the United States. These diseases currently have no cure and can only be managed by attempts to alleviate the symptoms. For decades, the field of gene therapy has promised a cure to these diseases. However technical hurdles regarding the safe and efficient delivery of therapeutic genes to cells and patients have limited this approach. Duchenne Muscular Dystrophy (DMD) is the most common hereditary monogenic disease and occurs in 1 in 3500 males. DMD is the result of inherited or spontaneous mutations in the dystrophin gene. Dystrophin is a key component of a protein complex that is responsible for regulating muscle cell integrity and function. DMD patients typically lose the ability to physically support themselves during childhood, become progressively weaker during the teenage years, and die in their twenties. Current experimental gene therapy strategies for DMD require repeated administration of transient gene delivery vehicles or rely on permanent integration of foreign genetic material into the genomic DNA. Both of these methods have serious safety concerns. Furthermore, these strategies have been limited by an inability to deliver the large and complex dystrophin gene sequence.

SUMMARY

The present invention is directed to a fusion protein comprising two heterologous polypeptide domains. The first polypeptide domain comprises a Clustered Regularly Interspaced Short Palindromic Repeats associated (Cas) protein and the second polypeptide domain has an activity selected from the group consisting of transcription activation activity, transcription repression activity, transcription release factor activity, histone modification activity, nuclease activity, nucleic acid association activity, methylase activity, and demethylase activity. The Cas protein may comprise Cas9. The Cas9 may comprise at least one amino acid mutation which knocks out nuclease activity of Cas9. The at least one amino acid mutation may be at least one of D10A and H840A. The Cas protein may comprise iCas9 (amino acids 36-1403 of SEQ ID NO: 1). The second polypeptide domain may have transcription activation activity. The second polypeptide domain may comprise at least one VP16 transcription activation domain repeat. The second polypeptide domain may comprise a VP16 tetramer ("VP64") or a p65 activation domain. The fusion protein may further comprise a linker connecting the first polypeptide domain to the second polypeptide domain. The fusion protein may comprise iCas9-VP64.

The present invention is directed to a DNA targeting system comprising said fusion protein and at least one guide RNA (gRNA). The at least one gRNA may comprise a 12-22 base pair complementary polynucleotide sequence of the target DNA sequence followed by a protospacer-adjacent motif. The at least one gRNA may target a promoter region of a gene, an enhancer region of a gene, or a transcribed region of a gene. The at least one gRNA may target an intron of a gene. The at least one gRNA may target an exon of a gene. The at least one gRNA may target a the promoter region of a gene selected from the group consisting of ASCL1, BRN2, MYT1L, NANOG, VEGFA, TERT, IL1B, ILIR2, IL1RN, HBG1, HBG2, and MYOD. The at least one gRNA may comprise at least one of SEQ ID NOs: 5-40, 65-144, 492-515, 540-563, and 585-625.

The present invention is directed to a DNA targeting system that binds to a dystrophin gene comprising Cas9 and at least one guide RNA (gRNA). The at least one gRNA may target an intron of the dystrophin gene. The at least one gRNA may target an exon of the dystrophin gene. The at least one guide RNA may comprise at least one of SEQ ID NOs: 5-40, 65-144, 492-515, 540-563, and 585-625. The DNA targeting system may comprise between one and ten different gRNAs.

The present invention is directed to an isolated polynucleotide encoding said fusion protein or said DNA targeting system.

The present invention is directed to a vector comprising said isolated polynucleotide.

The present invention is directed to a cell comprising said isolated polynucleotide or said vector.

The present invention is directed to a method of modulating mammalian gene expression in a cell. The method comprises contacting the cell with said fusion protein, said DNA targeting system, said isolated polynucleotide, or said vector. The gene expression may be induced.

The present invention is directed to a method of transdifferentiating or inducing differentiation of a cell. The method comprises contacting the cell with said fusion protein, said DNA targeting system, said isolated polynucleotide, or said vector. The cell may be a fibroblast cell or an induced pluripotent stem cells. The fibroblast cell may be transdifferentiated into a neuronal cell or a myogenic cell. The DNA targeting system may be contacted with the cell and at least one gRNA targets a promoter region of at least one gene selected from the group consisting of ASCL1, BRN2, MYOD1, and MYT1L. The DNA targeting system may comprise at least one gRNA that targets the promoter region of the ASCL1 gene and at least one gRNA that targets the promoter region of the BRN2 gene. The DNA targeting system may comprise between one and twenty different gRNAs. The DNA targeting system may comprise 8 or 16 different gRNAs. The DNA targeting system may comprise dCas9-VP64. The DNA targeting system may be delivered to the cell virally or non-virally.

The present invention is directed to a method of correcting a mutant gene in a cell. The method comprises administering to a cell containing said DNA targeting system, said isolated polynucleotide, or said vector. The correction of the mutant gene may comprise homology-directed repair. The method may further comprise administering to the cell a donor DNA. The mutant gene may comprise a frameshift mutation which causes a premature stop codon and a truncated gene product. The correction of the mutant gene may comprise nuclease mediated non-homologous end joining. The correction of the mutant gene may comprise a deletion of a premature stop codon, a disruption of a splice acceptor site, a deletion of one or more exons, or disruption of a splice donor sequence. The deletion of one or more exons may result in the correction of the reading frame.

The present invention is directed to a method of treating a subject in need thereof having a mutant dystrophin gene. The method comprises administering to the subject said DNA targeting system, said isolated polynucleotide, or said vector. The subject may be suffering from Duchenne muscular dystrophy.

The present invention is directed to a method of correcting a mutant dystrophin gene in a cell. The method comprises administering to a cell containing a mutant dystrophin gene said DNA targeting system, said isolated polynucleotide, said vector, or said cell. The mutant dystrophin gene may comprise a premature stop codon, disrupted reading frame via gene deletion, an aberrant splice acceptor site, or an aberrant splice donor site, and wherein the target region is upstream or downstream of the premature stop codon, disrupted reading frame, aberrant splice acceptor site, or the aberrant splice donor site. The correction of the mutant dystrophin gene may comprise homology-directed repair. The method may further comprise administering to the cell a donor DNA. The mutant dystrophin gene may comprise a frameshift mutation which causes a premature stop codon and a truncated gene product. The correction of the mutant dystrophin gene may comprise nuclease mediated non-homologous end joining. The correction of the mutant dystrophin gene may comprise a deletion of a premature stop codon, correction of a disrupted reading frame, or modulation of splicing by disruption of a splice acceptor site or disruption of a splice donor sequence. The correction of the mutant dystrophin gene may comprise a deletion of exons 45-55 or exon 51.

The present invention is directed to a kit comprising said fusion protein, said DNA targeting system, said isolated polynucleotide, said vector, or said cell.

The present invention is directed to a method of modulating mammalian gene expression in a cell. The method comprises contacting the cell with a polynucleotide encoding a DNA targeting system. The DNA targeting system comprises said fusion protein and at least one guide RNA (gRNA). The DNA targeting system may comprise between one and ten different gRNAs. The different gRNAs may bind to different target regions within the target gene. The target regions may be separated by at least one nucleotide. The target regions may be separated by about 15 to about 700 base pairs. Each of the different gRNAs may bind to at least one different target genes. The different target genes may be located on same chromosome. The different target genes may be located on different chromosomes. The at least one target region may be within a non-open chromatin region, an open chromatin region, a promoter region of the target gene, an enhancer region of the target gene, a transcribed region of the target gene, or a region upstream of a transcription start site of the target gene. The at least one target region may be located between about 1 to about 1000 base pairs upstream of a transcription start site of a target gene. The at least one target region may be located between about 1 to about 600 base pairs upstream of a transcription start site of a target gene. The gene expression may be induced. The DNA targeting system may comprise two different gRNAs, three different gRNAs, four different gRNAs, five different gRNAs, six different gRNAs, seven different gRNAs, eight different gRNAs, nine different gRNAs, or ten different gRNAs. The at least one guide RNA may target a promoter region of a gene selected from the group consisting of ASCL1, BRN2, MYT1L, NANOG, VEGFA, TERT, IL1B, ILIR2, IL1RN, HBG1, HBG2, and MYOD. The at least one guide RNA may comprise at least one of SEQ ID NOs: 5-40, 65-144, 492-515, 540-563, and 585-625. The at least one target region may be within an intron or an exon of a target gene.

The present invention is directed to a composition for inducing mammalian gene expression in a cell. The composition comprises said fusion protein and at least one guide RNA (gRNA).

The present invention is directed to a composition for inducing mammalian gene expression in a cell. The composition comprises an isolated polynucleotide sequence encoding said fusion protein and at least one guide RNA (gRNA). The at least one guide RNA may target a promoter region of a gene selected from the group consisting of ASCL1, BRN2, MYT1L, NANOG, VEGFA, TERT, IL1B, ILIR2, IL1RN, HBG1, HBG2, and MYOD. The at least one guide RNA may comprise at least one of SEQ ID NOs 5-40, 65-144, 492-515, 540-563, and 585-625.

The present invention is directed to a cell comprising said composition for inducing mammalian gene expression in a cell.

The present invention is directed to a kit comprising said composition for inducing mammalian gene expression in a cell or said cell comprising said composition for inducing mammalian gene expression in a cell.

The present invention is directed to a kit for inducing mammalian gene expression in a cell. The kit comprises said composition for inducing mammalian gene expression in a cell or said cell comprising said composition for inducing mammalian gene expression in a cell.

The present invention is directed to a composition for genome editing in a muscle of a subject. The composition comprises a modified adeno-associated virus (AAV) vector and a nucleotide sequence encoding a site-specific nuclease. The muscle is skeletal muscle or cardiac muscle. The modified AAV vector may have enhanced cardiac and skeletal muscle tissue tropism. The site-specific nuclease may comprise a zinc finger nuclease, a TAL effector nuclease, or a CRISPR/Cas9 system. The site-specific nuclease may bind a gene or locus in the cell of the muscle. The gene or locus may be dystrophin gene. The composition may further comprise a donor DNA or transgene.

The present invention is directed to a kit comprising said composition for genome editing in a muscle of a subject.

The present invention is directed to a method of genome editing in a muscle of a subject. The method comprises administering to the muscle said composition for genome editing in a muscle of a subject, wherein the muscle is skeletal muscle or cardiac muscle. The genome editing may comprise correcting a mutant gene or inserting a transgene. Correcting a mutant gene may comprise deleting, rearranging, or replacing the mutant gene. Correcting the mutant gene may comprise nuclease-mediated non-homologous end joining or homology-directed repair.

The present invention is directed to a method of treating a subject. The method comprises administering said composition for genome editing in a muscle of a subject to a muscle of the subject, wherein the muscle is skeletal muscle or cardiac muscle. The subject may be suffering from a skeletal muscle condition or a genetic disease. The subject may be suffering from Duchenne muscular dystrophy.

The present invention is directed to a method of correcting a mutant gene in a subject, the method comprises administering said composition for genome editing in a muscle of a subject. The muscle is skeletal muscle or cardiac muscle. The composition may be injected into the skeletal muscle of the subject. The composition may be injected systemically to the subject. The skeletal muscle may be tibialis anterior muscle.

The present invention is directed to a modified lentiviral vector for genome editing in a subject comprising a first polynucleotide sequence encoding said fusion protein and a second polynucleotide sequence encoding at least one sgRNA. The first polynucleotide sequence may be operably linked to a first promoter. The first promoter may be a constitutive promoter, an inducible promoter, a repressible promoter, or a regulatable promoter. The second polynucleotide sequence may encode between one and ten different sgRNAs. The second polynucleotide sequence may encode two different sgRNAs, three different sgRNAs, four different sgRNAs, five different sgRNAs, six different sgRNAs, seven different sgRNAs, eight different sgRNAs, nine different sgRNAs, or ten different sgRNAs. Each of the polynucleotide sequences encoding the different sgRNAs may be operably linked to a promoter. Each of the promoters operably linked to the different sgRNAs may be the same promoter. Each of the promoters operably linked to the different sgRNAs may be different promoters. The promoter may be a constitutive promoter, an inducible promoter, a repressible promoter, or a regulatable promoter. The sgRNA may bind to a target gene. Each of the sgRNA may bind to a different target region within one target loci. Each of the sgRNA may bind to a different target region within different gene loci. The fusion protein may comprise Cas9 protein or iCas9-VP64 protein. The fusion protein may comprise a VP64 domain, a p300 domain, or a KRAB domain. The two or more endogenous genes may be transcriptionally activated. The two or more endogenous genes may be repressed.

The present invention is directed to a method of activating an endogenous gene in a cell. The method comprises contacting a cell with said modified lentiviral vector. The endogenous gene may be transiently activated. The endogenous gene may be stably activated. The endogenous gene may be transiently repressed. The endogenous gene may be stably repressed. The fusion protein may be expressed at similar levels to the sgRNAs. The fusion protein may be expressed at different levels to the sgRNAs. The cell may be a primary human cell.

The present invention is directed to a method of multiplex gene editing in a cell. The method comprises contacting a cell with said modified lentiviral vector. The multiplex gene editing may comprise correcting at least one mutant gene or inserting a transgene. Correcting a mutant gene may comprise deleting, rearranging, or replacing the at least one mutant gene. Correcting the at least one mutant gene may comprise nuclease-mediated non-homologous end joining or homology-directed repair. The multiplex gene editing may comprise deleting at least one gene, wherein the gene is an endogenous normal gene or a mutant gene. The multiplex gene editing may comprise deleting at least two genes. The multiplex gene editing may comprise deleting between two and ten genes.

The present invention is directed to a method of modulating gene expression of at least one target gene in a cell. The method comprises contacting a cell with said modified lentiviral vector. The gene expression of at least two genes may be modulated. The gene expression of between two genes and ten genes may be modulated. The gene expression of the at least one target gene may be modulated when gene expression levels of the at least one target gene are increased or decreased compared to normal gene expression levels for the at least one target gene.

BRIEF DESCRIPTION OF THE DRAWINGS

FIG. 1A and FIG. 1B show an RNA-guided transcriptional activator was created by fusing the inactivated Cas9 (iCas9, D10A/H840A) to the VP64 transactivation domain. iCas9-VP64 recognizes genomic target sites through the hybridization of a guide RNA (gRNA) to a 20 bp target sequence. FIG. 1C shows expression plasmids for four gRNAs or crRNA/tracrRNAs targeted to sequences in the IL1RN promoter were co-transfected with the iCas9-VP64 expression plasmid into HEK293T cells. Activation of IL1RN expression was assessed by qRT-PCR. FIG. 1D shows four gRNA expression plasmids were co-transfected with iCas9-VP64 individually or in combination. Robust gene activation was observed by qRT-PCR only in response to the combination of gRNAs. FIG. 1E shows activation of IL1RN expression was confirmed by assessing secretion of the IL-1ra gene product into the media by ELISA. IL-1ra was only detected in three of the six samples treated with the combination of gRNAs. For FIG. 1C and FIG. 1E, data are shown as the mean±s.e.m. (n=3 independent experiments). Treatment with the combination of gRNAs was statistically different than all other treatments (*P<0.02) by Tukey's test. FIG. 1F shows RNA-seq was performed on samples treated with empty expression vector (n=2) or co-transfected with the expression plasmids for iCas9-VP64 and the four gRNAs targeting IL1RN (n=2). The only statistically significant changes in gene expression between these treatments were an increase in the four IL1RN isoforms (false discovery rate≤3×10-4) and a decrease in IL32 (false discovery rate=0.03).

FIG. 8A shows gRNA target sites in the human ASCL1 promoter (SEQ ID NO: 3) are conserved in the mouse ASCL1 promoter (SEQ ID NO: 4). Target sites are indicated by solid lines and the transcribed region is indicated by dashed line. FIG. 8B shows ASCL1 expression in MEFs increased at two days after iCas9-VP64/gRNA treatment as determined by qRT-PCR. FIGS. 8C-8H show that after 10 days in neural induction media, cells were stained for Ascl1 and Tuj1, an early marker of neuronal differentiation (FIGS. 8C-8D), or for Tuj1 and MAP2, a marker of more mature neuronal differentiation (FIGS. 8E-8F). FIGS. 8F-8G show that some Tuj1-positive cells adopted neuronal morphologies. FIG. 8G shows that a single cell was found to be positive for Tuj1 and MAP2. FIG. 8H shows Tuj1-positive cells were readily identified in the iCas9-VP64/gRNA-treated cultures (~0.05%) but were absent in controls. n=3 independent samples and data are represented as mean±standard error of the mean. gRNA 75/25 is significantly different than gRNA 50/50 and control (*P<0.01, Tukey's test).

FIG. 9A shows the iCas9-VP64 protein sequence (SEQ ID NO: 1) and FIG. 9B shows the sequence of the gRNA expression cassette with U6 promoter (SEQ ID NO: 2).

FIG. 11A and FIG. 11B show the validation of RNA-guided repair. FIG. 11A shows the Surveyor assay results of genomic DNA harvested from HEK 293T cells two days after Cas9 was co-transfected into the cells with empty vector (negative control) or gRNA. FIG. 11B shows the location of the gRNA target. FIG. 11C shows the expected cleavage sizes for each gRNA.

FIG. 16A shows sgRNA sequences were designed to bind sequences in the exon 45-55 mutational hotspot region of the dystrophin gene, such that gene editing could restore dystrophin expression from a wide variety of patient-specific mutations. Arrows within introns indicate sgRNA targets designed to delete entire exons from the genome. Arrows within exons indicate sgRNA targets designed to create targeted frameshifts in the dystrophin gene. FIG. 16B shows an example of frame correction following introduction of small insertions or deletions by NHEJ DNA repair in exon 51 using the CR3 sgRNA. FIG. 16B discloses SEQ ID NOS: 633-636, respectively, in order of appearance. FIG. 16C shows a schematic of multiplex sgRNA targets designed to delete exon 51 and restore the dystrophin reading frame in a patient mutation with the deletion of exons 48-50. FIG. 16D shows a schematic of multiplex sgRNA targets designed to delete the entire exon 45-55 region to address a variety of DMD patient mutations.

FIG. 19A shows a plasmid expressing a human-codon optimized SpCas9 protein linked to a GFP marker using a T2A ribosomal skipping peptide sequence was co-electroporated into human DMD myoblasts with one or two plasmids carrying sgRNA expression cassettes. FIG. 19B shows the indicated sgRNA expression cassettes were independently co-transfected into HEK293Ts with a separate plasmid expressing SpCas9 with (bottom) or without (top) a GFP marker linked to SpCas9 by a T2A ribosomal skipping peptide sequence. Gene modification frequencies were assessed at 3 days post-transfection by the Surveyor assay. FIG. 19C shows DMD myoblasts with deletions of exons 48-50 in the dystrophin gene were treated with sgRNAs that correct the dystrophin reading frame in these patient cells. Gene modification was assessed at 20 days post-electroporation in unsorted (bulk) or GFP+ sorted cells. FIG. 19D shows GFP expression in DMD myoblasts 3 days after electroporation with indicated expression plasmids. Transfection efficiencies and sorted cell populations are indicated by the gated region.

FIGS. 20A-20D show targeted frameshifts to restore the dystrophin reading frame using CRISPR/Cas9. FIG. 20A shows the 5' region of exon 51 was targeted using a sgRNA (SEQ ID NO: 637), CR3, that binds immediately upstream of the first out-of-frame stop codon. PAM: protospacer-adjacent motif. FIG. 20B shows the exon 51 locus was PCR amplified from HEK293T cells treated with SpCas9 and CR3 expression cassettes. Sequences of individual clones were determined by Sanger sequencing. The top sequence (bolded, exon in red) is the native, unmodified sequence. The number of clones for each sequence is indicated in parentheses. FIG. 20C shows summary of total gene editing efficiency and reading frame conversions resulting from gene modification shown in FIG. 20B. FIG. 20D shows western blot for dystrophin expression in human DMD myoblasts treated with SpCas9 and the CR3 sgRNA expression cassette (FIG. 19C) to create targeted frameshifts to restore the dystrophin reading frame. Dystrophin expression was probed using an antibody against the rod-domain of the dystrophin protein after 6 days of differentiation.

FIG. 21A shows end-point genomic PCR across the exon 51 locus in human DMD myoblasts with a deletion of exons 48-50. The top arrow indicates the expected position of full-length PCR amplicons and the two lower arrows indicate the expected position of PCR amplicons with deletions caused by the indicated sgRNA combinations. FIG. 21B shows PCR products from FIG. 21A were cloned and individual clones were sequenced to determine insertions and deletions present at the targeted locus (SEQ ID NOS: 424, 638, 425-428, 639 and 429-431, respectively, in order of appearance). The top row shows the wild-type unmodified sequence and the triangles indicate SpCas9 cleavage sites. At the right are representative chromatograms showing the sequences of the expected deletion junctions (SEQ ID NOS: 640-642, respectively, in order of appearance). FIG. 21C shows end-point RT-PCR analysis of dystrophin mRNA transcripts in CRISPR/Cas9-modified human Δ48-50 DMD myoblasts treated with the indicated sgRNAs. A representative chromatogram of the expected deletion PCR product is shown at the right. Asterisk: band resulting from hybridization of the deletion product strand to the unmodified strand. FIG. 21D shows rescue of dystrophin protein expression by CRISPR/Cas9 genome editing was assessed by western blot for the dystrophin protein with GAPDH as a loading control. The arrow indicates the expected restored dystrophin protein band.

FIGS. 22A-22D show deletion of the entire exon 45-55 region in human DMD myoblasts by multiplex CRISPR/Cas9 gene editing. FIG. 22A shows end-point genomic PCR of genomic DNA to detect deletion of the region between intron 44 and intron 55 after treating HEK293Ts or DMD myoblasts with the indicated sgRNAs. FIG. 22B shows individual clones of PCR products (SEQ ID NOS: 432, 643 and 433, respectively, in order of appearance) of the expected size for the deletions from DMD myoblasts in FIG. 22A were analyzed by Sanger sequencing to determine the sequences of genomic deletions present at the targeted locus. Below is a representative chromatograms showing the sequence of the expected deletion junctions (SEQ ID NO: 644). FIG. 22C shows end-point RT-PCR analysis of dystrophin mRNA transcripts in CRISPR/Cas9-modified human A48-50 DMD myoblasts treated with the indicated sgRNAs. A representative chromatogram of the expected deletion PCR product is shown at the right (SEQ ID NO: 645). FIG. 22D shows analysis of restored dystrophin protein expression by western blot following electroporation of DMD myoblasts with sgRNAs targeted to intron 44 and/or intron 55.

FIG. 23 shows verification of flow cytometry-based enrichment of gene-modified DMD myoblasts used for in vivo cell transplantation experiment. DMD myoblasts were treated with Cas9 with or without sgRNA expression vectors for CR1 and CR5 and sorted for GFP+ cells by flow cytometry. Deletions at the exon 51 locus were detected by end-point PCR using primers flanking the locus. Neg ctrl: DMD myoblasts treated with Cas9 only and sorted for GFP+ cells.

FIGS. 25A-25C show sections from muscles injected with untreated human DMD myoblasts. FIGS. 25D-25F show sections from muscles injected with CR1/5 treated human DMD myoblasts enriched by flow cytometry. White arrows indicate dystrophin positive fibers.

FIG. 26A shows results of a cytotoxicity assay in HEK293T cells treated with human-optimized SpCas9 and the indicated sgRNA constructs. Cytotoxicity is based on survival of GFP-positive cells that are co-transfected with the indicated nuclease. I-SceI is a well-characterized non-toxic meganuclease and GZF3 is a known toxic zinc finger nuclease. FIG. 26B shows surveyor analysis at off-target sites in sorted hDMD cells treated with expression cassettes encoding Cas9 the indicated sgRNAs. These three off-target sites tested in hDMD cells were identified from a panel of 50 predicted sites tested in HEK293T cells (FIG. 27 and Table 4). TGT: on-target locus for indicated sgRNA. OT:off-target locus. FIGS. 26C-26D show end-point nested PCR to detect chromosomal translocations in HEK293T cells treated with Cas9 and CR1 (FIG. 26C) or sorted hDMD cells treated with Cas9, CR1, and CR5 (FIG. 26D). The schematic depicts the relative location of nested primer pairs customized for each translocation event. The expected size of each band was estimated based on the primer size and the location of the predicted sgRNA cut site at each locus. Asterisks indicate bands detected at the expected size. The identities of the bands in FIG. 26C were verified by Sanger sequencing from each end (FIG. 30). A representative chromatogram for the P2/P5 translocation in HEK293T cells is shown (SEQ ID NO: 646).

FIG. 32A shows proliferating C2C12s were transduced with the indicated amount of virus and harvested at 4 days post-infection. Arrows indicate expected bands sizes resulting from Surveyor cleavage. FIG. 32B shows C2C12s were incubated in differentiation medium for 5 days and then transduced with the indicated amount of AAV-SASTG-ROSA virus in 24 well plates. Samples were collected at 10 days post-transduction. FIG. 32C shows the indicated amount of AAV-SASTG-ROSA was injected directly into the tibialis anterior of C57BL/6J mice and muscles were harvested 4 weeks post-infection. The harvested TA muscles were partitioned into 8 separate pieces for genomic DNA analysis, each shown in a separate lane.

FIG. 33 shows Rosa T2A opt DNA sequence (SEQ ID NO: 434) and Rosa T2A opt protein sequence (SEQ ID NO: 435).

FIGS. 34A and 34B show SASTG capsid DNA sequence (SEQ ID NO:436) and SASTG capsid peptide sequence (SEQ ID NO: 437).

FIG. 35 shows DZF16 ZFN target site sequence (SEQ ID NO: 442), DZF16-L6 left full amino acid sequence (SEQ ID NO: 443) and DZF16-R6 right full amino acid sequence (SEQ ID NO: 444).

FIG. 36 shows E51C3 ZFN target site sequence (SEQ ID NO: 445), E51C3-3L left full amino acid sequence (SEQ ID NO: 446) and E51C3-3R right full amino acid sequence (SEQ ID NO: 447).

FIG. 37 shows DZF15 ZFN target site sequence (SEQ ID NO: 448), DZF15-L6 left full amino acid sequence (SEQ ID NO: 449), DZF15-R6 right full amino acid sequence (SEQ ID NO: 450), DZF15-L5 left full amino acid sequence (SEQ ID NO: 451), DZF15-R5 right full amino acid sequence (SEQ ID NO: 452).

FIG. 38 shows E51C4 ZFN target site sequence (SEQ ID NO: 453), E51C4-4L left full amino acid sequence (SEQ ID NO: 454) and E51C4-4R right full amino acid sequence (SEQ ID NO: 455).

FIG. 40 shows the nucleotide sequences of SaCas9-NLS (with the NLS underlined) (SEQ ID NO: 459) and SaCas9 gRNA (SEQ ID NO: 460).

FIG. 41 shows the nucleotide sequences of NmCas9 (with the NLS 1 underlined, the NLS 2 underlined and bolded, and the HA tag bolded; SEQ ID NO: 461), NmCas9 short hairpin from Thomson PNAS 2013 (SEQ ID NO: 462), and NmCas9 long hairpin from Church Nature Biotech 2013 (SEQ ID NO: 463).

FIG. 42A shows constructs encoding unique Pol III promoters expressing sgRNAs targeting the AAVS1 locus or a construct containing the hU6 promoter immediately followed by poly-thymidine to terminate expression ("PolyT") were transfected into HEK293T cells. End-point RT-PCR was used to probe for expression of each indicated promoter/sgRNA construct two days post-transfection. –RT: no reverse transcriptase control. FIG. 42B shows HEK293Ts were transfected with expression vectors encoding the AAVS1 zinc-finger nuclease or Cas9-T2A-GFP and the indicated promoter/sgRNA expression cassettes and assessed for gene modification levels 3 days post-transfection using the Surveyor assay. FIG. 42C shows HEK293T cells were transduced with lentiviral constructs encoding the indicated Cas9-T2A-GFP constructs without sgRNAs and assessed for Cas9 expression by western blot 7 days post-transduction by probing for a FLAG epitope tag on the N-terminus of the Cas9 protein.

FIG. 43 discloses SEQ ID NOS: 661-672, respectively, in order of appearance.

FIG. 44A shows four sgRNAs targeting distinct genomic loci were cloned into a lentiviral vector expressing the active Cas9 nuclease. FIG. 44B shows HEK293Ts and primary human dermal fibroblasts were transduced with lentivirus expressing the indicated sgRNAs and assayed for cleavage events using the Surveyor assay. HEK293Ts were assayed 7 days post transduction. The human fibroblasts were assayed 10 days post transduction.

FIG. 48 shows a schematic representing the direct conversion of fibroblasts to neurons through ectopic expression of the BAM neuronal transcription factors.

FIG. 49A shows a schematic of the dCas9-VP64 construct. dCas9-VP64 is a catalytically inactive form of the Cas9 protein fused to a tetramer of the VP16 transcriptional activation domain. FIG. 49B is a schematic showing the mechanism of RNA-guided recruitment of dCas9-VP64 to a genomic target. FIG. 49C is a schematic of the experimental protocol to generate iNs with CRISPR/Cas9 transcription factors.

FIGS. 50A-50B shows endogenous ASCL1 expression at day 3 determined by qRT-PCR (FIG. 50A) or total ASCL1 protein detected by immunofluorescence in MEFs transduced with dCas9-VP64 and transfected with either gRNAs targeted to the ASCL1 promoter, ASCL1 cDNA, or luciferase (FIG. 50B). Asterisk (*) indicates significant ($p<0.05$) increase in ASCL1 expression with the co-delivery of 8 gRNAs compared to 4 gRNAs. Ectopic expression of ASCL1 produced more protein than induced by dCas9-VP64 and 8 gRNAs targeted to the Ascl1 promoter, but did not activate the endogenous locus by day 3 in culture.

FIG. 51A shows TUJ1 and MAP2-positive cells generated by ectopic BAM factors or by dCas9-VP64 and gRNAs targeted to the BRN2 and ASCL1 promoters. FIG. 51B shows cells with neuronal morphology expressing a hSyn-RFP reporter at day 11 in N3 medium.

FIGS. 52A-52B show activation of downstream targets of Ascl1 and Brn2, i.e., master regulatory genes, in iCas9-VP64-treated murine embryonic fibroblasts using dCas9-VP64 transcription factors to convert the fibroblasts to neurons. Mouse embryonic fibroblasts (MEFs) were transfected with a control GFP expression plasmid or the iCas9-VP64 expression plasmid and a combination of eight gRNA expression plasmids targeting ASCL1 and BRN2. The dCas9 transcription factors were delivered virally. After 10 days in neural induction media, cells were stained for Tuj1, an early marker of neuronal differentiation and MAP2, a marker of more mature neuronal differentiation. The conversion to neurons was efficient.

FIG. 53A shows Cas9-based effectors bind genomic sequences in the presence of a chimeric gRNA molecule consisting of a constant region that complexes with Cas9 preceded by an exchangeable 20 bp protospacer that confers target site specificity. FIG. 53A discloses SEQ ID NO: 673. FIG. 53B shows Cas9-based synthetic transcription factors repress transcription of a target gene by interfering with RNA polymerase activity or by binding within the promoter and blocking the binding sites of endogenous transcription factors. FIG. 53C shows targeting regulatory elements such as enhancers could also potentially block the expression of multiple distal genes.

FIG. 55A shows dCas9 and dCas9-KRAB repressors were delivered on a lentiviral vector. Single gRNAs were transiently transfected for screening. When assayed by quantitative RT-PCR at 3 days post-transfection, K562s expressing dCas9-KRAB achieve up to 80% repression of γ-globin (FIG. 55B), ε-globin (FIG. 55C), and β-globin (FIG. 55D) genes, as compared to control cells that received no gRNA treatment. FIG. 55E shows protein expression in cells expressing dCas9 or dCas9-KRAB and treated with Cr4 or Cr8 show mild repression of γ-globin expression at day 3, compared to β-actin controls.

FIG. 57A shows dCas9 and dCas9-KRAB repressors were co-expressed on a lentiviral vector with single gRNAs. When assayed by quantitative RT-PCR at 7 days post-transduction, K562s expressing dCas9-KRAB achieve up to 95% repression of γ-globin (FIG. 57B), ε-globin (FIG. 57C), and β-globin genes (FIG. 57D), as compared to control cells that received no lentiviral treatment.

FIGS. 61A-61C show the amino acid sequences of the dCas9 constructs. The legend for all FIGS. 61A-61C is shown in FIG. 61A. FIGS. 61A-61C disclose SEQ ID NOS: 674-676, respectively, in order of appearance.

FIG. 64A is a schematic showing how minidystrophin is integrated into the 5'UTR. FIG. 64B shows hygromycin-resistant clonal cell lines were isolated and screened by PCR for successful site-specific integrations at the 5'UTR using the primers shown in FIG. 64A. Asterisks indicate clones selected for further analysis in FIG. 64C. FIG. 64C shows clonally isolated DMD myoblasts with detected integration events were differentiated for 6 days and assessed for expression of an HA tag fused to the C terminus of minidystrophin.

DETAILED DESCRIPTION

Figure 1A:
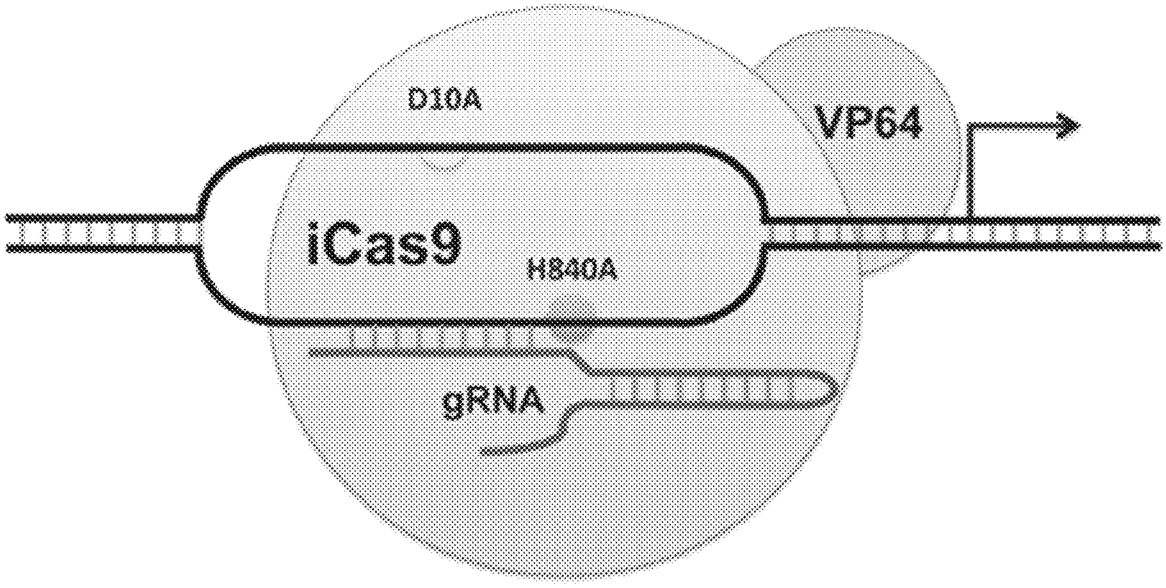
FIGS. 1A-1F show RNA-guided activation of the human IL1RN gene by iCas9-VP64.

As described herein, certain methods and engineered CRISPR/CRISPR-associated (Cas) 9-based system compositions have been discovered to be useful for altering the expression of genes, genome engineering, and correcting or reducing the effects of mutations in genes involved in genetic diseases. The CRISPR/Cas9-based system involves a Cas9 protein and at least one guide RNA, which provide the DNA targeting specificity for the system. In particular, the present disclosure describes a Cas9 fusion protein that combines the DNA sequence targeting function of the CRISPR/Cas9-based system with an additional activity, thus allowing changes in gene expression and/or epigenetic status. The system may also be used in genome engineering and correcting or reducing the effects of gene mutations.

The present disclosure also provides certain compositions and methods for delivering CRISPR/CRISPR-associated (Cas) 9-based system and multiple gRNAs to target one or more endogenous genes. Co-transfection of multiple sgR- NAs targeted to a single promoter allow for synergistic activation, however, co-transfection of multiple plasmids leads to variable expression levels in each cell due to differences in copy number. Additionally, gene activation following transfection is transient due to dilution of plasmid DNA over time. Moreover, many cell types are not easily transfected and transient gene expression may not be sufficient for inducing a therapeutic effect. To address these limitations, a single lentiviral system was developed to express Cas9 and up to four sgRNAs from independent promoters. A platform is disclosed that expresses Cas9 or dCas9 fusion proteins and up to four gRNAs from a single lentiviral vector. The lentiviral vector expresses a constitutive or inducible Cas9 or dCas9-VP64 in addition to one, two, three, or four gRNAs expressed from independent promoters. This system enables control of both the magnitude and timing of CRISPR/Cas9-based gene regulation. Furthermore, the lentiviral platform provides the potent and sustained levels of gene expression that will facilitate therapeutic applications of the CRISPR/Cas9 system in primary cells. Finally, this system may be used for editing multiple genes simultaneously, such as the concurrent knockout of several oncogenes.

The present disclosure also provides certain compositions and methods for delivering site-specific nucleases to skeletal muscle and cardiac muscle using modified adeno-associated virus (AAV) vectors. The site-specific nucleases, which may be engineered, are useful for altering the expression of genes, genome engineering, correcting or reducing the effects of mutations in genes involved in genetic diseases, or manipulating genes involved in other conditions affecting skeletal muscle or cardiac muscle or muscle regeneration. The engineered site-specific nucleases may include a zinc finger nuclease (ZFN), a TAL effector nuclease (TALEN), and/or a CRISPR/Cas9 system for genome editing. As described herein, genes in skeletal muscle tissue were successfully edited in vivo using this unique delivery system. The disclosed invention provides a means to rewrite the human genome for therapeutic applications and target model species for basic science applications.

Gene editing is highly dependent on cell cycle and complex DNA repair pathways that vary from tissue to tissue. Skeletal muscle is a very complex environment, consisting of large myofibers with more than 100 nuclei per cell. Gene therapy and biologics in general have been limited for decades by in vivo delivery hurdles. These challenges include stability of the carrier in vivo, targeting the right tissue, getting sufficient gene expression and active gene product, and avoiding toxicity that might overcome activity, which is common with gene editing tools. Other delivery vehicles, such as direct injection of plasmid DNA, work to express genes in skeletal muscle and cardiac muscle in other contexts, but do not work well with these site-specific nucleases for achieving detectable levels of genome editing.

While many gene sequences are unstable in AAV vectors and therefore undeliverable, these site-specific nucleases are surprisingly stable in the AAV vectors. When these site-specific nucleases are delivered and expressed, they remained active in the skeletal muscle tissue. The protein stability and activity of the site-specific nucleases are highly tissue type- and cell type-dependent. These active and stable nucleases are able to modify gene sequences in the complex environment of skeletal muscle. The current invention describes a way to deliver active forms of this class of therapeutics to skeletal muscle or cardiac muscle that is effective, efficient and facilitates successful genome modification.

The present disclosure also provides certain fusion epigenetic effector molecules, a dCas9-p300 fusion protein, which provides a robust and potentially more widely applicable tool for synthetic transcriptional modulation compared to the dCas9-VP64 fusion. The activated target genes to a substantially greater extent than the dCas9-VP64 fusion protein at all loci tested. In addition, the p300 has intrinsic endogenous activity at enhancers within the human genome. The dCas9-p300 fusion protein may be able to activate endogenous target gene promoters and enhancer regions.

The dCas9-p300 fusion protein can be used in human tissue culture cell lines to activate gene expression. This fusion protein may be used to direct the epigenetic state of target loci within human cells with precision and predictability in order to control differentiation, modulate cellular regulation, and apply innovative potential therapies. Current technologies are limited in the strength of activation and the extent and sustainability of epigenetic modulation; obstacles which may be obviated via utilization of this new fusion protein.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease.

"Cardiac muscle" or "heart muscle" as used interchangeably herein means a type of involuntary striated muscle found in the walls and histological foundation of the heart, the myocardium. Cardiac muscle is made of cardiomyocytes or myocardiocytes. Myocardiocytes show striations similar to those on skeletal muscle cells but contain only one, unique nucleus, unlike the multinucleated skeletal cells.

"Cardiac muscle condition" as used herein refers to a condition related to the cardiac muscle, such as cardiomyopathy, heart failure, arrhythmia, and inflammatory heart disease.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as homology-directed repair (HDR). Correcting or restoring a mutant gene may also include repairing a frameshift mutation that causes a premature stop codon, an aberrant splice acceptor site or an aberrant splice donor site, by generating a double stranded break in the gene that is then repaired using non-homologous end joining (NHEJ). NHEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

"Duchenne Muscular Dystrophy" or "DMD" as used interchangeably herein refers to a recessive, fatal, X-linked disorder that results in muscle degeneration and eventual death. DMD is a common hereditary monogenic disease and occurs in 1 in 3500 males. DMD is the result of inherited or spontaneous mutations that cause nonsense or frame shift mutations in the dystrophin gene. The majority of dystrophin mutations that cause DMD are deletions of exons that disrupt the reading frame and cause premature translation termination in the dystrophin gene. DMD patients typically lose the ability to physically support themselves during childhood, become progressively weaker during the teenage years, and die in their twenties.

"Dystrophin" as used herein refers to a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids.

"Exon 51" as used herein refers to the $51^{st}$ exon of the dystrophin gene. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

"Frameshift" or "frameshift mutation" as used interchangeably herein refers to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but not limited to DMD, hemophilia, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the site specific nuclease, such as with a CRISPR/Cas9-based systems, then the cellular machinery will repair the break by homologous recombination, which is enhanced several orders of magnitude in the presence of DNA cleavage. When the homologous DNA piece is absent, non-homologous end joining may take place instead.

"Genome editing" as used herein refers to changing a gene. Genome editing may include correcting or restoring a mutant gene. Genome editing may include knocking out a gene, such as a mutant gene or a normal gene. Genome editing may be used to treat disease or enhance muscle repair by changing the gene of interest.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

"Non-homologous end joining (NHEJ) pathway" as used herein refers to a pathway that repairs double-strand breaks in DNA by directly ligating the break ends without the need for a homologous template. The template-independent religation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Normal gene" as used herein refers to a gene that has not undergone a change, such as a loss, gain, or exchange of genetic material. The normal gene undergoes normal gene transmission and gene expression.

"Nuclease mediated NHEJ" as used herein refers to NHEJ that is initiated after a nuclease, such as a cas9, cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a non-functional protein.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Repeat variable diresidue" or "RVD" as used interchangeably herein refers to a pair of adjacent amino acid residues within a DNA recognition motif (also known as "RVD module"), which includes 33-35 amino acids, of a TALE DNA-binding domain. The RVD determines the nucleotide specificity of the RVD module. RVD modules may be combined to produce an RVD array. The "RVD array length" as used herein refers to the number of RVD modules that corresponds to the length of the nucleotide sequence within the TALEN target region that is recognized by a TALEN, i.e., the binding region.

"Site-specific nuclease" as used herein refers to an enzyme capable of specifically recognizing and cleaving DNA sequences. The site-specific nuclease may be engineered. Examples of engineered site-specific nucleases include zinc finger nucleases (ZFNs), TAL effector nucleases (TALENs), and CRISPR/Cas9-based systems.

"Skeletal muscle" as used herein refers to a type of striated muscle, which is under the control of the somatic nervous system and attached to bones by bundles of collagen fibers known as tendons. Skeletal muscle is made up of individual components known as myocytes, or "muscle cells", sometimes colloquially called "muscle fibers." Myocytes are formed from the fusion of developmental myoblasts (a type of embryonic progenitor cell that gives rise to a muscle cell) in a process known as myogenesis. These long, cylindrical, multinucleated cells are also called myofibers.

"Skeletal muscle condition" as used herein refers to a condition related to the skeletal muscle, such as muscular dystrophies, aging, muscle degeneration, wound healing, and muscle weakness or atrophy.

"Spacers" and "spacer region" as used interchangeably herein refers to the region within a TALEN or ZFN target region that is between, but not a part of, the binding regions for two TALENs or ZFNs.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene may be a mutated gene involved in a genetic disease.

"Target region" as used herein refers to the region of the target gene to which the site-specific nuclease is designed to bind and cleave.

"Transcription activator-like effector" or "TALE" as used herein refers to a protein structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence.

A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors, methyltransferases, integrases, nucleases, and recombinases.

"Transcription activator-like effector nucleases" or "TALENs" as used interchangeably herein refers to engineered fusion proteins of the catalytic domain of a nuclease, such as endonuclease FokI, and a designed TALE DNA-binding domain that may be targeted to a custom DNA sequence. A "TALEN monomer" refers to an engineered fusion protein with a catalytic nuclease domain and a designed TALE DNA-binding domain. Two TALEN monomers may be designed to target and cleave a TALEN target region.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of 2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode an iCas9-VP64 fusion protein comprising the amino acid sequence of SEQ ID NO: 1 or at least one gRNA nucleotide sequence of any one of SEQ ID NOs: 5-40, 65-144, 492-515, 540-563, and 585-625. Alternatively, the vector may encode Cas9 and at least one gRNA nucleotide sequence of any one of SEQ ID NOs: 5-40, 65-144, 492-515, 540-563, and 585-625.

"Zinc finger" as used herein refers to a protein structure that recognizes and binds to DNA sequences. The zinc finger domain is the most common DNA-binding motif in the human proteome. A single zinc finger contains approximately 30 amino acids and the domain typically functions by binding 3 consecutive base pairs of DNA via interactions of a single amino acid side chain per base pair.

"Zinc finger nuclease" or "ZFN" as used interchangeably herein refers to a chimeric protein molecule comprising at least one zinc finger DNA binding domain effectively linked to at least one nuclease or part of a nuclease capable of cleaving DNA when fully assembled.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. COMPOSITIONS FOR GENOME EDITING

The present invention is directed to compositions for genome editing, genomic alteration or altering gene expression of a target gene. The compositions may include a may include viral vector and fusion protein such as a site-specific nuclease or CRISPR/Cas9-system with at least one gRNA.

a. Compositions for Genome Editing in Muscle

The present invention is directed to a composition for genome editing a target gene in skeletal muscle or cardiac muscle of a subject. The composition includes a modified AAV vector and a nucleotide sequence encoding a site-specific nuclease. The composition delivers active forms of site-specific nucleases to skeletal muscle or cardiac muscle. The composition may further comprise a donor DNA or a transgene. These compositions may be used in genome editing, genome engineering, and correcting or reducing the effects of mutations in genes involved in genetic diseases and/or other skeletal or cardiac muscle conditions.

The target gene may be involved in differentiation of a cell or any other process in which activation, repression, or disruption of a gene may be desired, or may have a mutation such as a deletion, frameshift mutation, or a nonsense mutation. If the target gene has a mutation that causes a premature stop codon, an aberrant splice acceptor site or an aberrant splice donor site, the site-specific nucleases may be designed to recognize and bind a nucleotide sequence upstream or downstream from the premature stop codon, the aberrant splice acceptor site or the aberrant splice donor site. The site-specific nucleases may also be used to disrupt normal gene splicing by targeting splice acceptors and donors to induce skipping of premature stop codons or restore a disrupted reading frame. The site-specific nucleases may or may not mediate off-target changes to protein-coding regions of the genome.

3. CRISPR SYSTEM

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cas9 forms a complex with the 3' end of the sgRNA, and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the crRNA, i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed sgRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9:crRNA-tracrRNA complex.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Different Type II systems have differing PAM requirements. The *S. pyogenes* CRISPR system may have the PAM sequence for this Cas9 (SpCas9) as 5'-NRG-3', where R is either A or G, and characterized the specificity of this system in human cells. A unique capability of the CRISPR/Cas9 system is the straightforward ability to simultaneously target multiple distinct genomic loci by co-expressing a single Cas9 protein with two or more sgRNAs. For example, the *Streptococcus pyogenes* Type II system naturally prefers to use an "NGG" sequence, where "N" can be any nucleotide, but also accepts other PAM sequences, such as "NAG" in engineered systems (Hsu et al., *Nature Biotechnology* (2013) doi:10.1038/nbt.2647). Similarly, the Cas9 derived from *Neisseria meningitidis* (NmCas9) normally has a native PAM of NNNNGATT, but has activity across a variety of PAMs, including a highly degenerate NNNNGNNN PAM (Esvelt et al. *Nature Methods* (2013) doi:10.1038/nmeth.2681).

4. CRISPR/CAS9-BASED SYSTEM

Figure 53A:
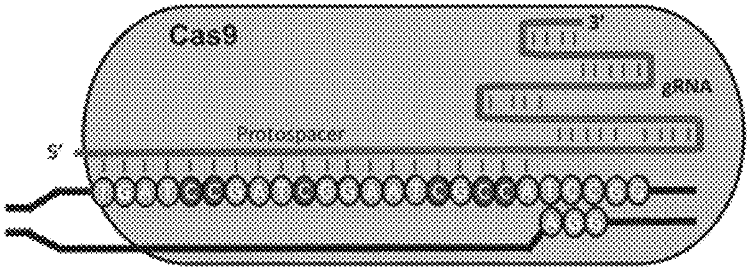
FIGS. 53A-53C show the CRISPR/Cas9 platform for control of mammalian gene regulation.

An engineered form of the Type II effector system of *Streptococcus pyogenes* was shown to function in human cells for genome engineering. In this system, the Cas9 protein was directed to genomic target sites by a synthetically reconstituted "guide RNA" ("gRNA", also used interchangeably herein as a chimeric single guide RNA ("sgRNA")), which is a crRNA-tracrRNA fusion that obviates the need for RNase III and crRNA processing in general (see FIG. 53A). Provided herein are CRISPR/Cas9-based engineered systems for use in genome editing and treating genetic diseases. The CRISPR/Cas9-based engineered systems may be designed to target any gene, including genes involved in a genetic disease, aging, tissue regeneration, or wound healing. The CRISPR/Cas9-based systems may include a Cas9 protein or Cas9 fusion protein and at least one gRNA. The Cas9 fusion protein may, for example, include a domain that has a different activity that what is endogenous to Cas9, such as a transactivation domain.

The target gene may be involved in differentiation of a cell or any other process in which activation of a gene may be desired, or may have a mutation such as a frameshift mutation or a nonsense mutation. If the target gene has a mutation that causes a premature stop codon, an aberrant splice acceptor site or an aberrant splice donor site, the CRISPR/Cas9-based system may be designed to recognize and bind a nucleotide sequence upstream or downstream from the premature stop codon, the aberrant splice acceptor site or the aberrant splice donor site. The CRISPR-Cas9-based system may also be used to disrupt normal gene splicing by targeting splice acceptors and donors to induce skipping of premature stop codons or restore a disrupted reading frame. The CRISPR/Cas9-based system may or may not mediate off-target changes to protein-coding regions of the genome.

a. Cas9

The CRISPR/Cas9-based system may include a Cas9 protein or a Cas9 fusion protein. Cas9 protein is an endonuclease that cleaves nucleic acid and is encoded by the CRISPR loci and is involved in the Type II CRISPR system. The Cas9 protein may be from any bacterial or archaea species, such as *Streptococcus pyogenes*. The Cas9 protein may be mutated so that the nuclease activity is inactivated. An inactivated Cas9 protein from *Streptococcus pyogenes* (iCas9, also referred to as "dCas9") with no endonuclease activity has been recently targeted to genes in bacteria, yeast, and human cells by gRNAs to silence gene expression through steric hindrance. As used herein, "iCas9" and "dCas9" both refer to a Cas9 protein that has the amino acid substitutions D10A and H840A and has its nuclease activity inactivated. For example, the CRISPR/Cas9-based system may include a Cas9 of SEQ ID NO: 459 or 461.

b. Cas9 Fusion Protein

The CRISPR/Cas9-based system may include a fusion protein. The fusion protein may comprise two heterologous polypeptide domains, wherein the first polypeptide domain comprises a Cas protein and the second polypeptide domain has an activity such as transcription activation activity, transcription repression activity, transcription release factor activity, histone modification activity, nuclease activity, nucleic acid association activity, methylase activity, or demethylase activity. The fusion protein may include a Cas9 protein or a mutated Cas9 protein, as described above, fused to a second polypeptide domain that has an activity such as transcription activation activity, transcription repression activity, transcription release factor activity, histone modification activity, nuclease activity, nucleic acid association activity, methylase activity, or demethylase activity.

(1) Transcription Activation Activity

The second polypeptide domain may have transcription activation activity, i.e., a transactivation domain. For example, gene expression of endogenous mammalian genes, such as human genes, may be achieved by targeting a fusion protein of iCas9 and a transactivation domain to mammalian promoters via combinations of gRNAs. The transactivation domain may include a VP16 protein, multiple VP16 proteins, such as a VP48 domain or VP64 domain, or p65 domain of NF kappa B transcription activator activity. For example, the fusion protein may be iCas9-VP64.

(2) Transcription Repression Activity

The second polypeptide domain may have transcription repression activity. The second polypeptide domain may have a Kruppel associated box activity, such as a KRAB domain, ERF repressor domain activity, Mxi1 repressor domain activity, SID4X repressor domain activity, Mad-SID repressor domain activity or TATA box binding protein activity. For example, the fusion protein may be dCas9-KRAB.

(3) Transcription Release Factor Activity

The second polypeptide domain may have transcription release factor activity. The second polypeptide domain may have eukaryotic release factor 1 (ERF1) activity or eukaryotic release factor 3 (ERF3) activity.

(4) Histone Modification Activity

The second polypeptide domain may have histone modification activity. The second polypeptide domain may have histone deacetylase, histone acetyltransferase, histone demethylase, or histone methyltransferase activity. The histone acetyltransferase may be p300 or CREB-binding protein (CBP) protein, or fragments thereof. For example, the fusion protein may be dCas9-p300.

(5) Nuclease Activity

The second polypeptide domain may have nuclease activity that is different from the nuclease activity of the Cas9 protein. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

(6) Nucleic Acid Association Activity

The second polypeptide domain may have nucleic acid association activity or nucleic acid binding protein-DNA-binding domain (DBD) is an independently folded protein domain that contains at least one motif that recognizes double- or single-stranded DNA. A DBD can recognize a specific DNA sequence (a recognition sequence) or have a general affinity to DNA. nucleic acid association region selected from the group consisting of helix-turn-helix region, leucine zipper region, winged helix region, winged helix-turn-helix region, helix-loop-helix region, immunoglobulin fold, B3 domain, Zinc finger, HMG-box, Wor3 domain, TAL effector DNA-binding domain.

(7) Methylase Activity

The second polypeptide domain may have methylase activity, which involves transferring a methyl group to DNA, RNA, protein, small molecule, cytosine or adenine. The second polypeptide domain may include a DNA methyltransferase.

(8) Demethylase Activity

The second polypeptide domain may have demethylase activity. The second polypeptide domain may include an enzyme that remove methyl (CH3-) groups from nucleic acids, proteins (in particular histones), and other molecules. Alternatively, the second polypeptide may covert the methyl group to hydroxymethylcytosine in a mechanism for demethylating DNA. The second polypeptide may catalyze this reaction. For example, the second polypeptide that catalyzes this reaction may be Tet1.

c. gRNA

The gRNA provides the targeting of the CRISPR/Cas9-based system. The gRNA is a fusion of two noncoding RNAs: a crRNA and a tracrRNA. The sgRNA may target any desired DNA sequence by exchanging the sequence encoding a 20 bp protospacer which confers targeting specificity through complementary base pairing with the desired DNA target. gRNA mimics the naturally occurring crRNA: tracrRNA duplex involved in the Type II Effector system. This duplex, which may include, for example, a 42-nucleotide crRNA and a 75-nucleotide tracrRNA, acts as a guide for the Cas9 to cleave the target nucleic acid. The "target region", "target sequence" or "protospacer" as used interchangeably herein refers to the region of the target gene to which the CRISPR/Cas9-based system targets. The CRISPR/Cas9-based system may include at least one gRNA, wherein the gRNAs target different DNA sequences. The target DNA sequences may be overlapping. The target sequence or protospacer is followed by a PAM sequence at the 3' end of the protospacer. Different Type II systems have differing PAM requirements. For example, the *Streptococcus pyogenes* Type II system uses an "NGG" sequence, where "N" can be any nucleotide.

The number of gRNA administered to the cell may be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 18 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA administered to the cell may be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, or 8 different gRNAs to at least 12 different gRNAs.

The gRNA may comprise a complementary polynucleotide sequence of the target DNA sequence followed by a PAM sequence. The gRNA may comprise a "G" at the 5' end of the complementary polynucleotide sequence. The gRNA may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by a PAM sequence. The PAM sequence may be "NGG", where "N" can be any nucleotide. The gRNA may target at least one of the promoter region, the enhancer region or the transcribed region of the target gene. The gRNA may include a nucleic acid sequence of at least one of SEQ ID NOs: 5-40, 65-144, 492-515, 540-563, 585-625, 462 (FIG. 40), 464 (FIG. 41), and 465 (FIG. 41).

The gRNA may target any nucleic acid sequence. The nucleic acid sequence target may be DNA. The DNA may be any gene. For example, the gRNA may target a gene, such as BRN2, MYT1L, ASCL1, NANOG, VEGFA, TERT, IL1B, ILIR2, IL1RN, HBG1, HBG2, MYOD1, OCT4, and DMD.

(1) Dystrophin

Dystrophin is a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane. The dystrophin gene is 2.2 megabases at locus Xp21. The primary transcription measures about 2,400 kb with the mature mRNA being about 14 kb. 79 exons code for the protein which is over 3500 amino acids. Normal skeleton muscle tissue contains only small amounts of dystrophin but its absence of abnormal expression leads to the development of severe and incurable symptoms. Some mutations in the dystrophin gene lead to the production of defective dystrophin and severe dystrophic phenotype in affected patients. Some mutations in the dystrophin gene lead to partially-functional dystrophin protein and a much milder dystrophic phenotype in affected patients.

DMD is the result of inherited or spontaneous mutations that cause nonsense or frame shift mutations in the dystrophin gene. Naturally occurring mutations and their consequences are relatively well understood for DMD. It is known that in-frame deletions that occur in the exon 45-55 region contained within the rod domain can produce highly functional dystrophin proteins, and many carriers are asymptomatic or display mild symptoms. Furthermore, more than 60% of patients may theoretically be treated by targeting exons in this region of the dystrophin gene. Efforts have been made to restore the disrupted dystrophin reading frame in DMD patients by skipping non-essential exons during mRNA splicing to produce internally deleted but functional dystrophin proteins. The deletion of internal dystrophin exons retain the proper reading frame but cause the less severe Becker muscular dystrophy.

(2) CRISPR/Cas9-Based System for Targeting Dystrophin

A CRISPR/Cas9-based system specific for dystrophin gene are disclosed herein. The CRISPR/Cas9-based system may include Cas9 and at least one gRNA to target the dystrophin gene. The CRISPR/Cas9-based system may bind and recognize a target region. The target regions may be chosen immediately upstream of possible out-of-frame stop codons such that insertions or deletions during the repair process restore the dystrophin reading frame by frame conversion. Target regions may also be splice acceptor sites or splice donor sites, such that insertions or deletions during the repair process disrupt splicing and restore the dystrophin reading frame by splice site disruption and exon exclusion. Target regions may also be aberrant stop codons such that insertions or deletions during the repair process restore the dystrophin reading frame by eliminating or disrupting the stop codon.

Single or multiplexed sgRNAs may be designed to restore the dystrophin reading frame by targeting the mutational hotspot at exons 45-55 and introducing either intraexonic small insertions and deletions, or large deletions of one or more exons. Following treatment with Cas9 and one or more sgRNAs, dystrophin expression may be restored in Duchenne patient muscle cells in vitro. Human dystrophin was detected in vivo following transplantation of genetically corrected patient cells into immunodeficient mice. Significantly, the unique multiplex gene editing capabilities of the CRISPR/Cas9 system enable efficiently generating large deletions of this mutational hotspot region that can correct up to 62% of patient mutations by universal or patient-specific gene editing approaches.

The CRISPR/Cas9-based system may use gRNA of varying sequences and lengths. Examples of gRNAs may be found in Table 6. The CRISPR/Cas9-based system may target a nucleic acid sequence of SEQ ID NOs: 65-144, or a complement thereof. The gRNA may include a nucleotide sequence selected from the group consisting of SEQ ID NO: 65-144, or a complement thereof. For example, the disclosed CRISPR/Cas9-based systems were engineered to mediate highly efficient gene editing at exon 51 of the dystrophin gene. These CRISPR/Cas9-based systems restored dystrophin protein expression in cells from DMD patients.

(a) Exons 51 and 45-55

Exon 51 is frequently adjacent to frame-disrupting deletions in DMD. Elimination of exon 51 from the dystrophin transcript by exon skipping can be used to treat approximately 15% of all DMD patients. This class of DMD mutations is ideally suited for permanent correction by NHEJ-based genome editing and HDR. The CRISPR/Cas9-based systems described herein have been developed for targeted modification of exon 51 in the human dystrophin gene. These CRISPR/Cas9-based systems were transfected into human DMD cells and mediated efficient gene modification and conversion to the correct reading frame. Protein restoration was concomitant with frame restoration and detected in a bulk population of CRISPR/Cas9-based system-treated cells. Similarly, the elimination of exons 45-55 of the dystrophin transcript can be used to treat approximately 62% of all DMD patients.

(3) AAV/CRISPR Constructs

Figure 39:
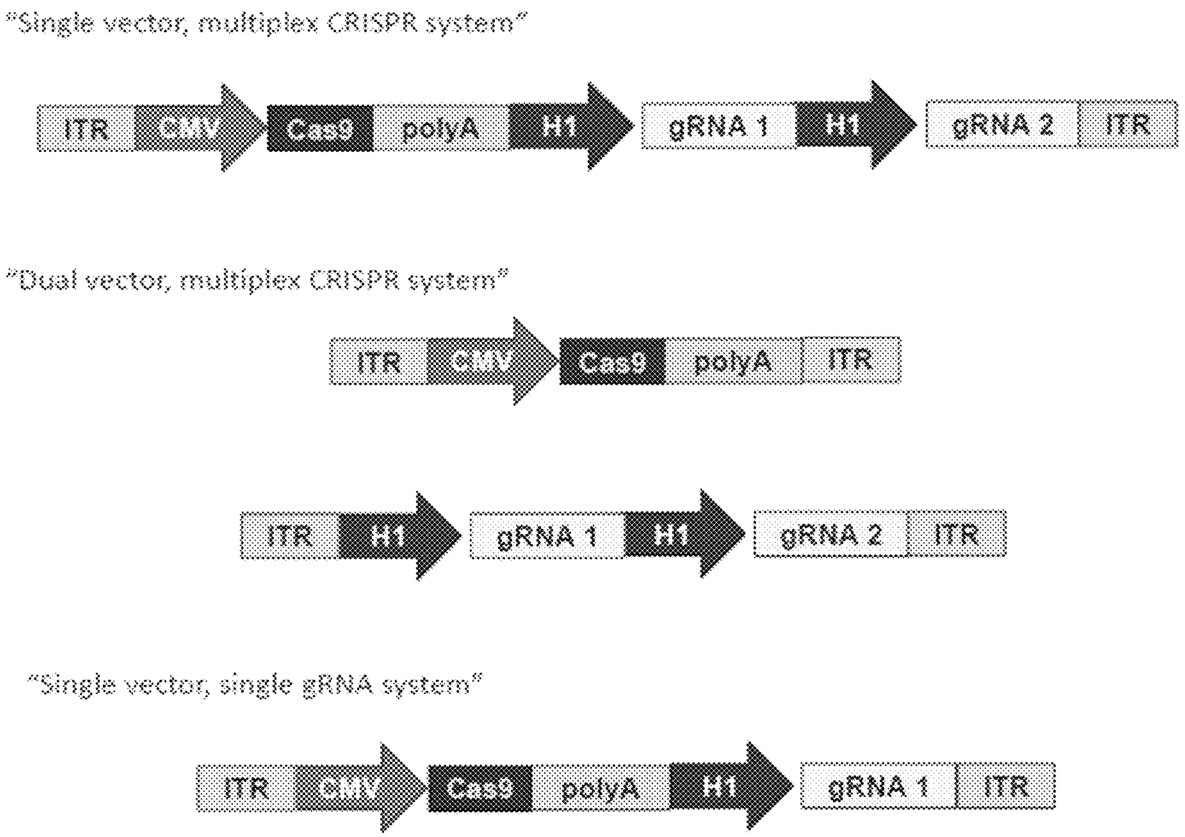
FIG. 39 shows schematic diagrams of a "Single vector, multiplex CRISPR system," Dual vector, multiplex CRISPR system," and "Single vector, single gRNA system."

AAV may be used to deliver CRISPRs using various construct configurations (see FIG. 39). For example, AAV may deliver Cas9 and gRNA expression cassettes on separate vectors. Alternatively, if the small Cas9 proteins, derived from species such as *Staphylococcus aureus* or *Neisseria meningitidis*, are used then both the Cas9 and up to two gRNA expression cassettes may be combined in a single AAV vector within the 4.7 kb packaging limit (see FIG. 39).

5. MULTIPLEX CRISPR/CAS9-BASED SYSTEM

The present disclosure is directed to a multiplex CRISPR/Cas9-Based System which includes a CRISPR/CRISPR-associated (Cas) 9-based system, such as Cas9 or dCas9, and multiple gRNAs to target one or more endogenous genes. This platform utilizes a convenient Golden Gate cloning method to rapidly incorporate up to four independent sgRNA expression cassettes into a single lentiviral vector. Each sgRNA was efficiently expressed and could mediate multiplex gene editing at diverse loci in immortalized and primary human cell lines. Transient transcriptional activation in cell lines stably expressing dCas9-VP64 was demonstrated to be tunable by synergistic activation with one to four sgRNAs. Furthermore, the single lentiviral vector can induce sustained and long-term endogenous gene expression in immortalized and primary human cells. This system allows for rapid assembly of a single lentiviral vector that enables efficient multiplex gene editing or activation in model and primary cell lines.

The multiplex CRISPR/Cas9-Based System provides potency of transcriptional activation and tunable induction of transcriptional activation. Readily generated by Golden Gate assembly, the final vector expresses a constitutive Cas9 or dCas9-VP64 in addition to one, two, three, or four sgRNAs expressed from independent promoters. Each promoter is capable of efficiently expressing sgRNAs that direct similar levels of Cas9 nuclease activity. Furthermore, lentiviral delivery of a single vector expressing Cas9 and four sgRNAs targeting independent loci resulted in simultaneous multiplex gene editing of all four loci. Tunable transcriptional activation at two endogenous genes in both transient and stable contexts was achieved using lentiviral delivery of Cas9 with or without sgRNAs. Highly efficient and long-term gene activation in primary human cells is accomplished. This system is therefore an attractive and efficient method to generate multiplex gene editing and long-term transcriptional activation in human cells.

The multiplex CRISPR/Cas9-Based System allows efficient multiplex gene editing for simultaneously inactivating multiple genes. The CRISPR/Cas9 system can simultaneously target multiple distinct genomic loci by co-expressing a single Cas9 protein with two or more sgRNAs, making this system uniquely suited for multiplex gene editing or synergistic activation applications. The CRISPR/Cas9 system greatly expedites the process of molecular targeting to new sites by simply modifying the expressed sgRNA molecule. The single lentiviral vector may be combined with methods for achieving inducible control of these components, either by chemical or optogenetic regulation, to facilitate investigation of the dynamics of gene regulation in both time and space.

The multiplex CRISPR/Cas9-based systems may transcriptionally activate two or more endogenous genes. The multiplex CRISPR/Cas9-based systems may transcriptionally repress two or more endogenous genes. For example, at least two endogenous genes, at least three endogenous genes, at least four endogenous genes, at least five endogenous genes, or at least ten endogenous genes may be activated or repressed by the multiplex CRISPR/Cas9-based system. Between two and fifteen genes, between two and ten genes, between two and five genes, between five and fifteen genes, or between five and ten genes may be activated or repressed by the multiplex CRISPR/Cas9-based system.

(1) Modified Lentiviral Vector

The multiplex CRISPR/Cas9-based system includes a modified lentiviral vector. The modified lentiviral vector includes a first polynucleotide sequence encoding a fusion protein and a second polynucleotide sequence encoding at least one sgRNA. The fusion protein may be the fusion protein of the CRISPR/Cas9-based system, as described above. The first polynucleotide sequence may be operably linked to a promoter. The promoter may be a constitutive promoter, an inducible promoter, a repressible promoter, or a regulatable promoter.

The second polynucleotide sequence encodes at least 1 sgRNA. For example, the second polynucleotide sequence may encode at least 1 sgRNA, at least 2 sgRNAs, at least 3 sgRNAs, at least 4 sgRNAs, at least 5 sgRNAs, at least 6 sgRNAs, at least 7 sgRNAs, at least 8 sgRNAs, at least 9 sgRNAs, at least 10 sgRNAs, at least 11 sgRNA, at least 12 sgRNAs, at least 13 sgRNAs, at least 14 sgRNAs, at least 15 sgRNAs, at least 16 sgRNAs, at least 17 sgRNAs, at least 18 sgRNAs, at least 19 sgRNAs, at least 20 sgRNAs, at least 25 sgRNA, at least 30 sgRNAs, at least 35 sgRNAs, at least 40 sgRNAs, at least 45 sgRNAs, or at least 50 sgRNAs. The second polynucleotide sequence may encode between 1 sgRNA and 50 sgRNAs, between 1 sgRNA and 45 sgRNAs, between 1 sgRNA and 40 sgRNAs, between 1 sgRNA and 35 sgRNAs, between 1 sgRNA and 30 sgRNAs, between 1 sgRNA and 25 different sgRNAs, between 1 sgRNA and 20 sgRNAs, between 1 sgRNA and 16 sgRNAs, between 1 sgRNA and 8 different sgRNAs, between 4 different sgRNAs and 50 different sgRNAs, between 4 different sgRNAs and 45 different sgRNAs, between 4 different sgRNAs and 40 different sgRNAs, between 4 different sgRNAs and 35 different sgRNAs, between 4 different sgRNAs and 30 different sgRNAs, between 4 different sgRNAs and 25 different sgRNAs, between 4 different sgRNAs and 20 different sgRNAs, between 4 different sgRNAs and 16 different sgRNAs, between 4 different sgRNAs and 8 different sgRNAs, between 8 different sgRNAs and 50 different sgRNAs, between 8 different sgRNAs and 45 different sgRNAs, between 8 different sgRNAs and 40 different sgRNAs, between 8 different sgRNAs and 35 different sgRNAs, between 8 different sgRNAs and 30 different sgRNAs, between 8 different sgRNAs and 25 different sgRNAs, between 8 different sgRNAs and 20 different sgRNAs, between 8 different sgRNAs and 16 different sgRNAs, between 16 different sgRNAs and 50 different sgRNAs, between 16 different sgRNAs and 45 different sgRNAs, between 16 different sgRNAs and 40 different sgRNAs, between 16 different sgRNAs and 35 different sgRNAs, between 16 different sgRNAs and 30 different sgRNAs, between 16 different sgRNAs and 25 different sgRNAs, or between 16 different sgRNAs and 20 different sgRNAs. Each of the polynucleotide sequences encoding the different sgRNAs may be operably linked to a promoter. The promoters that are operably linked to the different sgRNAs may be the same promoter. The promoters that are operably linked to the different sgRNAs may be different promoters. The promoter may be a constitutive promoter, an inducible promoter, a repressible promoter, or a regulatable promoter.

The at least one sgRNA may bind to a target gene or loci. If more than one sgRNA is included, each of the sgRNAs binds to a different target region within one target loci or each of the sgRNA binds to a different target region within different gene loci. The fusion protein may include Cas9 protein or iCas9-VP64 protein. The fusion protein may include a VP64 domain, a p300 domain, or a KRAB domain.

6. SITE-SPECIFIC NUCLEASES

The composition, as described above, includes a nucleotide sequence encoding a site-specific nuclease that binds and cleaves a target region. The site-specific nuclease may be engineered. For example, an engineered site-specific nuclease may be a CRISPR/Cas9-based system, a ZFN, or a TALEN. The site-specific nuclease may bind and cleave a gene or locus in the genome of a cell in the skeletal muscle or cardiac muscle. For example, the gene or locus may be the Rosa26 locus or the dystrophin gene.

a. CRISPR/Cas9-Based System

The CRISPR/Cas9-based system, as described above, may be used to introduce site-specific double strand breaks at targeted genomic loci.

b. Zinc Finger Nucleases (ZFN)

The site-specific nuclease may be a ZFN. A single zinc finger contains approximately 30 amino acids and the domain functions by binding 3 consecutive base pairs of DNA via interactions of a single amino acid side chain per base pair. The modular structure of the zinc finger motif permits the conjunction of several domains in series, allowing for the recognition and targeting of extended sequences in multiples of 3 nucleotides. These targeted DNA-binding domains can be combined with a nuclease domain, such as FokI, to generate a site-specific nuclease, called a "zinc finger nuclease" (ZFNs) that can be used to introduce site-specific double strand breaks at targeted genomic loci. This DNA cleavage stimulates the natural DNA-repair machinery, leading to one of two possible repair pathways, NHEJ and HDR. For example, the ZFN may target the Rosa26 locus (Perez-Pinera et al. Nucleic Acids Research (2012) 40:3741-3752) or a dystrophin gene. Examples of ZFNs are shown in Table 1 and FIGS. 35-38. In Table 1, the DNA recognition helices are underlined and "Fok ELD-S" and "Fok KKR-S" refers to the FokI nuclease domain that is fused to the zinc finger protein DNA-binding domains. In FIGS. 35-38, the target DNA sequence in the target sites (i.e., in SEQ ID NOs: 442, 445, 448, and 453) and the DNA recognition helices in the ZFN amino acid sequences (i.e., in SEQ ID NOs: 443, 444, 446, 447, 449-452, 454, and 455) are underlined, respectively.

TABLE 1

| Full amino acid sequences of identified ZFNs. |
|---|
| ZFN B left Fok ELD-S full amino acid sequence<br>(SEQ ID NO: 438)<br>MDYKDHDGDYKDHDIDYKDDDDKMAPKKKRKVGRLEPGEKPYKCPECGKS<br>FSRKDALRGHQRTHTGEKPYKCPECGKSFSHRTTLTNHQRTHTGEKPYKC<br>PECGKSFSQRNALAGHQRTHTGEKPYKCPECGKSFSHKNALQNHQRTHTG<br>EKPYKCPECGKSFSDPGHLVRHQRTHTGEKPYKCPECGKSFSTSGNLVRH<br>QRTHTGAAARALVKSELEEKKSELRHKLKYVPHEYIELIEIARNPTQDRI<br>LEMKVMEFFMKVYGYRGEHLGGSRKPDGAIYTVGSPIDYGVIVDTKAYSG<br>GYNLPIGQADEMERYVEENQTRDKHLNPNEWWKVYPSSVTEFKFLFVSGH<br>FKGNYKAQLTRLNHITNCNGAVLSVEELLIGGEMIKAGTLTLEEVRRKFN<br>NGEINF* |
| ZFN B right Fok KKR-S full amino acid sequence<br>(SEQ ID NO: 439)<br>MDYKDHDGDYKDHDIDYKDDDDKMAPKKKRKVGRLEPGEKPYKCPECGKS<br>FSQQRSLVGHQRTHTGEKPYKCPECGKSFSDKKDLTRHQRTHTGEKPYKC<br>PECGKSFSTSGHLVRHQRTHTGEKPYKCPECGKSFSQRAHLERHQRTHTG<br>EKPYKCPECGKSFSTSGSLVRHQRTHTGEKPYKCPECGKSFSTSGNLVRH<br>QRTHTGAAARALVKSELEEKKSELRHKLKYVPHEYIELIEIARNPTQDRI<br>LEMKVMEFFMKVYGYRGEHLGGSRKPDGAIYTVGSPIDYGVIVDTKAYSG<br>GYNLPIGQADEMQRYVKENQTRNKHINPNEWWKVYPSSVTEFKFLEVSGH<br>FKGNYKAQLTRLNRKTNCNGAVLSVEELLIGGEMIKAGTLTLEEVRRKFN<br>NGEINF* |
| ZFN J left Fok KKR-S full amino acid sequence<br>(SEQ ID NO: 440)<br>MDYKDHDGDYKDHDIDYKDDDDKMAPKKKRKVGRLEPGERPFQCRICMRN<br>FSSKQALAVHTRTHTGEKPFQCRICMRNFSQSTTLKRHLRTHTGEKPFQC<br>RICMRNFSRSDHLSLHLKTHLRGSQLVKSELEEKKSELRHKLKYVPHEYI<br>ELIEIARNPTQDRILEMKVMEFFMKVYGYRGEHLGGSRKPDGAIYTVGSP<br>IDYGVIVDTKAYSGGYNLPIGQADEMQRYVKENQTRNKHINPNEWWKVYP<br>SSVTEFKFLEVSGHFKGNYKAQLTRLNRKTNCNGAVLSVEELLIGGEMIK<br>AGTLTLEEVRRKFNNGEINF* |
| ZFN J right Fok ELD-S full amino acid sequence<br>(SEQ ID NO: 441)<br>MDYKDHDGDYKDHDIDYKDDDDKMAPKKKRKVGRLEPGERPFQCRICMRN<br>FSRRAHLQNHTRTHTGEKPFQCRICMRNFSQSTTLKRHLRTHTGEKPFQC<br>RICMRNFSDGGHLTRHLKTHLRGSQLVKSELEEKKSELRHKLKYVPHEYI<br>ELIEIARNPTQDRILEMKVMEFFMKVYGYRGEHLGGSRKPDGAIYTVGSP<br>IDYGVIVDTKAYSGGYNLPIGQADEMERYVEENQTRDKHLNPNEWWKVYP<br>SSVTEFKFLEVSGHFKGNYKAQLTRLNHITNCNGAVLSVEELLIGGEMIK<br>AGTLTLEEVRRKFNNGEINF* |

c. TAL Effector Nucleases (TALENs)

TALENs may be used to introduce site-specific double strand breaks at targeted genomic loci. Site-specific double-strand breaks are created when two independent TALENs bind to nearby DNA sequences, thereby permitting dimerization of FokI and cleavage of the target DNA. TALENs have advanced genome editing due to their high rate of successful and efficient genetic modification. This DNA cleavage may stimulate the natural DNA-repair machinery, leading to one of two possible repair pathways: homology-directed repair (TIDR) or the non-homologous end joining (NHEJ) pathway. The TALENs may be designed to target any gene involved in a genetic disease.

The TALENs may include a nuclease and a TALE DNA-binding domain that binds to the target gene in a TALEN target region. The target gene may have a mutation such as a frameshift mutation or a nonsense mutation. If the target gene has a mutation that causes a premature stop codon, the TALEN may be designed to recognize and bind a nucleotide sequence upstream or downstream from the premature stop codon. A "TALEN target region" includes the binding regions for two TALENs and the spacer region, which occurs between the binding regions. The two TALENs bind to different binding regions within the TALEN target region, after which the TALEN target region is cleaved. Examples of TALENs are described in International Patent Application No. PCT/US2013/038536, which is incorporated by reference in its entirety.

7. TRANSCRIPTIONAL ACTIVATORS

The composition, as described above, includes a nucleotide sequence encoding a transcriptional activator that activates a target gene. The transcriptional activator may be engineered. For example, an engineered transcriptional activator may be a CRISPR/Cas9-based system, a zinc finger fusion protein, or a TALE fusion protein.

a. CRISPR/Cas9-Based System

The CRISPR/Cas9-based system, as described above, may be used to activate transcription of a target gene with RNA. The CRISPR/Cas9-based system may include a fusion protein, as described above, wherein the second polypeptide domain has transcription activation activity or histone modification activity. For example, the second polypeptide domain may include VP64 or p300.

b. Zinc Finger Fusion Proteins

The transcriptional activator may be a zinc finger fusion protein. The zinc finger targeted DNA-binding domains, as described above, can be combined with a domain that has transcription activation activity or histone modification activity. For example, the domain may include VP64 or p300.

c. TALE Fusion Proteins

TALE fusion proteins may be used to activate transcription of a target gene. The TALE fusion protein may include a TALE DNA-binding domain and a domain that has transcription activation activity or histone modification activity. For example, the domain may include VP64 or p300.

8. COMPOSITIONS

The present invention is directed to a composition for altering gene expression and engineering or altering genomic DNA in a cell or subject. The composition may also include a viral delivery system.

a. Compositions for Genome Editing in Muscle

The present invention is directed to a composition for genome editing a target gene in skeletal muscle or cardiac muscle of a subject. The composition includes a modified AAV vector and a nucleotide sequence encoding a site-specific nuclease. The composition delivers active forms of site-specific nucleases to skeletal muscle or cardiac muscle. The composition may further comprise a donor DNA or a transgene. These compositions may be used in genome editing, genome engineering, and correcting or reducing the effects of mutations in genes involved in genetic diseases and/or other skeletal or cardiac muscle conditions.

The target gene may be involved in differentiation of a cell or any other process in which activation, repression, or disruption of a gene may be desired, or may have a mutation such as a deletion, frameshift mutation, or a nonsense mutation. If the target gene has a mutation that causes a premature stop codon, an aberrant splice acceptor site or an aberrant splice donor site, the site-specific nucleases may be designed to recognize and bind a nucleotide sequence upstream or downstream from the premature stop codon, the aberrant splice acceptor site or the aberrant splice donor site. The site-specific nucleases may also be used to disrupt normal gene splicing by targeting splice acceptors and donors to induce skipping of premature stop codons or restore a disrupted reading frame. The site-specific nucleases may or may not mediate off-target changes to protein-coding regions of the genome.

b. Adeno-Associated Virus Vectors

The composition, as described above, includes a modified adeno-associated virus (AAV) vector. The modified AAV vector may have enhanced cardiac and skeletal muscle tissue tropism. The modified AAV vector may be capable of delivering and expressing the site-specific nuclease in the cell of a mammal. For example, the modified AAV vector may be an AAV-SASTG vector (Piacentino et al. (2012) Human Gene Therapy 23:635-646). The modified AAV vector may deliver nucleases to skeletal and cardiac muscle in vivo. The modified AAV vector may be based on one or more of several capsid types, including AAV1, AAV2, AAV5, AAV6, AAV8, and AAV9. The modified AAV vector may be based on AAV2 pseudotype with alternative muscle-tropic AAV capsids, such as AAV2/1, AAV2/6, AAV2/7, AAV2/8, AAV2/9, AAV2.5 and AAV/SASTG vectors that efficiently transduce skeletal muscle or cardiac muscle by systemic and local delivery (Seto et al. Current Gene Therapy (2012) 12:139-151).

c. CRISPR/Cas9-Based System

The present disclosure also provides DNA targeting systems or compositions of at least one CRISPR/Cas9-based system, as described above. These compositions may be used in genome editing, genome engineering, and correcting or reducing the effects of mutations in genes involved in genetic diseases. The composition includes a CRISPR/Cas9-based system that includes a Cas9 protein or Cas9 fusion protein, as described above. The CRISPR/Cas9-based system may also include at least one gRNA, as described above.

d. Multiplex CRISPR/Cas9-Based System

The present disclosure also provides multiplex CRISPR/Cas9-based systems, as described above. These compositions may be used in genome editing, genome engineering, and correcting or reducing the effects of mutations in genes involved in genetic diseases. These compositions may be used to target more than one gene. The composition includes a modified lentiviral vector comprising a CRISPR/Cas9-based system that includes a Cas9 protein or Cas9 fusion protein, as described above and more than one gRNA, as described above.

9. METHODS OF USES

Potential applications of the compositions are diverse across many areas of science and biotechnology. The disclosed compositions may be used to repair genetic mutations that cause disease. The disclosed compositions may be used to disrupt genes such that gene disruption leads to increases in muscle regeneration or muscle strength, or decreases in muscle aging. The disclosed compositions may be used to introduce therapeutic genes to be expressed systemically from skeletal muscle or cardiac muscle, such as clotting factors or monoclonal antibodies. The disclosed compositions may be used to modulate mammalian gene expression. The disclosed compositions may be used to transdifferentiate or induce the differentiation of a cell or correct a mutant gene in a cell. Examples of activation of genes related to cell and gene therapy, genetic reprogramming, and regenerative medicine are provided. RNA-guided transcriptional activators may be used to reprogram cell lineage specification. Activation of endogenous genes encoding the key regulators of cell fate, rather than forced overexpression of these factors, may potentially lead to more rapid, efficient, stable, or specific methods for genetic reprogramming, transdifferentiation, and/or induced differentiation.

10. METHODS OF GENOME EDITING IN MUSCLE

The present disclosure is directed to a method of genome editing in a skeletal muscle or cardiac muscle of a subject. The method comprises administering to the skeletal muscle or cardiac muscle of the subject the composition for genome editing in skeletal muscle or cardiac muscle, as described above. The genome editing may include correcting a mutant gene or inserting a transgene. Correcting the mutant gene may include deleting, rearranging, or replacing the mutant gene. Correcting the mutant gene may include nuclease-mediated NHEJ or HDR.

11. METHODS OF USING CRISPR/CAS9-BASED SYSTEM

Potential applications of the CRISPR/Cas9-based system are diverse across many areas of science and biotechnology. The disclosed CRISPR/Cas9-based systems may be used to modulate mammalian gene expression. The disclosed CRISPR/Cas9-based systems may be used to transdifferentiate or induce differentiation of a cell or correct a mutant gene in a cell. Examples of activation of genes related to cell and gene therapy, genetic reprogramming, and regenerative medicine are provided. RNA-guided transcriptional activators may be used to reprogram cell lineage specification. Although reprogramming was incomplete and inefficient in these experiments, there are many ways by which this method could be improved, including repeated transfections of iCas9-VP64/gRNA combinations, stable expression of these factors, and targeting multiple genes, such as Brn2 and Mytl1 in addition to Ascl1 for transdifferentiation into a neuronal phenotype. Activation of endogenous genes encoding the key regulators of cell fate, rather than forced overexpression of these factors, may potentially lead to more rapid, efficient, stable, or specific methods for genetic reprogramming and transdifferentiation or induced differentiation of a cell. Finally, Cas9 fusions to other domains, including repressive and epigenetic-modifying domains, could provide a greater diversity of RNA-guided transcriptional regulators to complement other RNA-based tools for mammalian cell engineering.

a. Methods of Activating Gene Expression

The present disclosure provides a mechanism for activating the expression of endogenous genes, such as mammalian genes, based on targeting a transcriptional activator to promoters via RNA using a CRISPR/Cas9 based system, as described above. This is fundamentally different from previously described methods based on engineering sequence-specific DNA-binding proteins and may provide opportunities for targeted gene regulation. Because the generation of gRNA expression plasmids simply involves synthesizing two short custom oligonucleotides and one cloning step, it is possible to generate many new gene activators quickly and economically. The gRNAs can also be transfected directly to cells following in vitro transcription. Multiple gRNAs targeted to single promoters were shown, but simultaneous targeting of multiple promoters could also be possible. Recognition of genomic target sites with RNAs, rather than proteins, may also circumvent limitations of targeting epigenetically modified sites, such as methylated DNA.

In contrast to current methods based on engineering DNA-binding proteins, Cas9 fused to a transcriptional activation domain can be targeted by combinations of guide RNA molecules to induce the expression of endogenous human genes. This straightforward and versatile approach for targeted gene activation circumvents the need for engineering new proteins and allows for widespread synthetic gene regulation.

The method may include administering to a cell or subject a CRISPR/Cas9-based system, a polynucleotide or vector encoding said CRISPR/Cas9-based system, or DNA targeting systems or compositions of at least one CRISPR/Cas9-based system, as described above. The method may include administering a CRISPR/Cas9-based system, such as administering a Cas9 fusion protein containing transcription activation domain or a nucleotide sequence encoding said Cas9 fusion protein. The Cas9 fusion protein may include a transcription activation domain such as aVP16 protein or a transcription co-activator such as a p300 protein.

(1) dCas9-VP16

The Cas9 fusion protein may include a transcription activation domain such as aVP16 protein. The transcription activation domain may contain at least 1 VP16 protein, at least 2 VP16 proteins, at least 3 VP16 proteins, at least 4 VP16 proteins (i.e., a VP64 activator domain), at least 5 VP16 proteins, at least 6 VP16 proteins, at least 6 VP16 proteins, or at least 10 VP16 proteins. The Cas9 protein may be a Cas9 protein in which the nuclease activity is inactivated. For example, the Cas9 protein in the fusion protein may be iCas9 (amino acids 36-1403 of SEQ ID NO: 1), which includes the amino acid substitutions of D10A and H840A. The Cas9 fusion protein may be iCas9-VP64.

(2) dCas9-p300

The Cas9 fusion protein may include a transcription co-activation domain such as a p300 protein. The p300 protein (also known as EP300 or E1A binding protein p300) is encoded by the EP300 gene and regulates the activity of many genes in tissues throughout the body. The p300 protein plays a role in regulating cell growth and division, prompting cells to mature and assume specialized functions (differentiate) and preventing the growth of cancerous tumors. The p300 protein activates transcription by connecting transcription factors with a complex of proteins that carry out transcription in the cell's nucleus. The p300 interaction with transcription factors is managed by one or more of p300 domains: the nuclear receptor interaction domain (RID), the CREB and MYB interaction domain (KIX), the cysteine/histidine regions (TAZ1/CH and TAZ2/CH3) and the interferon response binding domain (IBiD). The last four domains, KIX, TAZ1, TAZ2 and IBiD of p300, each bind tightly to a sequence spanning both transactivation domains 9aaTADs of transcription factor p53. The protein functions as histone acetyltransferase that regulates transcription via chromatin remodeling, and is important in the processes of cell proliferation and differentiation. It mediates cAMP-gene regulation by binding specifically to phosphorylated CREB protein.

The p300 protein may activate Mothers against decapentaplegic homolog 7, MAF, TSG101, Peroxisome proliferator-activated receptor alpha, NPAS2, PAX6, DDX5, MYBL2, Mothers against decapentaplegic homolog 1, Mothers against decapentaplegic homolog 2, Lymphoid enhancer-binding factor 1, SNIP1, TRERF1, STAT3, EID1, RAR-related orphan receptor alpha, ELK1, HIF1A, ING5, Peroxisome proliferator-activated receptor gamma, SS18, TCF3, Zif268, Estrogen receptor alpha, GPS2, MyoD, YY1, ING4, PROX1, CITED1, HNF1A, MEF2C, MEF2D, MAML1, Twist transcription factor, PTMA, IRF2, DTX1, Flap structure-specific endonuclease 1, Myocyte-specific enhancer factor 2A, CDX2, BRCA1, HNRPU, STAT6, CITED2, RELA, TGS1, CEBPB, Mdm2, NCOA6, NFATC2, Thyroid hormone receptor alpha, BCL3, TFAP2A, PCNA, P53 and TAL1.

Figure 58:
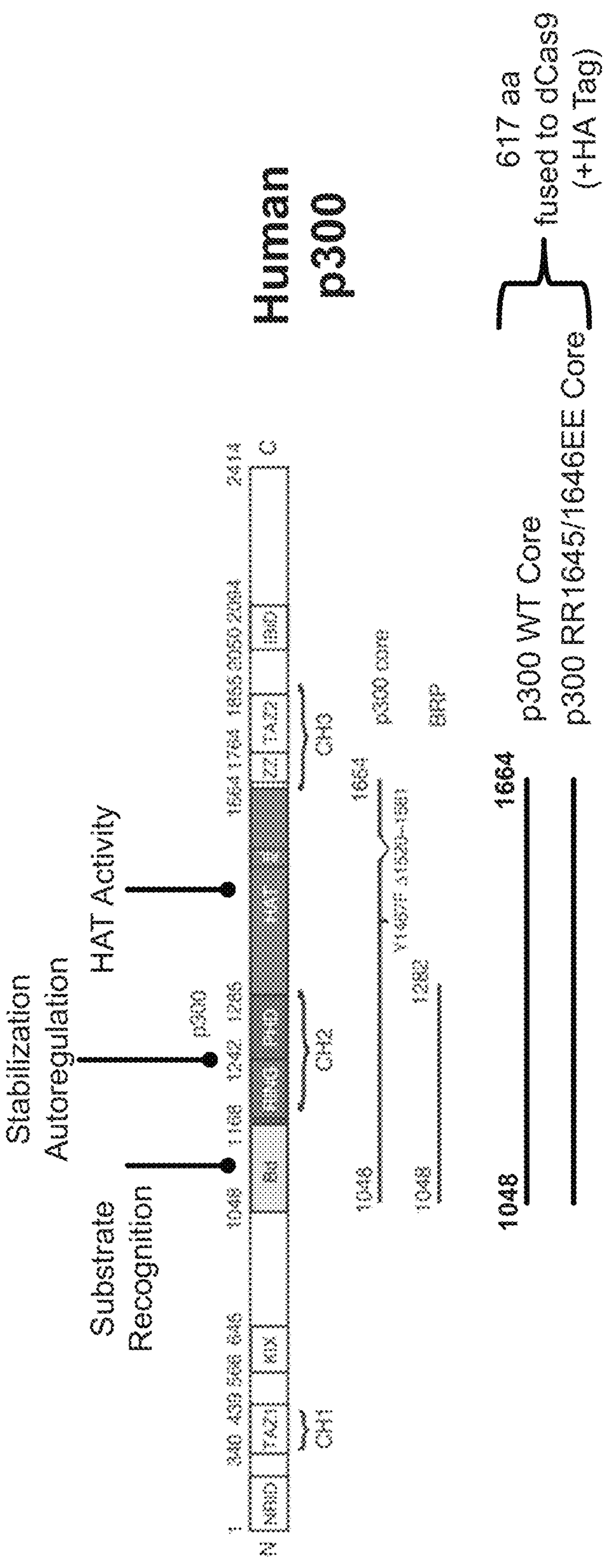
FIG. 58 shows that isolating the p300 HAT “Core” for targeted epigenetic modification of histones only via dCas9 fusion.

The transcription co-activation domain may include a human p300 protein or a fragment thereof. The transcription co-activation domain may include a wild-type human p300 protein or a mutant human p300 protein, or fragments thereof. The transcription co-activation domain may include the core lysine-acetyl transferase domain of the human p300 protein, i.e., the p300 HAT Core (also known as "p300 WT Core"; see FIG. 58). The Cas9 protein may be a Cas9 protein in which the nuclease activity is inactivated. For example, the Cas9 protein in the fusion protein may be iCas9 (amino acids 36-1403 of SEQ ID NO: 1), which includes the amino acid substitutions of D10A and H840A. The Cas9 fusion protein may be iCas9-p300 WT Core.

(3) gRNA

The method may also include administering to a cell or subject a CRISPR/Cas9-based system at least one gRNA, wherein the gRNAs target different DNA sequences. The target DNA sequences may be overlapping. The number of gRNA administered to the cell may be at least 1 gRNA, at least 2 different gRNAs, at least 3 different gRNAs at least 4 different gRNAs, at least 5 different gRNAs, at least 6 different gRNAs, at least 7 different gRNAs, at least 8 different gRNAs, at least 9 different gRNAs, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 18 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA administered to the cell may be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, 8 different gRNAs to at least 12 different gRNAs, at least 8 different gRNAs to at least 8 different gRNAs, The gRNA may comprise a complementary polynucleotide sequence of the target DNA sequence followed by NGG. The gRNA may comprise a "G" at the 5' end of the complementary polynucleotide sequence. The gRNA may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by NGG. The gRNA may target at least one of the promoter region, the enhancer region or the transcribed region of the target gene. The gRNA may include a nucleic acid sequence of at least one of SEQ ID NOs: 5-40, 65-144, 492-515, 540-563, and 585-625.

b. Methods of Repressing Gene Expression

Figure 53B:
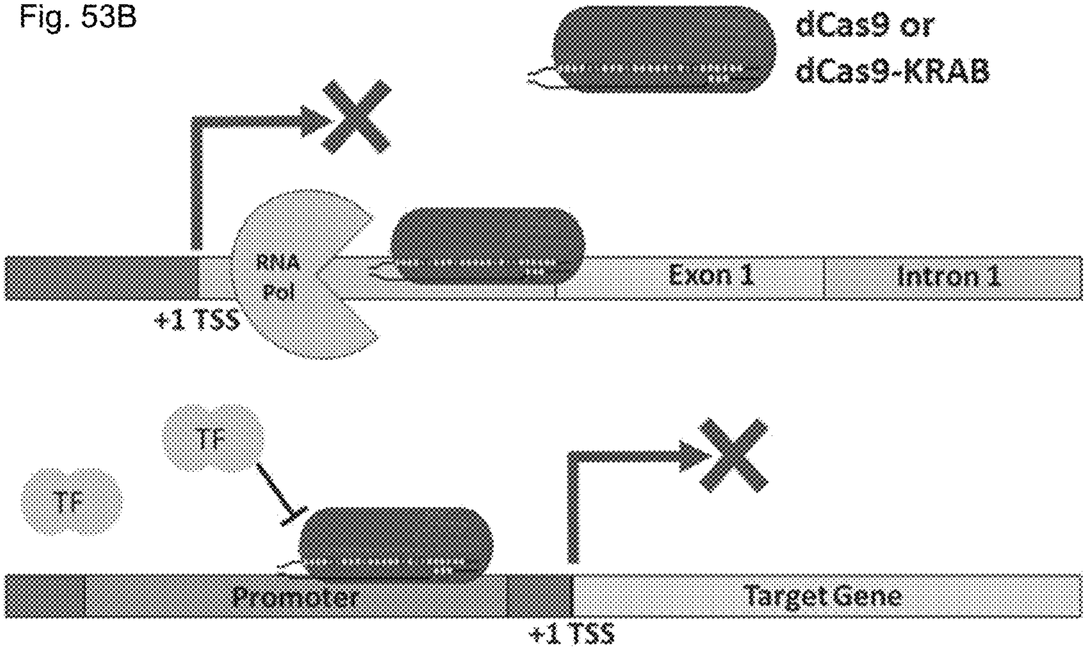
Figure 53C:
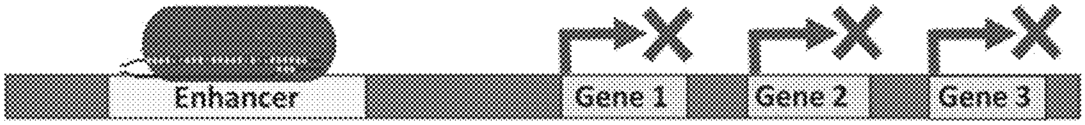

The present disclosure provides a mechanism for repressing the expression of endogenous genes, such as mammalian genes, based on targeting genomic regulatory elements, such as distal enhancers, via RNA using a CRISPR/Cas9 based system, as described above. The Cas9 fusion protein may include a transcriptional repressor, such as the KRAB repressor. The Cas9 fusion protein may be dCas9-KRAB. The dCas9-KRAB may additionally affect epigenetic gene regulation by recruiting heterochromatin-forming factors to the targeted locus. The CRISPR/dCas9-KRAB system may be used to repress the transcription of genes, but can also be used to target genomic regulatory elements which were previously inaccessible by traditional repression methods such as RNA interference (FIG. 53B). Delivering dCas9-KRAB with gRNAs targeted to a distal enhancer may disrupt expression of multiple genes regulated by the targeted enhancer (see FIG. 53C). The targeted enhancer may be any enhancer for a gene such as the HS2 enhancer.

a. Methods of Transdifferentiation or Induced Differentiation

The present disclosure provides a mechanism for transdifferentiating or inducing differentiation of cells by activating endogenous genes via RNA using a CRISPR/Cas9-based system, as described above.

(1) Transdifferentiation

The CRISPR/Cas9-based system may be used to transdifferentiate cells. Transdifferentiation, also known as lineage reprogramming or direct conversion, is a process where cells convert from one differentiated cell type to another without undergoing an intermediate pluripotent state or progenitor cell type. It is a type of metaplasia, which includes all cell fate switches, including the interconversion of stem cells. Transdifferentiation of cells has potential uses for disease modeling, drug discovery, gene therapy and regenerative medicine. Activation of endogenous genes, such as BRN2, MYT1L, ASCL1, NANOG, and/or MYOD1, using the CRISPR/Cas9 based system described above may lead to transdifferentiation of several cell types, such as fibroblasts, cardiomyocytes, hepatocytes, chondrocytes, mesenchymal progenitor cells, hematopoetic stem cells, or smooth muscle cells, into neuronal and myogenic phenotypes, respectively.

(2) Inducing Differentiation

The CRISPR/Cas9-based system may be used to induce differentiation of cells, such as stem cells, cardiomyocytes, hepatocytes, chondrocytes, mesenchymal progenitor cells, hematopoetic stem cells, or smooth muscle cells. For example, stem cells, such as embryonic stem cells or pluripotent stem cells, may be induced to differentiate into muscle cells or vascular endothelial cell, i.e., induce neuronal or myogenic differentiation.

12. USES OF MULTIPLEX CRISPR/CAS9-BASED SYSTEM

Figure 47:
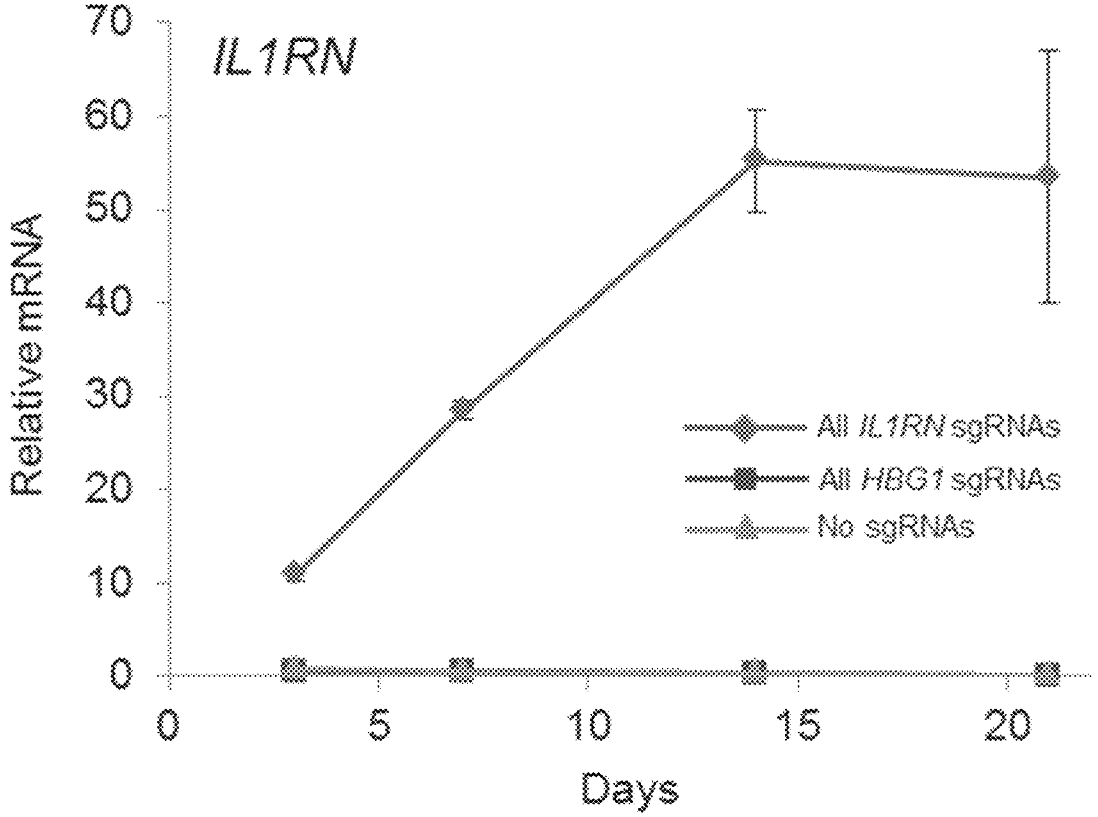
FIG. 47 shows IL1RN mRNA expression levels.

The multiplex CRISPR/Cas9-Based System takes advantage of the simplicity and low cost of sgRNA design and may be helpful in exploiting advances in high-throughput genomic research using CRISPR/Cas9 technology. For example, the single lentiviral vectors described here are useful in expressing Cas9 and numerous sgRNAs in difficult cell lines, such as primary fibroblasts described here (FIG. 47). The multiplex CRISPR/Cas9-Based System may be used in the same ways as the CRISPR/Cas9-Based System described above.

In addition to the described transcriptional activation and nuclease functionality, this system will be useful for expressing other novel Cas9-based effectors that control epigenetic modifications for diverse purposes, including interrogation of genome architecture and pathways of endogenous gene regulation. As endogenous gene regulation is a delicate balance between multiple enzymes, multiplexing Cas9 systems with different functionalities will allow for examining the complex interplay among different regulatory signals. The vector described here should be compatible with aptamer-modified sgRNAs and orthogonal Cas9s to enable independent genetic manipulations using a single set of sgRNAs.

The multiplex CRISPR/Cas9-Based System may be used to activate at least one endogenous gene in a cell. The method includes contacting a cell with the modified lentiviral vector. The endogenous gene may be transiently activated or stably activated. The endogenous gene may be transiently repressed or stably repressed. The fusion protein may be expressed at similar levels to the sgRNAs. The fusion protein may be expressed at different levels compared to the sgRNAs. The cell may be a primary human cell.

The multiplex CRISPR/Cas9-Based System may be used in a method of multiplex gene editing in a cell. The method includes contacting a cell with the modified lentiviral vector. The multiplex gene editing may include correcting a mutant gene or inserting a transgene. Correcting a mutant gene may include deleting, rearranging or replacing the mutant gene. Correcting the mutant gene may include nuclease-mediated non-homologous end joining or homology-directed repair. The multiplex gene editing may include deleting or correcting at least one gene, wherein the gene is an endogenous normal gene or a mutant gene. The multiplex gene editing may include deleting or correcting at least two genes. For example, at least two genes, at least three genes, at least four genes, at least five genes, at least six genes, at least seven genes, at least eight genes, at least nine genes, or at least ten genes may be deleted or corrected.

The multiplex CRISPR/Cas9-Based System may be used in a method of multiplex modulation of gene expression in a cell. The method includes contacting a cell with the modified lentiviral vector. The method may include modulating the gene expression levels of at least one gene. The gene expression of the at least one target gene is modulated when gene expression levels of the at least one target gene are increased or decreased compared to normal gene expression levels for the at least one target gene. The gene expression levels may be RNA or protein levels.

13. METHODS OF CORRECTING A MUTANT GENE AND TREATING A SUBJECT

The present disclosure is also directed to a method of correcting a mutant gene in a subject. The method comprises administering to the skeletal muscle or cardiac muscle of the subject the composition for genome editing in skeletal muscle or cardiac muscle, as described above. Use of the composition to deliver the site-specific nuclease to the skeletal muscle or cardiac muscle may restore the expression of a full-functional or partially-functional protein with a repair template or donor DNA, which can replace the entire gene or the region containing the mutation. The site-specific nuclease may be used to introduce site-specific double strand breaks at targeted genomic loci. Site-specific double-strand breaks are created when the site-specific nuclease binds to a target DNA sequences, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway.

The present disclosure is directed to genome editing with a site-specific nuclease without a repair template, which can efficiently correct the reading frame and restore the expression of a functional protein involved in a genetic disease. The disclosed site-specific nucleases may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active site-specific nucleases with an efficient gene editing method for the treatment of genetic diseases caused by mutations in nonessential coding regions that cause frameshifts, premature stop codons, aberrant splice donor sites or aberrant splice acceptor sites.

a. Nuclease Mediated Non-Homologous End Joining

Restoration of protein expression from an endogenous mutated gene may be through template-free NHEJ-mediated DNA repair. In contrast to a transient method targeting the target gene RNA, the correction of the target gene reading frame in the genome by a transiently expressed site-specific nuclease may lead to permanently restored target gene expression by each modified cell and all of its progeny.

Nuclease mediated NHEJ gene correction may correct the mutated target gene and offers several potential advantages over the HDR pathway. For example, NHEJ does not require a donor template, which may cause nonspecific insertional mutagenesis. In contrast to HDR, NHEJ operates efficiently in all stages of the cell cycle and therefore may be effectively exploited in both cycling and post-mitotic cells, such as muscle fibers. This provides a robust, permanent gene restoration alternative to oligonucleotide-based exon skipping or pharmacologic forced read-through of stop codons and could theoretically require as few as one drug treatment. NHEJ-based gene correction using a CRISPR/Cas9-based system, as well as other engineered nucleases including meganucleases and zinc finger nucleases, may be combined with other existing ex vivo and in vivo platforms for cell- and gene-based therapies, in addition to the plasmid electroporation approach described here. For example, delivery of a CRISPR/Cas9-based system by mRNA-based gene transfer or as purified cell permeable proteins could enable a DNA-free genome editing approach that would circumvent any possibility of insertional mutagenesis.

b. Homology-Directed Repair

Restoration of protein expression from an endogenous mutated gene may involve homology-directed repair. The method as described above further includes administrating a donor template to the cell. The donor template may include a nucleotide sequence encoding a full-functional protein or a partially-functional protein. For example, the donor template may include a miniaturized dystrophin construct, termed minidystrophin ("minidys"), a full-functional dystrophin construct for restoring a mutant dystrophin gene, or a fragment of the dystrophin gene that after homology-directed repair leads to restoration of the mutant dystrophin gene.

c. Methods of Correcting a Mutant Gene and Treating a Subject Using CRISPR/Cas9

The present disclosure is also directed to genome editing with the CRISPR/Cas9-based system to restore the expression of a full-functional or partially-functional protein with a repair template or donor DNA, which can replace the entire gene or the region containing the mutation. The CRISPR/Cas9-based system may be used to introduce site-specific double strand breaks at targeted genomic loci. Site-specific double-strand breaks are created when the CRISPR/Cas9-based system binds to a target DNA sequences using the gRNA, thereby permitting cleavage of the target DNA. The CRISPR/Cas9-based system has the advantage of advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway. For example, a CRISPR/Cas9-based system directed towards the dystrophin gene may include a gRNA having a nucleic acid sequence of any one of SEQ ID NOs: 65-115.

The present disclosure is directed to genome editing with CRISPR/Cas9-based system without a repair template, which can efficiently correct the reading frame and restore the expression of a functional protein involved in a genetic disease. The disclosed CRISPR/Cas9-based system and methods may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active CRISPR/Cas9-based system with an efficient gene editing method for the treatment of genetic diseases caused by mutations in nonessential coding regions that cause frameshifts, premature stop codons, aberrant splice donor sites or aberrant splice acceptor sites.

The present disclosure provides methods of correcting a mutant gene in a cell and treating a subject suffering from a genetic disease, such as DMD. The method may include administering to a cell or subject a CRISPR/Cas9-based system, a polynucleotide or vector encoding said CRISPR/Cas9-based system, or composition of said CRISPR/Cas9-based system as described above. The method may include administering a CRISPR/Cas9-based system, such as administering a Cas9 protein or Cas9 fusion protein containing a second domain having nuclease activity, a nucleotide sequence encoding said Cas9 protein or Cas9 fusion protein, and/or at least one gRNA, wherein the gRNAs target different DNA sequences. The target DNA sequences may be overlapping. The number of gRNA administered to the cell may be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNA, at least 15 different gRNA, at least 20 different gRNA, at least 30 different gRNA, or at least 50 different gRNA, as described above. The gRNA may include a nucleic acid sequence of at least one of SEQ ID NOs: 65-115. The method may involve homology-directed repair or non-homologous end joining.

14. METHODS OF TREATING A DISEASE

The present disclosure is directed to a method of treating a subject in need thereof. The method comprises administering to a tissue of a subject the composition for altering gene expression and engineering or altering genomic DNA in a cell or subject genome editing, as described above. The method may comprises administering to the skeletal muscle or cardiac muscle of the subject the composition for genome editing in skeletal muscle or cardiac muscle, as described above. The subject may be suffering from a skeletal muscle or cardiac muscle condition causing degeneration or weakness or a genetic disease. For example, the subject may be suffering from Duchenne muscular dystrophy, as described above.

a. Duchenne Muscular Dystrophy

The method, as described above, may be used for correcting the dystrophin gene and recovering full-functional or partially-functional protein expression of said mutated dystrophin gene. In some aspects and embodiments the disclosure provides a method for reducing the effects (e.g., clinical symptoms/indications) of DMD in a patient. In some aspects and embodiments the disclosure provides a method for treating DMD in a patient. In some aspects and embodiments the disclosure provides a method for preventing DMD in a patient. In some aspects and embodiments the disclosure provides a method for preventing further progression of DMD in a patient.

15. CONSTRUCTS AND PLASMIDS

The compositions, as described above, may comprise genetic constructs that encodes the CRISPR/Cas9-based system, as disclosed herein. The genetic construct, such as a plasmid, may comprise a nucleic acid that encodes the CRISPR/Cas9-based system, such as the Cas9 protein and Cas9 fusion proteins and/or at least one of the gRNAs. The compositions, as described above, may comprise genetic constructs that encodes the modified AAV vector and a nucleic acid sequence that encodes the site-specific nuclease, as disclosed herein. The genetic construct, such as a plasmid, may comprise a nucleic acid that encodes the site-specific nuclease. The compositions, as described above, may comprise genetic constructs that encodes the modified lentiviral vector, as disclosed herein. The genetic construct, such as a plasmid, may comprise a nucleic acid that encodes the Cas9-fusion protein and at least one sgRNA. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

The nucleic acid sequences may make up a genetic construct that may be a vector. The vector may be capable of expressing the fusion protein, such as the Cas9-fusion protein or site-specific nuclease, in the cell of a mammal. The vector may be recombinant. The vector may comprise heterologous nucleic acid encoding the fusion protein, such as the Cas9-fusion protein or site-specific nuclease. The vector may be a plasmid. The vector may be useful for transfecting cells with nucleic acid encoding the Cas9-fusion protein or site-specific nuclease, which the transformed host cell is cultured and maintained under conditions wherein expression of the Cas9-fusion protein or the site-specific nuclease system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cas9-based system or the site-specific nuclease and may further comprise an initiation codon, which may be upstream of the CRISPR/Cas9-based system or the site-specific nuclease coding sequence, and a stop codon, which may be downstream of the CRISPR/Cas9-based system or the site-specific nuclease coding sequence. The initiation and termination codon may be in frame with the CRISPR/Cas9-based system or the site-specific nuclease coding sequence. The vector may also comprise a promoter that is operably linked to the CRISPR/Cas9-based system or the site-specific nuclease coding sequence. The promoter operably linked to the CRISPR/Cas9-based system or the site-specific nuclease coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the CRISPR/Cas9-based system or the site-specific nuclease. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, CA).

The vector may also comprise an enhancer upstream of the CRISPR/Cas9-based system, i.e., the Cas9 protein or Cas9 fusion protein coding sequence or sgRNAs, or the site-specific nuclease. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cas9-based system, including the nucleic acid sequence encoding the Cas9 protein or Cas9 fusion protein and the nucleic acid sequence encoding the at least one gRNA comprising the nucleic acid sequence of at least one of SEQ ID NOs: 5-40, 65-144, 492-515, 540-563, and 585-625.

16. PHARMACEUTICAL COMPOSITIONS

The composition may be in a pharmaceutical composition. The pharmaceutical composition may comprise about 1 ng to about 10 mg of DNA encoding the CRISPR/Cas9-based system or CRISPR/Cas9-based system protein component, i.e., the Cas9 protein or Cas9 fusion protein. The pharmaceutical composition may comprise about 1 ng to about 10 mg of the DNA of the modified AAV vector and nucleotide sequence encoding the site-specific nuclease. The pharmaceutical composition may comprise about 1 ng to about 10 mg of the DNA of the modified lentiviral vector. The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition for genome editing in skeletal muscle or cardiac muscle at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

17. METHODS OF DELIVERY

Provided herein is a method for delivering the pharmaceutical formulations, preferably compositions described above, for providing genetic constructs. The delivery of the compositions may be the transfection or electroporation of the composition as a nucleic acid molecule that is expressed in the cell and delivered to the surface of the cell. The nucleic acid molecules may be electroporated using BioRad Gene Pulser Xcell or Amaxa Nucleofector IIb devices. Several different buffers may be used, including BioRad electroporation solution, Sigma phosphate-buffered saline product #D8537 (PBS), Invitrogen OptiMM I (OM), or Amaxa Nucleofector solution V (N.V.). Transfections may include a transfection reagent, such as Lipofectamine 2000.

Upon delivery of the composition to the tissue, and thereupon the vector into the cells of the mammal, the transfected cells will express the fusion protein, such as a CRISPR/Cas9-based system and/or a site-specific nuclease. The composition may be administered to a mammal to alter gene expression or to re-engineer or alter the genome. For example, the composition may be administered to a mammal to correct the dystrophin gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

a. CRISPR/Cas9-Based System

The vector encoding a CRISPR/Cas9-based system protein component, i.e., the Cas9 protein or Cas9 fusion protein, may be delivered to the mammal by DNA injection (also referred to as DNA vaccination) with and without in vivo electroporation, liposome mediated, nanoparticle facilitated, and/or recombinant vectors. The recombinant vector may be delivered by any viral mode. The viral mode may be recombinant lentivirus, recombinant adenovirus, and/or recombinant adeno-associated virus.

The nucleotide encoding a CRISPR/Cas9-based system protein component, i.e., the Cas9 protein or Cas9 fusion protein, may be introduced into a cell to genetically correct the target gene or alter gene expression of a gene, such as activate or repress endogenous genes. For example, a nucleotide encoding a CRISPR/Cas9-based system protein component, i.e., the Cas9 protein or Cas9 fusion protein, directed towards a mutant dystrophin gene by the gRNA may be introduced into a myoblast cell from a DMD patient. Alternatively, they may be introduced into a fibroblast cell from a DMD patient, and the genetically corrected fibroblast cell may be treated with MyoD to induce differentiation into myoblasts, which may be implanted into subjects, such as the damaged muscles of a subject to verify that the corrected dystrophin protein was functional and/or to treat the subject. The modified cells may also be stem cells, such as induced pluripotent stem cells, bone marrow-derived progenitors, skeletal muscle progenitors, human skeletal myoblasts from DMD patients, CD133+ cells, mesoangioblasts, and MyoD- or Pax7-transduced cells, or other myogenic progenitor cells. For example, the CRISPR/Cas9-based system may cause neuronal or myogenic differentiation of an induced pluripotent stem cell.

18. ROUTES OF ADMINISTRATION

The compositions may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gone guns", or other physical methods such as electroporation ("EP"), "hydrodynamic method", or ultrasound.

The composition may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus. The composition may be injected into the skeletal muscle or cardiac muscle. For example, the composition may be injected into the tibialis anterior muscle.

19. CELL TYPES

Any of these delivery methods and/or routes of administration could be utilized with a myriad of cell types, for example, those cell types currently under investigation for cell-based therapies. Cell types may be fibroblasts, pluripotent stem cells, cardiomyocytes, hepatocytes, chondrocytes, mesenchymal progenitor cells, hematopoetic stem cells, smooth muscle cells, or K562 human erythroid leukemia cell line.

a. DMD

Cell types currently under investigation for cell-based therapies of DMD include immortalized myoblast cells, such as wild-type and DMD patient derived lines, for example A48-50 DMD, DMD 8036 (del48-50), C25C14 and DMD-7796 cell lines, primal DMD dermal fibroblasts, induced pluripotent stem cells, bone marrow-derived progenitors, skeletal muscle progenitors, human skeletal myoblasts from DMD patients, CD133+ cells, mesoangioblasts, cardiomyocytes, hepatocytes, chondrocytes, mesenchymal progenitor cells, hematopoetic stem cells, smooth muscle cells, and MyoD- or Pax7-transduced cells, or other myogenic progenitor cells. Immortalization of human myogenic cells may be used for clonal derivation of genetically corrected myogenic cells. Cells may be modified ex vivo to isolate and expand clonal populations of immortalized DMD myoblasts that contain a genetically corrected dystrophin gene and are free of other nuclease-introduced mutations in protein coding regions of the genome. Alternatively, transient in vivo delivery of nucleases by non-viral or non-integrating viral gene transfer, or by direct delivery of purified proteins and gRNAs containing cell-penetrating motifs may enable highly specific correction in situ with minimal or no risk of exogenous DNA integration.

20. KITS

Provided herein is a kit, which may be used to edit a genome in skeletal muscle or cardiac muscle, such as correcting a mutant gene. The kit comprises a composition for genome editing in skeletal muscle or cardiac muscle, as described above, and instructions for using said composition. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The composition for genome editing in skeletal muscle or cardiac muscle may include a modified AAV vector and a nucleotide sequence encoding a site-specific nuclease, as described above. The site-specific nuclease may include a ZFN, a TALEN, or CRISPR/Cas9-based system, as described above, that specifically binds and cleaves a mutated gene. The site-specific nuclease, as described above, may be included in the kit to specifically bind and target a particular region in the mutated gene. The site-specific nuclease may be specific for a mutated dystrophin gene, as described above. The kit may further include donor DNA, a gRNA, or a transgene, as described above.

a. CRISPR/Cas9-Based System

Provided herein is a kit, which may be used to correct a mutated gene. The kit comprises at least one component for correcting a mutated gene and instructions for using the CRISPR/Cas9-based system. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

At least one component may include at least one CRISPR/Cas9-based system, as described above, which specifically targets a gene. The kit may include a Cas9 protein or Cas9 fusion protein, a nucleotide sequence encoding said Cas9 protein or Cas9 fusion protein, and/or at least one gRNA. The CRISPR/Cas9-based system, as described above, may be included in the kit to specifically bind and target a particular target region upstream, within or downstream of the coding region of the target gene. For example, a CRISPR/Cas9-based system may be specific for a promoter region of a target gene or a CRISPR/Cas9-based system may be specific for a mutated gene, for example a mutated dystrophin gene, as described above. The kit may include donor DNA, as described above.

21. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Materials and Methods

Cell Culture and Transfection.

HEK293T cells were obtained from the American Tissue Collection Center (ATCC) through the Duke University Cancer Center Facilities and were maintained in DMEM supplemented with 10% fetal bovine serum and 1% penicillin/streptomycin at 37° C. with 5% $CO_2$. HEK293T cells were transfected with Lipofectamine 2000 (Invitrogen) according to manufacturer's instructions. Transfection efficiencies were routinely higher than 80% as determined by fluorescence microscopy following delivery of a control eGFP expression plasmid. Cas9 expression plasmid was transfected at a mass ratio of 3:1 to either the individual gRNA expression plasmids or the identical amount of gRNA expression plasmid consisting of a mixture of equal amounts of the four gRNAs.

Primary mouse embryonic fibroblasts (PMEF-HL, Millipore, Billerica, MA) were seeded (75,000 per well) in 24-well TCPS plates (BD, Franklin Lakes, NJ) and maintained at 37° C. and 5% $CO_2$ in complete MEF medium consisting of high glucose DMEM supplemented with 10% Premium Select FBS (Atlanta Biologicals, Lawrenceville, GA), 25 μg $mL^{-1}$ gentamicin (Invitrogen), 1× GutaMAX, non-essential amino acids, sodium pyruvate, and β-mercaptoethanol (Invitrogen). MEF transfections were performed with a single 1 μg $cm^{-2}$ dose of total plasmid DNA, delivered as cationic nanocomplexes following electrostatic condensation with poly(CBA-ABOL) in serum- and antibiotic-free OptiMEM, as described previously (Adler et al. *Molecular therapy. Nucleic acids* 1, e32 (2012)). OptiMEM was replaced with complete MEF medium 4 hrs after transfection. 48 hrs after transfection, MEFs were processed for qRT-PCR, or the complete MEF medium was replaced with N3 neural induction medium containing: DMEM/F-12 (Invitrogen), 1× N-2 Supplement (Invitrogen), 10 ng $mL^{-1}$ human bFGF2 (Stemgent, Cambridge, MA), and 25 μg $mL^{-1}$ gentamicin (Invitrogen). A GFP reporter vector (pmax-GFP, 3486 bp, Amaxa, Cologne, Germany) was used to optimize transfection conditions. Cas9 expression plasmid was transfected at a mass ratio of 3:1 or 1:1 to an equal mixture of four gRNA expression plasmids.

Plasmids.

The plasmids encoding wild-type and H840A Cas9 were obtained from Addgene (Plasmid #39312 and Plasmid #39316; Jinek, et al. *Science* 337, 816-821 (2012)). H840A Cas9 was cloned into the vector pcDNA3.1 in frame with a FLAG epitope tag and a nuclear localization sequence (NLS) at the N-terminus with a primer pair that introduced the D10A mutation. The VP64 domain, an NLS, and an HA epitope tag were cloned in frame with the Cas9 ORF at the C-terminus (FIG. 1A, FIG. 9A). The tracrRNA and crRNA expression cassettes (Cong et al. *Science* 339, 819-823 (2013)) were ordered as gBlocks (Integrated DNA Technologies (IDT)) and cloned into a pZDonor plasmid (Sigma) with KpnI and SacII sites. A chimeric guide RNA expression cassette (Mali et al. *Science* 339, 823-826 (2013)) was also ordered as gBlocks with modifications to include a BbsI restriction site to facilitate rapid cloning of new guide RNA spacer sequences (FIG. 9B). The oligonucleotides containing the target sequences were obtained from IDT, hybridized, phosphorylated, and cloned in the appropriate plasmids using BbsI sites. The target sequences are provided in Table 2.

TABLE 2

Target sequences of gRNAs

| Target | Name | Sequence | SEQ ID NO |
|---|---|---|---|
| ASCL1 | CR1 | GCTGGGTGTCCCATTGAAA | 5 |
| | CR2 | CAGCCGCTCGCTGCAGCAG | 6 |
| | CR3 | TGGAGAGTTTGCAAGGAGC | 7 |
| | CR4 | GTTTATTCAGCCGGGAGTC | 8 |
| NANOG | CR1 | CGCCAGGAGGGGTGGGTCTA | 9 |
| | CR2 | CCTTGGTGAGACTGGTAGA | 10 |
| | CR3 | GTCTTCAGGTTCTGTTGCT | 11 |
| | CR4 | ATATTCCTGATTTAAAAGT | 12 |
| VEGFA | CR1 | TTAAAAGTCGGCTGGTAGC | 13 |
| | CR2 | CGGGCCGGGGGCGGGGTCC | 14 |
| | CR3 | GCCCGAGCCGCGTGTGGAA | 15 |
| | CR4 | CCTTCATTGCGGCGGGCTG | 16 |
| TERT | CR1 | CCGACCCCTCCCGGGTCCC | 17 |
| | CR2 | CAGGACCGCGCTTCCCACG | 18 |
| | CR3 | TGCACCCTGGGAGCGCGAG | 19 |
| | CR4 | CCGCACGCACCTGTTCCCA | 20 |
| IL1B | CR1 | AAAACAGCGAGGGAGAAAC | 21 |
| | CR2 | TTAACTTGATTGTGAAATC | 22 |
| | CR3 | AAAACAATGCATATTTGCA | 23 |
| | CR4 | AAAATCCAGTATTTTAATG | 24 |
| IL1R2 | CR1 | ACCCAGCACTGCAGCCTGG | 25 |
| | CR2 | AACTTATGCGGCGTTTCCT | 26 |
| | CR3 | TCACTTTAAAACCACCTCT | 27 |
| | CR4 | GCATCTTTTTCTCTTTAAT | 28 |
| IL1RN | CR1 | TGTACTCTCTGAGGTGCTC | 29 |
| | CR2 | ACGCAGATAAGAACCAGTT | 30 |
| | CR3 | CATCAAGTCAGCCATCAGC | 31 |
| | CR4 | GAGTCACCCTCCTGGAAAC | 32 |
| HBG1/2 | CR1 | GCTAGGGATGAAGAATAAA | 33 |
| | CR2 | TTGACCAATAGCCTTGACA | 34 |
| | CR3 | TGCAAATATCTGTCTGAAA | 35 |
| | CR4 | AAATTAGCAGTATCCTCTT | 36 |
| MYOD1 | CR1 | CCTGGGCTCCGGGGCGTTT | 37 |
| | CR2 | GGCCCCTGCGGCCACCCCG | 38 |
| | CR3 | CTCCCTCCCTGCCCGGTAG | 39 |
| | CR4 | AGGTTTGGAAAGGGCGTGC | 40 |

Western Blot.

Cells were lysed in 50 mM Tris-Cl (pH 7.4), 150 mM NaCl, 0.5% Triton X-100, and 0.1% SDS. Lysates were mixed with loading buffer, boiled for 5 min, and equal volumes of protein were run in NuPAGE® Novex 4-12% or 10% Bis-Tris Gel polyacrylamide gels and transferred to nitrocellulose membranes. Non-specific antibody binding was blocked with 50 mM Tris/150 mM NaCl/0.1% Tween-20 (TBS-T) with 5% nonfat milk for 30 min. The membranes were incubated with primary antibodies (HRP-conjugated anti-Flag (Cell Signaling, Cat #2044) in 5% BSA in TBS-T diluted 1:1000 overnight; anti-GAPDH (Cell Signaling, clone 14C10) in 5% milk in TBS-T diluted 1:5000 for 30 min; anti-ASCL1 (Santa Cruz, clone sc-48449) in 5% BSA diluted 1:500; or anti-g-globin (Santa Cruz, clone 51-7) in 5% milk diluted 1:500 and the membranes were washed with TBS-T for 30 min. Membranes labeled with primary antibodies were incubated with anti-rabbit HRP-conjugated antibody (Sigma-Aldrich) diluted 1:5000 for 30 min, anti-goat (1:3000) or anti-mouse (1:5000) and washed with TBS-T for 30 min. Membranes were visualized using the Immun-Star WesternC™ Chemiluminescence Kit (Bio-Rad) and images were captured using a ChemiDoc™ XRS+ System and processed using ImageLab software (Bio-Rad).

ELISA.

Serum-free culture media (OPTI-MEM) was collected and frozen at −80° C. Human IL-1ra secretion into culture media was quantified via enzyme-linked immunosorbent assay (ELISA), according to the manufacturer's protocols (R&D Systems, Cat. No. DY280). The standard curve was prepared by diluting recombinant human IL-1ra in OPTI-MEM and the IL-1ra in culture media was measured undiluted. The samples were concentrated about 8 fold via centrifugation through 3 kDa MWCO filters for 20 min (Amicon Ultra, Cat #UFC500396). Reported values were corrected by the concentration factor for each sample.

Optical density was measured at 450 nm, with a wavelength correction at 540 nm. Each standard and sample was assayed in duplicate. The duplicate readings were averaged and normalized by subtracting the average zero standard optical density. A standard curve was generated by log-transforming the data and performing a linear regression of the IL-1ra concentration versus the optical density. Reported values are the mean and standard error of the mean from three independent experiments (n=3) that were performed on different days with technical duplicates that were averaged for each experiment.

qRT-PCR.

Total RNA was isolated using the RNeasy Plus RNA isolation kit (Qiagen). cDNA synthesis was performed using the SuperScript® VILO™ cDNA Synthesis Kit (Invitrogen). Real-time PCR using PerfeCTa® SYBR® Green FastMix was performed with the CFX96 Real-Time PCR Detection System (Bio-Rad) with oligonucleotide primers reported in Table 3 that were designed using Primer3Plus software and purchased from IDT.

TABLE 3

Sequences of primers used for qRT-PCR.

| Target | Forward Primer | SEQ ID NO | Reverse Primer | SEQ ID NO |
|---|---|---|---|---|
| hASCL1 | GGAGCTTCTCGACTTCACCA | 41 | AACGCCACTGACAAGAAAGC | 53 |
| NANOG | GATTTGTGGGCCTGAAGAAA | 42 | CAGATCCATGGAGGAAGGAA | 54 |
| VEGFA | AAGGAGGAGGGCAGAATCAT | 43 | GGGTACTCCTGGAAGATGTCC | 55 |
| TERT | AAACCTTCCTCAGCTATGCCC | 44 | GTTTGCGACGCATGTTCCTC | 56 |
| IL1B | AGCTGATGGCCCTAAACAGA | 45 | AAGCCCTTGCTGTAGTGGTG | 57 |
| IL1R2 | CAGGAGGACTCTGGCACCTA | 46 | CGGCAGGAAAGCATCTGTAT | 58 |
| IL1RN | GGAATCCATGGAGGGAAGAT | 47 | TGTTCTCGCTCCAGGTCAGTG | 59 |
| HBG1/2 | GCTGAGTGAACTGCACTGTGA | 48 | GAATTCTTTGCCGAAATGGA | 60 |
| MYOD1 | CTCTCTGCTCCTTTGCCACA | 49 | GTGCTCTTCGGGTTTCAGGA | 61 |
| GAPDH | CAATGACCCCTTCATTGACC | 50 | TTGATTTTGGAGGGATCTCG | 62 |
| mASCL1 | GGAACAAGAGCTGCTGGACT | 51 | GTTTTTCTGCCTCCCCCATTT | 63 |
| mGAPDH | AACTTTGGCATTGTGGAAGG | 52 | GGATGCAGGGATGATGTTCT | 64 |

Figure 10A:
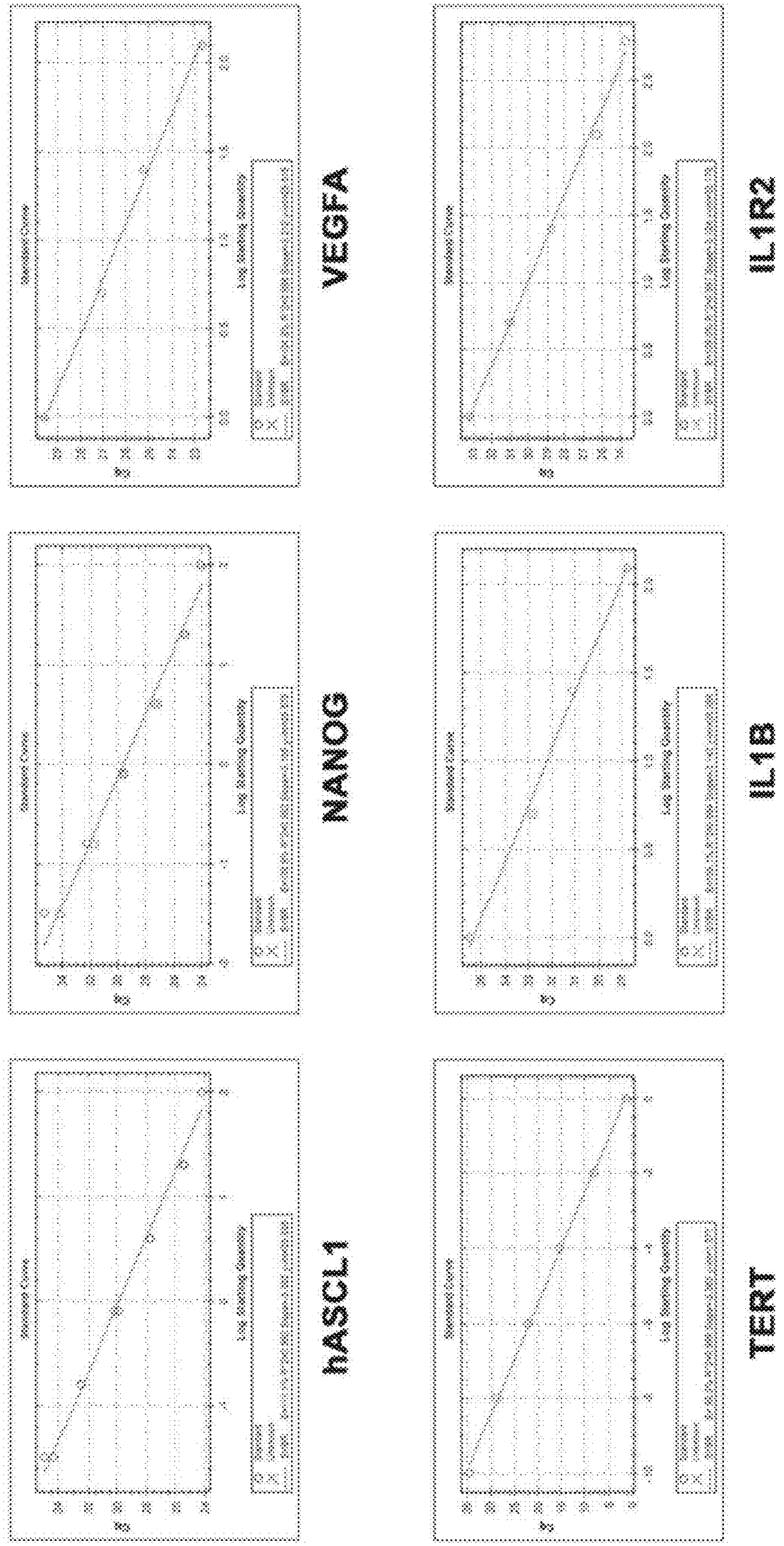
FIGS. 10A-10B show the standard curves for qRT-PCR. For each gene, the experimental sample with the highest expression level was diluted to create a standard curve that was assayed by qRT-PCR to ensure efficient amplification over an appropriate dynamic range. The efficiencies of all amplification reactions were within 90-115%.
Figure 10B:
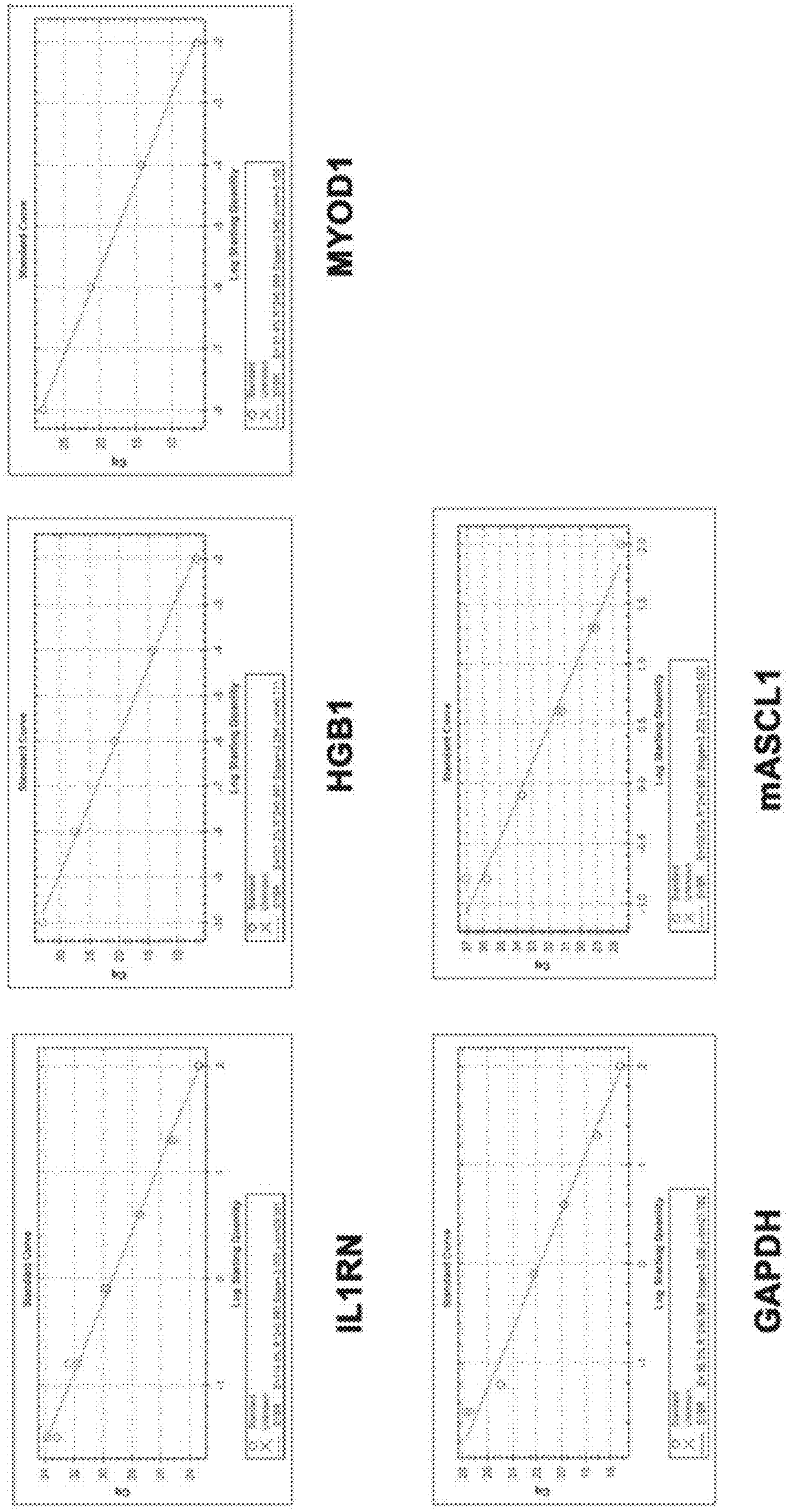

Primer specificity was confirmed by agarose gel electrophoresis and melting curve analysis. Reaction efficiencies over the appropriate dynamic range were calculated to ensure linearity of the standard curve (FIG. 10). The results are expressed as fold-increase mRNA expression of the gene of interest normalized to GAPDH expression by the $\Delta\Delta C_T$ method. Reported values are the mean and standard error of the mean from three independent experiments performed on different days (n=3) with technical duplicates that were averaged for each experiment.

RNA-Seq.

RNA seq libraries were constructed. Briefly, first strand cDNA was synthesized from oligo dT Dynabead® (Invitrogen) captured mRNA using SuperScript® VILO™ cDNA Synthesis Kit (Invitrogen). Second strand cDNA was synthesized using DNA Polymerase I (New England Biolabs). cDNA was purified using Agencourt AMPure XP beads (Beckman Coulter) and Nextera transposase (Illumina; 5 min at 55° C.) was used to simultaneously fragment and insert sequencing primers into the double-stranded cDNA. Transposition reactions were halted using QG buffer (Qiagen) and fragmented cDNA was purified on AMPure XP beads. Indexed sequencing libraries were generated by 6 cycles of PCR.

Libraries were sequenced using 50-bp single end reads on two lanes of an Illumina HiSeq 2000 instrument, generating between 29 million and 74 million reads per library. Reads were aligned to human RefSeq transcripts using Bowtie (Langmead et al. Genome biology 10, R25 (2009)). The statistical significance of differential expression, including correction for multiple hypothesis testing, was calculated using DESeq (Anders et al. Genome biology 11, R106 (2010)). Raw RNA-seq reads and the number of reads aligned to each RefSeq transcript have been deposited for public access in the Gene Expression Omnibus (GEO), with accession number currently pending.

Immunofluorescence Staining.

For detection of Tuj1 and MAP2 expression, transfected MEFs were fixed at day 10 of culture in N3 medium with 4% PFA (EMS, Hatfield, PA) at room temperature (RT) for 20 min. Cells were then incubated in blocking buffer containing 0.2% Triton X-100, 3% w/v BSA, and 10% goat serum (Sigma-Aldrich, Saint Louis, MO) for two hrs at room temperature with rabbit anti-Tuj1 (Covance, Princeton, New Jersey, clone TUJ1 1-15-79, 1:500) and mouse anti-MAP2 (BD, clone Ap20, 1:500), or for an additional 24 hrs at 4° C. with mouse anti-Ascl1 (BD clone 24B72D11.1, 1:100). The cells were then washed three times with PBS, incubated for 1 hr at room temperature in blocking buffer with Alexa Fluor 488 goat anti-mouse IgG and Alexa Fluor 594 goat anti-rabbit IgG (Invitrogen, 1:200), and washed three times with PBS. Stained MEFs were then scanned with a Nikon Eclipse TE2000-U inverted fluorescence microscope with a ProScanII motorized stage (Prior Scientific, Rockland, MA) to produce large mosaic images of each complete culture area. These mosaics were processed with a FIJI macro to automatically and uniformly threshold each image according to local contrast, exclude small debris, and to count the number of $Tuj1^+$ cells in each well.

Statistics.

Statistical analysis was performed by Tukey's test with alpha equal to 0.05 in JMP 10 Pro.

Example 2

Results

Figure 1B:
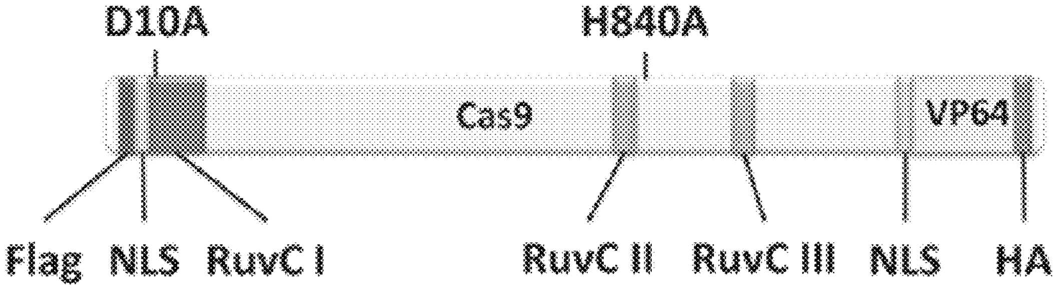
Figure 1C:
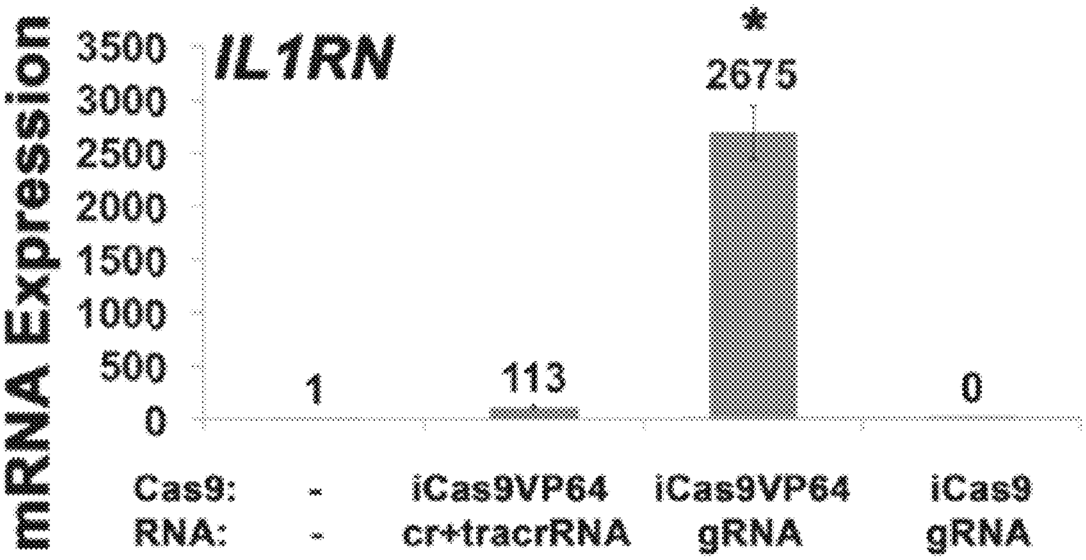
Figure 1D:
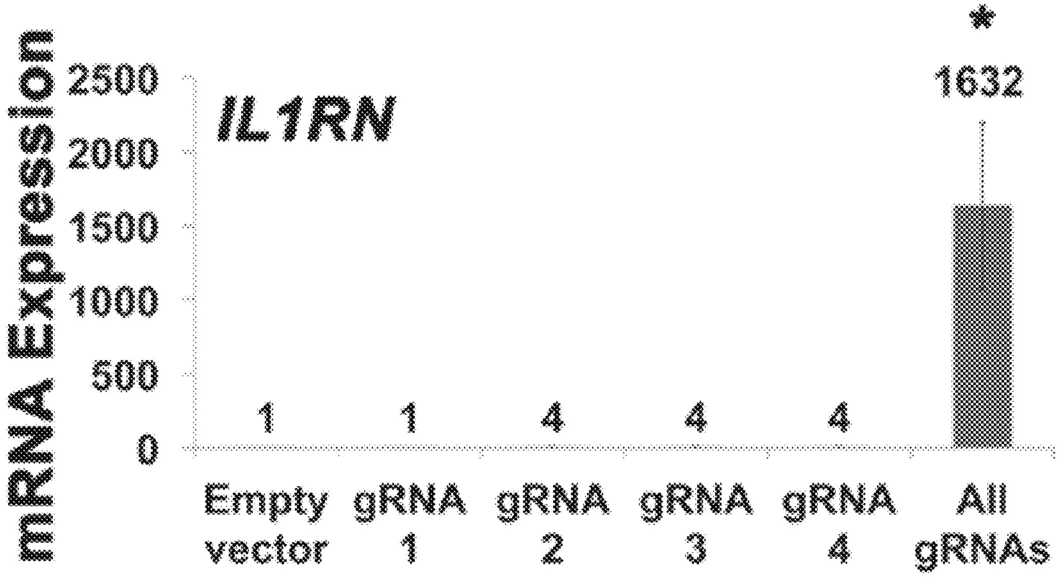
Figure 1E:
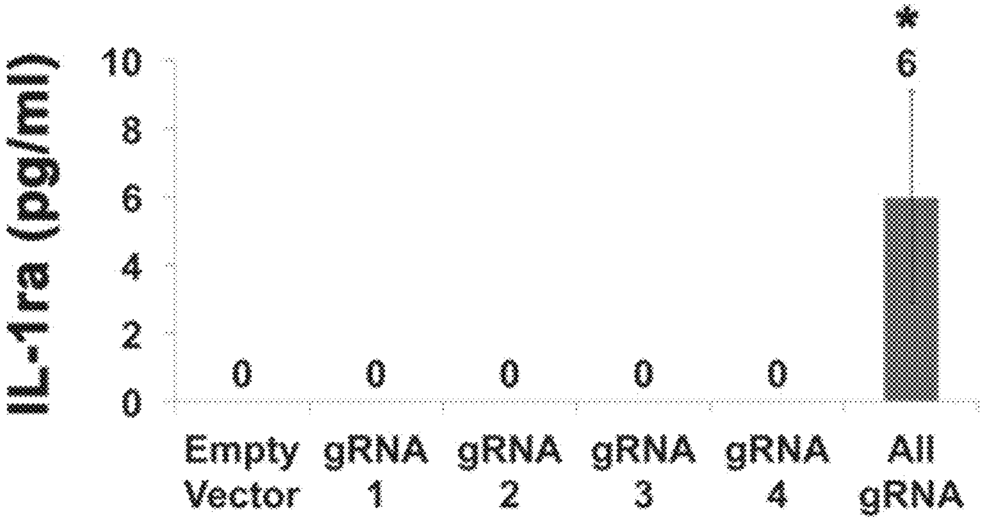
Figure 1F:
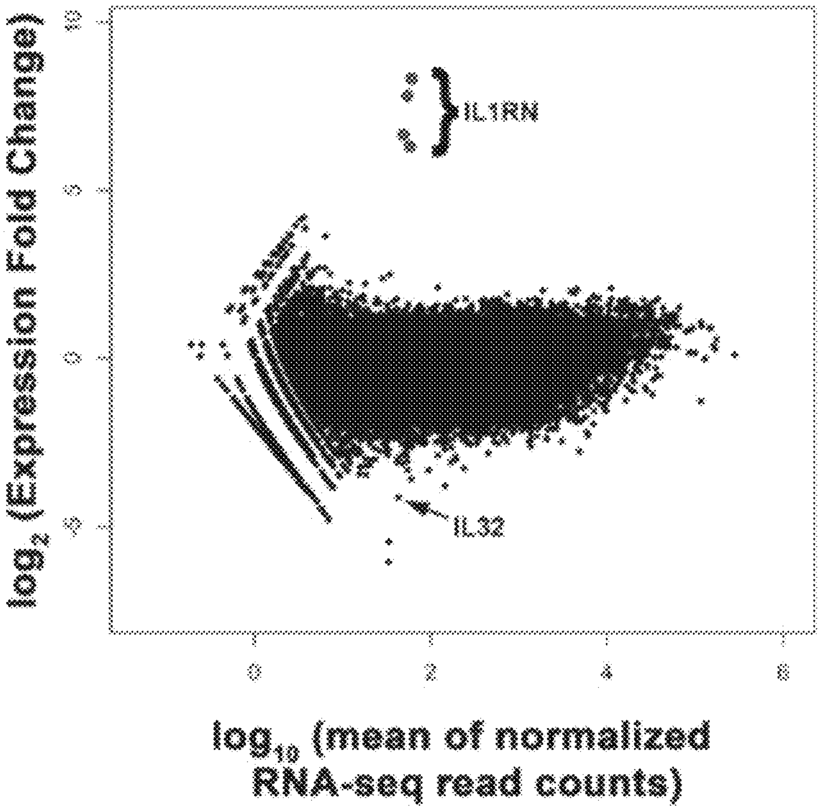
Figure 2A:
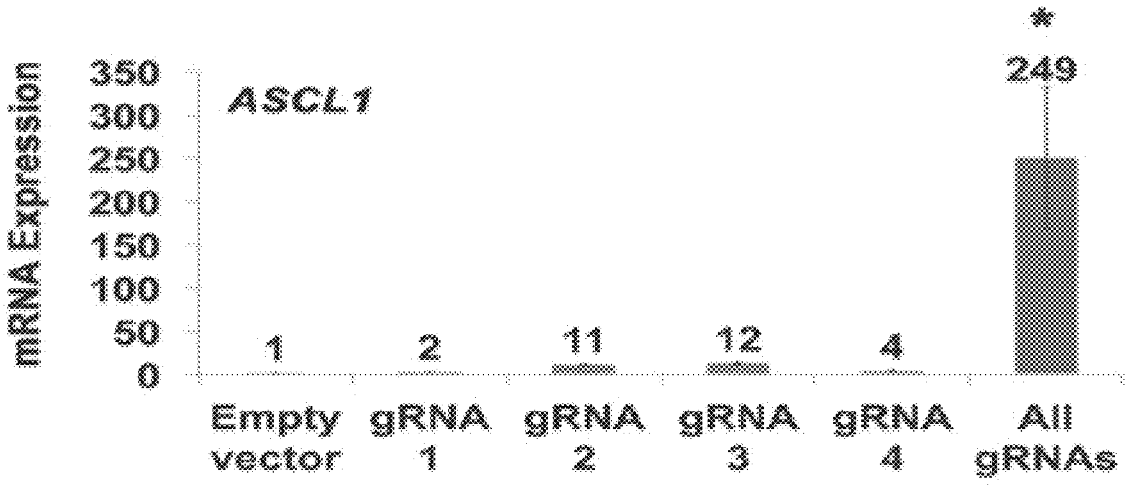
FIGS. 2A-2H show RNA-guided activation of human genes relevant to cell and gene therapy, genetic reprogramming, and regenerative medicine. HEK293T cells were transfected with the iCas9-VP64 expression plasmid and four gRNAs individually or in combination. Target gene expression was measured by qRT-PCR and normalized to GAPDH mRNA levels. Data are shown as the mean±s.e.m. (n=3 independent experiments). Treatment with the combination of gRNAs was statistically different than all other treatments (*P<0.05) by Tukey's test.
Figure 2B:
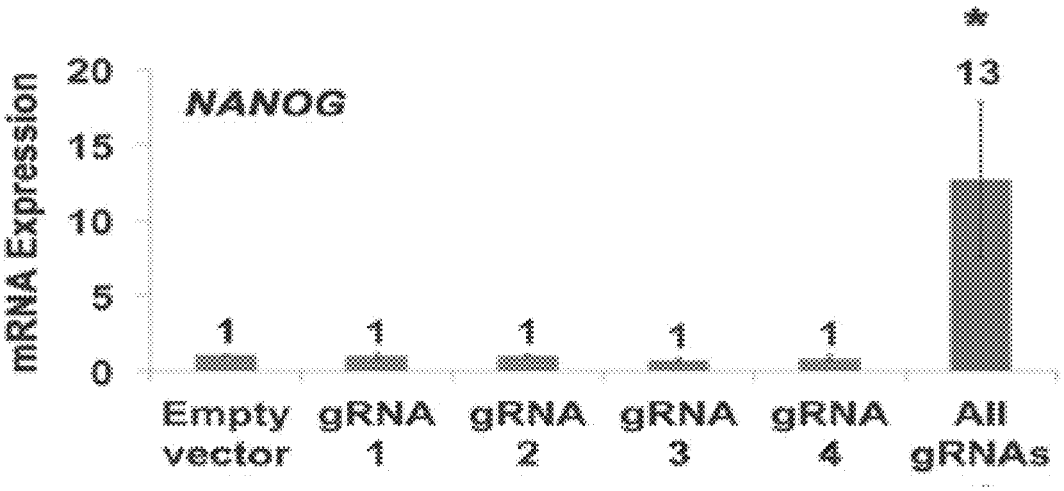
Figure 2C:
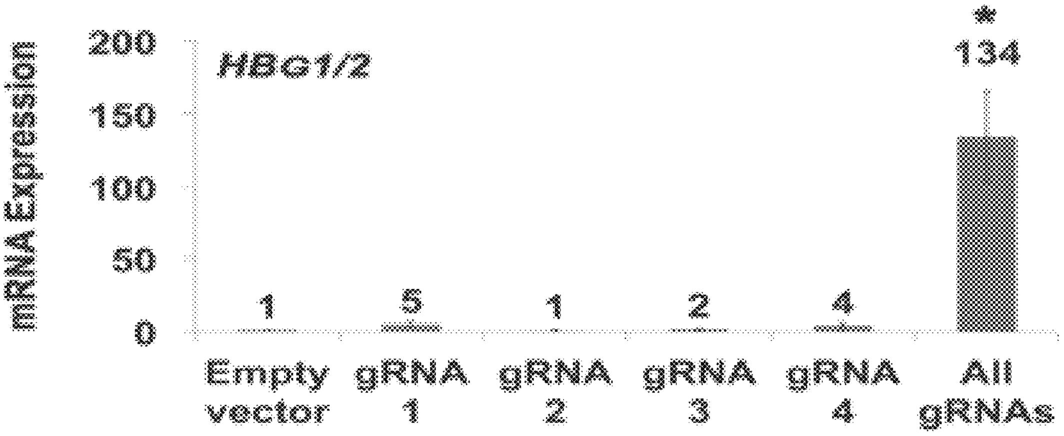
Figure 2D:
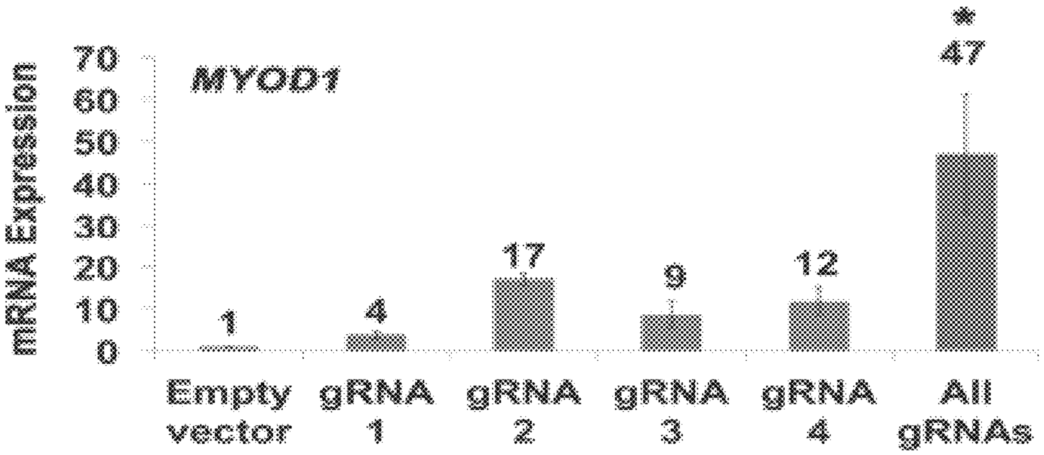
Figure 2E:
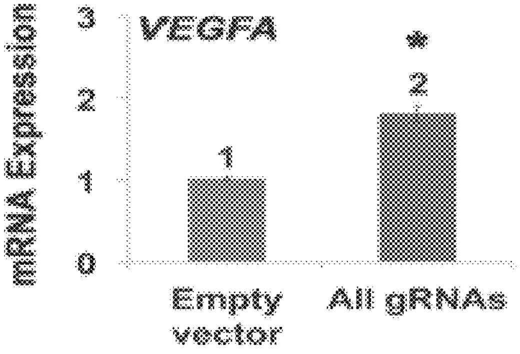
Figure 2F:
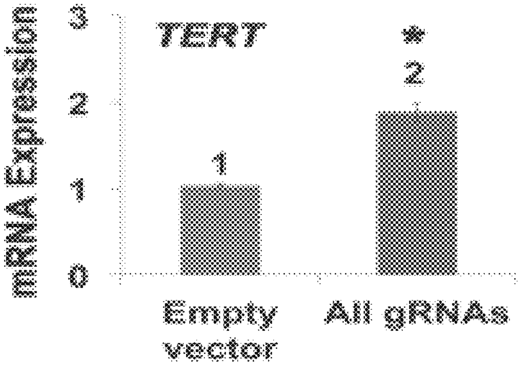
Figure 2G:
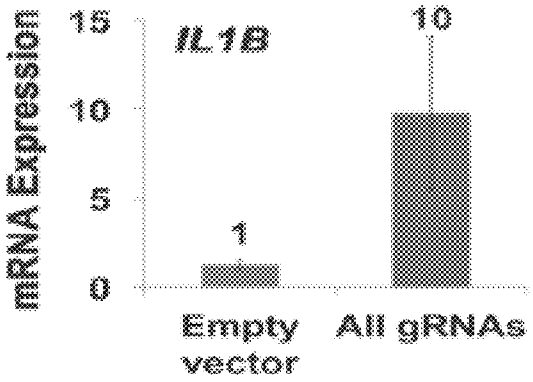
Figure 2H:
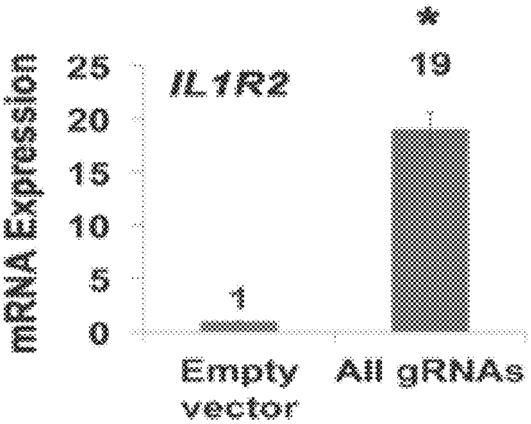
Figure 3:
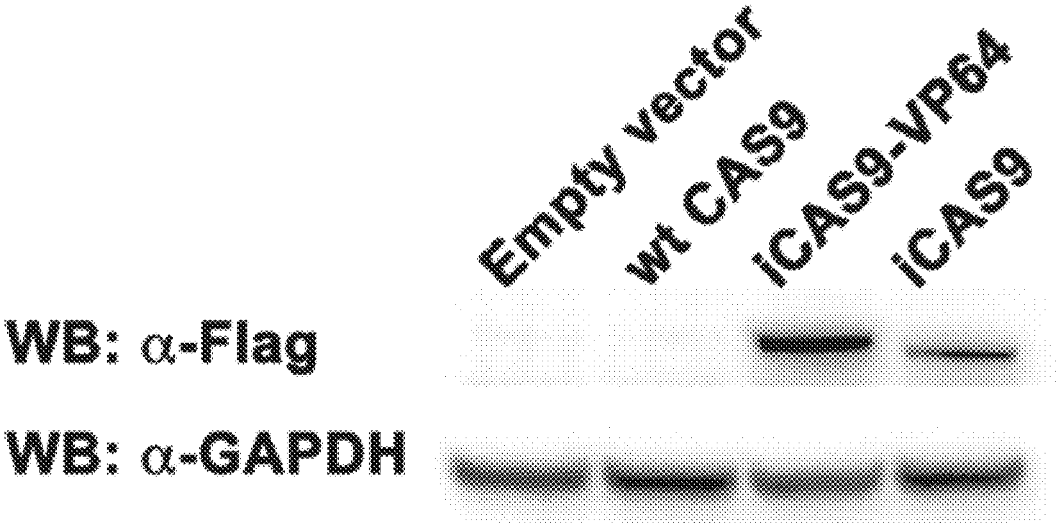
FIG. 3 shows expression of iCas9-VP64. Expression of iCas9-VP64 in transfected HEK293 cells was confirmed by western blot for the N-terminal Flag epitope tag. The wt Cas9 expression plasmid does not contain the epitope tag.
Figure 4A:
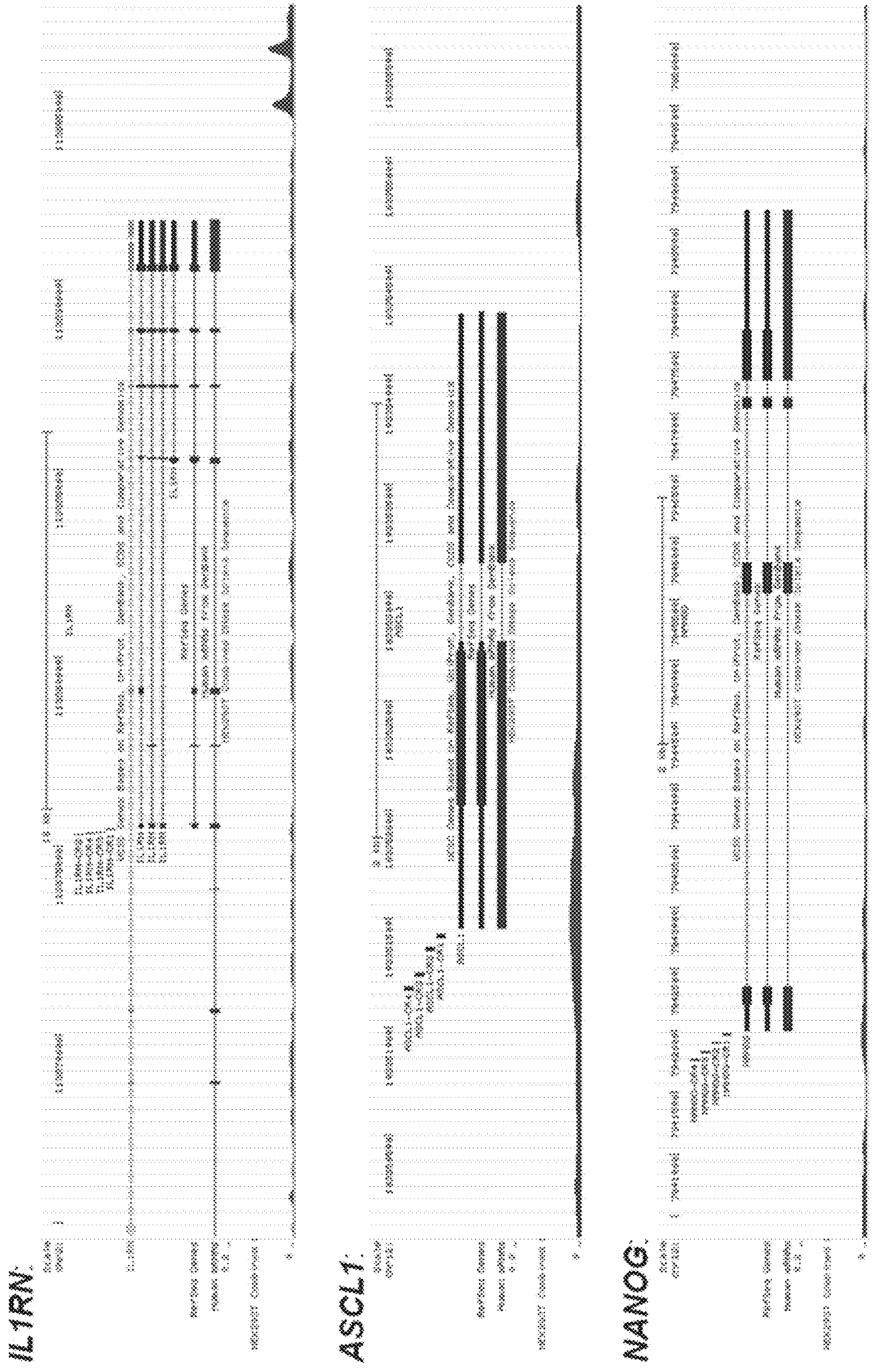
FIGS. 4A-4D show positions of gRNA target sites and DNAse hypersensitivity of human target genes. The four gRNA target sites for each locus are designated as custom tracks above each gene and DNase-seq data indicating DNAse-hypersensitive open chromatin regions is shown below each gene. DNase-seq was performed in HEK293T cells to identify DNase hypersensitive regions, as previously described (Song et al., *Cold Spring Harbor protocols* 2010, pdb prot5384 (2010); Song et al. *Genome Res* 21, 1757-1767 (2011)). The results show that open chromatin was not a requirement for gene activation by combinations of gRNAs with iCas9-VP64.
Figure 4B:
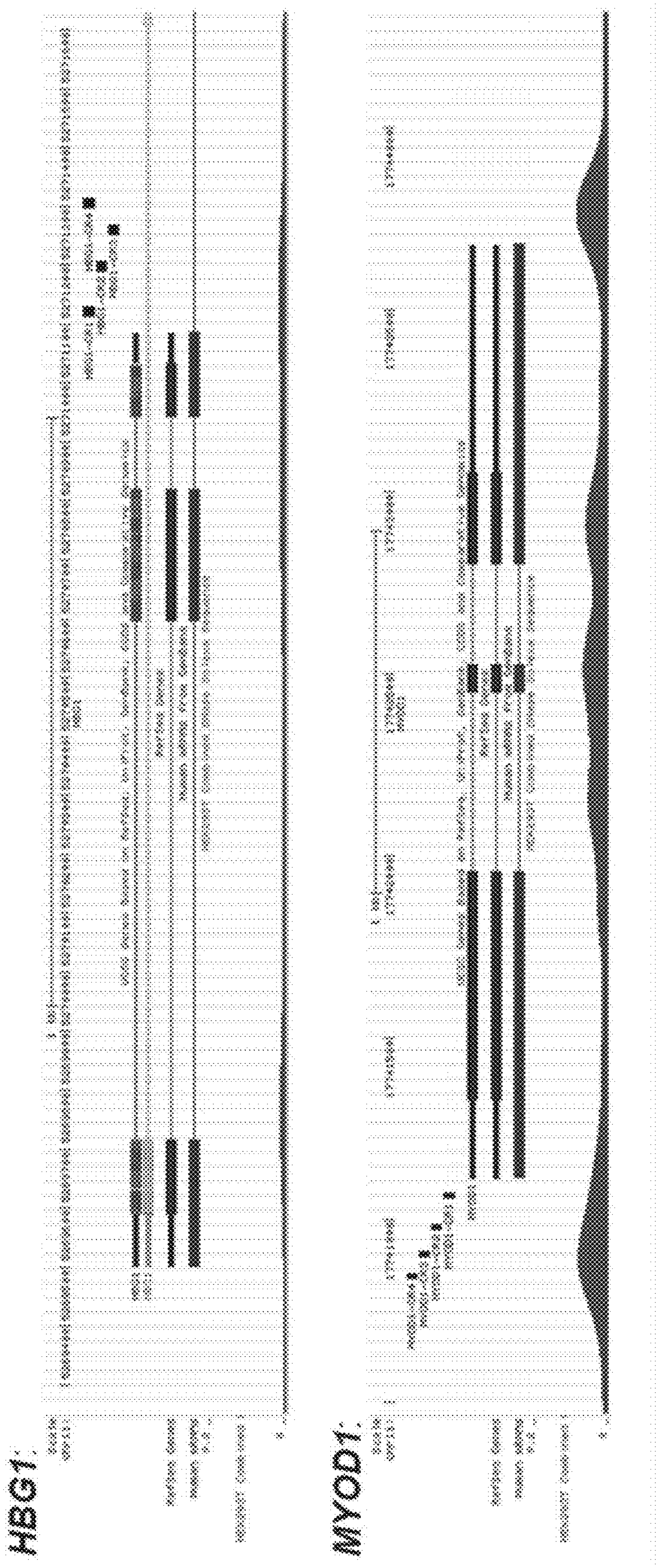
Figure 4C:
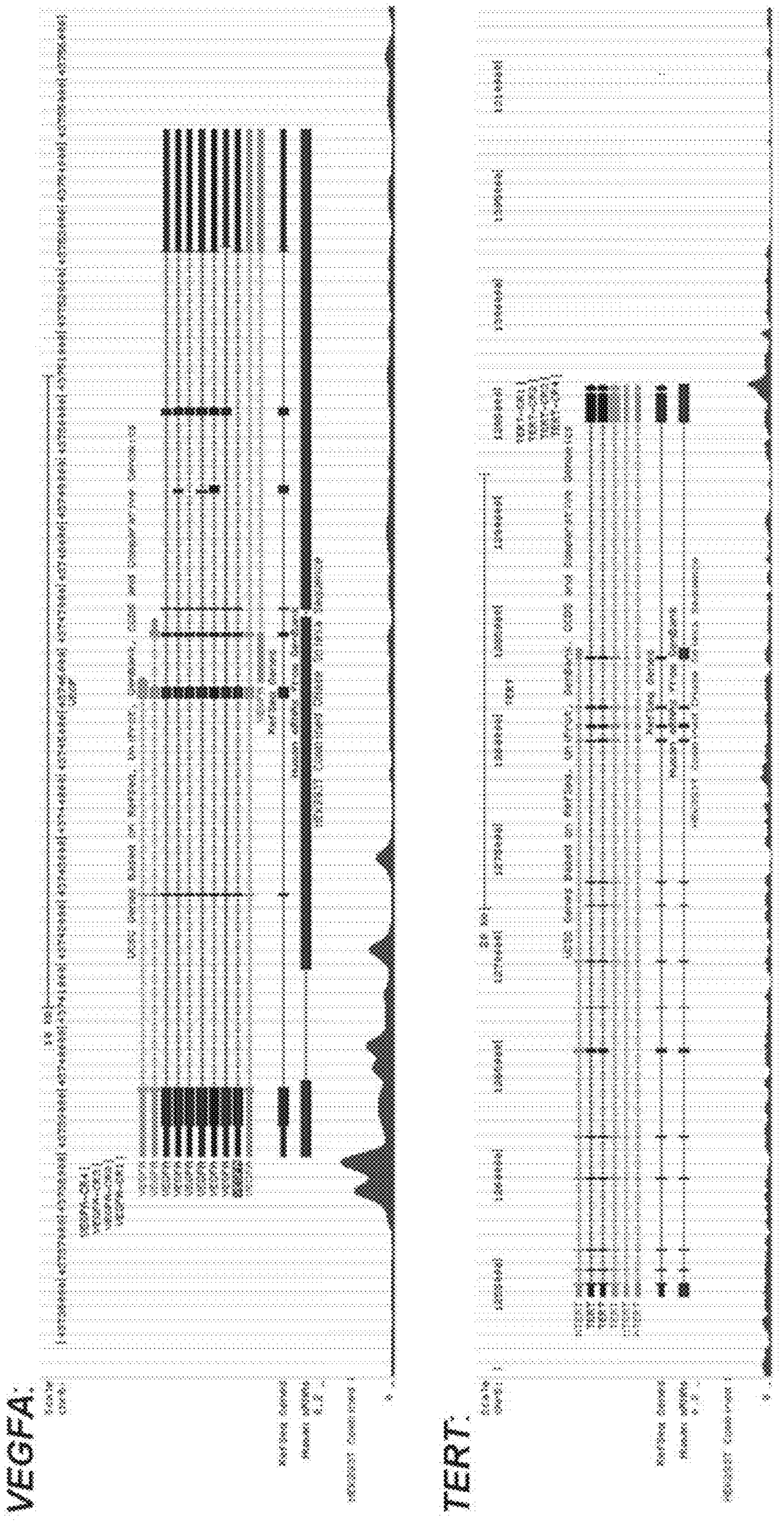
Figure 4D:
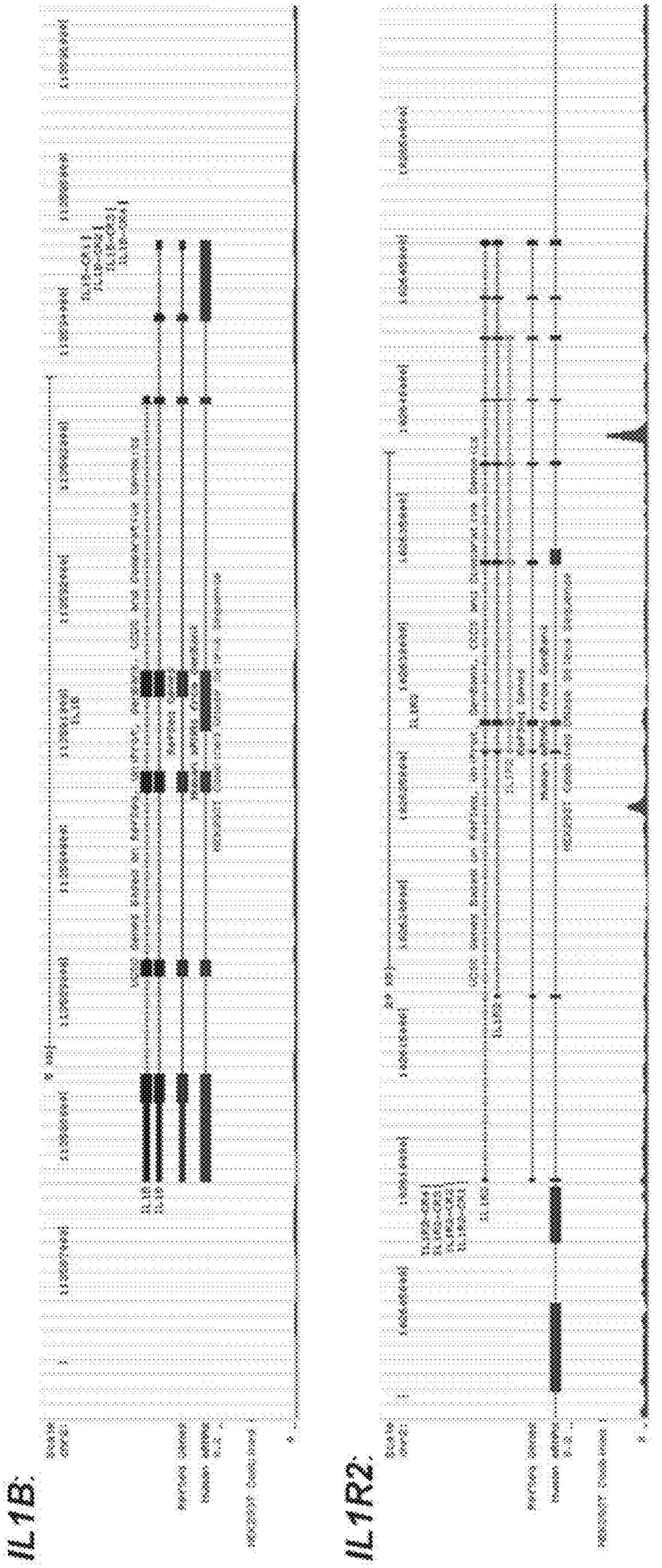
Figure 5:
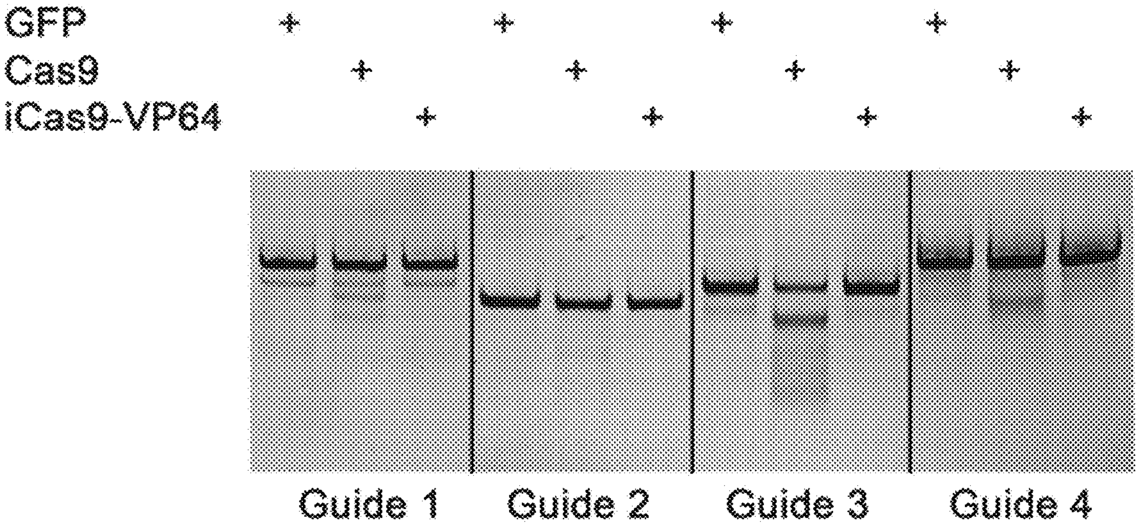
FIG. 5 shows the absence of nuclease activity by iCas9-VP64. Wild-type Cas9 or inactivated (D10A, H840A) iCas9-VP64 expression plasmids were co-transfected with expression plasmids for four different guide RNAs targeting the IL1RN promoter. Nuclease activity was determined by the Surveyor assay (Guschin et al., *Methods MolBiol* 649, 247-256 (2010)). The lower molecular weight bands indicative of nuclease activity and DNA repair by non-homologous end joining are only present following treatment with wild-type Cas9, supporting abrogation of nuclease activity by iCas9-VP64.

To create a CRISPR/Cas9-based transcriptional activation system, catalytic residues of Cas9 (D10A, H840A) were mutated to create iCas9 and genetically fused with a C-terminal VP64 acidic transactivation domain (FIGS. 1A and 1B). Robust expression of iCas9-VP64 was observed from the transfected plasmid in human embryonic kidney (HEK) 293T cells by western blot of the N-terminal Flag epitope tag (FIG. 3). The CRISPR system recognizes its target through base pairing of a 20 bp sequence in the gRNA to a complementary DNA target, which is followed by the NGG protospacer-adjacent motif (PAM) sequence, where N is any base pair. Combinations of synthetic transcription factors targeted to endogenous human promoters result in synergistic and robust activation of gene expression. Therefore four gRNA target sites followed by the NGG PAM sequence were identified in the promoter of the IL1RN gene within 500 bp of the transcriptional start site (FIG. 4, Table 2). To compare crRNA- and gRNA-based targeting strategies, the four target site sequences were introduced into crRNA and gRNA expression plasmids[17] and co-transfected with the iCas9-VP64 expression plasmid into HEK293T cells. Although substantial induction of IL1RN expression was observed by qRT-PCR in samples treated with the combination of crRNAs, much higher levels were achieved with the combination of gRNAs (FIG. 1C). No changes to gene expression were observed in cells treated with gRNAs and an expression plasmid for iCas9 without VP64, demonstrating the critical role of the activation domain in modulating gene expression (FIG. 1C). Nuclease activity at these target sites was confirmed to have been abrogated in the iCas9-VP64 system by performing the Surveyor assay to detect DNA repair events in samples treated with iCas9-VP64 and wild-type Cas9 (FIG. 5). By transfecting each of the four gRNAs individually or in combination, targeting multiple sites in the promoter with combinations of gRNAs showed robust increases in gene expression (FIG. 1D). High levels of IL1RN expression were observed only when the gRNA combinations were co-transfected with iCas9-VP64 (FIG. 1D), as seen with other classes of engineered transcription factors. Similarly, production of the IL-1 receptor antagonist (IL-1ra) protein, encoded by the IL1RN gene, was only observed in three of the six samples treated with the combination of gRNAs across three different experiments, whereas it was never detected in samples treated with single gRNAs or control plasmid (FIG. 1E). To examine the specificity of gene activation by iCas9-VP64, global gene expression of HEK293T cells treated with the combination of four gRNAs by RNA-seq was assessed (FIG. 1F). Notably, the only genes with significantly increased expression relative to control (false discovery rate$\leq 3\times10^{-4}$) were the four isoforms expressed from the IL1RN locus (FIG. 4), indicating a high level of specificity of gene activation.

Figure 6:
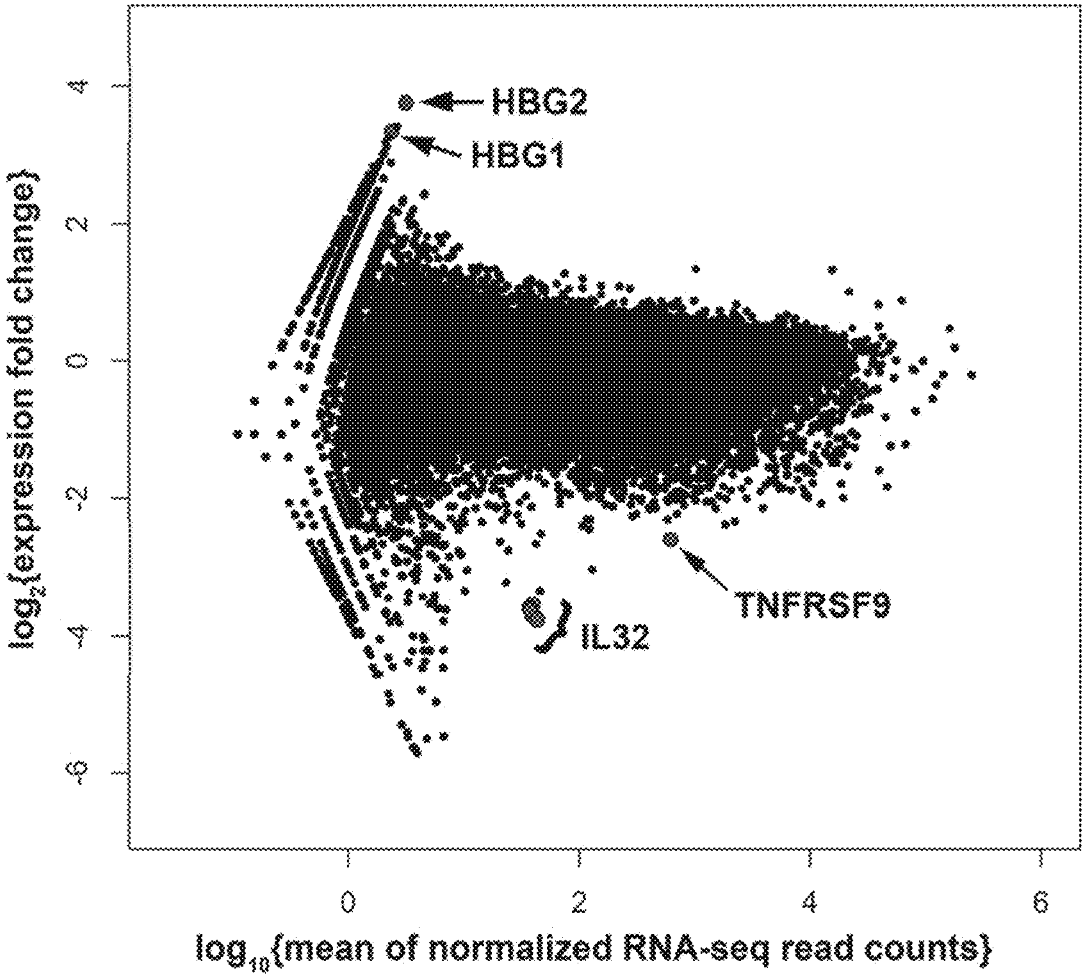
FIG. 6 shows RNA-seq for samples treated with gRNAs targeting HBG1 and HBG2. RNA-seq was performed on samples treated with a control empty expression vector (n=3) or cotransfected with the expression plasmids for iCas9-VP64 and the four gRNAs targeting HBG1 (n=2). Three of these gRNAs also target HBG2. Increases in both HBG1 and HBG2 relative to control were observed but were not statistically significant due to low expression levels. The only statistically significant changes in gene expression between these treatments were decreases in IL32 (false discovery rate=0.0007) and TNFRS9 (false discovery rate=0.002).
Figure 7:
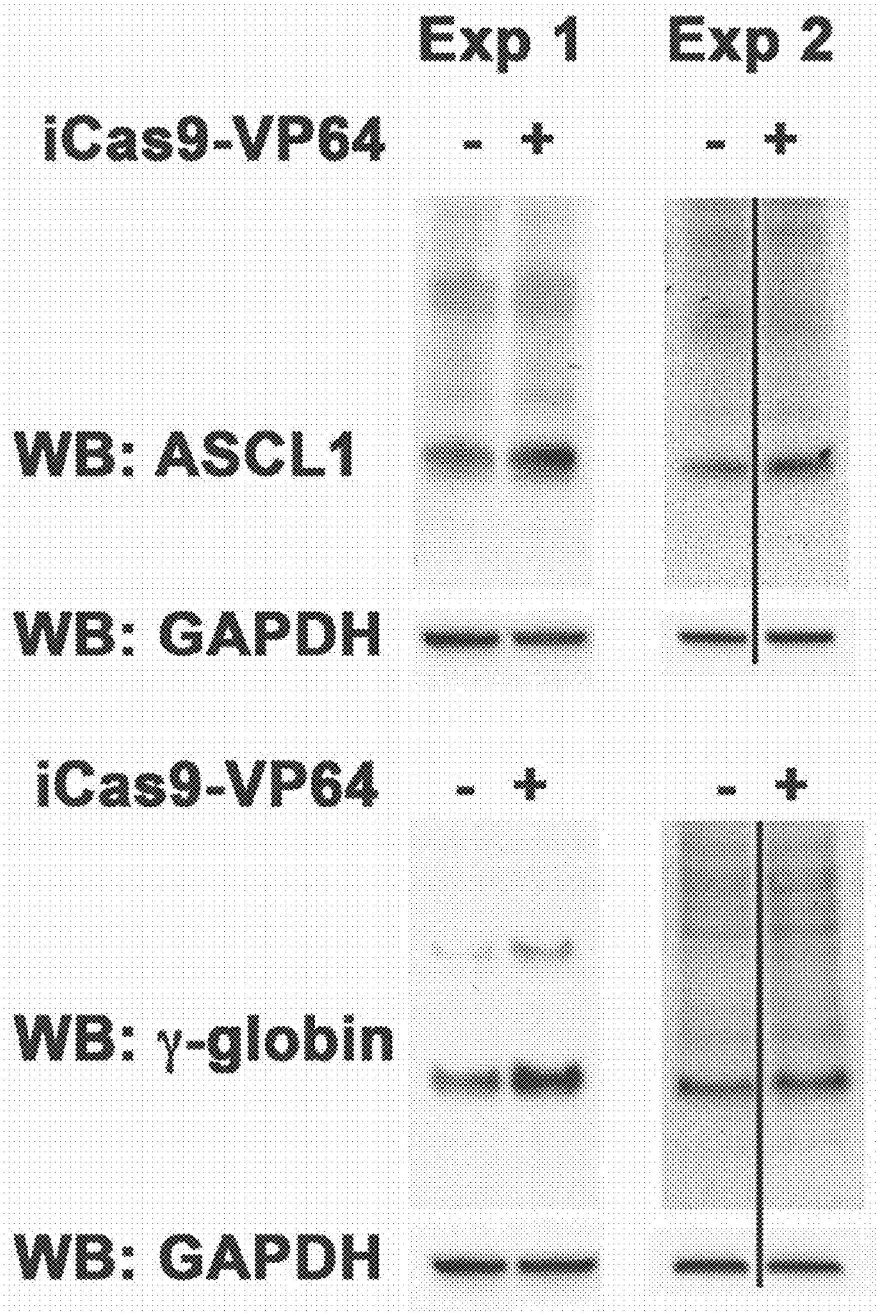
FIG. 7 shows upregulation of Ascl1 and γ-globin by iCas9-VP64. HEK293T cells were transfected with iCas9-VP64 and four gRNAs targeting the ASCL1 or HBG promoter. Levels of corresponding Ascl1 and γ-globin protein production were assessed by western blot. Low levels of these proteins were detectable in HEK293T cells and increases in expression were detectable following iCas9-VP64 treatment in two independent experiments.
Figure 8A:
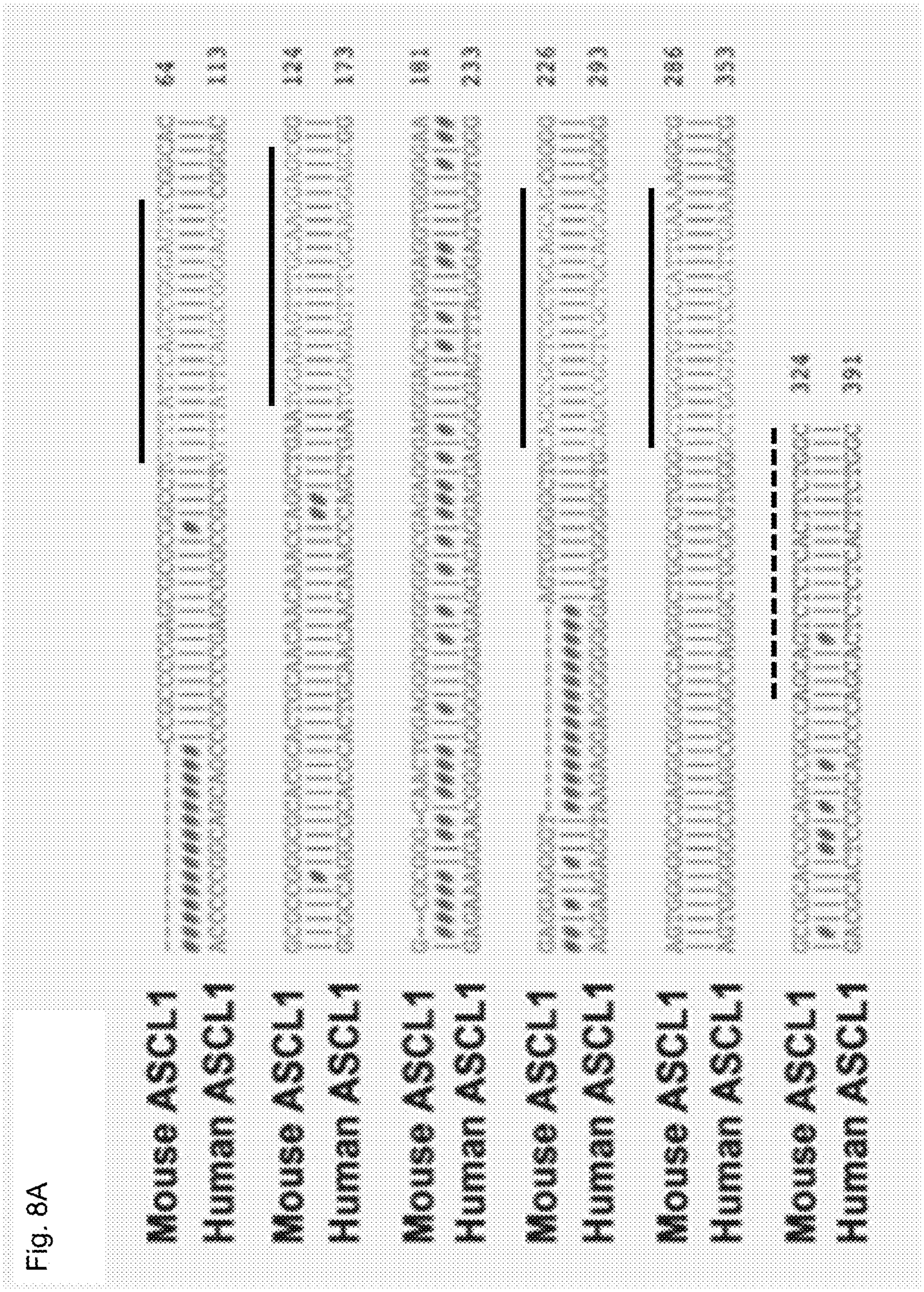
FIGS. 8A-8H show activation of downstream targets of Ascl1 in iCas9-VP64-treated murine embryonic fibroblasts. Mouse embryonic fibroblasts (MEFs) were transfected with a control GFP expression plasmid or the iCas9-VP64 expression plasmid and a combination of four gRNA expression plasmids targeting ASCL1 at a ratio of 50:50 or 75:25.
Figure 8B:
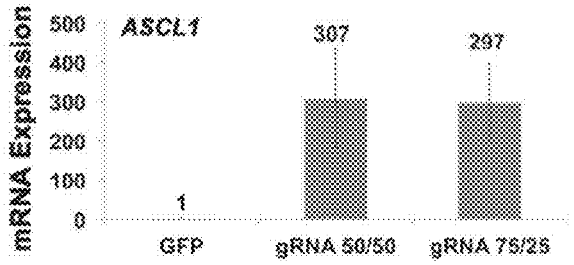
Figure 8C:
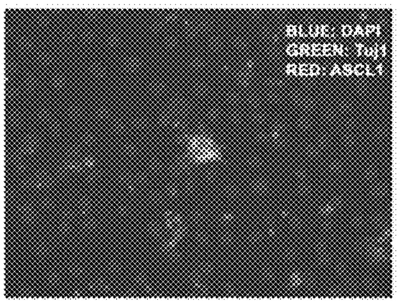
Figure 8D:
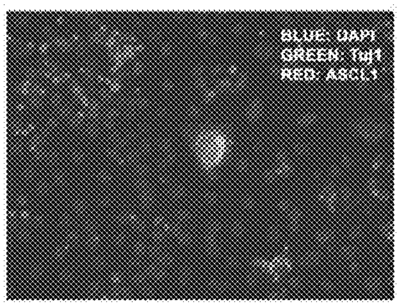
Figure 8E:
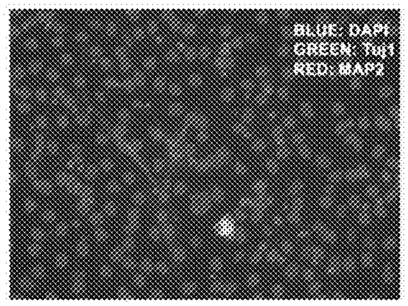
Figure 8F:
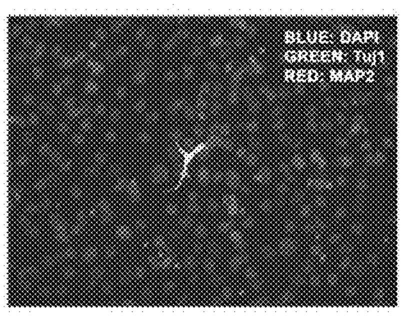
Figure 8G:
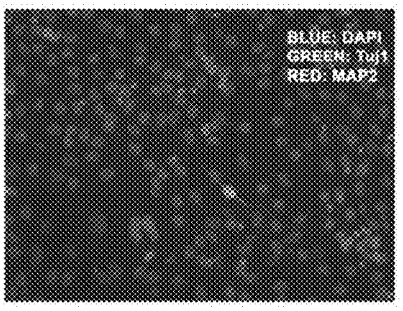
Figure 8H:
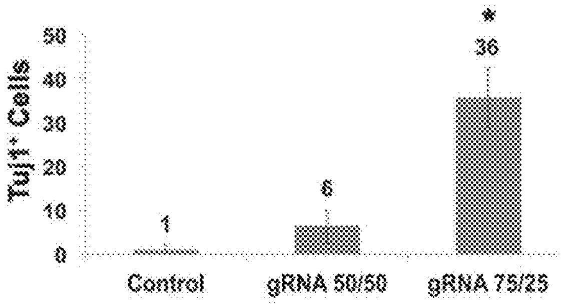

To demonstrate the general applicability of this system, four gRNAs were designed to target each of the promoters of eight other genes relevant to medicine and biotechnology, including ASCL1, NANOG, HBG12, MYOD, VEGFA, TERT, IL1B, and ILIR2 (FIG. 4, Table 2). Forced expression of ASCL1 and MYOD leads to transdifferentiation of several cell types into neuronal and myogenic phenotypes, respectively. NANOG is a marker of pluripotency and that is also used in genetic reprogramming strategies. Activation of the homologs HBG1 and HBG2, which encode γ-globin during fetal development, can be used as a therapeutic strategy to compensate for β-globin mutations in sickle cell disease. Up-regulation of VEGFA by synthetic transcription factors has been explored as a strategy to enhance tissue regeneration and wound healing. The forced expression of telomerase, encoded by the TERT gene, can be used to immortalize cell lines. IL1B encodes the IL-10 cytokine that mediates inflammation and autoimmunity. IL-10 signaling can be blocked by expression of IL-1ra or the decoy receptor encoded by ILIR2. Expression of each of these genes was enhanced by co-transfection of expression plasmids for iCas9-VP64 and the four gRNAs into HEK293T cells, as determined by qRT-PCR (FIGS. 2A-2H). In some cases expression of a single gRNA was sufficient to induce gene expression, but in all cases co-transfection of the four gRNAs led to synergistic effects (FIGS. 2A-2D). Notably, chromatin accessibility, as determined by DNase-seq, was not a predictor of successful gene activation (FIG. 4). RNA-seq was performed on cells transfected with iCas9-VP64 and the four gRNAs targeting HBG, three of which also target HBG2. This revealed specific and reproducible increases in expression of both HBG1 and HBG2, which cannot be distinguished by RNA-seq, although statistical significance was not achieved due to low total expression levels (FIG. 6). Increases in protein expression of Ascl1 and γ-globin following treatment with iCas9-VP64 and the four gRNAs were detected by western blot (FIG. 7), corroborating higher mRNA levels observed by qRT-PCR (FIGS. 2A-2H). Low baseline levels of Ascl1 and γ-globin protein expression were detectable in empty vector controls. As preliminary evidence that the activation of gene targets by iCas9-VP64 can lead to secondary changes in gene networks and cell phenotypes, expression plasmids for iCas9-VP64 and the four gRNAs targeting ASCL1 were co-transfected into murine embryonic fibroblasts (MEFs) (FIGS. 8A-8H). Forced expression of Ascl1 in MEFs has been shown to partially activate the neuronal gene network, including the downstream target Tuj1. Because the gRNA target sites are conserved in the human and mouse ASCL1 promoters (FIG. 8A), activation of ASCL1 expression was also observed in MEFs treated with plasmids encoding iCas9-VP64 and the four gRNAs (FIG. 8B). Furthermore, cells expressing Ascl1 and the neuronal marker Tuj1 were readily detected by immunofluorescence staining 12 days after transfection in the iCas9-VP64/gRNA-treated samples (FIGS. 8C-8H). No Tuj1-positive cells were observed in the cells treated with the control plasmid.

Thus far there has not been any comprehensive survey of the specificity of Cas9/CRISPR activity in mammalian cells. Using RNA-seq, targeted gene activation was shown to be exquisitely specific with no detectable off-target gene activation (FIG. 1F, FIG. 6). IL1RN and HBG1/2 were chosen for this specificity analysis as the gene products, IL-1ra and γ-globin, may not generate secondary effects on gene expression in HEK293T cells. Exploiting the synergistic activity of multiple weak transcriptional activators, in contrast to using a single strong activator, may increase specific gene regulation since it is unlikely that multiple adjacent off-target sites would exist at another locus. Interestingly, the IL32 gene was moderately downregulated (false discovery rate<0.03) in both the samples treated with iCas9-VP64 and either the IL1RN- or HBG1/2-targeted gRNAs compared to control samples treated with only an empty expression plasmid (FIG. 1F, FIG. 6). Because both the IL1RN and HBG1/2-targeted samples were similarly affected, it is unlikely that this is the result of off-target iCas9-VP64 activity related to the identity of the target sequences.

Figure 15:
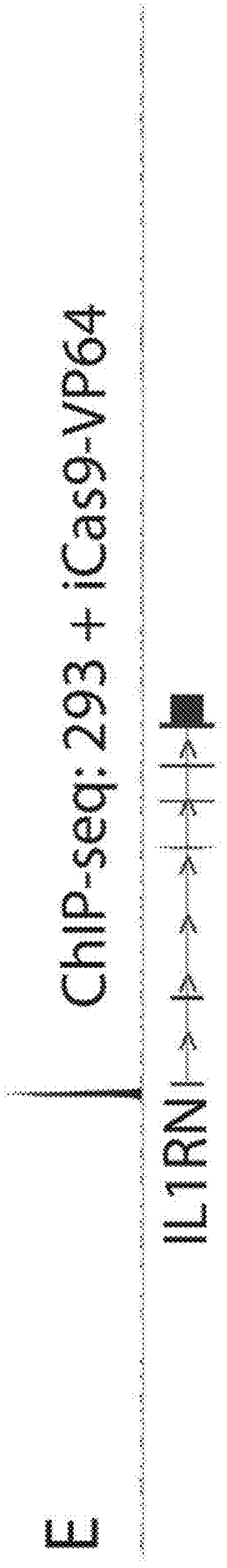
FIG. 15 shows ChIP sequencing data illustrating the specific binding of iCas9-VP64 targeting the IL1RN promoter. HEK 293T cells were transfected with iCas9-VP64 targeting the IL1RN promoter.

To evaluate the specificity with which iCas9-VP64 binds the genome, ChIP sequencing was performed using an anti-HA antibody on cells treated with iCas9-VP64 and four gRNAs targeting the IL1RN promoter. The experiment revealed that iCas9 targets the IL1RN promoter (FIG. 15). Moreover, the experiment revealed an extremely high level of specificity. The iCas9 had only 10 potential off-target binding sites (FDR<5%). To further query the specificity, RNA sequencing experiments were performed with iCas9 EGEMs and found that only IL1RN gene isoforms increased in expression relative to control (FDR≤3×10.4).

Example 3

CRISPRs Targeting the Dystrophin Gene—Methods and Materials

Plasmid Constructs.

The expression cassettes for the *S. pyogenes* sgRNA and human codon optimized Cas9 (hCas9) nuclease were used, as previously described (Perez-Pinera et al., *Nat Methods* 10:973-976 (2013)). In order to create a fluorescent reporter system to enrich CRISPR/Cas9-modified cells, a GeneBlock (IDT) was synthesized containing a portion of the 3' end of the Cas9 coding sequence fused to a T2A skipping peptide immediately upstream of a multiple cloning site and subsequently cloned into the hCas9 expression vector. An eGFP reporter gene was then cloned into the T2A vector to allow co-translation of Cas9 and eGFP proteins from the same expression vector (hCas9-T2A-GFP, SEQ ID NO: 116).

Cell Culture and Transfection.

HEK293T cells were obtained from the American Tissue Collection Center (ATCC) through the Duke Cell Culture Facility and were maintained in DMEM supplemented with 10% bovine calf serum and 1% penicillin/streptomycin. Immortalized myoblasts (Mamchaoui, K. et al. *Skelet Muscle* 1, 1-11 (2011)) (one from a wild-type donor, and two A48-50 DMD patient derived lines) were maintained in skeletal muscle media (PromoCell) supplemented with 20% bovine calf serum (Sigma), 50 μg/ml fetuin, 10 ng/ml human epidermal growth factor (Sigma), 1 ng/ml human basic fibroblast growth factor (Sigma), 10 μg/ml human insulin (Sigma), 1% GutaMAX (Invitrogen), and 1% penicillin/streptomycin (Invitrogen). Primary DMD dermal fibroblasts were obtained from the Coriell Cell repository (GM05162A, A46-50) and maintained in DMEM supplemented with 10% fetal bovine serum, 1 ng/mL human basic fibroblast growth factor, and 1% penicillin/streptomycin. All cell lines were maintained at 37° C. and 5% $CO_2$.

HEK293T cells were transfected with Lipofectamine 2000 (Invitrogen) with 400 ng of each expression vector according to the manufacturer's protocol in 24 well plates. Immortalized myoblasts and primary fibroblasts were transfected with 5 μg of each expression vector by electroporation using the Gene Pulser XCell (BioRad) with PBS as an electroporation buffer using optimized conditions for each line (FIGS. 1A-1F) (Ousterout et al. Mol Ther 21:1718-1726 (2013)). Transfection efficiencies were measured by delivering an eGFP expression plasmid (pmaxGFP, Clontech) and using flow cytometry. These efficiencies were routinely≥95% for HEK293T and ≥70% for the primary fibroblasts and immortalized myoblasts. For all experiments, the indicated mass of electroporated plasmid corresponds to the amount used for each CRISPR/Cas9-based system.

Cel-I Quantification of Endogenous Gene Modification (Surveyor Assay).

CRISPR/Cas9-based system-induced lesions at the endogenous target site were quantified using the Surveyor nuclease assay (Guschin, D. Y. et al. *Meth Mol Biol* 649, 247-256 (2010)), which can detect mutations characteristic of nuclease-mediated NHEJ. After transfection, cells were incubated for 3 or 10 days at 37° C. and genomic DNA was extracted using the DNeasy Blood and Tissue kit (QIAGEN). The target locus was amplified by 35 cycles of PCR with the AccuPrime High Fidelity PCR kit (Invitrogen) using primers specific to each locus (see Table 4), such as 5'-GAGTTTGGCTCAAATTGTTACTCTT-3' (SEQ ID NO: 626) and 5'-GGGAAATGGTCTAGGAGAGTAAAGT-3' (SEQ ID NO: 627).

TABLE 4

Summary of top 10 off target sites predicted in silico and activity at each site as detected by the Surveyor assay in HEK293T cells transfected with Cas9 and the indicated sgRNA expression cassettes. n.d.: not detected.

| SEQ ID NO. | Guide | Target | Sequence | PAM | Score | Chr | Gene | Intron/ Exon | #MMs | % indels |
|---|---|---|---|---|---|---|---|---|---|---|
| 67 | CR3 | Guide | GCCTACTCAGACTGTTACTC | — | — | — | — | — | — | — |
| 150 | | Target | tCCTACTCAGACTGTTACTC | TGG | — | X | DMD | Exon | 1 | 13.0 |
| 151 | | OT1 | tCCTACTCAcACTGTTACTC | AGG | 7.4 | 1 | STRIP1 | Intron | 2 | 9.3 |
| 152 | | OT2 | aCCTgCTCAcACTGTTACTC | CAG | 2.5 | 2 | ARHGAP25 | Intron | 3 | n.d. |
| 153 | | OT3 | GCaTtCTCAaACTGTTACTC | AGG | 2.4 | 13 | None | None | 3 | n.d. |
| 154 | | OT4 | GgaTtCTCAcACTGTTACTC | GGG | 1.3 | 14 | PGPEP1 | Exon | 4 | n.d. |
| 155 | | OT5 | aCaTACTtAtACTGTTACTC | TAG | 1.3 | 19 | MDGA2 | Intron | 4 | n.d. |
| 156 | | OT6 | tatTcCTaAGACTGTTACTC | AAG | 0.9 | 8 | LPPR1 | Intron | 5 | n.d. |
| 157 | | OT7 | aaggACTaAGACTGTTACTC | GGG | 0.9 | 9 | RNF122 | Intron | 5 | n.d. |
| 158 | | OT8 | GagctCTCAtACTGTTACTC | TAG | 0.8 | 3 | DNMBP | Exon | 5 | n.d. |
| 159 | | OT9 | GCaaAaTgAGACTGTTACTC | CAG | 0.8 | 5 | SLC12A2 | Intron | 4 | n.d. |
| 160 | | OT10 | cCtcAtTCAGACTGTTACTC | AAG | 0.8 | 4 | KCNIP4 | Intron | 4 | n.d. |
| 65 | CR1 | Guide | GATTGGCTTTGATTTCCCTA | — | — | — | — | — | — | — |
| 161 | | Target | cATTGGCTTTGATTTCCCTA | GGG | — | X | DMD | Intron | 1 | 8.3 |
| 162 | | OT1 | aATTGGCATTGATTTCCCTA | GAG | 7.1 | 16 | None | None | 2 | 0.8 |
| 163 | | OT2 | cATTGGCTTTaATTTCCCTA | TAG | 4.8 | 4 | None | None | 2 | n.d. |
| 164 | | OT3 | GATaGGCTgTGATTTCCCTA | GAG | 3.9 | 9 | None | None | 2 | n.d. |
| 165 | | OT4 | GAaTaGCcTTGATTTCCCTA | AAG | 2.4 | 1 | None | None | 3 | n.d. |
| 166 | | OT5 | aATTtGCTTTGATTTCCCTg | AGG | 1.5 | 1 | TIMM17A | Intron | 3 | n.d. |
| 167 | | OT6 | GATgtGCTTTGATTTCCCTt | GGG | 1.4 | 17 | MYO1D | Intron | 3 | n.d. |
| 168 | | OT7 | aATTGGtTTTaATTTCCCTA | AAG | 1.1 | 8 | PIK1A | Intron | 3 | n.d. |
| 169 | | OT8 | aATTGGgTTTGATTTCCCTt | TGG | 1.1 | 11 | MS4A1 | Intron | 3 | n.d. |
| 170 | | OT9 | GATgGGtTTTtATTTCCCTA | GAG | 1.0 | 11 | None | None | 3 | n.d. |
| 171 | | OT10 | GAaTGGtTTTGATTTCCCTg | GAG | 1.0 | 11 | None | None | 3 | n.d. |
| 69 | CR5 | Guide | GCAGTTGCCTAAGAACTGGT | — | — | — | — | — | — | — |
| 172 | | Target | aCAGTTGCCTAAGAACTGGT | GGG | — | X | DMD | Intron | 1 | 14.0 |
| 173 | | OT1 | cCAGTTGtCTAAGAACTGGg | GAG | 1.5 | 5 | NRG1 | Intron | 3 | n.d. |
| 174 | | OT2 | GCAGTTGCCTgtGAACTGGT | AGG | 1.4 | X | None | None | 2 | n.d. |
| 175 | | OT3 | GCAGaTGCagAAGAACTGGT | GAG | 1.4 | 19 | SMIM7 | Intron | 3 | n.d. |
| 176 | | OT4 | GCAGTTcCagAAGAACTGGT | GAG | 0.9 | 11 | GLB1L2 | Intron | 3 | n.d. |
| 177 | | OT5 | caAcTTGCCTAtGAACTGGT | AGG | 0.7 | 8 | ASAP1 | Intron | 4 | n.d. |
| 178 | | OT6 | aCAccTGCCTAAGAACTGGa | GGG | 0.7 | 11 | None | None | 4 | n.d. |
| 179 | | OT7 | tCAGgTGgCTAAGAACTGGg | TGG | 0.7 | 14 | NIN | Intron | 4 | n.d. |
| 180 | | OT8 | GaAGTTGgCcAAGAACTGGa | GAG | 0.6 | 7 | None | None | 4 | n.d. |
| 181 | | OT9 | GCtGcTGCCcAAGAACTGGc | AGG | 0.6 | 11 | AMOTL1 | Intron | 4 | n.d. |
| 182 | | OT10 | tCAGcTGgCTAAGAACgGGT | AAG | 0.6 | 7 | ACTR3C | Intron | 4 | n.d. |
| 70 | CR6 | Guide | GGGGCTCCACCCTCACGAGT | — | — | — | — | — | — | — |
| 183 | | Target | aGGGCTCCACCCTCACGAGT | GGG | — | X | DMD | Intron | 1 | 19.9 |
| 184 | | OT1 | GcaGCTCagCCCTCACGAGT | CAG | 0.8 | 3 | None | None | 4 | n.d. |
| 185 | | OT2 | GGGGCTtCAgCaTCACGAGT | GAG | 0.8 | 8 | None | None | 3 | n.d. |
| 186 | | OT3 | GGGGCTCtcCCCTCACtAGT | GAG | 0.6 | 8 | None | None | 3 | n.d. |
| 187 | | OT4 | GGGGaTCCACCtTCACcAGT | CAG | 0.6 | 2 | None | None | 3 | n.d. |
| 188 | | OT5 | aGGGCTggACCCTCACaAGT | AAG | 0.4 | 16 | AXIN1 | Intron | 4 | n.d. |
| 189 | | OT6 | tGGtCTCCtCCCcCACGAGT | GGG | 0.4 | 2 | None | None | 4 | n.d. |
| 190 | | OT7 | aGGGCTCCcaCCcCACGAGT | GAG | 0.3 | 5 | None | None | 4 | n.d. |
| 191 | | OT8 | GaGGCTCCAtaCTCACcAGT | GAG | 0.3 | 11 | None | None | 4 | n.d. |
| 192 | | OT9 | GGaGCTgCcCCtTCACGAGT | GGG | 0.3 | 3 | None | None | 4 | n.d. |
| 193 | | OT10 | atGaCTCCACCCTCAaGAGT | AAG | 0.3 | 8 | AGPAT5 | None | 4 | n.d. |
| 100 | CR36 | Guide | GCCTTCTTTATCCCCTATCG | — | — | — | — | — | — | — |
| 194 | | Target | GCCTTCTTTATCCCCTATCG | AGG | — | X | DMD | Intron | 0 | 20.6 |
| 195 | | OT1 | GtCTgCTgTgTCCCCTATCG | GGG | 1.3 | 21 | None | None | 4 | n.d. |
| 196 | | OT2 | cCCTTCTcTATCCCCTgTCG | TGG | 1.3 | 8 | None | None | 3 | n.d. |
| 197 | | OT3 | GCCTTCTTTATCCCCTcTCt | TGG | 0.9 | 10 | None | None | 2 | 0.5 |
| 198 | | OT4 | GCgcTCTTTtTCCCCTATCt | TAG | 0.6 | 16 | None | None | 4 | n.d. |
| 199 | | OT5 | GCCcTCTgTcTCCCCTgTCG | CAG | 0.5 | 1 | NFASC | None | 4 | n.d. |
| 200 | | OT6 | tCCATCTtTgTCCCCTATtG | AGG | 0.5 | 10 | None | None | 4 | n.d. |
| 201 | | OT7 | aCCtTCTCTcTCCCCTATaG | AGG | 0.5 | 5 | LOC100996485 | Intron | 4 | n.d. |
| 202 | | OT8 | GttTTCTTTtTCCCCTATgG | GAG | 0.5 | 3 | None | None | 4 | n.d. |
| 203 | | OT9 | tgCTTCTTaATCCCCTATCa | AAG | 0.4 | 7 | None | None | 4 | n.d. |
| 204 | | OT10 | aCCTTCTTacTCCCCTATCc | GGG | 0.4 | 10 | ADARB2 | None | 4 | n.d. |

The resulting PCR products were randomly melted and reannealed in a thermal cycler with the program: 95° C. for 240 s, followed by 85° C. for 60 s, 75° C. for 60 s, 65° C. for 60 s, 55° C. for 60 s, 45° C. for 60 s, 35° C. for 60 s, and 25° C. for 60 s with a −0.3° C./s rate between steps. Following reannealing, 8 μL of PCR product was mixed with 1 μL of Surveyor Nuclease S and 1 L of Enhancer S (Transgenomic) and incubated at 42° C. for 1 hr. After incubation, 6 μL of digestion product was loaded onto a 10% TBE polyacrylamide gel and run at 200V for 30 min. The gels were stained with ethidium bromide and quantified using ImageLab (Bio-Rad) by densitometry as previously described (Guschin, et al. *Meth MolBiol* 649, 247-256 (2010)).

Fluorescence-Activated Cell Sorting of Myoblasts.

DMD myoblasts were electroporated with 5 micrograms each of hCas9-T2A-GFP and sgRNA expression vectors and incubated at 37° C. and 5% $CO_2$. Three days after electroporation, cells were trypsinized and collected for FACS sorting using a FACSvantage II sorting machine. GFP-positive cells were collected and grown for analysis.

PCR-Based Assay to Detect Genomic Deletions.

The exon 51 or exon 45-55 loci were amplified from genomic DNA by PCR (Invitrogen AccuPrime High Fidelity PCR kit) using primers flanking each locus. The flanking primers were CelI-CR1/2-F and CelI-CR5-R for exon 51 or CelI-CR6-F and CelI-CR36-R for exon 45-55 analysis (Table 4). PCR products were separated on TAE-agarose gels and stained with ethidium bromide for analysis.

PCR-Based Detection of Translocations.

Loci with predicted possible translocations were amplified by a two-step nested PCR (Invitrogen AccuPrime High Fidelity PCR kit for each step) of genomic DNA from cells transfected with Cas9 alone (control) or Cas9 with sgRNA. In the first step, translocations that may occur at each on-target and off-target sgRNA target site were amplified by 35 cycles of PCR using combinations of Surveyor primers for each locus that were modified to include restriction sites to facilitate cloning and sequencing analysis (Table 4). One microliter of each PCR reaction was subjected to a second round of amplification by 35 rounds of PCR using nested primer sets custom designed for each individual predicted translocation (Table 4). Each second nested PCR primer binds within the same approximate region within the primary amplicon; however, each pair was optimized using Primer3 online bioinformatics software to ensure specific detection of each translocation. PCR amplicons corresponding to the expected length of predicted translocations and only present in cells treated with sgRNA were purified (QIAGEN Gel Extraction kit) and analyzed by Sanger sequencing.

mRNA Analysis.

Immortalized myoblasts were differentiated into myofibers by replacing the growth medium with DMEM supplemented with 1% insulin-transferrin-selenium (Invitrogen #51500056) and 1% penicillin/streptomycin (Invitrogen #15140) for 5 days before the cells were trypsinized and collected. Total RNA was isolated from these cells using the RNeasy Plus Mini Kit (QIAGEN) according to the manufacturer's instructions. RNA was reverse transcribed to cDNA using the VILO cDNA synthesis kit (Life Technologies #11754) and 1.5 micrograms of RNA for 2 hrs at 42° C. according to the manufacturer's instructions. The target loci were amplified by 35 cycles of PCR with the AccuPrime High Fidelity PCR kit (Invitrogen) using primers annealing to exons 44 and 52 to detect exon 51 deletion by CR1/5 or CR2/5 or primers annealing to exons 44 and 60 to detect exon 45-55 deletion by CR6/36 (Table 4). PCR products were run on TAE-agarose gels and stained with ethidium bromide for analysis. The resolved PCR bands were cloned and analyzed by Sanger sequencing to verify the expected exon junctions. Table 5 lists the sequences of primers used in Example 4.

TABLE 5

| SEQ ID NO. | Primer name | Primer sequence | Notes |
|---|---|---|---|
| 205 | CelI-CR1/2-F | GAGAGGTTATGTGGCTTTACCA | Forward Surveyor primer for CR1/2 |
| 206 | CelI-CR1-R | AAAAATGCTTCCCACTTTGC | Reverse Surveyor primer for CR1 |
| 207 | CelI-CR2-R | CTCATTCTCATGCCTGGACA | Reverse Surveyor primer for CR2 |
| 208 | CelI-CR3-F | GAGTTTGGCTCAAATTGTTACTCTT | Forward Surveyor primer for CR3 |
| 209 | CelI-CR3-R | GGGAAATGGTCTAGGAGAGTAAAGT | Reverse Surveyor primer for CR3 |
| 210 | CelI-CR4/31-F | GTTTGGCTCAAATTGTTACTCTTCA | Forward Surveyor primer for CR4 or CR31 |
| 211 | CelI-CR4/31-R | GTGAGAGTAATGTGTTTGCTGAGAG | Reverse Surveyor primer for CR4 or CR31 |
| 212 | CelI-CRS-F | CGGGCTTGGACAGAACTTAC | Forward Surveyor primer for CR5 |
| 213 | CelI-CR5-R | CTGCGTAGTGCCAAAACAAA | Reverse Surveyor primer for CR5 |
| 214 | CelI-CR6-F | TAATTTCATTGAAGAGTGGCTGAA | Forward Surveyor primer for CR6 |
| 215 | CelI-CR6-R | AAGCCCTGTGTGGTAGTAGTCAGT | Reverse Surveyor primer for CR6 |
| 216 | CelI-CR7-F | TGAGTCATGTTGGATAACCAGTCT | Forward Surveyor primer for CR7 |
| 217 | CelI-CR7-R | GAAGGTCAGGAACATACAATTCAA | Reverse Surveyor primer for CR7 |

TABLE 5-continued

| SEQ ID NO. | Primer name | Primer sequence | Notes |
|---|---|---|---|
| 218 | CelI-CR10/11-F | GATATGGGCATGTCAGTTTCATAG | Forward Surveyor primer for CR10 or CR11 |
| 219 | CelI-CR10/11-R | TGCTGTTGATTAATGGTTGATAGG | Reverse Surveyor primer for CR10 or CR11 |
| 220 | CelI-CR12/13-F | TTTTAAATTGCCATGTTTGTGTC | Forward Surveyor primer for CR12 or CR13 |
| 221 | CelI-CR12/13-R | ATGAATAACCTAATGGGCAGAAAA | Reverse Surveyor primer for CR12 or CR13 |
| 222 | CelI-CR14/15-F | TCAAGTCGCTTCATTTTGATAGAC | Forward Surveyor primer for CR14 or CR15 |
| 223 | CelI-CR14/15-R | CACAACAAAACATATAGCCAAAGC | Reverse Surveyor primer for CR14 or CR15 |
| 224 | CelI-CR16/17-F | TGCTGCTAAAATAACACAAATCAGT | Forward Surveyor primer for CR16 or CR17 |
| 225 | CelI-CR16/17-R | CTGTGCCTATTGTGGTTATCCTG | Reverse Surveyor primer for CR16 or CR17 |
| 226 | CelI-CR18/19-F | ATTGATCTGCAATACATGTGGAGT | Forward Surveyor primer for CR18 or CR19 |
| 227 | CelI-CR18/19-R | TTTGCCTCTGCTATTACAGTATGG | Reverse Surveyor primer for CR18 or CR19 |
| 228 | CelI-CR20/21-F | TGTAGGGTGGTTGGCTAAAATAAT | Forward Surveyor primer for CR20 or CR21 |
| 229 | CelI-CR20/21-R | TTTTTGCACAGTCAATAACACAAA | Reverse Surveyor primer for CR20 or CR21 |
| 230 | CelI-CR22/23-F | GGCTGGTCTCACAATTGTACTTTA | Forward Surveyor primer for CR22 or CR23 |
| 231 | CelI-CR22/23-R | CATTATGGACTGAAAATCTCAGCA | Reverse Surveyor primer for CR22 or CR23 |
| 232 | CelI-CR24/25-F | ATCATCCTAGCCATAACACAATGA | Forward Surveyor primer for CR24 or CR25 |
| 233 | CelI-CR24/25-R | TTCAGCTTTAACGTGATTTTCTGT | Reverse Surveyor primer for CR24 or CR25 |
| 234 | CelI-CR26/27-F | GGATTCAGAAGCTGTTTACGAAGT | Forward Surveyor primer for CR26 or CR27 |
| 235 | CelI-CR26/27-R | TTTAGCTGGATTGGAAAAACAAAT | Reverse Surveyor primer for CR26 or CR27 |
| 236 | CelI-CR28/29-F | AACTCACCCCATTGTTGGTATATT | Forward Surveyor primer for CR28 or CR29 |
| 237 | CelI-CR28/29-R | CCTTGTCCAAATACCGAAATACAT | Reverse Surveyor primer for CR28 or CR29 |
| 238 | CelI-CR33-F | CACATAATTCATGAACTTGGCTTC | Forward Surveyor primer for CR33 |
| 239 | CelI-CR33-R | TAGTAGCTGGGGAGGAAGATACAG | Reverse Surveyor primer for CR33 |
| 240 | CelI-CR34-F | TTTTGTTTTAATTGCGACTGTGT | Forward Surveyor primer for CR34 |
| 241 | CelI-CR34-R | AGAAAAGGGGTTTTCTTTTGACTT | Reverse Surveyor primer for CR34 |
| 242 | CelI-CR35-F | CATTGTGACTGGATGAGAAGAAAC | Forward Surveyor primer for CR35 |
| 243 | CelI-CR35-R | AACGGCTGTTATTAAAGTCCTCAG | Reverse Surveyor primer for CR35 |
| 244 | CelI-CR36-F | CAAGTCAGAAGTCACTTGCTTTGT | Forward Surveyor primer for CR36 |
| 245 | CelI-CR36-R | TTTTATGTGCAGGAATCAGTCTGT | Reverse Surveyor primer for CR36 |

TABLE 5-continued

| SEQ ID NO. | Primer name | Primer sequence | Notes |
|---|---|---|---|
| 246 | Dys-E44-F | TGGCGGCGTTTTCATTAT | Forward RT-PCR primer binding in exon 44 |
| 247 | Dys-E52-R | TTCGATCCGTAATGATTGTTCTAGCC | Reverse RT-PCR primer binding in exon 52 |
| 248 | Dys-E60-R | GGTCTTCCAGAGTGCTGAGG | Reverse RT-PCR primer binding in exon 60 |
| 249 | CR3-CelI-OT1-F | TGTGTGCTTCTGTACACATCATCT | Forward Surveyor primer for CR3 off-target 1 |
| 250 | CR3-CelI-OT1-R | AGATTTCAACCCTCAAAAACTGAG | Reverse Surveyor primer for CR3 off-target 1 |
| 251 | CR3-CelI-OT2-F | TAAACTCTTTCTTTTCCGCAATTC | Forward Surveyor primer for CR3 off-target 2 |
| 252 | CR3-CelI-OT2-R | CAAGGTGACCTGCTACCTAAAAAT | Reverse Surveyor primer for CR3 off-target 2 |
| 253 | CR3-CelI-OT3-F | TATGACCAAGGCTATGTGTTCACT | Forward Surveyor primer for CR3 off-target 3 |
| 254 | CR3-CelI-OT3-R | ACAGCCTCTCTCCAGTAACATTCT | Reverse Surveyor primer for CR3 off-target 3 |
| 255 | CR3-CelI-OT4-F | TATTCTTGCAGTGGTTTCACATTT | Forward Surveyor primer for CR3 off-target 4 |
| 256 | CR3-CelI-OT4-R | ATATTTTAAGCCAAGACCCAACAA | Reverse Surveyor primer for CR3 off-target 4 |
| 257 | CR3-CelI-OT5-F | CTTTCAACTGTCTGTCTGATTGCT | Forward Surveyor primer for CR3 off-target 5 |
| 258 | CR3-CelI-OT5-R | AACAGCCTCTCTTCATTGTTCTCT | Reverse Surveyor primer for CR3 off-target 5 |
| 259 | CR3-CelI-OT6-F | CTCTGGAACTTGTCTCTGTCTTGA | Forward Surveyor primer for CR3 off-target 6 |
| 260 | CR3-CelI-OT6-R | CTTTCCTGCGTTCTCATGTTACTA | Reverse Surveyor primer for CR3 off-target 6 |
| 261 | CR3-CelI-OT7-F | CCTTATATCCGTATCGCTCACTCT | Forward Surveyor primer for CR3 off-target 7 |
| 262 | CR3-CelI-OT7-R | CATATCTGTCTAACTTCCGCACAC | Reverse Surveyor primer for CR3 off-target 7 |
| 263 | CR3-CelI-OT8-F | ACAGGTGTTATGTTGTCTGCATCT | Forward Surveyor primer for CR3 off-target 8 |
| 264 | CR3-CelI-OT8-R | ACTCCATTCCCAGATTAGTTATGC | Reverse Surveyor primer for CR3 off-target 8 |
| 265 | CR3-CelI-OT9-F | CTGTTTTCTTTGTGAGAGTGGAGA | Forward Surveyor primer for CR3 off-target 9 |
| 266 | CR3-CelI-OT9-R | TGTAAGGTGGTCAAACTTGCTCTA | Reverse Surveyor primer for CR3 off-target 9 |
| 267 | CR3-CelI-OT10-F | TTTTTCCTAGTACCCACAGATTTTT | Forward Surveyor primer for CR3 off-target 10 |
| 268 | CR3-CelI-OT10-R | TCCCTGATTCTCTCATTTGTGTTA | Reverse Surveyor primer for CR3 off-target 10 |
| 269 | CR1-CelI-OT1-F | TTGGGAACATCAGAGAAAGTATGA | Forward Surveyor primer for CR1 off-target 1 |
| 270 | CR1-CelI-OT1-R | ACAAATTACAGTCTCCTGGGAAAG | Reverse Surveyor primer for CR1 off-target 1 |

TABLE 5-continued

| SEQ ID NO. | Primer name | Primer sequence | Notes |
|---|---|---|---|
| 271 | CR1-CelI-OT2-F | AGTAGCTTACCTTGGCAGAGAAAA | Forward Surveyor primer for CR1 off-target 2 |
| 272 | CR1-CelI-OT2-R | TGACATACTGTTACCCTTTGCAGT | Reverse Surveyor primer for CR1 off-target 2 |
| 273 | CR1-CelI-OT3-F | GAAAGGCTCAGTGAATGTTTGTT | Forward Surveyor primer for CR1 off-target 3 |
| 274 | CR1-CelI-OT3-R | CACTGCATCATCTCATTAAATCAA | Reverse Surveyor primer for CR1 off-target 3 |
| 275 | CR1-CelI-OT4-F | CCCATATATTCATGATTACCCACA | Forward Surveyor primer for CR1 off-target 4 |
| 276 | CR1-CelI-OT4-R | TATCAGAACGAGCACTAAAAGCAC | Reverse Surveyor primer for CR1 off-target 4 |
| 277 | CR1-CelI-OT5-F | TTGGGAGGCTGAGGTACAAG | Forward Surveyor primer for CR1 off-target 5 |
| 278 | CR1-CelI-OT5-R | GAATGAAAAACAAACAGAAGGTGA | Reverse Surveyor primer for CR1 off-target 5 |
| 279 | CR1-CelI-OT6-F | CTCCTCATCTGTACCCTTCAATCT | Forward Surveyor primer for CR1 off-target 6 |
| 280 | CR1-CelI-OT6-R | AGAGTGGCATCTAGTGTCAGTGAG | Reverse Surveyor primer for CR1 off-target 6 |
| 281 | CR1-CelI-OT7-F | TACCAAAAGCTTCTCCTGTTTACC | Forward Surveyor primer for CR1 off-target 7 |
| 282 | CR1-CelI-OT7-R | GTAAGTTGGATGGCCTATTCTTTG | Reverse Surveyor primer for CR1 off-target 7 |
| 283 | CR1-CelI-OT8-F | GAAGGAAATGCAAGGATACAAGAT | Forward Surveyor primer for CR1 off-target 8 |
| 284 | CR1-CelI-OT8-R | TGATTGAAAGAATCATTCCAGAAA | Reverse Surveyor primer for CR1 off-target 8 |
| 285 | CR1-CelI-OT9-F | TCAGAAGGAAAATTGAAATTGGTT | Forward Surveyor primer for CR1 off-target 9 |
| 286 | CR1-CelI-OT9-R | CAGATGTGTTCTTCATCATTCCTC | Reverse Surveyor primer for CR1 off-target 9 |
| 287 | CR1-CelI-OT10-F | TTCTCTTTAGGGAAAGCTCTCAAA | Forward Surveyor primer for CR1 off-target 10 |
| 288 | CR1-CelI-OT10-R | GGGTATAGATCATATGGAGGGAAG | Reverse Surveyor primer for CR1 off-target 10 |
| 289 | CR5-CelI-OT1-F | AGATGATCTGCCCACCTCAG | Forward Surveyor primer for CR5 off-target 1 |
| 290 | CR5-CelI-OT1-R | CTTTCTTCCTCATTTAGTGGCAAT | Reverse Surveyor primer for CR5 off-target 1 |
| 291 | CR5-CelI-OT2-F | ATGAATTGCAGATTGATGGTACTG | Forward Surveyor primer for CR5 off-target 2 |
| 292 | CR5-CelI-OT2-R | TCTCACCAAGAACCAAATTGTCTA | Reverse Surveyor primer for CR5 off-target 2 |
| 293 | CR5-CelI-OT3-F | GTAGGATACCTTGGCAACAGTCTT | Forward Surveyor primer for CR5 off-target 3 |
| 294 | CR5-CelI-OT3-R | TTAACGAATTGTGAGATTTGCTGT | Reverse Surveyor primer for CR5 off-target 3 |
| 295 | CR5-CelI-OT4-F | TCAGAAAGTCAAGTAGCACACACA | Forward Surveyor primer for CR5 off-target 4 |

TABLE 5-continued

| SEQ ID NO. | Primer name | Primer sequence | Notes |
|---|---|---|---|
| 296 | CR5-CelI-OT4-R | AGAAGCACACACTCAGGTAAAGC | Reverse Surveyor primer for CR5 off-target 4 |
| 297 | CR5-CelI-OT5-F | TCTTTGGGGGAATAATGACTAAAA | Forward Surveyor primer for CR5 off-target 5 |
| 298 | CR5-CelI-OT5-R | TTTGGCATTTATGGGAATAAAACT | Reverse Surveyor primer for CR5 off-target 5 |
| 299 | CR5-CelI-OT6-F | ACTAATTCTGGTCAAGCCCATCA | Forward Surveyor primer for CR5 off-target 6 |
| 300 | CR5-CelI-OT6-R | TTAAGACATCGGATGAACAGAAAG | Reverse Surveyor primer for CR5 off-target 6 |
| 301 | CR5-CelI-OT7-F | AGAAGCTTTCTGACATGATCTGC | Forward Surveyor primer for CR5 off-target 7 |
| 302 | CR5-CelI-OT7-R | TCAATTGCATTAGGACTTAGACCA | Reverse Surveyor primer for CR5 off-target 7 |
| 303 | CR5-CelI-OT8-F | GTTAAATTACCTGTGAAGCCCTTG | Forward Surveyor primer for CR5 off-target 8 |
| 304 | CR5-CelI-OT8-R | CGGAAAACAGATCCACTTTATGAT | Reverse Surveyor primer for CR5 off-target 8 |
| 305 | CR5-CelI-OT9-F | AAATCCACTGGAAACATCTTGAGT | Forward Surveyor primer for CR5 off-target 9 |
| 306 | CR5-CelI-OT9-R | AGTCTCTTCAGAATCATGCCCTAT | Reverse Surveyor primer for CR5 off-target 9 |
| 307 | CR5-CelI-OT10-F | GCTTGGTGGCACATACCTGTAG | Forward Surveyor primer for CR5 off-target 10 |
| 308 | CR5-CelI-OT10-R | GGTAGGTAGATTTGCTTGCTTGTT | Reverse Surveyor primer for CR5 off-target 10 |
| 309 | CR6-CelI-OT1-F | AGCTCTCAGCAGAGTAGGGATTTA | Forward Surveyor primer for CR6 off-target 1 |
| 310 | CR6-CelI-OT1-R | GTGAGTCTACTGCACCCCATC | Reverse Surveyor primer for CR6 off-target 1 |
| 311 | CR6-CelI-OT2-F | TGACACTGTGAAGTCAATTCTGTC | Forward Surveyor primer for CR6 off-target 2 |
| 312 | CR6-CelI-OT2-R | TCAAGAACTTGACAATGAGCAAAT | Reverse Surveyor primer for CR6 off-target 2 |
| 313 | CR6-CelI-OT3-F | TATCCGATCCACTGTTGTGTGT | Forward Surveyor primer for CR6 off-target 3 |
| 314 | CR6-CelI-OT3-R | CAGGAGACCCAAAACCACTCTAC | Reverse Surveyor primer for CR6 off-target 3 |
| 315 | CR6-CelI-OT4-F | TTGTTCTACAAATAGGGCTTCCTT | Forward Surveyor primer for CR6 off-target 4 |
| 316 | CR6-CelI-OT4-R | TGTTAAGTTTGGGCTTATGTTCCT | Reverse Surveyor primer for CR6 off-target 4 |
| 317 | CR6-CelI-OT5-F | CACAAGTCTCACTGCACAAACAT | Forward Surveyor primer for CR6 off-target 5 |
| 318 | CR6-CelI-OT5-R | TGACCCATGATTATCTCTCTTTGA | Reverse Surveyor primer for CR6 off-target 5 |
| 319 | CR6-CelI-OT6-F | TTCAGCTTCTGATTGGTTTTAATG | Forward Surveyor primer for CR6 off-target 6 |
| 320 | CR6-CelI-OT6-R | CCAATTCCTTAATTTTCCCTACAG | Reverse Surveyor primer for CR6 off-target 6 |

TABLE 5-continued

| SEQ ID NO. | Primer name | Primer sequence | Notes |
|---|---|---|---|
| 321 | CR6-CelI-OT7-F | ATCTCAGACCAGGAGGGAGAC | Forward Surveyor primer for CR6 off-target 7 |
| 322 | CR6-CelI-OT7-R | CCTCAGGGTCAGTACATTTTTCAG | Reverse Surveyor primer for CR6 off-target 7 |
| 323 | CR6-CelI-OT8-F | TTCTTAGGACATTGCTCCACATAC | Forward Surveyor primer for CR6 off-target 8 |
| 324 | CR6-CelI-OT8-R | GCAAACATAATGCAACTCGTAATC | Reverse Surveyor primer for CR6 off-target 8 |
| 325 | CR6-CelI-OT9-F | GCAAGGGAGTCTGTGTCTTTG | Forward Surveyor primer for CR6 off-target 9 |
| 326 | CR6-CelI-OT9-R | TCATTTAAGTGGCTGTTCTGTGTT | Reverse Surveyor primer for CR6 off-target 9 |
| 327 | CR6-CelI-OT10-F | ACAAAACAGAGAGAAAAGGCAGAG | Forward Surveyor primer for CR6 off-target 10 |
| 328 | CR6-CelI-OT10-R | GTTTTGATTTCTGGTGCCTACAG | Reverse Surveyor primer for CR6 off-target 10 |
| 329 | CR36-CelI-OT1-F | ACTGAAGCTGAAGCCCAGTC | Forward Surveyor primer for CR36 off-target 1 |
| 330 | CR36-CelI-OT1-R | ACATGAGCTCTCAGGTTTCTGAC | Reverse Surveyor primer for CR36 off-target 1 |
| 331 | CR36-CelI-OT2-F | TCAAACTTAGATGGTTCCCTATGTT | Forward Surveyor primer for CR36 off-target 2 |
| 332 | CR36-CelI-OT2-R | GTACCCTGAAAATGTAGGGTGACT | Reverse Surveyor primer for CR36 off-target 2 |
| 333 | CR36-CelI-OT3-F | CACTTCCCAAGTGAGGCAAT | Forward Surveyor primer for CR36 off-target 3 |
| 334 | CR36-CelI-OT3-R | CTATACTTGGGGCTGACTTGCTAC | Reverse Surveyor primer for CR36 off-target 3 |
| 335 | CR36-CelI-OT4-F | TCGTATAGGTTACTTTGGCTCACA | Forward Surveyor primer for CR36 off-target 4 |
| 336 | CR36-CelI-OT4-R | AGGGATCTTTACTCCTCAGTGTGT | Reverse Surveyor primer for CR36 off-target 4 |
| 337 | CR36-CelI-OT5-F | TGTAGAAGTTGGAATATCCTGCTG | Forward Surveyor primer for CR36 off-target 5 |
| 338 | CR36-CelI-OT5-R | GTCAACAATTTGATCTCAGGCTTC | Reverse Surveyor primer for CR36 off-target 5 |
| 339 | CR36-CelI-OT6-F | CTCAGTACTAAAGATGGACGCTTG | Forward Surveyor primer for CR36 off-target 6 |
| 340 | CR36-CelI-OT6-R | AATCATTTCAGTCTTCCCAACAAT | Reverse Surveyor primer for CR36 off-target 6 |
| 341 | CR36-CelI-OT7-F | GGGAATCACAGTAGATGTTTGTCA | Forward Surveyor primer for CR36 off-target 7 |
| 342 | CR36-CelI-OT7-R | AGACCAGGAGGTAAGAACATTTTG | Reverse Surveyor primer for CR36 off-target 7 |
| 343 | CR36-CelI-OT8-F | CCACATAGAAAGAGACTTGCAGAA | Forward Surveyor primer for CR36 off-target 8 |
| 344 | CR36-CelI-OT8-R | AGAGATGCCAAAAGAACAGTCAAT | Reverse Surveyor primer for CR36 off-target 8 |
| 345 | CR36-CelI-OT9-F | TGTGCCTTAGGCTATGTAAACTGT | Forward Surveyor primer for CR36 off-target 9 |

TABLE 5-continued

| SEQ ID NO. | Primer name | Primer sequence | Notes |
|---|---|---|---|
| 346 | CR36-CelI-OT9-R | AAACCCTTGTAACCAAAATTACCA | Reverse Surveyor primer for CR36 off-target 9 |
| 347 | CR36-Cell-OT10-F | TAACTGCATCAGAAGTCCTTGCTA | Forward Surveyor primer for CR36 off-target 10 |
| 348 | CR36-Cell-OT10-R | GGAGACCAAGCTGCTAAAGTCA | Reverse Surveyor primer for CR36 off-target 10 |
| 349 | CelI-CR3-F-nested | GTGGTGccgcggGAGTTTGGCTCAAATTGTTACTCTT | Nested PCR first round primers |
| 350 | CelI-CR3-R-nested | GTGGTGccgcggGGGAAATGGTCTAGGAGAGTAAAGT | Nested PCR first round primers |
| 351 | CelI-CR1-F-nested | GTGGTGccgcggGAGAGGTTATGTGGCTTTACCA | Nested PCR first round primers |
| 352 | CelI-CR1-R-nested | GTGGTGccgcggCTCATTCTCATGCCTGGACA | Nested PCR first round primers |
| 353 | CelI-CR5-F-nested | GTGGTGccgcggCGGGCTTGGACAGAACTTAC | Nested PCR first round primers |
| 354 | CelI-CR5-R-nested | GTGGTGccgcggCTGCGTAGTGCCAAAACAAA | Nested PCR first round primers |
| 355 | CelI-CR6-F-nested | GTGGTGccgcggTAATTTCATTGAAGAGTGGCTGAA | Nested PCR first round primers |
| 356 | CelI-CR6-R-nested | GTGGTGccgcggAAGCCCTGTGTGGTAGTAGTCAGT | Nested PCR first round primers |
| 357 | CelI-CR36-F-nested | GTGGTGccgcggCAAGTCAGAAGTCACTTGCTTTGT | Nested PCR first round primers |
| 358 | CelI-CR36-R-nested | GTGGTGccgcggTTTTATGTGCAGGAATCAGTCTGT | Nested PCR first round primers |
| 359 | CR3-CelI-OT1-F-nested | GTGGTGccgcggTGTGTGCTTCTGTACACATCATCT | Nested PCR first round primers |
| 360 | CR3-CelI-OT1-R-nested | GTGGTGccgcggAGATTTCAACCCTCAAAAACTGAG | Nested PCR first round primers |
| 361 | CR1-CelI-OT1-F-nested | GTGGTGccgcggTTGGGAACATCAGAGAAAGTATGA | Nested PCR first round primers |
| 362 | CR1-CelI-OT1-R-nested | GTGGTGccgcggACAAATTACAGTCTCCTGGGAAAG | Nested PCR first round primers |
| 363 | CR36-CelI-OT3-F-nested | GTGGTGccgcggCACTTCCCAAGTGAGGCAAT | Nested PCR first round primers |
| 364 | CR36-CelI-OT3-R-nested | GTGGTGccgcggCTATACTTGGGGCTGACTTGCTAC | Nested PCR first round primers |
| 365 | CR3-P1/P3-F | GTGGTGccgcggTTGGCTCTTTAGCTTGTGTTTC | Nested PCR second round primers |
| 366 | CR3-P1/P3-R | GTGGTGccgcggTGAGACTCCCAAAGGCAATC | Nested PCR second round primers |
| 367 | CR3-P1/P4-F | GTGGTGccgcggTTGGCTCTTTAGCTTGTGTTTC | Nested PCR second round primers |
| 368 | CR3-P1/P4-R | GTGGTGccgcggACTGAGGGGTGATCTTGGTG | Nested PCR second round primers |
| 369 | CR3-P2/P3-F | GTGGTGccgcggGCAGAGAAAGCCAGTCGGTA | Nested PCR second round primers |
| 370 | CR3-P2/P3-R | GTGGTGccgcggTGAGACTCCCAAAGGCAATC | Nested PCR second round primers |

TABLE 5-continued

| SEQ ID NO. | Primer name | Primer sequence | Notes |
|---|---|---|---|
| 371 | CR3-P2/P4-F | GTGGTGccgcggGCAGAGAAAGCCAGTCGGTA | Nested PCR second round primers |
| 372 | CR3-P2/P4-R | GTGGTGccgcggACTGAGGGGTGATCTTGGTG | Nested PCR second round primers |
| 373 | CR1-P1/P5-F | GTGGTGccgcggCCAGAGTTCCTAGGGCAGAG | Nested PCR second round primers |
| 374 | CR1-P1/P5-R | GTGGTGccgcggAGCTAGTCCCCACATTCCAC | Nested PCR second round primers |
| 375 | CR1-P1/P6-F | GTGGTGccgcggCCAGAGTTCCTAGGGCAGAG | Nested PCR second round primers |
| 376 | CR1-P1/P6-R | GTGGTGccgcggGGTGGAGGGAAACTTTAGGC | Nested PCR second round primers |
| 377 | CR1-P2/P5-F | GTGGTGccgcggCTCATTCTCATGCCTGGACA | Nested PCR second round primers |
| 378 | CR1-P2/P5-R | GTGGTGccgcggAGCTAGTCCCCACATTCCAC | Nested PCR second round primers |
| 379 | CR1-P2/P6-F | GTGGTGccgcggTCTCATGCCTGGACAAGTAACT | Nested PCR second round primers |
| 380 | CR1-P2/P6-R | GTGGTGccgcggGGTGGAGGGAAACTTTAGGC | Nested PCR second round primers |
| 381 | CR5-P3/P5-F | GTGGTGccgcggGGCTTGGACAGAACTTACCG | Nested PCR second round primers |
| 382 | CR5-P3/P5-R | GTGGTGccgcggCACCACTGTCTGCCTAAGGA | Nested PCR second round primers |
| 383 | CR5-P4/P6-F | GTGGTGccgcggGGCTTGGACAGAACTTACCG | Nested PCR second round primers |
| 384 | CR5-P4/P6-R | GTGGTGccgcggGGTGGAGGGAAACTTTAGGC | Nested PCR second round primers |
| 385 | CR5-P3/P5-F | GTGGTGccgcggCGTAGTGCCAAAACAAACAGT | Nested PCR second round primers |
| 386 | CR5-P3/P5-R | GTGGTGccgcggCACCACTGTCTGCCTAAGGA | Nested PCR second round primers |
| 387 | CR5-P4/P6-F | GTGGTGccgcggCGTAGTGCCAAAACAAACAGT | Nested PCR second round primers |
| 388 | CRS-P4/P6-R | GTGGTGccgcggGGTGGAGGGAAACTTTAGGC | Nested PCR second round primers |
| 389 | CR6-P1/P5-F | GTGGTGccgcggGCGAGGGCCTACTTGATATG | Nested PCR second round primers |
| 390 | CR6-P1/P5-R | GTGGTGccgcggCTTCCCAAGTGAGGCAATGC | Nested PCR second round primers |
| 391 | CR6-P1/P6-F | GTGGTGccgcggACGTTTTGTGCTGCTGTAACA | Nested PCR second round primers |
| 392 | CR6-P1/P6-R | GTGGTGccgcggCTGCAGGCACATTCTCTTCC | Nested PCR second round primers |
| 393 | CR6-P2/P5-F | GTGGTGccgcggGCCCTGTGTGGTAGTAGTCA | Nested PCR second round primers |
| 394 | CR6-P2/P5-R | GTGGTGccgcggCTTCCCAAGTGAGGCAATGC | Nested PCR second round primers |
| 395 | CR6-P2/P6-F | GTGGTGccgcggCAGTATTAAGGGGTGGGAGCT | Nested PCR second round primers |

TABLE 5-continued

| SEQ ID NO. | Primer name | Primer sequence | Notes |
|---|---|---|---|
| 396 | CR6-P2/P6-R | GTGGTGccgcggTCTCTTCCTCACACA GCTGA | Nested PCR second round primers |
| 397 | CR36-P3/P5-F | GTGGTGccgcggGGAGCTTGGAGGGA AGAGAA | Nested PCR second round primers |
| 398 | CR36-P3/P5-R | GTGGTGccgcggCTTCCCAAGTGAGGC AATGC | Nested PCR second round primers |
| 399 | CR36-P4/P6-F | GTGGTGccgcggATGGATGGGGAAGA CACTGG | Nested PCR second round primers |
| 400 | CR36-P4/P6-R | GTGGTGccgcggCTGCAGGCACATTCT CTTCC | Nested PCR second round primers |
| 401 | CR36-P3/P5-F | GTGGTGccgcggGGATGAAACAGGGC AGGAAC | Nested PCR second round primers |
| 402 | CR36-P3/P5-R | GTGGTGccgcggTTCCCAAGTGAGGCA ATGC | Nested PCR second round primers |
| 403 | CR36-P4/P6-F | GTGGTGccgcggTTTGCAGAGCCATGA TGAGG | Nested PCR second round primers |
| 404 | CR36-P4/P6-R | GTGGTGccgcggCGACAGCCAAAACA GCCG | Nested PCR second round primers |

Western Blot Analysis.

To assess dystrophin protein expression, immortalized myoblasts were differentiated into myofibers by replacing the growth medium with DMEM supplemented with 100 insulin-transferrin-selenium (Invitrogen) and 1% antibiotic/antimycotic (Invitrogen) for 4-7 days, such as 6 or 7 days. Fibroblasts were transdifferentiated into myoblasts by inducing MyoD overexpression and incubating the cells in DMEM supplemented with 1% insulin-transferrin-selenium (Invitrogen), 1% antibiotic/antimycotic (Invitrogen) and 3 g/mL doxycycline for 15 days. Dystrophin expression was assessed at 3 days after transfecting HEK293T cells. Cells were trypsinized, collected and lysed in RIPA buffer (Sigma) supplemented with a protease inhibitor cocktail (Sigma) and the total protein amount was quantified using the bicinchoninic acid assay according to the manufacturer's instructions (Pierce). Samples were then mixed with NuPAGE loading buffer (Invitrogen) and 5% 0-mercaptoethanol and heated to 85° C. for 10 minutes. Twenty-five micrograms of protein were separated on 4-12% NuPAGE Bis-Tris gels (Invitrogen) with MES buffer (Invitrogen). Proteins were transferred to nitrocellulose membranes for 1-2 hrs in transfer buffer containing 10-20% methanol, such as 10% methanol, and 0.01% SDS. The blot was then blocked for 1 hr with 5% milk-TBST at room temperature. Blots were probed with the following primary antibodies: MANDYS8 to detect dystrophin (1:100, Sigma D8168) and rabbit anti-GAPDH (1:5000, Cell Signaling 2118S). Blots were then incubated with mouse or rabbit horseradish peroxidase-conjugated secondary antibodies (Santa Cruz) and visualized using the ChemiDoc chemilumescent system (BioRad) and Western-C ECL substrate (BioRad).

Transplantation into Immunodeficient Mice.

All animal experiments were conducted under protocols approved by the Duke Institutional Animal Care & Use Committee. Cells were trypsinized, collected and washed in 1× Hank's Balanced Salt Solution (HBSS, Sigma). Two million cells were pelleted and resuspended in five μL 1×HBSS (Sigma) supplemented with cardiotoxin (Sigma #C9759) immediately prior to injection. These cells were transplanted into the hind limb tibialis anterior (TA) muscle of NOD.SCID.gamma (NSG) mice (Duke CCIF Breeding Core) by intramuscular injection. Four weeks after injection, mice were euthanized and the TA muscles were harvested.

Immunofluorescence Staining.

Harvested TA muscles were incubated in 30% glycerol overnight at 4° C. before mounting and freezing in Optimal Cutting Temperature compound. Serial 10 micron sections were obtained by cryosectioning of the embedded muscle tissue at −20° C. Cryosections were then washed in PBS to remove the OCT compound and subsequently blocked for 30-60 minutes at room temperature in PBS containing 10% heat-inactivated fetal bovine serum for spectrin detection or 5% heat-inactivated fetal bovine serum for dystrophin detection. Cryosections were incubated overnight at 4° C. with the following primary antibodies that are specific to human epitopes only: anti-spectrin (1:20, Leica NCL-SPEC1) or anti-dystrophin (1:2, Leica NCL-DYS3). After primary staining, spectrin or dystrophin expression was detected using a tyramide-based immunofluorescence signal amplification detection kit (Life Technologies, TSA Kit #22, catalog #T-20932). Briefly, cryosections were incubated with 1:200 goat anti-mouse biotin-XX secondary (Life Technologies #B2763) in blocking buffer for 1 hr at room temperature. The signal was then amplified using streptavidin-HRP conjugates (1:100, from TSA Kit) in blocking buffer for 1 hr at room temperature. Finally, cryosections were incubated with tyramide-AlexaFluor488 conjugates (1:100, TSA kit) in manufacturer-provided amplification buffer for 10 minutes at room temperature. Stained cryosections were then mounted in ProLong AntiFade (Life Technologies #P36934) and visualized with conventional fluorescence microscopy.

Cytotoxicity Assay.

To quantitatively assess potential sgRNA or SpCas9 nuclease-associated cytotoxicity, HEK293T cells were transfected with 10 ng of a GFP reporter and 100 ng SpCas9 expression vector and 100 ng sgRNA expression vector using Lipofectamine 2000 according to the manufacturer's instructions (Invitrogen). The percentage of GFP positive cells was assessed at 2 and 5 days by flow cytometry. The survival rate was calculated as the decrease in GFP positive cells from days 2 to 5 and normalized to cells transfected with an empty nuclease expression vector as described (Cornu et al., Meth Mol Biol 649:237-245 (2010)).

Example 4

CRISPRs Targeting the Dystrophin Gene—Results

The CRISPR/Cas9-based system was designed to target the dystrophin gene. Various gRNAs were chosen to target different regions of the human and mouse dystrophin gene based on NNNNN NNNNN NNNNN NNNNN NGG (SEQ ID NO: 677) and GNNNN NNNNN NNNNN NNNNN NNNNN NGG (SEQ ID NO: 678) (see Tables 6, 7 and 8).

TABLE 6

| Name (SEQ ID NO) | Species | Gene | Target | Strand | 19 bp for chimeric (add G on 5' end) | PAM |
|---|---|---|---|---|---|---|
| DCR1 (628) | Human | DMD | Intron 50 | + | attggctttgatttcccta (SEQ ID NO: 65) | GGG |
| DCR2 (66) | Human | DMD | Intron 50 | - | tgtagagtaagtcagccta (SEQ ID NO: 679) | TGG |
| DCR3 (629) | Human | DMD | Exon 51-55' | + | cctactcagactgttactc (SEQ ID NO: 67) | TGG |
| DCR4 (68) | Human | DMD | Exon 51-53 | + | ttggacagaacttaccgac (SEQ ID NO: 680) | TGG |
| DCR5 (630) | Human | DMD | Intron 51 | - | cagttgcctaagaactggt (SEQ ID NO: 69) | GGG |
| DCR6 (631) | Human | DMD | Intron 44 | - | GGGCTCCACCCTCACGAGT (SEQ ID NO: 70) | GGG |
| DCR7 (71) | Human | DMD | Intron 55 | + | TTTGCTTCGCTATAAAACG (SEQ ID NO: 681) | AGG |
| DCR8 (72) | Human | DMD | Exon 41 | + | TCTGAGGATGGGGCCGCAA (SEQ ID NO: 682) | TGG |
| DCR9 (73) | Human | DMD | Exon 44 | - | GATCTGTCAAATCGCCTGC (SEQ ID NO: 683) | AGG |
| DCR10 (74) | Human | DMD | Exon 45 | + | CCAGGATGGCATTGGGCAG (SEQ ID NO: 684) | CGG |
| DCR11 (75) | Human | DMD | Exon 45 | + | CTGAATCTGCGGTGGCAGG (SEQ ID NO: 685) | AGG |
| DCR12 (76) | Human | DMD | Exon 46 | - | TTCTTTTGTTCTTCTAGCc (SEQ ID NO: 686) | TGG |
| DCR13 (77) | Human | DMD | Exon 46 | + | GAAAAGCTTGAGCAAGTCA (SEQ ID NO: 687) | AGG |
| DCR14 (78) | Human | DMD | Exon 47 | + | GAAGAGTTGCCCCTGCGCC (SEQ ID NO: 688) | AGG |
| DCR15 (79) | Human | DMD | Exon 47 | + | ACAAATCTCCAGTGGATAA (SEQ ID NO: 689) | AGG |
| DCR16 (80) | Human | DMD | Exon 48 | - | TGTTTCTCAGGTAAAGCTC (SEQ ID NO: 690) | TGG |
| DCR17 (81) | Human | DMD | Exon 48 | + | GAAGGACCATTTGACGTTa (SEQ ID NO: 691) | AGG |
| DCR18 (82) | Human | DMD | Exon 49 | - | AACTGCTATTTCAGTTTCc (SEQ ID NO: 692) | TGG |
| DCR19 (83) | Human | DMD | Exon 49 | + | CCAGCCACTCAGCCAGTGA (SEQ ID NO: 693) | AGG |
| DCR20 (84) | Human | DMD | Exon 50 | + | gtatgcttttctgttaaag (SEQ ID NO: 694) | AGG |
| DCR21 (85) | Human | DMD | Exon 50 | + | CTCCTGGACTGACCACTAT (SEQ ID NO: 695) | TGG |

TABLE 6-continued

| Name (SEQ ID NO) | Species | Gene | Target | Strand | 19 bp for chimeric (add G on 5' end) | PAM |
|---|---|---|---|---|---|---|
| DCR22 (86) | Human | DMD | Exon 52 | + | GAACAGAGGCGTCCCCAGT (SEQ ID NO: 696) | TGG |
| DCR23 (87) | Human | DMD | Exon 52 | + | GAGGCTAGAACAATCATTA (SEQ ID NO: 697) | CGG |
| DCR24 (88) | Human | DMD | Exon 53 | + | ACAAGAACACCTTCAGAAC (SEQ ID NO: 698) | CGG |
| DCR25 (89) | Human | DMD | Exon 53 | - | GGTTTCTGTGATTTTCTTT (SEQ ID NO: 699) | TGG |
| DCR26 (90) | Human | DMD | Exon 54 | + | GGCCAAAGACCTCCGCCAG (SEQ ID NO: 700) | TGG |
| DCR27 (91) | Human | DMD | Exon 54 | + | TTGGAGAAGCATTCATAAA (SEQ ID NO: 701) | AGG |
| DCR28 (92) | Human | DMD | Exon 55 | - | TCGCTCACTCACCctgcaa (SEQ ID NO: 702) | AGG |
| DCR29 (93) | Human | DMD | Exon 55 | + | AAAAGAGCTGATGAAACAA (SEQ ID NO: 703) | TGG |
| DCR30 (94) | Human | DMD | 5'UTR/Exon 1 | + | TAcACTTTTCaAAATGCTT (SEQ ID NO: 704) | TGG |
| DCR31 (95) | Human | DMD | Exon 51 | + | gagatgatcatcaagcaga (SEQ ID NO: 705) | AGG |
| DCR32 (96) | Mouse | DMD | mdx mutation | + | ccttgaaagagcaaTaaaa (SEQ ID NO: 706) | TGG |
| DCR33 (97) | Human | DMD | Intron 44 | - | CACAAAAGTCAAATCGGAA (SEQ ID NO: 707) | TGG |
| DCR34 (98) | Human | DMD | Intron 44 | - | ATTTCAATATAAGATTCGG (SEQ ID NO: 708) | AGG |
| DCR35 (99) | Human | DMD | Intron 55 | - | CTTAAGCAATCCCGAACTC (SEQ ID NO: 709) | TGG |
| DCR36 (632) | Human | DMD | Intron 55 | - | CCTTCTTTATCCCCTATCG (SEQ ID NO: 100) | AGG |
| DCR40 (104) | Mouse | DMD | Exon 23 | - | aggccaaacctcggcttac (SEQ ID NO: 710) | NNGRR |
| DCR41 (105) | Mouse | DMD | Exon 23 | + | TTCGAAAATTTCAGgtaag (SEQ ID NO: 711) | NNGRR |
| DCR42 (106) | Mouse | DMD | Exon 23 | + | gcagaacaggagataacag (SEQ ID NO: 712) | NNGRRT |
| DCR43 (107) | Mouse | ACVR2B | Exon 1 | + | gcggccctcgcccttctct (SEQ ID NO: 713) | ggggat |
| DCR48 (108) | Human | DMD | Intron 45 | - | TAGTGATCGTGGATACGAG (SEQ ID NO: 714) | AGG |
| DCR49 (109) | Human | DMD | Intron 45 | - | TACAGCCCTCGGTGTATAT (SEQ ID NO: 715) | TGG |
| DCR50 (110) | Human | DMD | Intron 52 | - | GGAAGGAATTAAGCCCGAA (SEQ ID NO: 716) | TGG |
| DCR51 (111) | Human | DMD | Intron 53 | - | GGAACAGCTTTCGTAGTTG (SEQ ID NO: 718) | AGG |
| DCR52 (112) | Human | DMD | Intron 54 | + | ATAAAGTCCAGTGTCGATC (SEQ ID NO: 719) | AGG |
| DCR53 (113) | | | Intron 54 | + | AAAACCAGAGCTTCGGTCA (SEQ ID NO: 720) | AGG |

TABLE 6-continued

| Name (SEQ ID NO) | Species | Gene | Target | Strand | 19 bp for chimeric (add G on 5' end) | PAM |
|---|---|---|---|---|---|---|
| DCR54 (114) | Mouse | Rosa26 | ZFN region | + | GAGTCTTCTGGGCAGGCTTAA AGGCTAACC (SEQ ID NO: 720) | TGG |
| DCR55 (115) | Mouse | Rosa26 | mRNA | - | TCGGGTGAGCATGTCTTTAAT CTACCTCGA (SEQ ID NO: 721) | TGG |
| DCR49 (116) | Human | DMD | Ex 51 | - | gtgtcaccagagtaacagt (SEQ ID NO: 722) | ctgagt |
| DCR50 (117) | Human | DMD | Ex 51 | + | tgatcatcaagcagaaggt (SEQ ID NO: 723) | atgag |
| DCR60 (118) | Mouse | DMD | Exon 23 | + | AACTTCGAAAATTTCAGgta (SEQ ID NO: 724) | agccgagg |
| DCR61 (119) | Mouse | DMD | Intron 22 | + | gaaactcatcaaatatgcgt (SEQ ID NO: 725) | gttagtgt |
| DCR62 (120) | Mouse | DMD | Intron 22 | - | tcatttacactaacacgcat (SEQ ID NO: 726) | atttgatg |
| DCR63 (121) | Mouse | DMD | Intron 22 | + | gaatgaaactcatcaaatat (SEQ ID NO: 727) | gcgtgtta |
| DCR64 (122) | Mouse | DMD | Intron 23 | - | tcatcaatatctttgaagga (SEQ ID NO: 728) | ctctgggt |
| DCR65 (123) | Mouse | DMD | Intron 23 | - | tgttttcataggaaaaatag (SEQ ID NO: 729) | gcaagttg |
| DCR66 (124) | Mouse | DMD | Intron 23 | + | aattggaaaatgtgatggga (SEQ ID NO: 730) | aacagata |
| DCR67 (125) | Human | DMD | Exon 51 | + | atgatcatcaagcagaaggt (SEQ ID NO: 731) | atgagaaa |
| DCR68 (126) | Human | DMD | Exon 51 | + | agatgatcatcaagcagaag (SEQ ID NO: 732) | gtatgaga |
| DCR69 (127) | Human | DMD | Exon 51 | - | cattttctctcataccttct (SEQ ID NO: 733) | gcttgatg |
| DCR70 (128) | Human | DMD | Exon 51 | + | tcctactcagactgttactc (SEQ ID NO: 734) | tggtgaca |
| DCR71 (129) | Human | DMD | Exon 51 | - | acaggttgtgtcaccagagt (SEQ ID NO: 735) | aacagtct |
| DCR72 (130) | Human | DMD | Exon 51 | - | ttatcatttttctcatacc (SEQ ID NO: 736) | ttctgctt |
| DCR73 (131) | Human | DMD | Intron 51 | - | ttgcctaagaactggtggga (SEQ ID NO: 737) | aatggtct |
| DCR74 (132) | Human | DMD | Intron 51 | - | aaacagttgcctaagaactg (SEQ ID NO: 738) | gtgggaaa |
| DCR75 (133) | Human | DMD | Intron 51 | + | tttcccaccagttcttaggc (SEQ ID NO: 739) | aactgttt |
| DCR76 (134) | Human | DMD | Intron 50 | + | tggctttgatttccctaggg (SEQ ID NO: 740) | tccagctt |
| DCR77 (135) | Human | DMD | Intron 50 | - | tagggaaatcaaagccaatg (SEQ ID NO: 741) | aaacgttc |
| DCR78 (136) | Human | DMD | Intron 50 | - | gaccctagggaaatcaaagc (SEQ ID NO: 742) | caatgaaa |
| DCR79 (137) | Human | DMD | Intron 44 | - | TGAGGGCTCCACCCTCACGA (SEQ ID NO: 743) | GTGGGTTT |
| DCR80 (138) | Human | DMD | Intron 44 | - | AAGGATTGAGGGCTCCACCC (SEQ ID NO: 744) | TCACGAGT |

TABLE 6-continued

| Name (SEQ ID NO) | Species | Gene | Target | Strand | 19 bp for chimeric (add G on 5' end) | PAM |
|---|---|---|---|---|---|---|
| DCR81 (139) | Human | DMD | Intron 44 | - | GCTCCACCCTCACGAGTGGG (SEQ ID NO: 745) | TTTGGTTC |
| DCR82 (140) | Human | DMD | Intron 55 | - | TATCCCCTATCGAGGAAACC (SEQ ID NO: 746) | ACGAGTTT |
| DCR83 (141) | Human | DMD | Intron 55 | + | GATAAAGAAGGCCTATTTCA (SEQ ID NO: 747) | TAGAGTTG |
| DCR84 (142) | Human | DMD | Intron 55 | - | AGGCCTTCTTTATCCCCTAT (SEQ ID NO: 748) | CGAGGAAA |
| DCR85 (143) | Human | DMD | Intron 44 | - | TGAGGGCTCCACCCTCACGA (SEQ ID NO: 749) | GTGGGT |
| DCR86 (144) | Human | DMD | Intron 55 | + | GATAAAGAAGGCCTATTTCA (SEQ ID NO: 750) | TAGAGT |

TABLE 7

| Name | Notes | % Mod |
|---|---|---|
| DCR1 | Delete exon 51 | 6.6 |
| DCR2 | Delete exon 51 | 10.3 |
| DCR3 | Frameshift | 13 |
| DCR4 | Delete exon 51 | 11.9 |
| DCR5 | Delete exon 51 | 12.4 |
| DCR6 | As close to exon 44 as possible in intron 44 (in case of patient deletions) | 16.1 |
| DCR7 | As close to exon 56 as possible in intron 55 (in case of patient deletions) | 6.8 |
| DCR8 | Can correct exon 42-43 deletion (−1/+2) only, (−2/+1) is not correctable by this | 17.3 |
| DCR9 | Skip exon 44 (5') | 14.4 |
| DCR10 | Frameshift | 14.9 |
| DCR11 | Correct downstream of exon 45 | <1 |
| DCR12 | 5' splice acceptor/frameshift | <1 |
| DCR13 | Correct downstream of exon 46 | 16.9 |
| DCR14 | Frameshift | 17.2 |
| DCR15 | Correct downstream of exon 47 | 15.4 |
| DCR16 | Frameshift | 11.5 |
| DCR17 | Correct downstream of exon 48 | <1 |
| DCR18 | 5' splice acceptor/frameshift | 1.8 |
| DCR19 | Correct downstream of exon 49 | 33.7 |
| DCR20 | 5' splice acceptor | 14.9 |
| DCR21 | Correct downstream of exon 50 | 24.1 |

TABLE 7-continued

| Name | Notes | % Mod |
|---|---|---|
| DCR22 | Frameshift | 25.9 |
| DCR23 | Correct downstream of exon 52 | 25.2 |
| DCR24 | Frameshift (can only correct +1 frame) | 24.8 |
| DCR25 | Correct downstream of exon 53 | 2.6 |
| DCR26 | Frameshift | 24.5 |
| DCR27 | Correct downstream of exon 54 | 13.4 |
| DCR28 | 5' splice acceptor | 21.6 |
| DCR29 | Correct downstream of exon 55 | 19.2 |
| DCR30 | Integrate minidys in exon 1 | not tested |
| DCR31 | Correct downstream of exon 51 | 18.9 |
| DCR32 | Delete stop codon | not tested |
| DCR33 | Alternative to CR6 | 1.3 |
| DCR34 | Alternative to CR6 | 13.2 |
| DCR35 | Alternative to CR7 | 22.5 |
| DCR36 | Alternative to CR7 | 26.4 |
| DCR40 | Disrupt exon 23 5' splice donor (correct mdx mutation) | |
| DCR41 | Disrupt exon 23 5' splice donor (correct mdx mutation) | |
| DCR42 | Delete exon 53 mdx4cv mutation | |
| DCR43 | Disrupt myostatin receptor | |

TABLE 8

| Name | Cas9 | | Notes | Cas9 used |
|---|---|---|---|---|
| DCR49 | *S. Aureus* | | Frameshift in exon 51 | SaCas9 (from Zhang pX441) (NNGRRT PAM) |
| DCR50 | *S. Aureus* | | Disrupt 5' end of exon 51 | SaCas9 (from Zhang pX441) (NNGRR PAM) |
| DCR60 | *N. Meningitidis* | NNNNGANN | Target 3' splice donor of exon 23 to bypass mdx mutation | NmCas9 (NNNNGANN PAM) |
| DCR61 | *N. Meningitidis* | NNNNGNNT | Delete exon 23 and bypass mdx mutation | NmCas9 (NNNNGNNT PAM) |
| DCR62 | *N. Meningitidis* | NNNNGANN | Delete exon 23 and bypass mdx mutation | NmCas9 (NNNNGANN PAM) |
| DCR63 | *N. Meningitidis* | NNNNGTTN | Delete exon 23 and bypass mdx mutation | NmCas9 (NNNNGTTN PAM) |

TABLE 8-continued

| Name | Cas9 | | Notes | Cas9 used |
|---|---|---|---|---|
| DCR64 | *N. Meningitidis* | NNNNGNNT | Delete exon 23 and bypass mdx mutation | NmCas9 (NNNNGNNT PAM) |
| DCR65 | *N. Meningitidis* | NNNNGTTN | Delete exon 23 and bypass mdx mutation | NmCas9 (NNNNGTTN PAM) |
| DCR66 | *N. Meningitidis* | NNNNGANN | Delete exon 23 and bypass mdx mutation | NmCas9 (NNNNGANN PAM) |
| DCR67 | *N. Meningitidis* | NNNNGANN | Target 3' splice donor of exon 51 to skip exon | NmCas9 (NNNNGANN PAM) |
| DCR68 | *N. Meningitidis* | NNNNGANN | Target 3' splice donor of exon 51 to skip exon | NmCas9 (NNNNGANN PAM) |
| DCR69 | *N. Meningitidis* | NNNNGANN | Target 3' splice donor of exon 51 to skip exon | NmCas9 (NNNNGANN PAM) |
| DCR70 | *N. Meningitidis* | NNNNGANN | Frameshift in exon 51 | NmCas9 (NNNNGANN PAM) |
| DCR71 | *N. Meningitidis* | NNNNGNNT | Frameshift in exon 51 | NmCas9 (NNNNGNNT PAM) |
| DCR72 | *N. Meningitidis* | NNNNGNNT | Target 3' splice donor of exon 51 to skip exon | NmCas9 (NNNNGNNT PAM) |
| DCR73 | *N. Meningitidis* | NNNNGNNT | Delete exon 51 (bind as close to DCR5 as possible) | NmCas9 (NNNNGNNT PAM) |
| DCR74 | *N. Meningitidis* | NNNNGANN | Delete exon 51 (bind as close to DCR5 as possible) | NmCas9 (NNNNGANN PAM) |
| DCR75 | *N. Meningitidis* | NNNNGTTN | Delete exon 51 (bind as close to DCR5 as possible) | NmCas9 (NNNNGTTN PAM) |
| DCR76 | *N. Meningitidis* | NNNNGNNT | Delete exon 51 (bind as close to DCR1/2 as possible) | NmCas9 (NNNNGNNT PAM) |
| DCR77 | *N. Meningitidis* | NNNNGTTN | Delete exon 51 (bind as close to DCR1/2 as possible) | NmCas9 (NNNNGTTN PAM) |
| DCR78 | *N. Meningitidis* | NNNNGANN | Delete exon 51 (bind as close to DCR1/2 as possible) | NmCas9 (NNNNGANN PAM) |
| DCR79 | *N. Meningitidis* | NNNNGNNT | Delete exons 45-55-overlaps NNNNGTTN PAM, bind as close to DCR6 as possible | NmCas9 (NNNNGNNT PAM) |
| DCR80 | *N. Meningitidis* | NNNNGANN | Delete exons 45-55, bind as close to DCR6 as possible | NmCas9 (NNNNGANN PAM) |
| DCR81 | *N. Meningitidis* | NNNNGTTN | Delete exons 45-55, bind as close to DCR6 as possible | NmCas9 (NNNNGTTN PAM) |
| DCR82 | *N. Meningitidis* | NNNNGNNT | Delete exons 45-55, bind as close to DCR36 as possible-overlaps NNNNGTTN PAM | NmCas9 (NNNNGNNT PAM) |
| DCR83 | *N. Meningitidis* | NNNNGTTN | Delete exons 45-55, bind as close to DCR36 as possible | NmCas9 (NNNNGTTN PAM) |
| DCR84 | *N. Meningitidis* | NNNNGANN | Delete exons 45-55, bind as close to DCR36 as possible | NmCas9 (NNNNGANN PAM) |

TABLE 8-continued

| Name | Cas9 | | Notes | Cas9 used |
|---|---|---|---|---|
| DCR85 | *S. Aureus* | NNGRRT | Delete exons 45-55, bind as close to DCR6 as possible | SaCas9 (from Zhang pX441) (NNGRRT PAM) |
| DCR86 | *S. Aureus* | NNGRRT | Delete exons 45-55, bind as close to DCR36 as possible | SaCas9 (from Zhang pX441) (NNGRRT PAM) |

In particular, 400 ng of Cas9 was co-transfected into HEK 293T cells with either 400 ng of empty vector or gRNA that targets the region encompassing Exon 51, i.e., CR1, CR2, CR3, CR4, and CR5 (see FIG. 11B). Genomic DNA was harvested at 2 days post-transfection and analyzed using the Surveyor assay (see FIGS. 11A and 11C).

Figure 12:
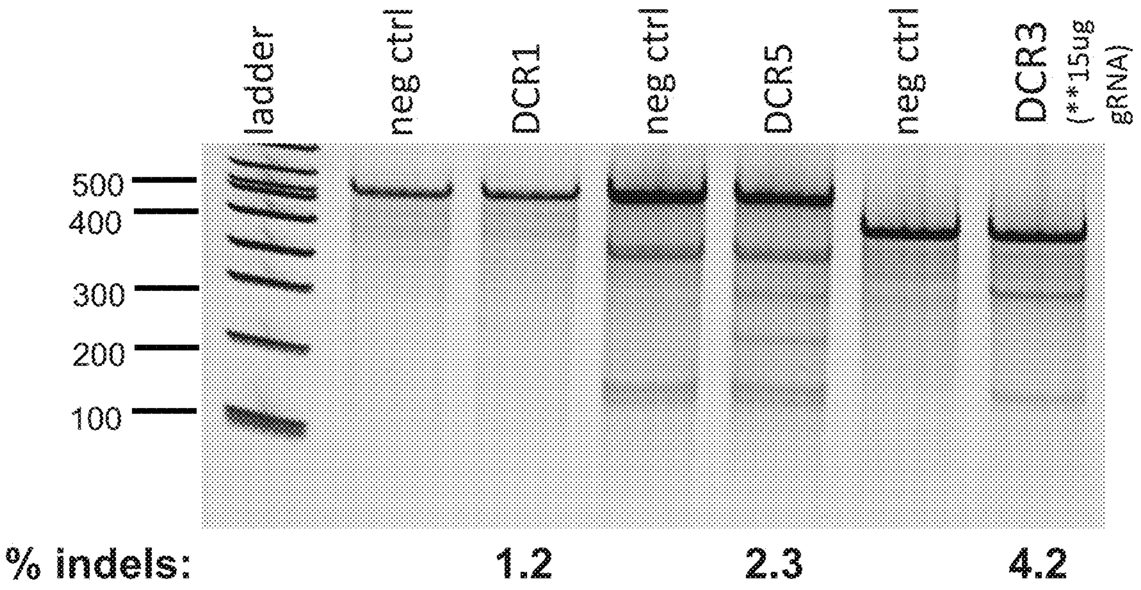
FIG. 12 shows RNA-guided repair in DMD 8036 (del48-50) cells as shown by Surveyor assay.
Figure 13:
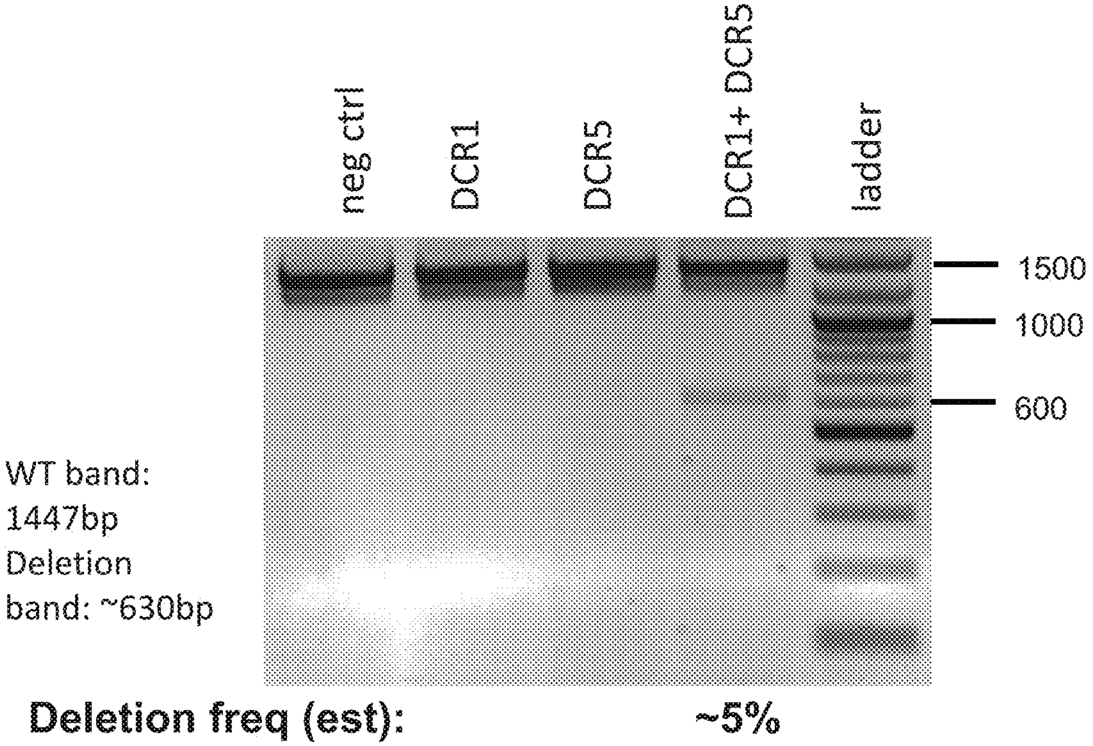
FIG. 13 shows RNA-guided repair in DMD 8036 (del48-50) cells as shown by PCR across the entire locus. The PCR of a wild-type dystrophin gene generates a fragment of 1447 bp in size, whereas PCR of the mutant gene in the DMD 8036 cell line shows a deletion of approximately 817 bp. The deletion band after introduction of the CRISPR/Cas9-based system was approximately 630 bp.
Figure 14:
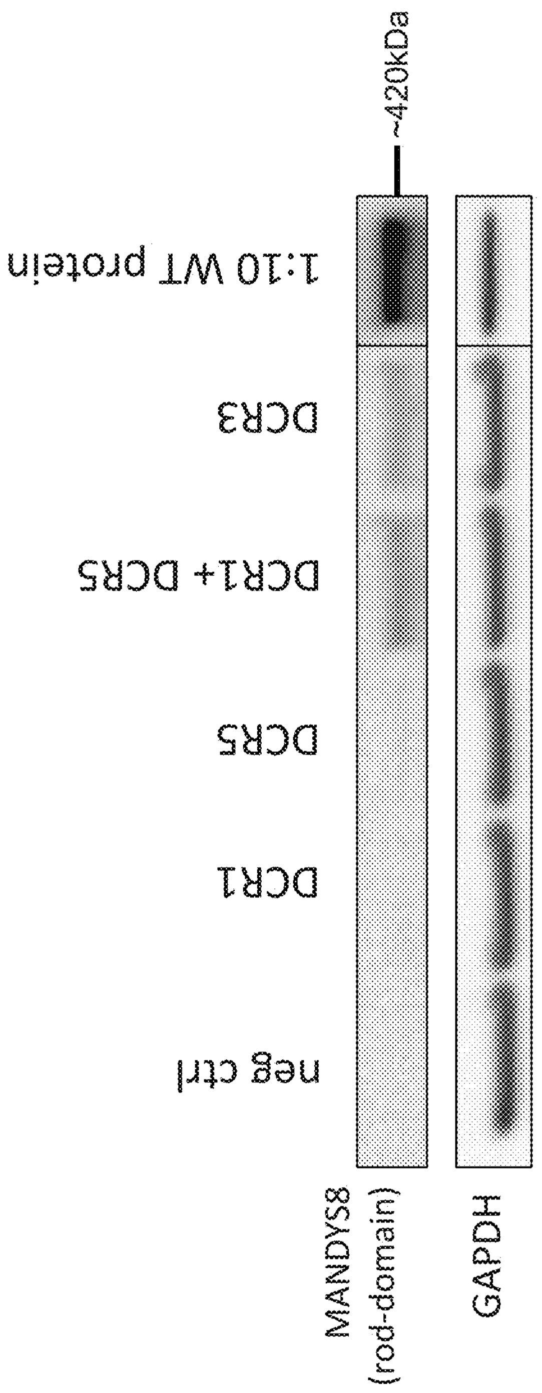
FIG. 14 shows RNA-guided repair in DMD 8036 (del48-50) cells as shown by Western blot with MANDYS8 (anti-dystrophin antibody) and GAPDH antibody (positive control).

The CRISPR/Cas9-based system was used in DMD 8036 (del48-50) cells to determine if the system could repair a mutant dystrophin gene. 5 μg of Cas9 was co-transfected into DMD 8036 (del48-50) cells with either 7.5 μg of empty vector or gRNA. In particular, 7.5 μg of CR1 ("DCR1"), 7.5 μg of CR5 ("DCR5"), 15 μg of CR3 ("DCR3") or 7.5 μg of a combination of CR1 and CR5 (DCR1+DCR5) were used. Genomic DNA was harvested at 3 days post-transfection and analyzed using the Surveyor assay (FIG. 12) or PCR analysis across the entire locus (FIG. 13). This locus was amplified by PCR using primers flanking the region containing the genomic targets for CR1 and CR5 (the forward primer: 5'-gagaggttatgtggctttacca (SEQ ID NO:457), the reverse primer: 5'-ctgcgtagtgccaaaacaaa (SEQ ID NO:458)), resulting in a 1447 bp band for the wild-type locus or an expected size of approximately 630 bp for the deleted locus. After 7 days of differentiation, western blot of the treated cells shows expression of dystrophin protein (see FIG. 14).

Example 5

Targeting CRISPR/Cas9 to Hotspot Mutations in the Human Dystrophin Gene

Figure 16A:
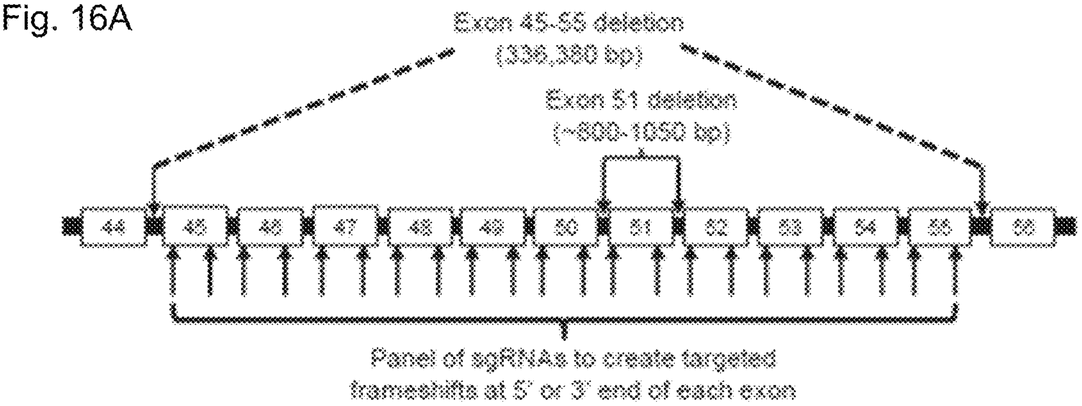
FIGS. 16A-16D show CRISPR/Cas9 targeting of the dystrophin gene.
Figure 16B:
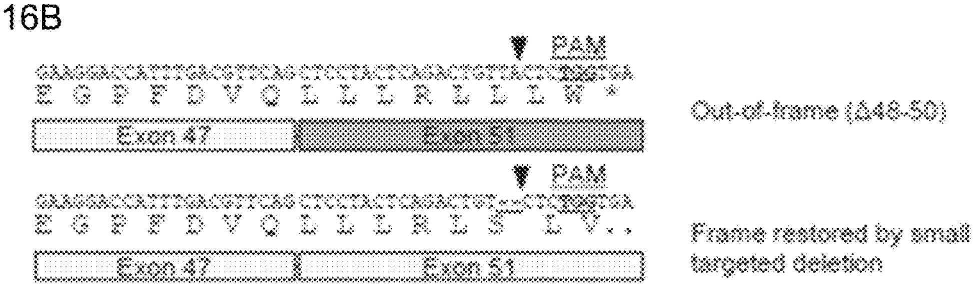
Figure 16C:
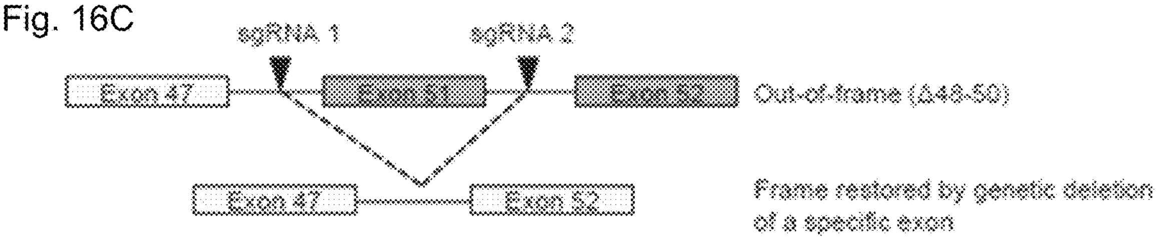
Figure 16D:
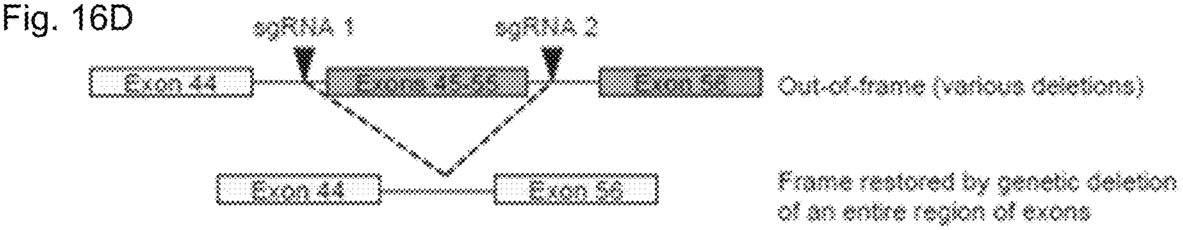

To utilize the CRISPR/Cas9 gene editing platform for correcting a wide range of dystrophin mutations, dozens of sgRNAs targeted to the hotspot mutation region between exons 45-55 were created (FIGS. 16A-16D). The *S. pyogenes* system that utilizes a human-codon optimized SpCas9 nuclease and a chimeric single-guide RNA (sgRNA) expression vector to guide efficient site-specific gene editing was used. Similar to Example 4 targeting exon 51 with TALENs, protospacers were selected to target the 5' and 3' ends of exons 45 through 55 which meet the 5'-NRG-3' PAM requirement of SpCas9. Small insertions or deletions created by NHEJ-based DNA repair within these exons can generate targeted frameshift mutations that address various dystrophin mutations surrounding each exon (FIGS. 16A-16B). For example, CR3 was designed to correct dystrophin mutations or deletions surrounding exon 51 by introducing small insertions or deletions in the 5' end of exon 51 to restore the downstream dystrophin reading frame (FIG. 16B). Additionally, sgRNAs were designed to employ the multiplex capability of the CRISPR/Cas9 system and specifically delete individual exons or a series of exons to restore the dystrophin reading frame, similar to the methods of oligonucleotide-based exon skipping. For this purpose, sgRNAs were targeted to the intronic regions surrounding exon 51 (FIG. 16C) or exons 45-55 (FIG. 16D). These sgRNAs were intentionally targeted to sites nearest to the downstream or upstream exon intended to be included in the resulting transcript to minimize the likelihood that the background patient deletion would include the intronic sgRNA target sites.

Example 6

Screening of sgRNAs Targeted to the Dystrophin Gene in Human Cells

Figure 17:
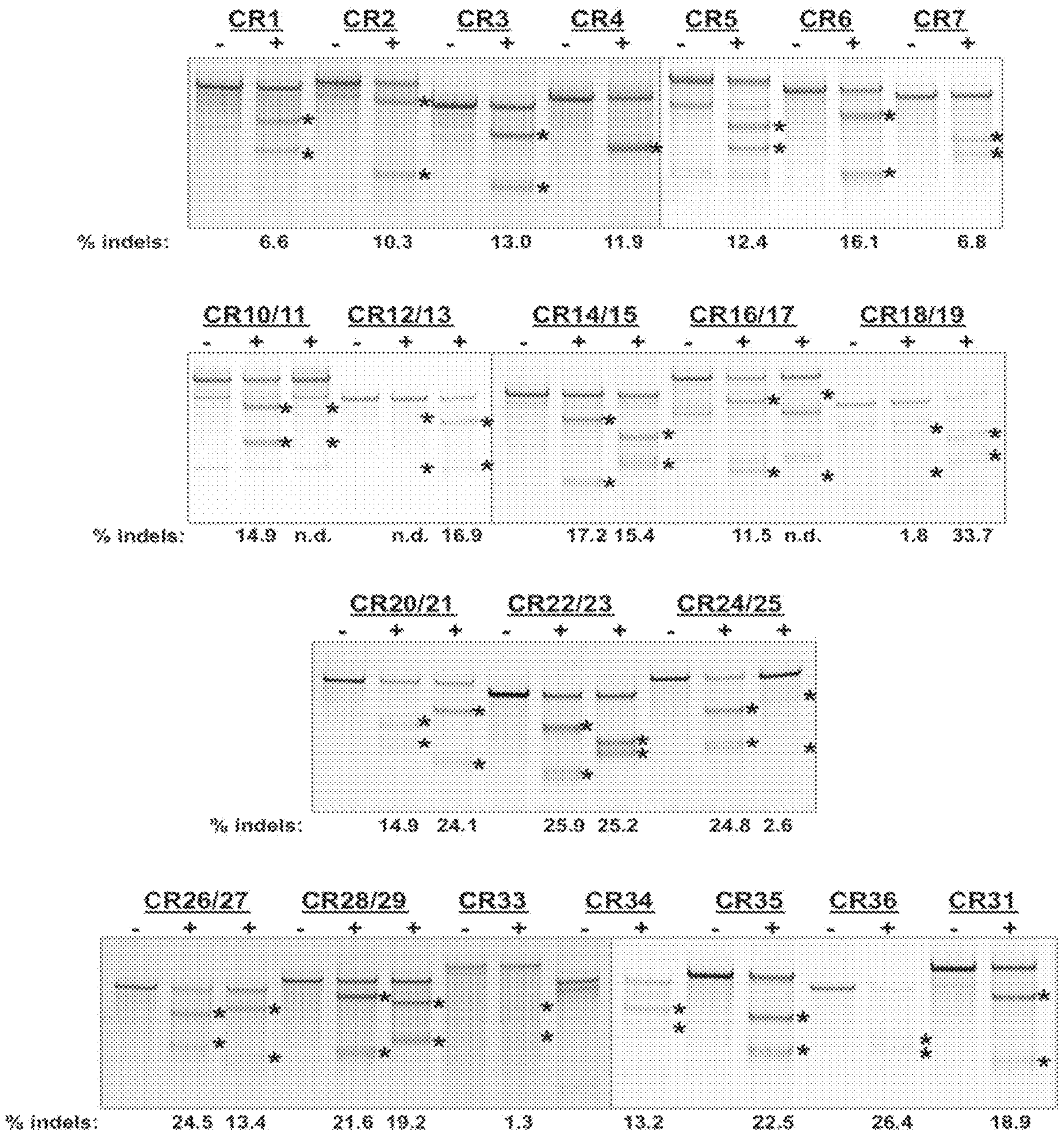
FIG. 17 shows images of TBE-PAGE gels used to quantify Surveyor assay results to measure day 3 gene modification in Table 7. Asterisks mark expected sizes of bands indicative of nuclease activity.
Figure 18:
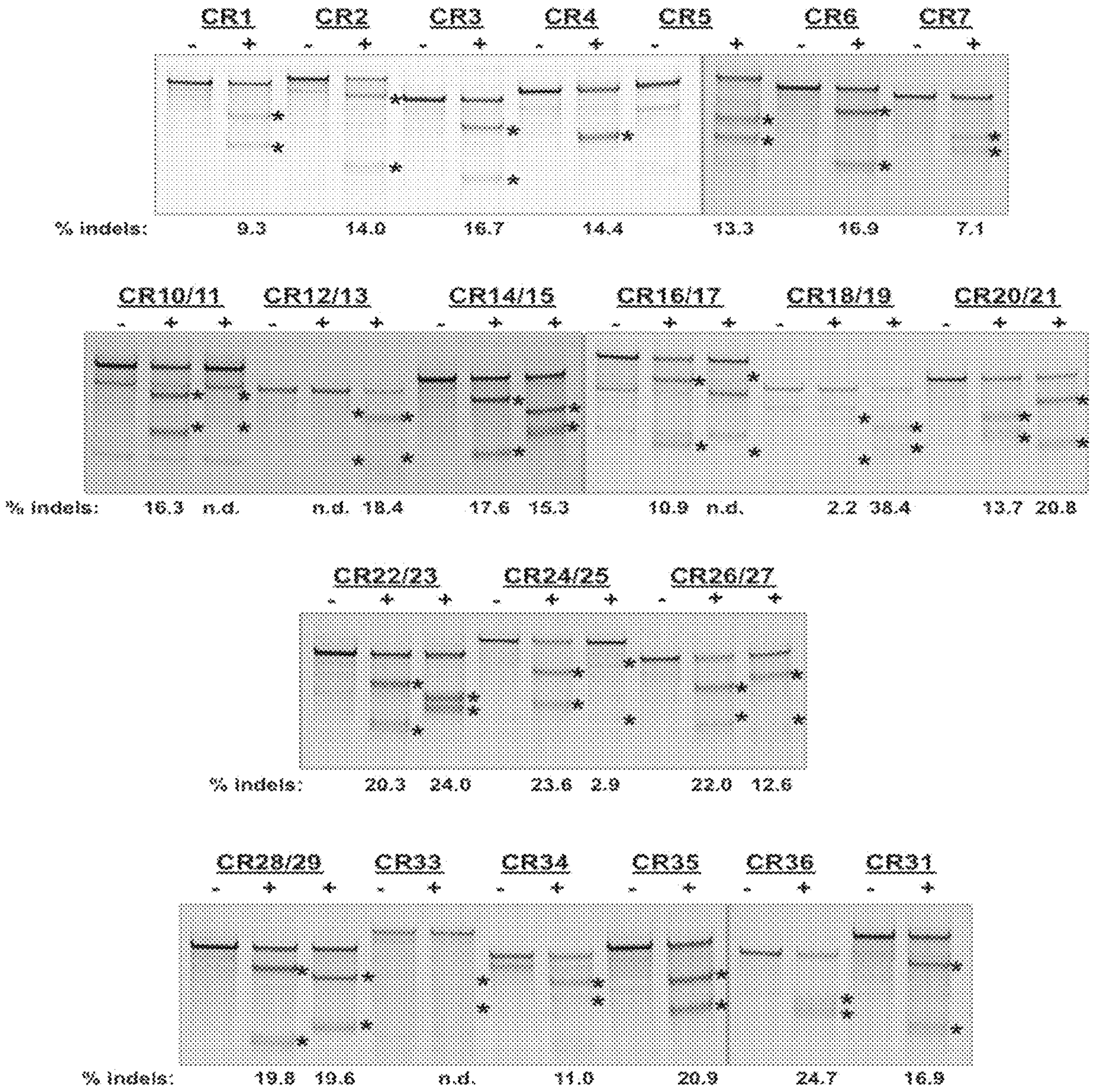
FIG. 18 shows images of TBE-PAGE gels used to quantify Surveyor assay results to measure day 10 gene modification in Table 7. Asterisks mark expected sizes of bands indicative of nuclease activity.

Gene editing frequency in the human HEK293T cell line was assessed to rapidly determine different sgRNA targeting efficiencies. HEK293Ts were transfected with constructs encoding human codon-optimized SpCas9 and the indicated sgRNA. Each sgRNA was designed to modify the dystrophin gene as indicated. The frequency of gene modification at day 3 or day 10 post-transfection was determined by the Surveyor assay. The ratio of measured Surveyor signal at day 3 and day 10 was calculated to quantify the stability of gene editing frequencies for each sgRNA in human cells. As quantified by the Surveyor assay 3 days post-transfection, 29/32 (~90%) of the sgRNAs tested were able to mediate highly efficient gene modification at the intended locus (Table 9, FIG. 17). The gene editing frequencies were stable for almost all of the sgRNAs (<25% signal change from day 3 to day 10, Table 9, FIG. 18), indicating that gene editing mediated by each individual sgRNA was well-tolerated. A notable exception is CR33, which had no detectable activity at day 10, although activity may be below the sensitivity of the Surveyor assay (est. ~1%).

TABLE 9

Measured activity of sgRNAs in human cells

| Target | sgRNA # | % modified alleles at day 3 | % modified alleles at day 10 | % change day 10/ day 3 |
|---|---|---|---|---|
| Multiplex deletion of exon 51 | | | | |
| Int 50 | CR1 | 6.6 | 9.3 | 41.8 |
| Int 50 | CR2 | 10.3 | 14.0 | 36.2 |
| Ex 51 | CR4 | 11.9 | 14.4 | 21.3 |
| Int 51 | CR5 | 12.4 | 13.3 | 7.8 |
| Multiplex deletion of exons 45-55 | | | | |
| Int 44 | CR6 | 16.1 | 16.9 | 4.3 |
| Int 44 | CR33 | 1.3 | <1 | n.d. |
| Int 44 | CR34 | 13.2 | 11.0 | −16.6 |
| Int 55 | CR7 | 6.8 | 7.1 | 5.3 |
| Int 55 | CR35 | 22.5 | 20.9 | −7.1 |
| Int 55 | CR36 | 26.4 | 24.7 | −6.4 |

TABLE 9-continued

| Measured activity of sgRNAs in human cells | | | | |
|---|---|---|---|---|
| Target | sgRNA # | % modified alleles at day 3 | % modified alleles at day 10 | % change day 10/ day 3 |
| Targeted frameshifts | | | | |
| Ex 45 | CR10 | 14.9 | 16.3 | 9.3 |
| Ex 45 | CR11 | <1 | <1 | n.d. |
| Ex 46 | CR12 | <1 | <1 | n.d. |
| Ex 46 | CR13 | 16.9 | 18.4 | 9.2 |
| Ex 47 | CR14 | 17.2 | 17.6 | 2.9 |
| Ex 47 | CR15 | 15.4 | 15.3 | −0.9 |
| Ex 48 | CR16 | 11.5 | 10.9 | −5.0 |
| Ex 48 | CR17 | <1 | <1 | n.d. |
| Ex 49 | CR18 | 1.8 | 2.2 | 20.1 |
| Ex 49 | CR19 | 33.7 | 38.4 | 13.9 |
| Ex 50 | CR20 | 14.9 | 13.7 | −7.6 |
| Ex 50 | CR21 | 24.1 | 20.8 | −13.5 |
| Ex 51 | CR3 | 13.0 | 16.7 | 28.0 |
| Ex 51 | CR31 | 18.9 | 16.9 | −10.2 |
| Ex 52 | CR22 | 25.9 | 20.3 | −21.6 |
| Ex 52 | CR23 | 25.2 | 24.0 | −4.8 |
| Ex 53 | CR24 | 24.8 | 23.6 | −4.6 |
| Ex 53 | CR25 | 2.6 | 2.9 | 9.5 |
| Ex 54 | CR26 | 24.5 | 22.0 | −10.1 |
| Ex 54 | CR27 | 13.4 | 12.6 | −5.9 |
| Ex 55 | CR28 | 21.6 | 19.8 | −8.4 |
| Ex 55 | CR29 | 19.2 | 19.6 | 2.2 |

Example 7

Figure 19A:
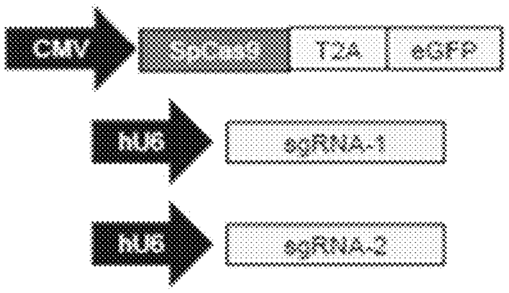
FIGS. 19A-19D show fluorescence-activated flow sorting to enrich genetically modified DMD myoblasts.
Figure 19B:
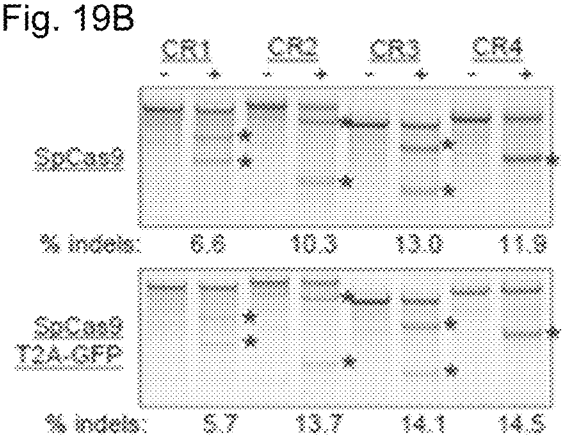
Figure 19C:
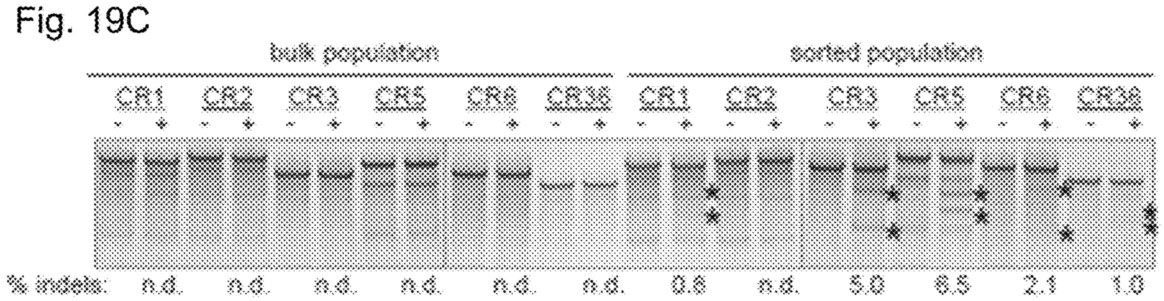
Figure 19D:
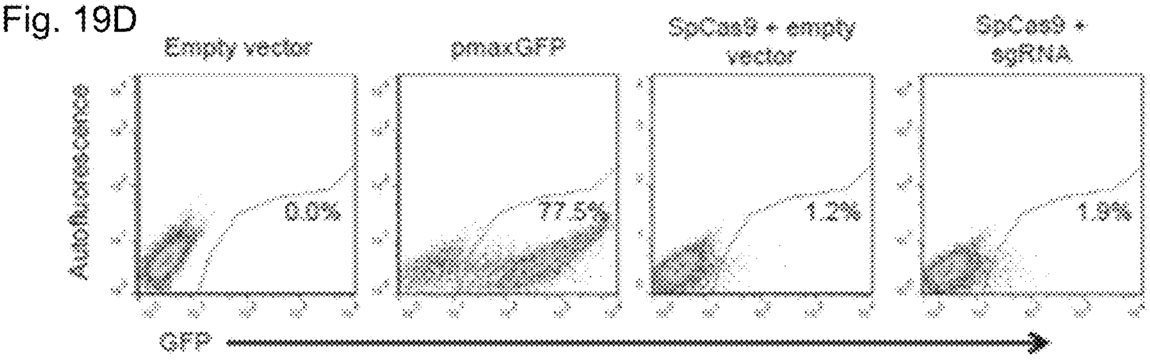

Enrichment of Gene-Edited Cells Using a Fluorescence-Based Reporter System sgRNAs were selected to correct specific mutations in DMD patient myoblast cell lines. After transfection into DMD myoblasts, unexpectedly low or undetectable gene modification activity was observed as measured by the Surveyor assay (FIG. 19C, bulk population). Flow cytometry was used to select for transfected cells co-expressing GFP through a 2A ribosomal skipping peptide linked to the SpCas9 protein (FIG. 19A). The addition of this fluorescent reporter to the SpCas9 expression vector did not seem to significantly impact gene editing activity in BEK293T cells (FIG. 19B). A low percentage of transfected myoblasts (~0.5-20%) expressed the fluorescent reporter at 3 days after electroporation, despite high transfection efficiencies of control GFP expression plasmids (typically >70%, FIG. 19D, pmaxGFP). Given the high levels of CRISPR/Cas9 activity in the easily transfected HEK293T line, inefficient transgene expression after electroporation of SpCas9-T2A-GFP and sgRNA constructs into the DMD cells may explain the low observed gene editing efficiencies in unsorted cells. After sorting the GFP-positive DMD myoblasts, a substantial increase was observed in detectable activity at most sgRNA target loci (FIG. 19C). Therefore, all subsequent experiments used cells sorted for SpCas9 expression by expression of this fluorescent reporter.

Example 8

Restoration of Dystrophin Expression by Targeted Frameshifts

Small insertions and deletions created by NHEJ DNA repair may be used to create targeted frameshifts to correct aberrant reading frames. A sgRNA, CR3, was designed to restore the dystrophin reading frame by introducing small insertions and deletions within exon 51 (FIGS. 16B, 20A). The types of insertions and deletions generated by CRISPR/Cas9 at this locus were assessed by Sanger sequencing of alleles from the genomic DNA of HEK293T cells co-transfected with expression plasmids for SpCas9 and the CR3 sgRNA (FIG. 20B). Notably, the insertions and deletions resulted in conversion to all three reading frames (FIGS. 20B, 20C). To demonstrate genetic correction in a relevant patient cell line, expression plasmids for SpCas9 and the CR3 sgRNA were electroporated into a DMD myoblast line with a deletion of exons 48-50 that is correctable by creating frameshifts in exon 51. The treated cells were sorted, verified to have gene modification activity by the Surveyor assay (CR3, FIG. 19C sorted population), and differentiated into myotubes to test for restored dystrophin expression. Expression of dystrophin protein was observed concomitant with the detectable nuclease activity (FIG. 20D). The *S. pyogenes* CRISPR/Cas9 system presents a powerful method to quickly generate targeted frameshifts to address a variety of patient mutations and restore expression of the human dystrophin gene.

Example 9

Figure 21A:
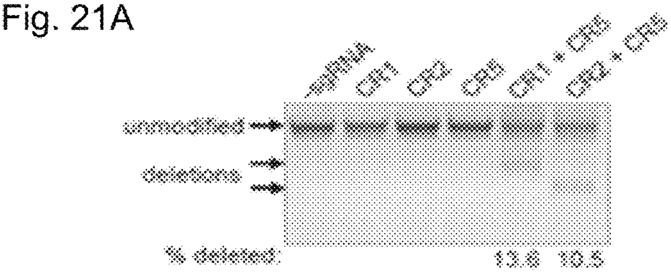
FIGS. 21A-21D show deletion of exon 51 from the human genome using multiplex CRISPR/Cas9 gene editing.
Figure 21B:
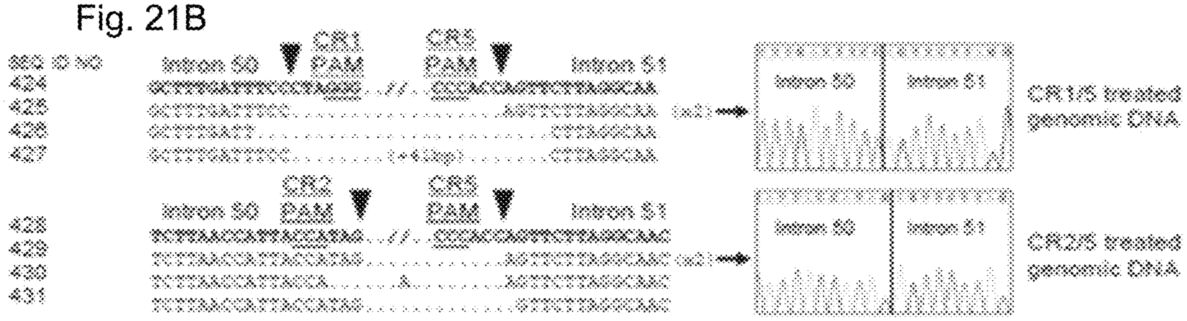
Figure 21C:
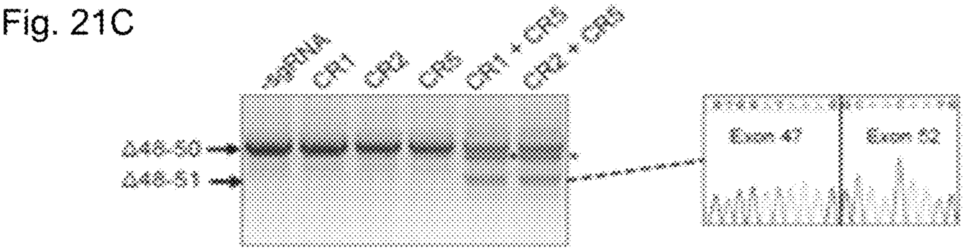
Figure 21D:

Multiplex CRISPR/Cas9 Gene Editing Mediates Genomic Deletion of Exon 51 and Rescues Dystrophin Protein Expression The multiplexing capability of the CRISPR/Cas9 system presents a novel method to efficiently generate genomic deletions of specific exons for targeted gene correction. DMD patient myoblasts with background deletions correctable by exon 51 skipping were treated with two combinations of sgRNAs flanking exon 51 (CR1/CR5 or CR2/CR5) and sorted to enrich for gene-edited cells as in FIGS. 19A-19D. As detected by end-point PCR of the genomic DNA from these treated cells, the expected genomic deletions were only present when both sgRNAs were electroporated into the cells with SpCas9 (FIG. 21A). Sanger sequencing confirmed the expected junction of the distal chromosomal segments (FIG. 21B) for both deletions. After differentiating the sorted myoblasts, a deletion of exon 51 from the mRNA transcript was detected only in the cells treated with both sgRNAs (FIG. 21C). Finally, restored dystrophin protein expression was detected in the treated cells concomitant with observed genome- and mRNA-level deletions of exon 51 (FIG. 21D).

Example 10

Dystrophin Rescue by a Multi-Exon Large Genomic Deletion

Although addressing patient-specific mutations is a powerful use of the CRISPR/Cas9 system, it would be advantageous to develop a single method that can address a myriad of common patient deletions. For example, a promising strategy is to exclude the entire exon 45-55 region as a method to correct up to 62% of known patient deletions. Multiplex CRISPR/Cas9-based gene editing was tested to determine if it may be able to generate efficient deletion of the exon 45-55 locus in human cells. After transfection into HEK293T cells, the expected deletion of ~336,000 bp was detected by PCR of the genomic DNA (FIG. 22A). Similarly, this deletion was detected by PCR of the genomic DNA from SpCas9/sgRNA-treated DMD patient cells harboring a background deletion of exons 48-50 of unknown length (FIG. 22A). Sanger sequencing of this deletion band from the genomic DNA of treated DMD cells revealed the expected junctions of intron 44 and intron 55 immediately adjacent to the sgRNA target sites (FIG. 22B). After differentiation of treated DMD cells, the expected deletion of exons 45-55 was detected in the dystrophin mRNA transcript and verified to be a fusion of exons 44 and 56 by Sanger sequencing (FIG. 22C). Restored protein expression was observed by western blot in the sorted cell populations containing the CRISPR/Cas9-induced deletion of exons 45-55 from the genome and resulting mRNA transcripts (FIG. 22D). These data demonstrate that multiplex CRISPR/Cas9 editing presents a single universal method to restore the dystrophin reading frame in more than 60% of DMD patient mutations.

Example 11

Transplantation of Corrected Myoblasts into Immunodeficient Mice

Figure 24:
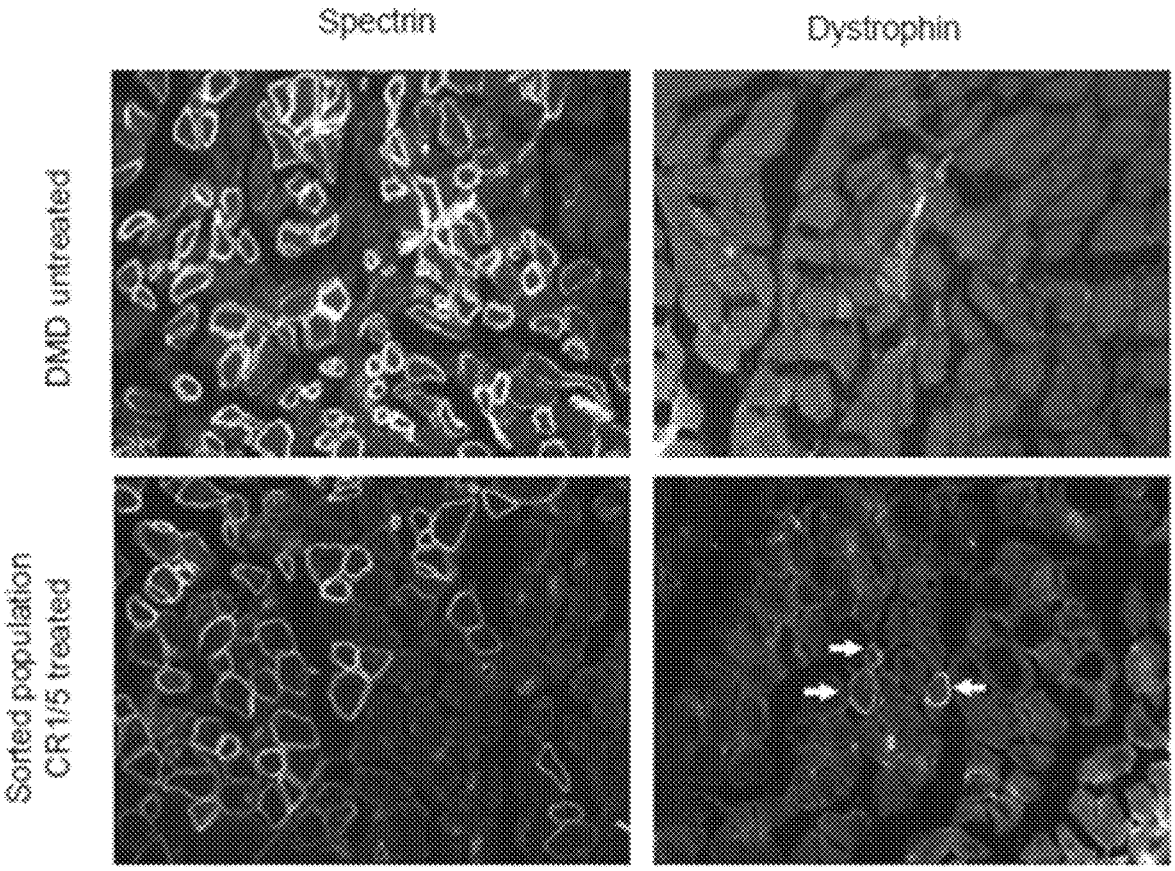
FIG. 24 shows expression of restored human dystrophin in vivo following transplantation of CRISPR/Cas9-treated human DMD myoblasts into immunodeficient mice. Human Δ48-50 DMD myoblasts were treated with SpCas9, CR1, and CR5 to delete exon 51 and sorted for GFP expression as shown in FIG. 19. These sorted cells and untreated control cells were injected into the hind limbs of immunodeficient mice and assessed for human-specific protein expression in muscle fibers after 4 weeks post-transplantation. Cryosections were stained with anti-human spectrin, which is expressed by both uncorrected and corrected myoblasts that have fused into mouse myofibers, or anti-human dystrophin antibodies as indicated. White arrows indicate muscle fibers positive for human dystrophin.
Figure 25A:
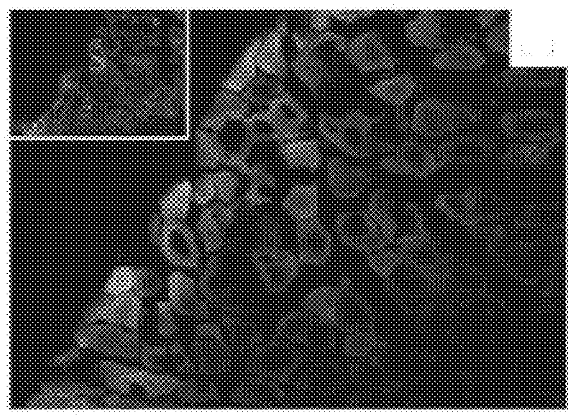
FIGS. 25A-25F show additional immunofluorescence images probing human dystrophin expression. Serial sections from regions stained with anti-human spectrin are shown inset in top left.
Figure 25B:
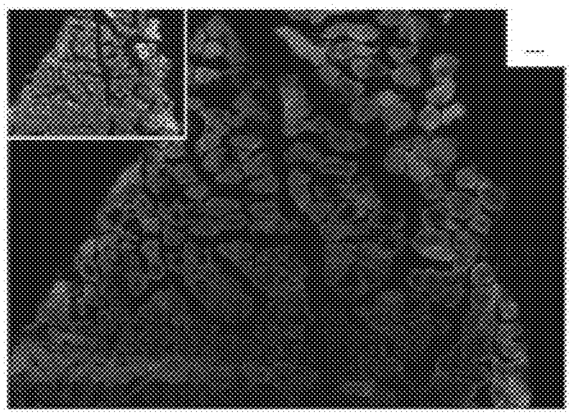
Figure 25C:
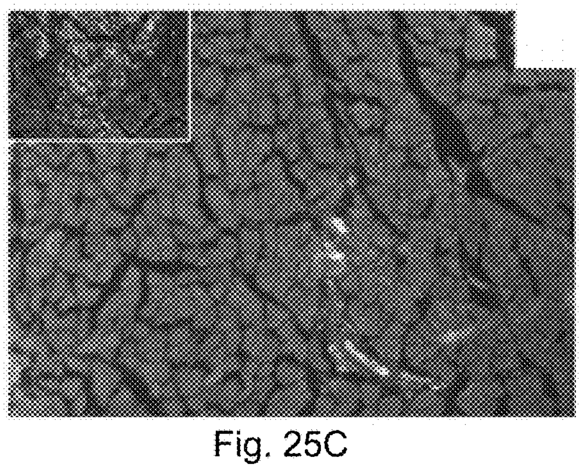
Figure 25D:
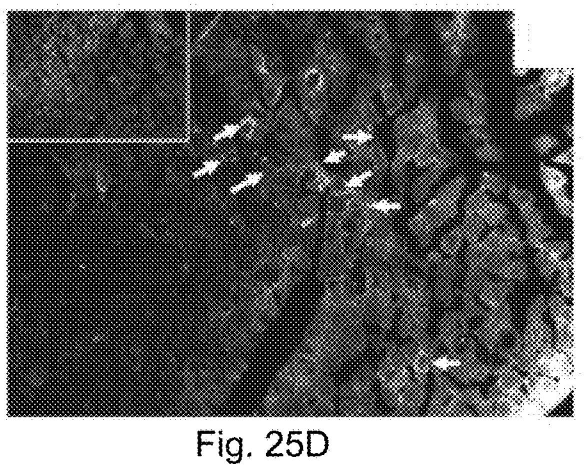
Figure 25E:
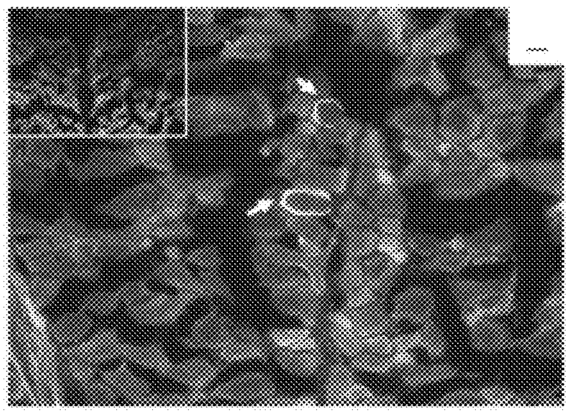
Figure 25F:
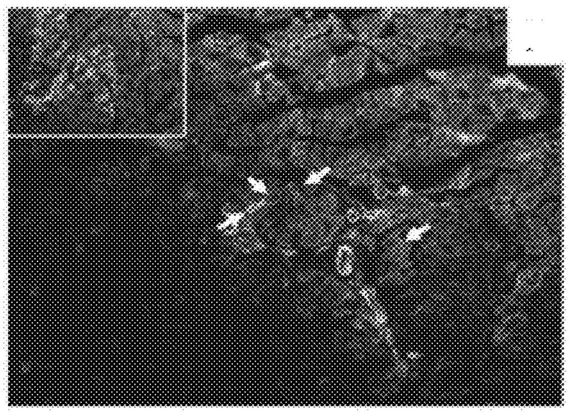

A promising method for DMD therapy is to correct a population of autologous patient muscle progenitor cells that can be engrafted into the patient's skeletal muscle tissue to rescue dystrophin expression. To demonstrate the ability of the corrected cells to express human dystrophin in vivo, a population of DMD myoblasts that were treated with sgRNAs CR1 and CR5, which flank exon 51, was transplanted and sorted for expression of GFP as before (FIGS. 19A-19D, FIG. 23). After 4 weeks, muscle fibers positive for human spectrin, which is expressed by both corrected and uncorrected cells, were detected in cryosections of injected muscle tissue (FIG. 24). A number of these fibers were also positive for human dystrophin with expression localized to the sarcolemma, demonstrating functional gene correction in these cells (FIG. 24, FIGS. 25A-25F). No fibers positive for human dystrophin were observed in sections from mice injected with the untreated DMD myoblasts (FIG. 24, FIGS. 25A-25F), indicating that the CRISPR/Cas9-modified cells were the source of human dystrophin expression.

Example 12

Off-Target and Cytotoxicity Analysis

Figures 26A, 26B, 26C, 26D:
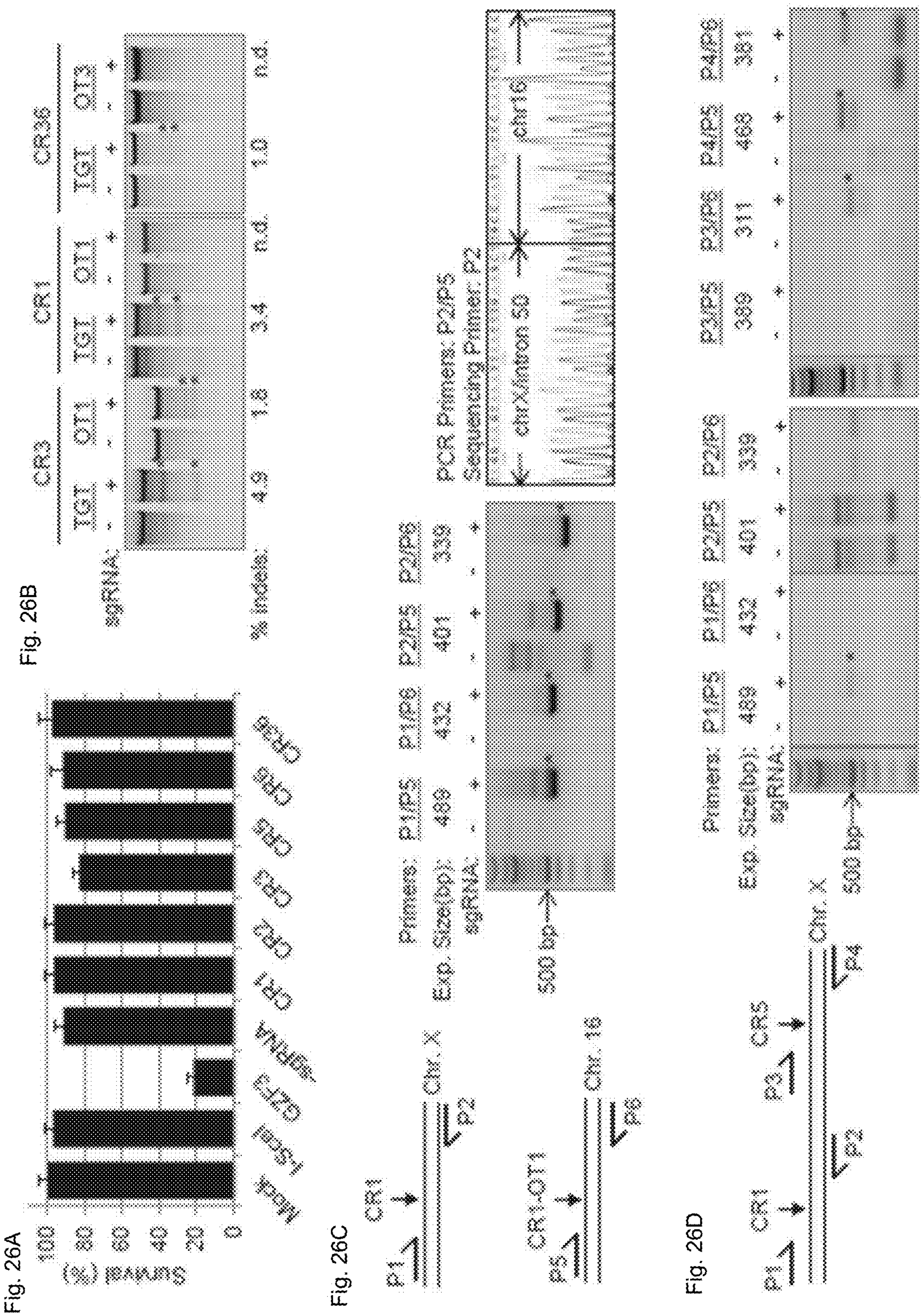
FIGS. 26A-26D show evaluation of CRISPR/Cas9 toxicity and off-target effects for CR1/CR5-mediated deletion of exon 51 in human cells.
Figure 27:
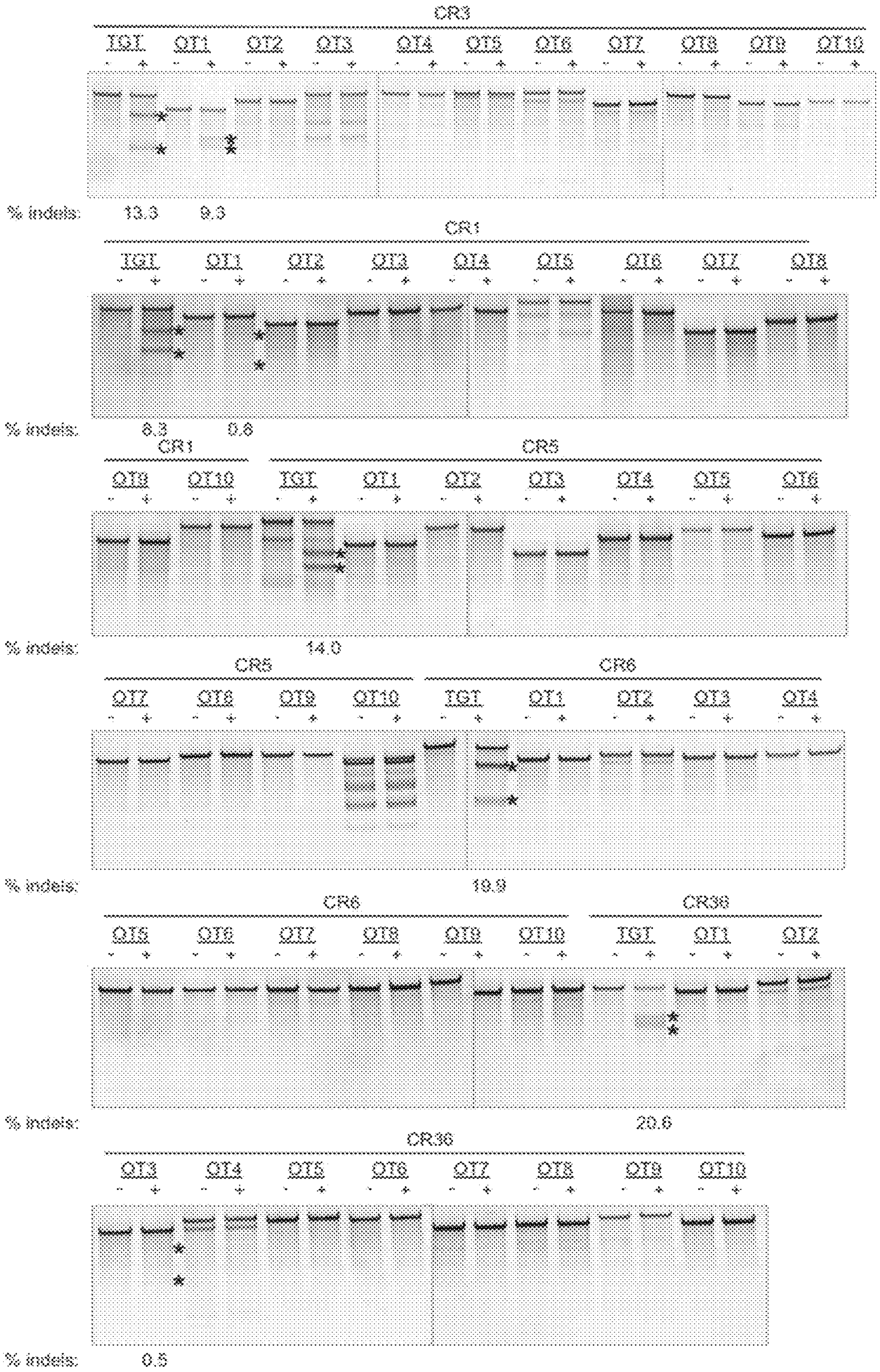
FIG. 27 shows images of TBE-PAGE gels used to quantify Surveyor assay results to measure on-target and off-target gene modification in Table 4. Asterisks mark expected sizes of bands indicative of nuclease activity.

The relative cytotoxicity of the CRISPR/Cas9 system was assessed in human cells for select sgRNAs by adapting a flow cytometry-based GFP retention assay as previously described (Ousterout et al., Mol Ther 21:1718-1726 (2013)). Minimal cytotoxicity was observed for SpCas9 co-expressed with or without sgRNAs after transfection into human cells (FIG. 26A). Publicly available tools are available to assess and prioritize potential CRISPR/Cas9 activity at off-target loci based on predicted positional bias of a given mismatch in the sgRNA protospacer sequence and the total number of mismatches to the intended target site (Hsu et al., Nat Biotechnol 31:827-826 (2013)). This public webserver was used to predict the most likely off-target sites for the sgRNAs used to correct the dystrophin gene in this study (Table 4). The top ten potential off-target sites were assessed by the Surveyor assay in HEK293T cells treated with SpCas9 and individual sgRNA expression cassettes for CR1, CR3, CR5, CR6, or CR36. CR1, CR3 and CR36 each had one of these ten predicted off-target loci demonstrate significant levels of gene modification (Table 4 and FIG. 27). Interestingly, the CR3 off-target sequence had substantial homology and similar modification frequencies to the intended on-target (9.3% at OT-1 vs. 13.3% at intended site (Table 4 and FIG. 27). Notably, CR3-OT1 was the only one of these three off-target sites to show significant levels of activity in the sorted hDMD cells by the Surveyor assay (FIG. 26B).

Figure 28A:
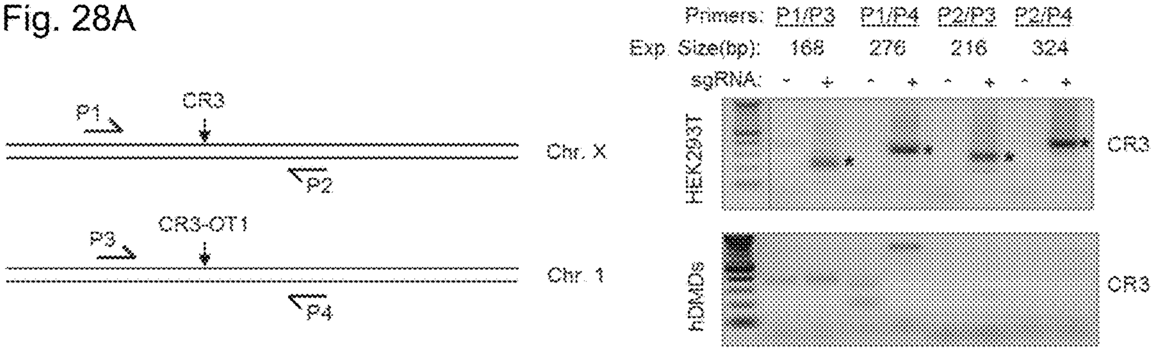
FIGS. 28A-28C show end-point nested PCR to detect chromosomal translocations caused by CRISPR/Cas9 off-target activity for CR3 and CR6/CR36 in human cells. Nested end-point PCR analysis was used to detect translocations in HEK293T or sorted hDMD cells treated with Cas9 and CR3 as indicated (FIG. 28A), HEK293T cells treated with Cas9 and CR36 alone (FIG. 28B), or sorted hDMD cells treated with Cas9, CR6, and CR36 expression cassettes (FIG. 28C). The second nested PCR reaction for translocation was amplified using custom primers for each predicted translocation locus to maximize specificity (See Table 4). The schematic depicts the relative location of nested primer pairs used to probe for the presence of translocations. Each possible translocation event was first amplified from genomic DNA isolated from cells treated with or without the indicated sgRNA(s). A second nested PCR reaction was performed using primers within the predicted PCR amplicons that would result from translocations. Expected size was estimated based on the indicated primer binding site and the predicted sgRNA cut site at each locus. * indicates bands detected at the expected size and verified by Sanger sequencing from each end. # indicates amplicons in which Sanger sequencing showed sequences other than the predicted translocation, likely a result of mispriming during the nested PCR.
Figure 28B:
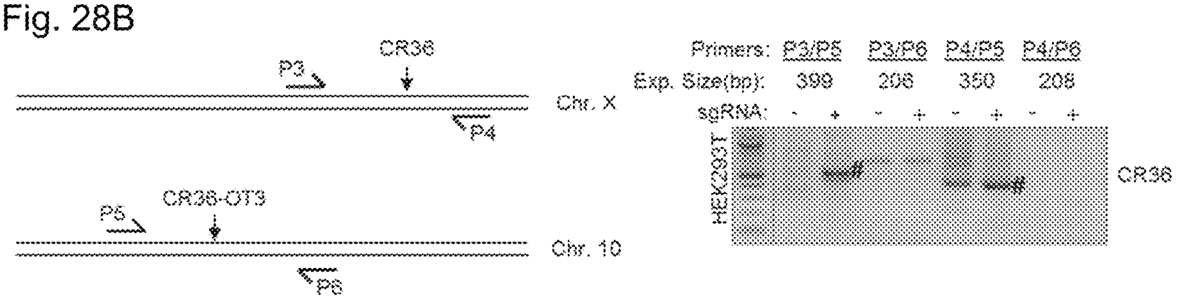
Figure 28C:
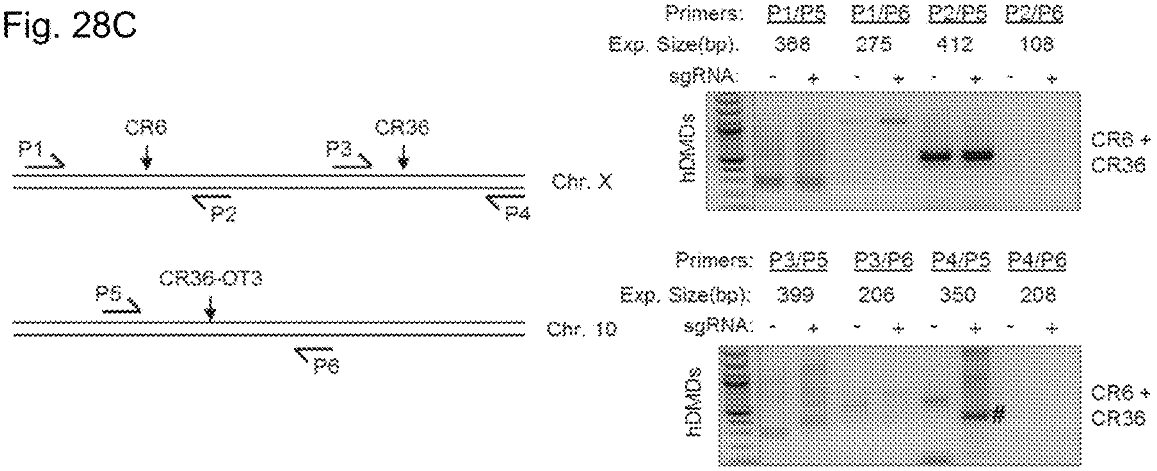
Figure 29:
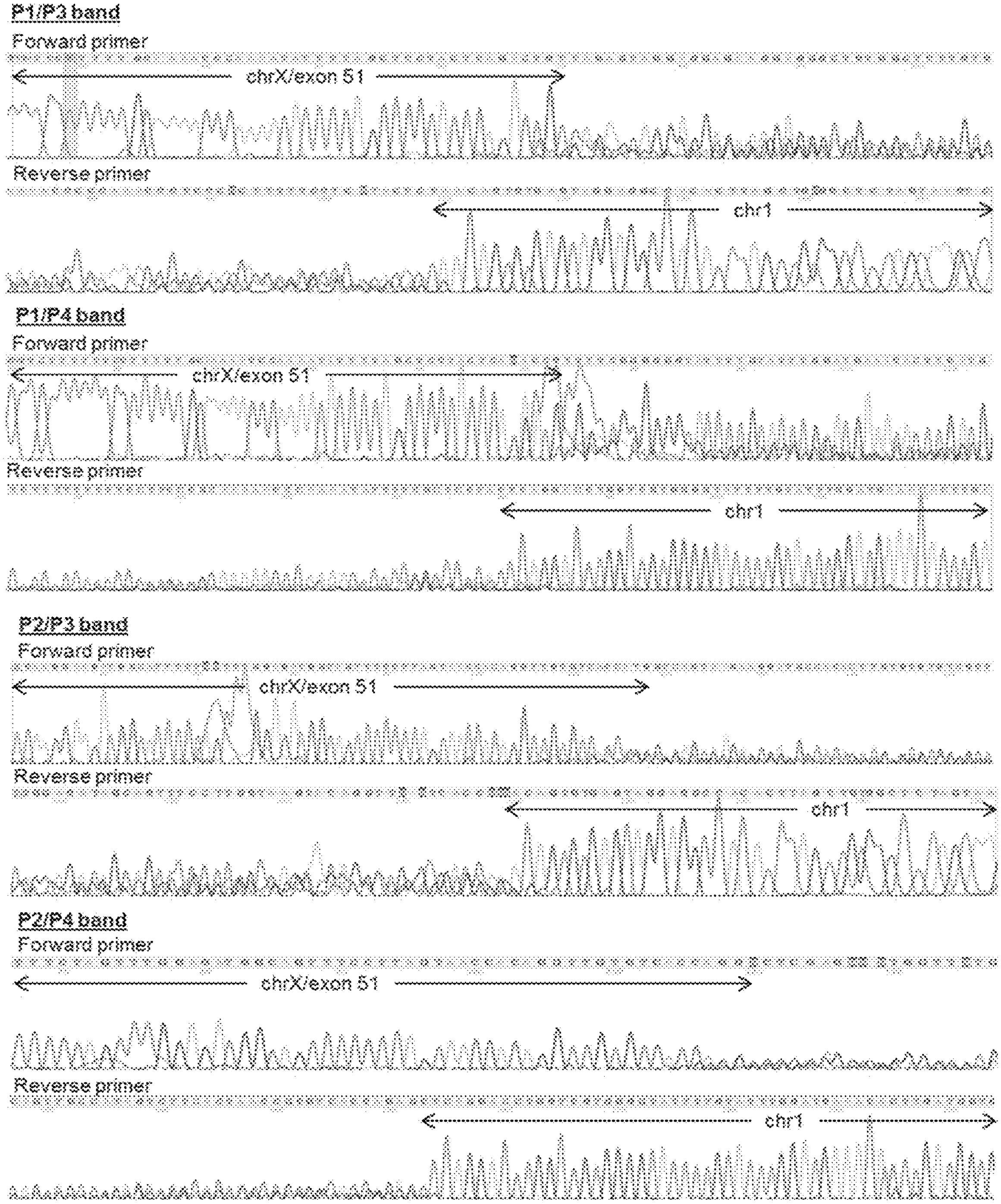
FIG. 29 shows Sanger sequencing chromatograms (SEQ ID NOS: 647-654, respectively, in order of appearance) for bands detected in FIGS. 28A-28C resulting from translocations between CR3 and CR3-OT1, on chromosomes X and 1, respectively, in HEK293T cells treated with Cas9 and CR3 gene cassettes. Arrows show regions of homology to the indicated chromosome nearby the expected break points caused by the appropriate sgRNAs. Note that sequencing reads become out of phase near the break point due to the error-prone nature of DNA repair by non-homologous end-joining.
Figure 30:
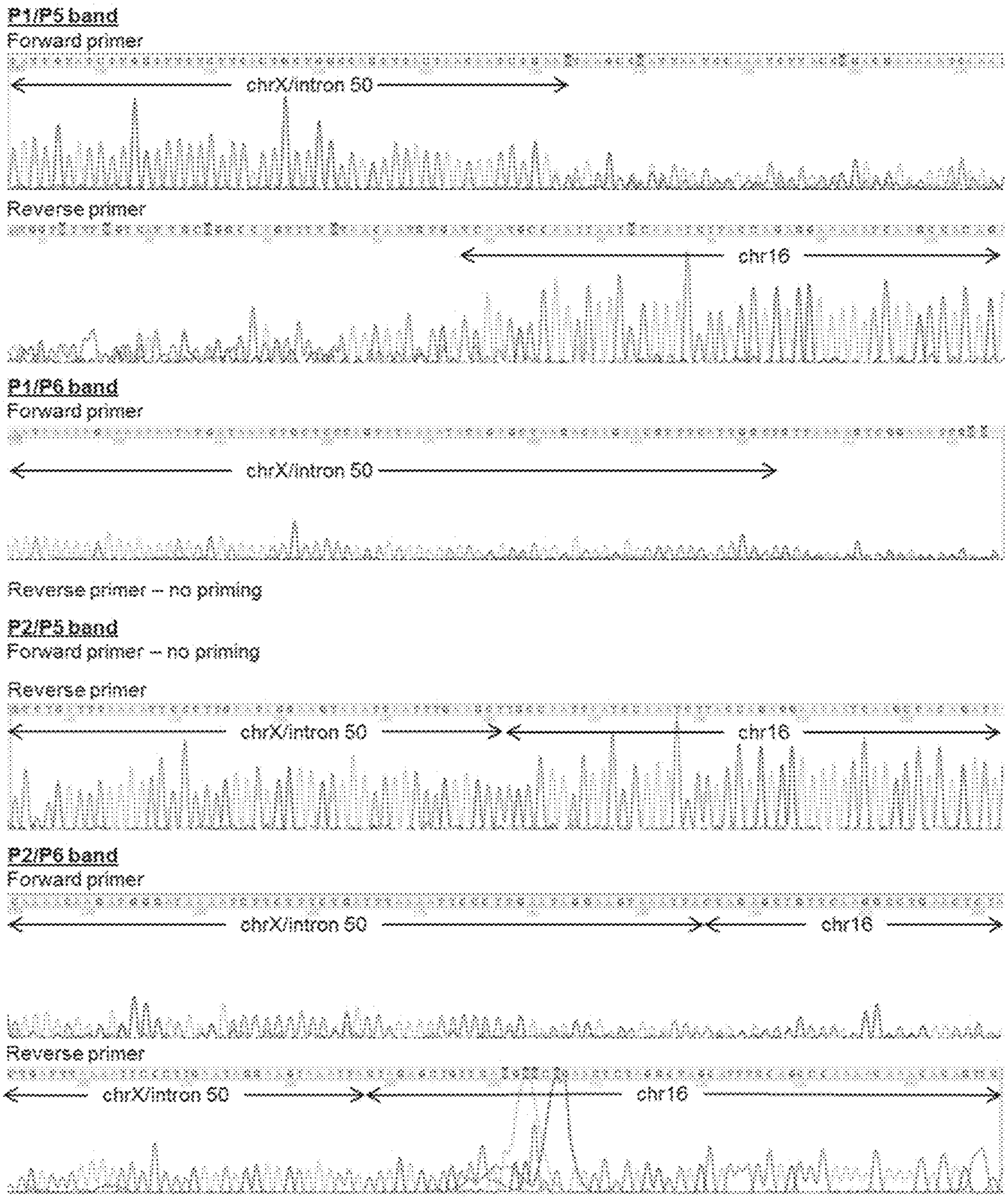
FIG. 30 shows Sanger sequencing chromatograms (SEQ ID NOS: 655-660, respectively, in order of appearance) for bands detected in FIG. 26C resulting from translocations between CR1 and CR1-OT1, on chromosomes X and 16, respectively, in HEK293T cells treated with Cas9 and CR1 gene cassettes. Arrows show regions of homology to the indicated chromosome nearby the expected break points caused by the appropriate sgRNAs. Note that sequencing reads become out of phase near the break point due to the error-prone nature of DNA repair by non-homologous end-joining.

Nuclease activity at off-target sites may cause unintended chromosomal rearrangements by distal re-ligation between cleaved target and off-target loci on distinct chromosomes. This presents a significant concern for deletion-based gene correction strategies due to the increased potential for off-target activity by using two or more nucleases, such as in multiplex CRISPR/Cas9 gene editing. Potential translocations were probed for using a highly sensitive nested genomic PCR assay to detect translocations at the validated off-target loci (Table 4) during both single and multiplex CRISPR/Cas9 editing strategies. Using this assay, translocations were readily detected between on-target and off-target sites in the model HEK293T cell line that also shows high levels of off-target activity (FIG. 26C and FIG. 28A, 28B). Sanger sequencing of the PCR amplicons confirmed the identity of the predicted translocation event for each primer pair (FIGS. 29-30). A subset of the translocations detected in the HEK293T cells were also detectable by nested PCR in the sorted hDMD myoblasts, although the signal was considerably weaker and the sequence identity was not confirmed due to low yield of product (FIG. 26D and FIGS. 28A, 28C). Translocations were not detected using this assay in HEK293T or sorted hDMD cells treated with CR6 or CR6/CR36, respectively, (FIGS. 28A-28C) that had low levels of off-target activity at CR6-OT3 only in HEK293T cells (Table 4). These results underscore the importance of selecting highly specific sgRNAs, particularly for multiplex editing applications, and show that this approach can benefit from ongoing efforts to improve the specificity of the CRISPR/Cas9 system. These data suggest that the selected sgRNAs are able to correct the dystrophin gene without significant toxicity and with only a single strongly predicted off-target site with detectable levels of activity.

Example 13

Discussion

Genome editing is a powerful tool for correcting genetic disease and the recent development of the CRISPR/Cas9 system is dramatically accelerating progress in this area. The correction of DMD, the most common genetic disease that also currently has no approved therapeutic options, was demonstrated. Many gene- and cell-based therapies for DMD are in preclinical development and clinical trials, and genome editing methods are compatible with many of these approaches. For example, genome editing may be combined with patient-specific cell-based therapies for DMD. The CRISPR/Cas9 system may function in human pluripotent stem cells and other human cell lines, as well as human skeletal myoblasts, as shown. Importantly, gene editing with CRISPR/Cas9 did not abolish the myogenic capacity of these cells, as demonstrated by efficient dystrophin expression in vitro and in vivo after transplantation into immunodeficient mice. Thus, this strategy should be compatible with cell-based therapies for DMD.

Additionally, an enriched pool of gene-corrected cells demonstrated expression of human dystrophin in vivo following engraftment into immunodeficient mice. CRISPR/Cas9 gene editing did not have significant toxic effects in human myoblasts as observed by stable gene editing frequencies and minimal cytotoxicity of several sgRNAs. However, gene editing activity was confirmed at three out of 50 predicted off-target sites across five sgRNAs and CRISPR/Cas9-induced chromosomal translocations between on-target and off-target sites were detectable. The CRISPR/Cas9 technology is an efficient and versatile method for correcting a significant fraction of dystrophin mutations and can serve as a general platform for treating genetic disease.

Additionally, direct transfection of the sgRNA and Cas9 mRNA, in contrast to the plasmid-based delivery method used here, may be used to increase specificity and safety by reducing the duration of Cas9 expression and eliminating the possibility of random plasmid integration. Alternatively, delivery of the CRISPR/Cas9 system directly to skeletal and/or cardiac muscle by viral, plasmid, or RNA delivery vectors may be used for in vivo genome editing and translation of this approach. The large size of *S. pyogenes* Cas9 gene (~4.2 kilobases) presents a challenge to its use in size-restricted adeno-associated viral vectors. However, Cas9 genes from other species, such as *N. meningitidis* and *S. thermophilus*, are short enough to efficiently package both Cas9 and sgRNA expression cassettes into single AAV vectors for in vivo gene editing applications.

The CRISPR/Cas9 system enabled efficient modification of nearly 90% of tested targets, consistent with other reports of robust activity of this system at diverse loci. The robustness and versatility of this technology is a significant advancement towards at-will creation of patient-specific gene editing. Low levels of dystrophin, including as little as 4% of wild-type expression, may be sufficient to improve survival, motor function, and cardiac function in a mouse model. The levels of CRISPR/Cas9 activity may be sufficient for therapeutic benefit.

The use of multiplexing with CRISPR/Cas9 to delete exons also presents a unique set of opportunities and challenges. The deletion of complete exons from the genome to restore dystrophin expression was performed, in contrast to restoring the reading frame of the dystrophin gene with small indels generated by NHEJ-based DNA repair following the action of a single nuclease. The protein product of the edited gene is predictable and already characterized in Becker muscular dystrophy patients with the naturally occurring deletion, in contrast to the random indels created by intraexonic action of a single nuclease that will lead to the creation of novel epitopes from each DNA repair event. Furthermore, the product resulting from the exon deletions will lead to restored dystrophin for every successful gene editing event, whereas modifying the gene with random indels within exons will only restore the reading frame in the one-third of editing events that leads to the correct reading frame.

All of the sgRNAs tested were not associated with significant cytotoxic effects in human cells. Three potential off-target sites out of 50 total tested sites for the five sgRNAs used were identified to restore dystrophin expression. Furthermore, chromosomal translocations between the intended on-target sites and these off-target sites were detectable by highly sensitive nested PCR assays in HEK293T cells expressing high levels of Cas9 and sgRNAs. Notably, the off-target activity and translocations identified in HEK293T cells, which is an immortalized and aneuploid cell line that expresses very high levels of Cas9 and sgRNA, did not occur at as high a level and in some cases were undetectable in the hDMD myoblasts. Importantly, this level of specificity may be tolerable given the severity of DMD, the lack of an apparent cytotoxic effect in human cells Example 14

An engineered AAV capsid, termed SASTG (FIG. 34; SEQ ID NOs: 436 and 437), was developed for enhanced cardiac and skeletal muscle tissue tropism (Piacentino et al. (2012) *Human Gene Therapy* 23:635-646). A ZFN targeting the Rosa26 locus ("Rosa26 ZFN"; FIG. 33; SEQ ID NO: 434 and 435) was shown to be highly active in mouse cells (Perez-Pinera et al. Nucleic Acids Research (2012) 40:3741-3752). AAV-SASTG vectors encoding the Rosa26 ZFN protein were designed and subsequently generated and purified by the UNC Viral Vector Core. The Surveyor assay (Guschin et al., *Methods Mol Biol* 649, 247-256 (2010)) was used to demonstrate NHEJ mutagenesis at the Rosa26 locus following delivery of AAV-SASTG Rosa26 ZFNs in cultured C2C12 myoblasts that were actively cycling or forced into differentiation by serum removal (not shown).

Figure 31:
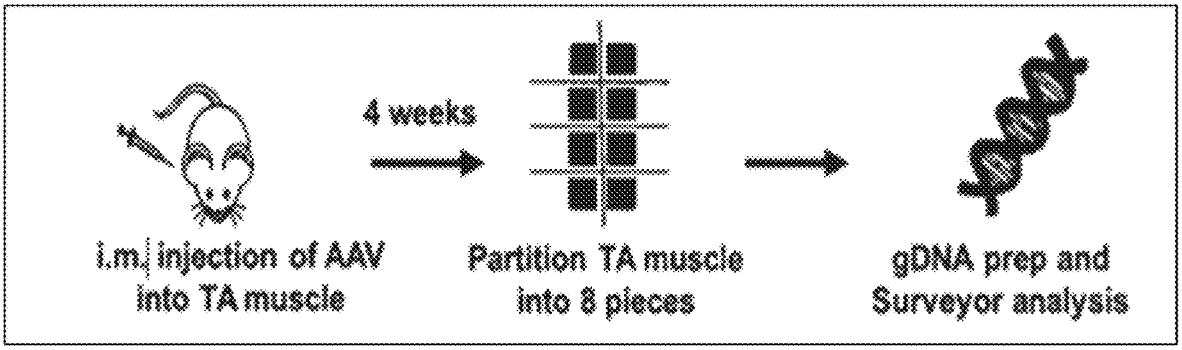
FIG. 31 shows an overview of in vivo AAV injections and tissue harvest.
Figures 32A, 32B, 32C:
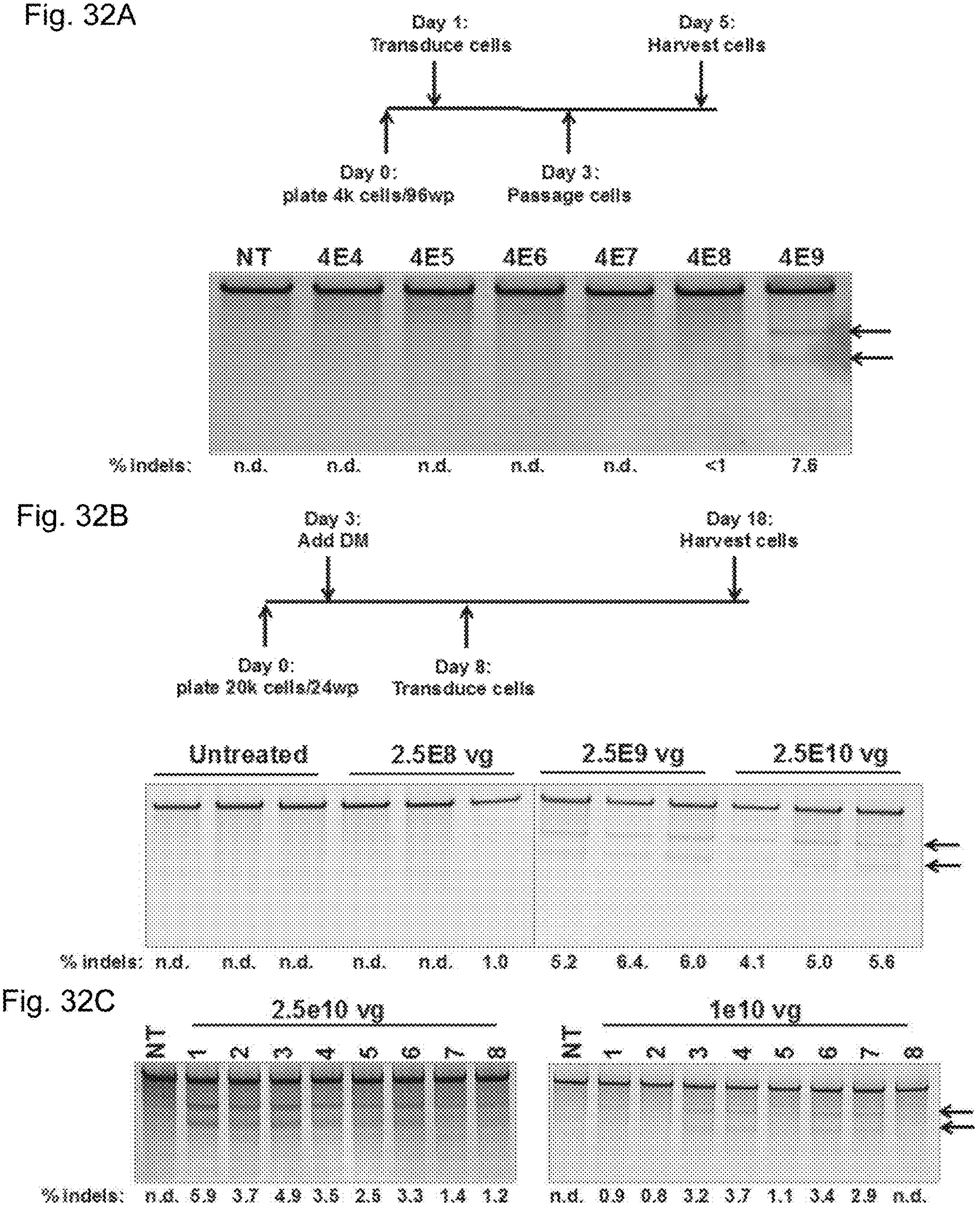
FIGS. 32A-32C show Surveyor analysis of Rosa26 ZFN activities in skeletal muscle in vitro and in vivo following delivery of AAV-SASTG-ROSA. Arrows indicate expected bands resulting from Surveyor cleavage. n.d.: not detected.

To verify that adult post-mitotic skeletal muscle were efficiently targeted by the Rosa26 ZFN following AAV transfer, AAV-SASTG vectors encoding the Rosa26 ZFN were injected directly into the tibialis anterior (TA) muscle of 6 week old C57BL6/J mice at titers of 1e10 vector genomes (vg) or 2.5e10 vg per muscle. Mice were sacrificed 4 weeks after injection and the TA muscles were harvested and partitioned into several fragments for genomic DNA extraction and analysis (FIG. 31). Genomic DNA was PCR amplified and subjected to the Surveyor assay to detect NHEJ mutations characteristic of ZFN mutagenesis at the Rosa26 target site (FIGS. 32A-32C). FIGS. 32A-32C show Surveyor analysis of Rosa26 ZFN activities in skeletal muscle in vitro and in vivo following delivery of AAV-SASTG-ROSA. Proliferating C2C12s were transduced with the indicated amount of virus and harvested at 4 days post-infection (FIG. 32A). C2C12s were incubated in differentiation medium for 5 days and then transduced with the indicated amount of AAV-SASTG-ROSA virus in 24 well plates (FIG. 32B). Samples were collected at 10 days post-transduction. The indicated amount of AAV-SASTG-ROSA was injected directly into the tibialis anterior of C57BL/6J mice and muscles were harvested 4 weeks post-infection. The harvested TA muscles were partitioned into 8 separate pieces for genomic DNA analysis, each shown in a separate lane (FIG. 32C). Notably, high levels of gene modification were detected in all fragments at the highest dose (2.5e10 vg).

Example 15

AAV-CRISPR Constructs for Targeting Mutant Dystrophin Genes

AAV constructs are designed to therapeutically correct mutations of the dystrophin gene that cause Duchenne muscular dystrophy and skeletal and cardiac muscle degeneration. CRISPR/Cas9 systems can be delivered using the AAV to restore the dystrophin reading frame by deleting exon 51, deleting exons 45-55, disrupting splice donor or acceptor sites, or creating frameshifts within exon 51 (Ousterout et al., Molecular Therapy 2013) to restore the dystrophin reading frame and protein expression. The CRISPR/Cas9 system will include a Cas9 having a sequence of SEQ ID NO: 64 or 114 (See FIGS. 40 and 41). gRNAs that could be combined with these Cas9s, targeting their respective PAM sequences, are provided (see FIGS. 40 and 41; see also Tables 2 and 3).

Example 16

Generation of Induced Neurons (iNs)

The generation of induced neurons (iNs) from other cell lineages has potential applications in regenerative medicine and the study of neurological diseases. The direct conversion of mouse embryonic fibroblasts (MEFs) to functional neuronal cells may occur through the delivery of a cocktail of three neuronal transcription factors—BRN2, ASCL1, and MYTL (BAM factors, FIG. 48). Other methods may include additional factors to induce various neuronal subtypes. These experiments require transcription factors to be delivered ectopically, and the activation of the corresponding endogenous loci to sustain the neuronal phenotype. The CRISPR/Cas9 system was engineered as a versatile transcription factor to activate endogenous genes in mammalian cells with the capacity to target any promoter in the genome through an RNA-guided mechanism (FIGS. 49A,49B).

Materials & Methods.

The CRISPR/Cas9-transcription factor was used to activate the endogenous genes encoding ASCL1 and BRN2 to directly reprogram MEFs to functional induced neurons.

Cell Culture:

MEFs were seeded in either 24-well TCPS plates or on poly-D-lysine/laminin-coated coverslips. Following transduction of dCas9-VP64 and transfection of the gRNAs (see Tables 10 and 11 for sequences of gRNAs), the cells were cultured in MEF medium (Adler et al. Mol Ther Nucleic Acids 1:e32 (2012)) for 24 hrs and then transferred to N3 neural induction medium (Vierbuchen et al. *Nature* 463: 1035-1041 (2010)) for the duration of the experiment (FIG. 49B).

TABLE 10 gRNAs for mouse ASCL1 (CR13):

| Oligo (5' to 3') | 5' overhang | | ASCL1 Target Sequence | | SEQ ID NO |
|---|---|---|---|---|---|
| CR13-1_S: | cacc | G | CAGCCGCTCGCTGCAGCAG (SEQ ID NO: 468) | | 492 |
| CR13-1_AS: | AAAC | | CTGCTGCAGCGAGCGGCTG (SEQ ID NO: 469) | C | 493 |
| CR13-2_S: | cacc | G | GCTGGGTGTCCCATTGAAA (SEQ ID NO: 470) | | 494 |
| CR13-2_A5: | AAAC | | TTTCAATGGGACACCCAGC (SEQ ID NO: 471) | C | 495 |
| CR13-3_S: | cacc | G | GTTTATTCAGCCGGGAGTC (SEQ ID NO: 472) | | 496 |
| CR13-3_AS: | AAAC | | GACTCCCGGCTGAATAAAC (SEQ ID NO: 473) | C | 497 |
| CR13-4_S: | cacc | G | TGGAGAGTTTGCAAGGAGC (SEQ ID NO: 474) | | 498 |
| CR13-4_AS: | AAAC | | GCTCCTTGCAAACTCTCCA (SEQ ID NO: 475) | C | 499 |
| CR13-5_S: | cacc | G | CCCTCCAGACTTTCCACCT (SEQ ID NO: 476) | | 500 |
| CR13-5_AS: | AAAC | | AGGTGGAAAGTCTGGAGGG (SEQ ID NO: 477) | C | 501 |
| CR13-6_S: | cacc | G | AATTTTCTTCCAAGTTCTC (SEQ ID NO: 478) | | 502 |
| CR13-6_AS: | AAAC | | GAGAACTTGGAAGAAAATT (SEQ ID NO: 479) | C | 503 |
| CR13-7_S: | cacc | G | CTGCGGAGAGAAGAAAGGG (SEQ ID NO: 480) | | 504 |
| CR13-7_AS: | AAAC | | CCCTTTCTTCTCTCCGCAG (SEQ ID NO: 481) | C | 505 |
| CR13-8_S: | cacc | G | AGAGCCACCCCCTGGCTCC (SEQ ID NO: 482) | | 506 |
| CR13-8_AS: | AAAC | | GGAGCCAGGGGGTGGCTCT (SEQ ID NO: 483) | C | 507 |
| CR13-9_S: | cacc | G | cgaagccaaccgcggcggg (SEQ ID NO: 484) | | 508 |
| CR13-9_AS: | AAAC | | cccgccgcggttggcttcg (SEQ ID NO: 485) | C | 509 |
| CR13-10_S: | cacc | G | agagggaagacgatcgccc (SEQ ID NO: 486) | | 510 |
| CR13-10_AS: | AAAC | | gggcgatcgtcttccctct (SEQ ID NO: 487) | C | 511 |
| CR13-11_S: | cacc | G | cccctttaactttcctccg (SEQ ID NO: 488) | | 512 |
| CR13-11_AS: | AAAC | | cggaggaaagttaaagggg (SEQ ID NO: 489) | C | 513 |
| CR13-12_S: | cacc | G | gcagccccgcttccttcaa (SEQ ID NO: 490) | | 514 |
| CR13-12_AS: | AAAC | | ttgaaggaagcggggctgc (SEQ ID NO: 491) | C | 515 |

TABLE 11

| gRNAs for mouse BRN2 (CR16): | | | | | |
|---|---|---|---|---|---|
| Oligo (5' to 3') | 5' overhang | | ASCL1 Target Sequence | | SEQ ID NO |
| CR16-1_S: | cacc | G | CGAGAGCGAGAGGAGGGAG (SEQ ID NO: 516) | | 540 |
| CR16-1_AS: | AAAC | | CTCCCTCCTCTCGCTCTCG (SEQ ID NO: 517) | C | 541 |
| CR16-2_S: | cacc | G | GAGAGAGCTTGAGAGCGCG (SEQ ID NO: 518) | | 542 |
| CR16-2_AS: | AAAC | | CGCGCTCTCAAGCTCTCTC (SEQ ID NO: 519) | C | 543 |
| CR16-3_S: | cacc | G | GGTGGAGGGGGCGGGGCCC (SEQ ID NO: 520) | | 544 |
| CR16-3_AS: | AAAC | | GGGCCCCGCCCCCTCCACC (SEQ ID NO: 521) | C | 545 |
| CR16-4_S: | cacc | G | GGTATCCACGTAAATCAAA (SEQ ID NO: 522) | | 546 |
| CR16-4_AS: | AAAC | | TTTGATTTACGTGGATACC (SEQ ID NO: 523) | C | 547 |
| CR16-5_S: | cacc | G | CCAATCACTGGCTCCGGTC (SEQ ID NO: 524) | | 548 |
| CR16-5_AS: | AAAC | | GACCGGAGCCAGTGATTGG (SEQ ID NO: 525) | C | 549 |
| CR16-6_S: | cacc | G | GGCGCCCGAGGGAAGAAGA (SEQ ID NO: 526) | | 550 |
| CR16-6_AS: | AAAC | | TCTTCTTCCCTCGGGCGCC (SEQ ID NO: 527) | C | 551 |
| CR16-7_S: | cacc | G | GGGTGGGGGTACCAGAGGA (SEQ ID NO: 528) | | 552 |
| CR16-7_AS: | AAAC | | TCCTCTGGTACCCCCACCC (SEQ ID NO: 529) | C | 553 |
| CR16-8_S: | cacc | G | CCGGGGACAGAAGAGAGGG (SEQ ID NO: 530) | | 554 |
| CR16-8_AS: | AAAC | | CCCTCTCTTCTGTCCCCGG (SEQ ID NO: 531) | C | 555 |
| CR16-9_S: | cacc | G | gagagagagtgggagaagc (SEQ ID NO: 532) | | 556 |
| CR16-9_AS: | AAAC | | gcttctcccactctctctc (SEQ ID NO: 533) | C | 557 |
| CR16-10_S: | cacc | G | aaagtaactgtcaaatgcg (SEQ ID NO: 534) | | 558 |
| CR16-10_AS: | AAAC | | cgcatttgacagttacttt (SEQ ID NO: 535) | C | 559 |
| CR16-11_S: | cacc | G | ttaaccagagcgcccagtc (SEQ ID NO: 536) | | 560 |
| CR16-11_AS: | AAAC | | gactgggcgctctggttaa (SEQ ID NO: 537) | C | 561 |
| CR16-12_S: | cacc | G | cgtcggagctgcccgctag (SEQ ID NO: 538) | | 562 |
| CR16-12_AS: | AAAC | | ctagcgggcagctccgacg (SEQ ID NO: 539) | C | 563 |

qRT-PCR & IF:

Activation of endogenous ASCL1 was assessed by qRT-PCR and immunofluorescence in MEFs on day 3 following delivery of either dCas9-VP64 and gRNAs, ASCL1 cDNA, or a negative control vector encoding luciferase. The generation of iNs was evaluated by TUJJ and MAP2 co-staining and identification of cells with neuronal morphology and extended processes.

Live Cell Reporters:

After 7-8 days in N3 medium, MEFs cultured on poly-D-lysine/laminin-coated coverslips were transduced with viruses carrying hSyn-RFP and MAP2-GCamP5 reporters to identify the most mature iNs for functional characterization via calcium imaging and electrophysiology (FIG. 49B).

Figure 52A:
FIG. 52A shows a cell with neuronal morphology positive for the GCaMP5 calcium indicator in the presence (bottom) or absence (top) of KCl in the culture medium.
Figure 52B:
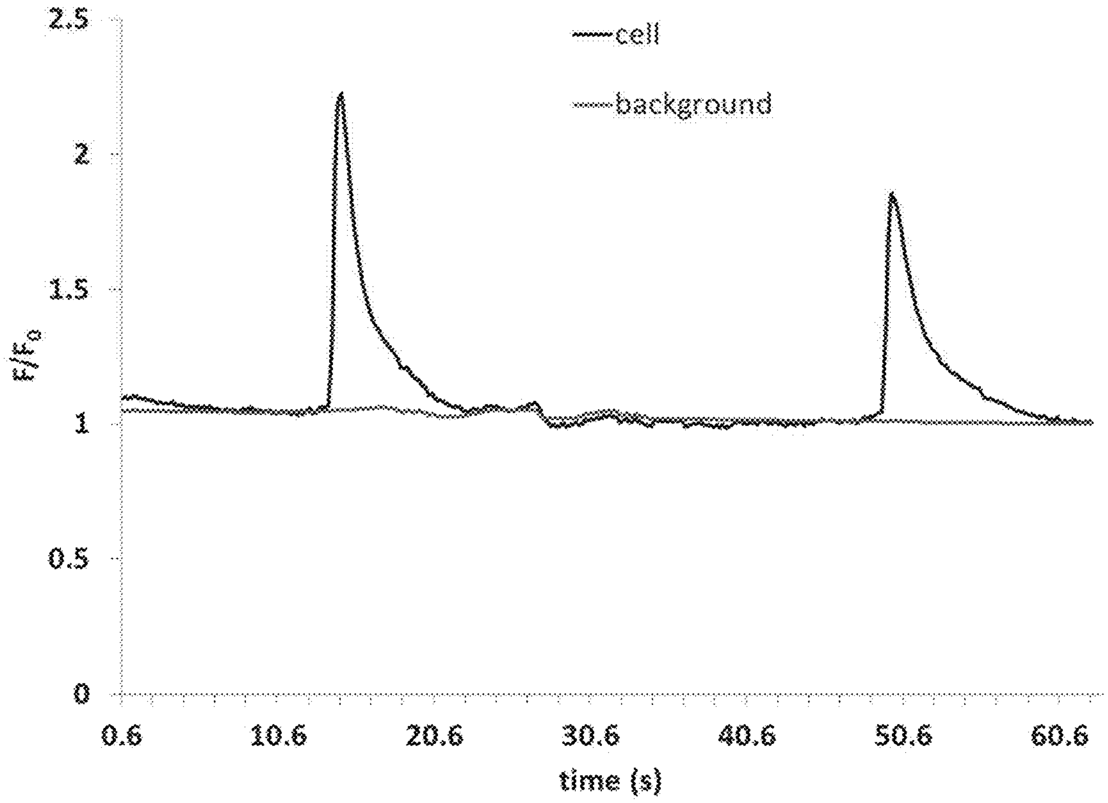
FIG. 52B shows a trace of normalized fluorescent intensity over time showing depolarization of the cell in response to KCl addition.

Results. dCas9-VP64 and gRNAs targeted to the ASCL1 promoter activated the endogenous gene in MEFs. Co-delivery of 8 gRNAs activated the endogenous gene 400-fold, a significant increase ($p<0.05$) over the 100-fold activation induced by the co-delivery of 4 gRNAs (FIG. 50A). Nuclear-localized Ascl1 protein was detected by immunofluorescence in MEFs. Ectopic Ascl1 expression produced more Ascl1 protein than dCas9-VP64 with either gRNA cocktail, but did not activate the endogenous locus by day 3 (FIG. 50A,50B). TUJ1 and MAP2 co-positive cells with extended processes were identified by immunofluorescence after 13 days in neurogenic medium following delivery of dCas9-VP64 and gRNAs targeting the ASCL1 and BRN2 promoters (FIG. 51A first row). A similar number of TUJJ and MAP2 co-positive cells were identified with ectopic expression of the BAM factors (FIG. 51A second row). Cells with a neuronal morphology expressing the hSyn-RFP reporter were visible in culture as early as day 11 in neurogenic medium (FIG. 51B). A cell expressing the MAP2-GCaMP5 calcium indicator exhibited KCl-induced depolarization detected with a fluorescent microscope (FIG. 52A,52B).

The direct conversion of mouse embryonic fibroblasts to TUJ1 and MAP2 co-positive cells with a neuronal morphology was accomplished through activation of endogenous BRN2 and ASCL1 by CRISPR/Cas9-based transcription factors. Though dCas9-VP64 produces less protein than ectopic expression of ASCL1 (FIG. 50B), the generation of neuronal-like cells is similar. The activation of the endogenous loci may induce a reprogramming cascade of events that is not mechanistically identical to that generated with ectopic expression.

dCas9-VP64 was able to penetrate heterochromatin and activated stably silenced endogenous genes, a characteristic of only a subset of "pioneer" transcription factors. As a result, converting cell lineage with CRISPR/Cas9-transcription factors may better overcome epigenetic barriers to reprogramming than ectopic expression of transcription factors, particularly in hard-to-reprogram cell-types, such as adult human cells. This may have clinical importance in the field of regenerative medicine, as it is often desired to use autologous sources in cell replacement therapies.

Example 17

Multiplex CRISPR/Cas9-Based Genome Engineering—Materials and Methods

Figure 42B:
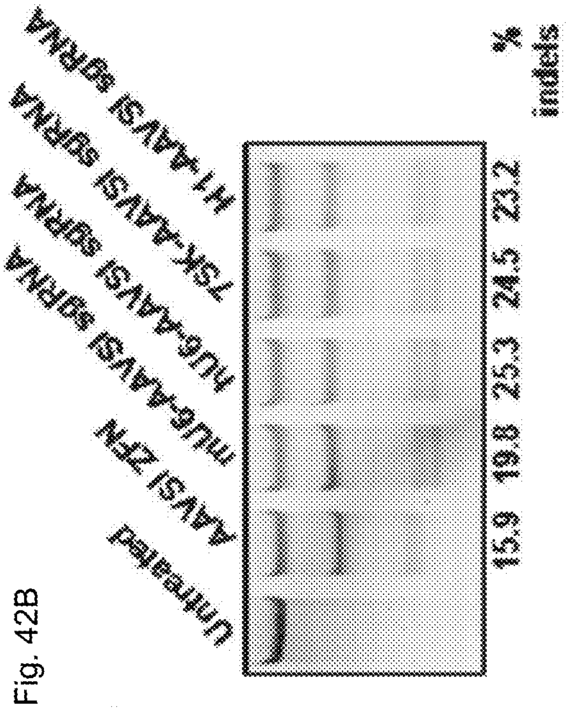
FIGS. 42A-42C show validation of sgRNA and lentiviral Cas9 expression constructs.
Figure 42A:
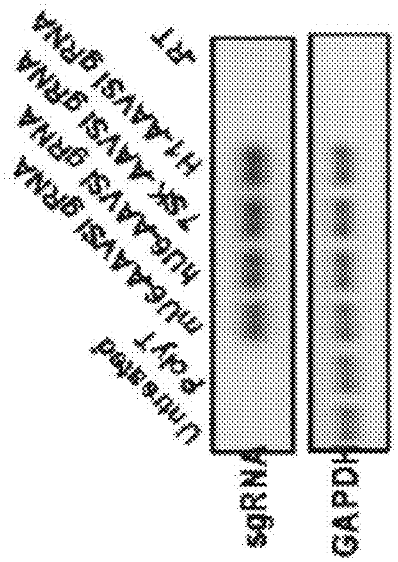

Plasmid constructs. The expression cassettes for the *S. pyogenes* sgRNA and human codon optimized Cas9 (hCas9) nuclease were used, as described above. Additional promoters for mU6 (Ohshima et al., Nucleic Acids Res 9:5145-5158 (1981)), H1 (Myslinski et al., Nucleic Acids Res 29:2502-2509 (2001)), and 7SK (Murphy et al., Cell 51:81-87 (1987)) pol-III promoters were synthesized using GeneBlocks (IDT) and cloned in place of the hU6 sgRNA expression cassette. A GeneBlock (IDT) was cloned onto the 3' end of the Cas9 coding sequence to fuse a T2A skipping peptide and eGFP gene immediately after Cas9 to monitor vector expression. The coding region for hCas9-T2A-GFP (SEQ ID NO: 145) was then transferred into a lentiviral expression vector containing the human ubiquitin C (hUbC) promoter to drive expression of hCas9-T2A-GFP, as well as restriction sites to facilitate Golden Gate cloning of sgRNA expression cassettes immediately upstream of the hUbC promoter (FIG. 42A).

Protocol for Assembly of Custom Lentiviral Vectors.

Assembly of custom lentiviral vectors expressing up to four sgRNAs of choice and active Cas9, dCas9, or dCas9-VP64 was accomplished in less than five days. The cloning method used the Golden Gate cloning and type IIS restriction enzymes that cleave outside their recognition sequence to create unique overhangs. Golden Gate assembly expedited cloning as all four expression cassettes were ligated into the final lentiviral vector in one step. The lentiviral vector expressed active Cas9, cCas9, or dCas9-VP64 in addition to one, two, three, or four sgRNAs expressed from independent promoters.

Step 1: Single stranded oligos containing each 20 bp protospacer were annealed in such a fashion to create sticky ends and were ligated into the desired pZDonor-promoter vector. Order two single stranded oligos for each desired genomic target. To anneal the complimentary oligos, mix 8 μL sense oligo+8 μL antisense oligo (both at 10 mM)+2 μL 10× ligase buffer. The oligos are melted and reannealed in a PCR machine with the program: 96° C. for 300 seconds, followed by 85° C. for 20 seconds, 75° C. for 20 seconds, 65° C. for 20 seconds, 55° C. for 20 seconds, 45° C. for 20 seconds, 35° C. for 20 seconds, and 25° C. for 20 seconds with a −0.3° C./second rate between steps. To phosphorylate the sticky ends, add 1 μL 25 mM ATP+1 microliter T4 Polynucleotide Kinase (NEB) and incubate at 37° C. for 60 minutes followed by 65° C. for 20 minutes to heat inactivate the enzyme. Each protospacer was ligated into the desired expression vector using T4 DNA ligase (NEB) incubated at 16C for 60 minutes using 50 ng of vector and 1 μL of annealed oligonucleotides in a 10 μL reaction volume according to manufacturer's instructions. Five microliters of each ligation was transformed into XL1 blue chemically competent bacteria (Agilent) following the manufacturer's instructions. Plate transformation onto LB agar plates containing 50 μg/mL kanamycin (Sigma) and incubate overnight at 37° C. In our experience, >90% of the colonies will contain the desired ligation product. Sequencing using the M13 reverse standard sequencing primer was performed to validate each final sgRNA construct prior to moving onto step 2.

Step 2: Construct the four promoter-gRNA cassettes into a lentiviral destination vector using Golden Gate assembly. After completion of step 1, there are four independent plasmids each expressing a different sgRNA from a different promoter. To assemble the four different promoter-sgRNA constructs into the desired destination vector, combine 200 ng of each sgRNA expression plasmid and desired lentiviral destination vector with 1 μL of T4 DNA ligase (NEB), 1 μL BsmBI FastDigest (Fisher Scientific), and 2 μL 10× T4 ligase buffer (NEB) in a 20 μL reaction volume. Incubate the reaction as follows: 37° C. for 10 minutes, 16C for 15 minutes, 37° C. for 30 minutes, 80° C. for 5 minutes. Transform 5 μL of ligation reaction into SURE 2 chemically competent cells (Agilent) following the manufacturer's instructions. Plate transformations onto LB agar plates containing 100 μg/mL ampicillin and incubate overnight at 37° C. Optionally, colonies can be screened by lacZ-based blue/white screening using IPTG and X-gal; however, in our experience, >90% of the transformants contain the proper ligation product. Due to the inverted repeats formed by the opposing sgRNA expression cassettes, the final constructs may be unstable and thus we recommend maintaining these plasmids in the SURE 2 cell line and screening the final plasmid with a test PCR using the sense primer 5'-TCGGGTTTATTACAGGGACAGCAG-3' (SEQ ID NO:464) and antisense primer 5'-TCTAAGGCCGAGTCTTATGAGCAG-3' (SEQ ID NO:465). These primers amplify across the four promoter-gRNA region. Due to the repetitive nature, a distinct banding pattern should be observed with the largest product approximately 1800 bp in size.

Cell Culture and Transfection.

HEK293T cells were obtained from the American Tissue Collection Center (ATCC, Manassas, VA) through the Duke University Cancer Center Facilities and were maintained in DMEM supplemented with 10% FBS and 1% penicillin streptomycin. Primary human dermal fibroblasts (Catalog ID: GM03348) were obtained from Coriell Institute (Camden, New Jersey) and were maintained in DMEM supplemented with 10% FBS and 1% penicillin streptomycin. All cells were cultured at 37° C. with 5% $CO_2$. HEK293T cells were transfected with Lipofectamine 2000 (Life Technologies) with 200 ng of each sgRNA expression vector (800 ng total pDNA) according to the manufacturer's protocol in 24 well plates.

Viral Production and Transduction.

All lentiviral vectors used is this study are second generation and were produced using standard viral production methods. Briefly, 3.5 million HEK293Ts were plated per 10 cm dish. The following day, cells were transfected by the calcium phosphate transfection method with 20 g of transfer vector, 6 g of pMD2G, and 10 μg psPAX2. The media was changed 12-14 hrs post transfection. The viral supernatant was collected 24 and 48 hrs after this media change, passed through a 0.45 micron filter and pooled. For transduction, the cell medium was replaced with viral supernatant supplemented with 4 μg/mL polybrene. The viral supernatant was exchanged for fresh medium 12-24 hrs later.

Reverse Transcription PCR.

RNA was isolated using the miRNeasy Mini RNA isolation kit (Qiagen). DNAse digestion was performed using the DNA-free Kit (Applied Biosystems). cDNA synthesis was performed using the SuperScript VILO cDNA Synthesis Kit (Invitrogen). cDNA was PCR amplified using Taq DNA polymerase (NEB) and the resulting product was run on TAE agarose gels. Images were captured using a ChemiDoc XRS+ System and processed using ImageLab software (Bio-Rad).

Quantitative Real Time PCR.

RNA was isolated using the RNeasy Plus RNA isolation kit (Qiagen). cDNA synthesis was performed using the SuperScript VILO cDNA Synthesis Kit (Invitrogen). Real-time PCR using PerfeCTa SYBR Green FastMix (Quanta Biosciences) was performed with the CFX96 Real-Time PCR Detection System (Bio-Rad). Primer specificity was confirmed by agarose gel electrophoresis and melting curve analysis. Reaction efficiencies over the appropriate dynamic range were calculated to ensure linearity of the standard curve. The results are expressed as fold-increase mRNA expression of the gene of interest normalized to β-Actin expression using the ΔΔCt method. Reported values are the mean and S.E.M. from two independent experiments (n=2) where technical replicates were averaged for each experiment.

Western Blot.

Cells were lysed in RIPA Buffer (Sigma) supplemented with protease inhibitor cocktail (Sigma). Protein concentration was measured using BCA protein assay reagent (Thermo Scientific) and BioTek Synergy 2 Multi-Mode Microplate Reader. Lysates were mixed with loading buffer and boiled for 5 min; 25 μg of protein were run in NuPage 10% Bis-Tris Gel polyacrylamide gels (Bio-Rad) and transferred to nitrocellulose membranes. Nonspecific antibody binding was blocked with TBST (50 mM Tris, 150 mM NaCl and 0.1% Tween-20) with 5% nonfat milk for 1 hr at room temperature. The membranes were incubated with primary antibodies: (anti-MyoD (1:250, Santa Cruz Sc-32758) in 5% BSA in TBST overnight at 4° C.; anti-Myogenin (1:250, Santa Cruz Sc-12732) in 5% BSA overnight at 4° C.; anti-FLAG-HRP (1:1000, Cell Signaling 2044) in 5% milk in TBST for 60 min at room temperature; anti-GAPDH (1:5000, Cell Signaling, clone 14C10) in 5% milk in TBST for 30 min at room temperature. Membranes were then washed three times with TBST for 15 minutes total. Membranes were incubated with anti-rabbit HRP-conjugated antibody (Sigma, A 6154) or anti-mouse HRP-conjugated antibody (Santa Cruz, SC-2005) diluted 1:5,000 for 30 min and washed with TBST three times for 15 min each. Membranes were visualized using the ImmunStar WesternC Chemiluminescence Kit (Bio-Rad) and images were captured using a ChemiDoc XRS+ System and processed using ImageLab software (Bio-Rad).

Cel-I Quantification of Endogenous Gene Modification.

CRISPR/Cas9 nuclease lesions at the endogenous target site were quantified using the Surveyor nuclease assay, which can detect mutations characteristic of nuclease-mediated NHEJ. After transfection or transduction, cells were incubated for 3-10 days at 37° C. and genomic DNA was extracted using the DNeasy Blood and Tissue kit (Qiagen). The target locus was amplified by 35 cycles of PCR with the AccuPrime High Fidelity PCR kit (Invitrogen). The resulting PCR products were randomly melted and reannealed in a PCR machine with the program: 95° C. for 240 seconds, followed by 85° C. for 60 seconds, 75° C. for 60 seconds, 65° C. for 60 seconds, 55° C. for 60 seconds, 45° C. for 60 seconds, 35° C. for 60 seconds, and 25° C. for 60 seconds with a −0.3° C./second rate between steps. Following re-annealing, 8 μL of PCR product was mixed with 1 μL of Surveyor Nuclease S and 1 μL of Enhancer S (Transgenomic, Omaha, NE) and incubated at 42° C. for 1 hr. After incubation, 6 μL of digestion product was loaded onto a 10% TBE polyacrylamide gel and run at 200 V for 30 minutes. The gels were stained with ethidium bromide and quantified using ImageLab (Bio-Rad) by densitometry (Perez-Pinera et al., Nucleic Acids Res 40:3741-3751 (2012)).

Statistical Analysis.

At least two independent experiments were compiled as means and standard errors of the mean. Effects were evaluated with multivariate ANOVA and Dunnett's post hoc test using JMP 10 Pro.

Example 18

Figure 42C:
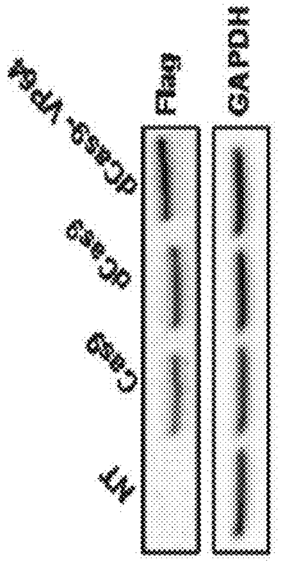

Development of a Single Lentiviral Vector for Multiplex CRISPR/Cas9 Applications A limitation of current CRISPR/Cas9 gene editing systems, particularly transactivator systems, is the simultaneous and efficient delivery of multiple sgRNAs and Cas9 protein for multiplex gene editing and synergistic gene activation applications, especially in difficult to transfect cell types. To overcome this limitation, we developed a single lentiviral vector that efficiently expresses Cas9 and up to four sgRNAs. In order to maximize the expression efficiency of each sgRNA, this vector expresses four sgRNAs from four independent pol III promoters (human U6 promoter, mouse U6 promoter, 7SK, and H1). We validated sgRNA expression from each promoter using end-point RT-PCR to detect a sgRNA targeting the AAVS1 locus (FIG. 42A). To test the activity of each sgRNA expression construct, we co-transfected each promoter construct expressing an sgRNA targeting AAVS1 independently with an active Cas9 expression construct into human HEK293T cells. Notably, we detected consistent and high levels of gene modification at the target locus for each sgRNA that are comparable to a well-characterized zinc-finger nuclease with high activity at the AAVS1 locus (FIG. 42B). Furthermore, lentiviral delivery of different Cas9-based constructs, including an active Cas9 nuclease, dead Cas9, and dead Cas9 fused to the VP64 transactivator domain, resulted in expression of full-length Cas9 protein in HEK293T cells as determined by western blot (FIG. 42C).

Figure 43:
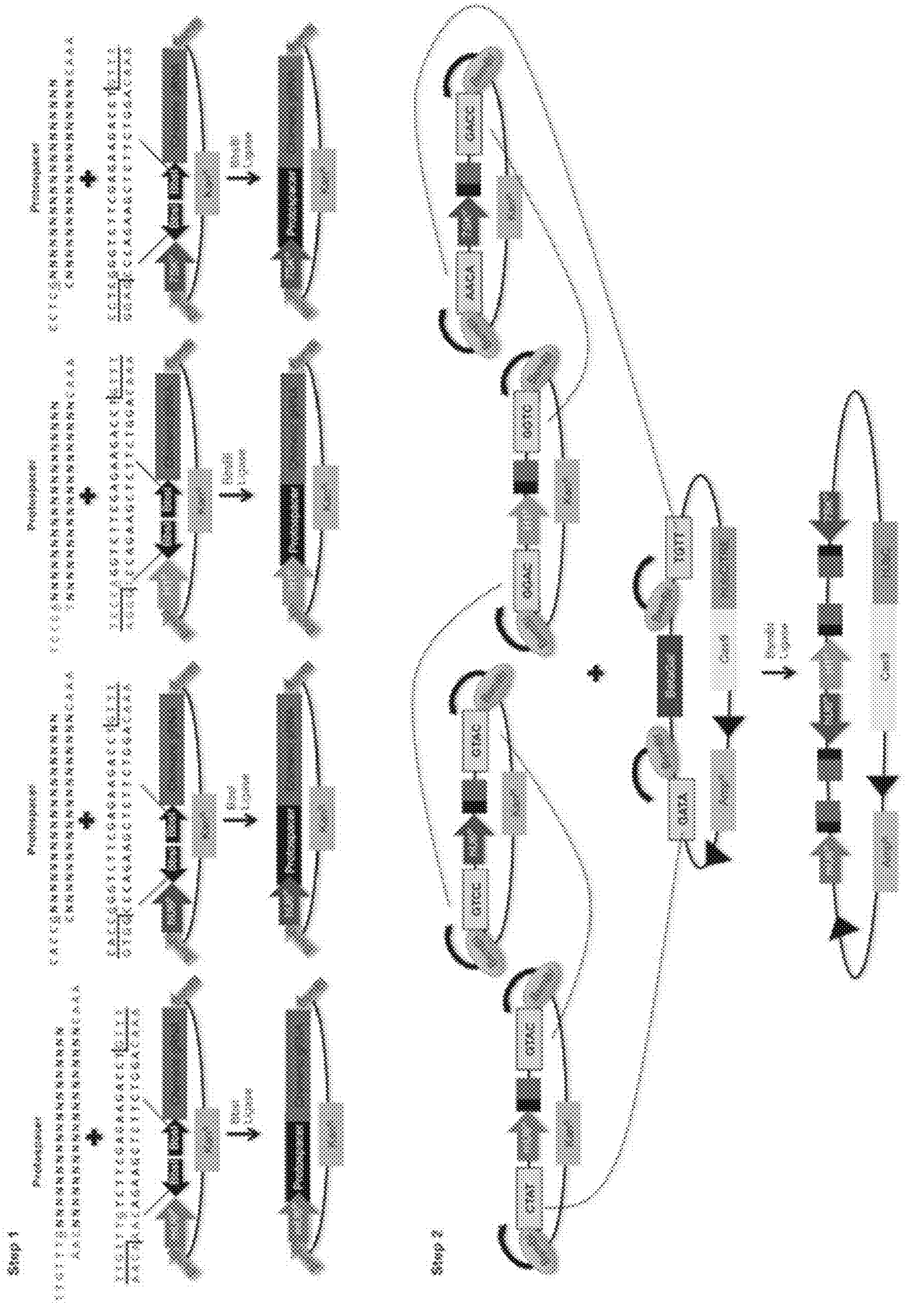
FIG. 43 shows Golden Gate assembly of single lentiviral CRISPR/Cas9 expression cassettes.

Using these components, we developed a Golden Gate cloning method to facilitate rapid and efficient cloning of multiple sgRNA expression cassettes into a single lentiviral vector expressing the desired Cas9 effector (FIG. 43). In the first step, oligonucleotides encoding sgRNA protospacer sequences are cloned independently into different expression vectors, each with a distinct promoter driving sgRNA expression. In the second step, each sgRNA expression construct is subcloned into a lentiviral Cas9 expression vector of choice by Golden Gate assembly. This strategy allows for robust and rapid cloning of up to four sgRNAs into a single lentiviral vector for gene editing or activation applications. To express less than four sgRNAs, a PolyT terminator sequence is cloned down-stream of unused promoters to prevent transcription from the unused promoters. Each vector co-expresses the choice Cas9 with eGFP via a 2A skipping peptide to enable fluorescence-activated flow sorting and enrichment of cells with a high multiplicity of infection. Finally, the entire region containing the sgRNA and Cas9 expression cassettes is flanked by loxP sites to mediate removal by Cre-lox excision.

Example 19

Figure 44A:
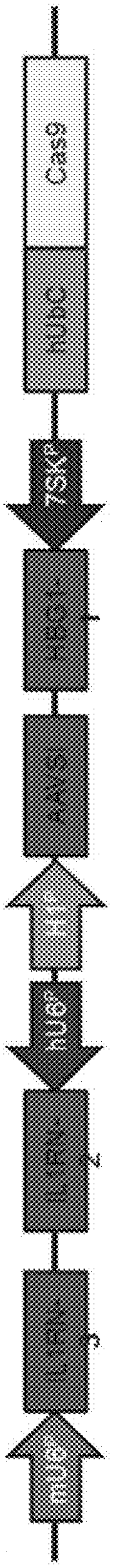
FIGS. 44A-44B show single lentiviral delivery of a multiplex CRISPR/Cas9 system.
Figure 44B:
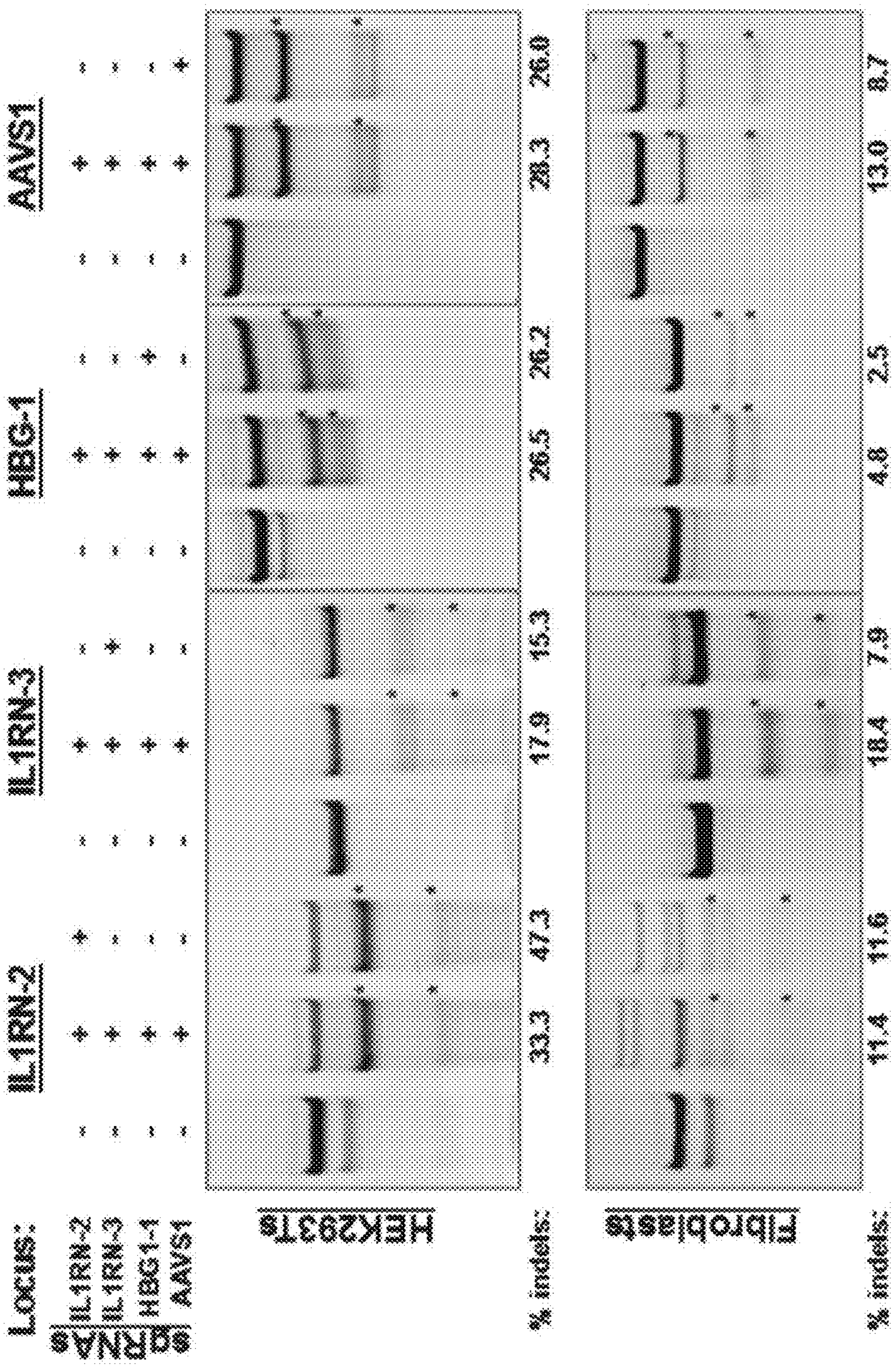

Validation of a Single Lentiviral sgRNA/Cas9 Expression Vector for Multiplex Genome Engineering To validate the independent activity of each sgRNA, we assembled a single lentiviral vector expressing active Cas9 and four sgRNAs, each targeting an independent loci (FIG. 44A). As control vectors, we assembled constructs expressing only one sgRNA along with polyT protospacers in the other three positions. We transduced HEK293Ts and primary fibroblasts with lentiviral vectors expressing the indicated sgRNAs and monitored gene modification frequencies at 7 or 10 days post-transduction, respectively (FIG. 44B). In both cell types, the single lentiviral vector mediated highly efficient multiplex editing at all four loci (FIG. 44B). Interestingly, expression of all four sgRNAs together resulted in higher modification frequencies than a single sgRNA alone at 3 out of 4 loci in fibroblasts (FIG. 44B). We observed efficient multiplex gene editing in fibroblasts, which are conventionally a difficult to transfect cell type. These data demonstrate that a single lentivirus can express four active sgRNAs efficiently and that this lentiviral platform can be used to target four distinct loci for multiplex CRISPR/Cas9 gene editing.

Example 20

Figure 45A:
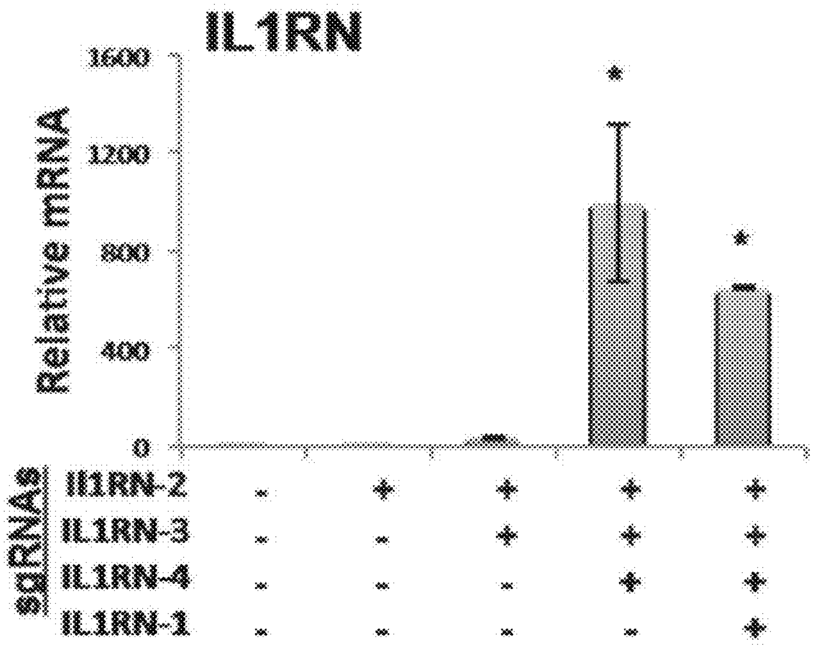
FIGS. 45A-45D show transient gene activation in HEK293Ts stably expressing dCas9-VP64. HEK293Ts were transduced with lentivirus to stably express dCas9-VP64 and were subsequently transfected with plasmid expressing the indicated sgRNA combinations. By varying the number of sgRNAs delivered, tunable endogenous gene activation of the endogenous IL1RN (FIG. 45A) and HBG1 (FIG. 45B) loci was achieved 3 days post transfection. Peak levels of endogenous IL1RN (FIG. 45C) and HBG1 (FIG. 45D) were observed 3-6 days post transfection and the level of activation returned to background levels between days 15-20. Importantly, the cell lines were able to reactive following a second transfection on day 20 albeit at a lower level than previously observed.
Figure 45B:
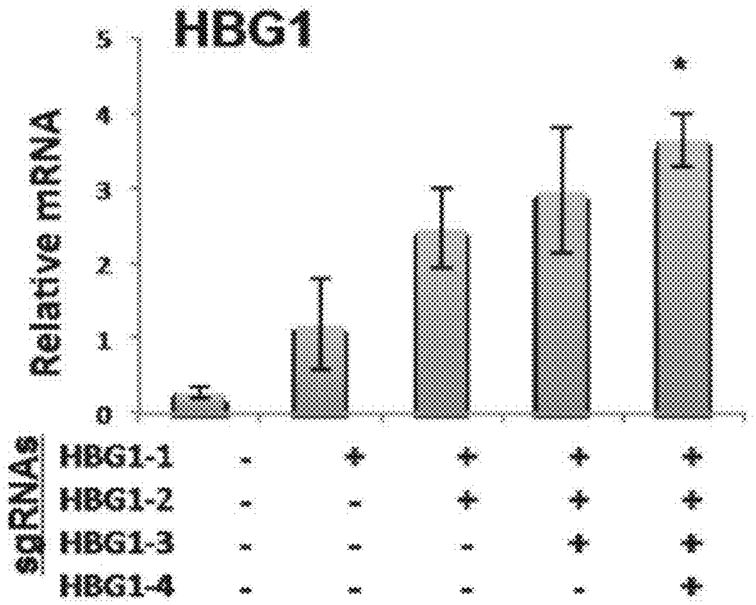
Figure 45C:
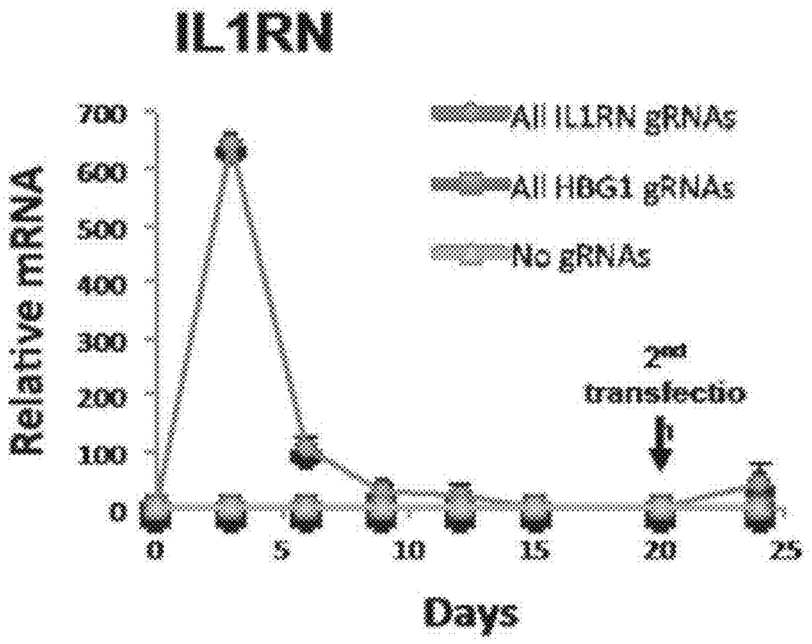
Figure 45D:
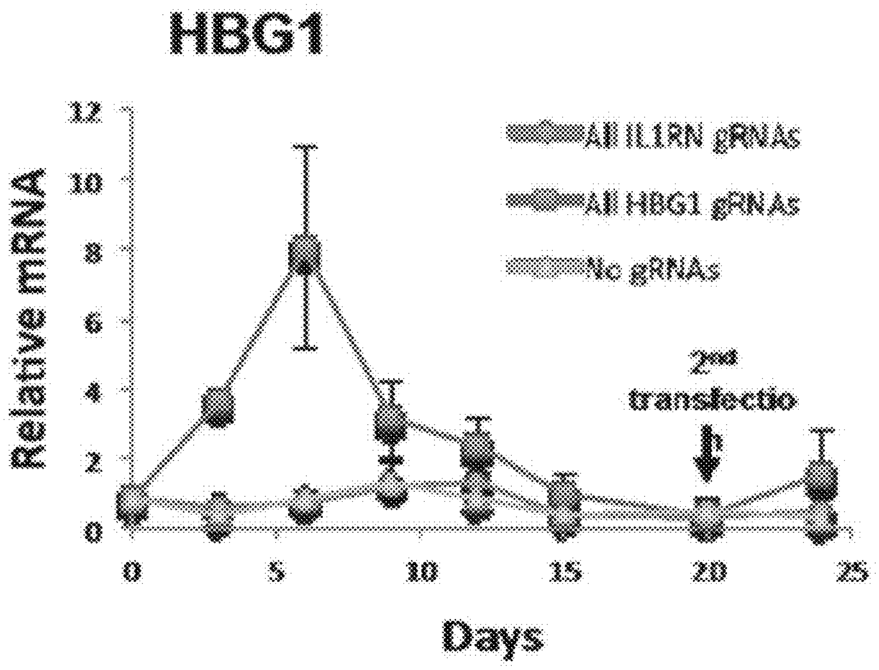

Transient RNA-Guided Gene Activation in Cell Lines Stably Expressing a Lentiviral Cas9-Based Transactivator Next, we were interested in developing a system that enables transient gene activation by transfecting sgRNAs into model cell lines stably expressing Cas9. HEK293Ts were transduced with different Cas9-T2A-GFP and GFP expression was monitored using flow cytometry. Following normal passaging every 2-3 days, each cell line exhibited stable GFP expression for up to 35 days post transduction. Transduced HEK293Ts were then transfected with one to four separate sgRNA expression constructs targeting either the IL1RN or HBG1 promoter. Transient transfection of these sgRNA constructs in stable dCas9-VP64 expressing cells lines resulted in tunable endogenous gene activation (FIGS. 45A,45B). Gene activation following transient transfection of sgRNA constructs in cells expressing dCas9-VP64 reached a maximum level of activation approximately 3-6 post-transfection and fell to undetectable levels by 20 days post-transfection (FIGS. 45C,45D). Furthermore, we were able to re-activate each gene by a second transfection of all four sgRNA constructs targeting each promoter, although activation levels were significantly lower than observed from the first transfection (FIGS. 45C, 45D). This reduction in activity after the second transfection may be due to reduced vector expression or competitive growth of untransduced cells. Despite this, these data demonstrate that lentiviral Cas9 combined with transient sgRNA delivery can be used as a versatile system to tunably and transiently activate and re-activate target genes in a Cas9 stably transduced cell line.

Example 21

Figure 46A:
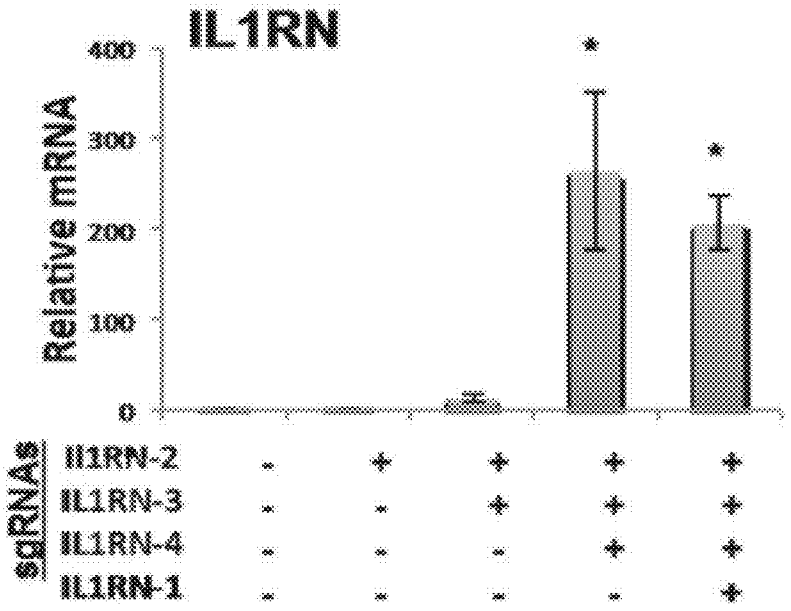
FIGS. 46A-46D show stable gene activation in HEK293Ts using a single lentiviral multiplex dCas9-VP64 vector. HEK293Ts were transduced with lentivirus to stably express dCas9-VP64 and the indicated combinations of gRNAs. By varying the number of sgRNAs delivered, tunable endogenous gene activation of the endogenous IL1RN (FIG. 46A) and HBG1 (FIG. 46B) loci was achieved 7 days post transduction. Peak levels of endogenous IL1RN (FIG. 46C) and HBG1 (FIG. 46D) were observed 6 days post transduction and the level of activation was sustained out to day 21.
Figure 46B:
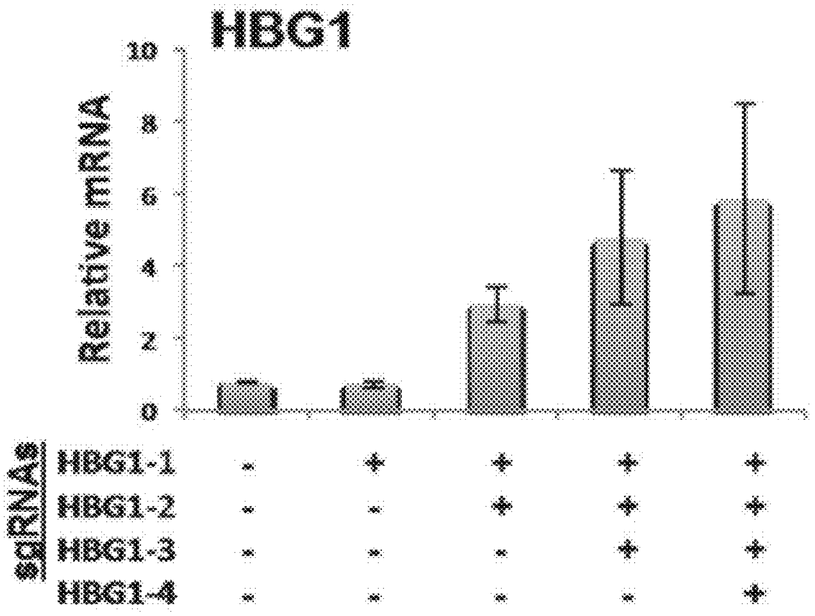
Figure 46C:
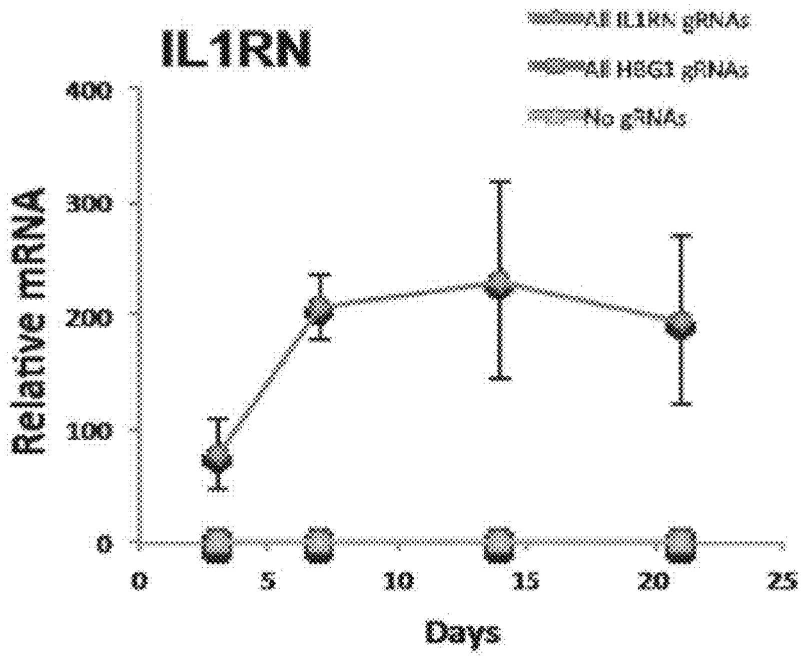
Figure 46D:
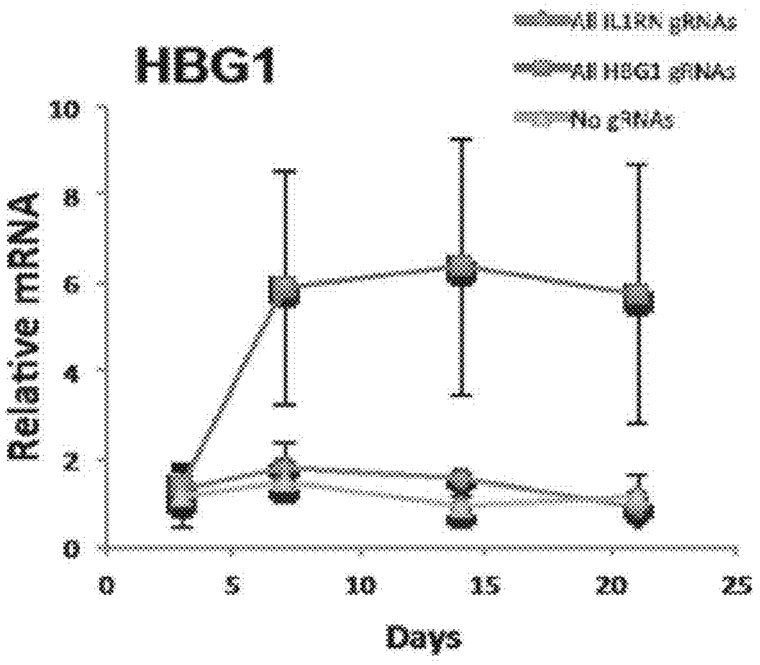

Stable Gene Activation in HEK293T Cells Using a Single Lentiviral sgRNA/Cas9 Transactivator Expression Vector Lentiviral delivery may enable stable, long-term gene activation by CRISPR/Cas9 transactivation. To test this, HEK293Ts were transduced using a single lentiviral vector encoding dCas9-VP64 and one to four sgRNA expression cassettes. Similar to our transient transfection results (FIGS. 45A-45D), we were able to tunably and robustly activate expression of endogenous IL1RN and HBG1 genes (FIGS. 46A,46B). Gene activation induced by co-transfection of HEK293T cells with dCas9-VP64 and four sgRNAs targeted to the IL1RN and HBG1 promoters peaked three-five days post-transfection and gene expression returned to background levels 15-20 days post-transfection FIGS. 45C and 45D. In contrast, lentiviral delivery of dCas9-VP64 and the same four IL1RN or HBG1-targeted sgRNAs induced sustained gene activation for more than 20 days post-transduction (FIGS. 46C,46D). Thus, single lentiviral delivery of multiplex dCas9-VP64 transactivators is a useful platform to efficiently and stably upregulate target endogenous genes.

Example 22 dCas9-KRAB—Targeting the HS2 Enhancer

Figure 54:
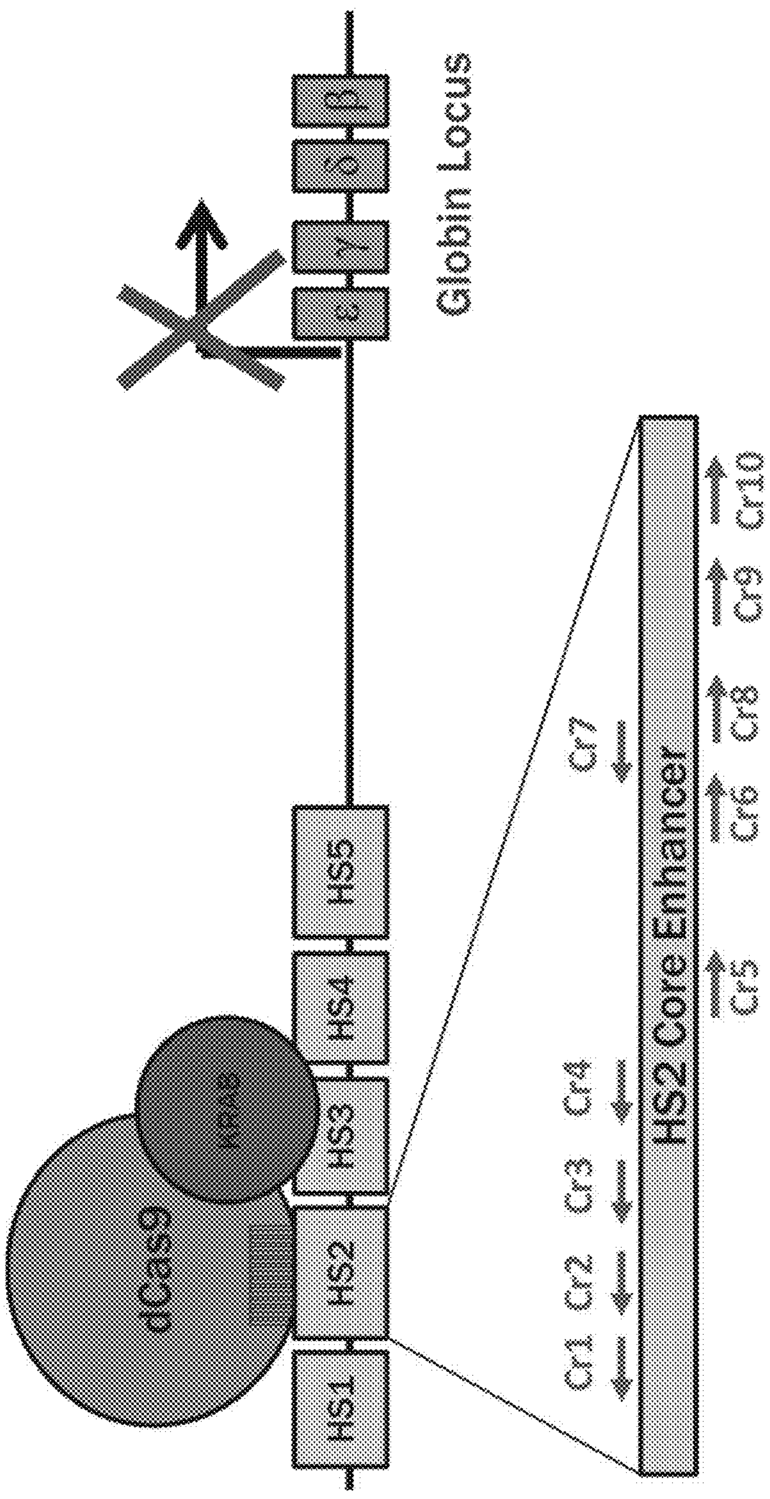
FIG. 54 shows targeting the HS2 enhancer using CRISPR/dCas9-KRAB. The HS2 region is a potent enhancer that distally regulates the expression of globin genes>10 kb downstream. A panel of single gRNAs was designed to target sites along the enhancer region.

The HS2 enhancer is a well-characterized distal regulatory element necessary for activation of the globin gene locus. dCas9-KRAB with gRNAs targeted to the HS2 enhancer were delivered to determine if this system would repress γ-, ε-, and β-globin expression in the K562 human erythroid leukemia cell line (FIG. 54). A panel of gRNAs was created targeting different sites along the core region of the HS2 enhancer (SEQ ID NO: 467). See Table 12.

TABLE 12

HS2 gRNA Target Sequences

| Cr# | Protospacer | Complete gRNA Sequence |
|---|---|---|
| 1 | gagacacacagaaatgtaac (SEQ ID NO: 564) | gagacacacagaaatgtaacgtaTAGAGCTAGAAATAGCAAGTTAAAATA AGGCTAGTCCGTTATCAACTTGAAAAAGTGGCACCGAGTCGG TGCTTTTTTTCC (SEQ ID NO: 585) |
| 2 | ggtggggcactgaccccgac (SEQ ID NO: 565) | ggtggggcactgaccccgacgtaTAGAGCTAGAAATAGCAAGTTAAAATA AGGCTAGTCCGTTATCAACTTGAAAAAGTGGCACCGAGTCGG TGCTTTTTTTCC (SEQ ID NO: 586) |
| 3 | ctagagtgatgactcctatc (SEQ ID NO: 566) | ctagagtgatgactcctatcgtttTAGAGCTAGAAATAGCAAGTTAAAATAA GGCTAGTCCGTTATCAACTTGAAAAAGTGGCACCGAGTCGGT GCTTTTTTTCC (SEQ ID NO: 587) |

TABLE 12-continued

HS2 gRNA Target Sequences

| Cr# | Protospacer | Complete gRNA Sequence |
|---|---|---|
| 4 | gactaaaactccacctcaaa (SEQ ID NO: 567) | gactaaaactccacctcaaagtaTAGAGCTAGAAATAGCAAGTTAAAATAAGGCTAGTCCGTTATCAACTTGAAAAAGTGGCACCGAGTCGGTGCTTTTTTTCC (SEQ ID NO: 588) |
| 5 | aatatgtcacattctgtctc (SEQ ID NO: 568) | aatatgtcacattctgtctcgtaTAGAGCTAGAAATAGCAAGTTAAAATAAGGCTAGTCCGTTATCAACTTGAAAAAGTGGCACCGAGTCGGTGCTTTTTTTCC (SEQ ID NO: 589) |
| 6 | ggactatgggaggtcactaa (SEQ ID NO: 569) | ggactatgggaggtcactaagtaTAGAGCTAGAAATAGCAAGTTAAAATAAGGCTAGTCCGTTATCAACTTGAAAAAGTGGCACCGAGTCGGTGCTTTTTTTCC (SEQ ID NO: 590) |
| 7 | gctcatgcttggactatggg (SEQ ID NO: 570) | gctcatgcttggactatggggtaTAGAGCTAGAAATAGCAAGTTAAAATAAGGCTAGTCCGTTATCAACTTGAAAAAGTGGCACCGAGTCGGTGCTTTTTTTCC (SEQ ID NO: 591) |
| 8 | gttctggccaggcccctgtc (SEQ ID NO: 571) | gttctggccaggcccctgtcgtaTAGAGCTAGAAATAGCAAGTTAAAATAAGGCTAGTCCGTTATCAACTTGAAAAAGTGGCACCGAGTCGGTGCTTTTTTTCC (SEQ ID NO: 592) |
| 9 | agtgccccacccccgccttc (SEQ ID NO: 572) | agtgccccacccccgccttcgtttTAGAGCTAGAAATAGCAAGTTAAAATAAGGCTAGTCCGTTATCAACTTGAAAAAGTGGCACCGAGTCGGTGCTTTTTTTCC (SEQ ID NO: 593) |
| 10 | gtggggcactgaccccgaca (SEQ ID NO: 573) | gtggggcactgaccccgacagtttTAGAGCTAGAAATAGCAAGTTAAAATAAGGCTAGTCCGTTATCAACTTGAAAAAGTGGCACCGAGTCGGTGCTTTTTTTCC (SEQ ID NO: 594) |
| 11 | aaccttctaagcaaaccttc (SEQ ID NO: 574) | aaccttctaagcaaaccttcgtaTAGAGCTAGAAATAGCAAGTTAAAATAAGGCTAGTCCGTTATCAACTTGAAAAAGTGGCACCGAGTCGGTGCTTTTTTTCC (SEQ ID NO: 595) |
| 12 | gttacacagaaccagaaggc (SEQ ID NO: 575) | gttacacagaaccagaaggcgtttTAGAGCTAGAAATAGCAAGTTAAAATAAGGCTAGTCCGTTATCAACTTGAAAAAGTGGCACCGAGTCGGTGCTTTTTTTCC (SEQ ID NO: 596) |
| 13 | gaaggttacacagaaccaga (SEQ ID NO: 576) | gaaggttacacagaaccagagtaTAGAGCTAGAAATAGCAAGTTAAAATAAGGCTAGTCCGTTATCAACTTGAAAAAGTGGCACCGAGTCGGTGCTTTTTTTCC (SEQ ID NO: 597) |
| 14 | agtcatgatgagtcatgctg (SEQ ID NO: 577) | agtcatgatgagtcatgctggtttTAGAGCTAGAAATAGCAAGTTAAAATAAGGCTAGTCCGTTATCAACTTGAAAAAGTGGCACCGAGTCGGTGCTTTTTTTCC (SEQ ID NO: 598) |
| 15 | gatgagtcatgctgaggctt (SEQ ID NO: 578) | gatgagtcatgctgaggcttgtaTAGAGCTAGAAATAGCAAGTTAAAATAAGGCTAGTCCGTTATCAACTTGAAAAAGTGGCACCGAGTCGGTGCTTTTTTTCC (SEQ ID NO: 599) |
| 16 | actctaggctgagaacatct (SEQ ID NO: 579) | actctaggctgagaacatctgtaTAGAGCTAGAAATAGCAAGTTAAAATAAGGCTAGTCCGTTATCAACTTGAAAAAGTGGCACCGAGTCGGTGCTTTTTTTCC (SEQ ID NO: 600) |
| 17 | gtccccagcaggatgcttac (SEQ ID NO: 580) | gtccccagcaggatgcttacgtaTAGAGCTAGAAATAGCAAGTTAAAATAAGGCTAGTCCGTTATCAACTTGAAAAAGTGGCACCGAGTCGGTGCTTTTTTTCC (SEQ ID NO: 601) |
| 18 | gccctgtaagcatcctgctg (SEQ ID NO: 581) | gccctgtaagcatcctgctggtttTAGAGCTAGAAATAGCAAGTTAAAATAAGGCTAGTCCGTTATCAACTTGAAAAAGTGGCACCGAGTCGGTGCTTTTTTTCC (SEQ ID NO: 602) |
| 19 | cagggcagatggcaaaaaaa (SEQ ID NO: 582) | cagggcagatggcaaaaaaagtaTAGAGCTAGAAATAGCAAGTTAAAATAAGGCTAGTCCGTTATCAACTTGAAAAAGTGGCACCGAGTCGGTGCTTTTTTTCC (SEQ ID NO: 603) |
| 20 | gaggtggagttttagtcagg (SEQ ID NO: 583) | gaggtggagttttagtcagggtaTAGAGCTAGAAATAGCAAGTTAAAATAAGGCTAGTCCGTTATCAACTTGAAAAAGTGGCACCGAGTCGGTGCTTTTTTTCC (SEQ ID NO: 604) |
| 21 | aaacggcatcataaagaaaa (SEQ ID NO: 584) | aaacggcatcataaagaaaagtttTAGAGCTAGAAATAGCAAGTTAAAATAAGGCTAGTCCGTTATCAACTTGAAAAAGTGGCACCGAGTCGGTGCTTTTTTTCC (SEQ ID NO: 605) |

Figure 55A:
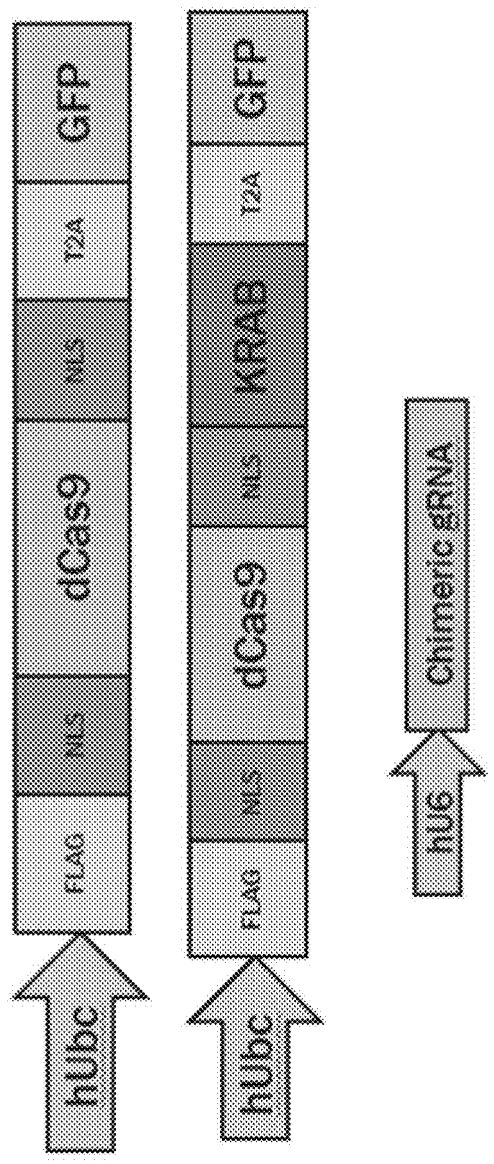
FIGS. 55A-55E that single gRNAs targeting the HS2 enhancer effect potent transcriptional repression of globin genes.
Figure 55B:
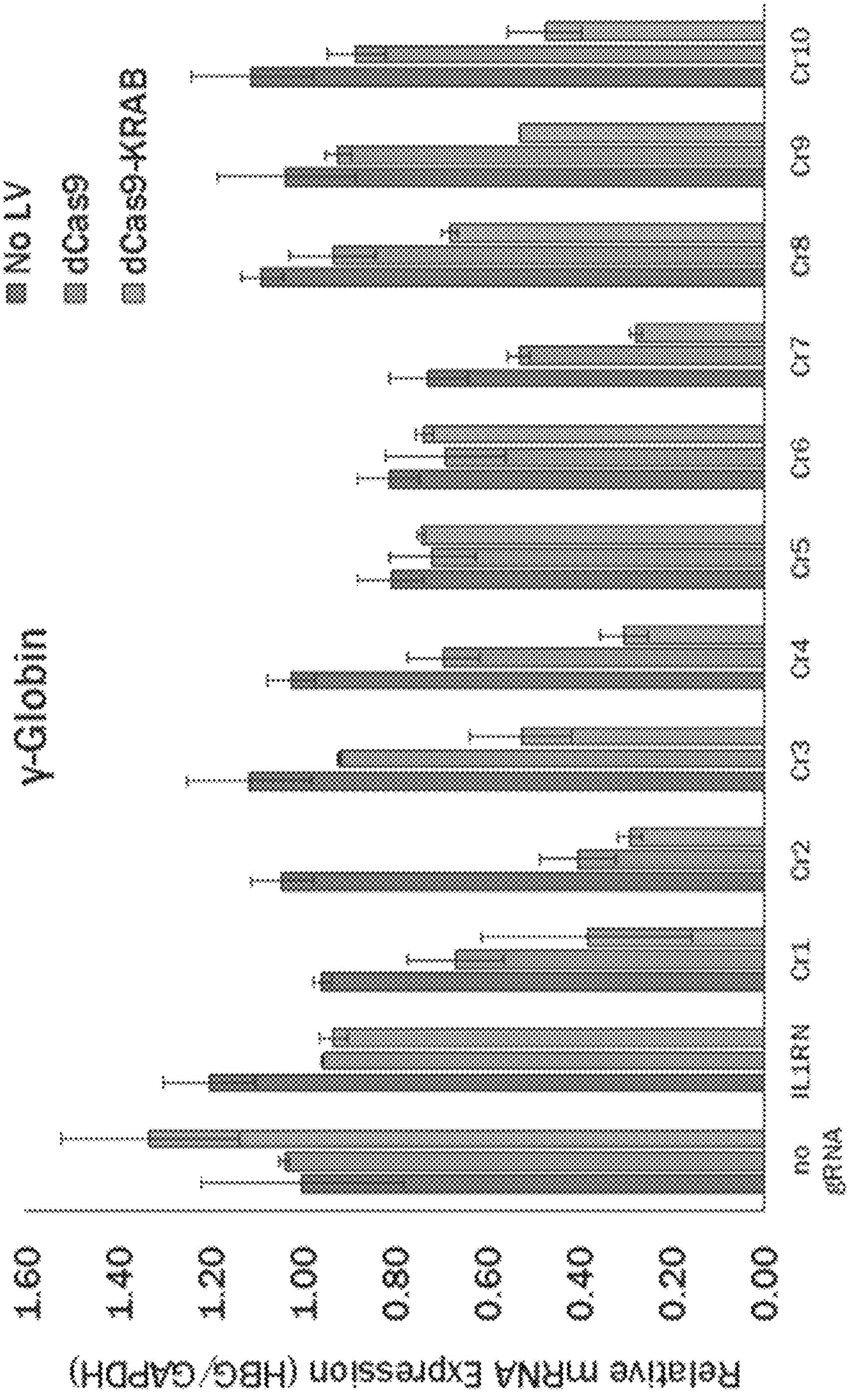
Figure 55C:
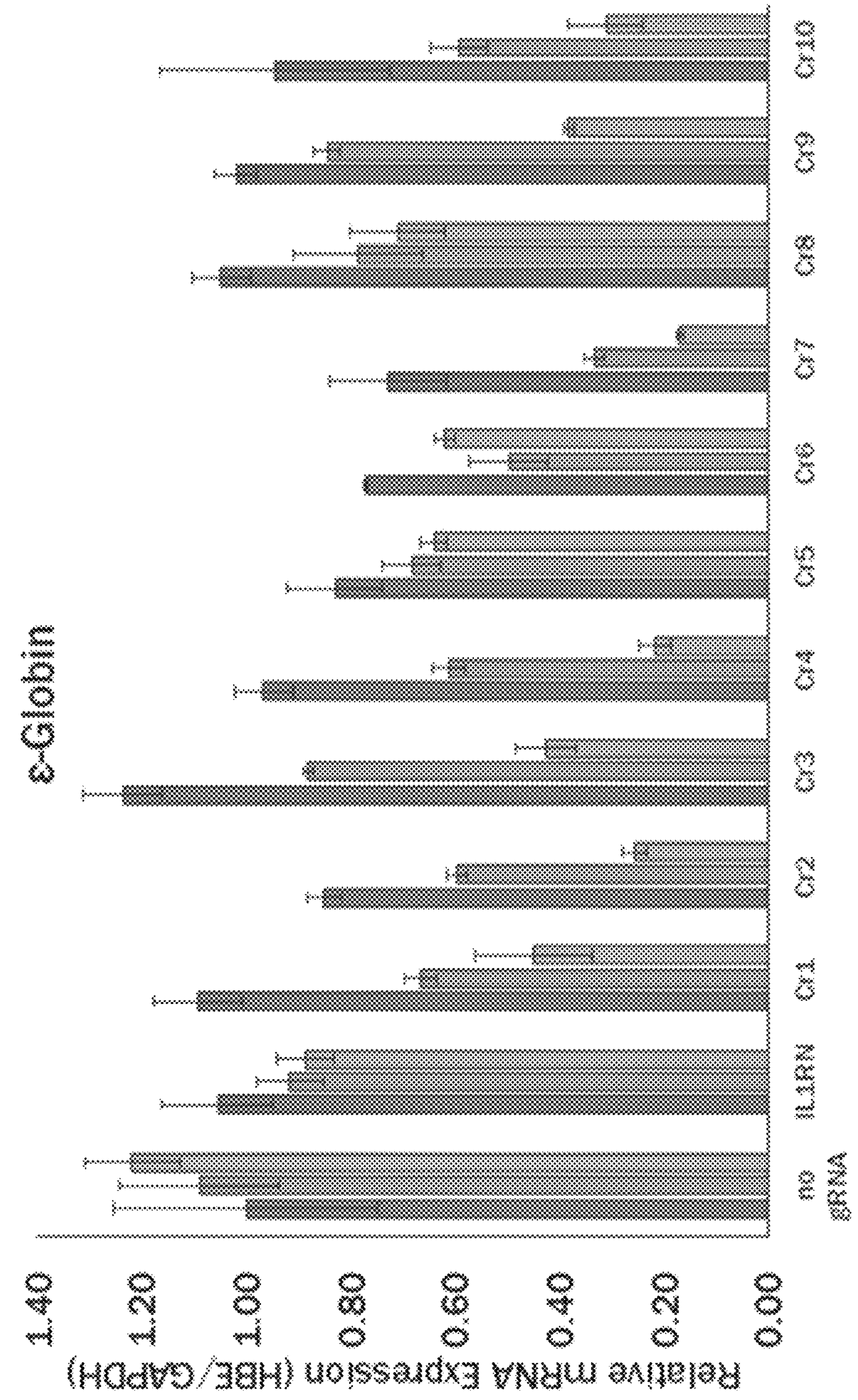
Figure 55D:
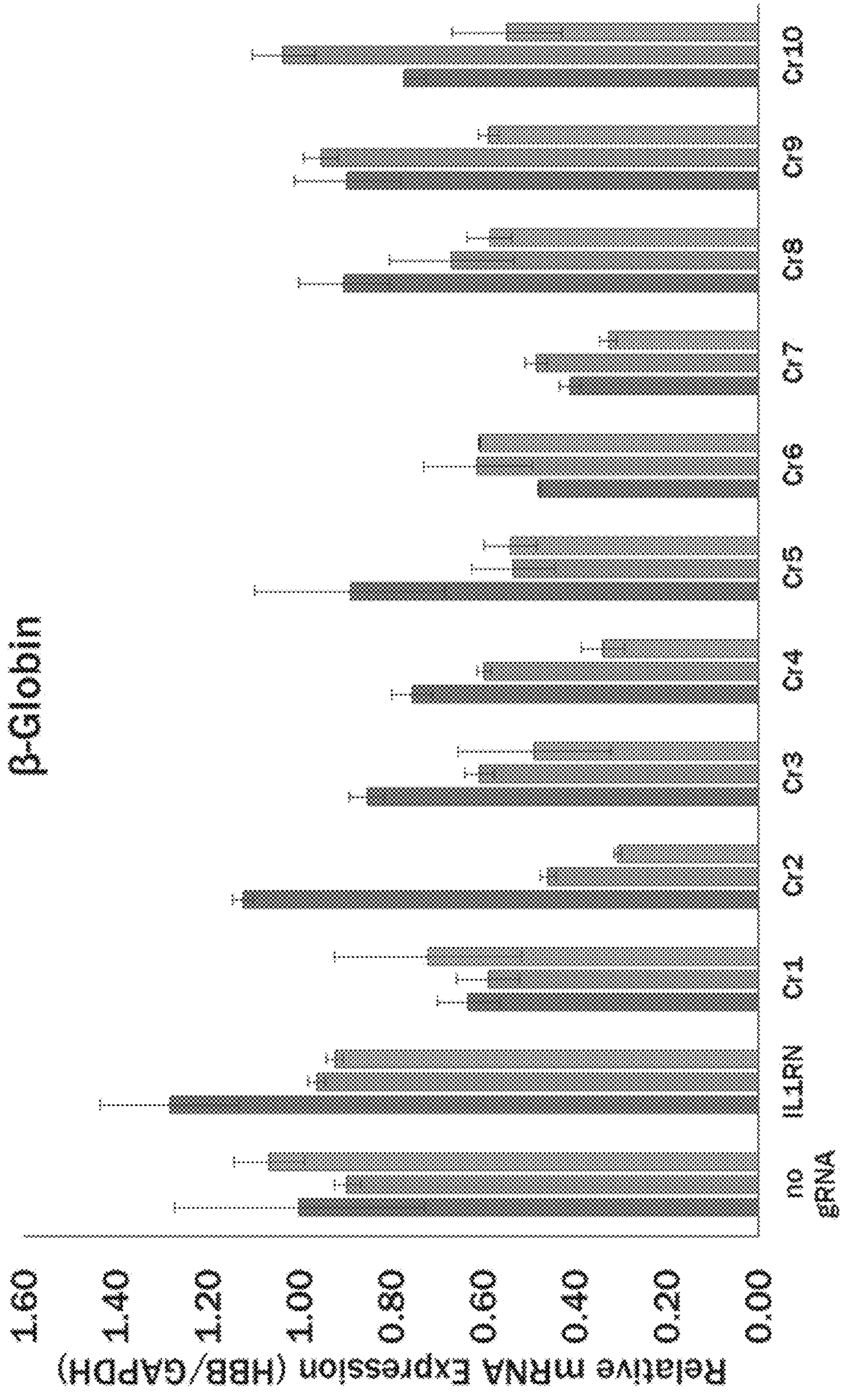
Figure 55E:
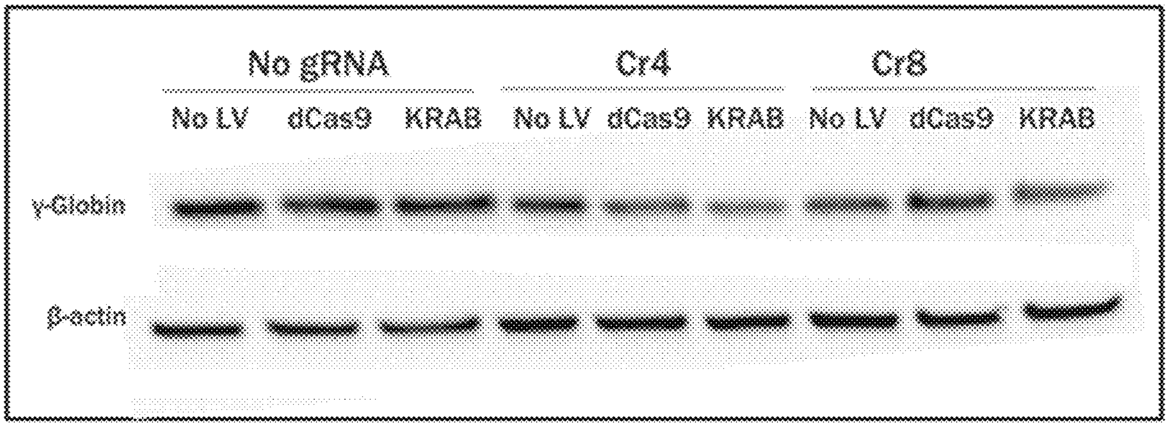
Figure 56A:
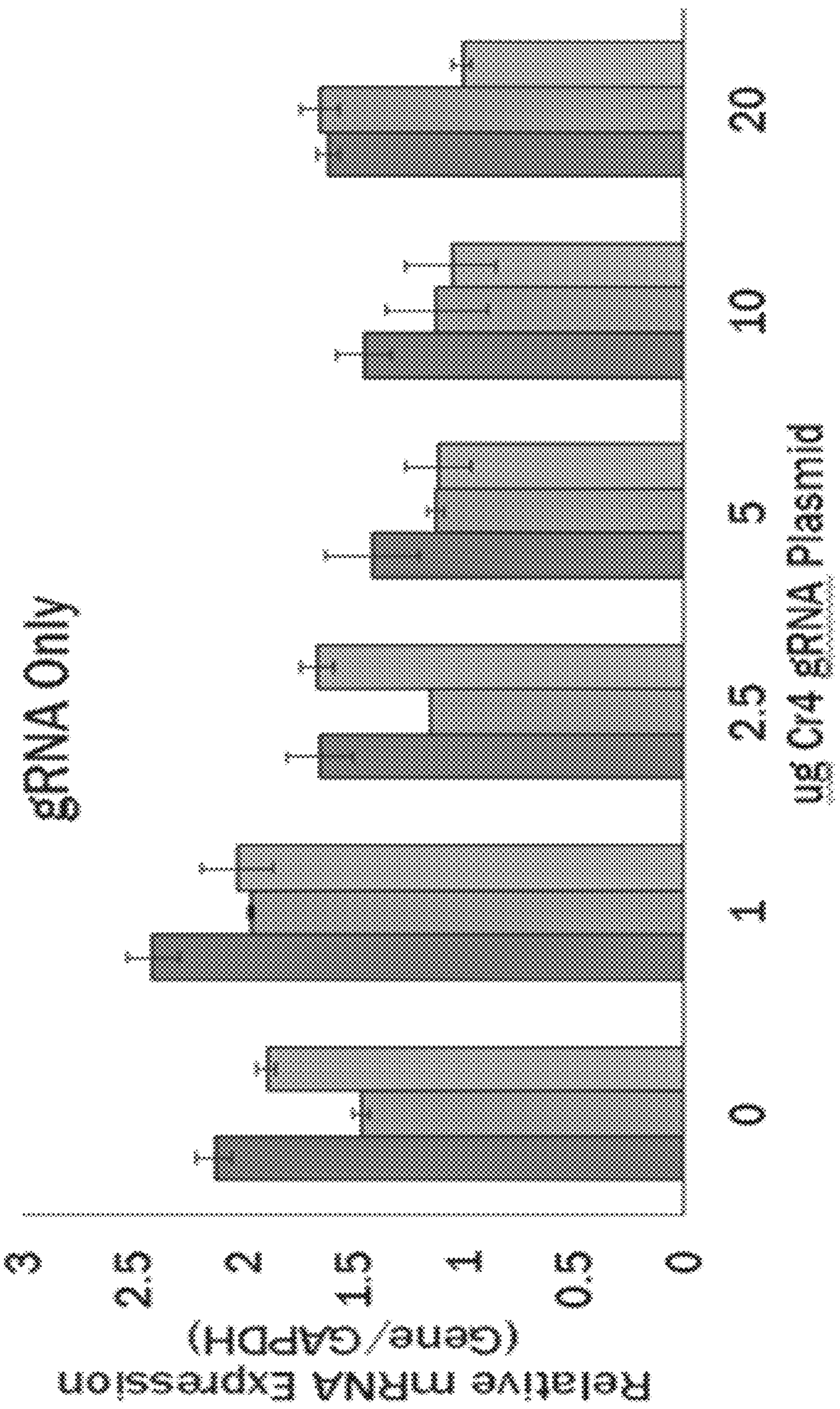
FIGS. 56A-56C expression of globin locus genes with varying doses of gRNA plasmid delivered to cells treated with no lentivirus (FIG. 56A), dCas9 lentivirus (FIG. 56B), or dCas9-KRAB lentivirus (FIG. 56C). Increasing the dose of Cr4 gRNA plasmid delivered enhanced repression in dCas9-KRAB treated cells, indicating that both the dCas9-KRAB effector and targeted gRNA play a role in achieving repression.
Figure 56B:
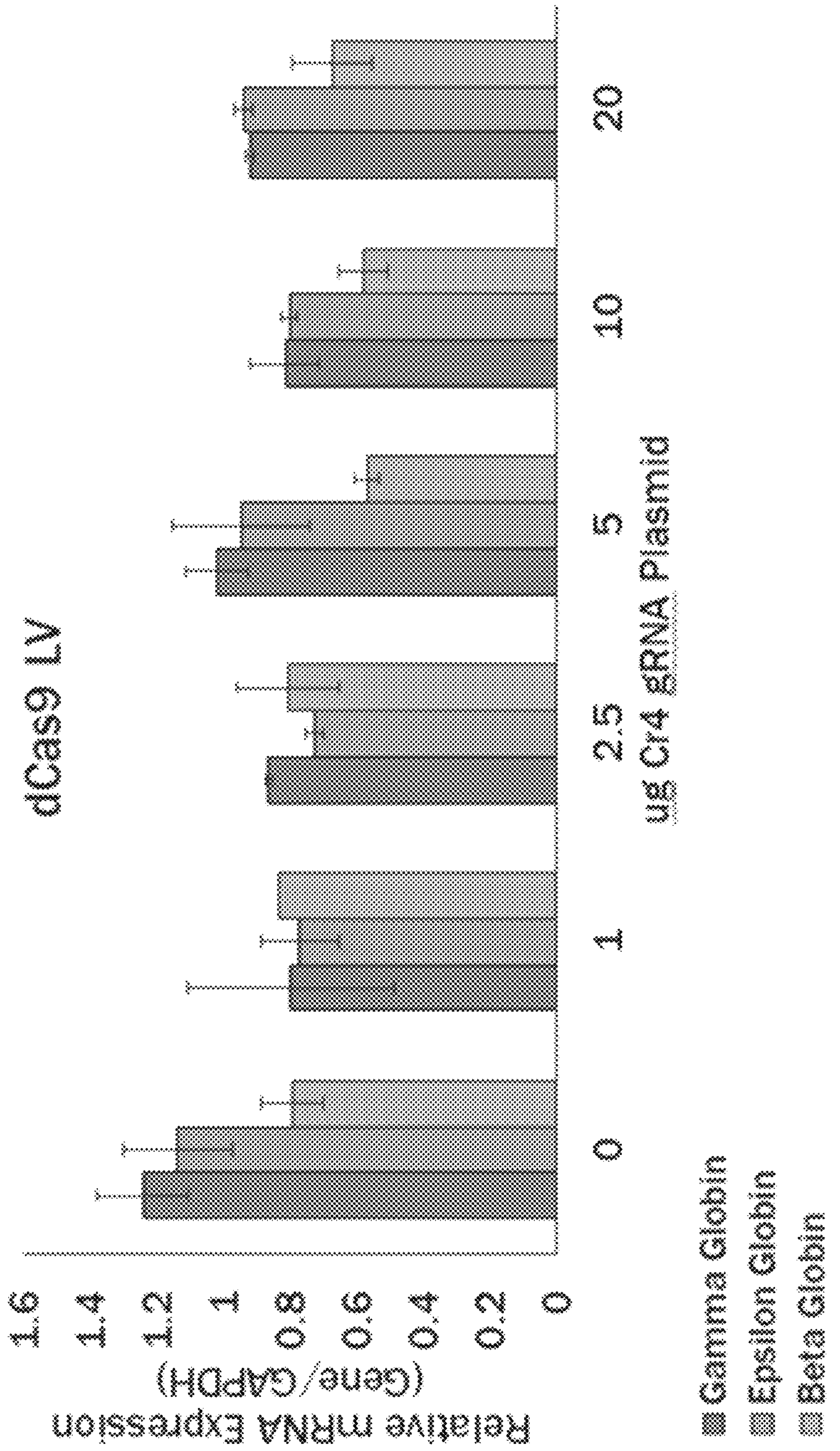
Figure 56C:
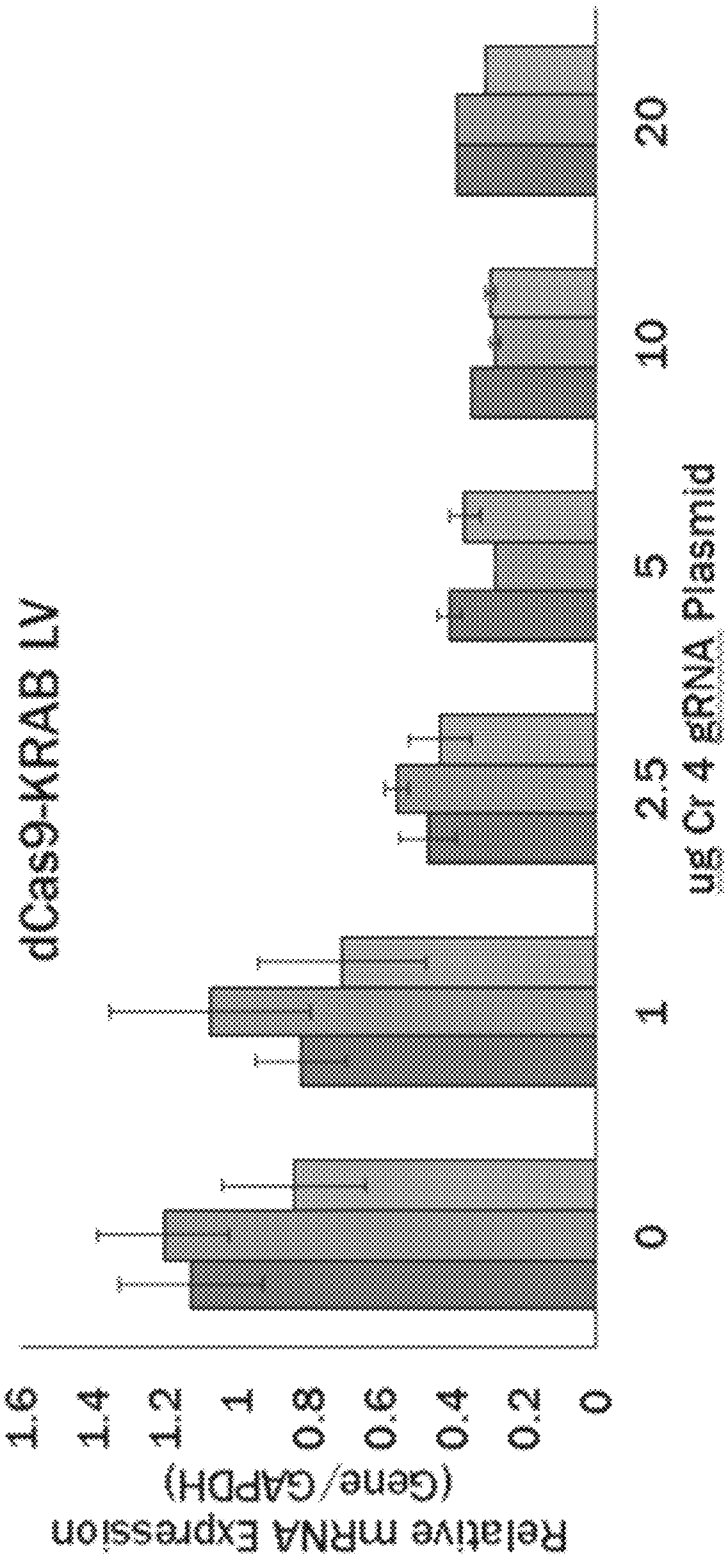

Screening single gRNAs at the globin locus by CRISPR/dCas9. dCas9 and dCas9-KRAB effectors were delivered lentivirally 5-8 days prior to electroporation with 5 μg of a plasmid encoding the U6-sgRNA expression (FIG. 55A). Cells that were not electroporated with gRNA (no gRNA) and cells treated with a gRNA targeting a different locus (IL1RN) were included as controls. Multiple gRNAs effected potent repression of ε-, γ-, and β-globin genes when assayed 3 days post-transfection, with up to 80% knockdown achieved (FIGS. 55B, 55C, 55D). Expressing a gRNA with either dCas9 or dCas9-KRAB inhibited gene expression at the globin locus. Generally, treatment with dCas9-KRAB resulted in stronger repression for a given gRNA compared to dCas9 alone, suggesting an important role for the KRAB domain in recruiting heterochromatin factors that enhance repression. The repression levels achieved are dependent on the amount of gRNA plasmid delivered by transfection only in the dCas9-KRAB treated cells (FIGS. 56A, 56B, 56C). Increasing the dose of Cr4 gRNA plasmid up to 10 μg increases silencing levels of the globin genes in dCas9-KRAB-treated cells.

Figure 57A:
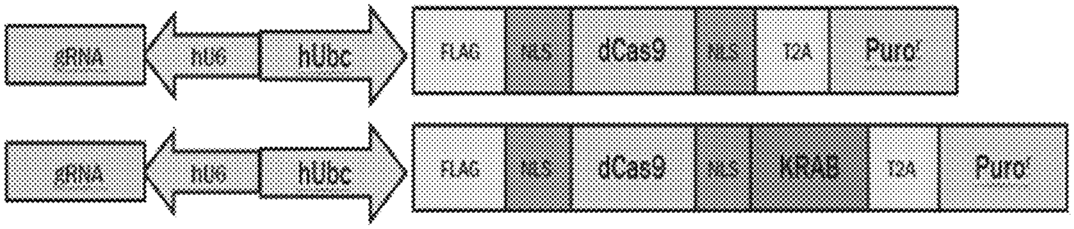
FIGS. 57A-57D show that stably delivering single gRNAs with dCas9-KRAB silences expression of the globin genes.
Figure 57B:
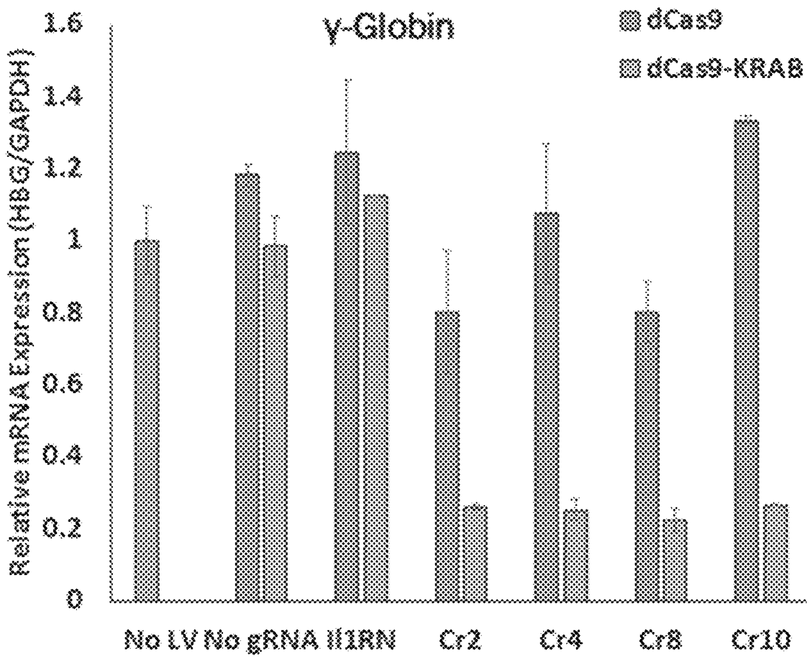
Figure 57C:
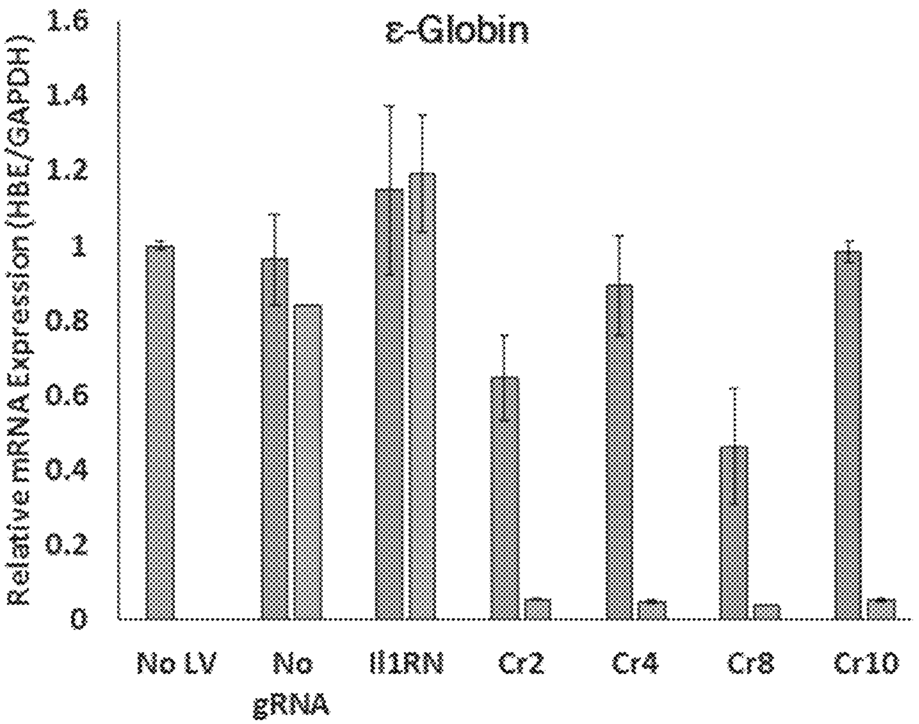
Figure 57D:
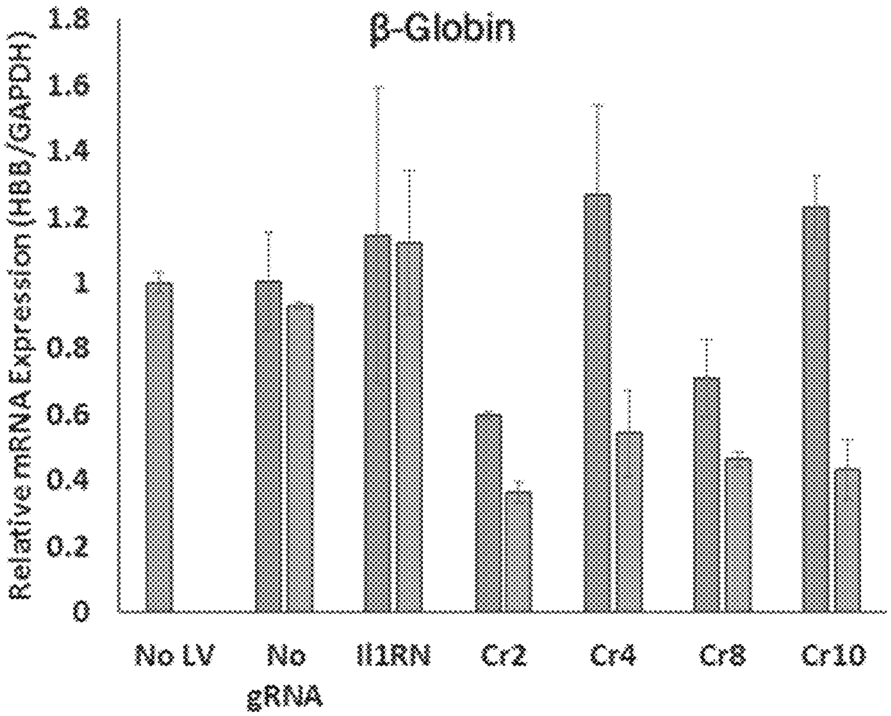

Stable Silencing of Globin Genes by dCas9-KRAB.

dCas9/dCas9-KRAB were co-expressed with single gRNAs lentivirally in K562s (FIG. 57A). Cells that were not treated with lentivirus (NT), treated with dCas9/dCas9-KRAB without a gRNA (no gRNA), and with dCas9/dCas9-KRAB and gRNA targeting a different locus (IL1RN) were included as controls. Cells treated with lentivirus were selected from days 4 to 7. Multiple gRNAs effected potent transcriptional repression of ε-, γ-, and β-globin genes when assayed 7 days after transduction, with up to 95% knockdown achieved (FIGS. 57B, 57C, 57D). Expression of ε-globin was silenced the most in response gRNAs targeted to the HS2 enhancer. Treatment with dCas9-KRAB with a gRNA resulted in dramatically more repression than treatment with dCas9 and gRNA.

These findings demonstrate that dCas9-KRAB targeted to the HS2 enhancer by gRNAs effects potent repression of the distal globin genes. This is the first example of targeted epigenetic control of distal regulatory elements in mammalian cells by the CRISPR/Cas9 system. Enhancers regulate development and disease, and this disclosure provides a method to probe and control enhancer function and may be used to determine the effects of dCas9-KRAB on local chromatin accessibility and genome-wide expression.

Example 23 dCas9-p300

Figure 59:
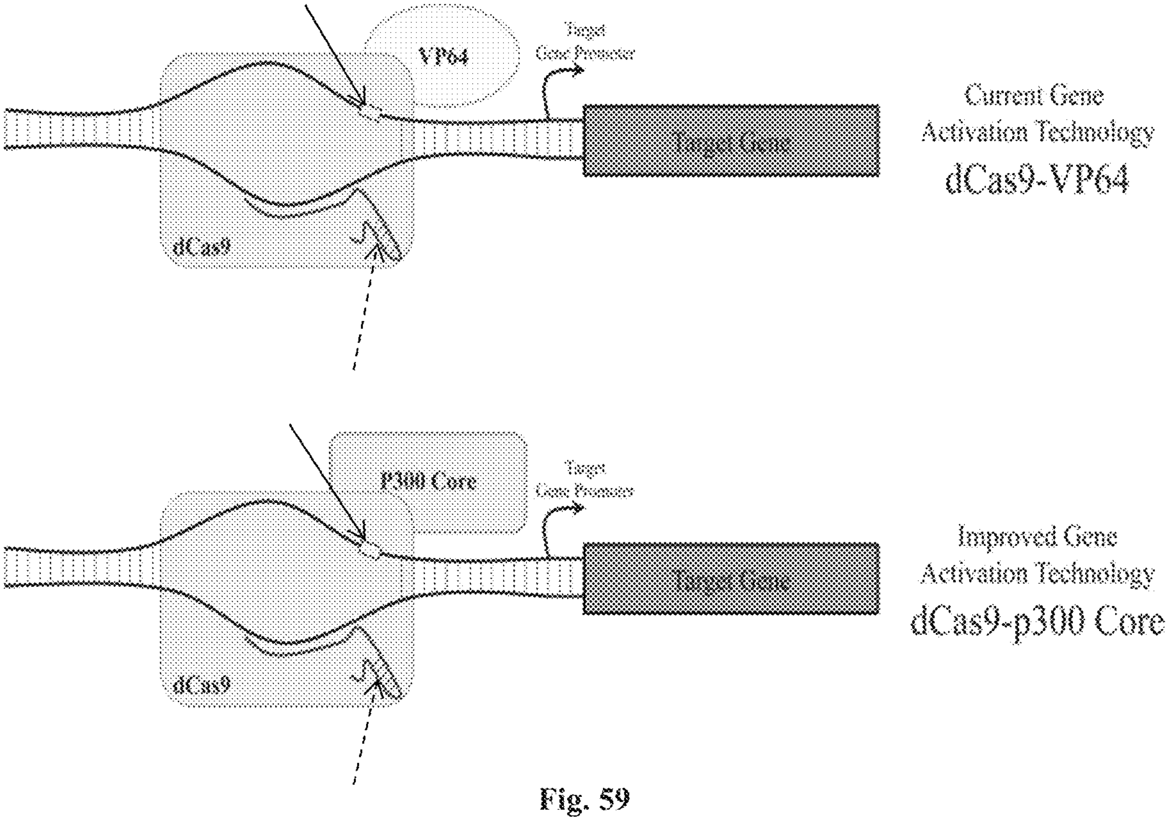
FIG. 59 shows a simplified schematic of *S. pyogenes* dCas9-VP64 fusion (top) and dCas9-p300 core fusion (bottom). The Protospacer Adjacent Motifs (PAM) are shown with arrows at target gene loci and synthetic guide RNA (gRNA) is shown with hatched arrows.

A dCas9-p300 fusion protein was designed and compared to dCas9-VP64 fusion protein (see FIG. 59). The amino acid constructs of dCas9 constructions are shown in FIG. 61A-61C. Cells from the Human Embryonic Kidney tissue culture line HEK293T (ATCC; CRL-11268) were seeded at a density of 1.5e5 cells per well in 24-well tissue culture dishes one day prior to transfection with Lipofectamine 2000 transfection reagent (Life Technologies). 24 hrs later cells were transfected with 1 μL Lipofectamine 2000, 375 ng dCas9 expression construct (dCas9, dCas9VP64, or dCas9p300 respectively), and 125 ng of pooled gRNA expression plasmids 4 each at equimolar ratios). Table 13 shows the RNA information.

TABLE 13 gRNA information

| Target Location | Protospacer Sequence (5'-3') | Genomic Location (GRCh38 Primary Assembly) | Reference |
|---|---|---|---|
| IL1RN Promoter | TGTACTCTCTGAGGTGCTC (SEQ ID NO: 606) | Chr2: 113117865-113117883 | Perez-Pinera et al., Nat Methods, 2013 |
| IL1RN Promoter | ACGCAGATAAGAACCAGTT (SEQ ID NO: 607) | Chr2: 113117714-113117732 | Perez-Pinera et al., Nat Methods, 2013 |
| IL1RN Promoter | CATCAAGTCAGCCATCAGC (SEQ ID NO: 608) | Chr2: 113117781-113117799 | Perez-Pinera et al., Nat Methods, 2013 |
| IL1RN Promoter | GAGTCACCCTCCTGGAAAC (SEQ ID NO: 609) | Chr2: 113117749-113117767 | Perez-Pinera et al., Nat Methods, 2013 |
| MyoD Promoter | CCTGGGCTCCGGGGCGTTT (SEQ ID NO: 610) | Chr11: 17719509-17719527 | Perez-Pinera et al., Nat Methods, 2013 |
| MyoD Promoter | GGCCCCTGCGGCCACCCCG (SEQ ID NO: 611) | Chr11: 17719422-17719440 | Perez-Pinera et al., Nat Methods, 2013 |
| MyoD Promoter | CTCCCTCCCTGCCCGGTAG (SEQ ID NO: 612) | Chr11: 17719350-17719368 | Perez-Pinera et al., Nat Methods, 2013 |
| MyoD Promoter | AGGTTTGGAAAGGGCGTGC (SEQ ID NO: 613) | Chr11: 17719290-17719308 | Perez-Pinera et al., Nat Methods, 2013 |

TABLE 13-continued

| gRNA information | | | |
|---|---|---|---|
| Target Location | Protospacer Sequence (5'-3') | Genomic Location (GRCh38 Primary Assembly) | Reference |
| Oct4 Promoter | ACTCCACTGCACTCCAGTCT (SEQ ID NO: 614) | Chr6:31170953-31170934 | Hu et al Nucleic Acids Res, 2014 |
| Oct4 Promoter | TCTGTGGGGGACCTGCACTG (SEQ ID NO: 615) | Chr6:31170885-31170866 | Hu et al Nucleic Acids Res, 2014 |
| Oct4 Promoter | GGGGCGCCAGTTGTGTCTCC (SEQ ID NO: 616) | Chr6:31170855-31170836 | Hu et al Nucleic Acids Res, 2014 |
| Oct4 Promoter | ACACCATTGCCACCACCATT (SEQ ID NO: 617) | Chr6:31170816-31170797 | Hu et al Nucleic Acids Res, 2014 |

The 3 days post-transfection cells were harvested and assayed by RT-QPCR for mRNA expression. The RT-QPCR primer sequences are listed in Table 14.

TABLE 14

| RT-QPCR Primers | | |
|---|---|---|
| Primer Target | Primer Sequence (5'-3') | Reference |
| GAPDH Forward | CAATGACCCCTTCATTGACC (SEQ ID NO: 618) | Perez-Pinera et al., Nat Methods, 2013 |
| GAPDH Reverse | TTGATTTTGGAGGGATCTCG (SEQ ID NO: 619) | Perez-Pinera et al., Nat Methods, 2013 |
| IL1RN Forward | GGAATCCATGGAGGGAAGAT (SEQ ID NO: 620) | Perez-Pinera et al., Nat Methods, 2013 |
| IL1RN Reverse | TGTTCTCGCTCAGGTCAGTG (SEQ ID NO: 621) | Perez-Pinera et al., Nat Methods, 2013 |
| MyoD Forward | CTCTCTGCTCCTTTGCCACA (SEQ ID NO: 622) | Perez-Pinera et al., Nat Methods, 2013 |
| MyoD Reverse | GTGCTCTTCGGGTTTCAGGA (SEQ ID NO: 623) | Perez-Pinera et al., Nat Methods, 2013 |
| Oct4 Forward | CGAAAGAGAAAGCGAACCAGTATCGAGAAC (SEQ ID NO: 624) | Hu et al., Nucleic Acids Res, 2014 |
| Oct4 Reverse | CGTTGTGCATAGTCGCTGCTTGATCGC (SEQ ID NO: 625) | Hu et al., Nucleic Acids Res, 2014 |

Figure 60A:
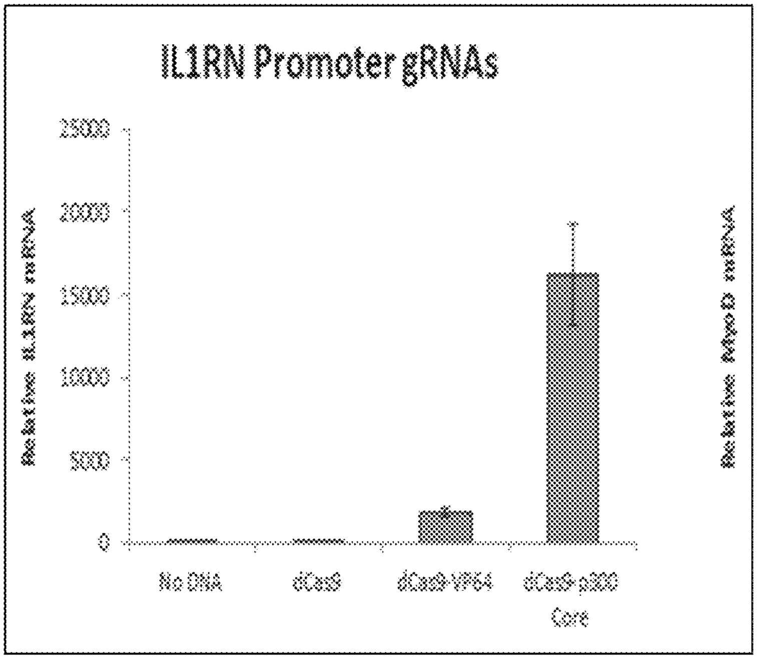
FIGS. 60A-60C show representative data at three human loci demonstrating the efficacy of activation using dCas9-p300 in relation to dCas9-VP64 and dCas9 without any fused effector domain in the human 293T cell culture line.
Figure 60B:
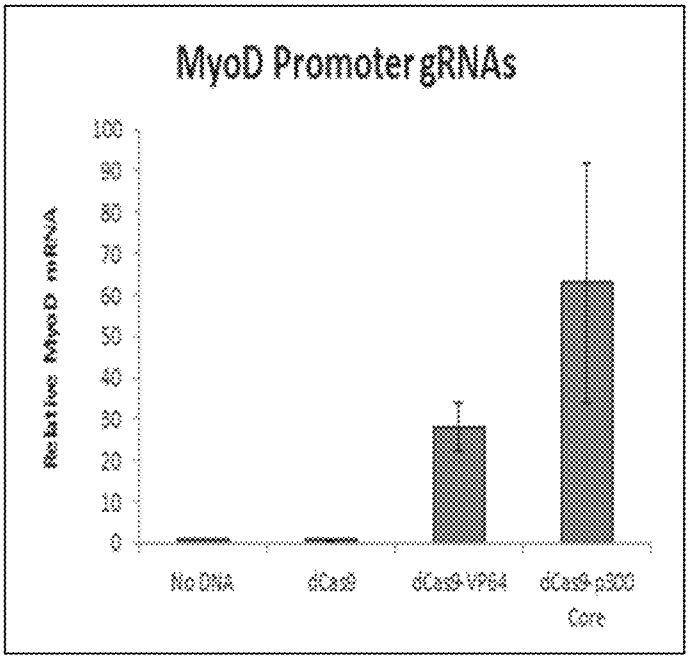
Figure 60C:
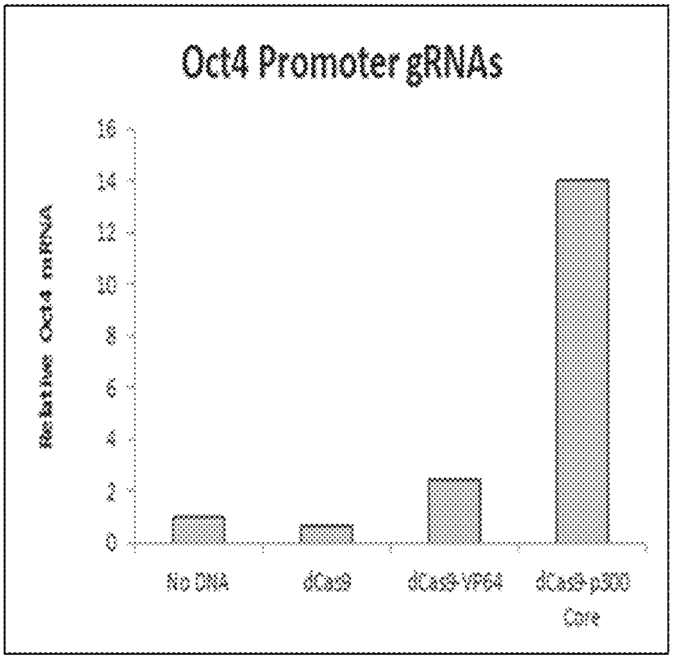

RT-QPCR was normalized to GAPDH expression using the $\Delta\Delta C_t$ method. Results are expressed as fold-increase expression of the gene of interest relative to cells treated with Lipofectamine only without DNA transfected ("No DNA") (See FIGS. 60A-60C).

Figure 62:
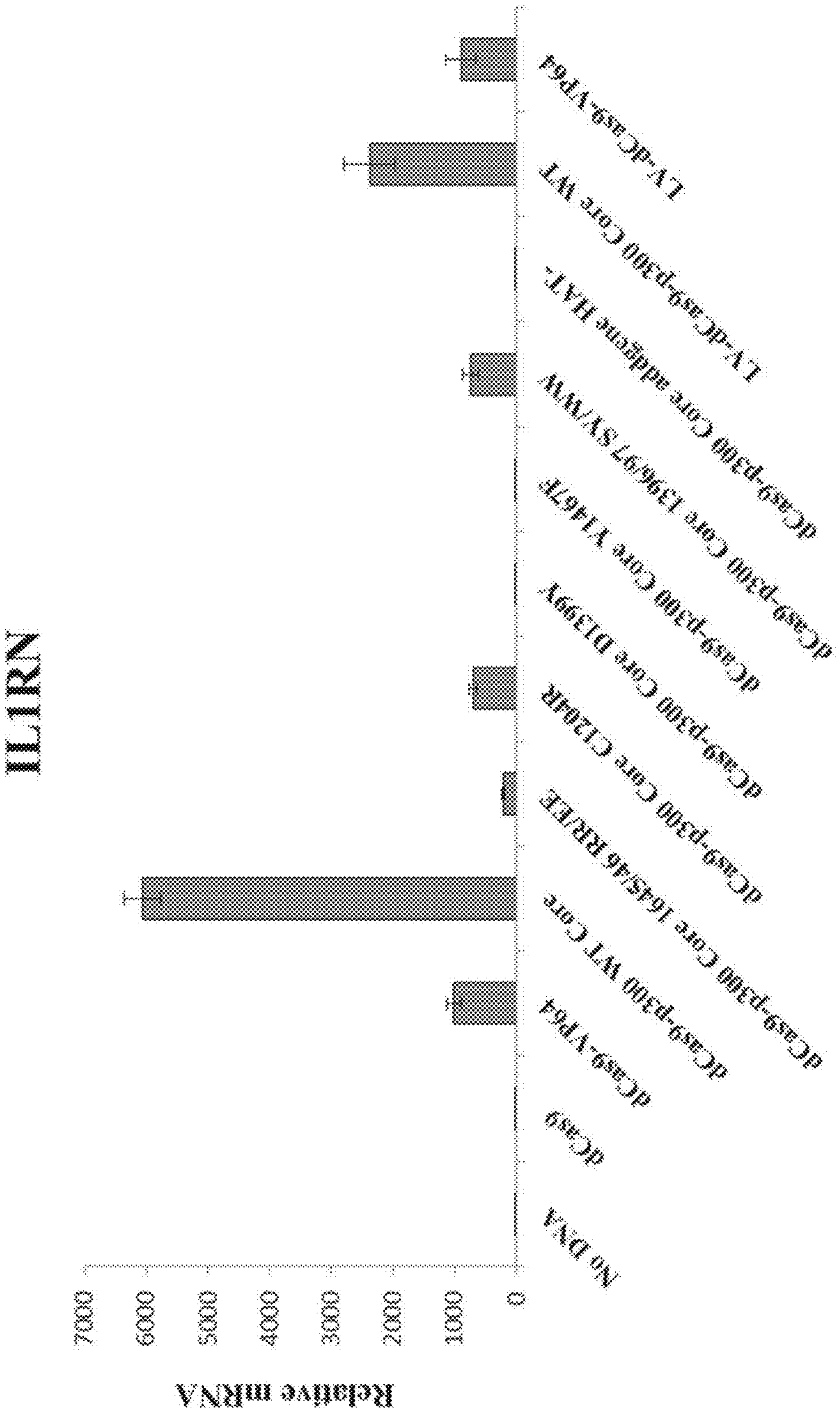
FIG. 62 shows that HAT-dCase9-p300 fusion proteins fail to activate gene expression.
Figure 63A:
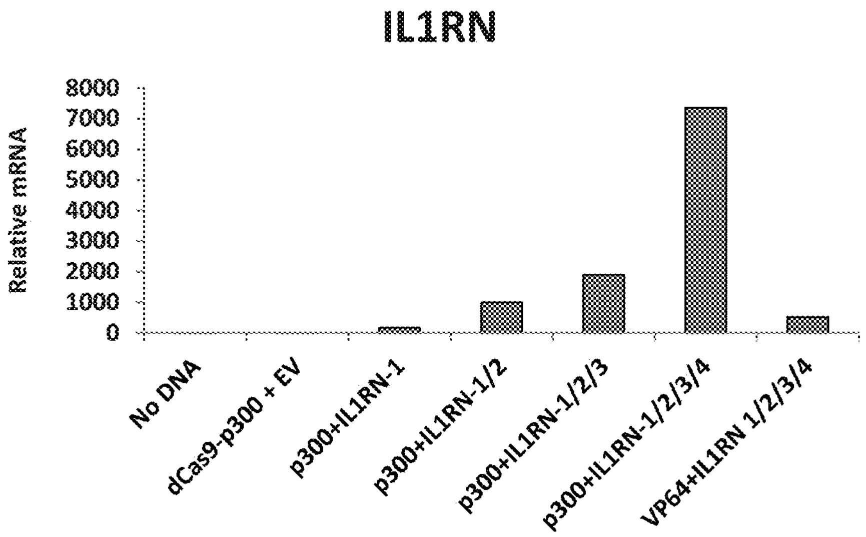
FIGS. 63A-63B show that gRNA’s also act synergistically with dCas9-p300 Core.
Figure 63B:
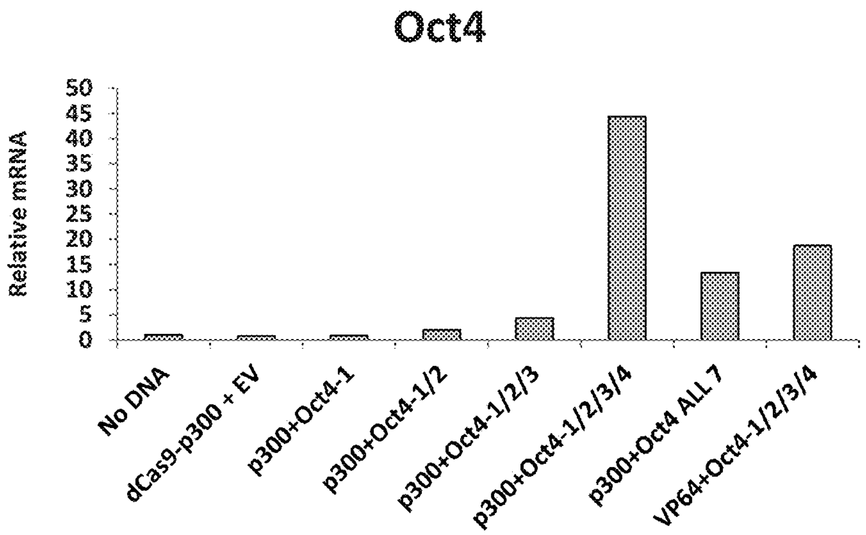

FIG. 62 shows that mutating residues in the p300 HAT domain causes a loss of its ability to activate gene expression. FIGS. 63A-63B show that multiple gRNAs work synergistically with dCas-9-p300, as showed with dCas-9-VP64.

Example 24

Figures 64A, 64B, 64C:
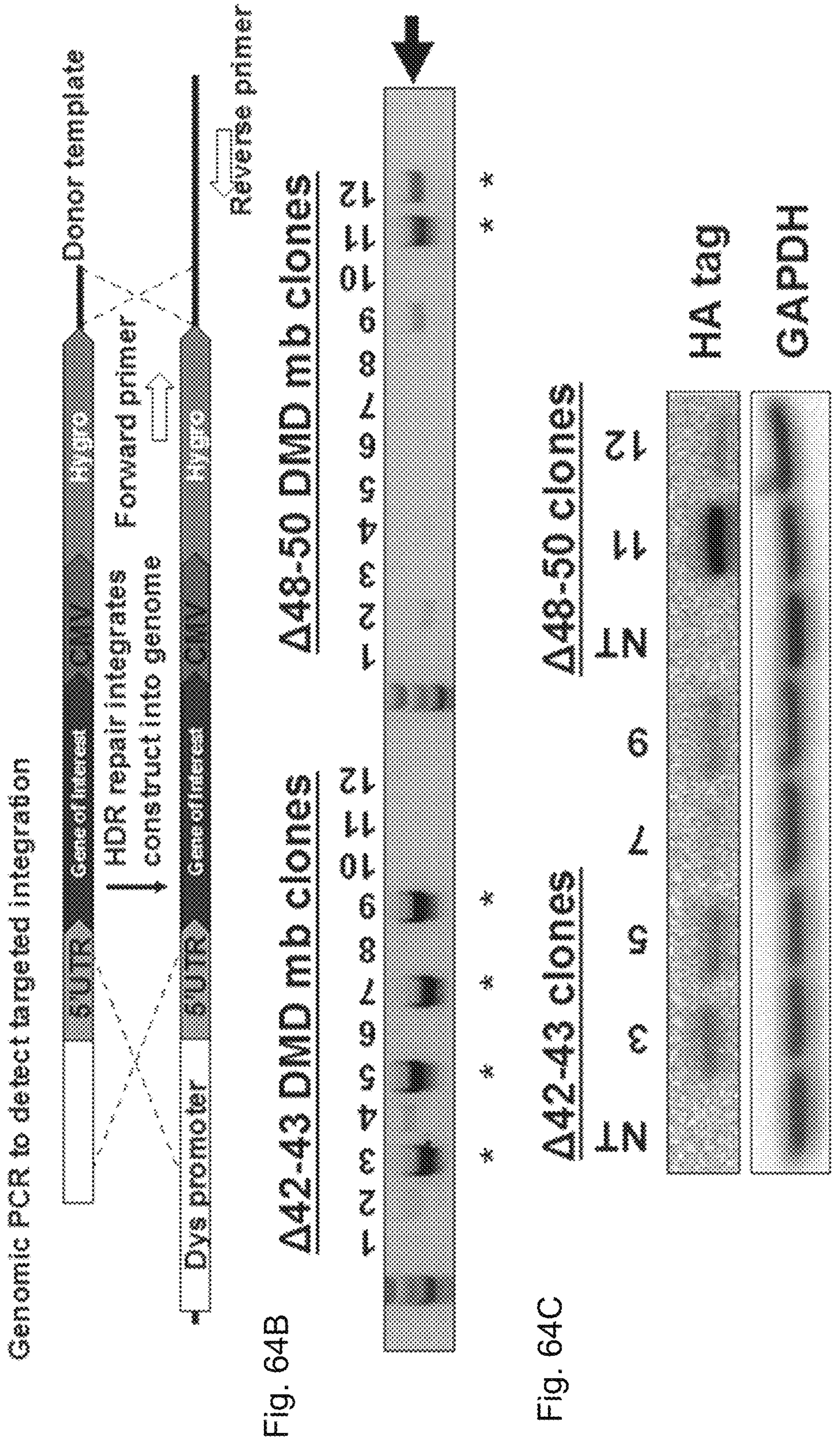
FIGS. 64A-64C show TALEN mediated integration of minidystrophin at the 5'UTR of the Dp427m skeletal muscle isoform of dystrophin in skeletal myoblast cell lines derived from human DMD patients carrying different deletions in the dystrophin gene. DMD patient cells were electroporated with constructs encoding a TALEN pair active at the 5'UTR locus and a donor template carrying the minidystrophin gene.

FIGS. 64A-64C show TALEN mediated integration of minidystrophin at the 5'UTR of the Dp427m skeletal muscle isoform of dystrophin in skeletal myoblast cell lines derived from human DMD patients carrying different deletions in the dystrophin gene. DMD patient cells were electroporated with constructs encoding a TALEN pair active at the 5'UTR locus and a donor template carrying the minidystrophin gene. FIG. 64A shows a schematic of how minidystrophin was integrated into the 5'UTR. FIG. 64B shows that hygromycin-resistant clonal cell lines were isolated and screened by PCR for successful site-specific integrations at the 5'UTR using the primers shown in FIG. 64A. Asterisks indicate clones selected for further analysis in FIG. 64C. FIG. 64C shows that clonally isolated DMD myoblasts with detected integration events were differentiated for 6 days and assessed for expression of an HA tag fused to the C terminus of minidystrophin.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

APPENDIX hCas9-T2A-GFP DNA sequence: SEQ ID NO: 145 (SpCas9 human optimized sequence, *HA tag*, T2A peptide, eGFP sequence)

gccaccATGGACAAGAAGTACTCCATTGGGCTCGATATCGGCACAAACAGCGTCGGCTGGGCCGTCATTACGGACGAGTA
CAAGGTGCCGAGCAAAAAATTCAAAGTTCTGGGCAATACCGATCGCCACAGCATAAAGAAGAACCTCATTGGCGCCCTCC
TGTTCGACTCCGGGGAGACGGCCGAAGCCACGCGGCTCAAAAGAACAGCACGGCGCAGATATACCCGCAGAAAGAATCGG
ATCTGCTACCTGCAGGAGATCTTTAGTAATGAGATGGCTAAGGTGGATGACTCTTTCTTCCATAGGCTGGAGGAGTCCTT
TTTGGTGGAGGAGGATAAAAAGCACGAGCGCCACCCAATCTTTGGCAATATCGTGGACGAGGTGGCGTACCATGAAAAGT
ACCCAACCATATATCATCTGAGGAAGAAGCTTGTAGACAGTACTGATAAGGCTGACTTGCGGTTGATCTATCTCGCGCTG
GCGCATATGATCAAATTTCGGGGACACTTCCTCATCGAGGGGGACCTGAACCCAGACAACAGCGATGTCGACAAACTCTT
TATCCAACTGGTTCAGACTTACAATCAGCTTTTCGAAGAGAACCCGATCAACGCATCCGGAGTTGACGCCAAAGCAATCC
TGAGCGCTAGGCTGTCCAAATCCCGGCGGCTCGAAAACCTCATCGCACAGCTCCCTGGGGAGAAGAAGAACGGCCTGTTT
GGTAATCTTATCGCCCTGTCACTCGGGCTGACCCCCAACTTTAAATCTAACTTCGACCTGGCCGAAGATGCCAAGCTTCA
ACTGAGCAAAGACACCTACGATGATGATCTCGACAATCTGCTGGCCCAGATCGGCGACCAGTACGCAGACCTTTTTTTGG
CGGCAAAGAACCTGTCAGACGCCATTCTGCTGAGTGATATTCTGCGAGTGAACACGGAGATCACCAAAGCTCCGCTGAGC
GCTAGTATGATCAAGCGCTATGATGAGCACCACCAAGACTTGACTTTGCTGAAGGCCCTTGTCAGACAGCAACTGCCTGA
GAAGTACAAGGAAATTTTCTTCGATCAGTCTAAAAATGGCTACGCCGGATACATTGACGGCGGAGCAAGCCAGGAGGAAT
TTTACAAATTTATTAAGCCCATCTTGGAAAAAATGGACGGCACCGAGGAGCTGCTGGTAAAGCTTAACAGAGAAGATCTG
TTGCGCAAACAGCGCACTTTCGACAATGGAAGCATCCCCCACCAGATTCACCTGGGCGAACTGCACGCTATCCTCAGGCG
GCAAGAGGATTTCTACCCCTTTTTGAAAGATAACAGGGAAAAGATTGAGAAAATCCTCACATTTCGGATACCCTACTATG
TAGGCCCCCTCGCCCGGGGAAATTCCAGATTCGCGTGGATGACTCGCAAATCAGAAGAGACCATCACTCCCTGGAACTTC
GAGGAAGTCGTGGATAAGGGGGCCTCTGCCCAGTCCTTCATCGAAAGGATGACTAACTTTGATAAAAATCTGCCTAACGA
AAAGGTGCTTCCTAAACACTCTCTGCTGTACGAGTACTTCACAGTTTATAACGAGCTCACCAAGGTCAAATACGTCACAG
AAGGGATGAGAAAGCCAGCATTCCTGTCTGGAGAGCAGAAGAAAGCTATCGTGGACCTCCTCTTCAAGACGAACCGGAAA
GTTACCGTGAAACAGCTCAAAGAAGACTATTTCAAAAAGATTGAATGTTTCGACTCTGTTGAAATCAGCGGAGTGGAGGA
TCGCTTCAACGCATCCCTGGGAACGTATCACGATCTCCTGAAAATCATTAAAGACAAGGACTTCCTGGACAATGAGGAGA
ACGAGGACATTCTTGAGGACATTGTCCTCACCCTTACGTTGTTTGAAGATAGGGAGATGATTGAAGAACGCTTGAAAACT
TACGCTCATCTCTTCGACGACAAAGTCATGAAACAGCTCAAGAGGCGCCGATATACAGGATGGGGGCGGCTGTCAAGAAA
ACTGATCAATGGGATCCGAGACAAGCAGAGTGGAAAGACAATCCTGGATTTTCTTAAGTCCGATGGATTTGCCAACCGGA
ACTTCATGCAGTTGATCCATGATGACTCTCTCACCTTTAAGGAGGACATCCAGAAAGCACAAGTTTCTGGCCAGGGGGAC
AGTCTTCACGAGCACATCGCTAATCTTGCAGGTAGCCCAGCTATCAAAAAGGGAATACTGCAGACCGTTAAGGTCGTGGA
TGAACTCGTCAAAGTAATGGGAAGGCATAAGCCCGAGAATATCGTTATCGAGATGGCCCGAGAGAACCAAACTACCCAGA
AGGGACAGAAGAACAGTAGGGAAAGGATGAAGAGGATTGAAGAGGGTATAAAAGAACTGGGGTCCCAAATCCTTAAGGAA
CACCCAGTTGAAAACACCCAGCTTCAGAATGAGAAGCTCTACCTGTACTACCTGCAGAACGGCAGGGACATGTACGTGGA
TCAGGAACTGGACATCAATCGGCTCTCCGACTACGACGTGGATCATATCGTGCCCCAGTCTTTTCTCAAAGATGATTCTA
TTGATAATAAAGTGTTGACAAGATCCGATAAAAATAGAGGGAAGAGTGATAACGTCCCCTCAGAAGAAGTTGTCAAGAAA
ATGAAAAATTATTGGCGGCAGCTGCTGAACGCCAAACTGATCACACAACGGAAGTTCGATAATCTGACTAAGGCTGAACG
AGGTGGCCTGTCTGAGTTGGATAAAGCCGGCTTCATCAAAAGGCAGCTTGTTGAGACACGCCAGATCACCAAGCACGTGG
CCCAAATTCTCGATTCACGCATGAACACCAAGTACGATGAAAATGACAAACTGATTCGAGAGGTGAAAGTTATTACTCTG
AAGTCTAAGCTGGTCTCAGATTTCAGAAAGGACTTTCAGTTTTATAAGGTGAGAGAGATCAACAATTACCACCATGCGCA
TGATGCCTACCTGAATGCAGTGGTAGGCACTGCACTTATCAAAAAATATCCCAAGCTTGAATCTGAATTTGTTTACGGAG
ACTATAAAGTGTACGATGTTAGGAAAATGATCGCAAAGTCTGAGCAGGAAATAGGCAAGGCCACCGCTAAGTACTTCTTT
TACAGCAATATTATGAATTTTTTCAAGACCGAGATTACACTGGCCAATGGAGAGATTCGGAAGCGACCACTTATCGAAAC
AAACGGAGAAACAGGAGAAATCGTGTGGGACAAGGGTAGGGATTTCGCGACAGTCCGGAAGGTCCTGTCCATGCCGCAGG
TGAACATCGTTAAAAAGACCGAAGTACAGACCGGAGGCTTCTCCAAGGAAAGTATCCTCCCGAAAAGGAACAGCGACAAG
CTGATCGCACGCAAAAAAGATTGGGACCCCAAGAAATACGGCGGATTCGATTCTCCTACAGTCGCTTACAGTGTACTGGT
TGTGGCCAAAGTGGAGAAAGGGAAGTCTAAAAAACTCAAAAGCGTCAAGGAACTGCTGGGCATCACAATCATGGAGCGAT
CAAGCTTCGAAAAAAACCCCATCGACTTTCTCGAGGCGAAAGGATATAAAGAGGTCAAAAAAGACCTCATCATTAAGCTT
CCCAAGTACTCTCTCTTTGAGCTTGAAAACGGCCGGAAACGAATGCTCGCTAGTGCGGGCGAGCTGCAGAAAGGTAACGA
GCTGGCACTGCCCTCTAAATACGTTAATTTCTTGTATCTGGCCAGCCACTATGAAAAGCTCAAAGGGTCTCCCGAAGATA
ATGAGCAGAAGCAGCTGTTCGTGGAACAACACAAACACTACCTTGATGAGATCATCGAGCAAATAAGCGAATTCTCCAAA
AGAGTGATCCTCGCCGACGCTAACCTCGATAAGGTGCTTTCTGCTTACAATAAGCACAGGGATAAGCCCATCAGGGAGCA
GGCAGAAAACATTATCCACTTGTTTACTCTGACCAACTTGGGCGCGCCTGCAGCCTTCAAGTACTTCGACACCACCATAG
ACAGAAAGCGGTACACCTCTACAAAGGAGGTCCTGGACGCCACACTGATTCATCAGTCAATTACGGGGCTCTATGAAACA
AGAATCGACCTCTCTCAGCTCGGTGGAGACAGCAGGGCTGACCCCAAGAAGAAGAGGAAGGTGGCTAGCGAGGGCAGAGG
AAGTCTTCTAACATGCGGTGACGTGGAGGAGAATCCCGGCCCTGgtacC*gtgagcaagggcgaggagctgttcaccgggg*
*tggtgcccatcctggtcgagctggacggcgacgtaaacggccacaagttcagcgtgtccggcgagggcgagggcgatgcc*
*acctacggcaagctgaccctgaagttcatctgcaccaccggcaagctgcccgtgccctggcccaccctcgtgaccaccct*
*gacctacggcgtgcagtgcttcagccgctaccccgaccacatgaagcagcacgacttcttcaagtccgccatgcccgaag*
*gctacgtccaggagcgcaccatcttcttcaaggacgacggcaactacaagacccgcgccgaggtgaagttcgagggcgac*
*accctggtgaaccgcatcgagctgaagggcatcgacttcaaggaggacggcaacatcctggggcacaagctggagtacaa*
*ctacaacagccacaacgtctatatcatggccgacaagcagaagaacggcatcaaggtgaacttcaagatccgccacaaca*
*tcgaggacggcagcgtgcagctcgccgaccactaccagcagaacacccccatcggcgacggccccgtgctgctgcccgac*
*aaccactacctgagcacccagtccgccctgagcaaagaccccaacgagaagcgcgatcacatggtcctgctggagttcgt*
*gaccgccgccgggatcactctcggcatggacgagctgtacaag*AccggTTAG AAV/Rosa26 construct (SEQ ID NO: 456)

ggggggggggggggggggttggccactccctctctgcgcgctcgctcgctcactgaggccgggcgaccaaaggtcgcccg
acgcccgggctttgcccgggcggcctcagtgagcgagcgagcgcgcagagagggagtggccaactccatcactaggggtt
cctagatctgaattcggtacccgttacataacttacggtaaatggcccgcctggctgaccgcccaacgacccccgcccat
tgacgtcaataatgacgtatgttcccatagtaacgccaatagggactttccattgacgtcaatgggtggagtatttacgg
taaactgcccacttggcagtacatcaagtgtatcatatgccaagtacgcccccctattgacgtcaatgacggtaaatggcc APPENDIX-continued cgcctggcattatgcccagtacatgaccttatgggactttcctacttggcagtacatctacgtattagtcatcgctatta
ccatggtgatgcggttttggcagtacatcaatgggcgtggatagcggtttgactcacggggatttccaagtctccacccc
attgacgtcaatgggagtttgttttggcaccaaaatcaacgggactttccaaaatgtcgtaacaactccgccccattgac
gcaaatgggcggtaggcgtgtacggtgggaggtctatataagcagagctcgtttagtgaaccgtcagatcgcctggagac
gccatccacgctgttttgacctccatagaagacaccgggaccgatccagcctccggactctagaggatccggtactcgag
gaactgaaaaaccagaaagttaactggtaagtttagtctttttgtcttttatttcaggtcccggatccggtggtggtgca
aatcaaagaactgctcctcagtggatgttgcctttacttctaggcctgtacggaagtgttacttctgctctaaaagctgc
ggaattgtacccgcggcccgggatccaccggTGGCTAGCgtctataggcccaccccccTTGGTGGAATTCGCCATGAGGTC
TGACTACAAAGACCATGACGGTGATTATAAAGATCATGACATCGATTACAAGGATGACGATGACAAGATGGCCCCCAAGA
AGAAGaggaaggtgggcctcgaGCCCGGAGAAAAACCGTACAAGTGCCCTGAGTGCGGGAAATCATTCTCCGACCCTGGG
GCGCTCGTCCGGCACCAAAGGACGCATACAGGGGAAAAGCCGTATAAGTGCCCCGAGTGTGGAAAGAGCTTCTCGCAGAG
AGCCCACCTTGAACGACACCAAAGAACACACACTGGTGAGAAACCCTATAAGTGTCCAGAGTGCGGCAAATCGTTTAGCA
GATCCGATGACTTGGTGCGCCACCAGCGGACACACACGGGTGAAAAGCCCTACAAATGCCCGGAGTGTGGGAAGTCGTTT
TCAAGGTCGGATCATCTGACTACCCATCAGCGCACCCATACGGGAGCggccgcccgcgccctGGTGAAGAGCGAGCTGGA
GGAGAAGAAGTCCGAGCTGCGGCACAAGCTGAAGTACGTGCCCCACGAGTACATCGAGCTGATCGAGATCGCCAGGAACC
CCACCCAGGACCGCATCCTGGAGATGAAGGTGATGGAGTTCTTCATGAAGGTGTACGGCTACAGGGGAGAGCACCTGGGC
GGAAGCAGAAAGCCTGACGGCGCCATCTATACAGTGGGCAGCCCCATCGATTACGGCGTGATCGTGGACACAAAGGCCTA
CAGCGGCGGCTACAATCTGCCTATCGGCCAGGCCGACGAGATGCAGAGATACGTGAAGGAGAACCAGACCCGGAATAAGC
ACATCAACCCCAACGAGTGGTGGAAGGTGTACCCTAGCAGCGTGACCGAGTTCAAGTTCCTGTTCGTGAGCGGCCACTTC
AAGGGCAACTACAAGGCCCAGCTGACCAGGCTGAACCGCAAAACCAACTGCAATGGCGCCGTGCTGAGCGTGGAGGAGCT
GCTGATCGGCGGCGAGATGATCAAAGCCGGCACCCTGACACTGGAGGAGGTGCGGCGCAAGTTCAACAACGGCGAGATCA
ACTTCGAGGGCAGAGGAAGTCTTCTAACATGCGGTGACGTGGAGGAGAATCCCGGCCCTAgatcTGACTACAAAGACCAT
GACGGTGATTATAAAGATCATGACATCGATTACAAGGATGACGATGACAAGATGGCCCCCAAGAAGAAGaggaaggtggg
cctcgagccGGGAGAGAAGCCGTACAAGTGTCCCGAATGTGGAAAGAGCTTCTCACAGTCGGGGGACCTTCGGCGCCACC
AGCGCACACATACTGGTGAAAAGCCGTATAAGTGTCCAGAATGTGGCAAATCATTCTCCACATCAGGGAGCCTGGTCAGG
CACCAGCGAACCCACACGGGTGAGAAGCCCTATAAGTGCCCCGAATGCGGGAAGTCCTTTTCGCAGAGAGCCCACTTGGA
GAGGCACCAGAGGACCCATACGGGGGAGAAACCTTACAAGTGCCCTGAATGCGGAAAGTCGTTCTCGACCCATCTGGATC
TCATCAGACATCAGAGAACGCACACTGGAGAGAAACCCTACAAATGTCCCGAGTGTGGGAAGTCGTTTAGCCGAAAGGAC
AATCTCAAAAACCATCAACGGACACACACGGGTGAAAAACCATACAAATGCCCGGAGTGCGGCAAATCGTTTTCCCAACT
TGCGCACTTGCGGGCACACCAACGCACGCATACTGGAGCGGCCGCccgcgcccCTGGTGAAGAGCGAGCTGGAGGAGAAGA
AGTCCGAGCTGCGGCACAAGCTGAAGTACGTGCCCCACGAGTACATCGAGCTGATCGAGATCGCCAGGAACCCCACCCAG
GACCGCATCCTGGAGATGAAGGTGATGGAGTTCTTCATGAAGGTGTACGGCTACAGGGGAGAGCACCTGGGCGGAAGCAG
AAAGCCTGACGGCGCCATCTATACAGTGGGCAGCCCCATCGATTACGGCGTGATCGTGGACACAAAGGCCTACAGCGGCG
GCTACAATCTGCCTATCGGCCAGGCCGACGAGATGGAGAGATACGTGGAGGAGAACCAGACACGGGATAAGCACCTCAAC
CCCAACGAGTGGTGGAAGGTGTACCCTAGCAGCGTGACCGAGTTCAAGTTCCTGTTCGTGAGCGGCCACTTCAAGGGCAA
CTACAAGGCCCAGCTGACCAGGCTGAACCACATCACCAACTGCAATGGCGCCGTGCTGAGCGTGGAGGAGCTGCTGATCG
GCGGCGAGATGATCAAAGCCGGCACCCTGACACTGGAGGAGGTGCGGCGCAAGTTCAACAACGGCGAGATCAACTTCTGA
TTAATTAACTAATCTAGAGTcgactagagctcgctgatcagcctcgactgtgccttctagttgccagccatctgttgttt
gcccctcccccgtgccttccttgaccctggaaggtgccactcccactgtcctttcctaataaaatgaggaaattgcatcg
cattgtctgagtaggtgtcattctattctggggggtggggtggggcaggacagcaagggggaggattgggaagacaatag
caggcatgctggggagagatctaggaacccctagtgatggagttggccactccctctctgcgcgctcgctcgctcactga
ggccgcccgggcaaagcccgggcgtcgggcgacctttggtcgcccggcctcagtgagcgagcgagcgcgcagagagggag
tggccaaccccccccccccccccctgcagcccagctgcattaatgaatcggccaacgcgcggggagaggcggtttgcgt
attgggcgctcttccgcttcctcgctcactgactcgctgcgctcggtcgttcggctgcggcgagcggtatcagctcactc
aaaggcggtaatacggttatccacagaatcaggggataacgcaggaaagaacatgtgagcaaaaggccagcaaaaggcca
ggaaccgtaaaaaggccgcgttgctggcgtttttccataggctccgcccccctgacgagcatcacaaaaatcgacgctca
agtcagaggtggcgaaacccgacaggactataaagataccaggcgtttccccctggaagctccctcgtgcgctctcctgt
tccgaccctgccgcttaccggatacctgtccgcctttctcccttcgggaagcgtggcgctttctcaatgctcacgctgta
ggtatctcagttcggtgtaggtcgttcgctccaagctgggctgtgtgcacgaaccccccgttcagcccgaccgctgcgcc
ttatccggtaactatcgtcttgagtccaacccggtaagacacgacttatcgccactggcagcagccactggtaacaggat
tagcagagcgaggtatgtaggcggtgctacagagttcttgaagtggtggcctaactacggctacactagaaggacagtat
ttggtatctgcgctctgctgaagccagttaccttcggaaaaagagttggtagctcttgatccggcaaacaaaccaccgct
ggtagcggtggtttttttgtttgcaagcagcagattacgcgcagaaaaaaaggatctcaagaagatcctttgatcttttc
tacggggtctgacgctcagtggaacgaaaactcacgttaagggattttggtcatgagattatcaaaaaggatcttcacct
agatccttttaaattaaaaatgaagttttaaatcaatctaaagtatatatgagtaaacttggtctgacagttaccaatgc
ttaatcagtgaggcacctatctcagcgatctgtctatttcgttcatccatagttgcctgactccccgtcgtgtagataac
tacgatacgggagggcttaccatctggccccagtgctgcaatgataccgcgagacccacgctcaccggctccagatttat
cagcaataaaccagccagccggaagggccgagcgcagaagtggtcctgcaactttatccgcctccatccagtctattaat
tgttgccgggaagctagagtaagtagttcgccagttaatagtttgcgcaacgttgttgccattgctacaggcatcgtggt
gtcacgctcgtcgtttggtatggcttcattcagctccggttcccaacgatcaaggcgagttacatgatcccccatgttgt
gcaaaaaagcggttagctccttcggtcctccgatcgttgtcagaagtaagttggccgcagtgttatcactcatggttatg
gcagcactgcataattctcttactgtcatgccatccgtaagatgcttttctgtgactggtgagtactcaaccaagtcatt
ctgagaatagtgtatgcggcgaccgagttgctcttgcccggcgtcaatacgggataataccgcgccacatagcagaactt
taaaagtgctcatcattggaaaacgttcttcggggcgaaaactctcaaggatcttaccgctgttgagatccagttcgatg
taacccactcgtgcacccaactgatcttcagcatcttttactttcaccagcgtttctgggtgagcaaaaacaggaaggca
aaatgccgcaaaaaagggaataagggcgacacggaaatgttgaatactcatactcttcctttttcaatattattgaagca
tttatcagggttattgtctcatgagcggatacatatttgaatgtatttagaaaaataaacaaataggggttccgcgcaca
tttccccgaaaagtgccacctgacgtctaagaaaccattattatcatgacattaacctataaaaataggcgtatcacgag
gccctttcgtctcgcgcgtttcggtgatgacggtgaaaacctctgacacatgcagctcccggagacggtcacagcttgtc
tgtaagcggatgccgggagcagacaagcccgtcagggcgcgtcagcgggtgttggcgggtgtcggggctggcttaactat
gcggcatcagagcagattgtactgagagtgcaccatatgcggtgtgaaataccgcacagatgcgtaaggagaaaataccg
catcaggaaattgtaaacgttaatattttgttaaaattcgcgttaaatttttgttaaatcagctcattttttaaccaata
ggccgaaatcggcaaaatcccttataaatcaaaagaatagaccgagatagggttgagtgttgttccagtttggaacaaga
gtccactattaaagaacgtggactccaacgtcaaagggcgaaaaaccgtctatcagggcgatggcccactacgtgaacca
tcaccctaatcaagttttttggggtcgaggtgccgtaaagcactaaatcggaaccctaaagggagcccccgatttagagc
ttgacggggaaagccggcgaacgtggcgagaaaggaagggaagaaagcgaaaggagcgggcgctagggcgctggcaagtg
tagcggtcacgctgcgcgtaaccaccacacccgccgcgcttaatgcgccgctacagggcgcgtcgcgccattcgccattc
aggctacgcaactgttgggaagggcgatcggtgcgggcctcttcgctattacgccagctggctgca APPENDIX-continued HS2 Enhancer Target Sequence (SEQ ID NO: 467)
taagcttcagtttttccttagttcctgttacatttctgtgtgtctccattagtgacctcccatagtccaagcatgagcag
ttctggccaggcccctgtcggggtcagtgccccacccccgccttctggttctgtgtaaccttctaagcaaaccttctggc
tcaagcacagcaatgctgagtcatgatgagtcatgctgaggcttagggtgtgtgcccagatgttctcagcctagagtgat
gactcctatctgggtccccagcaggatgcttacagggcagatggcaaaaaaaaggagaagctgaccacctgactaaaact
ccacctcaaacggcatcataaagaaaatggatgcctgagacagaatgtgacatattctagaatatatt dSpCas9-KRAB Sequence (SEQ ID NO: 466)
ATGGACTACAAAGACCATGACGGTGATTATAAAGATCATGACATCGATTACAAGGATGACGATGACAAGatggccccccaa
gaagaagaggaaggtgggccgcggaATGGACAAGAAGTACTCCATTGGGCTCGCCATCGGCACAAACAGCGTCGGCTGGG
CCGTCATTACGGACGAGTACAAGGTGCCGAGCAAAAAATTCAAAGTTCTGGGCAATACCGATCGCCACAGCATAAAGAAG
AACCTCATTGGCGCCCTCCTGTTCGACTCCGGGGAAACCGCCGAAGCCACGCGGCTCAAAAGAACAGCACGGCGCAGATA
TACCCGCAGAAAGAATCGGATCTGCTACCtgcaGGAGATCTTTAGTAATGAGATGGCTAAGGTGGATGACTCTTTCTTCC
ATAGGCTGGAGGAGTCCTTTTTGGTGGAGGAGGATAAAAAGCACGAGCGCCACCCAATCTTTGGCAATATCGTGGACGAG
GTGGCGTACCATGAAAAGTACCCAACCATATATCATCTGAGGAAGAAGCTTGTAGACAGTACTGATAAGGCTGACTTGCG
GTTGATCTATCTCGCGCTGGCGCATATGATCAAATTTCGGGGACACTTCCTCATCGAGGGGGACCTGAACCCAGACAACA
GCGATGTCGACAAACTCTTTATCCAACTGGTTCAGACTTACAATCAGCTTTTCGAAGAGAACCCGATCAACGCATCCGGA
GTTGACGCCAAAGCAATCCTGAGCGCTAGGCTGTCCAAATCCCGGCGGCTCGAAAACCTCATCGCACAGCTCCCTGGGGA
GAAGAAGAACGGCCTGTTTGGTAATCTTATCGCCCTGTCACTCGGGCTGACCCCCAACTTTAAATCTAACTTCGACCTGG
CCGAAGATGCCAAGCTTCAACTGAGCAAAGACACCTACGATGATGATCTCGACAATCTGCTGGCCCAGATCGGCGACCAG
TACGCAGACCTTTTTTTGGCGGCAAAGAACCTGTCAGACGCCATTCTGCTGAGTGATATTCTGCGAGTGAACACGGAGAT
CACCAAAGCTCCGCTGAGCGCTAGTATGATCAAGCGCTATGATGAGCACCACCAAGACTTGACTTTGCTGAAGGCCCTTG
TCAGACAGCAACTGCCTGAGAAGTACAAGGAAATTTTCTTCGATCAGTCTAAAAATGGCTACGCCGGATACATTGACGGC
GGAGCAAGCCAGGAGGAATTTTACAAATTTATTAAGCCCATCTTGGAAAAAATGGACGGCACCGAGGAGCTGCTGGTAAA
GCTTAACAGAGAAGATCTGTTGCGCAAACAGCGCACTTTCGACAATGGAAGCATCCCCCACCAGATTCACCTGGGCGAAC
TGCACGCTATCCTCAGGCGGCAAGAGGATTTCTACCCCTTTTTGAAAGATAACAGGGAAAAGATTGAGAAAATCCTCACA
TTTCGGATACCCTACTATGTAGGCCCCCTCGCCCGGGGAAATTCCAGATTCGCGTGGATGACTCGCAAATCAGAAGAGAC
CATCACTCCCTGGAACTTCGAGGAAGTCGTGGATAAGGGGGCCTCTGCCCAGTCCTTCATCGAAAGGATGACTAACTTTG
ATAAAAATCTGCCTAACGAAAAGGTGCTTCCTAAACACTCTCTGCTGTACGAGTACTTCACAGTTTATAACGAGCTCACC
AAGGTCAAATACGTCACAGAAGGGATGAGAAAGCCAGCATTCCTGTCTGGAGAGCAGAAGAAAGCTATCGTGGACCTCCT
CTTCAAGACGAACCGGAAAGTTACCGTGAAACAGCTCAAAGAAGACTATTTCAAAAAGATTGAATGTTTCGACTCTGTTG
AAATCAGCGGAGTGGAGGATCGCTTCAACGCATCCCTGGGAACGTATCACGATCTCCTGAAAATCATTAAAGACAAGGAC
TTCCTGGACAATGAGGAGAACGAGGACATTCTTGAGGACATTGTCCTCACCCTTACGTTGTTTGAAGATAGGGAGATGAT
TGAAGAACGCTTGAAAACTTACGCTCATCTCTTCGACGACAAAGTCATGAAACAGCTCAAGAGGCGCCGATATACAGGAT
GGGGGCGGCTGTCAAGAAAACTGATCAATGGgatcCGAGACAAGCAGAGTGGAAAGACAATCCTGGATTTTCTTAAGTCC
GATGGATTTGCCAACCGGAACTTCATGCAGTTGATCCATGATGACTCTCTCACCTTTAAGGAGGACATCCAGAAAGCACA
AGTTTCTGGCCAGGGGGACAGTCTTCACGAGCACATCGCTAATCTTGCAGGTAGCCCAGCTATCAAAAAGGGAATACTGC
AGACCGTTAAGGTCGTGGATGAACTCGTCAAAGTAATGGGAAGGCATAAGCCCGAGAATATCGTTATCGAGATGGCCCGA
GAGAACCAAACTACCCAGAAGGGACAGAAGAACAGTAGGGAAAGGATGAAGAGGATTGAAGAGGGTATAAAAGAACTGGG
GTCCCAAATCCTTAAGGAACACCCAGTTGAAAACACCCAGCTTCAGAATGAGAAGCTCTACCTGTACTACCTGCAGAACG
GCAGGGACATGTACGTGGATCAGGAACTGGACATCAATCGGCTCTCCGACTACGACGTGGATGCCATCGTGCCCCAGTCT
TTTCTCAAAGATGATTCTATTGATAATAAAGTGTTGACAAGATCCGATAAAAATAGAGGGAAGAGTGATAACGTCCCCTC
AGAAGAAGTTGTCAAGAAAATGAAAAATTATTGGCGGCAGCTGCTGAACGCCAAACTGATCACACAACGGAAGTTCGATA
ATCTGACTAAGGCTGAACGAGGTGGCCTGTCTGAGTTGGATAAAGCCGGCTTCATCAAAAGGCAGCTTGTTGAGACACGC
CAGATCACCAAgcacGTGGCCCAAATTCTCGATTCACGCATGAACACCAAGTACGATGAAAATGACAAACTGATTCGAGA
GGTGAAAGTTATTACTCTGAAGTCTAAGCTGGTCTCAGATTTCAGAAAGGACTTTCAGTTTTATAAGGTGAGAGAGATCA
ACAATTACCACCATGCGCATGATGCCTACCTGAATGCAGTGGTAGGCACTGCACTTATCAAAAAATATCCCAAGCTTGAA
TCTGAATTTGTTTACGGAGACTATAAAGTGTACGATGTTAGGAAAATGATCGCAAAGTCTGAGCAGGAAATAGGCAAGGC
CACCGCTAAGTACTTCTTTTACAGCAATATTATGAATTTTTTCAAGACCGAGATTACACTGGCCAATGGAGAGATTCGGA
AGCGACCACTTATCGAAACAAACGGAGAAACAGGAGAAATCGTGTGGGACAAGGGTAGGGATTTCGCGACAGTCCGGAAG
GTCCTGTCCATGCCGCAGGTGAACATCGTTAAAAAGACCGAAGTACAGACCGGAGGCTTCTCCAAGGAAAGTATCCTCCC
GAAAAGGAACAGCGACAAGCTGATCGCACGCAAAAAAGATTGGGACCCCAAGAAATACGGCGGATTCGATTCTCCTACAG
TCGCTTACAGTGTACTGGTTGTGGCCAAAGTGGAGAAAGGGAAGTCTAAAAAACTCAAAAGCGTCAAGGAACTGCTGGGC
ATCACAATCATGGAGCGATCAAGCTTCGAAAAAAACCCCATCGACTTTCTCGAGGCGAAAGGATATAAAGAGGTCAAAAA
AGACCTCATCATTAAGCTTCCCAAGTACTCTCTCTTTGAGCTTGAAAACGGCCGGAAACGAATGCTCGCTAGTGCGGGCG
AGCTGCAGAAAGGTAACGAGCTGGCACTGCCCTCTAAATACGTTAATTTCTTGTATCTGGCCAGCCACTATGAAAAGCTC
AAAGGGTCTCCCGAAGATAATGAGCAGAAGCAGCTGTTCGTGGAACAACACAAACACTACCTTGATGAGATCATCGAGCA
AATAAGCGAATTCTCCAAAAGAGTGATCCTCGCCGACGCTAACCTCGATAAGGTGCTTTCTGCTTACAATAAGCACAGGG
ATAAGCCCATCAGGGAGCAGGCAGAAAACATTATCCACTTGTTTACTCTGACCAACTTGGGCGCGCCTGCAGCCTTCAAG
TACTTCGACACCACCATAGACAGAAAGCGGTACACCTCTACAAAGGAGGTCCTGGACGCCACACTGATTCATCAGTCAAT
TACGGGGCTCTATGAAACAAGAATCGACCTCTCTCAGCTCGGTGGAGACAGCAGGGCTGACCCCAAGAAGAAGAGGAAGG
TGGctagCGATGCTAAGTCACTGACTGCCTGGTCCCGGACACTGGTGACCTTCAAGGATGTGTTTGTGGACTTCACCAGG
GAGGAGTGGAAGCTGCTGGACACTGCTCAGCAGATCCTGTACAGAAATGTGATGCTGGAGAACTATAAGAACCTGGTTTC
CTTGGGTTATCAGCTTACTAAGCCAGATGTGATCCTCCGGTTGGAGAAGGGAGAAGAGCCCTGGCTGGTGGAGAGAGAAA
TTCACCAAGAGACCCATCCTGATTCAGAGACTGCATTTGAAATCAAATCATCAGTTCCGAAAAAGAAACGCAAAGttGct
agCG

What is claimed is:

1. A fusion protein comprising two heterologous polypeptide domains, wherein the first polypeptide domain comprises a Clustered Regularly Interspaced Short Palindromic Repeats associated (Cas) protein comprising a Cas9 derived from *Streptococcus pyogenes* and the mutations D10A and H840A to inactivate the nuclease activity of Cas9, and wherein the second polypeptide domain comprises a p300 histone acetyltransferase effector domain comprising a wild-type human p300 protein or the core lysine-acetyltransferase domain of the human p300 protein.

2. The fusion protein of claim 1, wherein the Cas protein comprises amino acids 36-1403 of SEQ ID NO: 1.

3. The fusion protein of claim 1, wherein the p300 histone acetyltransferase effector domain comprises a wild-type human p300 protein.

4. The fusion protein of claim 1, wherein the p300 histone acetyltransferase effector domain comprises the core lysine-acetyltranserase domain of the human p300 protein.

5. The fusion protein of claim 1, wherein the fusion protein activates transcription of a target gene by activating regulatory elements.

6. The fusion protein of claim 5, wherein the regulatory elements comprise a promoter of the target gene.

7. The fusion protein of claim 5, wherein the regulatory elements comprise an enhancer of the target gene.

8. The fusion protein of claim 1, wherein the fusion protein further comprises a linker connecting the first polypeptide domain to the second polypeptide domain.

9. A kit comprising the fusion protein of claim 1.

10. An isolated polynucleotide encoding the fusion protein of claim 1.

11. A vector comprising the isolated polynucleotide of claim 10.

12. An isolated cell comprising the isolated polynucleotide of claim 10.

13. The fusion protein of claim 1, wherein the second polypeptide domain comprises amino acids 1422-2038 of SEQ ID NO: 676.

14. The fusion protein of claim 1, wherein the fusion protein comprises the amino acid sequence of SEQ ID NO: 676.

15. A method of modulating mammalian gene expression in a cell, the method comprises contacting the cell with the fusion protein of claim 1.

* * * * *

SEQUENCE LISTING

<160> NUMBER OF SEQ ID NOS: 750

<210> SEQ ID NO 1
<211> LENGTH: 1483
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 1

Met Asp Tyr Lys Asp His Asp Gly Asp Tyr Lys Asp His Asp Ile Asp
1 5 10 15

Tyr Lys Asp Asp Asp Asp Lys Met Ala Pro Lys Lys Lys Arg Lys Val
20 25 30

Gly Arg Gly Met Asp Lys Lys Tyr Ser Ile Gly Leu Ala Ile Gly Thr
35 40 45

Asn Ser Val Gly Trp Ala Val Ile Thr Asp Glu Tyr Lys Val Pro Ser
50 55 60

Lys Lys Phe Lys Val Leu Gly Asn Thr Asp Arg His Ser Ile Lys Lys
65 70 75 80

Asn Leu Ile Gly Ala Leu Leu Phe Asp Ser Gly Glu Thr Ala Glu Ala
85 90 95

Thr Arg Leu Lys Arg Thr Ala Arg Arg Arg Tyr Thr Arg Arg Lys Asn
100 105 110

Arg Ile Cys Tyr Leu Gln Glu Ile Phe Ser Asn Glu Met Ala Lys Val
115 120 125

Asp Asp Ser Phe Phe His Arg Leu Glu Glu Ser Phe Leu Val Glu Glu
130 135 140

Asp Lys Lys His Glu Arg His Pro Ile Phe Gly Asn Ile Val Asp Glu
145 150 155 160

Val Ala Tyr His Glu Lys Tyr Pro Thr Ile Tyr His Leu Arg Lys Lys
165 170 175

Leu Val Asp Ser Thr Asp Lys Ala Asp Leu Arg Leu Ile Tyr Leu Ala
180 185 190

Leu Ala His Met Ile Lys Phe Arg Gly His Phe Leu Ile Glu Gly Asp
195 200 205

Leu Asn Pro Asp Asn Ser Asp Val Asp Lys Leu Phe Ile Gln Leu Val
210 215 220

Gln Thr Tyr Asn Gln Leu Phe Glu Glu Asn Pro Ile Asn Ala Ser Gly
225 230 235 240

Val Asp Ala Lys Ala Ile Leu Ser Ala Arg Leu Ser Lys Ser Arg Arg
245 250 255

Leu Glu Asn Leu Ile Ala Gln Leu Pro Gly Glu Lys Lys Asn Gly Leu
260 265 270

Phe Gly Asn Leu Ile Ala Leu Ser Leu Gly Leu Thr Pro Asn Phe Lys
275 280 285

Ser Asn Phe Asp Leu Ala Glu Asp Ala Lys Leu Gln Leu Ser Lys Asp
290 295 300

Thr Tyr Asp Asp Asp Leu Asp Asn Leu Leu Ala Gln Ile Gly Asp Gln
305 310 315 320

Tyr Ala Asp Leu Phe Leu Ala Ala Lys Asn Leu Ser Asp Ala Ile Leu
325 330 335

Leu Ser Asp Ile Leu Arg Val Asn Thr Glu Ile Thr Lys Ala Pro Leu
340 345 350

Ser Ala Ser Met Ile Lys Arg Tyr Asp Glu His His Gln Asp Leu Thr
355 360 365

Leu Leu Lys Ala Leu Val Arg Gln Gln Leu Pro Glu Lys Tyr Lys Glu
370 375 380

```
Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
        435                 440                 445

Ile His Leu Gly Glu Leu His Ala Ile Leu Arg Arg Gln Glu Asp Phe
    450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
        515                 520                 525

Arg Met Thr Asn Phe Asp Lys Asn Leu Pro Asn Glu Lys Val Leu Pro
    530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
            580                 585                 590

Lys Val Thr Val Lys Gln Leu Lys Glu Asp Tyr Phe Lys Lys Ile Glu
        595                 600                 605

Cys Phe Asp Ser Val Glu Ile Ser Gly Val Glu Asp Arg Phe Asn Ala
    610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
        675                 680                 685

Arg Arg Tyr Thr Gly Trp Gly Arg Leu Ser Arg Lys Leu Ile Asn Gly
    690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
        755                 760                 765

Lys Lys Gly Ile Leu Gln Thr Val Lys Val Val Asp Glu Leu Val Lys
    770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
```

```
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
        835                 840                 845

Tyr Tyr Leu Gln Asn Gly Arg Asp Met Tyr Val Asp Gln Glu Leu Asp
    850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
        915                 920                 925

Gln Arg Lys Phe Asp Asn Leu Thr Lys Ala Glu Arg Gly Gly Leu Ser
    930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp  Phe Arg Lys Asp Phe  Gln Phe Tyr
        995                 1000                1005

Lys Val  Arg Glu Ile Asn Asn  Tyr His His Ala His  Asp Ala Tyr
    1010                1015                1020

Leu Asn  Ala Val Val Gly Thr  Ala Leu Ile Lys Lys  Tyr Pro Lys
    1025                1030                1035

Leu Glu  Ser Glu Phe Val Tyr  Gly Asp Tyr Lys Val  Tyr Asp Val
    1040                1045                1050

Arg Lys  Met Ile Ala Lys Ser  Glu Gln Glu Ile Gly  Lys Ala Thr
    1055                1060                1065

Ala Lys  Tyr Phe Phe Tyr Ser  Asn Ile Met Asn Phe  Phe Lys Thr
    1070                1075                1080

Glu Ile  Thr Leu Ala Asn Gly  Glu Ile Arg Lys Arg  Pro Leu Ile
    1085                1090                1095

Glu Thr  Asn Gly Glu Thr Gly  Glu Ile Val Trp Asp  Lys Gly Arg
    1100                1105                1110

Asp Phe  Ala Thr Val Arg Lys  Val Leu Ser Met Pro  Gln Val Asn
    1115                1120                1125

Ile Val  Lys Lys Thr Glu Val  Gln Thr Gly Gly Phe  Ser Lys Glu
    1130                1135                1140

Ser Ile  Leu Pro Lys Arg Asn  Ser Asp Lys Leu Ile  Ala Arg Lys
    1145                1150                1155

Lys Asp  Trp Asp Pro Lys Lys  Tyr Gly Gly Phe Asp  Ser Pro Thr
    1160                1165                1170

Val Ala  Tyr Ser Val Leu Val  Val Ala Lys Val Glu  Lys Gly Lys
    1175                1180                1185

Ser Lys  Lys Leu Lys Ser Val  Lys Glu Leu Leu Gly  Ile Thr Ile
    1190                1195                1200

Met Glu  Arg Ser Ser Phe Glu  Lys Asn Pro Ile Asp  Phe Leu Glu
    1205                1210                1215
```

```
Ala Lys  Gly Tyr Lys Glu Val  Lys Lys Asp Leu Ile  Ile Lys Leu
    1220                 1225                 1230

Pro Lys  Tyr Ser Leu Phe Glu  Leu Glu Asn Gly Arg  Lys Arg Met
    1235                 1240                 1245

Leu Ala  Ser Ala Gly Glu Leu  Gln Lys Gly Asn Glu  Leu Ala Leu
    1250                 1255                 1260

Pro Ser  Lys Tyr Val Asn Phe  Leu Tyr Leu Ala Ser  His Tyr Glu
    1265                 1270                 1275

Lys Leu  Lys Gly Ser Pro Glu  Asp Asn Glu Gln Lys  Gln Leu Phe
    1280                 1285                 1290

Val Glu  Gln His Lys His Tyr  Leu Asp Glu Ile Ile  Glu Gln Ile
    1295                 1300                 1305

Ser Glu  Phe Ser Lys Arg Val  Ile Leu Ala Asp Ala  Asn Leu Asp
    1310                 1315                 1320

Lys Val  Leu Ser Ala Tyr Asn  Lys His Arg Asp Lys  Pro Ile Arg
    1325                 1330                 1335

Glu Gln  Ala Glu Asn Ile Ile  His Leu Phe Thr Leu  Thr Asn Leu
    1340                 1345                 1350

Gly Ala  Pro Ala Ala Phe Lys  Tyr Phe Asp Thr Thr  Ile Asp Arg
    1355                 1360                 1365

Lys Arg  Tyr Thr Ser Thr Lys  Glu Val Leu Asp Ala  Thr Leu Ile
    1370                 1375                 1380

His Gln  Ser Ile Thr Gly Leu  Tyr Glu Thr Arg Ile  Asp Leu Ser
    1385                 1390                 1395

Gln Leu  Gly Gly Asp Pro Ile  Ala Gly Ser Lys Ala  Ser Pro Lys
    1400                 1405                 1410

Lys Lys  Arg Lys Val Gly Arg  Ala Asp Ala Leu Asp  Asp Phe Asp
    1415                 1420                 1425

Leu Asp  Met Leu Gly Ser Asp  Ala Leu Asp Asp Phe  Asp Leu Asp
    1430                 1435                 1440

Met Leu  Gly Ser Asp Ala Leu  Asp Asp Phe Asp Leu  Asp Met Leu
    1445                 1450                 1455

Gly Ser  Asp Ala Leu Asp Asp  Phe Asp Leu Asp Met  Leu Ile Asn
    1460                 1465                 1470

Tyr Pro  Tyr Asp Val Pro Asp  Tyr Ala Ser
    1475                 1480

<210> SEQ ID NO 2
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

gagggcctat ttcccatgat tccttcatat ttgcatatac gatacaaggc tgttagagag     60

ataattggaa ttaatttgac tgtaaacaca aagatattag tacaaaatac gtgacgtaga    120

aagtaataat ttcttgggta gtttgcagtt ttaaaattat gttttaaaat ggactatcat    180

atgcttatcg taacttgaaa gtatttcgat ttcttggctt tatatatctt gtggaaagga    240

cgaaacaccg ggtcttcgag aagacctgtt ttagagctag aaatagcaag ttaaaataag    300

gctagtccgt tatcaacttg aaaaagtggc accgagtcgg tgcttttttt               350
```

<210> SEQ ID NO 3
<211> LENGTH: 338
<212> TYPE: DNA
<213> ORGANISM: Homo sapiens

<400> SEQUENCE: 3

```
acccccggca gcagcccgcc ccgagcgcgc cgcctgttta ttcagccggg agtccggcac     60

gcgccaggcg cacgcactgc aacaacaaac ccagctgaat ggagagtttg caaggagcgg    120

gagaaaggaa cgggaggggg ggagaggaga ggaggagggg gagtttaggg agtgggtggg    180

aggaagaggt aagaggaggg gggggagtgg gggctgcagc cgctcgctgc agcagcgggg    240

agtggggggc gaggcggggc cagggctgcg cgtggggctg ggtgtcccat tgaaaaggcg    300

gacgcactcc ggcagcccag cactctctca cttctggc                            338
```

<210> SEQ ID NO 4
<211> LENGTH: 305
<212> TYPE: DNA
<213> ORGANISM: Mus musculus

<400> SEQUENCE: 4

```
ccgccccgag cgcgcggcct gtttattcag ccgggagtcc ggcacgcgcc gggcgcacgc     60

actgcaacaa caaaccaggc tgaatggaga gtttgcaagg agcgggcgcg ggcaactgga    120

gggggggggg gcgagaggga gggagctgag gaggtggggg aagaggaggg gtagtggggg    180

ctgcagccgc tcgctgcagc agcggggagt ggggggcgag gcggggccag ggctgcgcgt    240

ggggctgggt gtcccattga aaaggcggcc gcaccgcagc cgcccagcag tctctcactt    300

ctggc                                                                305
```

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5

```
gctgggtgtc ccattgaaa                                                  19
```

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6

```
cagccgctcg ctgcagcag                                                  19
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7

```
tggagagttt gcaaggagc                                                  19
```

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
gtttattcag ccgggagtc 19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
cgccaggagg ggtgggtcta 20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
ccttggtgag actggtaga 19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
gtcttcaggt tctgttgct 19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
atattcctga tttaaaagt 19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
ttaaaagtcg gctggtagc 19

<210> SEQ ID NO 14

<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
cgggccgggg gcggggtcc 19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
gcccgagccg cgtgtggaa 19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
ccttcattgc ggcgggctg 19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
ccgacccctc ccgggtccc 19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
caggaccgcg cttcccacg 19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
tgcaccctgg gagcgcgag 19

<210> SEQ ID NO 20
<211> LENGTH: 19

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
ccgcacgcac ctgttccca 19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
aaaacagcga gggagaaac 19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
ttaacttgat tgtgaaatc 19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
aaaacaatgc atatttgca 19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
aaaatccagt attttaatg 19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
acccagcact gcagcctgg 19

<210> SEQ ID NO 26
<211> LENGTH: 19
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 26
aacttatgcg gcgtttcct 19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
tcactttaaa accacctct 19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
gcatcttttt ctctttaat 19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
tgtactctct gaggtgctc 19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
acgcagataa gaaccagtt 19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
catcaagtca gccatcagc 19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
gagtcaccct cctggaaac 19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
gctagggatg aagaataaa 19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
ttgaccaata gccttgaca 19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
tgcaaatatc tgtctgaaa 19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
aaattagcag tatcctctt 19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
cctgggctcc ggggcgttt 19

<210> SEQ ID NO 38
<211> LENGTH: 19
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 38
ggcccctgcg gccaccccg 19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
ctccctccct gcccggtag 19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
aggtttggaa agggcgtgc 19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
ggagcttctc gacttcacca 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gatttgtggg cctgaagaaa 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
aaggaggagg gcagaatcat 20

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
aaaccttcct cagctatgcc c 21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
agctgatggc cctaaacaga 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
caggaggact ctggcaccta 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
ggaatccatg gagggaagat 20

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
gctgagtgaa ctgcactgtg a 21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
ctctctgctc ctttgccaca 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
caatgacccc ttcattgacc 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
ggaacaagag ctgctggact 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
aactttggca ttgtggaagg 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
aacgccactg acaagaaagc 20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
cagatccatg gaggaaggaa 20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gggtactcct ggaagatgtc c 21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
gtttgcgacg catgttcctc 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
aagcccttgc tgtagtggtg 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
cggcaggaaa gcatctgtat 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
tgttctcgct caggtcagtg 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
gaattctttg ccgaaatgga 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gtgctcttcg ggtttcagga 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
ttgattttgg agggatctcg 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
gtttttctgc ctccccattt 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
ggatgcaggg atgatgttct 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
gattggcttt gatttcccta 20

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
gtgtagagta agtcagccta tgg 23

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
gcctactcag actgttactc 20

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
gttggacaga acttaccgac tgg 23

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
gcagttgcct aagaactggt 20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
ggggctccac cctcacgagt 20

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
gtttgcttcg ctataaaacg agg 23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
gtctgaggat ggggccgcaa tgg 23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
ggatctgtca aatcgcctgc agg 23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
gccaggatgg cattgggcag cgg 23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
gctgaatctg cggtggcagg agg 23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
gttcttttgt tcttctagcc tgg 23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
ggaaaagctt gagcaagtca agg 23

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
ggaagagttg cccctgcgcc agg 23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
gacaaatctc cagtggataa agg 23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
gtgtttctca ggtaaagctc tgg 23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
ggaaggacca tttgacgtta agg 23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
gaactgctat ttcagtttcc tgg 23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
gccagccact cagccagtga agg 23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
ggtatgcttt tctgttaaag agg 23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
gctcctggac tgaccactat tgg 23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
ggaacagagg cgtccccagt tgg 23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
ggaggctaga acaatcatta cgg 23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
gacaagaaca ccttcagaac cgg 23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
gggtttctgt gattttcttt tgg 23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
gggccaaaga cctccgccag tgg 23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
gttggagaag cattcataaa agg 23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
gtcgctcact caccctgcaa agg 23

<210> SEQ ID NO 93

<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
gaaaagagct gatgaaacaa tgg 23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
gtacactttt caaaatgctt tgg 23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 95
ggagatgatc atcaagcaga agg 23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
gctttgaaag agcaataaaa tgg 23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
gcacaaaagt caaatcggaa tgg 23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 98
gatttcaata taagattcgg agg 23

<210> SEQ ID NO 99
<211> LENGTH: 23

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
gcttaagcaa tcccgaactc tgg 23

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
gccttcttta tcccctatcg 20

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (21)..(22)
<223> OTHER INFORMATION: a, c, t, g, unknown or other

<400> SEQUENCE: 104
gaggccaaac ctcggcttac nngrr 25

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (21)..(22)
<223> OTHER INFORMATION: a, c, t, g, unknown or other

<400> SEQUENCE: 105
gttcgaaaat ttcaggtaag nngrr 25

<210> SEQ ID NO 106
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (21)..(22)
<223> OTHER INFORMATION: a, c, t, g, unknown or other

<400> SEQUENCE: 106
ggcagaacag gagataacag nngrrt 26

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
ggcggccctc gcccttctct ggggat 26

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108
gtagtgatcg tggatacgag agg 23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
gtacagccct cggtgtatat tgg 23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
gggaaggaat taagcccgaa tgg 23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
gggaacagct ttcgtagttg agg 23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
gataaagtcc agtgtcgatc agg 23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
gaaaaccaga gcttcggtca agg 23

<210> SEQ ID NO 114
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
ggagtcttct gggcaggctt aaaggctaac ctgg 34

<210> SEQ ID NO 115
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
gtcgggtgag catgtcttta atctacctcg atgg 34

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
ggtgtcacca gagtaacagt ctgagt 26

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
gtgatcatca agcagaaggt atgag 25

<210> SEQ ID NO 118
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
gaacttcgaa aatttcaggt aagccgagg 29

<210> SEQ ID NO 119
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
ggaaactcat caaatatgcg tgttagtgt 29

<210> SEQ ID NO 120
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
gtcatttaca ctaacacgca tatttgatg 29

<210> SEQ ID NO 121
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
ggaatgaaac tcatcaaata tgcgtgtta 29

<210> SEQ ID NO 122
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
gtcatcaata tctttgaagg actctgggt 29

<210> SEQ ID NO 123
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
gtgttttcat aggaaaaata ggcaagttg 29

<210> SEQ ID NO 124
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
gaattggaaa atgtgatggg aaacagata 29

<210> SEQ ID NO 125
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
gatgatcatc aagcagaagg tatgagaaa 29

<210> SEQ ID NO 126
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
gagatgatca tcaagcagaa ggtatgaga 29

<210> SEQ ID NO 127
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127 gcatttttc tcataccttc tgcttgatg 29

<210> SEQ ID NO 128
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
gtcctactca gactgttact ctggtgaca 29

<210> SEQ ID NO 129
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
gacaggttgt gtcaccagag taacagtct 29

<210> SEQ ID NO 130
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
gttatcattt tttctcatac cttctgctt 29

<210> SEQ ID NO 131
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
gttgcctaag aactggtggg aaatggtct 29

<210> SEQ ID NO 132
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 132
gaaacagttg cctaagaact ggtgggaaa 29

<210> SEQ ID NO 133
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 133
gtttcccacc agttcttagg caactgttt 29

<210> SEQ ID NO 134
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 134
gtggctttga tttccctagg gtccagctt 29

<210> SEQ ID NO 135
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 135
gtagggaaat caaagccaat gaaacgttc 29

<210> SEQ ID NO 136

<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 136
ggaccctagg gaaatcaaag ccaatgaaa 29

<210> SEQ ID NO 137
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 137
gtgagggctc caccctcacg agtgggttt 29

<210> SEQ ID NO 138
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 138
gaaggattga gggctccacc ctcacgagt 29

<210> SEQ ID NO 139
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 139
ggctccaccc tcacgagtgg gtttggttc 29

<210> SEQ ID NO 140
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 140
gtatccccta tcgaggaaac cacgagttt 29

<210> SEQ ID NO 141
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 141
ggataaagaa ggcctatttc atagagttg 29

<210> SEQ ID NO 142
<211> LENGTH: 29

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
gaggccttct ttatccccta tcgaggaaa 29

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
gtgagggctc caccctcacg agtgggt 27

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
ggataaagaa ggcctatttc atagagt 27

<210> SEQ ID NO 145
<211> LENGTH: 4932
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145
gccaccatgg acaagaagta ctccattggg ctcgatatcg gcacaaacag cgtcggctgg 60
gccgtcatta cggacgagta caaggtgccg agcaaaaaat tcaaagttct gggcaatacc 120
gatcgccaca gcataaagaa gaacctcatt ggcgccctcc tgttcgactc cggggagacg 180
gccgaagcca cgcggctcaa aagaacagca cggcgcagat atacccgcag aaagaatcgg 240
atctgctacc tgcaggagat ctttagtaat gagatggcta aggtggatga ctctttcttc 300
cataggctgg aggagtcctt tttggtggag gaggataaaa agcacgagcg ccacccaatc 360
tttggcaata tcgtggacga ggtggcgtac catgaaaagt acccaaccat atatcatctg 420
aggaagaagc ttgtagacag tactgataag gctgacttgc ggttgatcta tctcgcgctg 480
gcgcatatga tcaaatttcg gggacacttc ctcatcgagg gggacctgaa cccagacaac 540
agcgatgtcg acaaactctt tatccaactg gttcagactt acaatcagct tttcgaagag 600
aacccgatca acgcatccgg agttgacgcc aaagcaatcc tgagcgctag gctgtccaaa 660
tcccggcggc tcgaaaacct catcgcacag ctccctgggg agaagaagaa cggcctgttt 720
ggtaatctta tcgccctgtc actcgggctg acccccaact ttaaatctaa cttcgacctg 780
gccgaagatg ccaagcttca actgagcaaa gacacctacg atgatgatct cgacaatctg 840
ctggcccaga tcggcgacca gtacgcagac cttttttggg cggcaaagaa cctgtcagac 900
gccattctgc tgagtgatat tctgcgagtg aacacggaga tcaccaaagc tccgctgagc 960

-continued

```
gctagtatga tcaagcgcta tgatgagcac caccaagact tgactttgct gaaggccctt   1020
gtcagacagc aactgcctga gaagtacaag gaaattttct tcgatcagtc taaaaatggc   1080
tacgccggat acattgacgg cggagcaagc caggaggaat tttacaaatt tattaagccc   1140
atcttggaaa aaatggacgg caccgaggag ctgctggtaa agcttaacag agaagatctg   1200
ttgcgcaaac agcgcacttt cgacaatgga agcatccccc accagattca cctgggcgaa   1260
ctgcacgcta tcctcaggcg gcaagaggat ttctacccct ttttgaaaga taacagggaa   1320
aagattgaga aaatcctcac atttcggata ccctactatg taggccccct cgcccgggga   1380
aattccagat tcgcgtggat gactcgcaaa tcagaagaga ccatcactcc ctggaacttc   1440
gaggaagtcg tggataaggg ggcctctgcc cagtccttca tcgaaaggat gactaacttt   1500
gataaaaatc tgcctaacga aaaggtgctt cctaaacact ctctgctgta cgagtacttc   1560
acagtttata acgagctcac caaggtcaaa tacgtcacag aagggatgag aaagccagca   1620
ttcctgtctg gagagcagaa gaaagctatc gtggacctcc tcttcaagac gaaccggaaa   1680
gttaccgtga aacagctcaa agaagactat ttcaaaaaga ttgaatgttt cgactctgtt   1740
gaaatcagcg gagtggagga tcgcttcaac gcatccctgg gaacgtatca cgatctcctg   1800
aaaatcatta aagacaagga cttcctggac aatgaggaga acgaggacat tcttgaggac   1860
attgtcctca cccttacgtt gtttgaagat agggagatga ttgaagaacg cttgaaaact   1920
tacgctcatc tcttcgacga caaagtcatg aaacagctca agaggcgccg atatacagga   1980
tgggggcggc tgtcaagaaa actgatcaat gggatccgag acaagcagag tggaaagaca   2040
atcctggatt ttcttaagtc cgatggattt gccaaccgga acttcatgca gttgatccat   2100
gatgactctc tcacctttaa ggaggacatc cagaaagcac aagtttctgg ccagggggac   2160
agtcttcacg agcacatcgc taatcttgca ggtagcccag ctatcaaaaa gggaatactg   2220
cagaccgtta aggtcgtgga tgaactcgtc aaagtaatgg gaaggcataa gcccgagaat   2280
atcgttatcg agatggcccg agagaaccaa actacccaga agggacagaa gaacagtagg   2340
gaaaggatga agaggattga agagggtata aaagaactgg ggtcccaaat ccttaaggaa   2400
cacccagttg aaaacaccca gcttcagaat gagaagctct acctgtacta cctgcagaac   2460
ggcagggaca tgtacgtgga tcaggaactg gacatcaatc ggctctccga ctacgacgtg   2520
gatcatatcg tgccccagtc ttttctcaaa gatgattcta ttgataataa agtgttgaca   2580
agatccgata aaaatagagg gaagagtgat aacgtcccct cagaagaagt tgtcaagaaa   2640
atgaaaaatt attggcggca gctgctgaac gccaaactga tcacacaacg gaagttcgat   2700
aatctgacta aggctgaacg aggtggcctg tctgagttgg ataaagccgg cttcatcaaa   2760
aggcagcttg ttgagacacg ccagatcacc aagcacgtgg cccaaattct cgattcacgc   2820
atgaacacca agtacgatga aaatgacaaa ctgattcgag aggtgaaagt tattactctg   2880
aagtctaagc tggtctcaga tttcagaaag gactttcagt tttataaggt gagagagatc   2940
aacaattacc accatgcgca tgatgcctac ctgaatgcag tggtaggcac tgcacttatc   3000
aaaaaatatc ccaagcttga atctgaattt gtttacggag actataaagt gtacgatgtt   3060
aggaaaatga tcgcaaagtc tgagcaggaa ataggcaagg ccaccgctaa gtacttcttt   3120
tacagcaata ttatgaattt tttcaagacc gagattacac tggccaatgg agagattcgg   3180
aagcgaccac ttatcgaaac aaacggagaa acaggagaaa tcgtgtggga caagggtagg   3240
gatttcgcga cagtccggaa ggtcctgtcc atgccgcagg tgaacatcgt taaaaagacc   3300
gaagtacaga ccggaggctt ctccaaggaa agtatcctcc cgaaaaggaa cagcgacaag   3360
```

```
ctgatcgcac gcaaaaaaga ttgggacccc aagaaatacg gcggattcga ttctcctaca   3420
gtcgcttaca gtgtactggt tgtggccaaa gtggagaaag ggaagtctaa aaaactcaaa   3480
agcgtcaagg aactgctggg catcacaatc atggagcgat caagcttcga aaaaaacccc   3540
atcgactttc tcgaggcgaa aggatataaa gaggtcaaaa aagacctcat cattaagctt   3600
cccaagtact ctctctttga gcttgaaaac ggccggaaac gaatgctcgc tagtgcgggc   3660
gagctgcaga aaggtaacga gctggcactg ccctctaaat acgttaattt cttgtatctg   3720
gccagccact atgaaaagct caaagggtct cccgaagata atgagcagaa gcagctgttc   3780
gtggaacaac acaaacacta ccttgatgag atcatcgagc aaataagcga attctccaaa   3840
agagtgatcc tcgccgacgc taacctcgat aaggtgcttt ctgcttacaa taagcacagg   3900
gataagccca tcagggagca ggcagaaaac attatccact tgtttactct gaccaacttg   3960
ggcgcgcctg cagccttcaa gtacttcgac accaccatag acagaaagcg gtacacctct   4020
acaaaggagg tcctggacgc cacactgatt catcagtcaa ttacggggct ctatgaaaca   4080
agaatcgacc tctctcagct cggtggagac agcagggctg accccaagaa gaagaggaag   4140
gtggctagcg agggcagagg aagtcttcta acatgcggtg acgtggagga gaatcccggc   4200
cctggtaccg tgagcaaggg cgaggagctg ttcaccgggg tggtgcccat cctggtcgag   4260
ctggacggcg acgtaaacgg ccacaagttc agcgtgtccg gcgagggcga gggcgatgcc   4320
acctacggca agctgaccct gaagttcatc tgcaccaccg gcaagctgcc cgtgccctgg   4380
cccaccctcg tgaccaccct gacctacggc gtgcagtgct tcagccgcta ccccgaccac   4440
atgaagcagc acgacttctt caagtccgcc atgcccgaag gctacgtcca ggagcgcacc   4500
atcttcttca aggacgacgg caactacaag acccgcgccg aggtgaagtt cgagggcgac   4560
accctggtga accgcatcga gctgaagggc atcgacttca aggaggacgg caacatcctg   4620
gggcacaagc tggagtacaa ctacaacagc cacaacgtct atatcatggc cgacaagcag   4680
aagaacggca tcaaggtgaa cttcaagatc cgccacaaca tcgaggacgg cagcgtgcag   4740
ctcgccgacc actaccagca gaacaccccc atcggcgacg gccccgtgct gctgcccgac   4800
aaccactacc tgagcaccca gtccgccctg agcaaagacc ccaacgagaa gcgcgatcac   4860
atggtcctgc tggagttcgt gaccgccgcc gggatcactc tcggcatgga cgagctgtac   4920
aagaccggtt ag                                                       4932
```

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
tcctactcag actgttactc tgg 23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
tcctactcac actgttactc agg 23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
acctgctcac actgttactc cag 23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 153
gcattctcaa actgttactc agg 23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 154
ggattctcac actgttactc ggg 23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 155
acatacttat actgttactc tag 23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
tattcctaag actgttactc aag 23

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
aaggactaag actgttactc ggg 23

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
gagctctcat actgttactc tag 23

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 159
gcaaaatgag actgttactc cag 23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 160
cctcattcag actgttactc aag 23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 161
cattggcttt gatttcccta ggg 23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 162
aattggcatt gatttcccta gag 23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
cattggcttt aatttcccta tag 23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 164
gataggctgt gatttcccta gag 23

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 165
gaatagcctt gatttcccta aag 23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 166
aatttgcttt gatttccctg agg 23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 167
gatgtgcttt gatttccctt ggg 23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 168
aattggtttt aatttcccta aag 23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 169
aattgggttt gatttccctt tgg 23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 170
gatgggtttt tatttcccta gag 23

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 171
gaatggtttt gatttccctg gag 23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 172
acagttgcct aagaactggt ggg 23

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 173
ccagttgtct aagaactggg gag 23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 174
gcagttgcct gtgaactggt agg 23

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 175
gcagatgcag aagaactggt gag 23

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 176
gcagttccag aagaactggt gag 23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
caacttgcct atgaactggt agg 23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 178
acacctgcct aagaactgga ggg 23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 179
tcaggtggct aagaactggg tgg 23

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 180
gaagttggcc aagaactgga gag 23

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 181
gctgctgccc aagaactggc agg 23

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 182
tcagctggct aagaacgggt aag 23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
agggctccac cctcacgagt ggg 23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
gcagctcagc cctcacgagt cag 23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 185
ggggcttcag catcacgagt gag 23

<210> SEQ ID NO 186

<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 186
ggggctctcc cctcactagt gag 23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 187
ggggatccac cttcaccagt cag 23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 188
agggctggac cctcacaagt aag 23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 189
tggtctcctc ccccacgagt ggg 23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 190
agggctccca ccccacgagt gag 23

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 191
gaggctccat actcaccagt gag 23

<210> SEQ ID NO 192
<211> LENGTH: 23

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 192
ggagctgccc cttcacgagt ggg 23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 193
atgactccac cctcaagagt aag 23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 194
gccttcttta tcccctatcg agg 23

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 195
gtctgctgtg tcccctatcg ggg 23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196
cccttctcta tcccctgtcg tgg 23

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197
gccttcttta tcccctctct tgg 23

<210> SEQ ID NO 198
<211> LENGTH: 23
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 198
gcgctctttt tcccctatct tag 23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
gccctctgtc tcccctgtcg cag 23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 200
tccatctttg tcccctattg agg 23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 201
accttctctc tcccctatag agg 23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 202
gttttctttt tcccctatgg gag 23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 203
tgcttcttaa tcccctatca aag 23

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
accttcttac tcccctatcc ggg 23

<210> SEQ ID NO 205
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
gagaggttat gtggctttac ca 22

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
aaaaatgctt cccactttgc 20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ctcattctca tgcctggaca 20

<210> SEQ ID NO 208
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
gagtttggct caaattgtta ctctt 25

<210> SEQ ID NO 209
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
gggaaatggt ctaggagagt aaagt 25

<210> SEQ ID NO 210
<211> LENGTH: 25
<212> TYPE: DNA
<213> ORGANISM: Artificial Sequence
<220> FEATURE:

<223> OTHER INFORMATION: Description of Artificial Sequence: Synthetic
primer

<400> SEQUENCE: 210
gtttggctca aattgttact cttca 25

<210> SEQ ID NO 211
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 211
gtgagagtaa tgtgtttgct gagag 25

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 212
cgggcttgga cagaacttac 20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 213
ctgcgtagtg ccaaaacaaa 20

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 214
taatttcatt gaagagtggc tgaa 24

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 215
aagccctgtg tggtagtagt cagt 24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 216
tgagtcatgt tggataacca gtct 24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 217
gaaggtcagg aacatacaat tcaa 24

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 218
gatatgggca tgtcagtttc atag 24

<210> SEQ ID NO 219
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 219
tgctgttgat taatggttga tagg 24

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 220
ttttaaattg ccatgtttgt gtc 23

<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 221
atgaataacc taatgggcag aaaa 24

<210> SEQ ID NO 222
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 222
tcaagtcgct tcattttgat agac 24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 223
cacaacaaaa catatagcca aagc 24

<210> SEQ ID NO 224
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 224
tgctgctaaa ataacacaaa tcagt 25

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 225
ctgtgcctat tgtggttatc ctg 23

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 226
attgatctgc aatacatgtg gagt 24

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 227
tttgcctctg ctattacagt atgg 24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 228
tgtagggtgg ttggctaaaa taat 24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 229
tttttgcaca gtcaataaca caaa 24

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 230
ggctggtctc acaattgtac ttta 24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 231
cattatggac tgaaaatctc agca 24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 232
atcatcctag ccataacaca atga 24

<210> SEQ ID NO 233
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 233
ttcagcttta acgtgatttt ctgt 24

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 234
ggattcagaa gctgtttacg aagt 24

<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 235
tttagctgga ttggaaaaac aaat 24

<210> SEQ ID NO 236
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 236
aactcacccc attgttggta tatt 24

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 237
ccttgtccaa ataccgaaat acat 24

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 238
cacataattc atgaacttgg cttc 24

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 239
tagtagctgg ggaggaagat acag 24

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 240
tttttgtttt aattgcgact gtgt 24

<210> SEQ ID NO 241
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 241
agaaaagggg ttttcttttg actt 24

<210> SEQ ID NO 242
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 242
cattgtgact ggatgagaag aaac 24

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
aacggctgtt attaaagtcc tcag 24

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
caagtcagaa gtcacttgct ttgt 24

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
ttttatgtgc aggaatcagt ctgt 24

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 246
tggcggcgtt ttcattat 18

<210> SEQ ID NO 247
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 247
ttcgatccgt aatgattgtt ctagcc 26

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 248
ggtcttccag agtgctgagg 20

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 249
tgtgtgcttc tgtacacatc atct 24

<210> SEQ ID NO 250
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 250
agatttcaac cctcaaaaac tgag 24

<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 251
taaactcttt cttttccgca attc 24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 252
caaggtgacc tgctacctaa aaat 24

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 253
tatgaccaag gctatgtgtt cact 24

<210> SEQ ID NO 254
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 254
acagcctctc tccagtaaca ttct 24

<210> SEQ ID NO 255
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 255
tattcttgca gtggtttcac attt 24

<210> SEQ ID NO 256
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 256
atattttaag ccaagaccca acaa 24

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 257
ctttcaactg tctgtctgat tgct 24

<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 258
aacagcctct cttcattgtt ctct 24

<210> SEQ ID NO 259
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 259
ctctggaact tgtctctgtc ttga 24

<210> SEQ ID NO 260
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 260
ctttcctgcg ttctcatgtt acta 24

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 261
ccttatatcc gtatcgctca ctct 24

<210> SEQ ID NO 262
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 262
catatctgtc taacttccgc acac 24

<210> SEQ ID NO 263
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 263
acaggtgtta tgttgtctgc atct 24

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 264
actccattcc cagattagtt atgc 24

<210> SEQ ID NO 265

<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
ctgttttctt tgtgagagtg gaga 24

<210> SEQ ID NO 266
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
tgtaaggtgg tcaaacttgc tcta 24

<210> SEQ ID NO 267
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
tttttcctag tacccacaga ttttt 25

<210> SEQ ID NO 268
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
tccctgattc tctcatttgt gtta 24

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ttgggaacat cagagaaagt atga 24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
acaaattaca gtctcctggg aaag 24

<210> SEQ ID NO 271
<211> LENGTH: 24

<212> TYPE: DNA
<213> ORGANISM: Artificial Sequence
<220> FEATURE:
<223> OTHER INFORMATION: Description of Artificial Sequence: Synthetic
primer

<400> SEQUENCE: 271
agtagcttac cttggcagag aaaa 24

<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 272
tgacatactg ttaccctttg cagt 24

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 273
gaaaggctca gtgaatgttt gtt 23

<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 274
cactgcatca tctcattaaa tcaa 24

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 275
cccatatatt catgattacc caca 24

<210> SEQ ID NO 276
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 276
tatcagaacg agcactaaaa gcac 24

<210> SEQ ID NO 277
<211> LENGTH: 20
<212> TYPE: DNA

<213> ORGANISM: Artificial Sequence
<220> FEATURE:
<223> OTHER INFORMATION: Description of Artificial Sequence: Synthetic
primer

<400> SEQUENCE: 277
ttgggaggct gaggtacaag 20

<210> SEQ ID NO 278
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 278
gaatgaaaaa caaacagaag gtga 24

<210> SEQ ID NO 279
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 279
ctcctcatct gtacccttca atct 24

<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 280
agagtggcat ctagtgtcag tgag 24

<210> SEQ ID NO 281
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 281
taccaaaagc ttctcctgtt tacc 24

<210> SEQ ID NO 282
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 282
gtaagttgga tggcctattc tttg 24

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
gaaggaaatg caaggataca agat 24

<210> SEQ ID NO 284
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
tgattgaaag aatcattcca gaaa 24

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
tcagaaggaa aattgaaatt ggtt 24

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
cagatgtgtt cttcatcatt cctc 24

<210> SEQ ID NO 287
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
ttctctttag ggaaagctct caaa 24

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
gggtatagat catatggagg gaag 24

<210> SEQ ID NO 289
<211> LENGTH: 20
<212> TYPE: DNA
<213> ORGANISM: Artificial Sequence
<220> FEATURE:

<223> OTHER INFORMATION: Description of Artificial Sequence: Synthetic
primer

<400> SEQUENCE: 289
agatgatctg cccacctcag 20

<210> SEQ ID NO 290
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 290
ctttcttcct catttagtgg caat 24

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 291
atgaattgca gattgatggt actg 24

<210> SEQ ID NO 292
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 292
tctcaccaag aaccaaattg tcta 24

<210> SEQ ID NO 293
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 293
gtaggatacc ttggcaacag tctt 24

<210> SEQ ID NO 294
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 294
ttaacgaatt gtgagatttg ctgt 24

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
tcagaaagtc aagtagcaca caca 24

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 296
agaagcacac actcaggtaa agc 23

<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 297
tctttggggg aataatgact aaaa 24

<210> SEQ ID NO 298
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 298
tttggcattt atgggaataa aact 24

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 299
actaattctg gtcaagccca tca 23

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 300
ttaagacatc ggatgaacag aaag 24

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 301
agaagctttc tgacatgatc tgc 23

<210> SEQ ID NO 302
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 302
tcaattgcat taggacttag acca 24

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 303
gttaaattac ctgtgaagcc cttg 24

<210> SEQ ID NO 304
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 304
cggaaaacag atccacttta tgat 24

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 305
aaatccactg gaaacatctt gagt 24

<210> SEQ ID NO 306
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 306
agtctcttca gaatcatgcc ctat 24

<210> SEQ ID NO 307
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 307
gcttggtggc acatacctgt ag 22

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 308
ggtaggtaga tttgcttgct tgtt 24

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 309
agctctcagc agagtaggga ttta 24

<210> SEQ ID NO 310
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 310
gtgagtctac tgcaccccat c 21

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 311
tgacactgtg aagtcaattc tgtc 24

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 312
tcaagaactt gacaatgagc aaat 24

<210> SEQ ID NO 313
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 313
tatccgatcc actgttgtgt gt 22

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 314
caggagaccc aaaaccactc tac 23

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 315
ttgttctaca aatagggctt cctt 24

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 316
tgttaagttt gggcttatgt tcct 24

<210> SEQ ID NO 317
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 317
cacaagtctc actgcacaaa cat 23

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 318
tgacccatga ttatctctct ttga 24

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 319
ttcagcttct gattggtttt aatg 24

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 320
ccaattcctt aattttccct acag 24

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 321
atctcagacc aggagggaga c 21

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 322
cctcagggtc agtacatttt tcag 24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 323
ttcttaggac attgctccac atac 24

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 324
gcaaacataa tgcaactcgt aatc 24

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 325
gcaagggagt ctgtgtcttt g 21

<210> SEQ ID NO 326
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 326
tcatttaagt ggctgttctg tgtt 24

<210> SEQ ID NO 327
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 327
acaaaacaga gagaaaaggc agag 24

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 328
gttttgattt ctggtgccta cag 23

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 329
actgaagctg aagcccagtc 20

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 330
acatgagctc tcaggtttct gac 23

<210> SEQ ID NO 331
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 331
tcaaacttag atggttccct atgtt 25

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 332
gtaccctgaa aatgtagggt gact 24

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 333
cacttcccaa gtgaggcaat 20

<210> SEQ ID NO 334
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 334
ctatacttgg ggctgacttg ctac 24

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 335
tcgtataggt tactttggct caca 24

<210> SEQ ID NO 336
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 336
agggatcttt actcctcagt gtgt 24

<210> SEQ ID NO 337
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 337
tgtagaagtt ggaatatcct gctg 24

<210> SEQ ID NO 338
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 338
gtcaacaatt tgatctcagg cttc 24

<210> SEQ ID NO 339
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 339
ctcagtacta aagatggacg cttg 24

<210> SEQ ID NO 340
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 340
aatcatttca gtcttcccaa caat 24

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 341
gggaatcaca gtagatgttt gtca 24

<210> SEQ ID NO 342
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 342
agaccaggag gtaagaacat tttg 24

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 343
ccacatagaa agagacttgc agaa 24

<210> SEQ ID NO 344

<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 344
agagatgcca aaagaacagt caat 24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 345
tgtgccttag gctatgtaaa ctgt 24

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 346
aaacccttgt aaccaaaatt acca 24

<210> SEQ ID NO 347
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 347
taactgcatc agaagtcctt gcta 24

<210> SEQ ID NO 348
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 348
ggagaccaag ctgctaaagt ca 22

<210> SEQ ID NO 349
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 349
gtggtgccgc gggagtttgg ctcaaattgt tactctt 37

<210> SEQ ID NO 350
<211> LENGTH: 37

<212> TYPE: DNA
<213> ORGANISM: Artificial Sequence
<220> FEATURE:
<223> OTHER INFORMATION: Description of Artificial Sequence: Synthetic
primer

<400> SEQUENCE: 350
gtggtgccgc gggggaaatg gtctaggaga gtaaagt 37

<210> SEQ ID NO 351
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 351
gtggtgccgc gggagaggtt atgtggcttt acca 34

<210> SEQ ID NO 352
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 352
gtggtgccgc ggctcattct catgcctgga ca 32

<210> SEQ ID NO 353
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 353
gtggtgccgc ggcgggcttg gacagaactt ac 32

<210> SEQ ID NO 354
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 354
gtggtgccgc ggctgcgtag tgccaaaaca aa 32

<210> SEQ ID NO 355
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 355
gtggtgccgc ggtaatttca ttgaagagtg gctgaa 36

<210> SEQ ID NO 356
<211> LENGTH: 36
<212> TYPE: DNA

<213> ORGANISM: Artificial Sequence
<220> FEATURE:
<223> OTHER INFORMATION: Description of Artificial Sequence: Synthetic
primer

<400> SEQUENCE: 356
gtggtgccgc ggaagccctg tgtggtagta gtcagt 36

<210> SEQ ID NO 357
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 357
gtggtgccgc ggcaagtcag aagtcacttg ctttgt 36

<210> SEQ ID NO 358
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 358
gtggtgccgc ggttttatgt gcaggaatca gtctgt 36

<210> SEQ ID NO 359
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 359
gtggtgccgc ggtgtgtgct tctgtacaca tcatct 36

<210> SEQ ID NO 360
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 360
gtggtgccgc ggagatttca accctcaaaa actgag 36

<210> SEQ ID NO 361
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 361
gtggtgccgc ggttgggaac atcagagaaa gtatga 36

<210> SEQ ID NO 362
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 362
gtggtgccgc ggacaaatta cagtctcctg ggaaag 36

<210> SEQ ID NO 363
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 363
gtggtgccgc ggcacttccc aagtgaggca at 32

<210> SEQ ID NO 364
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 364
gtggtgccgc ggctatactt ggggctgact tgctac 36

<210> SEQ ID NO 365
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 365
gtggtgccgc ggttggctct ttagcttgtg tttc 34

<210> SEQ ID NO 366
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 366
gtggtgccgc ggtgagactc ccaaaggcaa tc 32

<210> SEQ ID NO 367
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 367
gtggtgccgc ggttggctct ttagcttgtg tttc 34

<210> SEQ ID NO 368
<211> LENGTH: 32
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 368
gtggtgccgc ggactgaggg gtgatcttgg tg 32

<210> SEQ ID NO 369
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
gtggtgccgc gggcagagaa agccagtcgg ta 32

<210> SEQ ID NO 370
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
gtggtgccgc ggtgagactc ccaaaggcaa tc 32

<210> SEQ ID NO 371
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
gtggtgccgc gggcagagaa agccagtcgg ta 32

<210> SEQ ID NO 372
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
gtggtgccgc ggactgaggg gtgatcttgg tg 32

<210> SEQ ID NO 373
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
gtggtgccgc ggccagagtt cctagggcag ag 32

<210> SEQ ID NO 374
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 374
gtggtgccgc ggagctagtc cccacattcc ac 32

<210> SEQ ID NO 375
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 375
gtggtgccgc ggccagagtt cctagggcag ag 32

<210> SEQ ID NO 376
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 376
gtggtgccgc ggggtggagg gaaactttag gc 32

<210> SEQ ID NO 377
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 377
gtggtgccgc ggctcattct catgcctgga ca 32

<210> SEQ ID NO 378
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 378
gtggtgccgc ggagctagtc cccacattcc ac 32

<210> SEQ ID NO 379
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 379
gtggtgccgc ggtctcatgc ctggacaagt aact 34

<210> SEQ ID NO 380
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 380
gtggtgccgc ggggtggagg gaaactttag gc 32

<210> SEQ ID NO 381
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 381
gtggtgccgc ggggcttgga cagaacttac cg 32

<210> SEQ ID NO 382
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 382
gtggtgccgc ggcaccactg tctgcctaag ga 32

<210> SEQ ID NO 383
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 383
gtggtgccgc ggggcttgga cagaacttac cg 32

<210> SEQ ID NO 384
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 384
gtggtgccgc ggggtggagg gaaactttag gc 32

<210> SEQ ID NO 385
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 385
gtggtgccgc ggcgtagtgc caaaacaaac agt 33

<210> SEQ ID NO 386
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 386
gtggtgccgc ggcaccactg tctgcctaag ga 32

<210> SEQ ID NO 387
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 387
gtggtgccgc ggcgtagtgc caaaacaaac agt 33

<210> SEQ ID NO 388
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 388
gtggtgccgc ggggtggagg gaaactttag gc 32

<210> SEQ ID NO 389
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 389
gtggtgccgc gggcgagggc ctacttgata tg 32

<210> SEQ ID NO 390
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 390
gtggtgccgc ggcttcccaa gtgaggcaat gc 32

<210> SEQ ID NO 391
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 391
gtggtgccgc ggacgttttg tgctgctgta aca 33

<210> SEQ ID NO 392
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 392
gtggtgccgc ggctgcaggc acattctctt cc 32

<210> SEQ ID NO 393
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 393
gtggtgccgc gggccctgtg tggtagtagt ca 32

<210> SEQ ID NO 394
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 394
gtggtgccgc ggcttcccaa gtgaggcaat gc 32

<210> SEQ ID NO 395
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 395
gtggtgccgc ggcagtatta aggggtggga gct 33

<210> SEQ ID NO 396
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 396
gtggtgccgc ggtctcttcc tcacacagct ga 32

<210> SEQ ID NO 397
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 397
gtggtgccgc ggggagcttg gagggaagag aa 32

<210> SEQ ID NO 398
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 398
gtggtgccgc ggcttcccaa gtgaggcaat gc 32

<210> SEQ ID NO 399
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 399
gtggtgccgc ggatggatgg ggaagacact gg 32

<210> SEQ ID NO 400
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 400
gtggtgccgc ggctgcaggc acattctctt cc 32

<210> SEQ ID NO 401
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 401
gtggtgccgc ggggatgaaa cagggcagga ac 32

<210> SEQ ID NO 402
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 402
gtggtgccgc ggttcccaag tgaggcaatg c 31

<210> SEQ ID NO 403
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 403
gtggtgccgc ggtttgcaga gccatgatga gg 32

<210> SEQ ID NO 404
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 404
gtggtgccgc ggcgacagcc aaaacagccg 30

<210> SEQ ID NO 405
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 405
aaaatatttt agctcctact cagactgtta ctctggtgac acaa 44

<210> SEQ ID NO 406
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 406
ttgtgtcacc agagtaacag tctgagtagg agctaaaata tttt 44

<210> SEQ ID NO 407
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 407
tagctcctac tcagactgtt actctggtga cacaac 36

<210> SEQ ID NO 408
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 408
tagctcctac tcagactggt gacccaac 28

<210> SEQ ID NO 409
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 409
tagctcctac tctggtgaca caac 24

<210> SEQ ID NO 410
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 410
tagctcctac tcagactggt gacacaac 28

<210> SEQ ID NO 411
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 411
tagctcctac tcagac 16

<210> SEQ ID NO 412
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 412
tagctcctac tcagactgtt acacaac 27

<210> SEQ ID NO 413
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 413
tagctcctac tcagactgtg gtgaggtgac 30

<210> SEQ ID NO 414
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 414
tagctcctac tcagactctc tggtgacaca ac 32

<210> SEQ ID NO 415
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 415
tagctcctac tcagacctct ggtgacacaa c 31

<210> SEQ ID NO 416
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 416
tagctcctac tcaggctgtc tggtgacaca ac 32

<210> SEQ ID NO 417
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 417
tagctcctac tcagactact ctggtgacac aac 33

<210> SEQ ID NO 418
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 418
tagctcctac tcagactgtt gacacaac 28

<210> SEQ ID NO 419
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 419
ctggtgacac aac 13

<210> SEQ ID NO 420
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 420
tagctcctac tcagactgtt agacacaac 29

<210> SEQ ID NO 421
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 421
tagctcctac tcagactgct ctggtgacac aac 33

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 422
cagactgtta ctctggtgac 20

<210> SEQ ID NO 423

<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 423
cagaccacct gtggtctcct actggtgac 29

<210> SEQ ID NO 424
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 424
gctttgattt ccctaggg 18

<210> SEQ ID NO 425
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 425
gctttgattt ccagttctta ggcaa 25

<210> SEQ ID NO 426
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 426
gctttgattc ttaggcaa 18

<210> SEQ ID NO 427
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (13)..(53)
<223> OTHER INFORMATION: a, c, t, g, unknown or other

<400> SEQUENCE: 427
gctttgattt ccnnnnnnnn nnnnnnnnnn nnnnnnnnnn nnnnnnnnnn nnncttaggc 60
aa 62

<210> SEQ ID NO 428
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 428
tcttaaccat taccatag 18

<210> SEQ ID NO 429
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 429
tcttaaccat taccatagag ttcttaggca ac 32

<210> SEQ ID NO 430
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 430
tcttaaccat taccaaagtt cttaggcaac 30

<210> SEQ ID NO 431
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 431
tcttaaccat taccataggt tcttaggcaa c 31

<210> SEQ ID NO 432
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 432
gaaccaaacc cact 14

<210> SEQ ID NO 433
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 433
gaaccaaacc cacttagggg ataa 24

<210> SEQ ID NO 434
<211> LENGTH: 2328
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 434

```
atgaggtctg actacaaaga ccatgacggt gattataaag atcatgacat cgattacaag     60
gatgacgatg acaagatggc ccccaagaag aagaggaagg tgggcctcga gcccggagaa    120
aaaccgtaca agtgccctga gtgcgggaaa tcattctccg accctggggc gctcgtccgg    180
caccaaagga cgcatacagg ggaaaagccg tataagtgcc ccgagtgtgg aaagagcttc    240
tcgcagagag cccaccttga acgacaccaa agaacacaca ctggtgagaa accctataag    300
tgtccagagt gcggcaaatc gtttagcaga tccgatgact tggtgcgcca ccagcggaca    360
cacacgggtg aaaagcccta caaatgcccg gagtgtggga agtcgttttc aaggtcggat    420
catctgacta cccatcagcg cacccatacg ggagcggccg cccgcgccct ggtgaagagc    480
gagctggagg agaagaagtc cgagctgcgg cacaagctga agtacgtgcc ccacgagtac    540
atcgagctga tcgagatcgc caggaacccc acccaggacc gcatcctgga gatgaaggtg    600
atggagttct tcatgaaggt gtacggctac aggggagagc acctgggcgg aagcagaaag    660
cctgacggcg ccatctatac agtgggcagc ccccatcgatt acggcgtgat cgtggacaca    720
aaggcctaca gcggcggcta caatctgcct atcggccagg ccgacgagat gcagagatac    780
gtgaaggaga accagacccg gaataagcac atcaacccca acgagtggtg gaaggtgtac    840
cctagcagcg tgaccgagtt caagttcctg ttcgtgagcg gccacttcaa gggcaactac    900
aaggcccagc tgaccaggct gaaccgcaaa accaactgca atggcgccgt gctgagcgtg    960
gaggagctgc tgatcggcgg cgagatgatc aaagccggca ccctgacact ggaggaggtg   1020
cggcgcaagt tcaacaacgg cgagatcaac ttcgagggca gaggaagtct tctaacatgc   1080
ggtgacgtgg aggagaatcc cggccctaga tctgactaca aagaccatga cggtgattat   1140
aaagatcatg acatcgatta caaggatgac gatgacaaga tggcccccaa gaagaagagg   1200
aaggtgggcc tcgagccggg agagaagccg tacaagtgtc ccgaatgtgg aaagagcttc   1260
tcacagtcgg gggaccttcg gcgccaccag cgcacacata ctggtgaaaa gccgtataag   1320
tgtccagaat gtggcaaatc attctccaca tcagggagcc tggtcaggca ccagcgaacc   1380
cacacgggtg agaagcccta taagtgcccc gaatgcggga agtccttttc gcagagagcc   1440
cacttggaga ggcaccagag gacccatacg gggggagaaac cttacaagtg ccctgaatgc   1500
ggaaagtcgt tctcgaccca tctggatctc atcagacatc agagaacgca cactggagag   1560
aaaccctaca aatgtcccga gtgtgggaag tcgtttagcc gaaaggacaa tctcaaaaac   1620
catcaacgga cacacacggg tgaaaaacca tacaaatgcc cggagtgcgg caaatcgttt   1680
tcccaacttg cgcacttgcg ggcacaccaa cgcacgcata ctggagcggc cgcccgcgcc   1740
ctggtgaaga gcgagctgga ggagaagaag tccgagctgc ggcacaagct gaagtacgtg   1800
ccccacgagt acatcgagct gatcgagatc gccaggaacc ccacccagga ccgcatcctg   1860
gagatgaagg tgatggagtt cttcatgaag gtgtacggct acaggggaga gcacctgggc   1920
ggaagcagaa agcctgacgg cgccatctat acagtgggca gccccatcga ttacggcgtg   1980
atcgtggaca caaaggccta cagcggcggc tacaatctgc ctatcggcca ggccgacgag   2040
atgcagagat acgtggagga gaaccagaca cgggataagc acctcaaccc caacgagtgg   2100
tggaaggtgt accctagcag cgtgaccgag ttcaagttcc tgttcgtgag cggccacttc   2160
aagggcaact acaaggccca gctgaccagg ctgaaccaca tcaccaactg caatggcgcc   2220
gtgctgagcg tggaggagct gctgatcggc ggcgagatga tcaaagccgg caccctgaca   2280
ctggaggagg tgcggcgcaa gttcaacaac ggcgagatca acttctga                2328
```

<210> SEQ ID NO 435
<211> LENGTH: 775
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 435

Met Arg Ser Asp Tyr Lys Asp His Asp Gly Asp Tyr Lys Asp His Asp
1 5 10 15

Ile Asp Tyr Lys Asp Asp Asp Asp Lys Met Ala Pro Lys Lys Lys Arg
20 25 30

Lys Val Gly Leu Glu Pro Gly Glu Lys Pro Tyr Lys Cys Pro Glu Cys
35 40 45

Gly Lys Ser Phe Ser Asp Pro Gly Ala Leu Val Arg His Gln Arg Thr
50 55 60

His Thr Gly Glu Lys Pro Tyr Lys Cys Pro Glu Cys Gly Lys Ser Phe
65 70 75 80

Ser Gln Arg Ala His Leu Glu Arg His Gln Arg Thr His Thr Gly Glu
85 90 95

Lys Pro Tyr Lys Cys Pro Glu Cys Gly Lys Ser Phe Ser Arg Ser Asp
100 105 110

Asp Leu Val Arg His Gln Arg Thr His Thr Gly Glu Lys Pro Tyr Lys
115 120 125

Cys Pro Glu Cys Gly Lys Ser Phe Ser Arg Ser Asp His Leu Thr Thr
130 135 140

His Gln Arg Thr His Thr Gly Ala Ala Ala Arg Ala Leu Val Lys Ser
145 150 155 160

Glu Leu Glu Glu Lys Lys Ser Glu Leu Arg His Lys Leu Lys Tyr Val
165 170 175

Pro His Glu Tyr Ile Glu Leu Ile Glu Ile Ala Arg Asn Pro Thr Gln
180 185 190

Asp Arg Ile Leu Glu Met Lys Val Met Glu Phe Phe Met Lys Val Tyr
195 200 205

Gly Tyr Arg Gly Glu His Leu Gly Gly Ser Arg Lys Pro Asp Gly Ala
210 215 220

Ile Tyr Thr Val Gly Ser Pro Ile Asp Tyr Gly Val Ile Val Asp Thr
225 230 235 240

Lys Ala Tyr Ser Gly Gly Tyr Asn Leu Pro Ile Gly Gln Ala Asp Glu
245 250 255

Met Gln Arg Tyr Val Lys Glu Asn Gln Thr Arg Asn Lys His Ile Asn
260 265 270

Pro Asn Glu Trp Trp Lys Val Tyr Pro Ser Ser Val Thr Glu Phe Lys
275 280 285

Phe Leu Phe Val Ser Gly His Phe Lys Gly Asn Tyr Lys Ala Gln Leu
290 295 300

Thr Arg Leu Asn Arg Lys Thr Asn Cys Asn Gly Ala Val Leu Ser Val
305 310 315 320

Glu Glu Leu Leu Ile Gly Gly Glu Met Ile Lys Ala Gly Thr Leu Thr
325 330 335

Leu Glu Glu Val Arg Arg Lys Phe Asn Asn Gly Glu Ile Asn Phe Glu
340 345 350

Gly Arg Gly Ser Leu Leu Thr Cys Gly Asp Val Glu Glu Asn Pro Gly
355 360 365

```
Pro Arg Ser Asp Tyr Lys Asp His Asp Gly Asp Tyr Lys Asp His Asp
    370                 375                 380

Ile Asp Tyr Lys Asp Asp Asp Asp Lys Met Ala Pro Lys Lys Lys Arg
385                 390                 395                 400

Lys Val Gly Leu Glu Pro Gly Glu Lys Pro Tyr Lys Cys Pro Glu Cys
                405                 410                 415

Gly Lys Ser Phe Ser Gln Ser Gly Asp Leu Arg Arg His Gln Arg Thr
            420                 425                 430

His Thr Gly Glu Lys Pro Tyr Lys Cys Pro Glu Cys Gly Lys Ser Phe
        435                 440                 445

Ser Thr Ser Gly Ser Leu Val Arg His Gln Arg Thr His Thr Gly Glu
    450                 455                 460

Lys Pro Tyr Lys Cys Pro Glu Cys Gly Lys Ser Phe Ser Gln Arg Ala
465                 470                 475                 480

His Leu Glu Arg His Gln Arg Thr His Thr Gly Glu Lys Pro Tyr Lys
                485                 490                 495

Cys Pro Glu Cys Gly Lys Ser Phe Ser Thr His Leu Asp Leu Ile Arg
            500                 505                 510

His Gln Arg Thr His Thr Gly Glu Lys Pro Tyr Lys Cys Pro Glu Cys
        515                 520                 525

Gly Lys Ser Phe Ser Arg Lys Asp Asn Leu Lys Asn His Gln Arg Thr
    530                 535                 540

His Thr Gly Glu Lys Pro Tyr Lys Cys Pro Glu Cys Gly Lys Ser Phe
545                 550                 555                 560

Ser Gln Leu Ala His Leu Arg Ala His Gln Arg Thr His Thr Gly Ala
                565                 570                 575

Ala Ala Arg Ala Leu Val Lys Ser Glu Leu Glu Glu Lys Lys Ser Glu
            580                 585                 590

Leu Arg His Lys Leu Lys Tyr Val Pro His Glu Tyr Ile Glu Leu Ile
        595                 600                 605

Glu Ile Ala Arg Asn Pro Thr Gln Asp Arg Ile Leu Glu Met Lys Val
    610                 615                 620

Met Glu Phe Phe Met Lys Val Tyr Gly Tyr Arg Gly Glu His Leu Gly
625                 630                 635                 640

Gly Ser Arg Lys Pro Asp Gly Ala Ile Tyr Thr Val Gly Ser Pro Ile
                645                 650                 655

Asp Tyr Gly Val Ile Val Asp Thr Lys Ala Tyr Ser Gly Gly Tyr Asn
            660                 665                 670

Leu Pro Ile Gly Gln Ala Asp Glu Met Glu Arg Tyr Val Glu Glu Asn
        675                 680                 685

Gln Thr Arg Asp Lys His Leu Asn Pro Asn Glu Trp Trp Lys Val Tyr
    690                 695                 700

Pro Ser Ser Val Thr Glu Phe Lys Phe Leu Phe Val Ser Gly His Phe
705                 710                 715                 720

Lys Gly Asn Tyr Lys Ala Gln Leu Thr Arg Leu Asn His Ile Thr Asn
                725                 730                 735

Cys Asn Gly Ala Val Leu Ser Val Glu Glu Leu Leu Ile Gly Gly Glu
            740                 745                 750

Met Ile Lys Ala Gly Thr Leu Thr Leu Glu Glu Val Arg Arg Lys Phe
        755                 760                 765

Asn Asn Gly Glu Ile Asn Phe
    770                 775
```

<210> SEQ ID NO 436
<211> LENGTH: 4725
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 436
tggccactcc ctctatgcgc actcgctcgc tcggtggggc ctggcgacca aaggtcgcca 60
gacggacgtg ctttgcacgt ccggccccac cgagcgagcg agtgcgcata gagggagtgg 120
ccaactccat cactagaggt atggcagtga cgtaacgcga agcgcgcgaa gcgagaccac 180
gcctaccagc tgcgtcagca gtcaggtgac ccttttgcga cagtttgcga caccacgtgg 240
ccgctgaggg tatatattct cgagtgagcg aaccaggagc tccattttga ccgcgaaatt 300
tgaacgagca gcagccatgc cggggttcta cgagattgtc ctgaaggtcc cgagtgacct 360
ggacgagcac ctgccgggca tttctaactc gtttgttaac tgggtggccg agaaggaatg 420
ggagctgccg ccggattctg acatggatcc gaatctgatt gagcaggcac ccctgaccgt 480
ggccgaaaag cttcagcgcg agttcctggt ggagtggcgc cgcgtgagta aggccccgga 540
ggccctcttt tttgtccagt tcgaaaaggg ggagacctac ttccacctgc acgtgctgat 600
tgagaccatc ggggtcaaat ccatggtggt cggccgctac gtgagccaga ttaaagagaa 660
gctggtgacc cgcatctacc gcggggtcga gccgcagctt ccgaactggt tcgcggtgac 720
caaaacgcga aatggcgccg gggcgggaa caaggtggtg gacgactgct acatccccaa 780
ctacctgctc cccaagaccc agcccgagct ccagtgggcg tggactaaca tggaccagta 840
tttaagcgcc tgtttgaatc tcgcggagcg taaacggctg gtggcgcagc atctgacgca 900
cgtgtcgcag acgcaggagc agaacaaaga gaatcagaac cccaattctg acgcgccggt 960
catcaggtca aaaacctcag ccaggtacat ggagctggtc gggtggctgg tggaccgcgg 1020
gatcacgtca gaaaagcaat ggattcagga ggaccaggcc tcgtacatct ccttcaacgc 1080
cgcctccaac tcgcggtccc agatcaaggc cgcgctggac aatgcctcca agatcatgag 1140
cctgacaaag acggctccgg actacctggt gggcagcaac ccgccggagg acattaccaa 1200
aaatcggatc taccaaatcc tggagctgaa cgggtacgat ccgcagtacg cggcctccgt 1260
cttcctgggc tgggcgcaaa agaagttcgg gaagaggaac accatctggc tctttgggcc 1320
ggccacgacg ggtaaaacca acatcgcgga agccatcgcc cacgccgtgc ccttctacgg 1380
ctgcgtaaac tggaccaatg agaactttcc cttcaacgat tgcgtcgaca agatggtgat 1440
ctggtgggag gagggcaaga tgacggccaa ggtcgtggag agcgccaagg ccattctggg 1500
cggaagcaag gtgcgcgtgg accaaaagtg caagtcatcg gcccagatcg aacccactcc 1560
cgtgatcgtc acctccaaca ccaacatgtg cgccgtgatt gacgggaaca gcaccacctt 1620
cgagcatcag cagccgctgc aggaccggat gtttaaattt gaacttaccc gccgtttgga 1680
ccatgacttt gggaaggtca ccaaacagga agtaaaggac tttttccggt gggcttccga 1740
tcacgtgact gacgtggctc atgagttcta cgtcagaaag ggtggagcta agaaacgccc 1800
cgcctccaat gacgcggatg taagcgagcc aaaacggcag tgcacgtcac ttgcgcagcc 1860
gacaacgtca gacgcggaag caccggcgga ctacgcggac aggtaccaaa acaaatgttc 1920
tcgtcacgtg ggcatgaatc tgatgctttt tccctgtaaa acatgcgaga gaatgaatca 1980
aatttccaat gtctgtttta cgcatggtca aagagactgt ggggaatgct tccctggaat 2040
gtcagaatct caacccgttt ctgtcgtcaa aaagaagact tatcagaaac tgtgtccaat 2100

```
tcatcatatc ctgggaaggg cacccgagat tgcctgttcg gcctgcgatt tggccaatgt   2160
ggacttggat gactgtgttt ctgagcaata aatgacttaa accaggtatg gctgctgacg   2220
gttatcttcc agattggctc gaggacaacc tttctgaagg cattcgtgag tggtgggctc   2280
tgaaacctgg agtccctcaa cccaaagcga accaacaaca ccaggacaac cgtcggggtc   2340
ttgtgcttcc gggttacaaa tacctcggac ccggtaacgg actcgacaaa ggagagccgg   2400
tcaacgaggc ggacgcggca gccctcgaac acgacaaagc ttacgaccag cagctcaagg   2460
ccggtgacaa cccgtacctc aagtacaacc acgccgacgc cgagtttcag gagcgtcttc   2520
aagaagatac gtcttttggg ggcaaccttg gcagagcagt cttccaggcc aaaaagagga   2580
tccttgagcc tcttggtctg gttgaggaag cagctaaaac ggctcctgga aagaagaggc   2640
ctgtagatca gtctcctcag gaaccggact catcatctgg tgttggcaaa tcgggcaaac   2700
agcctgccag aaaaagacta aatttcggtc agactggcga ctcagagtca gtcccagacc   2760
ctcaacctct cggagaacca ccagcagccc ccacaagttt gggatctaat acaatggctt   2820
caggcggtgg cgcaccaatg gcagacaata acgagggtgc cgatggagtg ggtaattcct   2880
caggaaattg gcattgcgat tcccaatggc tgggcgacag agtcatcacc accagcacca   2940
gaacctgggc cctgcccact tacaacaacc atctctacaa gcaaatctcc agcgcttcaa   3000
cgggagcttc aaacgacaac cactactttg gctacagcac cccttggggg tattttgact   3060
ttaacagatt ccactgccac ttctcaccac gtgactggca gcgactcatt aacaacaact   3120
ggggattccg gcccaagaaa ctcagcttca agctcttcaa catccaagtt aaagaggtca   3180
cgcagaacga tggcacgacg actattgcca ataaccttac cagcacggtt caagtgttta   3240
cggactcgga gtatcagctc ccgtacgtgc tcgggtcggc gcaccaaggc tgtctcccgc   3300
cgtttccagc ggacgtcttc atggtccctc agtatggata cctcaccctg aacaacggaa   3360
gtcaagcggt gggacgctca tccttttact gcctggagta cttcccttcg cagatgctaa   3420
ggactggaaa taacttccaa ttcagctata ccttcgagga tgtacctttt cacagcagct   3480
acgctcacag ccagagtttg gatcgcttga tgaatcctct tattgatcag tatctgtact   3540
acctgaacag aacgcaagga acaacctctg gaacaaccaa ccaatcacgg ctgcttttta   3600
gccaggctgg gcctcagtct atgtctttgc aggccagaaa ttggctacct gggccctgct   3660
accggcaaca gagactttca aagactgcta acgacaacaa caacagtaac tttccttgga   3720
cagcggccag caaatatcat ctcaatggcc gcgactcgct ggtgaatcca ggaccagcta   3780
tggccagtca caaggacgat gaagaaaaat ttttccctat gcacggcaat ctaatatttg   3840
gcaaagaagg gacaacggca agtaacgcag aattagataa tgtaatgatt acggatgaag   3900
aagagattcg taccaccaat cctgtggcaa cagagcagta tggaactgtg gcaaataact   3960
tgcagagctc aaatacagct cccacgacta gaactgtcaa tgatcagggg gccttacctg   4020
gcatggtgtg gcaagatcgt gacgtgtacc ttcaaggacc tatctgggca aagattcctc   4080
acacggatgg acactttcat ccttctcctc tgatgggagg ctttggactg aaacatccgc   4140
ctcctcaaat catgatcaaa aatactccgg taccggcaaa tcctccgacg actttcagcc   4200
cggccaagtt tgcttcattt atcactcagt actccactgg acaggtcagc gtggaaattg   4260
agtgggagct acagaaagaa aacagcaaac gttggaatcc agagattcag tacacttcca   4320
actacaacaa gtctgttaat gtggacttta ctgtagacac taatggtgtt tatagtgaac   4380
ctcgccctat tggaacccgg tatctcacac gaaacttgta atcctggtta atcaataaac   4440
```

```
cgtttaattc gtttcagttg aactttggct cttgtgcact tcttatctta tcttgtttcc   4500

atggctactg cgtagataag cagcggcctg cggcgcttgc gcttcgcggt ttacaactgc   4560

tggttaatat ttaactctcg ccatacctct agtgatggag ttggccactc cctctatgcg   4620

cactcgctcg ctcggtgggg ccggacgtgc aaagcacgtc cgtctggcga cctttggtcg   4680

ccaggcccca ccgagcgagc gagtgcgcat agagggagtg gccaa                   4725


<210> SEQ ID NO 437
<211> LENGTH: 737
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Ser Phe Lys Leu Phe Asn Ile Gln
```

```
305                 310                 315                 320

Val Lys Glu Val Thr Gln Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Val Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Gly Thr Thr Ser Gly Thr Thr Asn Gln Ser Arg Leu Leu Phe
    450                 455                 460

Ser Gln Ala Gly Pro Gln Ser Met Ser Leu Gln Ala Arg Asn Trp Leu
465                 470                 475                 480

Pro Gly Pro Cys Tyr Arg Gln Gln Arg Leu Ser Lys Thr Ala Asn Asp
                485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Met His Gly Asn Leu Ile Phe
    530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys His Pro Pro Pro Gln Ile Met Ile Lys Asn Thr Pro Val Pro
                645                 650                 655

Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Asn
                725                 730                 735
```

Leu

<210> SEQ ID NO 438
<211> LENGTH: 406
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 438

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Arg Lys Asp Ala Leu Arg Gly His Gln Arg Thr His
    50                  55                  60

Thr Gly Glu Lys Pro Tyr Lys Cys Pro Glu Cys Gly Lys Ser Phe Ser
65                  70                  75                  80

His Arg Thr Thr Leu Thr Asn His Gln Arg Thr His Thr Gly Glu Lys
                85                  90                  95

Pro Tyr Lys Cys Pro Glu Cys Gly Lys Ser Phe Ser Gln Arg Asn Ala
            100                 105                 110

Leu Ala Gly His Gln Arg Thr His Thr Gly Glu Lys Pro Tyr Lys Cys
        115                 120                 125

Pro Glu Cys Gly Lys Ser Phe Ser His Lys Asn Ala Leu Gln Asn His
    130                 135                 140

Gln Arg Thr His Thr Gly Glu Lys Pro Tyr Lys Cys Pro Glu Cys Gly
145                 150                 155                 160

Lys Ser Phe Ser Asp Pro Gly His Leu Val Arg His Gln Arg Thr His
                165                 170                 175

Thr Gly Glu Lys Pro Tyr Lys Cys Pro Glu Cys Gly Lys Ser Phe Ser
            180                 185                 190

Thr Ser Gly Asn Leu Val Arg His Gln Arg Thr His Thr Gly Ala Ala
        195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
        275                 280                 285

Tyr Gly Val Ile Val Asp Thr Lys Ala Tyr Ser Gly Gly Tyr Asn Leu
    290                 295                 300

Pro Ile Gly Gln Ala Asp Glu Met Glu Arg Tyr Val Glu Glu Asn Gln
305                 310                 315                 320

Thr Arg Asp Lys His Leu Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350
```

```
Gly Asn Tyr Lys Ala Gln Leu Thr Arg Leu Asn His Ile Thr Asn Cys
        355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405


<210> SEQ ID NO 439
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Gln Gln Arg Ser Leu Val Gly His Gln Arg Thr His
    50                  55                  60

Thr Gly Glu Lys Pro Tyr Lys Cys Pro Glu Cys Gly Lys Ser Phe Ser
65                  70                  75                  80

Asp Lys Lys Asp Leu Thr Arg His Gln Arg Thr His Thr Gly Glu Lys
                85                  90                  95

Pro Tyr Lys Cys Pro Glu Cys Gly Lys Ser Phe Ser Thr Ser Gly His
            100                 105                 110

Leu Val Arg His Gln Arg Thr His Thr Gly Glu Lys Pro Tyr Lys Cys
        115                 120                 125

Pro Glu Cys Gly Lys Ser Phe Ser Gln Arg Ala His Leu Glu Arg His
    130                 135                 140

Gln Arg Thr His Thr Gly Glu Lys Pro Tyr Lys Cys Pro Glu Cys Gly
145                 150                 155                 160

Lys Ser Phe Ser Thr Ser Gly Ser Leu Val Arg His Gln Arg Thr His
                165                 170                 175

Thr Gly Glu Lys Pro Tyr Lys Cys Pro Glu Cys Gly Lys Ser Phe Ser
            180                 185                 190

Thr Ser Gly Asn Leu Val Arg His Gln Arg Thr His Thr Gly Ala Ala
        195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
        275                 280                 285

Tyr Gly Val Ile Val Asp Thr Lys Ala Tyr Ser Gly Gly Tyr Asn Leu
```

```
    290                 295                 300

Pro Ile Gly Gln Ala Asp Glu Met Gln Arg Tyr Val Lys Glu Asn Gln
305                 310                 315                 320

Thr Arg Asn Lys His Ile Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn Arg Lys Thr Asn Cys
        355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405


<210> SEQ ID NO 440
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Arg Pro Phe Gln Cys Arg Ile Cys Met
        35                  40                  45

Arg Asn Phe Ser Ser Lys Gln Ala Leu Ala Val His Thr Arg Thr His
    50                  55                  60

Thr Gly Glu Lys Pro Phe Gln Cys Arg Ile Cys Met Arg Asn Phe Ser
65                  70                  75                  80

Gln Ser Thr Thr Leu Lys Arg His Leu Arg Thr His Thr Gly Glu Lys
                85                  90                  95

Pro Phe Gln Cys Arg Ile Cys Met Arg Asn Phe Ser Arg Ser Asp His
            100                 105                 110

Leu Ser Leu His Leu Lys Thr His Leu Arg Gly Ser Gln Leu Val Lys
        115                 120                 125

Ser Glu Leu Glu Glu Lys Lys Ser Glu Leu Arg His Lys Leu Lys Tyr
    130                 135                 140

Val Pro His Glu Tyr Ile Glu Leu Ile Glu Ile Ala Arg Asn Pro Thr
145                 150                 155                 160

Gln Asp Arg Ile Leu Glu Met Lys Val Met Glu Phe Phe Met Lys Val
                165                 170                 175

Tyr Gly Tyr Arg Gly Glu His Leu Gly Gly Ser Arg Lys Pro Asp Gly
            180                 185                 190

Ala Ile Tyr Thr Val Gly Ser Pro Ile Asp Tyr Gly Val Ile Val Asp
        195                 200                 205

Thr Lys Ala Tyr Ser Gly Gly Tyr Asn Leu Pro Ile Gly Gln Ala Asp
    210                 215                 220

Glu Met Gln Arg Tyr Val Lys Glu Asn Gln Thr Arg Asn Lys His Ile
225                 230                 235                 240
```

```
Asn Pro Asn Glu Trp Trp Lys Val Tyr Pro Ser Ser Val Thr Glu Phe
                245                 250                 255

Lys Phe Leu Phe Val Ser Gly His Phe Lys Gly Asn Tyr Lys Ala Gln
            260                 265                 270

Leu Thr Arg Leu Asn Arg Lys Thr Asn Cys Asn Gly Ala Val Leu Ser
        275                 280                 285

Val Glu Glu Leu Leu Ile Gly Gly Glu Met Ile Lys Ala Gly Thr Leu
    290                 295                 300

Thr Leu Glu Glu Val Arg Arg Lys Phe Asn Asn Gly Glu Ile Asn Phe
305                 310                 315                 320


<210> SEQ ID NO 441
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Arg Pro Phe Gln Cys Arg Ile Cys Met
        35                  40                  45

Arg Asn Phe Ser Arg Arg Ala His Leu Gln Asn His Thr Arg Thr His
    50                  55                  60

Thr Gly Glu Lys Pro Phe Gln Cys Arg Ile Cys Met Arg Asn Phe Ser
65                  70                  75                  80

Gln Ser Thr Thr Leu Lys Arg His Leu Arg Thr His Thr Gly Glu Lys
                85                  90                  95

Pro Phe Gln Cys Arg Ile Cys Met Arg Asn Phe Ser Asp Gly Gly His
            100                 105                 110

Leu Thr Arg His Leu Lys Thr His Leu Arg Gly Ser Gln Leu Val Lys
        115                 120                 125

Ser Glu Leu Glu Glu Lys Lys Ser Glu Leu Arg His Lys Leu Lys Tyr
    130                 135                 140

Val Pro His Glu Tyr Ile Glu Leu Ile Glu Ile Ala Arg Asn Pro Thr
145                 150                 155                 160

Gln Asp Arg Ile Leu Glu Met Lys Val Met Glu Phe Phe Met Lys Val
                165                 170                 175

Tyr Gly Tyr Arg Gly Glu His Leu Gly Gly Ser Arg Lys Pro Asp Gly
            180                 185                 190

Ala Ile Tyr Thr Val Gly Ser Pro Ile Asp Tyr Gly Val Ile Val Asp
        195                 200                 205

Thr Lys Ala Tyr Ser Gly Gly Tyr Asn Leu Pro Ile Gly Gln Ala Asp
    210                 215                 220

Glu Met Glu Arg Tyr Val Glu Glu Asn Gln Thr Arg Asp Lys His Leu
225                 230                 235                 240

Asn Pro Asn Glu Trp Trp Lys Val Tyr Pro Ser Ser Val Thr Glu Phe
                245                 250                 255

Lys Phe Leu Phe Val Ser Gly His Phe Lys Gly Asn Tyr Lys Ala Gln
            260                 265                 270

Leu Thr Arg Leu Asn His Ile Thr Asn Cys Asn Gly Ala Val Leu Ser
        275                 280                 285
```

Val Glu Glu Leu Leu Ile Gly Gly Glu Met Ile Lys Ala Gly Thr Leu
    290                 295                 300

Thr Leu Glu Glu Val Arg Arg Lys Phe Asn Asn Gly Glu Ile Asn Phe
305                 310                 315                 320

<210> SEQ ID NO 442
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
caaactagaa atgccatctt ccttgatgtt ggaggtacct gc                          42

<210> SEQ ID NO 443
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Arg Lys Asp Ala Leu Arg Gly His Gln Arg Thr His
    50                  55                  60

Thr Gly Glu Lys Pro Tyr Lys Cys Pro Glu Cys Gly Lys Ser Phe Ser
65                  70                  75                  80

His Arg Thr Thr Leu Thr Asn His Gln Arg Thr His Thr Gly Glu Lys
                85                  90                  95

Pro Tyr Lys Cys Pro Glu Cys Gly Lys Ser Phe Ser Gln Arg Asn Ala
            100                 105                 110

Leu Ala Gly His Gln Arg Thr His Thr Gly Glu Lys Pro Tyr Lys Cys
        115                 120                 125

Pro Glu Cys Gly Lys Ser Phe Ser His Lys Asn Ala Leu Gln Asn His
    130                 135                 140

Gln Arg Thr His Thr Gly Glu Lys Pro Tyr Lys Cys Pro Glu Cys Gly
145                 150                 155                 160

Lys Ser Phe Ser Asp Pro Gly His Leu Val Arg His Gln Arg Thr His
                165                 170                 175

Thr Gly Glu Lys Pro Tyr Lys Cys Pro Glu Cys Gly Lys Ser Phe Ser
            180                 185                 190

Thr Ser Gly Asn Leu Val Arg His Gln Arg Thr His Thr Gly Ala Ala
        195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

```
Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
        275                 280                 285

Tyr Gly Val Ile Val Asp Thr Lys Ala Tyr Ser Gly Gly Tyr Asn Leu
    290                 295                 300

Pro Ile Gly Gln Ala Asp Glu Met Glu Arg Tyr Val Glu Glu Asn Gln
305                 310                 315                 320

Thr Arg Asp Lys His Leu Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn His Ile Thr Asn Cys
        355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405


<210> SEQ ID NO 444
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Gln Gln Arg Ser Leu Val Gly His Gln Arg Thr His
    50                  55                  60

Thr Gly Glu Lys Pro Tyr Lys Cys Pro Glu Cys Gly Lys Ser Phe Ser
65                  70                  75                  80

Asp Lys Lys Asp Leu Thr Arg His Gln Arg Thr His Thr Gly Glu Lys
                85                  90                  95

Pro Tyr Lys Cys Pro Glu Cys Gly Lys Ser Phe Ser Thr Ser Gly His
            100                 105                 110

Leu Val Arg His Gln Arg Thr His Thr Gly Glu Lys Pro Tyr Lys Cys
        115                 120                 125

Pro Glu Cys Gly Lys Ser Phe Ser Gln Arg Ala His Leu Glu Arg His
    130                 135                 140

Gln Arg Thr His Thr Gly Glu Lys Pro Tyr Lys Cys Pro Glu Cys Gly
145                 150                 155                 160

Lys Ser Phe Ser Thr Ser Gly Ser Leu Val Arg His Gln Arg Thr His
                165                 170                 175

Thr Gly Glu Lys Pro Tyr Lys Cys Pro Glu Cys Gly Lys Ser Phe Ser
            180                 185                 190

Thr Ser Gly Asn Leu Val Arg His Gln Arg Thr His Thr Gly Ala Ala
        195                 200                 205
```

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
        275                 280                 285

Tyr Gly Val Ile Val Asp Thr Lys Ala Tyr Ser Gly Gly Tyr Asn Leu
    290                 295                 300

Pro Ile Gly Gln Ala Asp Glu Met Gln Arg Tyr Val Lys Glu Asn Gln
305                 310                 315                 320

Thr Arg Asn Lys His Ile Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn Arg Lys Thr Asn Cys
        355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405

<210> SEQ ID NO 445
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (25)..(25)
<223> OTHER INFORMATION: May or may not be present

<400> SEQUENCE: 445
tatctgccca tgactggcgc aggga                                          25

<210> SEQ ID NO 446
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Arg Pro Phe Gln Cys Arg Ile Cys Met

-continued

```
        35                  40                  45

Arg Asn Phe Ser Ser Lys Gln Ala Leu Ala Val His Thr Arg Thr His
    50                  55                  60

Thr Gly Glu Lys Pro Phe Gln Cys Arg Ile Cys Met Arg Asn Phe Ser
65                  70                  75                  80

Gln Ser Thr Thr Leu Lys Arg His Leu Arg Thr His Thr Gly Glu Lys
                85                  90                  95

Pro Phe Gln Cys Arg Ile Cys Met Arg Asn Phe Ser Arg Ser Asp His
            100                 105                 110

Leu Ser Leu His Leu Lys Thr His Leu Arg Gly Ser Gln Leu Val Lys
        115                 120                 125

Ser Glu Leu Glu Glu Lys Lys Ser Glu Leu Arg His Lys Leu Lys Tyr
    130                 135                 140

Val Pro His Glu Tyr Ile Glu Leu Ile Glu Ile Ala Arg Asn Pro Thr
145                 150                 155                 160

Gln Asp Arg Ile Leu Glu Met Lys Val Met Glu Phe Phe Met Lys Val
                165                 170                 175

Tyr Gly Tyr Arg Gly Glu His Leu Gly Gly Ser Arg Lys Pro Asp Gly
            180                 185                 190

Ala Ile Tyr Thr Val Gly Ser Pro Ile Asp Tyr Gly Val Ile Val Asp
        195                 200                 205

Thr Lys Ala Tyr Ser Gly Gly Tyr Asn Leu Pro Ile Gly Gln Ala Asp
    210                 215                 220

Glu Met Gln Arg Tyr Val Lys Glu Asn Gln Thr Arg Asn Lys His Ile
225                 230                 235                 240

Asn Pro Asn Glu Trp Trp Lys Val Tyr Pro Ser Ser Val Thr Glu Phe
                245                 250                 255

Lys Phe Leu Phe Val Ser Gly His Phe Lys Gly Asn Tyr Lys Ala Gln
            260                 265                 270

Leu Thr Arg Leu Asn Arg Lys Thr Asn Cys Asn Gly Ala Val Leu Ser
        275                 280                 285

Val Glu Glu Leu Leu Ile Gly Gly Glu Met Ile Lys Ala Gly Thr Leu
    290                 295                 300

Thr Leu Glu Glu Val Arg Arg Lys Phe Asn Asn Gly Glu Ile Asn Phe
305                 310                 315                 320


<210> SEQ ID NO 447
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Arg Pro Phe Gln Cys Arg Ile Cys Met
        35                  40                  45

Arg Asn Phe Ser Arg Arg Ala His Leu Gln Asn His Thr Arg Thr His
    50                  55                  60

Thr Gly Glu Lys Pro Phe Gln Cys Arg Ile Cys Met Arg Asn Phe Ser
65                  70                  75                  80
```

```
Gln Ser Thr Thr Leu Lys Arg His Leu Arg Thr His Thr Gly Glu Lys
                85                  90                  95

Pro Phe Gln Cys Arg Ile Cys Met Arg Asn Phe Ser Asp Gly Gly His
            100                 105                 110

Leu Thr Arg His Leu Lys Thr His Leu Arg Gly Ser Gln Leu Val Lys
        115                 120                 125

Ser Glu Leu Glu Glu Lys Lys Ser Glu Leu Arg His Lys Leu Lys Tyr
    130                 135                 140

Val Pro His Glu Tyr Ile Glu Leu Ile Glu Ile Ala Arg Asn Pro Thr
145                 150                 155                 160

Gln Asp Arg Ile Leu Glu Met Lys Val Met Glu Phe Phe Met Lys Val
                165                 170                 175

Tyr Gly Tyr Arg Gly Glu His Leu Gly Gly Ser Arg Lys Pro Asp Gly
            180                 185                 190

Ala Ile Tyr Thr Val Gly Ser Pro Ile Asp Tyr Gly Val Ile Val Asp
        195                 200                 205

Thr Lys Ala Tyr Ser Gly Gly Tyr Asn Leu Pro Ile Gly Gln Ala Asp
    210                 215                 220

Glu Met Glu Arg Tyr Val Glu Glu Asn Gln Thr Arg Asp Lys His Leu
225                 230                 235                 240

Asn Pro Asn Glu Trp Trp Lys Val Tyr Pro Ser Ser Val Thr Glu Phe
                245                 250                 255

Lys Phe Leu Phe Val Ser Gly His Phe Lys Gly Asn Tyr Lys Ala Gln
            260                 265                 270

Leu Thr Arg Leu Asn His Ile Thr Asn Cys Asn Gly Ala Val Leu Ser
        275                 280                 285

Val Glu Glu Leu Leu Ile Gly Gly Glu Met Ile Lys Ala Gly Thr Leu
    290                 295                 300

Thr Leu Glu Glu Val Arg Arg Lys Phe Asn Asn Gly Glu Ile Asn Phe
305                 310                 315                 320
```

<210> SEQ ID NO 448
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 448

```
actagaaatg ccatcttcct tgatgttgga ggtacctgct ct                        42
```

<210> SEQ ID NO 449
<211> LENGTH: 406
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 449

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser His Arg Thr Thr Leu Thr Asn His Gln Arg Thr His
```

```
    50                  55                  60

Thr Gly Glu Lys Pro Tyr Lys Cys Pro Glu Cys Gly Lys Ser Phe Ser
65                  70                  75                  80

Gln Arg Asn Ala Leu Ala Gly His Gln Arg Thr His Thr Gly Glu Lys
                85                  90                  95

Pro Tyr Lys Cys Pro Glu Cys Gly Lys Ser Phe Ser His Lys Asn Ala
            100                 105                 110

Leu Gln Asn His Gln Arg Thr His Thr Gly Glu Lys Pro Tyr Lys Cys
        115                 120                 125

Pro Glu Cys Gly Lys Ser Phe Ser Asp Pro Gly His Leu Val Arg His
    130                 135                 140

Gln Arg Thr His Thr Gly Glu Lys Pro Tyr Lys Cys Pro Glu Cys Gly
145                 150                 155                 160

Lys Ser Phe Ser Thr Ser Gly Asn Leu Val Arg His Gln Arg Thr His
                165                 170                 175

Thr Gly Glu Lys Pro Tyr Lys Cys Pro Glu Cys Gly Lys Ser Phe Ser
            180                 185                 190

Gln Ser Ser Asn Leu Val Arg His Gln Arg Thr His Thr Gly Ala Ala
        195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
        275                 280                 285

Tyr Gly Val Ile Val Asp Thr Lys Ala Tyr Ser Gly Gly Tyr Asn Leu
    290                 295                 300

Pro Ile Gly Gln Ala Asp Glu Met Glu Arg Tyr Val Glu Glu Asn Gln
305                 310                 315                 320

Thr Arg Asp Lys His Leu Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn His Ile Thr Asn Cys
        355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405
```

<210> SEQ ID NO 450
<211> LENGTH: 406
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 450

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Gln Arg Asn Ala Leu Ala Gly His Gln Arg Thr His
    50                  55                  60

Thr Gly Glu Lys Pro Tyr Lys Cys Pro Glu Cys Gly Lys Ser Phe Ser
65                  70                  75                  80

Gln Gln Arg Ser Leu Val Gly His Gln Arg Thr His Thr Gly Glu Lys
                85                  90                  95

Pro Tyr Lys Cys Pro Glu Cys Gly Lys Ser Phe Ser Asp Lys Lys Asp
            100                 105                 110

Leu Thr Arg His Gln Arg Thr His Thr Gly Glu Lys Pro Tyr Lys Cys
        115                 120                 125

Pro Glu Cys Gly Lys Ser Phe Ser Thr Ser Gly His Leu Val Arg His
    130                 135                 140

Gln Arg Thr His Thr Gly Glu Lys Pro Tyr Lys Cys Pro Glu Cys Gly
145                 150                 155                 160

Lys Ser Phe Ser Gln Arg Ala His Leu Glu Arg His Gln Arg Thr His
                165                 170                 175

Thr Gly Glu Lys Pro Tyr Lys Cys Pro Glu Cys Gly Lys Ser Phe Ser
            180                 185                 190

Thr Ser Gly Ser Leu Val Arg His Gln Arg Thr His Thr Gly Ala Ala
        195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
        275                 280                 285

Tyr Gly Val Ile Val Asp Thr Lys Ala Tyr Ser Gly Gly Tyr Asn Leu
    290                 295                 300

Pro Ile Gly Gln Ala Asp Glu Met Gln Arg Tyr Val Lys Glu Asn Gln
305                 310                 315                 320

Thr Arg Asn Lys His Ile Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn Arg Lys Thr Asn Cys
        355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405
```

<210> SEQ ID NO 451
<211> LENGTH: 378
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 451

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Gln Arg Asn Ala Leu Ala Gly His Gln Arg Thr His
    50                  55                  60

Thr Gly Glu Lys Pro Tyr Lys Cys Pro Glu Cys Gly Lys Ser Phe Ser
65                  70                  75                  80

His Lys Asn Ala Leu Gln Asn His Gln Arg Thr His Thr Gly Glu Lys
                85                  90                  95

Pro Tyr Lys Cys Pro Glu Cys Gly Lys Ser Phe Ser Asp Pro Gly His
            100                 105                 110

Leu Val Arg His Gln Arg Thr His Thr Gly Glu Lys Pro Tyr Lys Cys
        115                 120                 125

Pro Glu Cys Gly Lys Ser Phe Ser Thr Ser Gly Asn Leu Val Arg His
    130                 135                 140

Gln Arg Thr His Thr Gly Glu Lys Pro Tyr Lys Cys Pro Glu Cys Gly
145                 150                 155                 160

Lys Ser Phe Ser Gln Ser Ser Asn Leu Val Arg His Gln Arg Thr His
                165                 170                 175

Thr Gly Ala Ala Ala Arg Ala Leu Val Lys Ser Glu Leu Glu Glu Lys
            180                 185                 190

Lys Ser Glu Leu Arg His Lys Leu Lys Tyr Val Pro His Glu Tyr Ile
        195                 200                 205

Glu Leu Ile Glu Ile Ala Arg Asn Pro Thr Gln Asp Arg Ile Leu Glu
    210                 215                 220

Met Lys Val Met Glu Phe Phe Met Lys Val Tyr Gly Tyr Arg Gly Glu
225                 230                 235                 240

His Leu Gly Gly Ser Arg Lys Pro Asp Gly Ala Ile Tyr Thr Val Gly
                245                 250                 255

Ser Pro Ile Asp Tyr Gly Val Ile Val Asp Thr Lys Ala Tyr Ser Gly
            260                 265                 270

Gly Tyr Asn Leu Pro Ile Gly Gln Ala Asp Glu Met Glu Arg Tyr Val
        275                 280                 285

Glu Glu Asn Gln Thr Arg Asp Lys His Leu Asn Pro Asn Glu Trp Trp
    290                 295                 300

Lys Val Tyr Pro Ser Ser Val Thr Glu Phe Lys Phe Leu Phe Val Ser
305                 310                 315                 320

Gly His Phe Lys Gly Asn Tyr Lys Ala Gln Leu Thr Arg Leu Asn His
                325                 330                 335

Ile Thr Asn Cys Asn Gly Ala Val Leu Ser Val Glu Glu Leu Leu Ile
            340                 345                 350

Gly Gly Glu Met Ile Lys Ala Gly Thr Leu Thr Leu Glu Glu Val Arg
        355                 360                 365
```

```
Arg Lys Phe Asn Asn Gly Glu Ile Asn Phe
    370                 375


<210> SEQ ID NO 452
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Gln Gln Arg Ser Leu Val Gly His Gln Arg Thr His
    50                  55                  60

Thr Gly Glu Lys Pro Tyr Lys Cys Pro Glu Cys Gly Lys Ser Phe Ser
65                  70                  75                  80

Asp Lys Lys Asp Leu Thr Arg His Gln Arg Thr His Thr Gly Glu Lys
                85                  90                  95

Pro Tyr Lys Cys Pro Glu Cys Gly Lys Ser Phe Ser Thr Ser Gly His
            100                 105                 110

Leu Val Arg His Gln Arg Thr His Thr Gly Glu Lys Pro Tyr Lys Cys
        115                 120                 125

Pro Glu Cys Gly Lys Ser Phe Ser Gln Arg Ala His Leu Glu Arg His
    130                 135                 140

Gln Arg Thr His Thr Gly Glu Lys Pro Tyr Lys Cys Pro Glu Cys Gly
145                 150                 155                 160

Lys Ser Phe Ser Thr Ser Gly Ser Leu Val Arg His Gln Arg Thr His
                165                 170                 175

Thr Gly Ala Ala Ala Arg Ala Leu Val Lys Ser Glu Leu Glu Glu Lys
            180                 185                 190

Lys Ser Glu Leu Arg His Lys Leu Lys Tyr Val Pro His Glu Tyr Ile
        195                 200                 205

Glu Leu Ile Glu Ile Ala Arg Asn Pro Thr Gln Asp Arg Ile Leu Glu
    210                 215                 220

Met Lys Val Met Glu Phe Phe Met Lys Val Tyr Gly Tyr Arg Gly Glu
225                 230                 235                 240

His Leu Gly Gly Ser Arg Lys Pro Asp Gly Ala Ile Tyr Thr Val Gly
                245                 250                 255

Ser Pro Ile Asp Tyr Gly Val Ile Val Asp Thr Lys Ala Tyr Ser Gly
            260                 265                 270

Gly Tyr Asn Leu Pro Ile Gly Gln Ala Asp Glu Met Gln Arg Tyr Val
        275                 280                 285

Lys Glu Asn Gln Thr Arg Asn Lys His Ile Asn Pro Asn Glu Trp Trp
    290                 295                 300

Lys Val Tyr Pro Ser Ser Val Thr Glu Phe Lys Phe Leu Phe Val Ser
305                 310                 315                 320

Gly His Phe Lys Gly Asn Tyr Lys Ala Gln Leu Thr Arg Leu Asn Arg
                325                 330                 335

Lys Thr Asn Cys Asn Gly Ala Val Leu Ser Val Glu Glu Leu Leu Ile
            340                 345                 350
```

Gly Gly Glu Met Ile Lys Ala Gly Thr Leu Thr Leu Glu Glu Val Arg
        355                 360                 365

Arg Lys Phe Asn Asn Gly Glu Ile Asn Phe
    370                 375

<210> SEQ ID NO 453
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (26)..(26)
<223> OTHER INFORMATION: May or may not be present

<400> SEQUENCE: 453
tgccatcttc cttgatgttg gaggta                                          26

<210> SEQ ID NO 454
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Arg Pro Phe Gln Cys Arg Ile Cys Met
        35                  40                  45

Arg Asn Phe Ser Ser Pro Ser Lys Leu Ala Arg His Thr Arg Thr His
    50                  55                  60

Thr Gly Glu Lys Pro Phe Gln Cys Arg Ile Cys Met Arg Asn Phe Ser
65                  70                  75                  80

Val Arg His Asn Leu Thr Arg His Leu Arg Thr His Thr Gly Glu Lys
                85                  90                  95

Pro Phe Gln Cys Arg Ile Cys Met Arg Asn Phe Ser Gln Arg Asn Asn
            100                 105                 110

Leu Gly Arg His Leu Lys Thr His Thr Gly Ala Ala Ala Arg Ala Leu
        115                 120                 125

Val Lys Ser Glu Leu Glu Glu Lys Lys Ser Glu Leu Arg His Lys Leu
    130                 135                 140

Lys Tyr Val Pro His Glu Tyr Ile Glu Leu Ile Glu Ile Ala Arg Asn
145                 150                 155                 160

Pro Thr Gln Asp Arg Ile Leu Glu Met Lys Val Met Glu Phe Phe Met
                165                 170                 175

Lys Val Tyr Gly Tyr Arg Gly Glu His Leu Gly Gly Ser Arg Lys Pro
            180                 185                 190

Asp Gly Ala Ile Tyr Thr Val Gly Ser Pro Ile Asp Tyr Gly Val Ile
        195                 200                 205

Val Asp Thr Lys Ala Tyr Ser Gly Gly Tyr Asn Leu Pro Ile Gly Gln 210 215 220

Ala Asp Glu Met Gln Arg Tyr Val Lys Glu Asn Gln Thr Arg Asn Lys
225 230 235 240

His Ile Asn Pro Asn Glu Trp Trp Lys Val Tyr Pro Ser Ser Val Thr
245 250 255

Glu Phe Lys Phe Leu Phe Val Ser Gly His Phe Lys Gly Asn Tyr Lys
260 265 270

Ala Gln Leu Thr Arg Leu Asn Arg Lys Thr Asn Cys Asn Gly Ala Val
275 280 285

Leu Ser Val Glu Glu Leu Leu Ile Gly Gly Glu Met Ile Lys Ala Gly
290 295 300

Thr Leu Thr Leu Glu Glu Val Arg Arg Lys Phe Asn Asn Gly Glu Ile
305 310 315 320

Asn Phe

<210> SEQ ID NO 455
<211> LENGTH: 322
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 455

Met Asp Tyr Lys Asp His Asp Gly Asp Tyr Lys Asp His Asp Ile Asp
1 5 10 15

Tyr Lys Asp Asp Asp Asp Lys Met Ala Pro Lys Lys Lys Arg Lys Val
20 25 30

Gly Arg Leu Glu Pro Gly Glu Arg Pro Phe Gln Cys Arg Ile Cys Met
35 40 45

Arg Asn Phe Ser Ile Pro Asn His Leu Ala Arg His Thr Arg Thr His
50 55 60

Thr Gly Glu Lys Pro Phe Gln Cys Arg Ile Cys Met Arg Asn Phe Ser
65 70 75 80

Gln Ser Ala His Leu Lys Arg His Leu Arg Thr His Thr Gly Glu Lys
85 90 95

Pro Phe Gln Cys Arg Ile Cys Met Arg Asn Phe Ser His His Asn Ser
100 105 110

Leu Thr Arg His Leu Lys Thr His Thr Gly Ala Ala Ala Arg Ala Leu
115 120 125

Val Lys Ser Glu Leu Glu Glu Lys Lys Ser Glu Leu Arg His Lys Leu
130 135 140

Lys Tyr Val Pro His Glu Tyr Ile Glu Leu Ile Glu Ile Ala Arg Asn
145 150 155 160

Pro Thr Gln Asp Arg Ile Leu Glu Met Lys Val Met Glu Phe Phe Met
165 170 175

Lys Val Tyr Gly Tyr Arg Gly Glu His Leu Gly Gly Ser Arg Lys Pro
180 185 190

Asp Gly Ala Ile Tyr Thr Val Gly Ser Pro Ile Asp Tyr Gly Val Ile
195 200 205

Val Asp Thr Lys Ala Tyr Ser Gly Gly Tyr Asn Leu Pro Ile Gly Gln
210 215 220

Ala Asp Glu Met Glu Arg Tyr Val Glu Glu Asn Gln Thr Arg Asp Lys
225 230 235 240

His Leu Asn Pro Asn Glu Trp Trp Lys Val Tyr Pro Ser Ser Val Thr 245 250 255

Glu Phe Lys Phe Leu Phe Val Ser Gly His Phe Lys Gly Asn Tyr Lys
260 265 270

Ala Gln Leu Thr Arg Leu Asn His Ile Thr Asn Cys Asn Gly Ala Val
275 280 285

Leu Ser Val Glu Glu Leu Leu Ile Gly Gly Glu Met Ile Lys Ala Gly
290 295 300

Thr Leu Thr Leu Glu Glu Val Arg Arg Lys Phe Asn Asn Gly Glu Ile
305 310 315 320

Asn Phe

<210> SEQ ID NO 456
<211> LENGTH: 6626
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 456
gggggggggg gggggggtt ggccactccc tctctgcgcg ctcgctcgct cactgaggcc 60
gggcgaccaa aggtcgcccg acgcccgggc tttgcccggg cggcctcagt gagcgagcga 120
gcgcgcagag agggagtggc caactccatc actaggggtt cctagatctg aattcggtac 180
ccgttacata acttacggta aatggcccgc ctggctgacc gcccaacgac ccccgcccat 240
tgacgtcaat aatgacgtat gttcccatag taacgccaat agggactttc cattgacgtc 300
aatgggtgga gtatttacgg taaactgccc acttggcagt acatcaagtg tatcatatgc 360
caagtacgcc ccctattgac gtcaatgacg gtaaatggcc cgcctggcat tatgcccagt 420
acatgacctt atgggacttt cctacttggc agtacatcta cgtattagtc atcgctatta 480
ccatggtgat gcggttttgg cagtacatca atgggcgtgg atagcggttt gactcacggg 540
gatttccaag tctccacccc attgacgtca atgggagttt gttttggcac caaaatcaac 600
gggactttcc aaaatgtcgt aacaactccg ccccattgac gcaaatgggc ggtaggcgtg 660
tacggtggga ggtctatata agcagagctc gtttagtgaa ccgtcagatc gcctggagac 720
gccatccacg ctgttttgac ctccatagaa gacaccggga ccgatccagc ctccggactc 780
tagaggatcc ggtactcgag gaactgaaaa accagaaagt taactggtaa gtttagtctt 840
tttgtctttt atttcaggtc ccggatccgg tggtggtgca aatcaaagaa ctgctcctca 900
gtggatgttg cctttacttc taggcctgta cggaagtgtt acttctgctc taaaagctgc 960
ggaattgtac ccgcggcccg ggatccaccg gtggctagcg tctataggcc cacccccttg 1020
gtggaattcg ccatgaggtc tgactacaaa gaccatgacg gtgattataa agatcatgac 1080
atcgattaca aggatgacga tgacaagatg gcccccaaga agaagaggaa ggtgggcctc 1140
gagcccggag aaaaaccgta caagtgccct gagtgcggga aatcattctc cgaccctggg 1200
gcgctcgtcc ggcaccaaag gacgcataca ggggaaaagc cgtataagtg ccccgagtgt 1260
ggaaagagct tctcgcagag agcccacctt gaacgacacc aaagaacaca cactggtgag 1320
aaaccctata agtgtccaga gtgcggcaaa tcgtttagca gatccgatga cttggtgcgc 1380
caccagcgga cacacacggg tgaaaagccc tacaaatgcc cggagtgtgg gaagtcgttt 1440
tcaaggtcgg atcatctgac tacccatcag cgcacccata cgggagcggc cgcccgcgcc 1500
ctggtgaaga gcgagctgga ggagaagaag tccgagctgc ggcacaagct gaagtacgtg 1560

-continued

```
ccccacgagt acatcgagct gatcgagatc gccaggaacc ccacccagga ccgcatcctg   1620
gagatgaagg tgatggagtt cttcatgaag gtgtacggct acaggggaga gcacctgggc   1680
ggaagcagaa agcctgacgg cgccatctat acagtgggca gccccatcga ttacggcgtg   1740
atcgtggaca caaaggccta cagcggcggc tacaatctgc ctatcggcca ggccgacgag   1800
atgcagagat acgtgaagga gaaccagacc cggaataagc acatcaaccc caacgagtgg   1860
tggaaggtgt accctagcag cgtgaccgag ttcaagttcc tgttcgtgag cggccacttc   1920
aagggcaact acaaggccca gctgaccagg ctgaaccgca aaaccaactg caatggcgcc   1980
gtgctgagcg tggaggagct gctgatcggc ggcgagatga tcaaagccgg caccctgaca   2040
ctggaggagg tgcggcgcaa gttcaacaac ggcgagatca acttcgaggg cagaggaagt   2100
cttctaacat gcggtgacgt ggaggagaat cccggcccta gatctgacta caaagaccat   2160
gacggtgatt ataaagatca tgacatcgat tacaaggatg acgatgacaa gatggccccc   2220
aagaagaaga ggaaggtggg cctcgagccg ggagagaagc cgtacaagtg tcccgaatgt   2280
ggaaagagct tctcacagtc gggggacctt cggcgccacc agcgcacaca tactggtgaa   2340
aagccgtata agtgtccaga atgtggcaaa tcattctcca catcagggag cctggtcagg   2400
caccagcgaa cccacacggg tgagaagccc tataagtgcc ccgaatgcgg gaagtccttt   2460
tcgcagagag cccacttgga gaggcaccag aggacccata cgggggagaa accttacaag   2520
tgccctgaat gcggaaagtc gttctcgacc catctggatc tcatcagaca tcagagaacg   2580
cacactggag agaaacccta caaatgtccc gagtgtggga agtcgtttag ccgaaaggac   2640
aatctcaaaa accatcaacg gacacacacg ggtgaaaaac catacaaatg cccggagtgc   2700
ggcaaatcgt tttcccaact tgcgcacttg cgggcacacc aacgcacgca tactggagcg   2760
gccgcccgcg ccctggtgaa gagcgagctg gaggagaaga agtccgagct gcggcacaag   2820
ctgaagtacg tgccccacga gtacatcgag ctgatcgaga tcgccaggaa ccccacccag   2880
gaccgcatcc tggagatgaa ggtgatggag ttcttcatga aggtgtacgg ctacagggga   2940
gagcacctgg gcggaagcag aaagcctgac ggcgccatct atacagtggg cagccccatc   3000
gattacggcg tgatcgtgga cacaaaggcc tacagcggcg gctacaatct gcctatcggc   3060
caggccgacg agatggagag atacgtggag gagaaccaga cacgggataa gcacctcaac   3120
cccaacgagt ggtggaaggt gtaccctagc agcgtgaccg agttcaagtt cctgttcgtg   3180
agcggccact tcaagggcaa ctacaaggcc cagctgacca ggctgaacca catcaccaac   3240
tgcaatggcg ccgtgctgag cgtggaggag ctgctgatcg gcggcgagat gatcaaagcc   3300
ggcaccctga cactggagga ggtgcggcgc aagttcaaca acggcgagat caacttctga   3360
ttaattaact aatctagagt cgactagagc tcgctgatca gcctcgactg tgccttctag   3420
ttgccagcca tctgttgttt gcccctcccc cgtgccttcc ttgaccctgg aaggtgccac   3480
tcccactgtc ctttcctaat aaaatgagga aattgcatcg cattgtctga gtaggtgtca   3540
ttctattctg gggggtgggg tggggcagga cagcaagggg gaggattggg aagacaatag   3600
caggcatgct ggggagagat ctaggaaccc ctagtgatgg agttggccac tccctctctg   3660
cgcgctcgct cgctcactga ggccgcccgg gcaaagcccg ggcgtcgggc gacctttggt   3720
cgcccggcct cagtgagcga gcgagcgcgc agagagggag tggccaaccc cccccccccc   3780
cccctgcag cccagctgca ttaatgaatc ggccaacgcg cggggagagg cggtttgcgt   3840
attgggcgct cttccgcttc ctcgctcact gactcgctgc gctcggtcgt tcggctgcgg   3900
cgagcggtat cagctcactc aaaggcggta atacggttat ccacagaatc aggggataac   3960
```

```
gcaggaaaga acatgtgagc aaaaggccag caaaaggcca ggaaccgtaa aaaggccgcg   4020
ttgctggcgt ttttccatag gctccgcccc cctgacgagc atcacaaaaa tcgacgctca   4080
agtcagaggt ggcgaaaccc gacaggacta taaagatacc aggcgtttcc ccctggaagc   4140
tccctcgtgc gctctcctgt tccgaccctg ccgcttaccg gatacctgtc cgcctttctc   4200
ccttcgggaa gcgtggcgct ttctcaatgc tcacgctgta ggtatctcag ttcggtgtag   4260
gtcgttcgct ccaagctggg ctgtgtgcac gaaccccccg ttcagcccga ccgctgcgcc   4320
ttatccggta actatcgtct tgagtccaac ccggtaagac acgacttatc gccactggca   4380
gcagccactg gtaacaggat tagcagagcg aggtatgtag gcggtgctac agagttcttg   4440
aagtggtggc ctaactacgg ctacactaga aggacagtat ttggtatctg cgctctgctg   4500
aagccagtta ccttcggaaa aagagttggt agctcttgat ccggcaaaca aaccaccgct   4560
ggtagcggtg gtttttttgt ttgcaagcag cagattacgc gcagaaaaaa aggatctcaa   4620
gaagatcctt tgatcttttc tacggggtct gacgctcagt ggaacgaaaa ctcacgttaa   4680
gggattttgg tcatgagatt atcaaaaagg atcttcacct agatcctttt aaattaaaaa   4740
tgaagtttta aatcaatcta aagtatatat gagtaaactt ggtctgacag ttaccaatgc   4800
ttaatcagtg aggcacctat ctcagcgatc tgtctatttc gttcatccat agttgcctga   4860
ctccccgtcg tgtagataac tacgatacgg gagggcttac catctggccc cagtgctgca   4920
atgataccgc gagacccacg ctcaccggct ccagatttat cagcaataaa ccagccagcc   4980
ggaagggccg agcgcagaag tggtcctgca actttatccg cctccatcca gtctattaat   5040
tgttgccggg aagctagagt aagtagttcg ccagttaata gtttgcgcaa cgttgttgcc   5100
attgctacag gcatcgtggt gtcacgctcg tcgtttggta tggcttcatt cagctccggt   5160
tcccaacgat caaggcgagt tacatgatcc cccatgttgt gcaaaaaagc ggttagctcc   5220
ttcggtcctc cgatcgttgt cagaagtaag ttggccgcag tgttatcact catggttatg   5280
gcagcactgc ataattctct tactgtcatg ccatccgtaa gatgcttttc tgtgactggt   5340
gagtactcaa ccaagtcatt ctgagaatag tgtatgcggc gaccgagttg ctcttgcccg   5400
gcgtcaatac gggataatac cgcgccacat agcagaactt taaaagtgct catcattgga   5460
aaacgttctt cggggcgaaa actctcaagg atcttaccgc tgttgagatc cagttcgatg   5520
taacccactc gtgcacccaa ctgatcttca gcatctttta ctttcaccag cgtttctggg   5580
tgagcaaaaa caggaaggca aaatgccgca aaaaagggaa taagggcgac acggaaatgt   5640
tgaatactca tactcttcct ttttcaatat tattgaagca tttatcaggg ttattgtctc   5700
atgagcggat acatatttga atgtatttag aaaaataaac aaataggggt tccgcgcaca   5760
tttccccgaa aagtgccacc tgacgtctaa gaaaccatta ttatcatgac attaacctat   5820
aaaaataggc gtatcacgag gccctttcgt ctcgcgcgtt tcggtgatga cggtgaaaac   5880
ctctgacaca tgcagctccc ggagacggtc acagcttgtc tgtaagcgga tgccgggagc   5940
agacaagccc gtcagggcgc gtcagcgggt gttggcgggt gtcggggctg gcttaactat   6000
gcggcatcag agcagattgt actgagagtg caccatatgc ggtgtgaaat accgcacaga   6060
tgcgtaagga gaaaataccg catcaggaaa ttgtaaacgt taatattttg ttaaaattcg   6120
cgttaaattt ttgttaaatc agctcatttt ttaaccaata ggccgaaatc ggcaaaatcc   6180
cttataaatc aaaagaatag accgagatag ggttgagtgt tgttccagtt tggaacaaga   6240
gtccactatt aaagaacgtg gactccaacg tcaaagggcg aaaaaccgtc tatcagggcg   6300
```

atggcccact acgtgaacca tcaccctaat caagtttttt ggggtcgagg tgccgtaaag 6360
cactaaatcg gaaccctaaa gggagccccc gatttagagc ttgacgggga aagccggcga 6420
acgtggcgag aaaggaaggg aagaaagcga aaggagcggg cgctagggcg ctggcaagtg 6480
tagcggtcac gctgcgcgta accaccacac ccgccgcgct taatgcgccg ctacagggcg 6540
cgtcgcgcca ttcgccattc aggctacgca actgttggga agggcgatcg gtgcgggcct 6600
cttcgctatt acgccagctg gctgca 6626

<210> SEQ ID NO 457
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 457
gagaggttat gtggctttac ca 22

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 458
ctgcgtagtg ccaaaacaaa 20

<210> SEQ ID NO 459
<211> LENGTH: 3252
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 459
atgaaaagga actacattct ggggctggac atcgggatta caagcgtggg gtatgggatt 60
attgactatg aaacaaggga cgtgatcgac gcaggcgtca gactgttcaa ggaggccaac 120
gtggaaaaca atgagggacg gagaagcaag aggggagcca ggcgcctgaa acgacggaga 180
aggcacagaa tccagagggt gaagaaactg ctgttcgatt acaacctgct gaccgaccat 240
tctgagctga gtggaattaa tccttatgaa gccagggtga aaggcctgag tcagaagctg 300
tcagaggaag agttttccgc agctctgctg cacctggcta agcgccgagg agtgcataac 360
gtcaatgagg tggaagagga caccggcaac gagctgtcta caaaggaaca gatctcacgc 420
aatagcaaag ctctggaaga gaagtatgtc gcagagctgc agctggaacg gctgaagaaa 480
gatggcgagg tgagagggtc aattaatagg ttcaagacaa gcgactacgt caaagaagcc 540
aagcagctgc tgaaagtgca gaaggcttac caccagctgg atcagagctt catcgatact 600
tatatcgacc tgctggagac tcggagaacc tactatgagg gaccaggaga agggagcccc 660
ttcggatgga aagacatcaa ggaatggtac gagatgctga tgggacattg cacctatttt 720
ccagaagagc tgagaagcgt caagtacgct tataacgcag atctgtacaa cgccctgaat 780
gacctgaaca acctggtcat caccagggat gaaaacgaga aactggaata ctatgagaag 840
ttccagatca tcgaaaacgt gtttaagcag aagaaaaagc ctacactgaa acagattgct 900

-continued

```
aaggagatcc tggtcaacga agaggacatc aagggctacc gggtgacaag cactggaaaa    960
ccagagttca ccaatctgaa agtgtatcac gatattaagg acatcacagc acggaaagaa   1020
atcattgaga acgccgaact gctggatcag attgctaaga tcctgactat ctaccagagc   1080
tccgaggaca tccaggaaga gctgactaac ctgaacagcg agctgaccca ggaagagatc   1140
gaacagatta gtaatctgaa ggggtacacc ggaacacaca acctgtccct gaaagctatc   1200
aatctgattc tggatgagct gtggcataca aacgacaatc agattgcaat ctttaaccgg   1260
ctgaagctgg tcccaaaaaa ggtggacctg agtcagcaga aagagatccc aaccacactg   1320
gtggacgatt tcattctgtc acccgtggtc aagcggagct tcatccagag catcaaagtg   1380
atcaacgcca tcatcaagaa gtacggcctg cccaatgata tcattatcga gctggctagg   1440
gagaagaaca gcaaggacgc acagaagatg atcaatgaga tgcagaaacg aaaccggcag   1500
accaatgaac gcattgaaga gattatccga actaccggga aagagaacgc aaagtacctg   1560
attgaaaaaa tcaagctgca cgatatgcag gagggaaagt gtctgtattc tctggaggcc   1620
atccccctgg aggacctgct gaacaatcca ttcaactacg aggtcgatca tattatcccc   1680
agaagcgtgt ccttcgacaa ttcctttaac aacaaggtgc tggtcaagca ggaagagaac   1740
tctaaaaagg gcaataggac tcctttccag tacctgtcta gttcagattc caagatctct   1800
tacgaaacct ttaaaaagca cattctgaat ctggccaaag gaaagggccg catcagcaag   1860
accaaaaagg agtacctgct ggaagagcgg gacatcaaca gattctccgt ccagaaggat   1920
tttattaacc ggaatctggt ggacacaaga tacgctactc gcggcctgat gaatctgctg   1980
cgatcctatt tccgggtgaa caatctggat gtgaaagtca agtccatcaa cggcgggttc   2040
acatcttttc tgaggcgcaa atggaagttt aaaaaggagc gcaacaaagg gtacaagcac   2100
catgccgaag atgctctgat tatcgcaaat gccgacttca tctttaagga gtggaaaaag   2160
ctggacaaag ccaagaaagt gatggagaac cagatgttcg aagagaagca ggccgaatct   2220
atgcccgaaa tcgagacaga acaggagtac aaggagattt tcatcactcc tcaccagatc   2280
aagcatatca aggatttcaa ggactacaag tactctcacc gggtggataa aaagcccaac   2340
agagagctga tcaatgacac cctgtatagt acaagaaaag acgataaggg gaataccctg   2400
attgtgaaca atctgaacgg actgtacgac aaagataatg acaagctgaa aaagctgatc   2460
aacaaaagtc ccgagaagct gctgatgtac caccatgatc ctcagacata tcagaaactg   2520
aagctgatta tggagcagta cggcgacgag aagaacccac tgtataagta ctatgaagag   2580
actgggaact acctgaccaa gtatagcaaa aaggataatg gccccgtgat caagaagatc   2640
aagtactatg ggaacaagct gaatgcccat ctggacatca cagacgatta ccctaacagt   2700
cgcaacaagg tggtcaagct gtcactgaag ccatacagat tcgatgtcta tctggacaac   2760
ggcgtgtata aatttgtgac tgtcaagaat ctggatgtca tcaaaaagga gaactactat   2820
gaagtgaata gcaagtgcta cgaagaggct aaaaagctga aaaagattag caaccaggca   2880
gagttcatcg cctcctttta caacaacgac ctgattaaga tcaatggcga actgtatagg   2940
gtcatcgggg tgaacaatga tctgctgaac cgcattgaag tgaatatgat tgacatcact   3000
taccgagagt atctggaaaa catgaatgat aagcgccccc ctcgaattat caaaacaatt   3060
gcctctaaga ctcagagtat caaaaagtac tcaaccgaca ttctgggaaa cctgtatgag   3120
gtgaagagca aaaagcaccc tcagattatc aaaaagggca gcggaggcaa gcgtcctgct   3180
gctactaaga aagctggtca agctaagaaa aagaaaggat cctacccata cgatgttcca   3240
gattacgctt aa                                                       3252
```

<210> SEQ ID NO 460
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 460
gttttagtac tctggaaaca gaatctacta aaacaaggca aaatgccgtg tttatctcgt 60
caacttgttg gcgagatttt ttt 83

<210> SEQ ID NO 461
<211> LENGTH: 3333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 461
atggtgccta agaagaagag aaaggtggct gccttcaaac ctaattcaat caactacatc 60
ctcggcctcg atatcggcat cgcatccgtc ggctgggcga tggtagaaat tgacgaagaa 120
gaaaacccca tccgcctgat tgatttgggc gtgcgcgtat ttgagcgtgc cgaagtaccg 180
aaaacaggcg actcccttgc catggcaagg cgtttggcgc gcagtgttcg ccgcctgacc 240
cgccgtcgcg cccaccgcct gcttcggacc cgccgcctat tgaaacgcga aggcgtatta 300
caagccgcca attttgacga aaacggcttg attaaatcct taccgaatac accatggcaa 360
cttcgcgcag ccgcattaga ccgcaaactg acgcctttag agtggtcggc agtcttgttg 420
catttaatca aacatcgcgg ctatttatcg caacggaaaa acgagggcga aactgccgat 480
aaggagcttg gcgctttgct taaaggcgta gccggcaatg cccatgcctt acagacaggc 540
gatttccgca caccggccga attggcttta aataaatttg agaaagaaag cggccatatc 600
cgcaatcagc gcagcgatta ttcgcatacg ttcagccgca aagatttaca ggcggagctg 660
attttgctgt ttgaaaaaca aaaagaattt ggcaatccgc atgtttcagg cggccttaaa 720
gaaggtattg aaaccctact gatgacgcaa cgccctgccc tgtccggcga tgccgttcaa 780
aaaatgttgg ggcattgcac cttcgaaccg gcagagccga aagccgctaa aaacacctac 840
acagccgaac gtttcatctg gctgaccaag ctgaacaacc tgcgtatttt agagcaaggc 900
agcgagcggc cattgaccga taccgaacgc gccacgctta tggacgagcc atacagaaaa 960
tccaaactga cttacgcaca agcccgtaag ctgctgggtt tagaagatac cgcctttttc 1020
aaaggcttgc gctatggtaa agacaatgcc gaagcctcaa cattgatgga aatgaaggcc 1080
taccatgcca tcagccgtgc actggaaaaa gaaggattga aagacaaaaa atccccatta 1140
aacctttctc ccgaattaca agacgaaatc ggcacggcat tctccctgtt caaaaccgat 1200
gaagacatta caggccgtct gaaagaccgt atacagcccg aaatcttaga agcgctgttg 1260
aaacacatca gcttcgataa gttcgtccaa atttccttga aagcattgcg ccgaattgtg 1320
cctctaatgg aacaaggcaa acgttacgat gaagcctgcg ccgaaatcta cggagaccat 1380
tacggcaaga agaatacgga agaaaagatt tatctgccgc cgattcccgc cgacgaaatc 1440
cgcaaccccg tcgtcttgcg cgccttatct caagcacgta aggtcattaa cggcgtggta 1500
cgccgttacg gctccccagc tcgtatccat attgaaactg caagggaagt aggtaaatcg 1560
tttaaagacc gcaaagaaat tgagaaacgc caagaagaaa accgcaaaga ccgggaaaaa 1620
gccgccgcca aattccgaga gtatttcccc aattttgtcg gagaacccaa atccaaagat 1680
attctgaaac tgcgcctgta cgagcaacaa cacggcaaat gcctgtattc gggcaaagaa 1740
atcaacttag gccgtctgaa cgaaaaaggc tatgtcgaaa tcgaccatgc cctgccgttc 1800
tcgcgcacat gggacgacag tttcaacaat aaagtactgg tattgggcag cgaaaaccaa 1860
aacaaaggca atcaaacccc ttacgaatac ttcaacggca aagacaacag ccgcgaatgg 1920
caggaattta aagcgcgtgt cgaaaccagc cgtttcccgc gcagtaaaaa acaacggatt 1980
ctgctgcaaa aattcgatga agacggcttt aaagaacgca atctgaacga cacgcgctac 2040
gtcaaccgtt tcctgtgtca atttgttgcc gaccgtatgc ggctgacagg taaaggcaag 2100
aaacgtgtct ttgcatccaa cggacaaatt accaatctgt tgcgcggctt ttggggattg 2160
cgcaaagtgc gtgcggaaaa cgaccgccat cacgccttgg acgccgtcgt cgttgcctgc 2220
tcgaccgttg ccatgcagca gaaaattacc cgttttgtac gctataaaga gatgaacgcg 2280
tttgacggta aaaccataga caaagaaaca ggagaagtgc tgcatcaaaa aacacacttc 2340
ccacaacctt gggaattttt cgcacaagaa gtcatgattc gcgtcttcgg caaaccggac 2400
ggcaaacccg aattcgaaga agccgatacc ctagaaaaac tgcgcacgtt gcttgccgaa 2460
aaattatcat ctcgccccga agccgtacac gaatacgtta cgccactgtt tgtttcacgc 2520
gcgcccaatc ggaagatgag cgggcaaggg catatggaga ccgtcaaatc cgccaaacga 2580
ctggacgaag gcgtcagcgt gttgcgcgta ccgctgacac agttaaaact gaaagacttg 2640
gaaaaaatgg tcaatcggga gcgcgaacct aagctatacg aagcactgaa agcacggctg 2700
gaagcacata aagacgatcc tgccaaagcc tttgccgagc cgttttacaa atacgataaa 2760
gcaggcaacc gcacccaaca ggtaaaagcc gtacgcgtag agcaagtaca gaaaaccggc 2820
gtatgggtgc gcaaccataa cggtattgcc gacaacgcaa ccatggtgcg cgtagatgtg 2880
tttgagaaag gcgacaagta ttatctggta ccgatttaca gttggcaggt agcgaaaggg 2940
attttgccgg atagggctgt tgtacaagga aaagatgaag aagattggca acttattgat 3000
gatagtttca actttaaatt ctcattacac cctaatgatt tagtcgaggt tataacaaaa 3060
aaagctagaa tgtttggtta ctttgccagc tgccatcgag gcacaggtaa tatcaatata 3120
cgcattcatg atcttgatca taaaattggc aaaaatggaa tactggaagg tatcggcgtc 3180
aaaaccgccc tttcattcca aaaataccaa attgacgaac tgggcaaaga aatcagacca 3240
tgccgtctga aaaaacgccc gcctgtccgt tacccatacg atgttccaga ttacgctgca 3300
gctccagcag cgaagaaaaa gaagctggat taa 3333

<210> SEQ ID NO 462
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 462
gttgtagctc cctttctcat ttcggaaacg aaatgagaac cgttgctaca ataaggccgt 60
ctgaaaagat gtgccgcaac gctctgcccc ttaaagcttc tgctttaagg ggcttttttt 120

<210> SEQ ID NO 463
<211> LENGTH: 144
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 463
gttgtagctc cctttctcat ttcgcagtgc tacaatgaaa attgtcgcac tgcgaaatga 60
gaaccgttgc tacaataagg ccgtctgaaa agatgtgccg caacgctctg ccccttaaag 120
cttctgcttt aaggggcttt tttt 144

<210> SEQ ID NO 464
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 464
tcgggtttat tacagggaca gcag 24

<210> SEQ ID NO 465
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 465
tctaaggccg agtcttatga gcag 24

<210> SEQ ID NO 466
<211> LENGTH: 4564
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 466
atggactaca aagaccatga cggtgattat aaagatcatg acatcgatta caaggatgac 60
gatgacaaga tggcccccaa gaagaagagg aaggtgggcc gcggaatgga caagaagtac 120
tccattgggc tcgccatcgg cacaaacagc gtcggctggg ccgtcattac ggacgagtac 180
aaggtgccga gcaaaaaatt caaagttctg ggcaataccg atcgccacag cataaagaag 240
aacctcattg gcgccctcct gttcgactcc ggggaaaccg ccgaagccac gcggctcaaa 300
agaacagcac ggcgcagata tacccgcaga aagaatcgga tctgctacct gcaggagatc 360
tttagtaatg agatggctaa ggtggatgac tctttcttcc ataggctgga ggagtccttt 420
ttggtggagg aggataaaaa gcacgagcgc cacccaatct ttggcaatat cgtggacgag 480
gtggcgtacc atgaaaagta cccaaccata tatcatctga ggaagaagct tgtagacagt 540
actgataagg ctgacttgcg gttgatctat ctcgcgctgg cgcatatgat caaatttcgg 600
ggacacttcc tcatcgaggg ggacctgaac ccagacaaca gcgatgtcga caaactcttt 660
atccaactgg ttcagactta caatcagctt ttcgaagaga acccgatcaa cgcatccgga 720
gttgacgcca aagcaatcct gagcgctagg ctgtccaaat cccggcggct cgaaaacctc 780
atcgcacagc tccctgggga gaagaagaac ggcctgtttg gtaatcttat cgccctgtca 840
ctcgggctga cccccaactt taaatctaac ttcgacctgg ccgaagatgc caagcttcaa 900

```
ctgagcaaag acacctacga tgatgatctc gacaatctgc tggcccagat cggcgaccag    960
tacgcagacc ttttttggc ggcaaagaac ctgtcagacg ccattctgct gagtgatatt    1020
ctgcgagtga acacggagat caccaaagct ccgctgagcg ctagtatgat caagcgctat    1080
gatgagcacc accaagactt gactttgctg aaggcccttg tcagacagca actgcctgag    1140
aagtacaagg aaattttctt cgatcagtct aaaaatggct acgccggata cattgacggc    1200
ggagcaagcc aggaggaatt ttacaaattt attaagccca tcttggaaaa aatggacggc    1260
accgaggagc tgctggtaaa gcttaacaga gaagatctgt tgcgcaaaca gcgcactttc    1320
gacaatggaa gcatccccca ccagattcac ctgggcgaac tgcacgctat cctcaggcgg    1380
caagaggatt tctacccctt tttgaaagat aacagggaaa agattgagaa aatcctcaca    1440
tttcggatac cctactatgt aggcccccctc gcccggggaa attccagatt cgcgtggatg    1500
actcgcaaat cagaagagac catcactccc tggaacttcg aggaagtcgt ggataagggg    1560
gcctctgccc agtccttcat cgaaaggatg actaactttg ataaaaatct gcctaacgaa    1620
aaggtgcttc ctaaacactc tctgctgtac gagtacttca cagtttataa cgagctcacc    1680
aaggtcaaat acgtcacaga agggatgaga aagccagcat tcctgtctgg agagcagaag    1740
aaagctatcg tggacctcct cttcaagacg aaccggaaag ttaccgtgaa acagctcaaa    1800
gaagactatt tcaaaaagat tgaatgtttc gactctgttg aaatcagcgg agtggaggat    1860
cgcttcaacg catccctggg aacgtatcac gatctcctga aaatcattaa agacaaggac    1920
ttcctggaca atgaggagaa cgaggacatt cttgaggaca ttgtcctcac ccttacgttg    1980
tttgaagata gggagatgat tgaagaacgc ttgaaaactt acgctcatct cttcgacgac    2040
aaagtcatga aacagctcaa gaggcgccga tatacaggat gggggcggct gtcaagaaaa    2100
ctgatcaatg ggatccgaga caagcagagt ggaaagacaa tcctggattt tcttaagtcc    2160
gatggatttg ccaaccggaa cttcatgcag ttgatccatg atgactctct cacctttaag    2220
gaggacatcc agaaagcaca agtttctggc caggggggaca gtcttcacga gcacatcgct    2280
aatcttgcag gtagcccagc tatcaaaaag ggaatactgc agaccgttaa ggtcgtggat    2340
gaactcgtca aagtaatggg aaggcataag cccgagaata tcgttatcga gatggcccga    2400
gagaaccaaa ctacccagaa gggacagaag aacagtaggg aaaggatgaa gaggattgaa    2460
gagggtataa aagaactggg gtcccaaatc cttaaggaac acccagttga aaacacccag    2520
cttcagaatg agaagctcta cctgtactac ctgcagaacg gcagggacat gtacgtggat    2580
caggaactgg acatcaatcg gctctccgac tacgacgtgg atgccatcgt gccccagtct    2640
tttctcaaag atgattctat tgataataaa gtgttgacaa gatccgataa aaatagaggg    2700
aagagtgata acgtcccctc agaagaagtt gtcaagaaaa tgaaaaatta ttggcggcag    2760
ctgctgaacg ccaaactgat cacacaacgg aagttcgata atctgactaa ggctgaacga    2820
ggtggcctgt ctgagttgga taaagccggc ttcatcaaaa ggcagcttgt tgagacacgc    2880
cagatcacca agcacgtggc ccaaattctc gattcacgca tgaacaccaa gtacgatgaa    2940
aatgacaaac tgattcgaga ggtgaaagtt attactctga agtctaagct ggtctcagat    3000
ttcagaaagg actttcagtt ttataaggtg agagagatca acaattacca ccatgcgcat    3060
gatgcctacc tgaatgcagt ggtaggcact gcacttatca aaaaatatcc caagcttgaa    3120
tctgaatttg tttacggaga ctataaagtg tacgatgtta ggaaaatgat cgcaaagtct    3180
gagcaggaaa taggcaaggc caccgctaag tacttctttt acagcaatat tatgaatttt    3240
```

```
ttcaagaccg agattacact ggccaatgga gagattcgga agcgaccact tatcgaaaca   3300

aacggagaaa caggagaaat cgtgtgggac aagggtaggg atttcgcgac agtccggaag   3360

gtcctgtcca tgccgcaggt gaacatcgtt aaaaagaccg aagtacagac cggaggcttc   3420

tccaaggaaa gtatcctccc gaaaaggaac agcgacaagc tgatcgcacg caaaaaagat   3480

tgggacccca agaaatacgg cggattcgat tctcctacag tcgcttacag tgtactggtt   3540

gtggccaaag tggagaaagg gaagtctaaa aaactcaaaa gcgtcaagga actgctgggc   3600

atcacaatca tggagcgatc aagcttcgaa aaaaacccca tcgactttct cgaggcgaaa   3660

ggatataaag aggtcaaaaa agacctcatc attaagcttc ccaagtactc tctctttgag   3720

cttgaaaacg gccggaaacg aatgctcgct agtgcgggcg agctgcagaa aggtaacgag   3780

ctggcactgc cctctaaata cgttaatttc ttgtatctgg ccagccacta tgaaaagctc   3840

aaagggtctc ccgaagataa tgagcagaag cagctgttcg tggaacaaca caaacactac   3900

cttgatgaga tcatcgagca aataagcgaa ttctccaaaa gagtgatcct cgccgacgct   3960

aacctcgata aggtgctttc tgcttacaat aagcacaggg ataagcccat cagggagcag   4020

gcagaaaaca ttatccactt gtttactctg accaacttgg gcgcgcctgc agccttcaag   4080

tacttcgaca ccaccataga cagaaagcgg tacacctcta caaaggaggt cctggacgcc   4140

acactgattc atcagtcaat tacggggctc tatgaaacaa gaatcgacct ctctcagctc   4200

ggtggagaca gcagggctga ccccaagaag aagaggaagg tggctagcga tgctaagtca   4260

ctgactgcct ggtcccggac actggtgacc ttcaaggatg tgtttgtgga cttcaccagg   4320

gaggagtgga agctgctgga cactgctcag cagatcctgt acagaaatgt gatgctggag   4380

aactataaga acctggtttc cttgggttat cagcttacta agccagatgt gatcctccgg   4440

ttggagaagg gagaagagcc ctggctggtg gagagagaaa ttcaccaaga gacccatcct   4500

gattcagaga ctgcatttga aatcaaatca tcagttccga aaaagaaacg caaagttgct   4560

agcg                                                                4564
```

<210> SEQ ID NO 467
<211> LENGTH: 388
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 467

```
taagcttcag tttttcctta gttcctgtta catttctgtg tgtctccatt agtgacctcc     60

catagtccaa gcatgagcag ttctggccag gcccctgtcg gggtcagtgc cccacccccg    120

ccttctggtt ctgtgtaacc ttctaagcaa accttctggc tcaagcacag caatgctgag    180

tcatgatgag tcatgctgag gcttagggtg tgtgcccaga tgttctcagc ctagagtgat    240

gactcctatc tgggtcccca gcaggatgct tacagggcag atggcaaaaa aaaggagaag    300

ctgaccacct gactaaaact ccacctcaaa cggcatcata aagaaaatgg atgcctgaga    360

cagaatgtga catattctag aatatatt                                       388
```

<210> SEQ ID NO 468
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 468
cagccgctcg ctgcagcag 19

<210> SEQ ID NO 469
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 469
ctgctgcagc gagcggctg 19

<210> SEQ ID NO 470
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 470
gctgggtgtc ccattgaaa 19

<210> SEQ ID NO 471
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 471
tttcaatggg acacccagc 19

<210> SEQ ID NO 472
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 472
gtttattcag ccgggagtc 19

<210> SEQ ID NO 473
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 473
gactcccggc tgaataaac 19

<210> SEQ ID NO 474
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 474
tggagagttt gcaaggagc 19

<210> SEQ ID NO 475
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 475
gctccttgca aactctcca 19

<210> SEQ ID NO 476
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 476
ccctccagac tttccacct 19

<210> SEQ ID NO 477
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 477
aggtggaaag tctggaggg 19

<210> SEQ ID NO 478
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 478
aattttcttc caagttctc 19

<210> SEQ ID NO 479
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 479
gagaacttgg aagaaaatt 19

<210> SEQ ID NO 480
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 480
ctgcggagag aagaaaggg 19

<210> SEQ ID NO 481
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 481
ccctttcttc tctccgcag 19

<210> SEQ ID NO 482
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 482
agagccaccc cctggctcc 19

<210> SEQ ID NO 483
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 483
ggagccaggg ggtggctct 19

<210> SEQ ID NO 484
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 484
cgaagccaac cgcggcggg 19

<210> SEQ ID NO 485
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 485
cccgccgcgg ttggcttcg 19

<210> SEQ ID NO 486
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 486
agagggaaga cgatcgccc 19

<210> SEQ ID NO 487
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 487
gggcgatcgt cttccctct 19

<210> SEQ ID NO 488
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 488
cccctttaac tttcctccg 19

<210> SEQ ID NO 489
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 489
cggaggaaag ttaaagggg 19

<210> SEQ ID NO 490
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 490
gcagccccgc ttccttcaa 19

<210> SEQ ID NO 491
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 491
ttgaaggaag cggggctgc 19

<210> SEQ ID NO 492
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 492
caccgcagcc gctcgctgca gcag 24

<210> SEQ ID NO 493
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 493
aaacctgctg cagcgagcgg ctgc 24

<210> SEQ ID NO 494
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 494
caccggctgg gtgtcccatt gaaa 24

<210> SEQ ID NO 495
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 495
aaactttcaa tgggacaccc agcc 24

<210> SEQ ID NO 496
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 496
caccggttta ttcagccggg agtc 24

<210> SEQ ID NO 497
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 497
aaacgactcc cggctgaata aacc 24

<210> SEQ ID NO 498
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 498
caccgtggag agtttgcaag gagc 24

<210> SEQ ID NO 499
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 499
aaacgctcct tgcaaactct ccac 24

<210> SEQ ID NO 500
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 500
caccgccctc cagactttcc acct 24

<210> SEQ ID NO 501
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 501
aaacaggtgg aaagtctgga gggc 24

<210> SEQ ID NO 502
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 502
caccgaattt tcttccaagt tctc 24

<210> SEQ ID NO 503
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 503
aaacgagaac ttggaagaaa attc 24

<210> SEQ ID NO 504
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 504
caccgctgcg gagagaagaa aggg 24

<210> SEQ ID NO 505
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 505 aaacccctt cttctctccg cagc 24

<210> SEQ ID NO 506
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 506
caccgagagc cacccccctgg ctcc 24

<210> SEQ ID NO 507
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 507
aaacggagcc agggggtggc tctc 24

<210> SEQ ID NO 508
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 508
caccgcgaag ccaaccgcgg cggg 24

<210> SEQ ID NO 509
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 509
aaaccccgcc gcggttggct tcgc 24

<210> SEQ ID NO 510
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 510
caccgagagg gaagacgatc gccc 24

<210> SEQ ID NO 511

<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 511
aaacgggcga tcgtcttccc tctc 24

<210> SEQ ID NO 512
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 512
caccgcccct ttaactttcc tccg 24

<210> SEQ ID NO 513
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 513
aaaccggagg aaagttaaag gggc 24

<210> SEQ ID NO 514
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 514
caccggcagc cccgcttcct tcaa 24

<210> SEQ ID NO 515
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 515
aaacttgaag gaagcggggc tgcc 24

<210> SEQ ID NO 516
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 516
cgagagcgag aggagggag 19

<210> SEQ ID NO 517
<211> LENGTH: 19

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 517
ctccctcctc tcgctctcg 19

<210> SEQ ID NO 518
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 518
gagagagctt gagagcgcg 19

<210> SEQ ID NO 519
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 519
cgcgctctca agctctctc 19

<210> SEQ ID NO 520
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 520
ggtggagggg gcggggccc 19

<210> SEQ ID NO 521
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 521
gggccccgcc ccctccacc 19

<210> SEQ ID NO 522
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 522
ggtatccacg taaatcaaa 19

<210> SEQ ID NO 523
<211> LENGTH: 19
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 523
tttgatttac gtggatacc 19

<210> SEQ ID NO 524
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
ccaatcactg gctccggtc 19

<210> SEQ ID NO 525
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
gaccggagcc agtgattgg 19

<210> SEQ ID NO 526
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
ggcgcccgag ggaagaaga 19

<210> SEQ ID NO 527
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tcttcttccc tcgggcgcc 19

<210> SEQ ID NO 528
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
gggtgggggt accagagga 19

<210> SEQ ID NO 529
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 529
tcctctggta cccccaccc 19

<210> SEQ ID NO 530
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 530
ccggggacag aagagaggg 19

<210> SEQ ID NO 531
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 531
ccctctcttc tgtccccgg 19

<210> SEQ ID NO 532
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 532
gagagagagt gggagaagc 19

<210> SEQ ID NO 533
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 533
gcttctccca ctctctctc 19

<210> SEQ ID NO 534
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 534
aaagtaactg tcaaatgcg 19

<210> SEQ ID NO 535
<211> LENGTH: 19
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 535
cgcatttgac agttacttt 19

<210> SEQ ID NO 536
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 536
ttaaccagag cgcccagtc 19

<210> SEQ ID NO 537
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 537
gactgggcgc tctggttaa 19

<210> SEQ ID NO 538
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 538
cgtcggagct gcccgctag 19

<210> SEQ ID NO 539
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 539
ctagcgggca gctccgacg 19

<210> SEQ ID NO 540
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 540
caccgcgaga gcgagaggag ggag 24

<210> SEQ ID NO 541
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 541
aaacctccct cctctcgctc tcgc 24

<210> SEQ ID NO 542
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 542
caccggagag agcttgagag cgcg 24

<210> SEQ ID NO 543
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 543
aaaccgcgct ctcaagctct ctcc 24

<210> SEQ ID NO 544
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 544
caccgggtgg agggggcggg gccc 24

<210> SEQ ID NO 545
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 545
aaacgggccc cgccccctcc accc 24

<210> SEQ ID NO 546
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 546
caccgggtat ccacgtaaat caaa 24

<210> SEQ ID NO 547
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 547
aaactttgat ttacgtggat accc 24

<210> SEQ ID NO 548
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 548
caccgccaat cactggctcc ggtc 24

<210> SEQ ID NO 549
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 549
aaacgaccgg agccagtgat tggc 24

<210> SEQ ID NO 550
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 550
caccgggcgc ccgagggaag aaga 24

<210> SEQ ID NO 551
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 551
aaactcttct tccctcgggc gccc 24

<210> SEQ ID NO 552
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 552
caccggggtg ggggtaccag agga 24

<210> SEQ ID NO 553
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 553
aaactcctct ggtaccccca cccc 24

<210> SEQ ID NO 554
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 554
caccgccggg gacagaagag aggg 24

<210> SEQ ID NO 555
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 555
aaacccctct cttctgtccc cggc 24

<210> SEQ ID NO 556
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 556
caccggagag agagtgggag aagc 24

<210> SEQ ID NO 557
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 557
aaacgcttct cccactctct ctcc 24

<210> SEQ ID NO 558
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 558
caccgaaagt aactgtcaaa tgcg 24

<210> SEQ ID NO 559
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 559
aaaccgcatt tgacagttac tttc 24

<210> SEQ ID NO 560
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 560
caccgttaac cagagcgccc agtc 24

<210> SEQ ID NO 561
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 561
aaacgactgg gcgctctggt taac 24

<210> SEQ ID NO 562
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 562
caccgcgtcg gagctgcccg ctag 24

<210> SEQ ID NO 563
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 563
aaacctagcg ggcagctccg acgc 24

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 564
gagacacaca gaaatgtaac 20

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 565
ggtggggcac tgaccccgac 20

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 566
ctagagtgat gactcctatc 20

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 567
gactaaaact ccacctcaaa 20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 568
aatatgtcac attctgtctc 20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 569
ggactatggg aggtcactaa 20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 570
gctcatgctt ggactatggg 20

<210> SEQ ID NO 571
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 571
gttctggcca ggcccctgtc 20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 572
agtgccccac ccccgccttc 20

<210> SEQ ID NO 573
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 573
gtggggcact gaccccgaca 20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 574
aaccttctaa gcaaaccttc 20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 575
gttacacaga accagaaggc 20

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 576
gaaggttaca cagaaccaga 20

<210> SEQ ID NO 577
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 577
agtcatgatg agtcatgctg 20

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 578
gatgagtcat gctgaggctt 20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 579
actctaggct gagaacatct 20

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 580
gtccccagca ggatgcttac 20

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 581
gccctgtaag catcctgctg 20

<210> SEQ ID NO 582
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 582
cagggcagat ggcaaaaaaa 20

<210> SEQ ID NO 583
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 583
gaggtggagt tttagtcagg 20

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 584
aaacggcatc ataaagaaaa 20

<210> SEQ ID NO 585
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 585
gagacacaca gaaatgtaac gttttagagc tagaaatagc aagttaaaat aaggctagtc 60
cgttatcaac ttgaaaaagt ggcaccgagt cggtgctttt tttcc 105

<210> SEQ ID NO 586
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 586
ggtggggcac tgaccccgac gttttagagc tagaaatagc aagttaaaat aaggctagtc 60
cgttatcaac ttgaaaaagt ggcaccgagt cggtgctttt tttcc 105

<210> SEQ ID NO 587
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 587
ctagagtgat gactcctatc gttttagagc tagaaatagc aagttaaaat aaggctagtc 60
cgttatcaac ttgaaaaagt ggcaccgagt cggtgctttt tttcc 105

<210> SEQ ID NO 588
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 588
gactaaaact ccacctcaaa gttttagagc tagaaatagc aagttaaaat aaggctagtc 60
cgttatcaac ttgaaaaagt ggcaccgagt cggtgctttt tttcc 105

<210> SEQ ID NO 589
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 589
aatatgtcac attctgtctc gttttagagc tagaaatagc aagttaaaat aaggctagtc 60
cgttatcaac ttgaaaaagt ggcaccgagt cggtgctttt tttcc 105

<210> SEQ ID NO 590
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 590
ggactatggg aggtcactaa gttttagagc tagaaatagc aagttaaaat aaggctagtc 60
cgttatcaac ttgaaaaagt ggcaccgagt cggtgctttt tttcc 105

<210> SEQ ID NO 591
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 591
gctcatgctt ggactatggg gttttagagc tagaaatagc aagttaaaat aaggctagtc 60
cgttatcaac ttgaaaaagt ggcaccgagt cggtgctttt tttcc 105

<210> SEQ ID NO 592
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 592
gttctggcca ggcccctgtc gttttagagc tagaaatagc aagttaaaat aaggctagtc 60
cgttatcaac ttgaaaaagt ggcaccgagt cggtgctttt tttcc 105

<210> SEQ ID NO 593
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 593
agtgccccac ccccgccttc gttttagagc tagaaatagc aagttaaaat aaggctagtc 60
cgttatcaac ttgaaaaagt ggcaccgagt cggtgctttt tttcc 105

<210> SEQ ID NO 594
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 594
gtggggcact gaccccgaca gttttagagc tagaaatagc aagttaaaat aaggctagtc 60
cgttatcaac ttgaaaaagt ggcaccgagt cggtgctttt tttcc 105

<210> SEQ ID NO 595
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 595
aaccttctaa gcaaaccttc gttttagagc tagaaatagc aagttaaaat aaggctagtc 60
cgttatcaac ttgaaaaagt ggcaccgagt cggtgctttt tttcc 105

<210> SEQ ID NO 596
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 596
gttacacaga accagaaggc gttttagagc tagaaatagc aagttaaaat aaggctagtc 60
cgttatcaac ttgaaaaagt ggcaccgagt cggtgctttt tttcc 105

<210> SEQ ID NO 597
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 597
gaaggttaca cagaaccaga gttttagagc tagaaatagc aagttaaaat aaggctagtc 60
cgttatcaac ttgaaaaagt ggcaccgagt cggtgctttt tttcc 105

<210> SEQ ID NO 598
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 598
agtcatgatg agtcatgctg gttttagagc tagaaatagc aagttaaaat aaggctagtc 60
cgttatcaac ttgaaaaagt ggcaccgagt cggtgctttt tttcc 105

<210> SEQ ID NO 599
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 599
gatgagtcat gctgaggctt gttttagagc tagaaatagc aagttaaaat aaggctagtc 60
cgttatcaac ttgaaaaagt ggcaccgagt cggtgctttt tttcc 105

<210> SEQ ID NO 600
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 600
actctaggct gagaacatct gttttagagc tagaaatagc aagttaaaat aaggctagtc 60
cgttatcaac ttgaaaaagt ggcaccgagt cggtgctttt tttcc 105

<210> SEQ ID NO 601
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 601
gtccccagca ggatgcttac gttttagagc tagaaatagc aagttaaaat aaggctagtc 60
cgttatcaac ttgaaaaagt ggcaccgagt cggtgctttt tttcc 105

<210> SEQ ID NO 602
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 602
gccctgtaag catcctgctg gttttagagc tagaaatagc aagttaaaat aaggctagtc 60
cgttatcaac ttgaaaaagt ggcaccgagt cggtgctttt tttcc 105

<210> SEQ ID NO 603
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 603
cagggcagat ggcaaaaaaa gttttagagc tagaaatagc aagttaaaat aaggctagtc 60
cgttatcaac ttgaaaaagt ggcaccgagt cggtgctttt tttcc 105

<210> SEQ ID NO 604
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 604
gaggtggagt tttagtcagg gttttagagc tagaaatagc aagttaaaat aaggctagtc 60
cgttatcaac ttgaaaaagt ggcaccgagt cggtgctttt tttcc 105

<210> SEQ ID NO 605
<211> LENGTH: 105
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 605
aaacggcatc ataaagaaaa gttttagagc tagaaatagc aagttaaaat aaggctagtc 60
cgttatcaac ttgaaaaagt ggcaccgagt cggtgctttt tttcc 105

<210> SEQ ID NO 606
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 606
tgtactctct gaggtgctc 19

<210> SEQ ID NO 607
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 607
acgcagataa gaaccagtt 19

<210> SEQ ID NO 608
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 608
catcaagtca gccatcagc 19

<210> SEQ ID NO 609
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 609
gagtcaccct cctggaaac 19

<210> SEQ ID NO 610
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 610
cctgggctcc ggggcgttt 19

<210> SEQ ID NO 611
<211> LENGTH: 19

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 611
ggcccctgcg gccaccccg 19

<210> SEQ ID NO 612
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 612
ctccctccct gcccggtag 19

<210> SEQ ID NO 613
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 613
aggtttggaa agggcgtgc 19

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 614
actccactgc actccagtct 20

<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 615
tctgtggggg acctgcactg 20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 616
ggggcgccag ttgtgtctcc 20

<210> SEQ ID NO 617
<211> LENGTH: 20
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 617
acaccattgc caccaccatt 20

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 618
caatgacccc ttcattgacc 20

<210> SEQ ID NO 619
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 619
ttgattttgg agggatctcg 20

<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 620
ggaatccatg gagggaagat 20

<210> SEQ ID NO 621
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 621
tgttctcgct caggtcagtg 20

<210> SEQ ID NO 622
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 622
ctctctgctc ctttgccaca 20

<210> SEQ ID NO 623
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 623
gtgctcttcg ggtttcagga 20

<210> SEQ ID NO 624
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 624
cgaaagagaa agcgaaccag tatcgagaac 30

<210> SEQ ID NO 625
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 625
cgttgtgcat agtcgctgct tgatcgc 27

<210> SEQ ID NO 626
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 626
gagtttggct caaattgtta ctctt 25

<210> SEQ ID NO 627
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 627
gggaaatggt ctaggagagt aaagt 25

<210> SEQ ID NO 628
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 628
gattggcttt gatttcccta ggg 23

<210> SEQ ID NO 629
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 629
gcctactcag actgttactc tgg 23

<210> SEQ ID NO 630
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
gcagttgcct aagaactggt ggg 23

<210> SEQ ID NO 631
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
ggggctccac cctcacgagt ggg 23

<210> SEQ ID NO 632
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
gccttcttta tcccctatcg agg 23

<210> SEQ ID NO 633
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
gaaggaccat ttgacgttca gctcctactc agactgttac tctggtga 48

<210> SEQ ID NO 634
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Glu Gly Pro Phe Asp Val Gln Leu Leu Leu Arg Leu Leu Leu Trp
1               5                   10                  15

<210> SEQ ID NO 635
<211> LENGTH: 46
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 635
gaaggaccat ttgacgttca gctcctactc agactgtctc tggtga 46

<210> SEQ ID NO 636
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Glu Gly Pro Phe Asp Val Gln Leu Leu Leu Arg Leu Ser Leu Val
1 5 10 15

<210> SEQ ID NO 637
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
gccuacucag acuguuacuc 20

<210> SEQ ID NO 638
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
cccaccagtt cttaggcaa 19

<210> SEQ ID NO 639
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
cccaccagtt cttaggcaac 20

<210> SEQ ID NO 640
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
tttgatttcc agttcttagg 20

<210> SEQ ID NO 641
<211> LENGTH: 19
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 641
attaccatag agttcttag 19

<210> SEQ ID NO 642
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 642
gtggataaag gcaacaatg 19

<210> SEQ ID NO 643
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 643
cctcgatagg ggataa 16

<210> SEQ ID NO 644
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 644
accaaaccca cttaggggat aaa 23

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 645
ggtatcttaa ggacctccaa g 21

<210> SEQ ID NO 646
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 646
taggaagtaa attaatttga agcttgccaa ttaatccaaa tcttacc 47

<210> SEQ ID NO 647
<211> LENGTH: 83
<212> TYPE: DNA
<213> ORGANISM: Artificial Sequence
<220> FEATURE:
<223> OTHER INFORMATION: Description of Artificial Sequence: Synthetic primer

<400> SEQUENCE: 647
tttccttttt gcaaaaccca aaatatttta gctcctactc agactgttag agtaggagga 60
gaaggagggc tgtggctctt gtg 83

<210> SEQ ID NO 648
<211> LENGTH: 83
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other

<400> SEQUENCE: 648
aaaaccccca aaccctcccn ctttttcctc ntactctaac agtgtgagta ggaggccaca 60
cttagctgng gctctagtaa gtc 83

<210> SEQ ID NO 649
<211> LENGTH: 94
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (50)..(50)
<223> OTHER INFORMATION: a, c, t, g, unknown or other

<400> SEQUENCE: 649
cttctttttt cctttttgca aaaacccaaa atattttagc tcctactcan accgttttcg 60
gggggtattt tgtatttgga tgaaacactt gatg 94

<210> SEQ ID NO 650
<211> LENGTH: 93
<212> TYPE: DNA
<213> ORGANISM: Artificial Sequence
<220> FEATURE:
<223> OTHER INFORMATION: Description of Artificial Sequence: Synthetic
primer

<400> SEQUENCE: 650
tcttcttttt tccttcccgc aaaaacccaa aatattttcg ctcctactca ggacctggtc 60
gtggggtatt ttgtatttgg atgaaacact tga 93

<210> SEQ ID NO 651
<211> LENGTH: 104
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (21)..(22)
<223> OTHER INFORMATION: a, c, t, g, unknown or other

<400> SEQUENCE: 651
tcaaggaaga tggcatttct nntttggaga tggcagtttc cttagtaacc acaggttgtg 60
tcaccatggc cagtaagaag gatgccacac ttgtgtgtgt cgct 104

<210> SEQ ID NO 652
<211> LENGTH: 86
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (42)..(44)
<223> OTHER INFORMATION: a, c, t, g, unknown or other

<400> SEQUENCE: 652
ttggagatag cagtttcctt ggtaagtaca ggttnntcac cnnnacagtg tgagtaggag 60
gccacactta gctgtggctc tagtaa 86

<210> SEQ ID NO 653
<211> LENGTH: 71
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (61)..(63)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other

<400> SEQUENCE: 653
tttctagttt ggagatggca gtttccttag taaccacagg ttgtgtcacc aggnctcgag 60
nnntggttnt g 71

<210> SEQ ID NO 654
<211> LENGTH: 87
<212> TYPE: DNA
<213> ORGANISM: Artificial Sequence
<220> FEATURE:
<223> OTHER INFORMATION: Description of Artificial Sequence: Synthetic primer

<400> SEQUENCE: 654
cagttgccat agtcttcact aaccgcgtca ccagagctca ggacctggtc gtggggtatt 60
ttgtatttgg atgaaacact tgatggt 87

<210> SEQ ID NO 655
<211> LENGTH: 92
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: modified_base
<222> LOCATION: (59)..(59)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other

<400> SEQUENCE: 655
tattgtatct tggtttttct tcactgctgg ccagtttact aacaatctga antaagccna 60
ttaatccaaa tcttaccnga cgaaaaatca aa 92

<210> SEQ ID NO 656
<211> LENGTH: 89
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other

<400> SEQUENCE: 656
atggtntttn gtcattgcng gccagttttn taacaatgtg atcaatgcca attaatncaa 60
atcttaccag aggaaaaatc aagccacag 89

<210> SEQ ID NO 657
<211> LENGTH: 94
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (93)..(94)
<223> OTHER INFORMATION: a, c, t, g, unknown or other

<400> SEQUENCE: 657
aataaaaaga aaaaaatatg ataaactgct cccagtataa aatacagagc taagacaaga 60
acgtttcatt ggctgttaaa agtcggaaat cgnn 94

<210> SEQ ID NO 658
<211> LENGTH: 94

<212> TYPE: DNA
<213> ORGANISM: Artificial Sequence
<220> FEATURE:
<223> OTHER INFORMATION: Description of Artificial Sequence: Synthetic primer

<400> SEQUENCE: 658
ttctgattta aaattccctt gaataggaag taaattaatt tgaagcttgc caattaatcc 60
aaatcttacc agaggaaaaa tcaagccaca gata 94

<210> SEQ ID NO 659
<211> LENGTH: 90
<212> TYPE: DNA
<213> ORGANISM: Artificial Sequence
<220> FEATURE:
<223> OTHER INFORMATION: Description of Artificial Sequence: Synthetic primer

<400> SEQUENCE: 659
caaaacaaga tgggataaaa tcttctttct gatttaaaat tcccttgaat aggaagtaaa 60
ttactagagc tgttcaaggc ctgaactcta 90

<210> SEQ ID NO 660
<211> LENGTH: 96
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (49)..(49)
<223> OTHER INFORMATION: a, c, t, g, unknown or other
<220> FEATURE:
<221> NAME/KEY: modified_base
<222> LOCATION: (51)..(52)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other

<400> SEQUENCE: 660
ctgatttaaa attcccttga ataggaagta aattactaga gctgttcang nncngaactc 60
taggctagca tttccagccc aaaacaaaca cagttc 96

<210> SEQ ID NO 661
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (8)..(26)
<223> OTHER INFORMATION: a, c, t, g, unknown or other

<400> SEQUENCE: 661
ttgtttgnnn nnnnnnnnnn nnnnnn 26

<210> SEQ ID NO 662
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (6)..(24)
<223> OTHER INFORMATION: a, c, t, g, unknown or other

<400> SEQUENCE: 662
caccgnnnnn nnnnnnnnnn nnnn 24

<210> SEQ ID NO 663
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (6)..(24)
<223> OTHER INFORMATION: a, c, t, g, unknown or other

<400> SEQUENCE: 663
tcccannnnn nnnnnnnnnn nnnn 24

<210> SEQ ID NO 664
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (6)..(24)
<223> OTHER INFORMATION: a, c, t, g, unknown or other

<400> SEQUENCE: 664
cctcgnnnnn nnnnnnnnnn nnnn 24

<210> SEQ ID NO 665
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 665
aaacnnnnnn nnnnnnnnnn nnncaa 26

<210> SEQ ID NO 666
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 666
aaacnnnnnn nnnnnnnnnn nnnc 24

<210> SEQ ID NO 667

<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 667
aaacnnnnnn nnnnnnnnnn nnnt 24

<210> SEQ ID NO 668
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 668
aaacnnnnnn nnnnnnnnnn nnnc 24

<210> SEQ ID NO 669
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 669
ttgtttgtct tcgagaagac ctgttt 26

<210> SEQ ID NO 670
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 670
caccgggtct tcgagaagac ctgttt 26

<210> SEQ ID NO 671
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 671
tcccaggtct tcgagaagac ctgttt 26

<210> SEQ ID NO 672
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 672
cctcgggtct tcgagaagac ctgttt 26

<210> SEQ ID NO 673
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 673
ggcctaccgc taaggctagc ctagt 25

<210> SEQ ID NO 674
<211> LENGTH: 1411
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 674

Met Asp Tyr Lys Asp His Asp Gly Asp Tyr Lys Asp His Asp Ile Asp
1 5 10 15

Tyr Lys Asp Asp Asp Asp Lys Met Ala Pro Lys Lys Lys Arg Lys Val
20 25 30

Gly Arg Gly Met Asp Lys Lys Tyr Ser Ile Gly Leu Ala Ile Gly Thr
35 40 45

Asn Ser Val Gly Trp Ala Val Ile Thr Asp Glu Tyr Lys Val Pro Ser
50 55 60

Lys Lys Phe Lys Val Leu Gly Asn Thr Asp Arg His Ser Ile Lys Lys
65 70 75 80

Asn Leu Ile Gly Ala Leu Leu Phe Asp Ser Gly Glu Thr Ala Glu Ala
85 90 95

Thr Arg Leu Lys Arg Thr Ala Arg Arg Arg Tyr Thr Arg Arg Lys Asn
100 105 110

Arg Ile Cys Tyr Leu Gln Glu Ile Phe Ser Asn Glu Met Ala Lys Val
115 120 125

Asp Asp Ser Phe Phe His Arg Leu Glu Glu Ser Phe Leu Val Glu Glu
130 135 140

Asp Lys Lys His Glu Arg His Pro Ile Phe Gly Asn Ile Val Asp Glu
145 150 155 160

Val Ala Tyr His Glu Lys Tyr Pro Thr Ile Tyr His Leu Arg Lys Lys
165 170 175

Leu Val Asp Ser Thr Asp Lys Ala Asp Leu Arg Leu Ile Tyr Leu Ala
180 185 190

Leu Ala His Met Ile Lys Phe Arg Gly His Phe Leu Ile Glu Gly Asp
195 200 205

Leu Asn Pro Asp Asn Ser Asp Val Asp Lys Leu Phe Ile Gln Leu Val
210 215 220

Gln Thr Tyr Asn Gln Leu Phe Glu Glu Asn Pro Ile Asn Ala Ser Gly
225 230 235 240

Val Asp Ala Lys Ala Ile Leu Ser Ala Arg Leu Ser Lys Ser Arg Arg
245 250 255

Leu Glu Asn Leu Ile Ala Gln Leu Pro Gly Glu Lys Lys Asn Gly Leu
260 265 270

Phe Gly Asn Leu Ile Ala Leu Ser Leu Gly Leu Thr Pro Asn Phe Lys
275 280 285

Ser Asn Phe Asp Leu Ala Glu Asp Ala Lys Leu Gln Leu Ser Lys Asp
290 295 300

Thr Tyr Asp Asp Asp Leu Asp Asn Leu Leu Ala Gln Ile Gly Asp Gln
305 310 315 320

Tyr Ala Asp Leu Phe Leu Ala Ala Lys Asn Leu Ser Asp Ala Ile Leu
325 330 335

Leu Ser Asp Ile Leu Arg Val Asn Thr Glu Ile Thr Lys Ala Pro Leu
340 345 350

Ser Ala Ser Met Ile Lys Arg Tyr Asp Glu His His Gln Asp Leu Thr
355 360 365

Leu Leu Lys Ala Leu Val Arg Gln Gln Leu Pro Glu Lys Tyr Lys Glu
370 375 380

Ile Phe Phe Asp Gln Ser Lys Asn Gly Tyr Ala Gly Tyr Ile Asp Gly
385 390 395 400

Gly Ala Ser Gln Glu Glu Phe Tyr Lys Phe Ile Lys Pro Ile Leu Glu
405 410 415

Lys Met Asp Gly Thr Glu Glu Leu Leu Val Lys Leu Asn Arg Glu Asp
420 425 430

Leu Leu Arg Lys Gln Arg Thr Phe Asp Asn Gly Ser Ile Pro His Gln
435 440 445

Ile His Leu Gly Glu Leu His Ala Ile Leu Arg Arg Gln Glu Asp Phe
450 455 460

Tyr Pro Phe Leu Lys Asp Asn Arg Glu Lys Ile Glu Lys Ile Leu Thr
465 470 475 480

Phe Arg Ile Pro Tyr Tyr Val Gly Pro Leu Ala Arg Gly Asn Ser Arg
485 490 495

Phe Ala Trp Met Thr Arg Lys Ser Glu Glu Thr Ile Thr Pro Trp Asn
500 505 510

Phe Glu Glu Val Val Asp Lys Gly Ala Ser Ala Gln Ser Phe Ile Glu
515 520 525

Arg Met Thr Asn Phe Asp Lys Asn Leu Pro Asn Glu Lys Val Leu Pro
530 535 540

Lys His Ser Leu Leu Tyr Glu Tyr Phe Thr Val Tyr Asn Glu Leu Thr
545 550 555 560

Lys Val Lys Tyr Val Thr Glu Gly Met Arg Lys Pro Ala Phe Leu Ser
565 570 575

Gly Glu Gln Lys Lys Ala Ile Val Asp Leu Leu Phe Lys Thr Asn Arg
580 585 590

Lys Val Thr Val Lys Gln Leu Lys Glu Asp Tyr Phe Lys Lys Ile Glu
595 600 605

Cys Phe Asp Ser Val Glu Ile Ser Gly Val Glu Asp Arg Phe Asn Ala
610 615 620

Ser Leu Gly Thr Tyr His Asp Leu Leu Lys Ile Ile Lys Asp Lys Asp
625 630 635 640

Phe Leu Asp Asn Glu Glu Asn Glu Asp Ile Leu Glu Asp Ile Val Leu
645 650 655

Thr Leu Thr Leu Phe Glu Asp Arg Glu Met Ile Glu Glu Arg Leu Lys
660 665 670

Thr Tyr Ala His Leu Phe Asp Asp Lys Val Met Lys Gln Leu Lys Arg
675 680 685

```
Arg Arg Tyr Thr Gly Trp Gly Arg Leu Ser Arg Lys Leu Ile Asn Gly
    690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
        755                 760                 765

Lys Lys Gly Ile Leu Gln Thr Val Lys Val Val Asp Glu Leu Val Lys
    770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
        835                 840                 845

Tyr Tyr Leu Gln Asn Gly Arg Asp Met Tyr Val Asp Gln Glu Leu Asp
    850                 855                 860

Ile Asn Arg Leu Ser Asp Tyr Asp Val Asp His Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
        915                 920                 925

Gln Arg Lys Phe Asp Asn Leu Thr Lys Ala Glu Arg Gly Gly Leu Ser
    930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp  Phe Arg Lys Asp Phe  Gln Phe Tyr
        995                 1000                1005

Lys Val  Arg Glu Ile Asn Asn  Tyr His His Ala His  Asp Ala Tyr
    1010                1015                1020

Leu Asn  Ala Val Val Gly Thr  Ala Leu Ile Lys Lys  Tyr Pro Lys
    1025                1030                1035

Leu Glu  Ser Glu Phe Val Tyr  Gly Asp Tyr Lys Val  Tyr Asp Val
    1040                1045                1050

Arg Lys  Met Ile Ala Lys Ser  Glu Gln Glu Ile Gly  Lys Ala Thr
    1055                1060                1065

Ala Lys  Tyr Phe Phe Tyr Ser  Asn Ile Met Asn Phe  Phe Lys Thr
    1070                1075                1080

Glu Ile  Thr Leu Ala Asn Gly  Glu Ile Arg Lys Arg  Pro Leu Ile
    1085                1090                1095

Glu Thr  Asn Gly Glu Thr Gly  Glu Ile Val Trp Asp  Lys Gly Arg
```

1100 1105 1110

Asp Phe Ala Thr Val Arg Lys Val Leu Ser Met Pro Gln Val Asn
1115 1120 1125

Ile Val Lys Lys Thr Glu Val Gln Thr Gly Gly Phe Ser Lys Glu
1130 1135 1140

Ser Ile Leu Pro Lys Arg Asn Ser Asp Lys Leu Ile Ala Arg Lys
1145 1150 1155

Lys Asp Trp Asp Pro Lys Lys Tyr Gly Gly Phe Asp Ser Pro Thr
1160 1165 1170

Val Ala Tyr Ser Val Leu Val Val Ala Lys Val Glu Lys Gly Lys
1175 1180 1185

Ser Lys Lys Leu Lys Ser Val Lys Glu Leu Leu Gly Ile Thr Ile
1190 1195 1200

Met Glu Arg Ser Ser Phe Glu Lys Asn Pro Ile Asp Phe Leu Glu
1205 1210 1215

Ala Lys Gly Tyr Lys Glu Val Lys Lys Asp Leu Ile Ile Lys Leu
1220 1225 1230

Pro Lys Tyr Ser Leu Phe Glu Leu Glu Asn Gly Arg Lys Arg Met
1235 1240 1245

Leu Ala Ser Ala Gly Glu Leu Gln Lys Gly Asn Glu Leu Ala Leu
1250 1255 1260

Pro Ser Lys Tyr Val Asn Phe Leu Tyr Leu Ala Ser His Tyr Glu
1265 1270 1275

Lys Leu Lys Gly Ser Pro Glu Asp Asn Glu Gln Lys Gln Leu Phe
1280 1285 1290

Val Glu Gln His Lys His Tyr Leu Asp Glu Ile Ile Glu Gln Ile
1295 1300 1305

Ser Glu Phe Ser Lys Arg Val Ile Leu Ala Asp Ala Asn Leu Asp
1310 1315 1320

Lys Val Leu Ser Ala Tyr Asn Lys His Arg Asp Lys Pro Ile Arg
1325 1330 1335

Glu Gln Ala Glu Asn Ile Ile His Leu Phe Thr Leu Thr Asn Leu
1340 1345 1350

Gly Ala Pro Ala Ala Phe Lys Tyr Phe Asp Thr Thr Ile Asp Arg
1355 1360 1365

Lys Arg Tyr Thr Ser Thr Lys Glu Val Leu Asp Ala Thr Leu Ile
1370 1375 1380

His Gln Ser Ile Thr Gly Leu Tyr Glu Thr Arg Ile Asp Leu Ser
1385 1390 1395

Gln Leu Gly Gly Asp Pro Lys Lys Lys Arg Lys Val Gly
1400 1405 1410

<210> SEQ ID NO 675
<211> LENGTH: 1483
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 675

Met Asp Tyr Lys Asp His Asp Gly Asp Tyr Lys Asp His Asp Ile Asp
1 5 10 15

Tyr Lys Asp Asp Asp Asp Lys Met Ala Pro Lys Lys Lys Arg Lys Val
20 25 30

```
Gly Arg Gly Met Asp Lys Lys Tyr Ser Ile Gly Leu Ala Ile Gly Thr
        35                  40                  45

Asn Ser Val Gly Trp Ala Val Ile Thr Asp Glu Tyr Lys Val Pro Ser
    50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
    130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
    210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
    290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350

Ser Ala Ser Met Ile Lys Arg Tyr Asp Glu His His Gln Asp Leu Thr
        355                 360                 365

Leu Leu Lys Ala Leu Val Arg Gln Gln Leu Pro Glu Lys Tyr Lys Glu
    370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
        435                 440                 445

Ile His Leu Gly Glu Leu His Ala Ile Leu Arg Arg Gln Glu Asp Phe
```

```
    450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
        515                 520                 525

Arg Met Thr Asn Phe Asp Lys Asn Leu Pro Asn Glu Lys Val Leu Pro
    530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
            580                 585                 590

Lys Val Thr Val Lys Gln Leu Lys Glu Asp Tyr Phe Lys Lys Ile Glu
        595                 600                 605

Cys Phe Asp Ser Val Glu Ile Ser Gly Val Glu Asp Arg Phe Asn Ala
    610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
        675                 680                 685

Arg Arg Tyr Thr Gly Trp Gly Arg Leu Ser Arg Lys Leu Ile Asn Gly
    690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
        755                 760                 765

Lys Lys Gly Ile Leu Gln Thr Val Lys Val Val Asp Glu Leu Val Lys
    770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
        835                 840                 845

Tyr Tyr Leu Gln Asn Gly Arg Asp Met Tyr Val Asp Gln Glu Leu Asp
    850                 855                 860

Ile Asn Arg Leu Ser Asp Tyr Asp Val Asp Ala Ile Val Pro Gln Ser
865                 870                 875                 880
```

Phe Leu Lys Asp Asp Ser Ile Asp Asn Lys Val Leu Thr Arg Ser Asp
885 890 895

Lys Asn Arg Gly Lys Ser Asp Asn Val Pro Ser Glu Glu Val Val Lys
900 905 910

Lys Met Lys Asn Tyr Trp Arg Gln Leu Leu Asn Ala Lys Leu Ile Thr
915 920 925

Gln Arg Lys Phe Asp Asn Leu Thr Lys Ala Glu Arg Gly Gly Leu Ser
930 935 940

Glu Leu Asp Lys Ala Gly Phe Ile Lys Arg Gln Leu Val Glu Thr Arg
945 950 955 960

Gln Ile Thr Lys His Val Ala Gln Ile Leu Asp Ser Arg Met Asn Thr
965 970 975

Lys Tyr Asp Glu Asn Asp Lys Leu Ile Arg Glu Val Lys Val Ile Thr
980 985 990

Leu Lys Ser Lys Leu Val Ser Asp Phe Arg Lys Asp Phe Gln Phe Tyr
995 1000 1005

Lys Val Arg Glu Ile Asn Asn Tyr His His Ala His Asp Ala Tyr
1010 1015 1020

Leu Asn Ala Val Val Gly Thr Ala Leu Ile Lys Lys Tyr Pro Lys
1025 1030 1035

Leu Glu Ser Glu Phe Val Tyr Gly Asp Tyr Lys Val Tyr Asp Val
1040 1045 1050

Arg Lys Met Ile Ala Lys Ser Glu Gln Glu Ile Gly Lys Ala Thr
1055 1060 1065

Ala Lys Tyr Phe Phe Tyr Ser Asn Ile Met Asn Phe Phe Lys Thr
1070 1075 1080

Glu Ile Thr Leu Ala Asn Gly Glu Ile Arg Lys Arg Pro Leu Ile
1085 1090 1095

Glu Thr Asn Gly Glu Thr Gly Glu Ile Val Trp Asp Lys Gly Arg
1100 1105 1110

Asp Phe Ala Thr Val Arg Lys Val Leu Ser Met Pro Gln Val Asn
1115 1120 1125

Ile Val Lys Lys Thr Glu Val Gln Thr Gly Gly Phe Ser Lys Glu
1130 1135 1140

Ser Ile Leu Pro Lys Arg Asn Ser Asp Lys Leu Ile Ala Arg Lys
1145 1150 1155

Lys Asp Trp Asp Pro Lys Lys Tyr Gly Gly Phe Asp Ser Pro Thr
1160 1165 1170

Val Ala Tyr Ser Val Leu Val Val Ala Lys Val Glu Lys Gly Lys
1175 1180 1185

Ser Lys Lys Leu Lys Ser Val Lys Glu Leu Leu Gly Ile Thr Ile
1190 1195 1200

Met Glu Arg Ser Ser Phe Glu Lys Asn Pro Ile Asp Phe Leu Glu
1205 1210 1215

Ala Lys Gly Tyr Lys Glu Val Lys Lys Asp Leu Ile Ile Lys Leu
1220 1225 1230

Pro Lys Tyr Ser Leu Phe Glu Leu Glu Asn Gly Arg Lys Arg Met
1235 1240 1245

Leu Ala Ser Ala Gly Glu Leu Gln Lys Gly Asn Glu Leu Ala Leu
1250 1255 1260

Pro Ser Lys Tyr Val Asn Phe Leu Tyr Leu Ala Ser His Tyr Glu
1265 1270 1275

Lys Leu Lys Gly Ser Pro Glu Asp Asn Glu Gln Lys Gln Leu Phe
1280 1285 1290

Val Glu Gln His Lys His Tyr Leu Asp Glu Ile Ile Glu Gln Ile
1295 1300 1305

Ser Glu Phe Ser Lys Arg Val Ile Leu Ala Asp Ala Asn Leu Asp
1310 1315 1320

Lys Val Leu Ser Ala Tyr Asn Lys His Arg Asp Lys Pro Ile Arg
1325 1330 1335

Glu Gln Ala Glu Asn Ile Ile His Leu Phe Thr Leu Thr Asn Leu
1340 1345 1350

Gly Ala Pro Ala Ala Phe Lys Tyr Phe Asp Thr Thr Ile Asp Arg
1355 1360 1365

Lys Arg Tyr Thr Ser Thr Lys Glu Val Leu Asp Ala Thr Leu Ile
1370 1375 1380

His Gln Ser Ile Thr Gly Leu Tyr Glu Thr Arg Ile Asp Leu Ser
1385 1390 1395

Gln Leu Gly Gly Asp Pro Ile Ala Gly Ser Lys Ala Ser Pro Lys
1400 1405 1410

Lys Lys Arg Lys Val Gly Arg Ala Asp Ala Leu Asp Asp Phe Asp
1415 1420 1425

Leu Asp Met Leu Gly Ser Asp Ala Leu Asp Asp Phe Asp Leu Asp
1430 1435 1440

Met Leu Gly Ser Asp Ala Leu Asp Asp Phe Asp Leu Asp Met Leu
1445 1450 1455

Gly Ser Asp Ala Leu Asp Asp Phe Asp Leu Asp Met Leu Ile Asn
1460 1465 1470

Tyr Pro Tyr Asp Val Pro Asp Tyr Ala Ser
1475 1480

<210> SEQ ID NO 676
<211> LENGTH: 2048
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 676

Met Asp Tyr Lys Asp His Asp Gly Asp Tyr Lys Asp His Asp Ile Asp
1 5 10 15

Tyr Lys Asp Asp Asp Asp Lys Met Ala Pro Lys Lys Lys Arg Lys Val
20 25 30

Gly Arg Gly Met Asp Lys Lys Tyr Ser Ile Gly Leu Ala Ile Gly Thr
35 40 45

Asn Ser Val Gly Trp Ala Val Ile Thr Asp Glu Tyr Lys Val Pro Ser
50 55 60

Lys Lys Phe Lys Val Leu Gly Asn Thr Asp Arg His Ser Ile Lys Lys
65 70 75 80

Asn Leu Ile Gly Ala Leu Leu Phe Asp Ser Gly Glu Thr Ala Glu Ala
85 90 95

Thr Arg Leu Lys Arg Thr Ala Arg Arg Arg Tyr Thr Arg Arg Lys Asn
100 105 110

Arg Ile Cys Tyr Leu Gln Glu Ile Phe Ser Asn Glu Met Ala Lys Val
115 120 125

Asp Asp Ser Phe Phe His Arg Leu Glu Glu Ser Phe Leu Val Glu Glu
130 135 140

```
Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
    210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
    290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350

Ser Ala Ser Met Ile Lys Arg Tyr Asp Glu His His Gln Asp Leu Thr
        355                 360                 365

Leu Leu Lys Ala Leu Val Arg Gln Gln Leu Pro Glu Lys Tyr Lys Glu
    370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
        435                 440                 445

Ile His Leu Gly Glu Leu His Ala Ile Leu Arg Arg Gln Glu Asp Phe
    450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
        515                 520                 525

Arg Met Thr Asn Phe Asp Lys Asn Leu Pro Asn Glu Lys Val Leu Pro
    530                 535                 540

Lys His Ser Leu Leu Tyr Glu Tyr Phe Thr Val Tyr Asn Glu Leu Thr
545                 550                 555                 560
```

```
Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
            580                 585                 590

Lys Val Thr Val Lys Gln Leu Lys Glu Asp Tyr Phe Lys Lys Ile Glu
        595                 600                 605

Cys Phe Asp Ser Val Glu Ile Ser Gly Val Glu Asp Arg Phe Asn Ala
    610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
        675                 680                 685

Arg Arg Tyr Thr Gly Trp Gly Arg Leu Ser Arg Lys Leu Ile Asn Gly
    690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
        755                 760                 765

Lys Lys Gly Ile Leu Gln Thr Val Lys Val Val Asp Glu Leu Val Lys
    770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
        835                 840                 845

Tyr Tyr Leu Gln Asn Gly Arg Asp Met Tyr Val Asp Gln Glu Leu Asp
    850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
        915                 920                 925

Gln Arg Lys Phe Asp Asn Leu Thr Lys Ala Glu Arg Gly Gly Leu Ser
    930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
```

980 985 990

Leu Lys Ser Lys Leu Val Ser Asp Phe Arg Lys Asp Phe Gln Phe Tyr
995 1000 1005

Lys Val Arg Glu Ile Asn Asn Tyr His His Ala His Asp Ala Tyr
1010 1015 1020

Leu Asn Ala Val Val Gly Thr Ala Leu Ile Lys Lys Tyr Pro Lys
1025 1030 1035

Leu Glu Ser Glu Phe Val Tyr Gly Asp Tyr Lys Val Tyr Asp Val
1040 1045 1050

Arg Lys Met Ile Ala Lys Ser Glu Gln Glu Ile Gly Lys Ala Thr
1055 1060 1065

Ala Lys Tyr Phe Phe Tyr Ser Asn Ile Met Asn Phe Phe Lys Thr
1070 1075 1080

Glu Ile Thr Leu Ala Asn Gly Glu Ile Arg Lys Arg Pro Leu Ile
1085 1090 1095

Glu Thr Asn Gly Glu Thr Gly Glu Ile Val Trp Asp Lys Gly Arg
1100 1105 1110

Asp Phe Ala Thr Val Arg Lys Val Leu Ser Met Pro Gln Val Asn
1115 1120 1125

Ile Val Lys Lys Thr Glu Val Gln Thr Gly Gly Phe Ser Lys Glu
1130 1135 1140

Ser Ile Leu Pro Lys Arg Asn Ser Asp Lys Leu Ile Ala Arg Lys
1145 1150 1155

Lys Asp Trp Asp Pro Lys Lys Tyr Gly Gly Phe Asp Ser Pro Thr
1160 1165 1170

Val Ala Tyr Ser Val Leu Val Val Ala Lys Val Glu Lys Gly Lys
1175 1180 1185

Ser Lys Lys Leu Lys Ser Val Lys Glu Leu Leu Gly Ile Thr Ile
1190 1195 1200

Met Glu Arg Ser Ser Phe Glu Lys Asn Pro Ile Asp Phe Leu Glu
1205 1210 1215

Ala Lys Gly Tyr Lys Glu Val Lys Lys Asp Leu Ile Ile Lys Leu
1220 1225 1230

Pro Lys Tyr Ser Leu Phe Glu Leu Glu Asn Gly Arg Lys Arg Met
1235 1240 1245

Leu Ala Ser Ala Gly Glu Leu Gln Lys Gly Asn Glu Leu Ala Leu
1250 1255 1260

Pro Ser Lys Tyr Val Asn Phe Leu Tyr Leu Ala Ser His Tyr Glu
1265 1270 1275

Lys Leu Lys Gly Ser Pro Glu Asp Asn Glu Gln Lys Gln Leu Phe
1280 1285 1290

Val Glu Gln His Lys His Tyr Leu Asp Glu Ile Ile Glu Gln Ile
1295 1300 1305

Ser Glu Phe Ser Lys Arg Val Ile Leu Ala Asp Ala Asn Leu Asp
1310 1315 1320

Lys Val Leu Ser Ala Tyr Asn Lys His Arg Asp Lys Pro Ile Arg
1325 1330 1335

Glu Gln Ala Glu Asn Ile Ile His Leu Phe Thr Leu Thr Asn Leu
1340 1345 1350

Gly Ala Pro Ala Ala Phe Lys Tyr Phe Asp Thr Thr Ile Asp Arg
1355 1360 1365

Lys Arg Tyr Thr Ser Thr Lys Glu Val Leu Asp Ala Thr Leu Ile
1370 1375 1380

His Gln Ser Ile Thr Gly Leu Tyr Glu Thr Arg Ile Asp Leu Ser
1385 1390 1395

Gln Leu Gly Gly Asp Pro Ile Ala Gly Ser Lys Ala Ser Pro Lys
1400 1405 1410

Lys Lys Arg Lys Val Gly Arg Ala Ile Phe Lys Pro Glu Glu Leu
1415 1420 1425

Arg Gln Ala Leu Met Pro Thr Leu Glu Ala Leu Tyr Arg Gln Asp
1430 1435 1440

Pro Glu Ser Leu Pro Phe Arg Gln Pro Val Asp Pro Gln Leu Leu
1445 1450 1455

Gly Ile Pro Asp Tyr Phe Asp Ile Val Lys Ser Pro Met Asp Leu
1460 1465 1470

Ser Thr Ile Lys Arg Lys Leu Asp Thr Gly Gln Tyr Gln Glu Pro
1475 1480 1485

Trp Gln Tyr Val Asp Asp Ile Trp Leu Met Phe Asn Asn Ala Trp
1490 1495 1500

Leu Tyr Asn Arg Lys Thr Ser Arg Val Tyr Lys Tyr Cys Ser Lys
1505 1510 1515

Leu Ser Glu Val Phe Glu Gln Glu Ile Asp Pro Val Met Gln Ser
1520 1525 1530

Leu Gly Tyr Cys Cys Gly Arg Lys Leu Glu Phe Ser Pro Gln Thr
1535 1540 1545

Leu Cys Cys Tyr Gly Lys Gln Leu Cys Thr Ile Pro Arg Asp Ala
1550 1555 1560

Thr Tyr Tyr Ser Tyr Gln Asn Arg Tyr His Phe Cys Glu Lys Cys
1565 1570 1575

Phe Asn Glu Ile Gln Gly Glu Ser Val Ser Leu Gly Asp Asp Pro
1580 1585 1590

Ser Gln Pro Gln Thr Thr Ile Asn Lys Glu Gln Phe Ser Lys Arg
1595 1600 1605

Lys Asn Asp Thr Leu Asp Pro Glu Leu Phe Val Glu Cys Thr Glu
1610 1615 1620

Cys Gly Arg Lys Met His Gln Ile Cys Val Leu His His Glu Ile
1625 1630 1635

Ile Trp Pro Ala Gly Phe Val Cys Asp Gly Cys Leu Lys Lys Ser
1640 1645 1650

Ala Arg Thr Arg Lys Glu Asn Lys Phe Ser Ala Lys Arg Leu Pro
1655 1660 1665

Ser Thr Arg Leu Gly Thr Phe Leu Glu Asn Arg Val Asn Asp Phe
1670 1675 1680

Leu Arg Arg Gln Asn His Pro Glu Ser Gly Glu Val Thr Val Arg
1685 1690 1695

Val Val His Ala Ser Asp Lys Thr Val Glu Val Lys Pro Gly Met
1700 1705 1710

Lys Ala Arg Phe Val Asp Ser Gly Glu Met Ala Glu Ser Phe Pro
1715 1720 1725

Tyr Arg Thr Lys Ala Leu Phe Ala Phe Glu Glu Ile Asp Gly Val
1730 1735 1740

Asp Leu Cys Phe Phe Gly Met His Val Gln Glu Tyr Gly Ser Asp
1745 1750 1755

Cys Pro Pro Pro Asn Gln Arg Arg Val Tyr Ile Ser Tyr Leu Asp
1760 1765 1770

```
Ser Val  His Phe Phe Arg Pro  Lys Cys Leu Arg Thr  Ala Val Tyr
    1775                 1780                 1785

His Glu  Ile Leu Ile Gly Tyr  Leu Glu Tyr Val Lys  Lys Leu Gly
    1790                 1795                 1800

Tyr Thr  Thr Gly His Ile Trp  Ala Cys Pro Pro Ser  Glu Gly Asp
    1805                 1810                 1815

Asp Tyr  Ile Phe His Cys His  Pro Pro Asp Gln Lys  Ile Pro Lys
    1820                 1825                 1830

Pro Lys  Arg Leu Gln Glu Trp  Tyr Lys Lys Met Leu  Asp Lys Ala
    1835                 1840                 1845

Val Ser  Glu Arg Ile Val His  Asp Tyr Lys Asp Ile  Phe Lys Gln
    1850                 1855                 1860

Ala Thr  Glu Asp Arg Leu Thr  Ser Ala Lys Glu Leu  Pro Tyr Phe
    1865                 1870                 1875

Glu Gly  Asp Phe Trp Pro Asn  Val Leu Glu Glu Ser  Ile Lys Glu
    1880                 1885                 1890

Leu Glu  Gln Glu Glu Glu Glu  Arg Lys Arg Glu Glu  Asn Thr Ser
    1895                 1900                 1905

Asn Glu  Ser Thr Asp Val Thr  Lys Gly Asp Ser Lys  Asn Ala Lys
    1910                 1915                 1920

Lys Lys  Asn Asn Lys Lys Thr  Ser Lys Asn Lys Ser  Ser Leu Ser
    1925                 1930                 1935

Arg Gly  Asn Lys Lys Lys Pro  Gly Met Pro Asn Val  Ser Asn Asp
    1940                 1945                 1950

Leu Ser  Gln Lys Leu Tyr Ala  Thr Met Glu Lys His  Lys Glu Val
    1955                 1960                 1965

Phe Phe  Val Ile Arg Leu Ile  Ala Gly Pro Ala Ala  Asn Ser Leu
    1970                 1975                 1980

Pro Pro  Ile Val Asp Pro Asp  Pro Leu Ile Pro Cys  Asp Leu Met
    1985                 1990                 1995

Asp Gly  Arg Asp Ala Phe Leu  Thr Leu Ala Arg Asp  Lys His Leu
    2000                 2005                 2010

Glu Phe  Ser Ser Leu Arg Arg  Ala Gln Trp Ser Thr  Met Cys Met
    2015                 2020                 2025

Leu Val  Glu Leu His Thr Gln  Ser Gln Asp Tyr Pro  Tyr Asp Val
    2030                 2035                 2040

Pro Asp  Tyr Ala Ser
    2045
```

<210> SEQ ID NO 677
<211> LENGTH: 23
<212> TYPE: DNA
<213> ORGANISM: Artificial Sequence
<220> FEATURE:
<223> OTHER INFORMATION: Description of Artificial Sequence: Dystrophin gene reference sequence
<220> FEATURE:
<221> NAME/KEY: modified_base
<222> LOCATION: (1)..(21)
<223> OTHER INFORMATION: a, c, t, g, unknown or other

<400> SEQUENCE: 677
nnnnnnnnnn nnnnnnnnnn ngg 23

<210> SEQ ID NO 678
<211> LENGTH: 23
<212> TYPE: DNA
<213> ORGANISM: Artificial Sequence
<220> FEATURE:
<223> OTHER INFORMATION: Description of Artificial Sequence: Dystrophin
gene reference sequence
<220> FEATURE:
<221> NAME/KEY: modified_base
<222> LOCATION: (2)..(21)
<223> OTHER INFORMATION: a, c, t, g, unknown or other

<400> SEQUENCE: 678
gnnnnnnnnn nnnnnnnnnn ngg 23

<210> SEQ ID NO 679
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 679
gtgtagagta agtcagccta 20

<210> SEQ ID NO 680
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 680
gttggacaga acttaccgac 20

<210> SEQ ID NO 681
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 681
gtttgcttcg ctataaaacg 20

<210> SEQ ID NO 682
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 682
gtctgaggat ggggccgcaa 20

<210> SEQ ID NO 683
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 683
ggatctgtca aatcgcctgc 20

<210> SEQ ID NO 684

<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 684
gccaggatgg cattgggcag 20

<210> SEQ ID NO 685
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 685
gctgaatctg cggtggcagg 20

<210> SEQ ID NO 686
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 686
gttcttttgt tcttctagcc 20

<210> SEQ ID NO 687
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 687
ggaaaagctt gagcaagtca 20

<210> SEQ ID NO 688
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 688
ggaagagttg cccctgcgcc 20

<210> SEQ ID NO 689
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 689
gacaaatctc cagtggataa 20

<210> SEQ ID NO 690
<211> LENGTH: 20

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 690
gtgtttctca ggtaaagctc 20

<210> SEQ ID NO 691
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 691
ggaaggacca tttgacgtta 20

<210> SEQ ID NO 692
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 692
gaactgctat ttcagtttcc 20

<210> SEQ ID NO 693
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 693
gccagccact cagccagtga 20

<210> SEQ ID NO 694
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 694
ggtatgcttt tctgttaaag 20

<210> SEQ ID NO 695
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 695
gctcctggac tgaccactat 20

<210> SEQ ID NO 696
<211> LENGTH: 23
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 696
ggaacagagg cgtccccagt tgg 23

<210> SEQ ID NO 697
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 697
ggaggctaga acaatcatta 20

<210> SEQ ID NO 698
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 698
gacaagaaca ccttcagaac 20

<210> SEQ ID NO 699
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 699
gggtttctgt gattttcttt 20

<210> SEQ ID NO 700
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 700
gggccaaaga cctccgccag 20

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 701
gttggagaag cattcataaa 20

<210> SEQ ID NO 702
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 702
gtcgctcact caccctgcaa 20

<210> SEQ ID NO 703
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 703
gaaaagagct gatgaaacaa 20

<210> SEQ ID NO 704
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 704
gtacactttt caaaatgctt 20

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 705
ggagatgatc atcaagcaga 20

<210> SEQ ID NO 706
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 706
gctttgaaag agcaataaaa 20

<210> SEQ ID NO 707
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 707
gcacaaaagt caaatcggaa 20

<210> SEQ ID NO 708
<211> LENGTH: 20
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 708
gatttcaata taagattcgg 20

<210> SEQ ID NO 709
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 709
gcttaagcaa tcccgaactc 20

<210> SEQ ID NO 710
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 710
gaggccaaac ctcggcttac 20

<210> SEQ ID NO 711
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 711
gttcgaaaat ttcaggtaag 20

<210> SEQ ID NO 712
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 712
ggcagaacag gagataacag 20

<210> SEQ ID NO 713
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 713
ggcggccctc gcccttctct 20

<210> SEQ ID NO 714
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 714
gtagtgatcg tggatacgag 20

<210> SEQ ID NO 715
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 715
gtacagccct cggtgtatat 20

<210> SEQ ID NO 716
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 716
gggaaggaat taagcccgaa 20

<210> SEQ ID NO 717
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 717
gggaacagct ttcgtagttg 20

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 718
gataaagtcc agtgtcgatc 20

<210> SEQ ID NO 719
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 719
gaaaaccaga gcttcggtca 20

<210> SEQ ID NO 720
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 720
ggagtcttct gggcaggctt aaaggctaac c 31

<210> SEQ ID NO 721
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 721
gtcgggtgag catgtcttta atctacctcg a 31

<210> SEQ ID NO 722
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 722
ggtgtcacca gagtaacagt 20

<210> SEQ ID NO 723
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 723
gtgatcatca agcagaaggt 20

<210> SEQ ID NO 724
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 724
gaacttcgaa aatttcaggt a 21

<210> SEQ ID NO 725
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 725
ggaaactcat caaatatgcg t 21

<210> SEQ ID NO 726
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 726
gtcatttaca ctaacacgca t 21

<210> SEQ ID NO 727
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 727
ggaatgaaac tcatcaaata t 21

<210> SEQ ID NO 728
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 728
gtcatcaata tctttgaagg a 21

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 729
gtgttttcat aggaaaaata g 21

<210> SEQ ID NO 730
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 730
gaattggaaa atgtgatggg a 21

<210> SEQ ID NO 731
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 731
gatgatcatc aagcagaagg t 21

<210> SEQ ID NO 732
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 732
gagatgatca tcaagcagaa g 21

<210> SEQ ID NO 733
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 733 gcatttttc tcataccttc t 21

<210> SEQ ID NO 734
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 734
gtcctactca gactgttact c 21

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 735
gacaggttgt gtcaccagag t 21

<210> SEQ ID NO 736
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 736
gttatcattt tttctcatac c 21

<210> SEQ ID NO 737
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 737
gttgcctaag aactggtggg a 21

<210> SEQ ID NO 738
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 738
gaaacagttg cctaagaact g 21

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 739
gtttcccacc agttcttagg c 21

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 740
gtggctttga tttccctagg g 21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 741
gtagggaaat caaagccaat g 21

<210> SEQ ID NO 742
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 742
ggaccctagg gaaatcaaag c 21

<210> SEQ ID NO 743
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 743
gtgagggctc caccctcacg a 21

<210> SEQ ID NO 744
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 744
gaaggattga gggctccacc c 21

<210> SEQ ID NO 745
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 745
ggctccaccc tcacgagtgg g 21

<210> SEQ ID NO 746
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 746
gtatccccta tcgaggaaac c 21

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 747
ggataaagaa ggcctatttc a 21

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 748
gaggccttct ttatccccta t 21

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 749
gtgagggctc caccctcacg a 21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 750
ggataaagaa ggcctatttc a 21